(12) United States Patent
Kanda et al.

(10) Patent No.: US 7,605,272 B2
(45) Date of Patent: Oct. 20, 2009

(54) IGF-1R INHIBITOR

(75) Inventors: Yutaka Kanda, Tokyo (JP); Hiromi Ando, Naka-gun (JP); Keiko Kawashima, Numazu (JP); Takamasa Sugita, Sakai (JP); Masayo Suzuki, Tokyo (JP); Hisashi Tagaya, Sunto-gun (JP); Tomoyuki Nakazato, Sunto-gun (JP); Yoshinori Yamashita, Tokyo (JP); Takeshi Takahashi, Numazu (JP); Shinji Nara, Sunto-gun (JP); Hiroaki Nakamura, Sunto-gun (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 236 days.

(21) Appl. No.: 11/814,753

(22) PCT Filed: Jan. 27, 2006

(86) PCT No.: PCT/JP2006/301341

§ 371 (c)(1),
(2), (4) Date: Jul. 25, 2007

(87) PCT Pub. No.: WO2006/080450

PCT Pub. Date: Aug. 3, 2006

(65) Prior Publication Data

US 2009/0054508 A1     Feb. 26, 2009

(30) Foreign Application Priority Data

Jan. 27, 2005   (JP)   ............... 2005-020158

(51) Int. Cl.
| | |
|---|---|
| C07D 231/56 | (2006.01) |
| C07D 211/06 | (2006.01) |
| C07D 413/10 | (2006.01) |
| C07D 403/10 | (2006.01) |
| A61K 31/416 | (2006.01) |
| A61K 31/4439 | (2006.01) |
| A61K 31/496 | (2006.01) |
| A61K 31/5355 | (2006.01) |
| A61K 31/5377 | (2006.01) |

(52) U.S. Cl. ............... 548/362.5; 544/140; 544/371; 546/199; 514/234.5; 514/254.06; 514/322; 514/406

(58) Field of Classification Search ............... 548/362.5
See application file for complete search history.

(56) References Cited

U.S. PATENT DOCUMENTS

| | | | |
|---|---|---|---|
| 7,470,717 B2 * | 12/2008 | Ohta et al. ............... 514/406 |
| 2002/0091116 A1 | 7/2002 | Zhu et al. | |
| 2004/0127538 A1 | 7/2004 | Oinuma et al. | |
| 2005/0137171 A1 | 6/2005 | Cherrier et al. | |
| 2005/0208582 A1 | 9/2005 | Ohi et al. | |
| 2005/0261339 A1 | 11/2005 | Ohi et al. | |
| 2005/0282880 A1 | 12/2005 | Oinuma et al. | |
| 2006/0058366 A1 | 3/2006 | Kanai et al. | |
| 2006/0281789 A1 | 12/2006 | Shiotsu et al. | |
| 2007/0117856 A1 | 5/2007 | Ohta et al. | |

FOREIGN PATENT DOCUMENTS

| | | |
|---|---|---|
| JP | 02-032059 | 2/1990 |
| JP | 2003-503481 | 1/2003 |
| WO | WO 01/02369 | 1/2001 |
| WO | WO 01/53268 | 7/2001 |
| WO | WO 02/10137 | 2/2002 |
| WO | WO 03/018022 | 3/2003 |
| WO | WO 03/035065 | 5/2003 |
| WO | WO 2004/050088 | 6/2004 |
| WO | WO 2004/094388 | 11/2004 |
| WO | WO 2005/012257 | 2/2005 |
| WO | WO 2005/012258 | 2/2005 |
| WO | WO 2005/094823 | 10/2005 |
| WO | WO 2007/058626 | 5/2007 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007], retrieved from the internet, URL; http://en.wikipedia.org/wiki/Cancer.*
Chemical Abstracts 163493q, vol. 89 (1978) 570 citing Khimiya Geterosiklicheskikh Soedinenii, vol. 7 (1978) 957-9.

* cited by examiner

*Primary Examiner*—Rei-Tsang Shiao
*Assistant Examiner*—Shawquia Young
(74) *Attorney, Agent, or Firm*—Fitzpatrick, Cella, Harper & Scinto

(57) ABSTRACT

The present invention provides a type I insulin-like growth factor receptor (IGF-1R) inhibitor comprising, as an active ingredient, an indazole derivative represented by Formula (I):

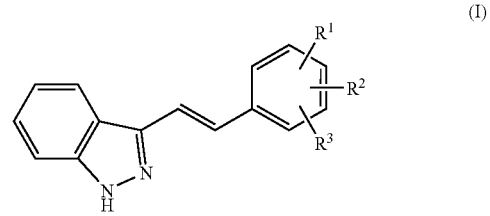

{wherein $R^1$ represents —$NR^4R^5$ [wherein $R^4$ represents a hydrogen atom or the like, $R^5$ represents substituted or unsubstituted lower alkyl, —$C(=O)R^6$ (wherein $R^6$ represents substituted or unsubstituted lower alkyl, substituted or unsubstituted aryl or the like), or the like], or the like, and $R^2$ and $R^3$ may be the same or different and each represents a hydrogen atom, hydroxy, substituted or unsubstituted lower alkoxy, or the like} or a pharmaceutically acceptable salt thereof, and the like.

16 Claims, No Drawings

IGF-1R INHIBITOR

TECHNICAL FIELD

The present invention relates to a type I insulin-like growth factor receptor (IGF-1R) inhibitor comprising, as an active ingredient, an indazole derivative or a pharmaceutically acceptable salt thereof and the like.

BACKGROUND ART

IGF-1R is a receptor tyrosine kinase which has a structure extremely similar to that of an insulin receptor and is a heterotetramer consisting of 2 extracellular α subunits and 2 transmembrane β subunits [EMBO Journal, vol. 5, p. 2503 (1986); Annual Review of Biochemistry, vol. 69, p. 373 (2000)]. By binding insulin-like growth factor-1 or 2, which is a ligand of IGF-1R, to its α subunits, the β subunits having kinase domain activate and thereby causes activation of IGF-1R. The activated IGF-1R phosphorylates many important proximal substrates such as insulin receptor substrate-1 or 2, and activates Akt, which is a serine-threonine kinase, via phosphatidylinositol-3 kinase or activates mitogen-activated protein kinase (MAPK) [Endocrinology, vol. 142, p. 1073 (2001)]. A signal pathway of Akt or MAPK is known to take an important role in transformation, proliferation, survival, infiltration and transfer of cells [Current Cancer Drug Targets, vol. 4, p. 235 (2004); and Molecular Pathology, vol. 54, p. 149 (2001)]. Also, signals sent from IGF-1R are known to protect cancer cells from cell-killing effect by chemotherapy or actinotherapy and are thought to be an important factor of drug tolerance [Breast Cancer Research and Treatment, vol. 56, p. 1 (1999); Cancer Research, vol. 57, p. 3079 (1997)]. Therefore, blocking these signal pathways is considered as an effective method for cancer treatment.

In many cancer cells (such as lung cancer, colon cancer, pancreatic cancer, mammary cancer, prostatic cancer, hepatic cancer, melanoma, brain tumor, multiple myeloma and leukemia), increase of expression of IGF-1R or activation of IGF-1R is known to be observed [Endocrine Reviews, vol. 21, p. 215 (2000); Nature Reviews Cancer, vol. 4, p. 505 (2004)]. Also, in rare cases, amplification of chromosomes, in which IGF-1R exist, are also known in mammary cancer or melanoma [Genes Chromosomes Cancer, vol. 11, p. 63 (1994)].

Therefore, IGF-1R is thought to be an effective target for cancer treatment and IGF-1R inhibitor is thought to be an useful therapeutic agent for various cancers.

Heretofore, staurosporine has been widely known as a kinase inhibitor [Biochemical & Biophysical Research Communications, vol. 135, p. 397 (1986)]. However, staurosporine non-selectively inhibits too much kinase and therefore, when administered, it leads animals such as mice to death. On the other hand, it has been reported that imatinib developed as a selective kinase inhibitor exhibits low toxicity and high clinical effect to chronic leukemia patients by selectively inhibiting Abl (Ableson) kinase [New England Journal of Medicine, vol. 345, p. 645 (2002)].

As an IGF-1R inhibitor, a pyrimidine derivative (WO03/018021, WO03/018022, WO04/080980), a pyrrolopyrimidine derivative (WO04/043962, WO02/92599), a cyclic urea derivative (WO04/070050), a 1-phenyltetrahydronaphtalene derivative (WO04/065996) and the like are known. Also, as an indazole derivative, various compounds have been known.

In Patent Document 1, a compound represented by Formula (IA):

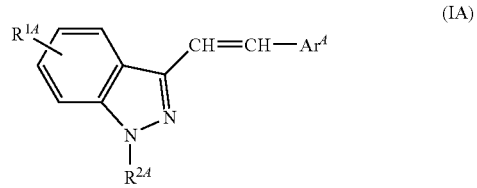

(IA)

{wherein $R^{1A}$ represents a hydrogen atom, nitro, $NR^{1A1}R^{1A2}$ [wherein $R^{1A1}$ and $R^{1A2}$ may be the same or different and each represents a hydrogen atom, substituted or unsubstituted lower alkyl, lower alkanoyl (the carbon number in the lower alkanoyl is 1 to 6) or the like] or the like, $R^{2A}$ represents a hydrogen atom or the like, $Ar^4$ represents pyridyl, substituted or unsubstituted 2-oxochromenyl [the 2-oxochromenyl is bonded to ethenyl (—CH=CH—) on its benzene ring and the substituent(s) on the 2-oxochromenyl is lower alkyl having 1 to 6 carbon atom(s) or lower alkoxy having 1 to 6 carbon atom(s)], phenyl or substituted phenyl [substituents $Q^{1A}$, $Q^{2A}$ and $Q^{3A}$ on the substituted phenyl may be the same or different and each represents a hydrogen atom, halogen, hydroxy, nitro, nitroso, carboxy, lower alkyl having 1 to 6 carbon atom(s), lower alkoxy having 1 to 6 carbon atom(s), lower alkoxycarbonyl having 1 to 6 carbon atom(s), $NR^{3A1}R^{3A2}$ (wherein $R^{3A1}$ and $R^{3A2}$ have the same meanings as $R^{1A1}$ and $R^{1A2}$ defined above, respectively), or $O(CH_2)_{nA}NR^{3A3}R^{3A4}$ (wherein nA represents an integer of 1 to 6 and $R^{3A3}$ and $R^{3A4}$ have the same meanings as $R^{1A1}$ and $R^{1A2}$ defined above, respectively), or any two from the groups $Q^{1A}$, $Q^{2A}$ and $Q^{3A}$ are combined together to form —$O(CR^{3A5}R^{3A6})O$— (wherein two terminal oxygen atoms are bonded to the phenyl group at adjacent carbon atoms on the phenyl group and $R^{3A5}$ and $R^{3A6}$ may be the same or different and each represents a hydrogen atom or lower alkyl having 1 to 6 carbon atom(s), or $R^{3A5}$ and $R^{3A6}$ are combined together to form alkylene having 4 or 5 carbon atoms), provided that the $Q^{1A}$, $Q^{2A}$ and $Q^{3A}$ which are the substituents on the substituted phenyl are not simultaneously hydrogen atoms)} is disclosed.

In Patent Document 2, a compound having suppressive activity on cell differentiation represented by Formula (IB):

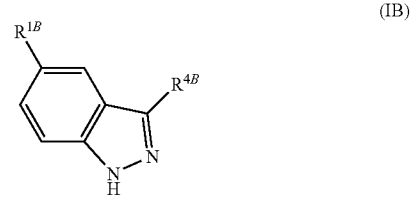

(IB)

[wherein $R^{4B}$ represents CH=CH—$R^{4B1}$ (wherein $R^{4B1}$ represents substituted or unsubstituted alkyl, substituted or unsubstituted aryl, a substituted or unsubstituted heterocyclic group, or the like) and $R^{1B}$ represents alkyl, aryl, CH=CH—$R^{1B1}$ (wherein $R^{1B1}$ represents substituted or unsubstituted aryl, substituted or unsubstituted heteroaryl, or the like)] is disclosed.

In Patent Documents 3 and 4, a compound having inhibitory activity against c-jun N-terminal Kinase (JNK) represented by Formula (IC):

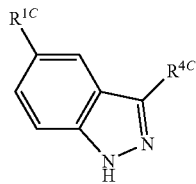

(IC)

[wherein $R^{4C}$ represents CH=CH—$R^{4C1}$ (wherein $R^{4C1}$ represents substituted or unsubstituted aryl, substituted or unsubstituted heteroaryl, or the like) and $R^{1C}$ represents halogen, hydroxy, amino, or the like] is disclosed. Also, a therapeutic agent for diseases associated with asbestos comprising, as an active ingredient, a compound of Patent Document 3 or 4 is known (WO2005/046594).

In Patent Document 5, a compound having inhibitory activity against JNK represented by Formula (ID):

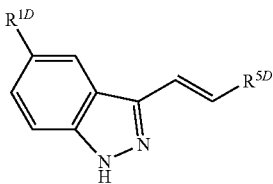

(ID)

[wherein $R^{1D}$ represents a hydrogen atom, $NR^{1D1}R^{1D2}$ (wherein $R^{1D1}$ and $R^{1D2}$ may be the same or different and each represents a hydrogen atom, substituted or unsubstituted lower alkanoyl, or the like), or the like and $R^{5D}$ represents substituted or unsubstituted aryl or the like] is disclosed.

Also, in Patent Document 6, an indazole derivative having inhibitory activity against JNK is disclosed.

In Non-patent Document 1, a compound represented by Formula (IE):

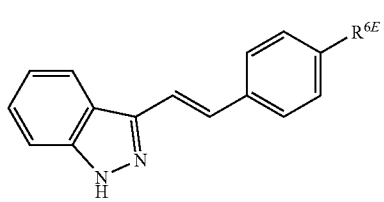

(IE)

(wherein $R^{6E}$ represents methoxy or nitro) is disclosed.

In Patent Document 7, a compound represented by Formula (IF):

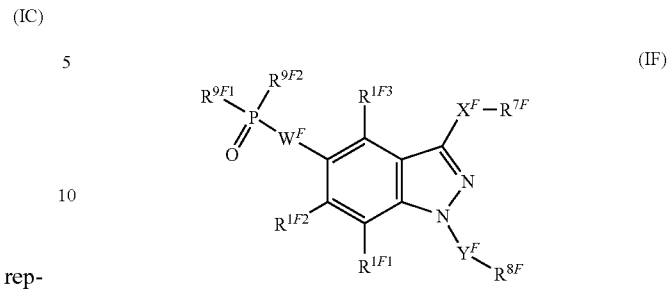

(IF)

[wherein $W^F$ represents a bond, or the like, $X^F$ represents a single bond, C=O, or the like, $Y^F$ represents a single bond, C=O, or the like, $R^{7F}$ represents a hydrogen atom, alkyl optionally having substituent(s), or the like, $R^{8F}$ represents a hydrogen atom, or the like, $R^{1F1}$, $R^{1F2}$ and $R^{1F3}$, which may be the same or different and each represents a hydrogen atom, halogen, or the like and $R^{11F1}$ and $R^{11F2}$ may be the same or different and each represents a hydrogen atom, alkyl optionally having substituent(s), or the like] is disclosed.

In Patent Document 8, a compound useful as an antitumor agent represented by Formula (IG):

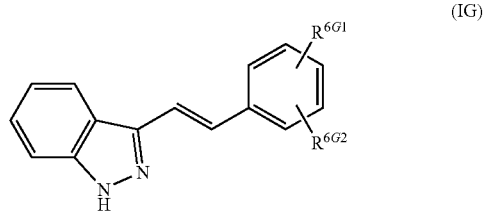

(IG)

[wherein $R^{6G1}$ represents $CONR^{10G1}R^{10G2}$ (wherein $R^{10G1}$ and $R^{10G2}$ may be the same or different and each represents a hydrogen atom, substituted or unsubstituted lower alkyl, or the like), or the like, $R^{6G2}$ represents a hydrogen atom, substituted or unsubstituted lower alkyl or the like] is disclosed.

In Patent Document 9, a compound having inhibitory activity against protein kinase represented by Formula (IH):

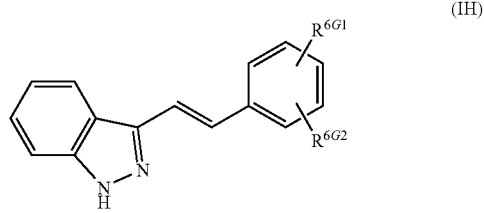

(IH)

[wherein $R^{6H1}$, $R^{6H2}$ and $R^{6H3}$ may be the same or different and each represents $OR^{11H}$ (wherein $R^{11H}$ represents a hydrogen atom, substituted or unsubstituted lower alkyl, or the like), or the like] ia disclosed.

In Patent Document 10, Fms like tyrosine kinase 3 (Flt-3) inhibitor comprising, as an active ingredient, a compound represented by Formula (IJ):

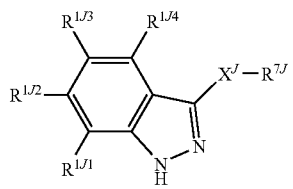

(IJ)

[wherein $X^J$ represents $(CH_2)_{nJ1}CH=CH(CH_2)_{nJ2}$ (wherein nJ1 and nJ2 may be the same or different and each represents an integer of 0 to 4), or the like, $R^{7J}$ represents substituted or unsubstituted aryl, or the like, $R^{1J1}$, $R^{1J2}$, $R^{1J3}$ and $R^{1J4}$ may be the same or different and each represents $NR^{12J1}R^{12J2}$ (wherein $R^{12J1}$ and $R^{12J2}$ may be the same or different and each represents a hydrogen atom, substituted or unsubstituted lower alkyl, or the like), or the like] is disclosed.

[Patent Document 1] Japanese published Unexamined Patent Application No. 32059/1990
[Patent Document 2] WO01/53268
[Patent Document 3] WO02/10137
[Patent Document 4] WO2004/094388
[Patent Document 5] WO2004/050088
[Patent Document 6] WO03/101968
[Patent Document 7] US2005/0137171
[Patent Document 8] WO2005/012257
[Patent Document 9] WO2005/012258
[Patent Document 10] WO2005/094823
[Non-patent Document 1] Khimiya Geterotsiklicheskikh Soedinenii, vol. 7, p. 957-959, 1978

DISCLOSURE OF THE INVENTION

Problems to be Solved by the Invention

An object of the present invention is to provide an IGF-1R inhibitor comprising, as an active ingredient, an indazole derivative or a pharmaceutically acceptable salt thereof, and the like.

Means for Solving the Problems

The present invention relates to the following (1) to (58).
(1) An IGF-1R inhibitor comprising, as an active ingredient, an indazole derivative represented by Formula (I):

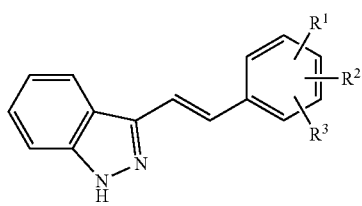

(I)

< wherein $R^1$ represents cyano, substituted or unsubstituted lower alkyl, substituted or unsubstituted lower alkoxy, substituted or unsubstituted lower alkylthio, —$NR^4R^5$ {wherein $R^4$ represents a hydrogen atom or substituted or unsubstituted lower alkyl, and $R^5$ represents a hydrogen atom, substituted or unsubstituted lower alkyl, a substituted or unsubstituted heterocyclic group, —C(=S)NH$_2$, —C(=O)$R^6$ [wherein $R^6$ represents a hydrogen atom, substituted or unsubstituted lower alkyl, substituted or unsubstituted lower alkoxy, substituted or unsubstituted aryl, a substituted or unsubstituted heterocyclic group, or —$NR^{7a}R^{7b}$ (wherein $R^{7a}$ and $R^{7b}$ may be the same or different and each represents a hydrogen atom, substituted or unsubstituted lower alkyl, substituted or unsubstituted lower alkoxy, substituted or unsubstituted aryl or a substituted or unsubstituted heterocyclic group, or $R^{7a}$ and $R^{7b}$ are combined together with the adjacent nitrogen atom thereto to form a substituted or unsubstituted heterocyclic group)] or —S(O)$_2R^8$ (wherein $R^8$ represents substituted or unsubstituted lower alkyl or substituted or unsubstituted aryl), or $R^4$ and $R^5$ are combined together with the adjacent nitrogen atom thereto to form nitro, a substituted or unsubstituted heterocyclic group, —N=CH—$R^{18}$ (wherein $R^{18}$ represents substituted or unsubstituted aryl, or a substituted or unsubstituted heterocyclic group), or —N=CH—$NR^{9a}R^{9b}$ (wherein $R^{9a}$ and $R^{9b}$ may be the same or different and each represents a hydrogen atom or lower alkyl)} or —C(=O) $NR^{10a}R^{10b}$ (wherein $R^{10a}$ and $R^{10b}$ have the same meanings as $R^{7a}$ and $R^{7b}$ defined above, respectively), and $R^2$ and $R^3$ may be the same or different and each represents a hydrogen atom, halogen, nitro, hydroxy, cyano, carboxy, substituted or unsubstituted lower alkyl, substituted or unsubstituted lower alkoxy, substituted or unsubstituted lower alkoxycarbonyl, a substituted or unsubstituted heterocyclic group, mono- or di-(substituted or unsubstituted lower alkyl)amino, or —$CX^1X^1$—$NR^{11a}R^{11b}$ (wherein $R^{11a}$ and $R^{11b}$ have the same meanings as $R^{7a}$ and $R^{7b}$ defined above, respectively, and $X^1$ and $X^2$ each represents a hydrogen atom, or $X^1$ and $X^2$ are combined together to represent an oxygen atom), or when $R^2$ and $R^3$ are on the adjacent carbon atoms, $R^2$ and $R^3$ may be combined to form methylenedioxy or ethylenedioxy, or when $R^1$ and $R^2$ are on the adjacent carbon atom thereto, $R^1$ and $R^2$ may be combined to form

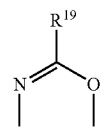

(wherein $R^{19}$ represents a hydrogen atom, substituted or unsubstituted lower alkyl, or a substituted or unsubstituted heterocyclic group)>, or a pharmaceutically acceptable salt thereof.

(2) An IGF-1R inhibitor comprising, as an active ingredient, an indazole derivative represented by Formula (Ia):

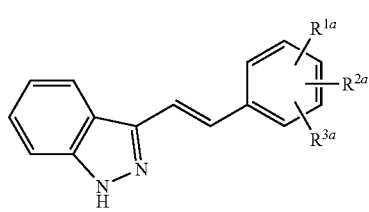

(Ia)

<wherein $R^{1a}$ represents cyano, substituted or unsubstituted lower alkyl, substituted or unsubstituted lower alkoxy, substituted or unsubstituted lower alkylthio, —$NR^{4a}R^{5a}$ {wherein $R^{4a}$ has the same meaning as $R^4$ defined above, and $R^{5a}$ represents a hydrogen atom, substituted or unsubstituted lower alkyl, —C(=O)$R^{6a}$ [wherein $R^{6a}$ represents a hydrogen atom, substituted or unsubstituted lower alkyl, substituted or unsubstituted lower alkoxy, substituted or unsubstituted aryl, a substituted or unsubstituted heterocyclic group, or —$NR^{7c}R^{7d}$ (wherein $R^{7c}$ and $R^{7d}$ may be the same or different and each represents a hydrogen atom, substituted or unsubstituted lower alkyl, substituted or unsubstituted aryl, or a substituted or unsubstituted heterocyclic group, or $R^{7c}$ and $R^{7d}$ are combined together with the adjacent nitrogen atom thereto to form a substituted or unsubstituted heterocyclic group)] or —S(O)$_2R^{8a}$ (wherein $R^{8a}$ has the same meaning as $R^8$ defined above), or $R^{4a}$ and $R^{5a}$ are combined together with the adjacent nitrogen atom thereto to form nitro, a substituted or unsubstituted heterocyclic group, or —N=CH—$NR^{9c}R^{9d}$ (wherein $R^{9c}$ and $R^{9d}$ have the same meanings as $R^{9a}$ and $R^{9b}$ defined above, respectively)}, or —C(=O)$NR^{10c}R^{11d}$ (wherein $R^{10c}$ and $R^{10d}$ have the same meanings as $R^{10a}$ and $R^{10b}$ defined above, respectively), and $R^{2a}$ and $R^{3a}$ may be the same or different and each represents a hydrogen atom, halogen, nitro, hydroxy, cyano, carboxy, substituted or unsubstituted lower alkyl, substituted or unsubstituted lower alkoxy, substituted or unsubstituted lower alkoxycarbonyl, mono- or di-(substituted or unsubstituted lower alkyl)amino, or —C(=O)$NR^{11c}R^{11d}$ (wherein $R^{11c}$ and $R^{11d}$ have the same meanings as $R^{11a}$ and $R^{11b}$ defined above, respectively), or when $R^{2a}$ and $R^{3a}$ are on the adjacent carbon atoms, $R^{2a}$ and $R^{3a}$ may be combined to form methylenedioxy or ethylenedioxy>, or a pharmaceutically acceptable salt thereof.

(3) An IGF-1R inhibitor comprising, as an active ingredient, an indazole derivative represented by Formula (Ib):

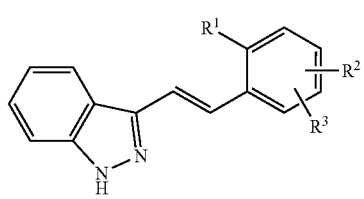

(Ib)

(wherein $R^1$, $R^2$ and $R^3$ have the same meanings as defined above, respectively) or a pharmaceutically acceptable salt thereof.

(4) An IGF-1R inhibitor comprising, as an active ingredient, an indazole derivative represented by Formula (Ic):

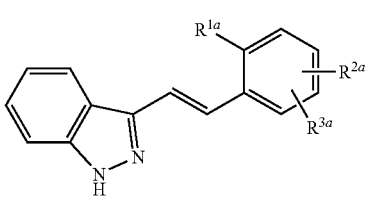

(Ic)

(wherein $R^{1a}$, $R^{2a}$ and $R^{3a}$ have the same meanings as defined above, respectively) or a pharmaceutically acceptable salt thereof.

(5) A method for inhibiting IGF-1R comprising administering an effective amount of the indazole derivative or the pharmaceutically acceptable salt thereof according to any of the above (1) to (4).

(6) Use of the indazole derivative or the pharmaceutically acceptable salt thereof according to any of the above (1) to (4) for the manufacture of IGF-1R inhibitor.

(7) An indazole derivative represented by Formula (II):

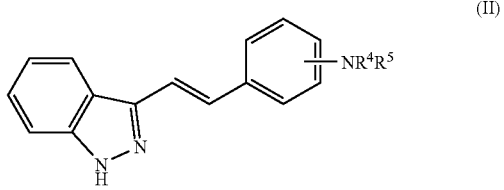

(II)

(wherein $R^4$ and $R^5$ have the same meanings as defined above, respectively) or a pharmaceutically acceptable salt thereof.

(8) An indazole derivative represented by Formula (IIa):

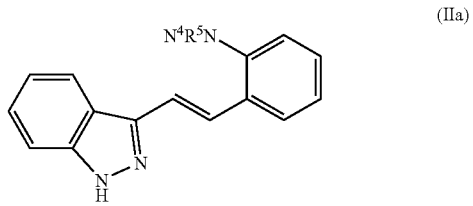

(IIa)

(wherein $R^4$ and $R^5$ have the same meanings as defined above, respectively) or a pharmaceutically acceptable salt thereof.

(9) The indazole derivative or the pharmaceutically acceptable salt thereof according to the above (8), wherein $R^4$ is a hydrogen atom.

(10) The indazole derivative or the pharmaceutically acceptable salt thereof according to the above (8) or (9), wherein $R^5$ is substituted or unsubstituted lower alkyl.

(11) The indazole derivative or the pharmaceutically acceptable salt thereof according to the above (8) or (9), wherein $R^5$ is benzyl.

(12) The indazole derivative or the pharmaceutically acceptable salt thereof according to the above (8) or (9), wherein $R^5$ is —C(=O)$R^6$ (wherein $R^6$ has the same meaning as defined above).

(13) The indazole derivative or the pharmaceutically acceptable salt thereof according to the above (8) or (9), wherein $R^5$ is —C(=O)$R^{6b}$ (wherein $R^{6b}$ represents substituted or unsubstituted lower alkyl).

(14) The indazole derivative or the pharmaceutically acceptable salt thereof according to the above (8) or (9), wherein $R^5$ is —C(=O)$R^{6c}$ (wherein $R^6$ represents substituted or unsubstituted aryl).

(15) The indazole derivative or the pharmaceutically acceptable salt thereof according to the above (8) or (9), wherein $R^5$ is —C(=O)$R^{6d}$ (wherein $R^{6d}$ represents a substituted or unsubstituted heterocyclic group).

(16) The indazole derivative or the pharmaceutically acceptable salt thereof according to the above (8) or (9), wherein $R^5$ is —S(O)$_2R^8$ (wherein $R^8$ has the same meaning as defined above).

(17) The indazole derivative or the pharmaceutically acceptable salt thereof according to the above (8), wherein $R^4$ and $R^5$ are hydrogen atoms.

(18) An indazole derivative represented by Formula (III):

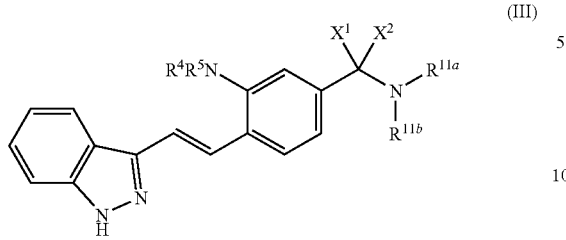

(III)

(wherein $X^1$, $X^2$, $R^4$, $R^5$, $R^{11a}$ and $R^{11b}$ have the same meanings as defined above, respectively) or a pharmaceutically acceptable salt thereof.

(19) An indazole derivative represented by Formula (IIIa):

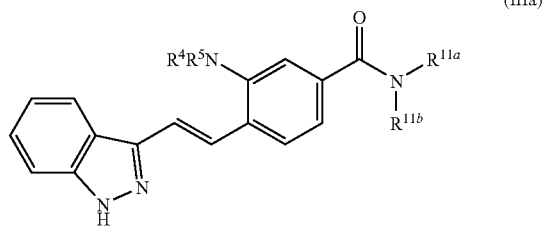

(IIIa)

(wherein $R^4$, $R^5$, $R^{11a}$ and $R^{11b}$ have the same meanings as defined above, respectively) or a pharmaceutically acceptable salt thereof.

(20) An indazole derivative represented by Formula (IIIb):

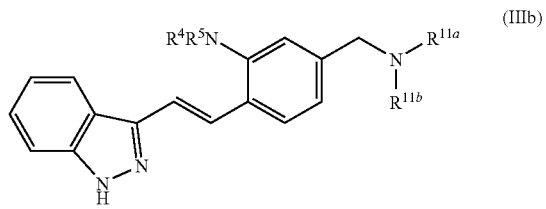

(IIIb)

(wherein $R^4$, $R^5$, $R^{11a}$ and $R^{11b}$ have the same meanings as defined above, respectively) or a pharmaceutically acceptable salt thereof.

(21) The indazole derivative or the pharmaceutically acceptable salt thereof according to any of the above (18) to (20), wherein $R^{11a}$ and $R^{11b}$ are combined together with the adjacent nitrogen atom thereto to form a substituted or unsubstituted heterocyclic group.

(22) The indazole derivative or the pharmaceutically acceptable salt thereof according to any of the above (18) to (20), wherein $R^{11a}$ and $R^{11b}$ may be the same or different and each is substituted or unsubstituted lower alkyl.

(23) The indazole derivative or the pharmaceutically acceptable salt thereof according to any of the above (18) to (22); wherein $R^4$ is a hydrogen atom and $R^5$ is —C(=O)$R^{6d}$ (wherein $R^{6d}$ has the same meaning as defined above).

(24) The indazole derivative or the pharmaceutically acceptable salt thereof according to any of the above (18) to (22), wherein $R^4$ and $R^5$ are combined together with the adjacent nitrogen atom thereto to form nitro.

(25) The indazole derivative or the pharmaceutically acceptable salt thereof according to any of the above (18) to (22), wherein $R^4$ and $R^5$ are hydrogen atoms.

(26) An indazole derivative represented by Formula (IV):

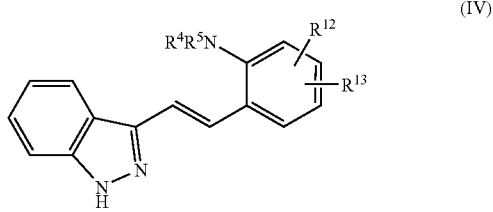

(IV)

[wherein $R^4$ and $R^5$ have the same meanings as defined above, respectively, and $R^{12}$ and $R^{13}$ may be the same or different and each represents a hydrogen atom, halogen ($R^{12}$ and $R^{13}$ do not simultaneously represent hydrogen atoms), nitro, hydroxy, cyano, carboxy, substituted or unsubstituted lower alkyl, substituted or unsubstituted lower alkoxy, substituted or unsubstituted lower alkoxycarbonyl, or mono- or di-(substituted or unsubstituted lower alkyl)amino, or when $R^{12}$ and $R^{13}$ are on the adjacent carbon atom, $R^{12}$ and $R^{13}$ are combined to form methylenedioxy or ethylenedioxy] or a pharmaceutically acceptable salt thereof.

(27) The indazole derivative or the pharmaceutically acceptable salt thereof according to the above (26), wherein $R^{12}$ is methoxy and $R^{13}$ is a hydrogen atom.

(28) The indazole derivative or the pharmaceutically acceptable salt thereof according to the above (26), wherein $R^{12}$ and $R^{13}$ are methoxy.

(29) The indazole derivative or the pharmaceutically acceptable salt thereof according to any of the above (26) to (28), wherein $R^4$ and $R^5$ are hydrogen atoms.

(30) The indazole derivative or the pharmaceutically acceptable salt thereof according to any of the above (26) to (28), wherein $R^4$ is a hydrogen atom and $R^5$ is —C(=O)$R^{6c}$ (wherein $R^{6c}$ has the same meaning as defined above).

(31) An indazole derivative represented by Formula (V):

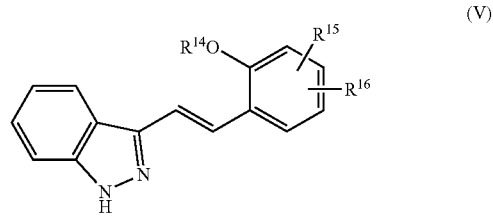

(V)

(wherein $R^{14}$ represents substituted or unsubstituted lower alkyl, and $R^{15}$ and $R^{16}$ may be the same or different and each represents a hydrogen atom, substituted or unsubstituted lower alkyl, or substituted or unsubstituted lower alkoxy, or when $R^{15}$ and $R^{16}$ are on the adjacent carbon atoms, $R^{15}$ and $R^{16}$ may be combined to form methylenedioxy or ethylenedioxy) or a pharmaceutically acceptable salt thereof.

(32) The indazole derivative or the pharmaceutically acceptable salt thereof according to the above (31), wherein $R^{15}$ and $R^{16}$ are hydrogen atoms.

(33) An indazole derivative represented by Formula (VI):

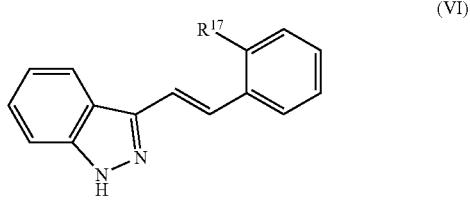

[wherein $R^{17}$ represents cyano, substituted or unsubstituted lower alkyl, substituted or unsubstituted lower alkylthio, or —C(=O)NR$^{10a}$R$^{10b}$ (wherein R$^{10a}$ and R$^{10b}$ have the same meanings as defined above, respectively)] or a pharmaceutically acceptable salt thereof.

(34) The indazole derivative or the pharmaceutically acceptable salt thereof according to the above (33), wherein $R^{17}$ is —C(=O)NR$^{10a}$R$^{10b}$ (wherein R$^{10a}$ and R$^{10b}$ have the same meanings as defined above, respectively).

(35) The indazole derivative or the pharmaceutically acceptable salt thereof according to the above (33), wherein $R^{17}$ is —C(=O)NR$^{10e}$R$^{10f}$ (wherein R$^{10e}$ represents a hydrogen atom and R$^{10f}$ represents substituted or unsubstituted lower alkyl).

(36) An indazole derivative represented by Formula (VII):

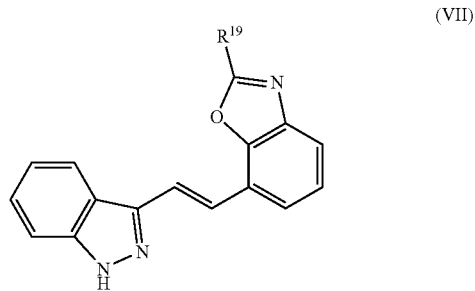

(wherein $R^{19}$ has the same meaning as defined above) or a pharmaceutically acceptable salt thereof.

(37) An IGF-1R inhibitor comprising, as an active ingredient, the indazole derivative or the pharmaceutically acceptable salt thereof according to any of the above (7) to (36).

(38) A pharmaceutical composition comprising, as an active ingredient, the indazole derivative or the pharmaceutically acceptable salt thereof according to any of the above (7) to (36).

(39) An antitumor agent comprising, as an active ingredient, the indazole derivative or the pharmaceutically acceptable salt thereof according to any of the above (7) to (36).

(40) A therapeutic agent for hematopoietic tumor comprising, as an active ingredient, the indazole derivative or the pharmaceutically acceptable salt thereof according to any of the above (7) to (36).

(41) A therapeutic agent for solid carcinoma comprising, as an active ingredient, the indazole derivative or the pharmaceutically acceptable salt thereof according to any of the above (7) to (36).

(42) A therapeutic agent for multiple myeloma comprising, as an active ingredient, the indazole derivative or the pharmaceutically acceptable salt thereof according to any of the above (7) to (36).

(43) The therapeutic agent for solid carcinoma according to the above (41), wherein the solid carcinoma is a mammary cancer, uterine body cancer, uterine cervix cancer, prostatic cancer, bladder cancer, renal cancer, gastric cancer, esophageal cancer, hepatic cancer, biliary tract cancer, colon cancer, rectal cancer, pancreatic cancer, lung cancer, head and neck cancer, or cancer derived from osteosarcoma, melanoma or brain neoplasm.

(44) The therapeutic agent for solid carcinoma according to the above (41), wherein the solid carcinoma is a colon cancer or pancreatic cancer.

(45) A method for inhibiting IGF-1R comprising administering an effective amount of the indazole derivative or the pharmaceutically acceptable salt thereof according to any of the above (7) to (36);

(46) A method for treating tumor comprising administering an effective amount of the indazole derivative or the pharmaceutically acceptable salt thereof according to any of the above (7) to (36).

(47) A method for treating hematopoietic tumor comprising administering an effective amount of the indazole derivative or the pharmaceutically acceptable salt thereof according to any of the above (7) to (36).

(48) A method for treating solid carcinoma comprising administering an effective amount of the indazole derivative or the pharmaceutically acceptable salt thereof according to any of the above (7) to (36).

(49) A method for treating multiple myeloma comprising administering an effective amount of the indazole derivative or the pharmaceutically acceptable salt thereof according to any of the above (7) to (36).

(50) The method for treating solid carcinoma according to the above (48), wherein the solid carcinoma is a mammary cancer, uterine body cancer, uterine cervix cancer, prostatic cancer, bladder cancer, renal cancer, gastric cancer, esophageal cancer, hepatic cancer, biliary tract cancer, colon cancer, rectal cancer, pancreatic cancer, lung cancer, head and neck cancer, or cancer derived from osteosarcoma, melanoma or brain neoplasm.

(51) The method for treating solid carcinoma according to the above (48), wherein the solid carcinoma is a colon cancer or pancreatic cancer.

(52) Use of the indazole derivative or the pharmaceutically acceptable salt thereof according to any of the above (7) to (36) for the manufacture of IGF-1R inhibitor.

(53) Use of the indazole derivative or the pharmaceutically acceptable salt thereof according to any of the above (7) to (36) for the manufacture of an antitumor agent.

(54) Use of the indazole derivative or the pharmaceutically acceptable salt thereof according to any of the above (7) to (36) for the manufacture of a therapeutic agent for hematopoietic tumor.

(55) Use of the indazole derivative or the pharmaceutically acceptable salt thereof according to any of the above (7) to (36) for the manufacture of a therapeutic agent for solid carcinoma.

(56) Use of the indazole derivative or the pharmaceutically acceptable salt thereof according to any of the above (7) to (36) for the manufacture of a therapeutic agent for multiple myeloma.

(57) Use of the indazole derivative or the pharmaceutically acceptable salt thereof according to any of the above (7) to (36) for the manufacture of a therapeutic agent for a mammary cancer, uterine body cancer, uterine cervix cancer, prostatic cancer, bladder cancer, renal cancer, gastric cancer, esophageal cancer, hepatic cancer, biliary tract cancer, colon cancer, rectal cancer, pancreatic cancer, lung cancer, head and neck cancer, or cancer derived from osteosarcoma, melanoma or brain neoplasm.

(58) Use of the indazole derivative or the pharmaceutically acceptable salt thereof according to any of the above (7) to (36) for the manufacture of a therapeutic agent for a colon cancer or pancreatic cancer.

EFFECT OF THE INVENTION

The present invention provides an IGF-1R inhibitor comprising, as an active ingredient, an indazole derivative or a pharmaceutically acceptable salt thereof, and the like.

BEST MODE FOR CARRYING OUT THE INVENTION

The compounds represented by Formulae (I), (Ia), (Ib), (Ic), (II), (IIa), (III), (IIIa), (IIIb), (IV), (V), (VI) and (VII) are hereinafter referred to as Compound (I), (Ia), (Ib), (Ic), (II), (IIa), (III), (IIIa), (IIIb), (IV), (V), (VI) and (VII), respectively. The same is true for compounds represented by other formula numbers.

In the definitions for each groups in Formulae (I), (Ia), (Ib), (Ic), (II), (IIa), (III), (IIIa), (IIIb), (IV), (v), (VI) and (VII):

(i) The halogen includes each atoms of fluorine, chlorine, bromine and iodine.

(ii) Examples of the lower alkyl and the lower alkyl moieties of the lower alkoxy, lower alkoxycarbonyl, lower alkylthio and mono- or di-(lower alkyl)amino include, for example, linear, branched, cyclic alkyl or alkyl comprising these alkyls in combination, having 1 to 10 carbon atom(s). More specific examples thereof are as follows.

(ii-a) Examples of the linear or branched lower alkyl include, for example, methyl, ethyl, n-propyl, isopropyl, n-butyl, isobutyl, sec-butyl, tert-butyl, n-pentyl, neopentyl, n-hexyl, n-heptyl, n-octyl, n-nonyl, n-decyl or the like;

(ii-b) examples of the cyclic lower alkyl include, for example, cyclopropyl, cyclobutyl, cyclopentyl, cyclohexyl, cycloheptyl, cyclooctyl, cyclodecyl, noradamantyl, adamantyl, bicyclo[2.2.1]heptyl, bicyclo[2.2.2]octyl, bicyclo[3.3.0]octyl, bicyclo[3.3.1]nonyl or the like; and (ii-c) examples of the lower alkyl comprising linear or branched alkyl and cyclic alkyl in combination include, for example, cyclopropylmethyl, cyclopentylmethyl, cyclooctylethyl and the like.

Two lower alkyl moieties of di-(lower alkyl)amino may be the same or different.

(iii) Examples of the aryl include, for example, monocyclic aryls or fused aryl in which two or more rings are fused and more specific examples include aryl having 6 to 14 carbon atoms as ring-constituting members, such as phenyl, naphthyl, indenyl or anthryl.

(iv) Examples of the heterocyclic group include, for example, a heteroaromatic group, heteroalicyclic group or the like.

(iv-a) Examples of the heteroaromatic group include, for example, monocyclic heteroaromatic group, fused heteroaromatic group in which two or more rings are fused, or the like. The type and number of the heteroatom contained in heteroaromatic group are not specifically limited and the heteroaromatic group may contain, for example, one or more heteroatoms selected from a group consisting of a nitrogen atom, sulfur atom and oxygen atom. More specific examples include heteroaromatic group having 5 to 14 atoms as ring-constituting members, such as furyl, thienyl, pyrrolyl, imidazolyl, pyrazolyl, triazolyl, tetrazolyl, oxazolyl, isoxazolyl, oxadiazolyl, thiazolyl, pyridyl, pyrazinyl, pyrimidinyl, pyridazinyl, triazinyl, indolyl, indazolyl, benzimidazolyl, benzofuryl, benzothienyl, benzoxazolyl, benzothiazolyl, quinolyl, isoquinolyl, phthalazinyl, naphthyridinyl, quinoxalinyl, quinazolinyl, cinnolinyl, purinyl, coumarinyl, thienothienyl, or thiadiazolyl; and (iv-b) examples of the heteroalicyclic group include, for example, monocyclic heteroalicyclic group, fused heteroalicyclic group in which two or more rings are fused, or the like. The type and number of the heteroatom contained in heteroalicyclic groups are not specifically limited and the heteroalicyclic group may contain, for example, one or more heteroatoms selected from a group consisting of a nitrogen atom, sulfur atom and oxygen atom. More specific examples include, heteroalicyclic group having 3 to 14 atoms as ring-constituting members, such as pyrrolidinyl, 2,5-dioxopyrrolidinyl, thiazolidinyl, oxazolidinyl, piperidyl, 1,2-dihydropyridyl, piperazinyl, homopiperazinyl, morpholinyl, thiomorpholinyl, pyrazolinyl, oxazolinyl, dioxolanyl, tetrahydropyranyl, tetrahydrothiopyranyl, tetrahydrofuryl, tetrahydroquinolyl, tetrahydroisoquinolyl, tetrahydroquinoxalinyl, octahydroquinolyl, dihydroindolyl, 1,3-dioxoisoindolinyl and dihydrothiazolyl.

(v) Examples of the heterocyclic group formed together with the adjacent nitrogen atom include 5- or 6-membered monocyclic heteroalicyclic group containing at least one nitrogen atom (the monocyclic heteroalicyclic group may further contain any other of a nitrogen atom, oxygen atom and sulfur atom), bicyclic or tricyclic fused heterocyclic group containing at least one nitrogen atom in which 3- to 8-membered rings are fused (the fused heterocyclic group may further contain any other of a nitrogen atom, oxygen atom, sulfur atom), or the like. More specific examples include, for example, pyrrolidinyl, piperidino, piperazinyl, morpholino, thiomorpholino, homopiperidino, homopiperazinyl, tetrahydropyridyl, tetrahydroquinolyl, tetrahydroisoquinolyl, isoindolinyl, pyrrolinyl, imidazolidinyl, pyrrolyl, pyridinecarboxamido, naphtalenedicarboxamido, 3,4,5,6-tetrahydrophtalimido, 1,2-cyclopentenedicarboxyImido, thienopyrrolidinyl, or the like.

(vi) Examples of the substituents in the substituted lower alkyl, substituted lower alkoxy, substituted lower alkoxycarbonyl, substituted lower alkylthio and mono- or di-(substituted lower alkyl)amino, which may be the same or different and in number of 1 to 3, include (vi-a) halogen;
(vi-b) hydroxy;
(vi-c) substituted or unsubstituted lower alkoxy (the substituent(s) in the substituted lower alkoxy, which is 1 to 3 in number, is for example, halogen, hydroxy or the like);
(vi-d) oxo;
(vi-e) carboxy;
(vi-f) lower alkoxycarbonyl;
(vi-g) heteroaroyl;
(vi-h) arylsulfonyl;
(vi-i) substituted or unsubstituted aryl [the substituent(s) in the substituted aryl, which is 1 to 3 in number, is for example, nitro, carboxy, lower alkyl, lower alkoxy, lower alkoxycarbonyl, or the like];
(vi-j) a substituted or unsubstituted heterocyclic group (the substituent(s) in the substituted heterocyclic group, which is 1 to 3 in number, is for example, nitro, carboxy, lower alkyl, lower alkoxy, lower alkoxycarbonyl, or the like);

(vi-k) CONR$^{20a}$R$^{20b}$ {wherein R$^{20a}$ and R$^{20b}$ may be the same or different and each represents a hydrogen atom or substituted or unsubstituted lower alkyl [the substituent(s) in the substituted lower alkyl, which is 1 to 3 in number, is for example, halogen, amino, mono- or di-(lower alkyl)amino, hydroxy, oxo, nitro, cyano, carboxy, lower alkanoyl, lower alkoxycarbonyl, aroyl, substituted or unsubstituted lower alkoxy (the substituent(s) in the substituted lower alkoxy, which is 1 to 3 in number, is for example, hydroxy, or the like) or the like], or R$^{20a}$ and R$^{20b}$ are combined together with the adjacent nitrogen atom thereto to form a substituted or unsubstituted heterocyclic group [the substituent(s) in the substituted heterocyclic group formed together with the adjacent nitrogen atom thereto, which is 1 to 3 in number, is for example, halogen, hydroxy, oxo, nitro, cyano, carboxy, lower alkanoyl, lower alkoxycarbonyl, aralkyl, aroyl, substituted or unsubstituted lower alkyl (the substituent(s) in the substituted lower alkyl, which is 1 to 3 in number, is for example, hydroxy or the like), substituted or unsubstituted lower alkoxy (the substituent(s) in the substituted lower alkoxy, which is 1 to 3 in number, is for example, hydroxy, or the like), or the like]};

(vi-l) NR$^{21a}$R$^{21b}$ (wherein R$^{21a}$ and R$^{21b}$ have the same meanings as R$^{20a}$ and R$^{21b}$ defined above, respectively);

(vi-m) lower alkanoylamino;

(vi-n) N-(lower alkanoyl)-N-(lower alkyl)amino;

(vi-o) lower alkanoyl;

(vi-p) cyano;

(vi-q) lower alkylsulfonyl, or the like.

In the definition of the substituents (vi) in the substituted lower alkyl, substituted lower alkoxy, substituted lower alkoxycarbonyl, substituted lower alkylthio and mono- or di-(substituted lower alkyl)amino, the halogen has the same meaning as (i) defined above; the lower alkyl and the lower alkyl moiety of the lower alkoxy, lower alkoxycarbonyl and N-(lower alkanoyl)-N-(lower alkyl)amino have the same meanings as (ii) defined above, respectively; the aryl and the aryl moiety of the aralkyl, aroyl and arylsulfonyl have the same meanings as (iii) defined above, respectively; the heterocyclic group has the same meaning as (iv) defined above; the heteroaryl moiety of the heteroaroyl has the same meaning as (iv-a) defined above; the heterocyclic group formed together with the adjacent nitrogen atom thereto has the same meaning as (v) defined above.

(vii) Examples of the lower alkanoyl and the lower alkanoyl moiety of the lower alkanoylamino and N-(lower alkanoyl)-N-(lower alkyl)amino include, for example, linear, branched or cyclic alkanoyl or alkanoyl comprising these alkanoyls in combination, having 1 to 8 carbon atom(s) such as formyl, acetyl, propionyl, butyryl, isobutyryl, valeryl, isovaleryl, pivaloyl, hexanoyl, heptanoyl, octanoyl, cyclopropylcarbonyl, cyclobutylcarbonyl, cyclopropylcarbonyl, cyclopropylmethylcarbonyl, cyclohexylcarbonyl, 1-methylcyclopropylcarbonyl or cycloheptylcarbonyl.

(viii) The alkylene moiety of the aralkyl has the same meaning as the group formed by removing one hydrogen atom from the linear or branched lower alkyl (ii-a) defined above.

(ix) Examples of the substituents in the substituted aryl, substituted heterocyclic group or substituted heterocyclic group formed together with the adjacent nitrogen atom thereto, which may be the same or different and in number of 1 to 3, include (ix-a) halogen;

(ix-b) nitro;

(ix-c) nitroso;

(ix-d) carboxy;

(ix-e) cyano;

(ix-f) lower alkylthio;

(ix-g) lower alkylsulfonyl;

(ix-h) substituted or unsubstituted lower alkyl [the substituent(s) in the substituted lower alkyl has the same meaning as the above (vi)];

(ix-i) substituted or unsubstituted lower alkenyl [the substituent(s) in the substituted lower alkenyl has the same meaning as the substituent (vi) in the above substituted lower alkyl];

(ix-j) substituted or unsubstituted lower alkynyl [the substituent(s) in the substituted lower alkynyl has the same meaning as the substituent (vi) in the above substituted lower alkyl];

(ix-k) substituted or unsubstituted lower alkoxycarbonyl [the substituent(s) in the substituted lower alkoxycarbonyl has the same meaning as (vi) defined above];

(ix-l) substituted or unsubstituted lower alkanoyl [the substituent(s) in the substituted lower alkanoyl has the same meaning as (vi) defined above];

(ix-m) substituted or unsubstituted aryl [the substituent(s) in the substituted aryl, which is 1 to 3 in number, is for example, halogen, hydroxy, nitro, cyano, carboxy, lower alkanoyl, lower alkoxycarbonyl, aralkyl, aroyl, substituted or unsubstituted lower alkyl (the substituent(s) in the substituted lower alkyl which is 1 to 3 in number, is for example, hydroxy or the like), substituted or unsubstituted lower alkoxy (the substituent(s) in the substituted lower alkoxy is for example, hydroxy or the like), or the like];

(ix-n) NR$^{22a}$R$^{22b}$ {wherein R$^{22a}$ and R$^{22b}$ may be the same or different and each represents a hydrogen atom, lower alkylsulfonyl, substituted or unsubstituted lower alkyl [the substituent(s) in the substituted lower alkyl has the same meaning as (vi) defined above], substituted or unsubstituted lower alkenyl [the substituent(s) in the substituted lower alkenyl has the same meaning as (ix-i) defined above], substituted or unsubstituted lower alkynyl [the substituent(s) in the substituted lower alkynyl has the same meaning as (ix-j) defined above], substituted or unsubstituted lower alkoxy [the substituent(s) in the substituted lower alkoxy has the same meaning as (vi) defined above], substituted or unsubstituted lower alkanoyl [the substituent(s) in the substituted lower alkanoyl has the same meaning as (ix-1) defined above], substituted or unsubstituted aryl [the substituent(s) in the substituted aryl which is 1 to 3 in number, is for example, halogen, hydroxy, amino, nitro, cyano, carboxy, lower alkanoyl, lower alkoxycarbonyl, aralkyl, aroyl, substituted or unsubstituted lower alkyl (the substituent(s) in the substituted lower alkyl, which is 1 to 3 in number, is for example hydroxy, or the like), substituted or unsubstituted lower alkoxy (the substituent(s) in the substituted lower alkoxy, which is 1 to 3 in number, is for example hydroxy, or the like) or the like], substituted or unsubstituted aroyl [the substituent(s) in the substituted aroyl, which is 1 to 3 in number, is for example halogen, hydroxy, amino, nitro, cyano, carboxy, lower alkanoyl, lower alkoxycarbonyl, aralkyl, aroyl, substituted or unsubstituted lower alkyl (the substituent(s) in the substituted lower alkyl, which is 1 to 3 in number, is for example, hydroxy, or the like), or substituted or unsubstituted lower alkoxy (the substituent(s) in the substituted lower alkoxy, which is 1 to 3 in number, is for example, hydroxy, or the like) or the like], substituted or unsubstituted heteroaroyl [the substituent(s) in the substituted heteroaroyl, which is 1 to 3 in number, is for example halogen, hydroxy, amino, nitro, cyano, carboxy, lower alkanoyl, lower alkoxycarbonyl, aralkyl, aroyl, substituted or unsubstituted lower alkyl (the substituent(s) in the substituted lower alkyl, which is 1 to 3 in number, is for example, hydroxy, or the like), substituted or unsubstituted lower alkoxy (the substituent(s) in the substituted lower alkoxy, which is 1 to 3 in number, is for example, hydroxy, or the like) or the like], or a substituted or unsubstituted heterocyclic group [the substituent(s) in the substituted-heterocyclic group, which is 1 to 3 in number, is for example halogen, hydroxy, nitro, cyano, carboxy, lower alkanoyl, lower alkoxycarbonyl, aralkyl, aroyl, substituted or unsubstituted lower alkyl (the substituent(s) in the substituted lower alkyl, which is 1 to 3 in number, is for example, hydroxy, or the like), substituted or unsubstituted lower alkoxy (the substituent(s) in the substituted lower alkoxy, which is 1 to 3 in number, is for example, hydroxy, or the like) or the like], or $R^{22a}$ and $R^{22b}$ are combined together with the adjacent nitrogen atom thereto to form a substituted or unsubstituted heterocyclic group [the substituent(s) in the substituted heterocyclic group, formed together with the adjacent nitrogen atom, which is 1 to 3 in number, is for example halogen, amino, nitro, hydroxy, oxo, cyano, carboxy, lower alkoxycarbonyl, aralkyl, aroyl, heteroaroyl, substituted or unsubstituted lower alkyl (the substituent(s) in the substituted lower alkyl, which is 1 to 3 in number, is for example, hydroxy, lower alkoxy, or the like), substituted or unsubstituted lower alkoxy (the substituent(s) in the substituted lower alkoxy, which is 1 to 3 in number, is for example, hydroxy, lower alkoxy or the like), substituted or unsubstituted lower alkanoyl (the substituent(s) in the substituted lower alkanoyl which is 1 to 3 in number, is for example, amino, hydroxy, lower alkoxy, lower alkanoylamino, N-(lower alkanoyl)-N-(lower alkyl) amino, or the like), substituted or unsubstituted heteroalicyclic carbonyl (the substituent(s) in the substituted heteroalicyclic carbonyl, which is 1 to 3 in number, is for example, halogen, hydroxy, oxo, lower alkyl, lower alkoxy or the like), or the like]}

(ix-o) $CONR^{23a}R^{23b}$ (wherein $R^{23a}$ and $R^{23b}$ have the same meanings as $R^{22a}$ and $R^{22b}$ defined above, respectively);

(ix-p) $OR^{24}$ {wherein $R^{24}$ represents a hydrogen atom, substituted or unsubstituted lower alkyl [the substituent(s) in the substituted lower alkyl has the same meaning as (vi) defined above], substituted or unsubstituted aryl [the substituent(s) in the substituted aryl which is 1 to 3 in number, is for example, halogen, hydroxy, nitro, cyano, carboxy, lower alkanoyl, lower alkoxycarbonyl, aralkyl, aroyl, substituted or unsubstituted lower alkyl (the substituent(s) in the substituted lower alkyl which is 1 to 3 in number, is for example, hydroxy, or the like), substituted or unsubstituted lower alkoxy (the substituent(s) in the substituted lower alkoxy which is 1 to 3 in number, is for example, hydroxy, or the like)], or a substituted or unsubstituted heterocyclic group [the substituent(s) in the substituted heterocyclic group, which is 1 to 3 in number, is for example, halogen, hydroxy, nitro, cyano, carboxy, lower alkanoyl, lower alkoxycarbonyl, aralkyl, aroyl, substituted or unsubstituted lower alkyl (the substituent(s) in the substituted lower alkyl, which is 1 to 3 in number, is for example, hydroxy or the like), substituted or unsubstituted lower alkoxy (the substituent(s) in the substituted lower alkoxy, which is 1 to 3 in number, is for example, hydroxy or the like) or the like]};

(ix-q) substituted or unsubstituted heteroaroyl (the substituent(s) in the substituted heteroaroyl, which is 1 to 3 in number, is for example, halogen, hydroxy, oxo, lower alkyl, lower alkoxy, or the like);

(ix-r) substituted or unsubstituted heteroalicyclic carbonyl (the substituent(s) in the substituted heteroalicyclic carbonyl, which is 1 to 3 in number, is for example, halogen, hydroxy, oxo, lower alkyl, lower alkoxy or the like), or the like.

The substituent(s) in the substituted heterocyclic group and the substituent(s) in the substituted heterocyclic group formed with the adjacent nitrogen atom may be, in addition to (ix-a) to (ix-r), the following (ix-s) or (ix-t):

(ix-s) oxo;

(ix-t) $—O(CR^{25a}R^{25b})_nO—$ (wherein $R^{25a}$ and $R^{25b}$ may be the same or different and each represents a hydrogen atom, or lower alkyl, n represents 2 or 3 and the two terminal oxygen atoms are combined on the same carbon atom in the substituent(s) in the substituted heterocyclic group and the substituent(s) in the substituted heterocyclic group formed with the adjacent nitrogen atom).

In the definition of the substituents (ix) in the substituted aryl, substituted heterocyclic group and substituted heterocyclic group formed together with the adjacent nitrogen atom, the halogen has the same meaning as (i) defined above; the lower alkyl and the lower alkyl moiety of the lower alkoxy, lower alkoxycarbonyl, lower alkylthio, lower alkylsulfonyl and N-(lower alkanoyl)-N-(lower alkyl)amino have the same meanings as (ii) defined above; the aryl and the aryl moiety of the aroyl and aralkyl have the same meanings as (iii) defined above; the heterocyclic group has the same meaning as (iv) defined above; the heteroaryl moiety of the heteroaroyl has the same meaning as (iv-a) defined above; the heteroalicyclic moiety of the heteroalicyclic carbonyl has the same meaning as (iv-b) defined above; the heterocyclic group formed together with the adjacent nitrogen atom has the same meaning as (v) defined above; the lower alkanoyl and the lower alkanoyl moiety of the lower alkanoylamino and N-(lower alkanoyl)-N-(lower alkyl)amino have the same meanings as (vii) defined above; and the alkylene moiety of the aralkyl has the same meaning as (viii) defined above.

(x) Examples of the lower alkenyl include, for example, linear or branched alkenyl having 2 to 10 carbon atoms such as vinyl, allyl, 1-propenyl, 1-butenyl, 3-butenyl, 2-pentenyl, 4-pentenyl, 2-hexenyl, 5-hexenyl, 2-decenyl and 9-decenyl.

(xi) Examples of the lower alkynyl include, for example, linear or branched alkynyl having 2 to 10 carbon atoms such as ethynyl, 2-propynyl, 3-butynyl, 4-pentynyl, 5-hexynyl and 9-decynyl.

Examples of the pharmaceutically acceptable salts of Compound (I), (Ia), (Ib), (Ic), (II), (IIa), (III), (IIIa), (IIIb), (IV), (V), (VI) and (VII) include, for example, pharmaceutically acceptable acid addition salts, metal salts, ammonium salts, organic amine addition salts, amino acid addition salts, or the like. The acid addition salts include, for example, inorganic acid salts such as hydrochlorides, sulfates and phosphates; organic acid salts such as acetates, trifluoroacetates, maleates, fumarates, tartrates, citrates, lactates, aspartates and glutamates; or the like. The metal salts include, for example, alkali metal salts such as sodium salts and potassium salts; alkaline earth metal salts such as magnesium salts and calcium salts; as well as aluminum salts and zinc salts.

The ammonium salts include, for example, salts of ammonium, tetramethylammonium, or the like. The organic amine addition salts include, for example, addition salts of morpholine, piperidine, or the like. The amino acid addition salts include, for example, addition salts of lysine, glycine, phenylalanine, or the like.

The hematopoietic tumor refers to tumors typically in hemocytes. Examples of pathosis based on the hematopoietic tumor include leukemia such as chronic myeloid leukemia and acute myeloid leukemia; myeloma such as multiple myeloma; lymphoma; or the like.

Examples of the solid carcinoma include, for example, mammary cancer, uterine body cancer, uterine cervix cancer, prostatic cancer, bladder cancer, renal cancer, gastric cancer, esophageal cancer, hepatic cancer, biliary tract cancer, colon cancer, rectal cancer, pancreatic cancer, lung cancer, head and neck cancer, cancer derived from osteosarcoma, melanoma, brain neoplasm or the like.

Next, production methods of Compounds (II), (IIa), (III), (IIIa), (IIIb), (IV), (V), (VI) and (VII) will be described below.

Production Method 1

Compound (II) can be produced using Compound (A) obtained in a similar manner to the known method [e.g., J. Org. Chem., vol. 52, p. 19 (1987); Can. J. Chem., vol. 51, p. 792 (1973)] according to the following process:

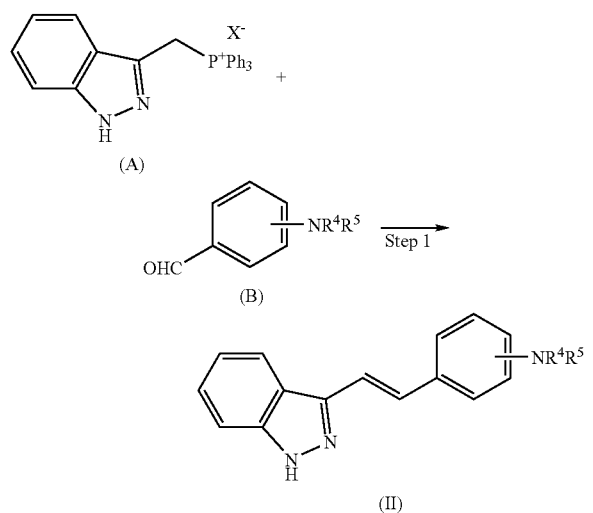

(wherein $R^4$ and $R^5$ have the same meanings as defined above, respectively, Ph represents phenyl, and X represents each atoms of chlorine, bromine and iodine)

Step 1

Compound (II) can be obtained by reacting Compound (A) with Compound (B) in the presence of a base, in a solvent such as methanol, ethanol, tetrahydrofuran (THF) and N,N-dimethylformamide (DMF), or a mixture of these solvents.

Potassium carbonate, potassium tert-butoxide, sodium hydride, 1,8-diazabicyclo[5.4.0]undec-7-en (DBU) or the like may be used as the base. To Compound (A), 1 to 10 equivalent(s) of Compound (B) and the base are used, respectively. The reaction is usually performed at temperatures between 0 and 100° C. for 1 to 72 hours.

In the above Step 1, Compounds (IIa), (III), (IIIa), (IIIb), (IV), (V), (VI) and (VII) can be synthesized by using corresponding benzaldehyde derivatives in place of Compound (B).

Production Method 2

Compound (II) can also be produced according to the following Production Method 2.

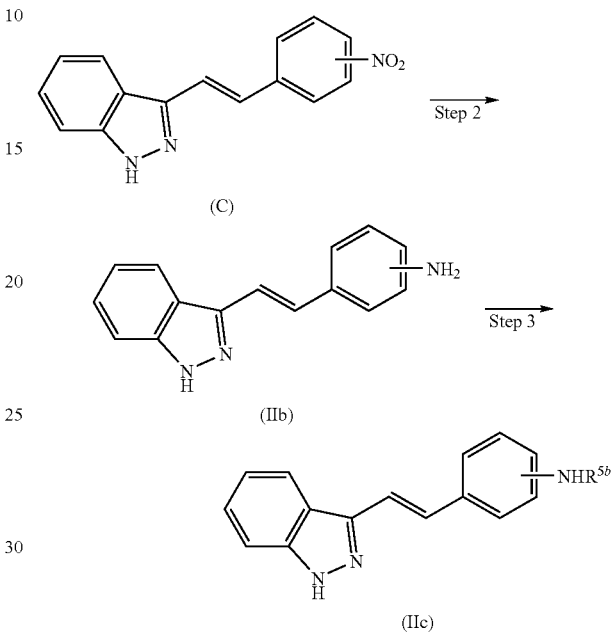

[wherein $R^{5b}$ represents —C(=O)$R^6$ (wherein $R^6$ has the same meaning as defined above)]

Step 2

Compound (IIb) can be obtained by treating Compound (C) with a reducing agent such as tin or iron, in the presence of an acid such as concentrated hydrochloric acid or acetic acid, in a solvent such as water or ethanol, or a mixed solvent thereof, or without solvent, or by subjecting Compound (C) to reduction, in the presence of a catalyst such as palladium/carbon, platinum dioxide and Raney nickel, under hydrogen atomosphere or in the presence of hydrogen donor such as hydrazine hydrate or ammonium formate, in a solvent such as water, methanol, ethanol, THF and DMF, or a mixed solvent thereof.

To Compound (C), 1 to 20 equivalent(s) of the reducing agent such as tin or iron, 0.5 to 100 weight % of the catalyst and 1 to 100 equivalent(s) of the hydrogen donor are preferably used. The reaction is usually performed at temperatures between 0 to 100° C. for 1 to 72 hours.

Step 3

Compound (IIc) can be obtained by reacting Compound (IIb) with Compound (D) represented by $R^6$COCl (wherein $R^6$ has the same meaning as defined above) or Compound (E) represented by ($R^6$CO)$_2$O (wherein $R^6$ has the same meaning as defined above) in the presence of a base such as triethylamine, pyridine, 4-dimethylaminopyridine, polyvinylpyridine, 4-morpholinomethyl polystyrene, 4-piperidino polystyrene, or by reacting with Compound (F) δ 6 represented by $R^6CO_2H$ (wherein $R^6$ has the same meaning as defined above) in a presence of a condensing agent such as dicyclohexylcarbodiimide (DCC), 1-(3-dimethylaminopropyl)-3-ethylcarbodiimide hydrochloride (EDC) and polymer-bound 1-(3-dimethylaminopropyl)-3-ethylcarbodiimide or an activating agent such as 1-hydroxybenzotriazole and N-hydroxysuccinimide, in a solvent such as dichloromethane, THF, 1,4-dioxane, DMF or N-methylpiperidone or a mixed solvent thereof.

To Compound (IIb), 1 to 20 equivalent(s) of the base, Compound (D) or Compound (E), condensing agent, activating agent or Compound (F) are used, respectively. The reaction is usually performed at temperatures between −20 and 80° C. for 30 minutes to 24 hours.

Production Method 3

Compound (VIa) can be produced according to the following Production Method 3.

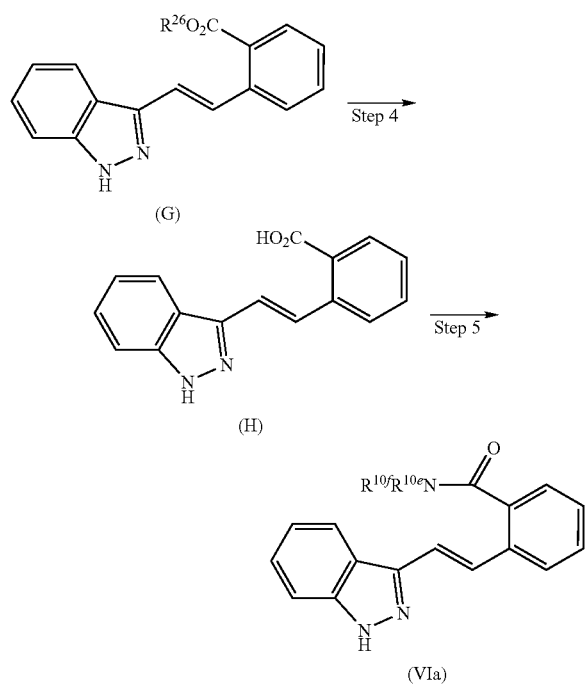

(wherein $R^{10e}$ and $R^{10f}$ have the same meanings as defined above, respectively, and $R^{26}$ represents substituted or unsubstituted lower alkyl)

Step 4

Compound (H) can be obtained by hydrolyzing Compound (G), in the presence of a base such as sodium hydroxide or an acid such as hydrochloric acid, in water or a mixed solvent of water and methanol, ethanol, THF, or the like.

To Compound (G), 0.1 to 10 equivalent(s) of the acid or the base are used. The reaction is usually performed at temperatures between 20 to 100° C. for 1 to 24 hours.

Step 5

Compound (VIa) can be obtained by reacting Compound (H) with Compound (J) represented by $HNR^{10e}R^{10f}$ (wherein $R^{10e}$ and $R^{10f}$ have the same meanings as defined above, respectively), in the presence of a condensing agent such as DCC, EDC, polymer-bound 1-(3-dimethylaminopropyl)-3-ethylcarbodiimide, triphenylphosphine oxide.trifluoromethanesulfonic anhydride and an activating agent such as 1-hydroxybenzotriazole and N-hydroxysuccinimide, in a solvent such as dichloromethane, THF, 1,4-dioxane, DMF or N-methylpiperidone or a mixed solvent thereof.

To Compound (H), 1 to 20 equivalent(s) of the condensing agent, activating agent and Compound (J) are preferably used, respectively. The reaction is usually performed at temperatures between −20 and 80° C. for 30 minutes to 24 hour(s). Depending upon the type of Compound (J), the salts can be prepared by mixing with the activating agent, and then are used for the reaction.

Transformation of functional groups in Compound (II) and the starting material can also be carried out by other known methods [for example, Comprehensive Organic Transformations, R. C. Larock, (1989)] in addition to the above steps.

Compound (II) having a desired functional group at a desired position can be obtained by carrying out the above steps in any suitable combination thereof.

Compound (I), (Ia), (Ib), (Ic), (IIa), (III), (IIIa), (IIIb), (IV), (V), (VI) and (VII) can be obtained according to the production method of the above Compound (II) or in a similar manner to the known methods.

Isolation and purification of the products in the above-mentioned production methods can be carried out by an appropriate combination of usual methods used in organic synthesis, such as filtration, extraction, washing, drying, concentration, crystallization and various chromatography. Intermediates can also be used in the subsequent reaction step without further purification.

There can be isomers such as positional isomers, geometrical isomers or optical isomers in Compound (I), (Ia), (Ib) and (Ic). All possible isomers including these isomers and mixtures of the isomers in any ratio can be used in the present invention.

There can be isomers such as positional isomers, geometrical isomers or optical isomers in Compound (II), (IIa), (III), (IIIa), (IIIb), (IV), (V), (VI) and (VII). All possible isomers including these isomers and mixtures of the isomers in any ratio can be used in the present invention.

When it is desired to obtain salts of Compound (I), (Ia), (Ib), (Ic), (II), (IIa), (III), (IIIa), (IIIb), (IV), (V), (VI) and (VII) in the case where they are obtained in forms of salts, they may be purified as they are and when they are obtained in free forms, they are dissolved or suspended in an appropriate solvent followed by adding an acid, a base or the like thereto to form a salt.

There can be isomers such as positional isomers, geometrical isomers or optical isomers in Compound (I), (Ia), (Ib) and (Ic). All possible isomers including these isomers and mixtures of the isomers in any ratio can be used in the present invention.

There can be isomers such as positional isomers, geometrical isomers or optical isomers in Compound (II), (IIa), (III), (IIIa), (IIIb), (IV), (V), (VI) and (VII). All possible isomers including these isomers and mixtures of the isomers in any ratio can be used in the present invention.

Compound (II), (IIa), (III), (IIIa), (IIIb), (IV); (V), (VI) and (VII) or pharmaceutically acceptable salts thereof may exist in the form of adducts with water or solvents. These adducts are also included in the present invention.

There can be isomers such as positional isomers, geometrical isomers or optical isomers in Compound (I), (Ia), (Ib) and (Ic). All possible isomers including these isomers and mixtures of the isomers in any ratio can be used in the present invention.

Specific examples of Compound (I), (Ia), (Ib), (Ic), (II), (IIa), (III), (IIIa), (IIIb), (IV), (V), (VI) and (VII) are, for example, Compounds 1 to 342. (See Table 1 to 7)

Me, Et and Ts in the Tables 1 to 7 represent methyl, ethyl and p-toluenesulfonyl, respectively.

TABLE 1
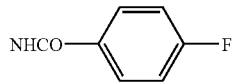
| Compound Number | R$^A$ | Salt |
|---|---|---|
| 1 | NO$_2$ | |
| 2 | NH$_2$ | |
| 3 | 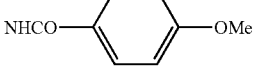 | |
| 4 | 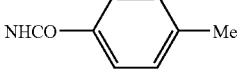 | |
| 5 | 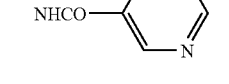 | |
| 6 | 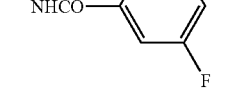 | |
| 7 | 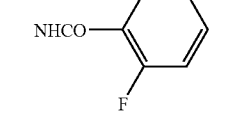 | |
| 8 | 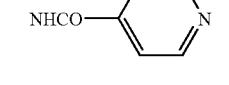 | |
| 9 | NHCOMe | |
| 10 | 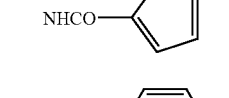 | |
| 11 | 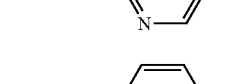 | |
| 12 | 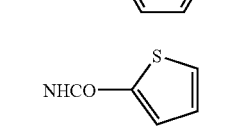 | |
| 13 |  | |
| 14 |  | |
TABLE 1-continued
| Compound Number | R$^A$ | Salt |
|---|---|---|
| 15 |  | |
| 16 | 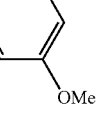 | |
| 17 |  | |
| 18 | NHCOCHMe$_2$ | |
| 19 |  | |
| 20 |  | |
| 21 | NHCONHEt | |
| 22 |  | |
| 23 |  | |
| 24 | 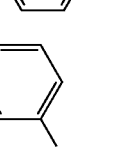 | |
| 25 |  | |
| 26 |  | |
| 27 |  | |

TABLE 1-continued

[Structure: 1H-indazole connected via vinyl (CH=CH) to a phenyl group bearing $R^A$ at ortho position]

| Compound Number | $R^A$ | Salt |
|---|---|---|
| 28 | NHCO-(pyrazin-2-yl) | |
| 29 | NHCO-(1-methyl-pyrrol-2-yl) | |
| 30 | NHCO-(2-methylphenyl) | |
| 31 | NHCO-(thiophen-3-yl) | |
| 32 | NHCO-(tetrahydrofuran-2-yl) | |
| 33 | NHCO-cyclopropyl | |
| 34 | NHCO-(5-bromothiophen-2-yl) | |
| 35 | NHCO-morpholin-4-yl | |
| 36 | NHCO-(thiazol-4-yl) | |
| 37 | NHCO-(isoxazol-5-yl) | |
| 38 | NMeCO-phenyl | |
| 39 | NHCOCH$_2$CH$_2$-(thiophen-2-yl) | |
| 40 | NHCO-(5-methylthiophen-2-yl) | |
| 41 | NHCO-(3-methylthiophen-2-yl) | |
| 42 | NHCO-(1H-pyrrol-2-yl) | |
| 43 | NHCO-(5-acetylthiophen-2-yl) | |
| 44 | NHCO-cyclobutyl | |
| 45 | NHCO-C(OH)(Et)(Et) | |
| 46 | NHCO-(benzo[b]thiophen-2-yl) | |
| 47 | CONH-phenyl | |
| 48 | CO-(4-amino-pyrazol-1-yl) | |
| 49 | NHCO-(benzofuran-2-yl) | |
| 50 | NHCO-(1H-indol-2-yl) | |
| 51 | NHCO-(5-nitrothiophen-2-yl) | |

TABLE 1-continued

| Compound Number | $R^A$ | Salt |
|---|---|---|
| 52 | 1-methyl-4-nitro-pyrrol-2-yl-NHCO- | |
| 53 | 4-methoxy-thiophen-3-yl-NHCO- | |
| 54 | 3-chloro-thiophen-2-yl-NHCO- | |
| 55 | 1-methyl-indol-2-yl-NHCO- | |
| 56 | 5-amino-thiophen-2-yl-NHCO- | |
| 57 | thieno[3,2-b]thiophen-2-yl-NHCO- | |
| 58 | 5-chloro-3-methyl-benzothiophen-2-yl-NHCO- | |
| 59 | 2-trifluoromethyl-5-methyl-furan-3-yl-NHCO- | |
| 60 | thiophen-2-yl-NHSO$_2$- | |
| 61 | 5-(thiophene-2-carboxamido)-thiophen-2-yl-NHCO- | |
| 62 | 5-(isobutyramido)-thiophen-2-yl-NHCO- | |
| 63 | 5-nitro-furan-2-yl-NHCO- | |
| 64 | 3-nitro-phenyl-NHCO- | |
| 65 | 4-nitro-phenyl-NHCO- | |
| 66 | 3-methyl-5-nitro-thiophen-2-yl-NHCO- | |
| 67 | 5-amino-3-methyl-thiophen-2-yl-NHCO- | |
| 68 | 5-(acetamido)-thiophen-2-yl-NHCO- | |
| 69 | 3-amino-phenyl-NHCO- | |
| 70 | 4-amino-phenyl-NHCO- | |
| 71 | 4-methyl-1,2,3-thiadiazol-5-yl-NHCO- | |

TABLE 1-continued

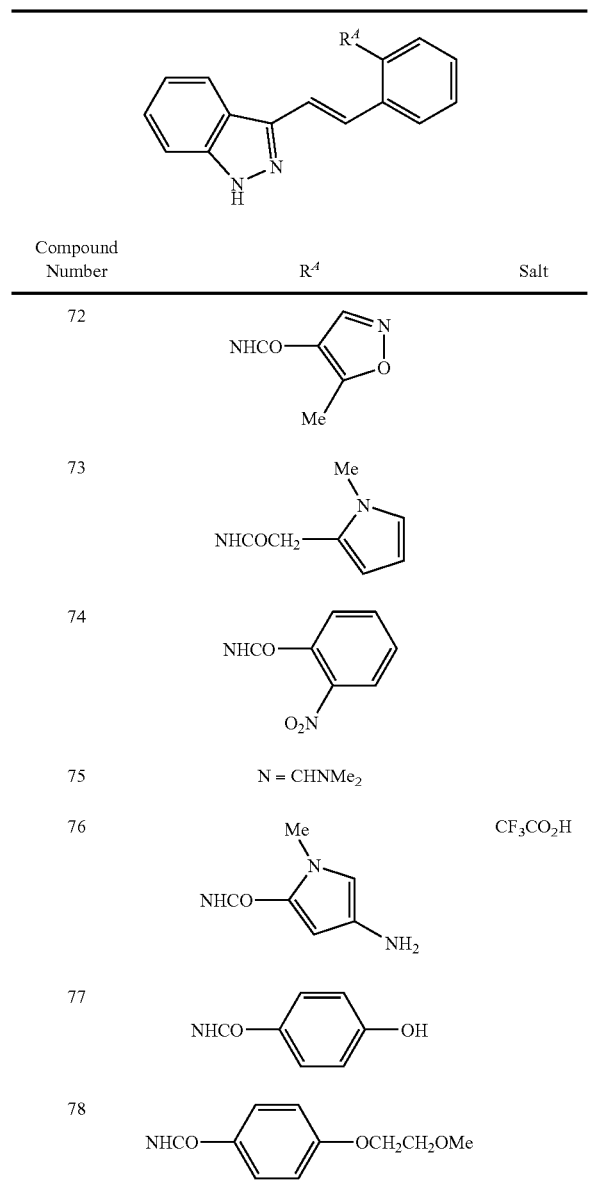

| Compound Number | R^A | Salt |
|---|---|---|
| 72 | NHCO-(5-Me-isoxazol-4-yl) | |
| 73 | NHCOCH2-(1-Me-pyrrol-2-yl) | |
| 74 | NHCO-(2-O2N-phenyl) | |
| 75 | N=CHNMe2 | |
| 76 | NHCO-(1-Me-4-NH2-pyrrol-2-yl) | CF3CO2H |
| 77 | NHCO-(4-OH-phenyl) | |
| 78 | NHCO-(4-OCH2CH2OMe-phenyl) | |

TABLE 1-continued

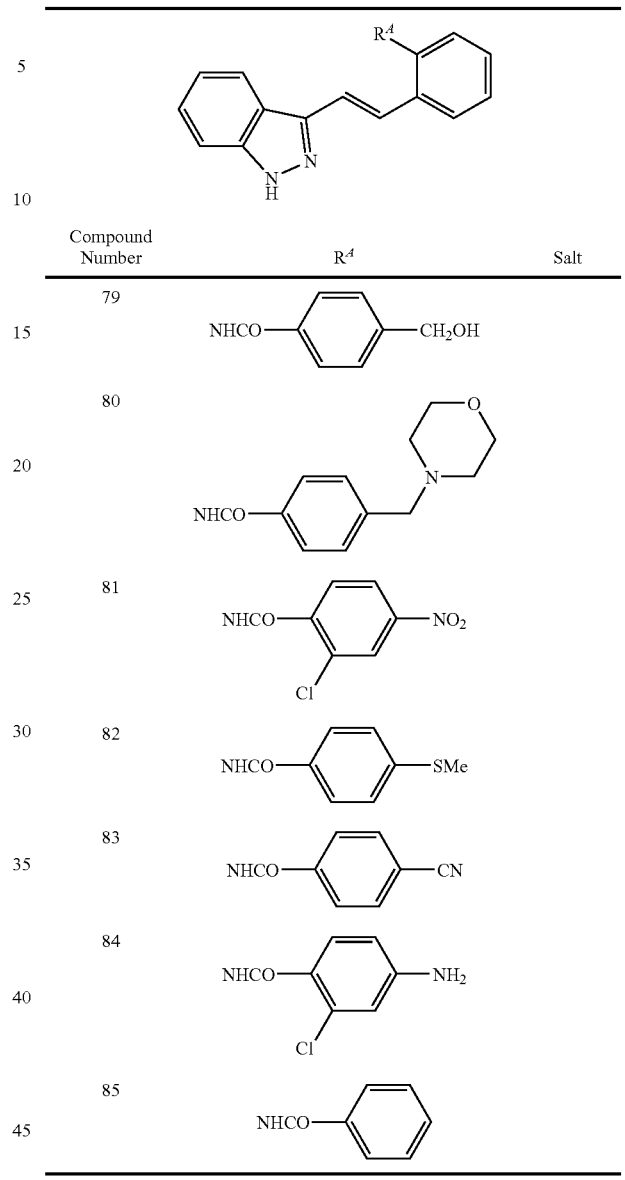

| Compound Number | R^A | Salt |
|---|---|---|
| 79 | NHCO-(4-CH2OH-phenyl) | |
| 80 | NHCO-(4-(morpholinomethyl)phenyl) | |
| 81 | NHCO-(2-Cl-4-NO2-phenyl) | |
| 82 | NHCO-(4-SMe-phenyl) | |
| 83 | NHCO-(4-CN-phenyl) | |
| 84 | NHCO-(2-Cl-4-NH2-phenyl) | |
| 85 | NHCO-phenyl | |

TABLE 2

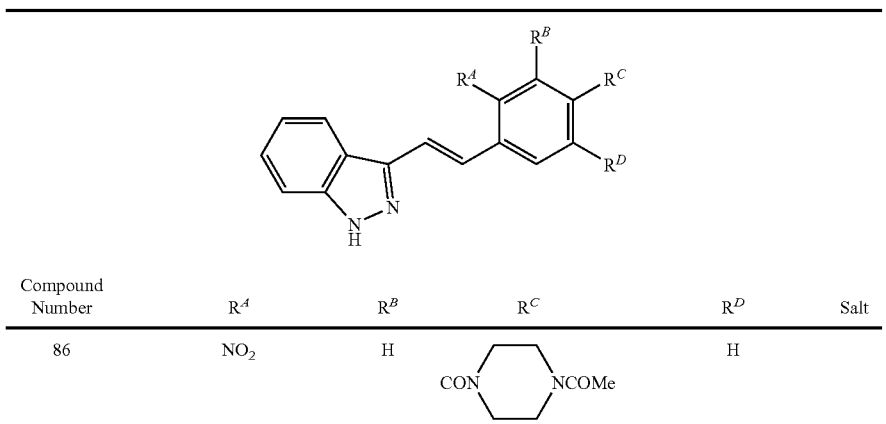

| Compound Number | R^A | R^B | R^C | R^D | Salt |
|---|---|---|---|---|---|
| 86 | NO2 | H | CON(piperazinyl)NCOMe | H | |

TABLE 2-continued

| Compound Number | R$^A$ | R$^B$ | R$^C$ | R$^D$ | Salt |
|---|---|---|---|---|---|
| 87 | NH$_2$ | H | CON(piperazine)NCOMe | H | |
| 88 | 3-Me-thiophen-2-yl-NHCO– | H | CON(piperazine)NCOMe | H | |
| 89 | thiophen-2-yl-CH$_2$CONH– | H | CON(piperazine)NCOMe | H | |
| 90 | benzothiophen-2-yl-NHCO– | H | CON(piperazine)NCOMe | H | |
| 91 | 1-Me-pyrrol-2-yl-NHCO– | H | CON(piperazine)NCOMe | H | |
| 92 | NH$_2$ | H | OMe | OMe | |
| 93 | NH$_2$ | OMe | H | H | |
| 94 | 3-Me-thiophen-2-yl-NHCO– | OMe | H | H | |
| 95 | 3-Me-thiophen-2-yl-NHCO– | H | OMe | OMe | |
| 96 | 1-Me-pyrrol-2-yl-NHCO– | H | OMe | OMe | |
| 97 | 3-Me-thiophen-2-yl-NHCO– | H | CO$_2$Me | H | |

TABLE 2-continued

| Compound Number | R^A | R^B | R^C | R^D | Salt |
|---|---|---|---|---|---|
| 98 | NHCO-(3-Me-thiophen-2-yl) | H | CO₂H | H | |
| 99 | NHCO-(3-Me-thiophen-2-yl) | H | CO-piperazinyl | H | |
| 100 | NHCO-(3-Me-thiophen-2-yl) | H | CO-morpholinyl | H | |
| 101 | NHCO-(3-Me-thiophen-2-yl) | H | CONEt₂ | H | |
| 102 | NHCO-(3-Me-thiophen-2-yl) | H | CO-(3-aminopyrrolidin-1-yl) | H | |
| 103 | NHCO-(3-Me-thiophen-2-yl) | H | H | OCH₂CH₂N-morpholinyl | |
| 104 | NHCO-(1-Me-pyrrol-2-yl) | H | H | OCH₂CH₂N-morpholinyl | |
| 105 | NHCO-(3-Me-thiophen-2-yl) | H | NMe₂ | H | |
| 106 | NHCO-(5-amino-thiophen-2-yl) | H | H | OCH₂CH₂N-morpholinyl | |

TABLE 2-continued
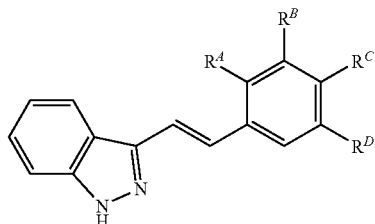
| Compound Number | R$^A$ | R$^B$ | R$^C$ | R$^D$ | Salt |
|---|---|---|---|---|---|
| 107 | 1-Me-pyrrol-2-yl-NHCO | H | NMe$_2$ | H | |
| 108 | 3-Me-thiophen-2-yl-NHCO | H | CH$_2$OH | H | |
| 109 | 1-Me-pyrrol-2-yl-NHCO | OMe | H | H | |
| 110 | 3-Me-thiophen-2-yl-NHCO | H | H | OH | |
| 111 | 3-Me-thiophen-2-yl-NHCO | H | CON(4-aminopiperidin-1-yl) | H | |
| 112 | 3-Me-thiophen-2-yl-NHCO | H | CONHCH$_2$CH$_2$CH$_3$ | H | |
| 113 | 3-Me-thiophen-2-yl-NHCO | H | CONMeEt | H | |
| 114 | 3-Me-thiophen-2-yl-NHCO | H | CONHCH$_2$CH$_2$OH | H | |
| 115 | 3-Me-thiophen-2-yl-NHCO | H | CO-morpholin-4-yl | H | HCl |

TABLE 2-continued

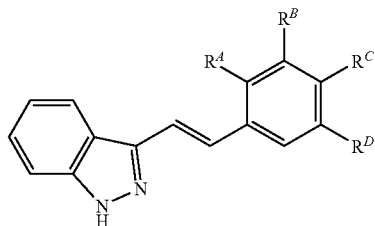

| Compound Number | R$^A$ | R$^B$ | R$^C$ | R$^D$ | Salt |
|---|---|---|---|---|---|
| 116 | 3-Me-2-thienyl-NHCO- | H | CO-pyrrolidinyl | H | |
| 117 | 3-Me-2-thienyl-NHCO- | H | CONMe$_2$ | H | |
| 118 | 3-Me-2-thienyl-NHCO- | H | CONH-cyclopropyl | H | |
| 119 | 3-Me-2-thienyl-NHCO- | H | CO-N(1,4-dioxa-8-azaspiro[4.5]decyl) | H | |
| 120 | 3-Me-2-thienyl-NHCO- | H | CO-N(4-OMe-piperidinyl) | H | |
| 121 | 3-Me-2-thienyl-NHCO- | H | CH$_2$OMe | H | |
| 122 | 3-Me-2-thienyl-NHCO- | H | CO-N(4-SO$_2$Me-piperidinyl) | H | |
| 123 | 1-Me-2-pyrrolyl-NHCO- | H | CO-morpholinyl | H | |
| 124 | 3-Me-2-thienyl-NHCO- | H | CONEt$_2$ | H | HCl |

TABLE 2-continued

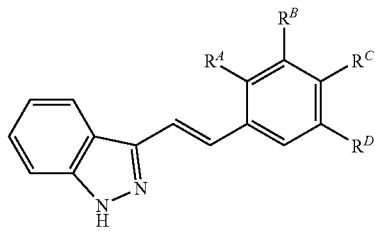

| Compound Number | R^A | R^B | R^C | R^D | Salt |
|---|---|---|---|---|---|
| 125 | NHCO-(3-Me-thiophen-2-yl) | H | CONMe₂ | H | HCl |
| 126 | NHCO-(3-Me-thiophen-2-yl) | H | CON(4-Me-piperazin-1-yl) | H | |
| 127 | NHCO-(3-Me-thiophen-2-yl) | H | CON(4-OMe-piperidin-1-yl) | H | HCl |
| 128 | NHCO-(3-Me-thiophen-2-yl) | H | CON(4-Me-piperazin-1-yl) | H | HCl |
| 129 | NHCO-(3-Me-thiophen-2-yl) | H | CON(1,4-dioxa-8-azaspiro[4.5]dec-8-yl) | H | HCl |

TABLE 3

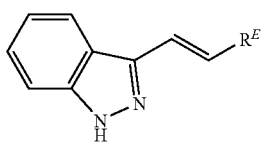

| Compound Number | R^E | Salt |
|---|---|---|
| 130 | 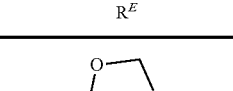 | |

TABLE 3-continued

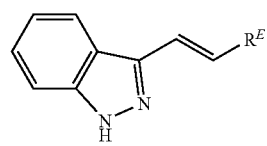

| Compound Number | R^E | Salt |
|---|---|---|
| 131 | (6-(N-methylpyrrole-2-carboxamido)benzo[1,3]dioxol-5-yl) | |

TABLE 3-continued

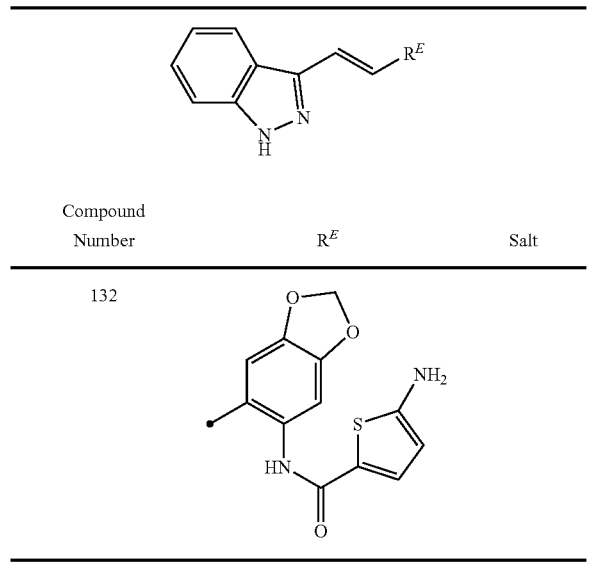

| Compound Number | $R^E$ | Salt |
|---|---|---|
| 132 | 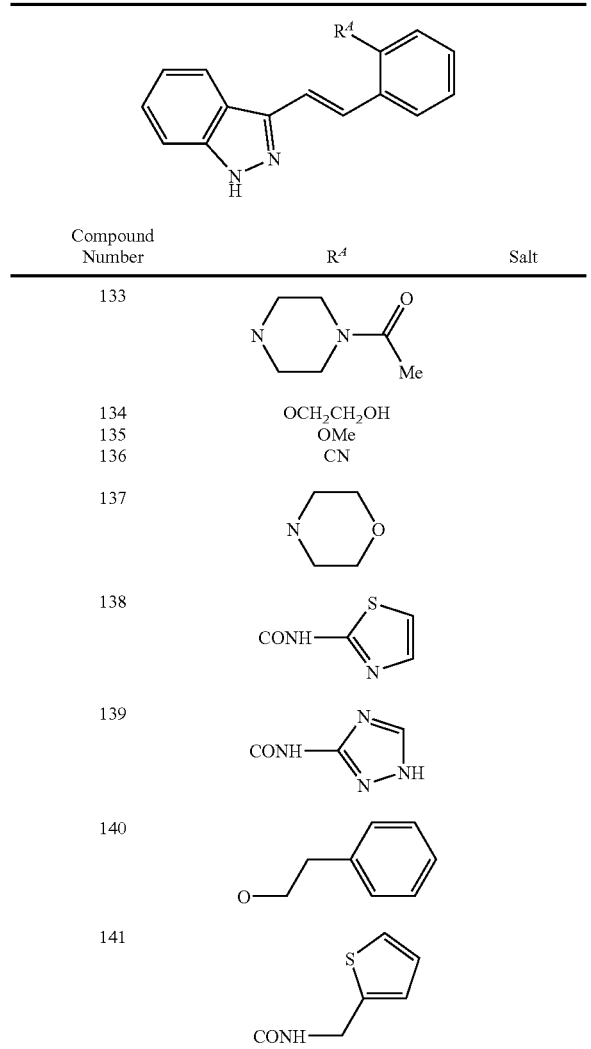 | |

TABLE 4

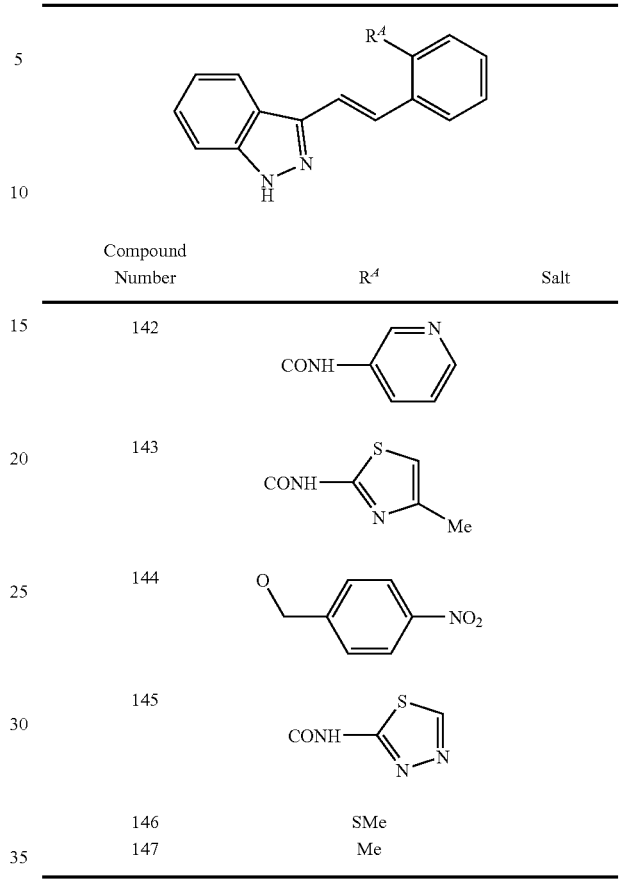

| Compound Number | $R^A$ | Salt |
|---|---|---|
| 133 | (N-acetylpiperazinyl) | |
| 134 | $OCH_2CH_2OH$ | |
| 135 | OMe | |
| 136 | CN | |
| 137 | (morpholinyl) | |
| 138 | CONH-(thiazol-2-yl) | |
| 139 | CONH-(1H-1,2,4-triazol-3-yl) | |
| 140 | O-CH₂CH₂-phenyl | |
| 141 | (thiophen-2-yl)-CH₂-NHCO- | |

TABLE 4-continued

| Compound Number | $R^A$ | Salt |
|---|---|---|
| 142 | CONH-(pyridin-3-yl) | |
| 143 | CONH-(4-methylthiazol-2-yl) | |
| 144 | O-CH₂-(4-nitrophenyl) | |
| 145 | CONH-(1,3,4-thiadiazol-2-yl) | |
| 146 | SMe | |
| 147 | Me | |

TABLE 5

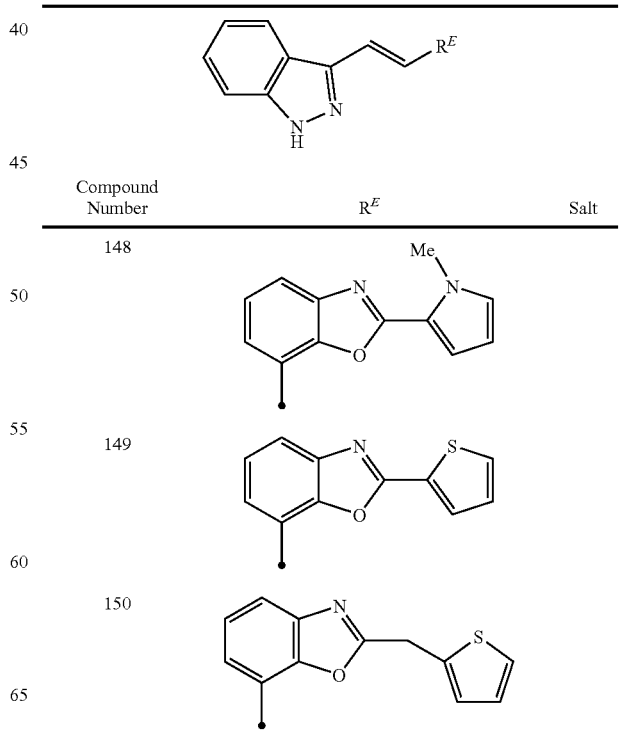

| Compound Number | $R^E$ | Salt |
|---|---|---|
| 148 | (7-substituted benzoxazol-2-yl)-(1-methylpyrrol-2-yl) | |
| 149 | (7-substituted benzoxazol-2-yl)-(thiophen-2-yl) | |
| 150 | (7-substituted benzoxazol-2-yl)-CH₂-(thiophen-2-yl) | |

TABLE 5-continued

Structure: 1H-indazole-3-yl-CH=CH-R^E

| Compound Number | R^E | Salt |
|---|---|---|
| 151 | 2-(benzo[1,3]dioxol-5-yl)-phthalimide | |
| 152 | 2-(benzo[1,3]dioxol-5-yl)-4-amino-phthalimide | |
| 153 | 2-(benzo[1,3]dioxol-5-yl)-5-amino-phthalimide | |
| 154 | 2-(3-chlorophenyl)-phthalimide | |

TABLE 6-1

Structure: 1H-indazole-3-yl-CH=CH-(2-R^A-phenyl)

| Compound Number | R^A | Salt |
|---|---|---|
| 155 | NH-pyrazinyl | |
| 156 | NHCO-(2-methylphenyl) | |
| 157 | NHCO-(3-methyl-4-nitrophenyl) | |
| 158 | NHCO-(3-methyl-4-aminophenyl) | |
| 159 | phthalimido | |
| 160 | N=CH-(3-methylthiophen-2-yl) | |
| 161 | NHCSNH$_2$ | |
| 162 | pyrrol-1-yl | |
| 163 | NH-pyrimidin-2-yl | |
| 164 | NH-pyridin-2-yl | |
| 165 | NH-(5-ethoxycarbonyl-thiazol-2-yl) | |

TABLE 6-1-continued
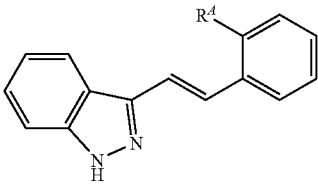
| Compound Number | R^A | Salt |
|---|---|---|
| 166 | 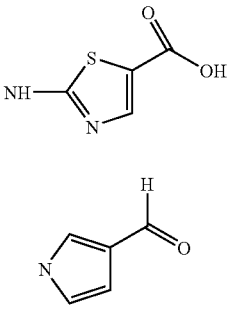 | |
| 167 | 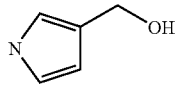 | |
| 168 | 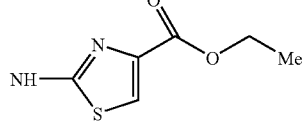 | |
| 169 | 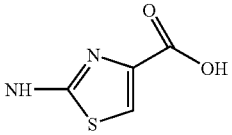 | |
| 170 | 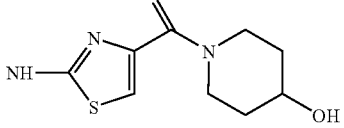 | |
| 171 | 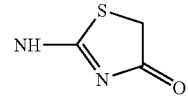 | |
| 172 | 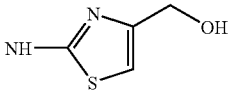 | |
| 173 | 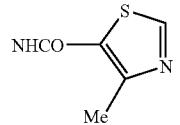 | |
| 174 | 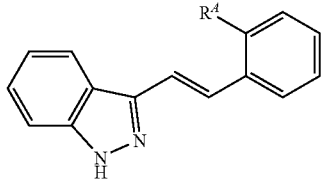 | |
TABLE 6-1-continued
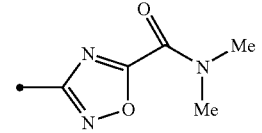
| Compound Number | R^A | Salt |
|---|---|---|
| 175 | 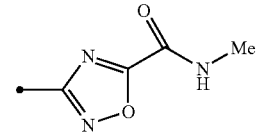 | |
| 176 | 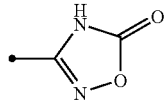 | |
| 177 | 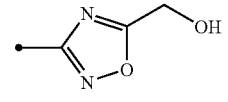 | |
| 178 | 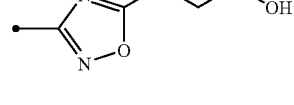 | |
| 179 | 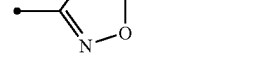 | |
| 180 |  | |
| 181 | 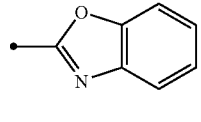 | |
| 182 | 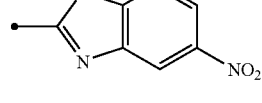 | |
| 183 | | |
| 184 | | |

TABLE 6-1-continued
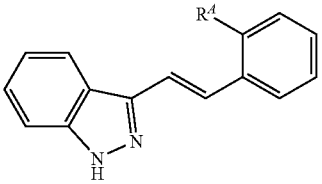
| Compound Number | R^A | Salt |
|---|---|---|
| 185 | 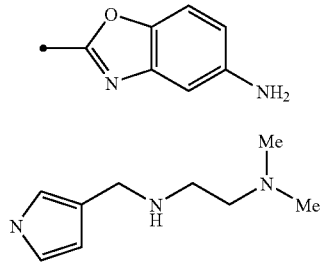 | |
| 186 | 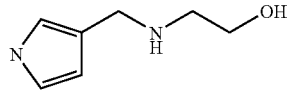 | |
| 187 | 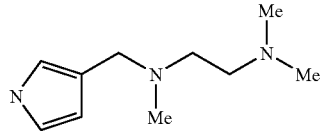 | |
| 188 | 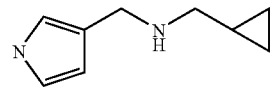 | |
| 189 | 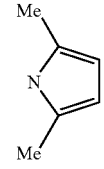 | |
| 190 | 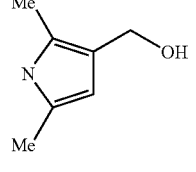 | |
| 191 | 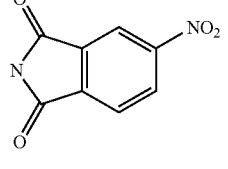 | |
| 192 | 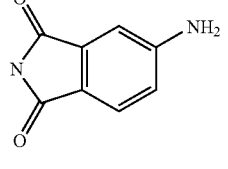 | |
| 193 | 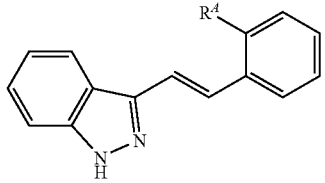 | |
TABLE 6-1-continued
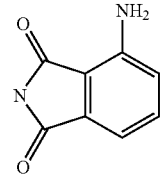
| Compound Number | R^A | Salt |
|---|---|---|
| 194 | 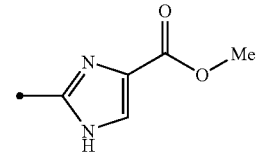 | |
| 195 | 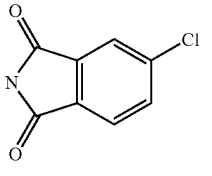 | |
| 196 | 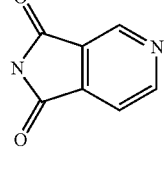 | |
| 197 | 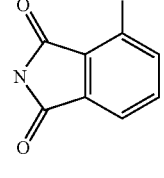 | |
| 198 | 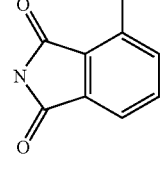 | HCl |
| 199 | | |
| 200 | | |

TABLE 6-1-continued
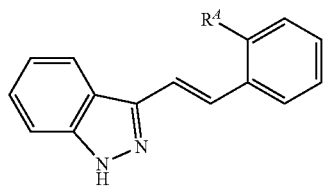
| Compound Number | R<sup>4</sup> | Salt |
|---|---|---|
| 201 | 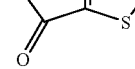 | |
| 202 | 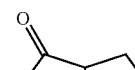 | |
| 203 |  | |
| 204 |  | |
| 205 | 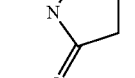 | |
| 206 | 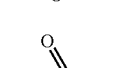 | |
| 207 | 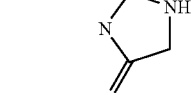 | |
| 208 | 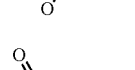 | |
TABLE 6-1-continued
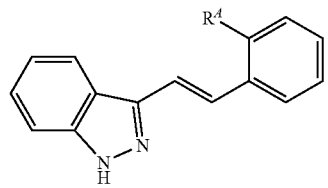
| Compound Number | R<sup>4</sup> | Salt |
|---|---|---|
| 209 | | |
| 210 | | |
| 211 | | |
| 212 | | |
| 213 | | |
| 214 | | |
| 215 | NHCO—C₆H₄—SO₂Me | |
| 216 | | |

TABLE 7

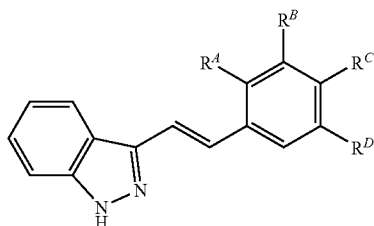

| Compound Number | R$^A$ | R$^B$ | R$^C$ | R$^D$ | Salt |
|---|---|---|---|---|---|
| 217 | 1-methyl-2-(NHCO)pyrrole | H | CO-morpholine | H | HCl |
| 218 | 3-methyl-2-(NHCO)thiophene | H | CO-piperazine-N-CHO | H | HCl |
| 219 | 3-methyl-2-(NHCO)thiophene | H | CO-N(4-hydroxypiperidine) | H | HCl |
| 220 | 3-methyl-2-(NHCO)thiophene | H | CO-N(3-hydroxypyrrolidine) | H | HCl |
| 221 | 3-methyl-2-(NHCO)thiophene | H | CO-N(3-aminopyrrolidine) | H | 2HCl |
| 222 | 3-methyl-2-(NHCO)thiophene | H | CO-N(4-methanesulfonylpiperazine) | H | HCl |
| 223 | 3-methyl-2-(NHCO)thiophene | H | CO-N(2,6-dimethylmorpholine) | H | |
| 224 | 3-methyl-2-(NHCO)thiophene | H | CH$_2$N-morpholine | H | 2HCl |
| 225 | 3-methyl-2-(NHCO)thiophene | H | H | N-morpholine | 2HCl |

TABLE 7-continued
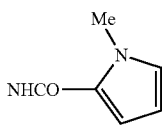
| Compound Number | R^A | R^B | R^C | R^D | Salt |
|---|---|---|---|---|---|
| 226 | 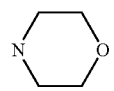 | H | H | 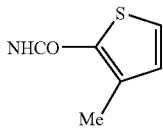 | 2HCl |
| 227 | 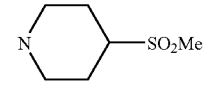 | H | H | 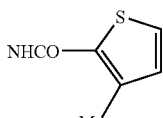 | 2HCl |
| 228 | 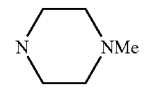 | H | H | 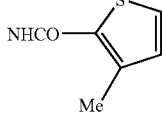 | |
| 229 | 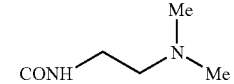 | H | 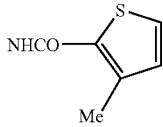 | H | HCl |
| 230 | 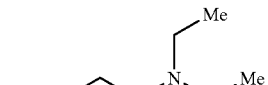 | H | 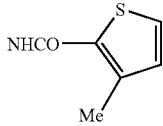 | H | HCl |
| 231 | 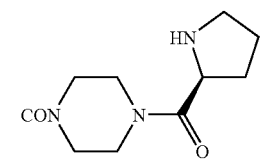 | H | 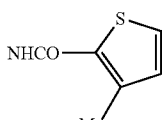 | H | |
| 232 | 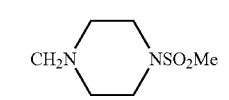 | H | 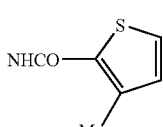 | H | |
| 233 | 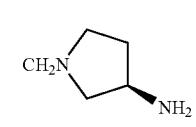 | H | 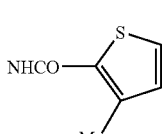 | H | |
| 234 | 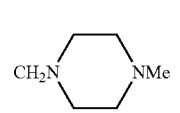 | H |  | H | |

TABLE 7-continued

| Compound Number | R^A | R^B | R^C | R^D | Salt |
|---|---|---|---|---|---|
| 235 | NHCO-(3-Me-thiophen-2-yl) | H | CH₂-(1-piperidinyl-4-SO₂Me) | H | |
| 236 | NHCO-(3-Me-thiophen-2-yl) | H | CH₂NH-CH₂CH₂-N(Et)(Me) with extra Et | H | |
| 237 | NHCO-(3-Me-thiophen-2-yl) | H | H | O-CH₂CH₂-N(Et)(Me) | |
| 238 | NHCO-(3-Me-thiophen-2-yl) | H | H | N-CH₂CH₂-morpholine, CH₂CH₂OMe | |
| 239 | NHCO-(3-Me-thiophen-2-yl) | H | CH₂-(4-(2-hydroxyethyl)piperazin-1-yl) | H | |
| 240 | NHCO-(3-Me-thiophen-2-yl) | H | CONH-(piperidin-4-yl) | H | 2HCl |
| 241 | NHCO-(3-Me-thiophen-2-yl) | H | CON(CH₂CH₂NMe₂)(CH₂CH₂OMe) | H | 2HCl |
| 242 | NHCO-(3-Me-thiophen-2-yl) | H | CH₂-(piperazin-1-yl) | H | |

TABLE 7-continued

| Compound Number | R^A | R^B | R^C | R^D | Salt |
|---|---|---|---|---|---|
| 243 | NHCO-(3-Me-thiophen-2-yl) | OMe | O-CH2CH2-N(pyrrolidin-3-yl-NH2) | H | |
| 244 | NHCO-(3-Me-thiophen-2-yl) | H | CH2N(piperazinyl)-C(O)-CH2-OMe | H | |
| 245 | NHCO-(3-Me-thiophen-2-yl) | H | CH2NH-CH2CH2-N(morpholinyl) | H | |
| 246 | NHCO-(1-Me-pyrrol-2-yl) | H | morpholinyl | H | 2HCl |
| 247 | NHCO-(3-Me-thiophen-2-yl) | H | morpholinyl | H | HCl |
| 248 | NHCO-(3-Me-thiophen-2-yl) | H | CH2N(piperazinyl)-C(O)-CH2-OH | H | |
| 249 | NHCO-(3-Me-thiophen-2-yl) | H | CON(CH2CH2-OMe)(CH2CH2-N-morpholinyl) | H | |
| 250 | phthalimido | H | H | F | |

TABLE 7-continued

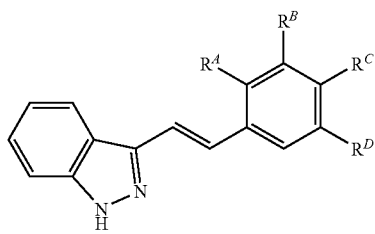

| Compound Number | $R^A$ | $R^B$ | $R^C$ | $R^D$ | Salt |
|---|---|---|---|---|---|
| 251 | NHCO-(3-Me-thiophen-2-yl) | H | OCH₂CH₂-morpholine | H | |
| 252 | NHCO-(3-Me-thiophen-2-yl) | H | CH₂N(Me)CH₂CH₂OMe | H | |
| 253 | NHCO-(3-Me-thiophen-2-yl) | H | CH₂N(CH₂CH₂OH)CH₂CH₂-morpholine | H | |
| 254 | 3-amino-phthalimido | H | H | F | |
| 255 | NHCO-(3-Me-thiophen-2-yl) | H | CON(CH₂CH₂OH)CH₂CH₂NEt₂ | H | |
| 256 | NHCO-(3-Me-thiophen-2-yl) | H | CON(CH₂CH₂OH)CH₂CH₂CH₂OMe | H | |
| 257 | NHCO-(thiophen-2-yl) | H | Cl | H | |
| 258 | phthalimido | H | Cl | H | |

TABLE 7-continued

| Compound Number | R$^A$ | R$^B$ | R$^C$ | R$^D$ | Salt |
|---|---|---|---|---|---|
| 259 | 3-methyl-2-thiophenecarboxamido (NHCO-thiophene-Me) | H | CON(CH₂CH₂OH)(CH₂CH₂-morpholine) | H | |
| 260 | 3-methyl-2-thiophenecarboxamido | H | CON(Me)(CH₂CH₂OMe) | H | |
| 261 | 3-methyl-2-thiophenecarboxamido | OMe | OMe | H | |
| 262 | 3-methyl-2-thiophenecarboxamido | H | 4-methylpiperazin-1-yl | H | |
| 263 | 3-methyl-2-thiophenecarboxamido | OMe | OCH₂CH₂N(Et)₂ | H | |
| 264 | 3-methyl-2-thiophenecarboxamido | H | CH₂NH-(piperidin-4-yl) | H | |
| 265 | 3-methyl-2-thiophenecarboxamido | H | F | H | |
| 266 | 3-methyl-2-thiophenecarboxamido | OMe | OCH₂CH₂-morpholine | H | |

TABLE 7-continued

| Compound Number | R^A | R^B | R^C | R^D | Salt |
|---|---|---|---|---|---|
| 267 | NHCO-(3-Me-thiophen-2-yl) | H | -N(CH2CH2-morpholine)(CH2CH2OMe) | H | |
| 268 | NHCO-(3-Me-thiophen-2-yl) | H | CH2N(piperazine)CH2CH2CN | H | |
| 269 | NHCO-(3-Me-thiophen-2-yl) | H | CH2N(piperazine)C(O)Me | H | |
| 270 | NHCO-(3-Me-thiophen-2-yl) | H | CH2N(piperazine)C(O)H | H | |
| 271 | NHCO-(3-Me-thiophen-2-yl) | H | CH2N(piperazine)CH2CH2OMe | H | |
| 272 | NHCO-(3-Me-thiophen-2-yl) | H | N(piperazine)SO2Me | H | |
| 273 | NHCO-(3-Me-thiophen-2-yl) | H | N(piperazine)CH2CH2OH | H | |
| 274 | NHCO-(3-Me-thiophen-2-yl) | H | N(piperazine)NH | H | |
| 275 | NHCO-(3-Me-thiophen-2-yl) | H | OCH2CH2OMe | H | |

TABLE 7-continued

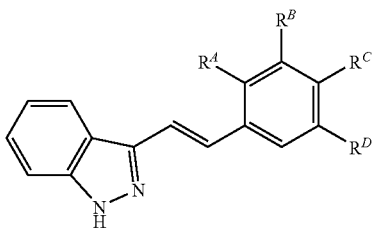

| Compound Number | R$^A$ | R$^B$ | R$^C$ | R$^D$ | Salt |
|---|---|---|---|---|---|
| 276 | phthalimido | H | CO-morpholine | H | |
| 277 | 3-methylthiophene-2-NHCO- | H | CH$_2$N(piperazine)-N-CH$_2$CH$_2$CH$_2$OH | H | |
| 278 | 3-methylthiophene-2-NHCO- | H | CH$_2$N(pyrrolidine)-NHMe | H | |
| 279 | 3-methylthiophene-2-NHCO- | H | piperazine-N-CH$_2$CH$_2$OMe | H | |
| 280 | 3-methylthiophene-2-NHCO- | H | N(Me)CH$_2$CH$_2$OH | H | |
| 281 | 3-methylthiophene-2-NHCO- | H | CON(piperazine)-N-CH$_2$CH$_2$OH | H | |
| 282 | 3-methylthiophene-2-NHCO- | H | CONH-CH$_2$CH$_2$-N-morpholine | H | |
| 283 | 3-methylthiophene-2-NHCO- | H | CON(pyrrolidine)-NHMe | H | |

TABLE 7-continued

| Compound Number | R^A | R^B | R^C | R^D | Salt |
|---|---|---|---|---|---|
| 284 | 3-methyl-2-thiophenecarboxamido (NHCO-thiophene-Me) | H | N(Me)CH₂CH₂N(Me)CH₂CH₂OMe | H | |
| 285 | phthalimido | H | CON(Me)₂ | H | |
| 286 | phthalimido | H | CON(piperazine)CH₂CH₂OH | H | |
| 287 | phthalimido | H | CON(piperazine)N-Me | H | |
| 288 | 3-amino-phthalimido | H | CON(morpholine) | H | |
| 289 | 2-thiophenecarboxamido (NHCO-thiophene) | H | CON(piperazine)CH₂CH₂OH | H | |
| 290 | benzamido (HNOC-phenyl) | H | CON(piperazine)CH₂CH₂OH | H | |
| 291 | 2-furancarboxamido (NHCO-furan) | H | CON(piperazine)CH₂CH₂CH₂OH | H | |

TABLE 7-continued

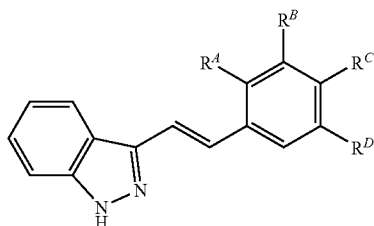

| Compound Number | R$^A$ | R$^B$ | R$^C$ | R$^D$ | Salt |
|---|---|---|---|---|---|
| 292 | NHCO-(3-Me-thiophen-2-yl) | H | O-(CH$_2$)$_3$-morpholinyl | OMe | |
| 293 | NHCO-(3-Me-thiophen-2-yl) | H | O-(CH$_2$)$_2$-morpholinyl | OMe | |
| 294 | NHCO-(3-Me-thiophen-2-yl) | H | CH$_2$N-pyrrolidin-3-yl-NMe$_2$ | H | |
| 295 | NHCO-(3-Me-thiophen-2-yl) | H | CON-pyrrolidin-3-yl-NMe$_2$ | H | |
| 296 | NHCO-(3-Me-thiophen-2-yl) | H | CH$_2$N-piperidin-4-yl-morpholinyl | H | |
| 297 | NHCO-(3-Me-thiophen-2-yl) | H | CON(Me)-piperidin-4-yl-NH | H | |
| 298 | NHCO-(3-Me-thiophen-2-yl) | H | O-(CH$_2$)$_3$-N(Me)-CH$_2$CH$_2$OMe | OMe | |
| 299 | phthalimido | H | piperazin-1-yl-CH$_2$CH$_2$OH | H | |
| 300 | NHCO-(3-Me-thiophen-2-yl) | H | O-(CH$_2$)$_3$-NEt$_2$ | OMe | |

TABLE 7-continued

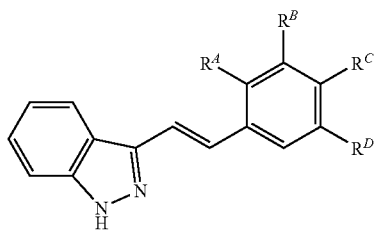

| Compound Number | $R^A$ | $R^B$ | $R^C$ | $R^D$ | Salt |
|---|---|---|---|---|---|
| 301 | NHCO-(3-Me-thiophen-2-yl) | H | 1-(acetamido)-4-piperidinecarbonyl (Me-CO-NH-piperidin-4-yl-CO-N) | H | |
| 302 | NHCO-(3-Me-thiophen-2-yl) | H | CH₂-piperazin-N-CH₂-CH(OH)-CH₂OH | H | |
| 303 | NHCO-(3-Me-thiophen-2-yl) | H | COHN-(1-acetyl-piperidin-4-yl) | H | |
| 304 | NHCO-(3-Me-thiophen-2-yl) | H | CH₂-piperazin-N-CH₂CH₂CH₂-OMe | H | |
| 305 | NHCO-(1-Me-pyrrol-2-yl) | H | N(Me)-CH₂CH₂-OH | H | |
| 306 | 4-amino-phthalimid-N-yl | H | CH₂-piperazin-N-CH₂CH₂CH₂-OH | H | |
| 307 | 4-amino-phthalimid-N-yl | H | CH₂-piperazin-N-CH₂CH₂-OH | H | |
| 308 | NHCO-(1-Me-pyrrol-2-yl) | H | N(CH₂CH₂-morpholin-N-yl)(CH₂CH₂-OH) | H | |

TABLE 7-continued

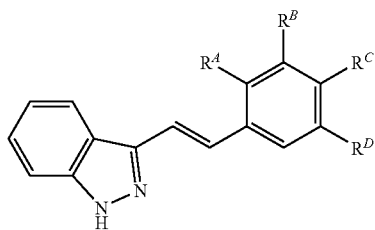

| Compound Number | R<sup>A</sup> | R<sup>B</sup> | R<sup>C</sup> | R<sup>D</sup> | Salt |
|---|---|---|---|---|---|
| 309 | 4-amino-phthalimidyl | H | CON(piperazinyl)-CH₂CH₂CH₂OMe | H | |
| 310 | 4-amino-isoindolin-1-on-yl | H | CON(4-methoxypiperidinyl) | H | |
| 311 | 3-methyl-2-thienylcarbonylamino (NHCO-) | H | CH₂N(4-(2-hydroxyethyl)piperidinyl) | H | |
| 312 | 3-methyl-2-thienylcarbonylamino | H | CH₂N(piperazinyl)-CH₂C(Me)₂OH | H | |
| 313 | 3-methyl-2-thienylcarbonylamino | H | CH₂N(piperazinyl)-CH₂CH₂C(O)Me | H | |
| 314 | 4-amino-isoindolin-1-on-yl | H | CH₂N(piperazinyl)-CH₂CH₂CH₂OH | H | |
| 315 | 4-amino-phthalimidyl | H | CON(piperazinyl)-N-Me | H | |

TABLE 7-continued
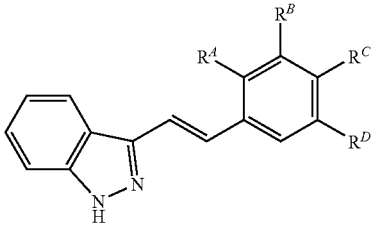
| Compound Number | R^A | R^B | R^C | R^D | Salt |
|---|---|---|---|---|---|
| 316 | 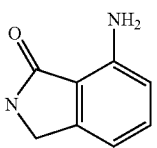 | H | 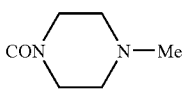 | H | |
| 317 | 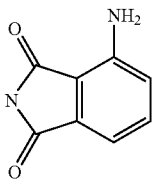 | H | 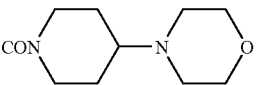 | H | |
| 318 | 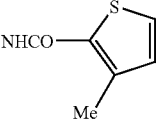 | H | 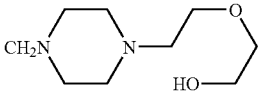 | H | |
| 319 | 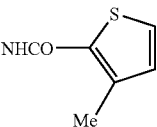 | H | 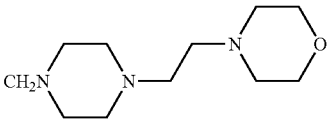 | H | |
| 320 | 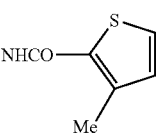 | H | 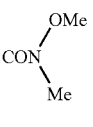 | H | |
| 321 | 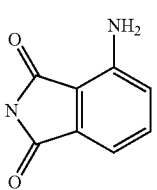 | H | 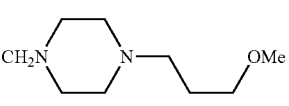 | H | |
| 322 | 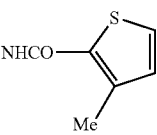 | H | 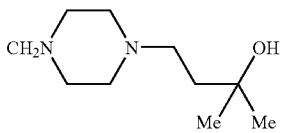 | H | |
| 323 | 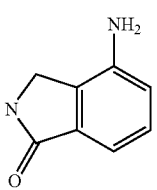 | H | 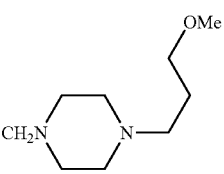 | H | |

TABLE 7-continued

| Compound Number | R^A | R^B | R^C | R^D | Salt |
|---|---|---|---|---|---|
| 324 | 4-amino-isoindolin-1(3H)-one | H | CO-morpholine | H | |
| 325 | 4-amino-phthalimide | H | CO-N(4-methoxypiperidine) | H | |
| 326 | 4-amino-phthalimide | H | CON(Me)Me | H | |
| 327 | 3-methyl-thiophene-2-carboxamido (NHCO) | H | CON(Me)CH₂CH₂OH | H | |
| 328 | 3-methyl-thiophene-2-carboxamido (NHCO) | H | CON(Me)-(1-methylpiperidin-4-yl) | H | |
| 329 | 3-methyl-thiophene-2-carboxamido (NHCO) | H | CH₂N-(4-methyl-3-oxopiperazin-1-yl) | H | |
| 330 | 3-methyl-thiophene-2-carboxamido (NHCO) | H | CH₂N-((R)-3-hydroxypyrrolidin-1-yl) | H | |

TABLE 7-continued
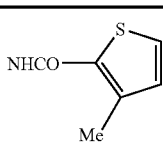
| Compound Number | R^A | R^B | R^C | R^D | Salt |
|---|---|---|---|---|---|
| 331 | 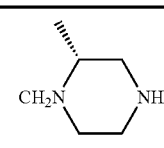 | H | 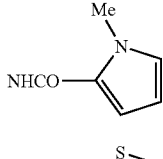 | H | |
| 332 | 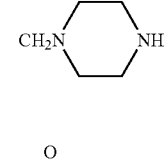 | H | 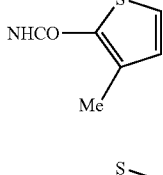 | H | |
| 333 | 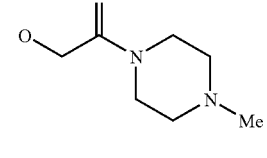 | OMe | 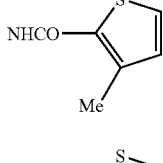 | H | |
| 334 | 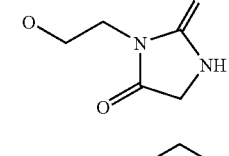 | OMe | 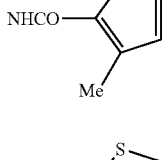 | H | |
| 335 | 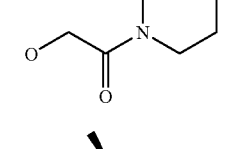 | OMe | 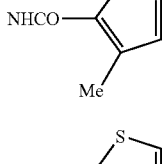 | H | |
| 336 | 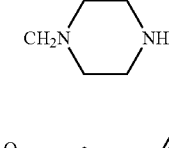 | H | 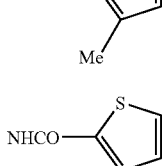 | H | |
| 337 | 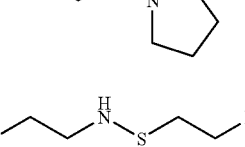 | OMe | 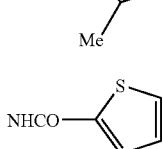 | H | |
| 338 | 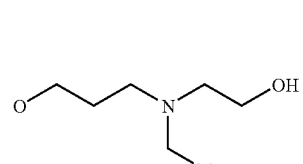 | OMe | 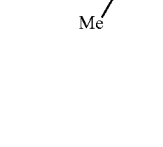 | H | |
| 339 | 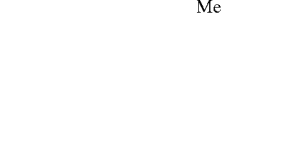 | OMe | | H | |

TABLE 7-continued

| Compound Number | R^A | R^B | R^C | R^D | Salt |
|---|---|---|---|---|---|
| 340 | NHCO-(3-Me-thiophen-2-yl) | OMe | -O-(CH2)3-N-[(2S)-2-(hydroxymethyl)pyrrolidin-1-yl] | H | |
| 341 | NHCO-(3-Me-thiophen-2-yl) | OMe | -O-(CH2)3-N-(3-oxopiperazin-1-yl) | H | |
| 342 | NHCO-(3-Me-thiophen-2-yl) | OMe | -O-(CH2)3-N-morpholinyl | H | |
| 343 | NHCO-(3-Me-thiophen-2-yl) | OMe | -O-CH2-C(=O)-N-[(3R)-3-hydroxypyrrolidin-1-yl] | H | |
| 344 | NHCO-(3-Me-thiophen-2-yl) | OMe | -O-(CH2)3-N-(4-hydroxypiperidin-1-yl) | H | |
| 345 | 4-amino-isoindolin-1-one (NH2 on ring, CH2N) | H | piperazine-N-CH2CH2-OH | H | |
| 346 | NHCO-(3-Me-thiophen-2-yl) | OMe | -O-(CH2)3-N-[(3S)-3-aminopyrrolidin-1-yl] | H | |
| 347 | NHCO-(3-Me-thiophen-2-yl) | OMe | -O-(CH2)3-N(Me)-CH2CH2-OH | H | |

TABLE 7-continued

[Structure: 1H-indazole-3-yl vinyl phenyl with substituents R^A, R^B, R^C, R^D]

| Compound Number | R^A | R^B | R^C | R^D | Salt |
|---|---|---|---|---|---|
| 348 | NHCO-(3-Me-thiophen-2-yl) | OMe | O-propyl-N-(pyrrolidinyl with Me, NHMe, OMe substituents) | H | |
| 349 | NHCO-(3-Me-thiophen-2-yl) | OMe | O-ethyl-N-(4-OH-piperidinyl) | H | |
| 350 | NHCO-(3-Me-thiophen-2-yl) | OMe | O-propyl-N-(4-CH2OH-piperidinyl) | H | |

TABLE 8

[Structure: 1H-indazole-3-yl vinyl phenyl with R^A]

| Compound Number | R^A | Salt |
|---|---|---|
| 351 | NHCO-(3-Me-benzothiophen-2-yl) | |
| 352 | NHCO-(1-Me-imidazol-2-yl) | |
| 353 | NHCO-(4-Br-3-Me-thiophen-2-yl) | |

TABLE 8-continued

[Structure: 1H-indazole-3-yl vinyl phenyl with R^A]

| Compound Number | R^A | Salt |
|---|---|---|
| 354 | NHCO-(5-(SO2Me)-thiophen-2-yl) | |

Next, pharmacological activities of typical compounds will be illustrated below with reference to the test examples.

TEST EXAMPLE 1

Cytostatic Activity on Blood Carcinoma Cell Line and Solid Carcinoma Cell Line which has been Reported as IGF-Dependent.

The cytostatic rates of a test compound on human multiple myeloma cell lines NCI-H929 and KMS-11, were determined in the following manner.

For culturing NCI-H929, Roswell Park Memorial Institute's Medium (RPMI) 1640 (Gibco, Catalog No. 11875-093) containing 15% fetal bovine serum (Gibco, Catalog No.

10099-141), 1 mmol/L sodium pyruvate (Gibco, Catalog No. 11360-070), 10 mmol/L HEPES (Gibco, Catalog No. 15630-80), 4.5 g/L glucose (Sigma, Catalog No. G8769), 0.05 mmol/L 2-mercaptethanol (Nacalai Tesque, Catalog No. 21418-42) and penicillin/streptomycin (1:1) (Gibco, Catalog No. 15140-122) was used. For culturing KMS-11 cell, RPMI 1640 medium containing 10% fetal bovine serum and penicillin/streptomycin (1:1) was used. Each 80 μL of the NCI-H929 cell having a concentration of $1 \times 10^5$ cells/mL (or the KMS-11 cell having a concentration of $7.5 \times 10^4$ cells/mL) was inoculated to wells of a TC MICROWELL 96U plate (Nalge Nunc International, Catalog No. 163320) and was cultured in a 5% carbon dioxide gas incubator at 37° C. for 24 hours. Each 20 μL of a solution of the test compound in dimethyl sulfoxide (DMSO) which was prepared to make the final concentration to 1 μmol/L or 10 μmol/L, was added to each well. Each 20 μL of DMSO was added to the control well and the blank well to a final concentration of 0.1%. After adding the test compound, the cells were incubated in a 5% carbon dioxide gas incubator at 37° C. for 72 hours except for the blank well. After adding 20 μL of WST-1 reagent {4-[3-(4-iodophenyl)-2-(4-nitrophenyl)-2H-5-tetrazolio]-1,3-benzene disulfonate sodium salt} (Roche Diagnostics K.K., Catalog No. 1644807), which was diluted to 50% by RPMI medium to each well, the cells were further incubated at 37° C. for 2 hours. Then, the absorbances at 450 nm (reference wavelength: 690 nm) were measured with a microplate spectrophotometer SPECTRA max 340PC (Molecular Devices Corporation). The relative growth (%) of a well to which the test compound had been added and cultured for 72 hours was determined while setting the absorbance of a well to which not the test compound but DMSO alone had been added and cultured for 72 hours (control) as 100% and that of a well where the drugs are added (blank) as 0%. The cytostatic rate (%) of the test compound was determined by subtracting the calculated relative growth from 100. The higher the cytostatic rate, the stronger the test compound exhibits cytostatic activity on the cell.

The cytostatic rates of the test compound on the human pancreatic cancer cell line AsPC-1 and the human colon cancer cell line Colo205 were determined in the following manner.

For culturing AsPC-1, RPMI 1640 medium containing 20% fetal bovine serum, 1 mmol/L sodium pyruvate, 10 mmol/L HEPES, 4.5 g/L glucose and penicillin/streptomycin (1:1). The Colo205 cell was cultured using RPMI 1640 medium containing 10% fetal bovine serum, 1 mmol/L sodium pyruvate, 10 mmol/L HEPES, 4.5 g/L glucose and penicillin/streptomycin (1:1) was used. Each 80 μL of the AsPC-1 cell having a concentration of $5 \times 10^4$ cells/mL (or the Colo205 having a concentration of $5 \times 10^4$ cells/mL) was inoculated to wells of a TC MICROWELL 96F plate (Nalge Nunc International, Catalog No. 167008) and was cultured in a 5% carbon dioxide gas incubator at 37° C. for 24 hours. Each 20 μL of a solution of the test compound in DMSO which was prepared to make the final concentration to 1 μmol/L or 10 μmol/L, was added to each well. Each 20 μL of DMSO was added to the control well and the blank well to a final concentration of 0.1%. After adding the test compound, the cell was incubated in a 5% carbon dioxide gas incubator at 37° C. for 72 hours except for the blank well. After adding 20 μL of WST-1 reagent which was diluted to 50% by RPMI medium to each well, the cells were further incubated at 37° C. for 2 hours. Then, the absorbances at 450 nm (reference wavelength: 690 nm) were determined with a microplate spectrophotometer SPECTRA max 340PC. The cytostatic rate (%) was then determined in the similar manner to the above multiple myeloma cell lines.

The results of Test Example 1 are shown in Tables 9-1 to 9-8.

TABLE 9-1

| Compound Number | cytostatic rate (%) | | | |
|---|---|---|---|---|
| | H929 (10 μmol/L) | KMS-11 (10 μmol/L) | AsPC-1 (10 μmol/L) | Colo205 (10 μmol/L) |
| 1 | 105.1 | 80.2 | | |
| 3 | 114.9 | 118.1 | | |
| 4 | 114.5 | 129.9 | | |
| 5 | 116.3 | 128.7 | | |
| 6 | 115.1 | 119.8 | | |
| 7 | 115.4 | 120.9 | | |
| 8 | 117.7 | 126.1 | | |
| 9 | 59.0 | 99.8 | | |
| 10 | 113.2 | 102.4 | | |
| 11 | 116.3 | 120.5 | | |
| 12 | 117.5 | 119.6 | | |
| 13 | 115.5 | 104.7 | | |
| 14 | 113.5 | 109.9 | | |
| 15 | 93.6 | 95.1 | | |
| 16 | 64.7 | 85.2 | | |
| 17 | 115.1 | 127.0 | | |
| 18 | 112.7 | 124.1 | | |
| 19 | 131.8 | 109.7 | | |
| 20 | 129.8 | 107.2 | | |
| 21 | 113.7 | 94.0 | | |
| 23 | 130.0 | 109.0 | | |
| 24 | 115.5 | 109.7 | | |
| 25 | 116.0 | 105.7 | | |
| 27 | 119.1 | 114.0 | | |
| 28 | 116.2 | 109.3 | | |
| 29 | 117.0 | 111.9 | 66.1 | 114.1 |
| 30 | 115.4 | 115.1 | | |
| 31 | 114.0 | 117.2 | | |
| 32 | 112.7 | 125.5 | | |
| 33 | 108.0 | 115.1 | | |
| 34 | 112.8 | 115.7 | | |
| 35 | 109.7 | 124.7 | | |
| 36 | 112.4 | 116.3 | | |
| 37 | 111.7 | 112.4 | | |
| 38 | 65.0 | | | |
| 39 | 68.8 | 91.0 | | |

TABLE 9-2

| Compound Number | cytostatic rate (%) | | | |
|---|---|---|---|---|
| | H929 (10 μmol/L) | KMS-11 (10 μmol/L) | AsPC-1 (10 μmol/L) | Colo205 (10 μmol/L) |
| 40 | 125.1 | 108.5 | | |
| 41 | 121.1 | 109.0 | 85.5 | 115.3 |
| 42 | 125.8 | 109.2 | | |
| 43 | 113.0 | 112.5 | | |
| 44 | 115.1 | 112.6 | | |
| 45 | 115.0 | 98.3 | | |
| 46 | 118.4 | 115.2 | 120.2 | 112.2 |
| 47 | 100.2 | 92.1 | | |
| 48 | 111.1 | 90.1 | | |
| 52 | 118.8 | 128.4 | | |
| 53 | 113.9 | 125.7 | | |
| 54 | 118.4 | 125.6 | | |
| 55 | 114.6 | 132.1 | | |
| 56 | 115.7 | 133.7 | | |
| 57 | 117.3 | 141.2 | | |
| 58 | 69.8 | 118.7 | | |
| 59 | 110.4 | 106.4 | | |
| 60 | 63.9 | 102.7 | | |
| 61 | 123.8 | | | |
| 62 | 120.4 | | | |
| 63 | 108.9 | 124.7 | | |
| 64 | 108.5 | 123.7 | | |

TABLE 9-2-continued

| Compound Number | cytostatic rate (%) | | | |
|---|---|---|---|---|
| | H929 (10 μmol/L) | KMS-11 (10 μmol/L) | AsPC-1 (10 μmol/L) | Colo205 (10 μmol/L) |
| 65 | 108.8 | 120.0 | | |
| 66 | 110.7 | 114.5 | | |
| 67 | 118.9 | 100.1 | | |
| 68 | 114.1 | 112.0 | | |
| 69 | 115.9 | 113.7 | | |
| 70 | 114.7 | 112.8 | | |
| 71 | 115.0 | 114.4 | | |
| 73 | 80.0 | 90.4 | | |
| 76 | 108.8 | 126.0 | | |
| 77 | 110.6 | 126.3 | | |
| 78 | 114.5 | 107.4 | | |
| 83 | 114.5 | 107.4 | | |
| 84 | 113.2 | 107.4 | | |
| 85 | 134.1 | 124.0 | 125.2 | 116.5 |
| 86 | 116.2 | 126.3 | | |
| 87 | 95.0 | 78.1 | | |

TABLE 9-3

| Compound Number | cytostatic rate (%) | | | |
|---|---|---|---|---|
| | H929 (10 μmol/L) | KMS-11 (10 μmol/L) | AsPC-1 (10 μmol/L) | Colo205 (10 μmol/L) |
| 88 | 115.7 | | | |
| 89 | 113.5 | 137.6 | | |
| 90 | 114.3 | 135.8 | | |
| 91 | 115.4 | 143.6 | | |
| 92 | 70.1 | | | |
| 94 | 124.8 | 142.7 | | |
| 95 | 121.4 | 138.2 | | |
| 96 | 117.3 | 117.0 | | |
| 97 | | 100.2 | | |
| 98 | 66.3 | | | |
| 99 | | 118.4 | | |
| 100 | 121.5 | 114.9 | 107.8 | 121.4 |
| 101 | | 117.0 | | |
| 102 | 125.3 | | | |
| 103 | 129.8 | | | |
| 104 | 130.1 | | | |
| 105 | 120.2 | 120.5 | | |
| 106 | 112.1 | 115.3 | | |
| 107 | 118.6 | 119.1 | | |
| 108 | 123.1 | 110.5 | 87.9 | 120.6 |
| 109 | 115.8 | 116.9 | 114.2 | 123.1 |
| 110 | 116.1 | 118.3 | | |
| 111 | 119.8 | 111.6 | | |
| 112 | | 125.5 | | |
| 113 | | 121.0 | | |
| 115 | 120.0 | 115.5 | 108.7 | 121.6 |
| 116 | 118.3 | 114.0 | | |
| 117 | 119.3 | 114.9 | | |
| 118 | 115.7 | 113.6 | | |
| 119 | 116.7 | 115.5 | | |
| 120 | 115.5 | 114.2 | | |
| 130 | 126.3 | | | |
| 131 | 121.5 | | | |
| 132 | 108.1 | 111.7 | | |

TABLE 9-4

| Compound Number | cytostatic rate (%) | | | |
|---|---|---|---|---|
| | H929 (10 μmol/L) | KMS-11 (10 μmol/L) | AsPC-1 (10 μmol/L) | Colo205 (10 μmol/L) |
| 133 | 62.9 | | | |
| 134 | 92.8 | 52.5 | | |
| 136 | 87.7 | 38.4 | | |

TABLE 9-4-continued

| Compound Number | cytostatic rate (%) | | | |
|---|---|---|---|---|
| | H929 (10 μmol/L) | KMS-11 (10 μmol/L) | AsPC-1 (10 μmol/L) | Colo205 (10 μmol/L) |
| 137 | 114.0 | 51.2 | | |
| 138 | 113.9 | 101.4 | | |
| 140 | 103.9 | 58.9 | | |
| 141 | 113.8 | 116.7 | | |
| 142 | 104.3 | 84.9 | | |
| 145 | 125.6 | 116.3 | | |
| 151 | 103.5 | 83.2 | | |
| 152 | 121.8 | 115.7 | 72.1 | 86.7 |
| 153 | 122.0 | 128.8 | 77.0 | 114.1 |
| 156 | 115.4 | 115.1 | | |
| 158 | 113.1 | 107.6 | | |
| 159 | 104.0 | 75.5 | | |
| 161 | 113.3 | 92.8 | | |
| 168 | 105.6 | | | |
| 174 | 108.8 | 82.6 | | |
| 193 | 124.3 | 167.0 | | |
| 194 | 119.0 | 142.8 | 75.3 | 97.9 |
| 195 | 110.6 | 97.7 | | |
| 213 | 126.6 | 120.9 | | |
| 216 | 109.4 | 90.9 | | |

TABLE 9-5

| Compound Number | cytostatic rate (%) | | | |
|---|---|---|---|---|
| | H929 (1 μmol/L) | KMS-11 (1 μmol/L) | AsPC-1 (10 μmol/L) | Colo205 (10 μmol/L) |
| 217 | 112.9 | 128.1 | 91.9 | 122.0 |
| 218 | 111.8 | 106.4 | | |
| 219 | 111.3 | 108.2 | | |
| 220 | 110.5 | 97.9 | | |
| 222 | 118.1 | 108.2 | 113.7 | 123.3 |
| 223 | 118.6 | 119.8 | | |
| 224 | 119.1 | 119.1 | | |
| 227 | 112.6 | 52.9 | | |
| 228 | 113.6 | 58.0 | | |
| 229 | 121.4 | 66.8 | | |
| 230 | 124.2 | 93.8 | | |
| 231 | 121.5 | 80.2 | | |
| 232 | 123.7 | 115.5 | | |
| 233 | 118.2 | 101.7 | 89.1 | 123.3 |
| 234 | 118.5 | 110.6 | | |
| 235 | 115.4 | 109.2 | | |
| 236 | 123.1 | 139.2 | | |
| 237 | 119.8 | 143.9 | | |
| 238 | 126.4 | 132.4 | | |
| 239 | 114.9 | 151.6 | 101.5 | 121.4 |
| 240 | 105.1 | 67.0 | | |
| 241 | 112.0 | 118.0 | 103.6 | 121.4 |
| 242 | 111.1 | 106.2 | 87.1 | 119.7 |
| 244 | 126.9 | 123.5 | | |
| 245 | 126.2 | 118.1 | 101.9 | 120.9 |
| 246 | 126.7 | 128.9 | | |
| 247 | 126.6 | 133.0 | 117.3 | 122.7 |
| 248 | 114.3 | 112.8 | | |
| 249 | 113.4 | 113.1 | | |
| 251 | 112.5 | 114.1 | | |
| 252 | 120.1 | 112.9 | | |
| 253 | 119.2 | 108.9 | 100.0 | 121.6 |
| 254 | 115.5 | 81.2 | | |
| 255 | 121.4 | 97.6 | | |
| 256 | 122.4 | 105.2 | | |
| 259 | 117.8 | 103.5 | | |
| 260 | 118.9 | 118.5 | | |

TABLE 9-6 cytostatic rate (%)

| Compound Number | H929 (1 μmol/L) | KMS-11 (1 μmol/L) | AsPC-1 (10 μmol/L) | Colo205 (10 μmol/L) |
|---|---|---|---|---|
| 261 | 115.3 | 120.8 | | |
| 262 | 119.1 | 118.8 | | |
| 263 | 116.0 | 126.2 | 103.4 | 120.5 |
| 264 | 110.9 | 58.5 | | |
| 265 | 115.1 | 96.9 | | |
| 266 | 117.6 | 130.8 | | |
| 267 | 118.1 | 133.8 | | |
| 268 | 117.7 | 129.1 | | |
| 269 | 119.0 | 132.0 | | |
| 270 | 120.6 | 129.0 | | |
| 271 | 118.8 | 123.2 | | |
| 272 | 120.1 | 135.4 | | |
| 273 | 115.4 | 111.0 | | |
| 274 | 114.4 | 108.1 | | |
| 275 | 117.9 | 115.7 | | |
| 277 | 119.3 | 107.1 | | |
| 278 | 111.6 | 102.9 | | |
| 279 | 111.8 | 111.3 | | |
| 280 | 112.2 | 109.0 | | |
| 281 | 128.0 | 114.7 | | |
| 282 | 129.5 | 122.9 | | |
| 283 | 127.8 | 115.5 | | |
| 284 | 121.2 | 130.8 | | |
| 288 | 117.8 | 109.4 | 94.5 | 120.1 |
| 289 | 101.5 | 73.6 | | |
| 290 | 93.8 | | | |
| 292 | 112.7 | 121.5 | | |
| 293 | 110.4 | 118.7 | | |
| 294 | 117.6 | 115.5 | | |
| 295 | 118.2 | 117.8 | | |
| 296 | 117.0 | 112.5 | | |
| 297 | 116.5 | 94.5 | | |
| 298 | 117.4 | 109.7 | | |
| 300 | 119.4 | 115.8 | | |
| 301 | 118.8 | 100.1 | | |
| 302 | 115.1 | 99.4 | | |
| 303 | 115.0 | 106.4 | | |
| 304 | 114.9 | 104.6 | | |

TABLE 9-7 cytostatic rate (%)

| Compound Number | H929 (1 μmol/L) | KMS-11 (1 μmol/L) | AsPC-1 (10 μmol/L) | Colo205 (10 μmol/L) |
|---|---|---|---|---|
| 305 | 117.7 | 110.2 | | |
| 306 | 115.5 | 112.2 | | |
| 307 | 114.2 | 109.5 | | |
| 308 | 118.3 | 128.1 | | |
| 309 | 115.3 | 112.7 | | |
| 310 | 105.3 | | | |
| 311 | 117.1 | 110.8 | | |
| 312 | 115.1 | 108.2 | 101.1 | 120.3 |
| 313 | 115.2 | 107.9 | | |
| 315 | 112.8 | 105.5 | | |
| 317 | 114.1 | 104.8 | | |
| 318 | 122.1 | 102.1 | 103.0 | 120.4 |
| 319 | 122.4 | 102.6 | | |
| 320 | 122.8 | 112.1 | | |
| 321 | 121.7 | 102.3 | | |
| 322 | 122.0 | 106.0 | | |
| 323 | 107.6 | 73.8 | | |
| 325 | 118.4 | 100.1 | | |
| 326 | 118.5 | 102.1 | | |
| 327 | 115.5 | 98.0 | | |
| 328 | 115.6 | 105.1 | | |
| 329 | 131.9 | 115.6 | | |
| 330 | 131.3 | 112.4 | | |
| 331 | 116.1 | 102.2 | | |
| 332 | 113.9 | 89.9 | | |

TABLE 9-7-continued cytostatic rate (%)

| Compound Number | H929 (1 μmol/L) | KMS-11 (1 μmol/L) | AsPC-1 (10 μmol/L) | Colo205 (10 μmol/L) |
|---|---|---|---|---|
| 333 | 118.1 | 119.0 | | |
| 334 | 110.8 | 97.5 | | |
| 335 | 117.0 | 109.6 | | |
| 336 | 131.0 | 115.1 | | |
| 337 | 120.5 | 121.1 | | |
| 338 | 119.7 | 122.1 | | |
| 339 | 119.0 | 118.0 | | |
| 340 | 121.4 | 117.5 | | |
| 341 | 119.6 | 123.8 | | |
| 342 | 118.7 | 122.6 | | |
| 343 | 127.5 | 79 | | |
| 344 | 132.9 | 117.1 | | |

TABLE 9-8 cytostatic rate (%)

| Compound Number | H929 (1 μmol/L) | KMS-11 (1 μmol/L) | AsPC-1 (10 μmol/L) | Colo205 (10 μmol/L) |
|---|---|---|---|---|
| 346 | 114.2 | 97.2 | | |
| 347 | 116.4 | 116.5 | | |
| 348 | 115.8 | 116.7 | | |
| 349 | 116.3 | 117.2 | | |
| 350 | 117.2 | 117.2 | | |
| 352 | 108.0 | 84.8 | | |
| 353 | 104.2 | 77.4 | | |

TEST EXAMPLE 2

IGF-1R Inhibitory Activity

The IGF-1R inhibitory activity was measured in the following manner.

As IGF-1R, active recombinant enzyme (Catalog No. 14-465) purchased from Upstate Co., was used. To 96 well plate (FIA-PLATE BLACK 96 well FALT-BOTTOM HIGH BINDING, Greiner Bio-one, Catalog No. 655077) coated with NeutroAvidin (Pierce, Catalog No. 31000), biotinylated polyglutamic acid-tyrosine peptide (Nihon Schering K.K., Catalog No. 61GT0BAA) was immobilized and then blocked with 0.25% gelatin to be used as a plate for measuring the kinase reaction. Separately was prepared a solution containing at final concentrations, IGF-1R (200 μg/L), Tris.HCl(pH 7.5)(20 mmol/L), $Na_3VO_4$(0.1 mmol/L), $MgCl_2$(1 mmol/L), $MnCl_2$(10 mmol/L), ATP(10 mmol/L), 2-mercaptoethanol (0.04%), BSA(Bovine Serum Albumin) (0.1%), DMSO (0.1%), test compound (10 μmol/L). The solution (each 50 μL) was added to the well of the plate for measuring the kinase reaction and then, enzyme reaction was performed for 30 minutes at 24° C. The plate was washed with TBS-T [10 mmol/L Tris Cl (pH 7.5), 150 mmol/L NaCl, 0.05% Tween 20 (Bio-Rad, Catalog No. 170-6531)] 4 times, then reacted with europium-labeled anti-phosphotyrosine antibody, further washed with TBS-T 4 times and then, measured with time-resolved fluoroimmunoassay (excitation wavelength 340 nm, measuring wavelength 615 nm). The value of a well to which the test compound had not been added was considered as 100% and that of a well where the enzyme and the test compound had not been added was considered as 0%. The relative activity (%) of the well which was added with enzyme and the test compound was measured and by subtracting the calculated value from 100, IGF-1R inhibitory activity of the test compound (%) was determined.

The results of Test Example 2 are shown in Tables 10-1 to 10-5.

TABLE 10-1 inhibitory activity (%) at 10 μmol/L

| Compound Number | inhibitory activity (%) |
|---|---|
| 1 | 71.2 |
| 3 | 99.1 |
| 4 | 98.5 |
| 5 | 99.1 |
| 6 | 97.8 |
| 7 | 98.6 |
| 8 | 99.5 |
| 9 | 74.3 |
| 10 | 99.1 |
| 11 | 99.4 |
| 12 | 96.1 |
| 13 | 96.9 |
| 14 | 96.5 |
| 15 | 55.4 |
| 16 | 59.2 |
| 17 | 98.3 |
| 18 | 96.4 |
| 19 | 95.3 |
| 20 | 97.3 |
| 21 | 88.2 |
| 23 | 95.4 |
| 24 | 97.4 |
| 25 | 86.0 |
| 26 | 67.8 |
| 27 | 99.3 |
| 28 | 95.2 |
| 29 | 97.9 |
| 30 | 97.6 |
| 31 | 99.7 |
| 32 | 98.6 |
| 33 | 92.4 |
| 34 | 99.2 |
| 35 | 98.4 |
| 36 | 98.6 |
| 37 | 99.1 |
| 38 | 93.0 |
| 39 | 59.1 |
| 40 | 98.8 |
| 41 | 98.6 |
| 42 | 98.9 |
| 43 | 96.3 |
| 44 | 98.0 |
| 45 | 97.4 |
| 46 | 97.8 |
| 47 | 90.1 |
| 48 | 99.3 |
| 49 | 102.7 |
| 50 | 98.5 |
| 51 | 100.1 |
| 52 | 98.5 |
| 53 | 98.9 |
| 54 | 96.7 |
| 55 | 98.9 |
| 56 | 99.3 |
| 57 | 98.3 |
| 58 | 86.0 |
| 59 | 86.3 |
| 60 | 77.4 |
| 61 | 94.5 |
| 62 | 95.7 |
| 63 | 99.2 |
| 64 | 97.0 |
| 65 | 97.9 |
| 66 | 93.6 |
| 67 | 95.6 |
| 68 | 97.4 |
| 69 | 101.4 |
| 70 | 100.7 |
| 71 | 99.4 |

TABLE 10-1-continued inhibitory activity (%) at 10 μmol/L

| Compound Number | inhibitory activity (%) |
|---|---|
| 72 | 82.7 |
| 73 | 88.0 |
| 74 | 97.6 |
| 75 | 90.4 |
| 76 | 99.2 |
| 77 | 101.4 |
| 78 | 100.1 |
| 79 | 97.2 |
| 80 | 96.6 |

TABLE 10-2 inhibitory activity (%) at 10 μmol/L

| Compound Number | inhibitory activity (%) |
|---|---|
| 81 | 60.7 |
| 82 | 84.7 |
| 83 | 96.3 |
| 84 | 100.2 |
| 85 | 99.5 |
| 86 | 97.8 |
| 87 | 92.6 |
| 88 | 97.5 |
| 89 | 98.4 |
| 90 | 97.0 |
| 91 | 98.7 |
| 92 | 66.5 |
| 93 | 70.6 |
| 94 | 95.4 |
| 95 | 97.2 |
| 96 | 100.0 |
| 97 | 97.1 |
| 98 | 98.4 |
| 99 | 97.4 |
| 100 | 98.6 |
| 101 | 100.0 |
| 102 | 97.8 |
| 103 | 97.0 |
| 104 | 98.3 |
| 105 | 94.8 |
| 107 | 92.8 |
| 108 | 95.0 |
| 109 | 102.6 |
| 110 | 96.3 |
| 111 | 98.1 |
| 112 | 98.5 |
| 113 | 98.6 |
| 114 | 92.0 |
| 115 | 100.1 |
| 116 | 103.3 |
| 117 | 101.2 |
| 118 | 101.7 |
| 119 | 101.5 |
| 120 | 97.5 |
| 121 | 98.6 |
| 123 | 95.9 |
| 124 | 98.9 |
| 125 | 100.9 |
| 126 | 98.8 |
| 127 | 101.9 |
| 128 | 98.8 |
| 129 | 99.9 |
| 130 | 98.3 |
| 131 | 94.1 |
| 132 | 98.0 |

TABLE 10-3 inhibitory activity (%) at 10 μmol/L

| Compound Number | inhibitory activity (%) |
|---|---|
| 133 | 70.4 |
| 134 | 93.4 |
| 135 | 86.6 |
| 136 | 85.3 |
| 137 | 94.3 |
| 138 | 97.2 |
| 139 | 93.9 |
| 140 | 92.1 |
| 141 | 97.1 |
| 142 | 92.8 |
| 143 | 94.9 |
| 145 | 93.4 |
| 146 | 78.3 |
| 149 | 70.0 |
| 151 | 100.3 |
| 152 | 99.5 |
| 153 | 99.8 |
| 154 | 97.1 |
| 155 | 97.9 |
| 156 | 97.6 |
| 157 | 96.0 |
| 158 | 99.5 |
| 159 | 99.9 |
| 160 | 98.4 |
| 161 | 95.9 |
| 162 | 101.7 |
| 163 | 100.4 |
| 164 | 99.1 |
| 165 | 93.8 |
| 167 | 94.1 |
| 168 | 99.0 |
| 169 | 88.4 |
| 170 | 69.8 |
| 171 | 87.2 |
| 173 | 97.8 |
| 174 | 102.8 |
| 175 | 100.0 |
| 176 | 100.1 |
| 177 | 99.4 |
| 178 | 71.1 |
| 179 | 99.6 |
| 180 | 98.1 |
| 181 | 98.9 |
| 182 | 97.9 |
| 183 | 59.1 |
| 185 | 93.2 |
| 186 | 101.6 |
| 187 | 98.2 |
| 188 | 99.4 |
| 189 | 101.8 |
| 190 | 96.9 |
| 191 | 102.2 |
| 192 | 92.3 |
| 193 | 100.5 |
| 194 | 102.4 |
| 195 | 100.2 |
| 196 | 99.8 |
| 197 | 101.4 |
| 198 | 87.2 |
| 199 | 99.4 |
| 200 | 67.5 |
| 201 | 99.1 |
| 202 | 85.9 |
| 203 | 101.3 |
| 204 | 99.8 |
| 205 | 89.8 |
| 206 | 101.2 |
| 207 | 98.1 |
| 208 | 96.1 |
| 209 | 99.5 |
| 210 | 96.5 |
| 211 | 86.7 |

TABLE 10-4 inhibitory activity (%) at 10 μmol/L

| Compound Number | inhibitory activity (%) |
|---|---|
| 212 | 83.6 |
| 213 | 99.0 |
| 215 | 81.2 |
| 216 | 96.5 |
| 217 | 96.6 |
| 218 | 98.6 |
| 219 | 99.4 |
| 220 | 99.3 |
| 221 | 95.8 |
| 222 | 98.7 |
| 223 | 100.8 |
| 224 | 100.1 |
| 225 | 95.0 |
| 226 | 97.8 |
| 227 | 98.9 |
| 228 | 100.1 |
| 229 | 99.3 |
| 230 | 98.9 |
| 231 | 99.7 |
| 232 | 100.7 |
| 233 | 106.4 |
| 234 | 101.7 |
| 235 | 98.3 |
| 236 | 99.5 |
| 237 | 100.4 |
| 238 | 97.1 |
| 239 | 101.1 |
| 240 | 103.3 |
| 241 | 101.0 |
| 242 | 102.1 |
| 244 | 101.7 |
| 245 | 99.9 |
| 246 | 100.2 |
| 247 | 101.6 |
| 248 | 100.5 |
| 249 | 100.3 |
| 250 | 98.9 |
| 251 | 101.5 |
| 252 | 100.9 |
| 253 | 98.7 |
| 254 | 99.5 |
| 255 | 100.1 |
| 256 | 100.0 |
| 257 | 101.8 |
| 258 | 100.2 |
| 259 | 102.5 |
| 260 | 101.6 |
| 261 | 100.8 |
| 262 | 103.0 |
| 263 | 100.9 |
| 264 | 101.7 |
| 265 | 98.4 |
| 266 | 102.8 |
| 267 | 100.3 |
| 268 | 101.4 |
| 269 | 100.7 |
| 270 | 100.1 |
| 271 | 102.5 |
| 272 | 101.1 |
| 273 | 103.5 |
| 274 | 104.2 |
| 275 | 98.6 |
| 276 | 99.6 |
| 277 | 99.5 |
| 278 | 100.1 |
| 279 | 98.2 |
| 280 | 97.6 |
| 281 | 97.2 |
| 282 | 99.2 |
| 283 | 101.1 |
| 284 | 97.5 |
| 285 | 99.0 |
| 286 | 96.1 |
| 287 | 97.1 |

TABLE 10-4-continued inhibitory activity (%) at 10 μmol/L

| Compound Number | inhibitory activity (%) |
|---|---|
| 288 | 97.9 |
| 289 | 93.5 |
| 290 | 95.7 |
| 291 | 97.7 |
| 292 | 97.2 |
| 293 | 98.9 |

TABLE 10-5 inhibitory activity (%) at 10 μmol/L

| Compound Number | inhibitory activity (%) |
|---|---|
| 294 | 98.2 |
| 295 | 97.2 |
| 296 | 99.9 |
| 297 | 101.3 |
| 298 | 94.2 |
| 299 | 92.9 |
| 300 | 97.2 |
| 301 | 98.3 |
| 302 | 100.8 |
| 303 | 100.5 |
| 304 | 102.5 |
| 305 | 100.3 |
| 306 | 100.3 |
| 307 | 100.2 |
| 308 | 99.1 |
| 309 | 97.1 |
| 310 | 97.9 |
| 311 | 103.5 |
| 312 | 105.0 |
| 313 | 100.7 |
| 314 | 101.8 |
| 315 | 105.5 |
| 316 | 103.4 |
| 317 | 102.7 |
| 318 | 94.7 |
| 319 | 100.4 |
| 320 | 102.1 |
| 321 | 100.8 |
| 322 | 99.1 |
| 323 | 105.8 |
| 324 | 101.7 |
| 325 | 100.2 |
| 326 | 102.6 |
| 327 | 100.8 |
| 328 | 97.9 |
| 329 | 104.8 |
| 330 | 101.7 |
| 331 | 103.4 |
| 332 | 102.6 |
| 333 | 108.7 |
| 334 | 101.6 |
| 335 | 102.0 |
| 336 | 101.3 |
| 337 | 97.4 |
| 338 | 99.0 |
| 339 | 103.6 |
| 340 | 103.2 |
| 341 | 104.7 |
| 342 | 101.6 |
| 343 | 98.4 |
| 344 | 97.4 |
| 345 | 105.4 |
| 346 | 113.6 |
| 347 | 105.7 |
| 348 | 108.6 |
| 349 | 101.9 |
| 350 | 111.0 |

TABLE 10-5-continued inhibitory activity (%) at 10 μmol/L

| Compound Number | inhibitory activity (%) |
|---|---|
| 351 | 99.1 |
| 352 | 102.7 |
| 353 | 101.5 |
| 354 | 97.1 |

Compound (I), (Ia), (Ib), (Ic), (II), (IIa), (III), (IIIa), (IIIb), (IV), (V), (VI) and (VII) or pharmaceutically acceptable salts thereof may be used as they are but it is desirable to provide them as various pharmaceutical formulations. Also, the pharmaceutical formulations are to be used for animals and humans.

The pharmaceutical formulation associated with the present invention may comprise, as active ingredients, Compound (I), (Ia), (Ib), (Ic), (II), (IIa), (III), (IIIa), (IIIb), (IV), (V), (VI) and (VII) or pharmaceutically acceptable salts thereof as they are or as mixtures with other active ingredients for treatments. The pharmaceutical formulation of the present invention can be manufactured by mixing the active ingredient with one or more pharmaceutically acceptable carrier(s) and by the method well known in the technical field of the pharmaceutics.

As the administration route, it is desirable to use the most effective route for treatment, such as orally or parenterally. Examples of the parenteral administration include intravenous administration, or the like.

Examples of the administration form include, for example, tablets, powders, granules, syrups, injections and the like.

In the manufacture of liquid preparation, such as syrups, which is suitable for oral administration, water, saccharides such as sucrose, sorbitol and fructose, glycols such as polyethyleneglycol and propyleneglycol, oil such as sesame oil, olive oil and soybean oil, antiseptics such as p-hydroxybenzoate, flavors such as strawberry flavor and peppermint flavor can be used. In the manufacture of tablets, powders and granules, excipients such as lactose, glucose, sucrose and mannitol, disintegrators such as starch and sodium alginate, lubricants such as magnesium stearate and talc, binders such as polyvinyl alcohol, hydroxypropyl cellulose and gelatin, surfactants such as fatty acid ester and plasticizers such as glycerin etc. may be used.

Preparation suitable for parenteral administration preferably consists of a sterilized aqueous preparation comprising active compound which is isotonic to blood of the recipient. For example, in the case of an injection, a solution for injection is prepared using a carrier consisting of a salt solution, a glucose solution or a mixture of a salt solution and a glucose solution, or the like.

In such a parenteral preparation, it is also possible to add one or more auxiliary component(s) selected from diluents, antiseptics, flavors, excipients, disintegrators, lubricants, binders, surfactants, plasticizers, etc. which were exemplified above for an oral preparation.

The dose and frequency of administering Compound (I), (Ia), (Ib), (Ic), (II), (IIa), (III), (IIIa), (IIIb), (IV), (V), (VI) and (VII) or pharmaceutically acceptable salts thereof vary depending on the dosage form, age, body weight of the patient and symptom to be treated or its seriousness, etc. In general, they may be orally administered in an amount of 0.01 mg to 1 g/adult, preferably in an amount of 0.05 to 50 mg/adult per day, once or several times a day. When administered parenterally, intravenously, or the like, they may be administered, for example, in an amount of 0.001 to 100 mg/adult, preferably in an amount of 0.01 to 10 mg/adult per day, once or several times a day. However, the amount and the frequency of the administration may vary depending upon the above various conditions.

The present invention will be illustrated in further detail with Examples below which by no means limit the scope of the present invention.

EXAMPLE 1

(E)-3-[2-(2-nitrophenyl)vinyl]-1H-indazole (Compound 1)

(1H-indazol-3-ylmethyl)triphenylphosphonium iodide (3.12 g, 6.00 mmol) was dissolved in methanol (50 mL) and the solution was added with o-nitrobenzaldehyde (1.00 g, 6.60 mmol) and potassium carbonate (2.82 g, 20.40 mmol), followed by stirring at room temperature for 1 hour. The reaction mixture was added with water. The precipitated solid was collected by filtration and then dried. The obtained solid was triturated in methanol to obtain Compound 1 (1.05 g, 76%).

$^1$H-NMR (270 MHz, DMSO-$d_6$) δ 7.25 (t, J=7.4 Hz, 1H), 7.41 (t, J=7.4 Hz, 1H), 7.52-7.63 (m, 2H), 7.69 (s, 1H), 7.74-7.79 (m, 1H), 7.80 (d, J=16.3 Hz, 1H), 8.02 (dd, J=1.3 Hz, 8.2 Hz, 1H), 8.06-8.14 (m, 2H).

APCI-MS (m/z); 266 [M+H]$^+$

EXAMPLE 2

(E)-2-[2-(1H-indazol-3-yl)vinyl]phenylamine (Compound 2)

(E)-3-[2-(2-nitrophenyl)vinyl]-1H-indazole (4 g, 15.08 mmol) obtained in Example 1 was dissolved in ethanol (68 mL), and the solution was added with tin (3.85 g, 32.40 mmol) and concentrated hydrochloric acid (34 mL, 400 mmol) under ice-cooling, followed by stirring at 40° C. for 3 hours. To the reaction mixture, 6 mol/L aqueous sodium hydroxide solution was added to neutralize the mixture under ice-cooling. Then the mixture was filtered. The filtrate was added with saturated aqueous sodium hydrogencarbonate solution and extracted with ethyl acetate. The organic layer was washed with water and saturated brine, dried over anhydrous magnesium sulfate and then the solvent was evaporated under reduced pressure. The residue was triturated in ethyl acetate to obtain Compound 2 (2.98 g, 84%).

$^1$H-NMR (300 MHz, DMSO-$d_6$) δ 5.29 (s, 2H), 6.59 (t, J=7.2 Hz, 1H), 6.70 (d, J=7.9 Hz, 1H), 6.96-7.01 (m, 1H), 7.18 (t, J=7.2 Hz, 1H), 7.28 (d, J=16.3 Hz, 1H), 7.35-7.40 (m, 1H), 7.49-7.54 (m, 2H), 7.56 (d, J=16.3 Hz, 1H), 8.21 (d, J=8.3 Hz, 1H), 13.05 (br, 1H).

APCI-MS (m/z); 236 [M+H]$^+$

EXAMPLE 3

(E)-4-fluoro-N-{2-[2-(1H-indazol-3-yl)vinyl]phenyl}benzamide (Compound 3)

(E)-2-[2-(1H-indazol-3-yl)vinyl]phenylamine (60 mg, 0.26 mmol) obtained in Example 2 was dissolved in THF (1.5 mL) and the solution was added with triethylamine (71 μL, mmol) and p-fluorobenzoylchloride (45 μL, 0.38 mmol), followed by stirring at room temperature for 30 minutes. Further, the reaction mixture was added with potassium carbonate and stirred for a while. Then, the solid precipitated by adding water to the mixture was collected by filtration and the solid was triturated in ethanol to obtain Compound 3 (57 mg, 62%).

$^1$H-NMR (300 MHz, DMSO-$d_6$) δ 7.03 (t, J=7.7 Hz, 1H), 7.31-7.47 (m, 6H), 7.48-7.54 (m, 2H), 7.59 (d, J=16.8 Hz, 1H), (d, J=8.1 Hz, 1H), 7.95-7.98 (m, 1H), 8.14 (dd, J=8.4, 8.4 Hz, 2H), 10.30 (s, 1H), 13.15 (br, 1H).

APCI-MS (m/z); 358 [M+H]$^+$

EXAMPLE 4

(E)-N-{2-[2-(1H-indazol-3-yl)vinyl]phenyl}-4-methoxybenzamide (Compound 4)

In a similar manner to Example 3, Compound 4 (66 mg, 70%) was obtained from (E)-2-[2-(1H-indazol-3-yl)vinyl]phenylamine (60 mg, 0.26 mmol), triethylamine (71 μL, 0.51 mmol) and p-methoxybenzoylchloride (65 mg, 0.38 mmol).

$^1$H-NMR (300 MHz, DMSO-$d_6$) δ 3.85 (s, 3H), 7.02 (t, J=7.7 Hz, 1H), 7.09 (d, J=8.8 Hz, 2H), 7.30-7.35 (m, 4H), 7.46-7.52 (m, 1H), 7.49 (d, J=16.9 Hz, 1H), 7.60 (d, J=16.9 Hz, 1H), 7.90 (d, J=8.4 Hz, 1H), 7.94-7.97 (m, 1H), 8.04 (d, J=8.8 Hz, 2H), 10.10 (s, 1H), 13.10 (br, 1H).

APCI-MS (m/z); 370 [M+H]$^+$

EXAMPLE 5

(E)-N-{2-[2-(1H-indazol-3-yl)vinyl]phenyl}-4-methylbenzamide (Compound 5)

In a similar manner to Example 3, Compound 5 (66.3 mg, 37%) was obtained from (E)-2-[2-(1H-indazol-3-yl)vinyl]phenylamine (119 mg, 0.51 mmol), triethyamine (141 μL, 1.01 mmol) and p-toluoylchloride (141 μL, 1.01 mmol).

$^1$H-NMR (270 MHz, DMSO-$d_6$) δ 2.40 (s, 3H), 7.03 (t, J=7.6 Hz, 1H), 7.30-7.38 (m, 5H), 7.46-7.53 (m, 1H), 7.49 (d, J=16.8 Hz, 1H), 7.60 (d, J=16.8 Hz, 1H), 7.91-7.98 (m, 5H), 10.19 (s, 1H), 13.10 (br, 1H).

APCI-MS (m/z); 354 [M+H]$^+$

EXAMPLE 6

(E)-N-{2-[2-(1H-indazol-3-yl)vinyl]phenyl}nicotinamide (Compound 6)

In a similar manner to Example 3, Compound 6 (80 mg, 79%) was obtained from (E)-2-[2-(1H-indazol-3-yl)vinyl]phenylamine (70 mg, 0.30 mmol), triethylamine (125 μL, 0.89 mmol) and nicotinoyl chloride hydrochloride (80 mg, 0.45 mmol).

$^1$H-NMR (300 MHz, DMSO-$d_6$) δ 7.03 (t, J=7.5 Hz, 1H), 7.31-7.43 (m, 4H), 7.59-7.65 (m, 4H), 7.93 (d, J=8.3 Hz, 1H), 7.95-7.99 (m, 2H), 8.78 (dd, J=4.8, 4.8 Hz, 1H), 9.21 (d, J=1.3 Hz, 1H), 10.49 (s, 1H), 13.14 (br, 1H).

APCI-MS (m/z); 341 [M+H]$^+$

EXAMPLE 7

(E)-3-fluoro-N-{2-[2-(1H-indazol-3-yl)vinyl]phenyl}benzamide (Compound 7)

In a similar manner to Example 3, Compound 7 (72 mg, 79%) was obtained from (E)-2-[2-(1H-indazol-3-yl)vinyl]phenylamine (60 mg, 0.26 mmol), triethylamine (71 μL, 0.51 mmol) and 3-fluorobenzoyl chloride (47 μL, 0.38 mmol).

¹H-NMR (300 MHz, DMSO-d$_6$) δ 7.02 (t, J=7.7 Hz, 1H), 7.31-7.37 (m, 4H), 7.48-7.64 (m, 5H), 7.83-7.99 (m, 4H), 10.37 (s, 1H), 13.12 (br, 1H).

APCI-MS (m/z); 358 [M+H]$^+$

EXAMPLE 8

(E)-2-fluoro-N-{2-[2-(1H-indazol-3-yl)vinyl]phenyl}benzamide (Compound 8)

In a similar manner to Example 3, Compound 8 (72 mg, 79%) was obtained from (E)-2-[2-(1H-indazol-3-yl)vinyl]phenylamine (60 mg, 0.26 mmol), triethylamine (71 μL, 0.51 mmol) and 2-fluorobenzoyl chloride (45.4 μL, 0.38 mmol).

¹H-NMR (300 MHz, DMSO-d$_6$) δ 7.14 (t, J=8.1 Hz, 1H), 7.34-7.60 (m, 9H), 7.69 (d, J=16.5 Hz, 1H), 7.73-7.79 (m, 1H), 7.96 (m, 1H), 8.19 (d, J=8.1 Hz, 1H), 10.27 (s, 1H), 13.21 (br, 1H).

APCI-MS (m/z); 358 [M+H]$^+$

EXAMPLE 9

(E)-N-{2-[2-(1H-indazol-3-yl)vinyl]phenyl}acetamide (Compound 9)

In a similar manner to Example 3, Compound 9 (10 mg, 14%) was obtained from (E)-2-[2-(1H-indazol-3-yl)vinyl]phenylamine (60 mg, 0.26 mmol), triethylamine (71 μL, 0.51 mmol) and acetyl chloride (54 μL, 0.76 mmol).

¹H-NMR (300 MHz, DMSO-d$_6$) δ 2.11 (s, 3H), 7.18-7.27 (m, 3H), 7.29-7.43 (m, 2H), 7.49-7.56 (m, 2H), 7.59 (d, J=16.5 Hz, 1H), 7.87 (d, J=7.0 Hz, 1H), 8.09 (d, J=8.1 Hz, 1H), 9.77 (s, 1H), 13.16 (br, 1H).

APCI-MS (m/z); 278 [M+H]$^+$

EXAMPLE 10

(E)-N-{2-[2-(1H-indazol-3-yl)vinyl]phenyl}isonicotinamide (Compound 10)

In a similar manner to Example 3, Compound 10 (42 mg, 48%) was obtained from (E)-2-[2-(1H-indazol-3-yl)vinyl]phenylamine (60 mg, 0.26 mmol), triethylamine (71 μL, 0.51 mmol) and isonicotinoyl chloride (68 mg, 0.38 mmol).

¹H-NMR (300 MHz, DMSO-d$_6$) δ 7.05 (t, J=7.2 Hz, 1H), 7.31-7.38 (m, 4H), 7.50-7.56 (m, 3H), 7.90-7.99 (m, 4H), 8.82 (d, J=5.9 Hz, 2H), 10.57 (s, 1H), 13.14 (br, 1H).

APCI-MS (m/z); 341 [M+H]$^+$

EXAMPLE 11

(E)-N-{2-[2-(1H-indazol-3-yl)vinyl]phenyl}furan-2-carboxamide (Compound 11)

In a similar manner to Example 3, Compound 11 (63 mg, 75%) was obtained from (E)-2-[2-(1H-indazol-3-yl)vinyl]phenylamine (60 mg, 0.26 mmol), triethylamine (71 μL, 0.51 mmol) and 2-furancarbonyl chloride (37 μL, 0.38 mmol).

¹H-NMR (300 MHz, DMSO-d$_6$) δ 6.73 (dd, J=3.5, 3.5 Hz, 1H), 7.09 (t, J=7.9 Hz, 1H), 7.31-7.37 (m, 4H), 7.51 (d, J=16.7 Hz, 1H), 7.51-7.57 (m, 1H), 7.60 (d, J=16.7 Hz, 1H), 7.94-7.97 (m, 4H), 10.2 (br, 1H).

APCI-MS (m/z); 330 [M+H]$^+$

EXAMPLE 12

(E)-N-{2-[2-(1H-indazol-3-yl)vinyl]phenyl}pyridine-2-carboxamide (Compound 12)

In a similar manner to Example 3, Compound 12 (68 mg, 79%) was obtained from (E)-2-[2-(1H-indazol-3-yl)vinyl]phenylamine (60 mg, 0.26 mmol), triethylamine (71 μL, 0.51 mmol) and picolinoyl chloride (91 mg, 0.51 mmol).

¹H-NMR (300 MHz, DMSO-d$_6$) δ 7.11 (t, J=7.5 Hz, 1H), 7.28-7.39 (m, 3H), 7.47-7.55 (m, 2H), 7.66 (s, 1H), 7.69-7.74 (m, 2H), 7.90 (d, J=7.7 Hz, 1H), 8.05-8.13 (m, 2H), 8.19 (d, J=7.7 Hz, 1H), 8.77 (d, J=4.59 Hz, 1H), 10.69 (s, 1H), 13.16 (br, 1H).

APCI-MS (m/z); 341 [M+H]$^+$

EXAMPLE 13

(E)-3-[2-(2-benzyloxyphenyl)vinyl]-1H-indazole (Compound 13)

(1H-indazol-3-ylmethyl)triphenylphosphonium bromide (150 mg, 0.32 mmol) was dissolved in methanol (2 mL) and the solution was added with o-benzyloxybenzaldehyde (55 μL, 0.35 mmol) and potassium carbonate (88 mg, 0.63 mmol), followed by stirring at room temperature for 2 hours. The reaction mixture was added with saturated aqueous sodium hydrogencarbonate solution, and extracted with ethyl acetate. Then, the organic layer was sequentially washed with water and saturated brine, and was dried over anhydrous magnesium sulfate and the solvent was evaporated under reduced pressure. The residue was triturated in a mixed solvent of ethyl acetate/hexane (2/1) to obtain Compound 13 (39.3 mg, 38%).

¹H-NMR (300 MHz, DMSO-d$_6$) δ 5.23 (s, 2H), 7.02 (t, J=7.7 Hz, 1H), 7.11-7.18 (m, 2H), 7.29 (t, J=7.7 Hz, 1H), 7.35-7.48 (m, 4H), 7.51-7.58 (m, 4H), 7.80 (d, J=7.7 Hz, 1H), 7.82 (d, J=16.9 Hz, 1H), 7.90 (d, J=8.3 Hz, 1H), 13.10 (br, 1H).

APCI-MS (m/z); 327 [M+H]$^+$

EXAMPLE 14

(E)-N-{2-[2-(1H-indazol-3-yl)vinyl]phenyl}thiophene-2-carboxamide (Compound 14)

In a similar manner to Example 3, Compound 14 (58 mg, 66%) was obtained from (E)-2-[2-(1H-indazol-3-yl)vinyl]phenylamine (60 mg, 0.26 mmol), triethylamine (71 μL, 0.51 mmol) and 2-thiophenecarbonyl chloride (41 μL, 0.38 mmol).

¹H-NMR (300 MHz, DMSO-d$_6$) δ 7.05 (t, J=7.7 Hz, 1H), 7.27 (dd, J=5.0, 5.0 Hz, 1H), 7.32-7.37 (m, 4H), 7.50-7.56 (m, 2H), 7.62 (d, J=16.7 Hz, 1H), 7.89 (dd, J=5.0, 5.0 Hz, 1H), 7.94-8.00 (m, 2H), 8.10 (d, J=3.1 Hz, 1H), 10.32 (s, 1H), 13.14 (br, 1H).

ESI-MS (m/z); 346 [M+H]$^+$

EXAMPLE 15

(E)-N-{2-[2-(1H-indazol-3-yl)vinyl]phenyl}-2-phenylacetamide (Compound 15)

In a similar manner to Example 3, Compound 15 (54 mg, 60%) was obtained from (E)-2-[2-(1H-indazol-3-yl)vinyl]phenylamine (60 mg, 0.26 mmol), triethylamine (71 μL, 0.51 mmol) and phenylacetyl chloride (51 μL, 0.38 mmol).

¹H-NMR (300 MHz, DMSO-d$_6$) δ 3.73 (s, 2H), 7.16-7.31 (m, 5H), 7.37-7.42 (m, 5H), 7.49-7.57 (m, 2H), 7.60 (d, J=16.8 Hz, 1H), 7.88 (d, J=6.4 Hz, 1H), 8.03 (d, J=7.9 Hz, 1H), 10.01 (s, 1H), 13.19 (br, 1H).
ESI-MS (m/z); 354 [M+H]$^+$

EXAMPLE 16

(E)-N-{2-[2-(1H-indazol-3-yl)vinyl]phenyl}benzenesulfonamide (Compound 16)

In a similar manner to Example 3, Compound 16 (32 mg, 33%) was obtained from (E)-2-[2-(1H-indazol-3-yl)vinyl]phenylamine (60 mg, 0.26 mmol), triethylamine (71 µL, 0.51 mmol) and benzenesulfonyl chloride (49 µL, 0.38 mmol).
¹H-NMR (300 MHz, DMSO-d$_6$) δ 7.00 (dd, J=7.9, 7.9 Hz, 1H), 7.18-7.32 (m, 4H), 7.35-7.49 (m, 4H), 7.54 (d, J=9.7 Hz, 1H), 7.56 (d, J=16.3 Hz, 1H), 7.64 (m, 2H), 8.82 (dd, J=7.9, 7.9 Hz, 1H), 8.01 (d, J=8.1 Hz, 1H), 10.02 (s, 1H), 13.15 (br, 1H).
APCI-MS (m/z); 376 [M+H]$^+$

EXAMPLE 17

(E)-4-dimethylamino-N-{2-[2-(1H-indazol-3-yl)vinyl]phenyl}benzamide (Compound 17)

In a similar manner to Example 3, Compound 17 (86 mg, 88%) was obtained from (E)-2-[2-(1H-indazol-3-yl)vinyl]phenylamine (60 mg, 0.26 mmol), triethylamine (71 µL, 0.51 mmol) and 4-dimethylaminobenzoyl chloride (94 mg, 0.51 mmol).
¹H-NMR (300 MHz, DMSO-d$_6$) δ 3.01 (s, 6H), 6.78 (d, J=9.0 Hz, 2H), 7.02 (t, J=7.9 Hz, 1H), 7.32 (m, 4H), 7.49 (d, J=16.7 Hz, 1H), 7.51 (t, J=4.2 Hz, 1H), 7.60 (d, J=16.7 Hz, 1H), 7.91-7.96 (m, 4H), 9.89 (s, 1H), 13.09 (br, 1H).
APCI-MS (m/z); 383 [M+H]$^+$

EXAMPLE 18

(E)-N-{2-[2-(1H-indazol-3-yl)vinyl]phenyl}isobutylamide (Compound 18)

In a similar manner to Example 3, Compound 18 (56 mg, 72%) was obtained from (E)-2-[2-(1H-indazol-3-yl)vinyl]phenylamine (60 mg, 0.26 mmol), triethylamine (71 µL, 0.51 mmol) and isobutyryl chloride (54 µL, 0.51 mmol).
¹H-NMR (300 MHz, DMSO-d$_6$) δ 1.17 (d, J=6.8 Hz, 6H), 2.73 (m, 1H), 7.19 (t, J=7.5 Hz, 1H), 7.26-7.30 (m, 3H), 7.39 (t, J=7.5 Hz, 1H), 7.48 (d, J=16.7 Hz, 1H), 7.56 (d, J=8.3 Hz, 1H), 7.57 (d, J=16.7 Hz, 1H), 7.89 (d, J=4.5 Hz, 1H), 8.09 (d, J=8.1 Hz, 1H), 9.68 (s, 1H).
APCI-MS (m/z); 306 [M+H]$^+$

EXAMPLE 19

(E)-N-{2-[2-(1H-indazol-3-yl)vinyl]phenyl}-3-methoxybenzamide (Compound 19)

In a similar manner to Example 3, Compound 19 (69 mg, 73%) was obtained from (E)-2-[2-(1H-indazol-3-yl)vinyl]phenylamine (60 mg, 0.26 mmol), triethylamine (71 µL, 0.51 mmol) and 3-methoxybenzoyl chloride (72 µL, 0.51 mmol).
¹H-NMR (270 MHz, DMSO-d$_6$) δ 3.85 (s, 3H), 7.03 (t, J=7.6 Hz, 1H), 7.18 (dd, J=8.2, 8.2 Hz, 1H), 7.32-7.37 (m, 4H), 7.45-7.55 (m, 3H), 7.62 (d, J=16.8 Hz, 1H), 7.63 (m, 2H), 7.96 (m, 2H), 10.26 (s, 1H), 13.13 (br, 1H).
APCI-MS (m/z); 370 [M+H]$^+$

EXAMPLE 20

(E)-N-{2-[2-(1H-indazol-3-yl)vinyl]phenyl}-2-methoxybenzamide (Compound 20)

In a similar manner to Example 3, Compound 20 (25 mg, 26%) was obtained from (E)-2-[2-(1H-indazol-3-yl)vinyl]phenylamine (60 mg, 0.26 mmol), triethylamine (71 µL, 0.51 mmol) and 2-methoxybenzoyl chloride (76 µL, 0.51 mmol).
¹H-NMR (270 MHz, DMSO-d$_6$) δ 3.89 (s, 3H), 7.09-7.16 (m, 2H), 7.21-7.41 (m, 4H), 7.48-7.58 (m, 3H), 7.71-7.79 (m, 2H), 7.86-7.91 (m, 2H), 8.07 (d, J=8.2 Hz, 1H), 10.10 (s, 1H), 13.20 (br, 1H).
APCI-MS (m/z); 370 [M+H]$^+$

EXAMPLE 21

(E)-1-ethyl-3-{2-[2-(1H-indazol-3-yl)vinyl]phenyl}urea (Compound 21)

A solution of (E)-2-[2-(1H-indazol-3-yl)vinyl]phenylamine (60 mg, 0.26 mmol) in THF (1.5 mL) was added with triethylamine (11 µL, 0.08 mmol) and ethyl isocyanate (40.3 µL, 0.51 mmol), followed by stirring at room temperature for 5 hours. Further, the reaction mixture was added with potassium carbonate, stirred for 30 minutes and added with water. The precipitated solid was collected by filtration and the solid was triturated in ethanol to obtain Compound 21 (53 mg, 68%).
¹H-NMR (270 MHz, DMSO-d$_6$) δ 1.07 (t, J=7.3 Hz, 3H), 3.08-3.19 (m, 2H), 6.48 (m, 1H), 7.05 (t, J=7.4 Hz, 1H), 7.16-7.25 (m, 2H), 7.36-7.39 (m, 1H), 7.42 (d, J=4.95 Hz, 1H), 7.55 (d, J=8.6 Hz, 1H), 7.66 (t, J=7.9 Hz, 1H), 7.74 (d, J=7.6 Hz, 1H), 8.10 (d, J=8.3 Hz, 2H), 9.02 (s, 1H), 13.10 (br, 1H).
APCI-MS (m/z); 307 [M+H]$^+$

EXAMPLE 22

(E)-1-{2-[2-(1H-indazol-3-yl)vinyl]phenyl}-3-phenylurea (Compound 22)

In a similar manner to Example 21, Compound 22 (79 mg, 88%) was obtained from (E)-2-[2-(1H-indazol-3-yl)vinyl]phenylamine (60 mg, 0.26 mmol), triethylamine (11 µL, 0.077 mmol) and phenyl isocyanate (34 µL, 0.31 mmol).
¹H-NMR (270 MHz, DMSO-d$_6$) δ 6.97 (t, J=7.3 Hz, 1H), 7.14 (t, J=7.3 Hz, 2H), 7.29 (m, 3H), 7.38 (t, J=8.2 Hz, 1H), 7.47-7.57 (m, 4H), 7.60 (d, J=16.4 Hz, 1H), 7.72-7.76 (m, 1H), 7.81 (d, J=7.8 Hz, 1H), 8.12 (d, J=8.1 Hz, 1H), 8.38 (s, 1H), 9.02 (s, 1H), 13.18 (br, 1H).
APCI-MS (m/z); 355 [M+H]$^+$

EXAMPLE 23

(E)-N-{2-[2-(1H-indazol-3-yl)vinyl]phenyl}cyclohexanecarboxamide (Compound 23)

In a similar manner to Example 3, Compound 23 (71 mg, 93%) was obtained from (E)-2-[2-(1H-indazol-3-yl)vinyl]phenylamine (60 mg, 0.26 mmol), triethylamine (71 µL, 0.51 mmol) and cyclohexanecarbonyl chloride (68 µL, 0.51 mmol).
¹H-NMR (270 MHz, DMSO-d$_6$) δ 1.47-1.93 (m, 10H), 2.50 (m, 1H), 7.16 (t, J=7.3 Hz, 1H), 7.24-7.35 (m, 3H), 7.38

(dd, J=6.9, 6.9 Hz, 1H), 7.44 (d, J=16.8 Hz, 1H), 7.56 (m, 1H), 7.59 (d, J=16.8 Hz, 1H), 7.87 (t, J=5.0 Hz, 1H), 8.04 (d, J=8.1 Hz, 1H), 9.62 (s, 1H).

APCI-MS (m/z); 346 [M+H]$^+$

EXAMPLE 24

(E)-N-{2-[2-(1H-indazol-3-yl)vinyl]phenyl}cyclopentanecarboxamide (Compound 24)

In a similar manner to Example 3, Compound 24 (61 mg, 73%) was obtained from (E)-2-[2-(1H-indazol-3-yl)vinyl]phenylamine (60 mg, 0.26 mmol), triethylamine (71 μL, 0.51 mmol) and cyclopentanecarbonyl chloride (62 μL, 0.51 mmol).

$^1$H-NMR (270 MHz, DMSO-d$_6$) δ 1.60-1.91 (m, 8H), 1.91-2.95 (m, 1H), 7.18 (t, J=7.4 Hz, 1H), 7.25-7.30 (m, 2H), 7.36-7.49 (m, 1H), 7.45 (d, J=16.8 Hz, 1H), 7.54-7.62 (m, 2H), 7.57 (d, J=16.8 Hz, 1H), 7.88 (t, J=4.8 Hz, 1H), 8.09 (d, J=8.2 Hz, 1H), 9.69 (s, 1H).

APCI-MS (m/z); 332 [M+H]$^+$

EXAMPLE 25

(E)-N-{2-[2-(1H-indazol-3-yl)vinyl]phenyl}-2-(thiophen-2-yl)acetamide (Compound 25)

In a similar manner to Example 3, Compound 25 (57 mg, 62%) was obtained from (E)-2-[2-(1H-indazol-3-yl)vinyl]phenylamine (60 mg, 0.26 mmol), triethylamine (71 μL, 0.51 mmol) and thiophen-2-ylacetyl chloride (63 μL, 0.51 mmol).

$^1$H-NMR (270 MHz, DMSO-d$_6$) δ 3.98 (s, 2H), 6.98 (dd, J=5.43, 5.43 Hz, 1H), 7.05 (m, 1H), 7.19 (t, J=7.7 Hz, 1H), 7.26-7.32 (m, 2H), 7.32-7.43 (m, 3H), 7.49 (d, J=16.6 Hz, 1H), 7.42-7.54 (m, 1H), 7.60 (d, J=16.6 Hz, 1H), 7.87-7.91 (m, 1H), 8.02 (d, J=8.2 Hz, 1H), 10.04 (s, 1H), 13.18 (br, 1H).

APCI-MS (m/z); 360 [M+H]$^+$

EXAMPLE 26

(E)-N-benzyl-N-{2-[2-(1H-indazol-3-yl)vinyl]phenyl}amine (Compound 26)

(E)-2-[2-(1H-indazol-3-yl)vinyl]phenylamine (60 mg, 0.26 mmol) was dissolved in dichloroethane and the solution was added with benzaldehyde (28 μL, 0.28 mmol), sodium triacetoxyborohydride (81 mg, 0.38 mmol) and acetic acid (15 mL, 0.25 mmol), followed by stirring at room temperature for 13 hours. The reaction mixture was added with water and extracted with ethyl acetate. The organic layer was sequentially washed with water and saturated brine, dried over anhydrous magnesium sulfate and the solvent was evaporated under reduced pressure. A crude product was purified by silica gel chromatography [ethyl acetate/hexane=1/8 to 1/1] and further crystallized from ethyl acetate to obtain Compound 26 (31.1 mg, 38%).

$^1$H-NMR (270 MHz, DMSO-d$_6$) δ 4.48 (d, J=5.5 Hz, 2H), 6.35-6.37 (m, 1H), 6.45 (d, J=8.1 Hz, 1H), 6.60 (t, J=7.3 Hz, 1H), 6.99 (t, J=7.3 Hz, 1H), 7.17-7.23 (m, 2H), 7.28-7.42 (m, 6H), 7.51-7.56 (m, 2H), 7.72 (d, J=16.4 Hz, 1H), 8.22 (d, J=8.1 Hz, 1H), 13.1 (br, 1H).

APCI-MS (m/z); 326 [M+H]$^+$

EXAMPLE 27

(E)-3-dimethylamino-N-{2-[2-(1H-indazol-3-yl)vinyl]phenyl}benzamide (Compound 27)

In a similar manner to Example 3, Compound 27 (52 mg, 53%) was obtained from (E)-2-[2-(1H-indazol-3-yl)vinyl]phenylamine (60 mg, 0.26 mmol), triethylamine (71 μL, 0.51 mmol) and 3-dimethylaminobenzoyl chloride (113 mg, mmol).

$^1$H-NMR (270 MHz, DMSO-d$_6$) δ 2.97 (s, 6H), 6.94-6.98 (m, 1H), (t, J=7.6 Hz, 1H), 7.31-7.37 (m, 7H), 7.50 (m, 1H), (d, J=16.8 Hz, 1H), 7.63 (d, J=16.8 Hz, 1H), 7.96 (d, J=8.9 Hz, 1H), 7.97 (m, 1H), 10.16 (s, 1H), 13.1 (br, 1H).

APCI-MS (m/z); 383 [M+H]$^+$

EXAMPLE 28

(E)-N-{2-[2-(1H-indazol-3-yl)vinyl]phenyl}pyrazine-2-carboxamide (Compound 28)

(E)-2-[2-(1H-indazol-3-yl)vinyl]phenylamine (60 mg, 0.26 mmol) was dissolved in THF (5 mL) and the solution was added with 2-pyrazinecarboxylic acid (38 mg, 0.31 mmol), 1-hydroxybenzotriazole monohydrate (51 mg, 0.33 mmol), 4-methylmorpholine (47 μL, 0.51 mmol) and EDC (68 mg, 0.36 mmol), followed by stirring at room temperature for 3 hours. The reaction mixture was added with saturated aqueous sodium hydrogencarbonate solution and extracted with ethyl acetate. The organic layer was sequentially washed with water and saturated brine, dried over anhydrous magnesium sulfate and the solvent was evaporated under reduced pressure. The residue was triturated in ethanol to obtain Compound 28 (25 mg, 30%).

$^1$H-NMR (270 MHz, DMSO-d$_6$) δ 7.09 (t, J=7.6 Hz, 1H), 7.33-7.37 (m, 3H), 7.47-7.54 (m, 2H), 7.58-7.63 (m, 1H), 7.65 (d, J=16.7 Hz, 1H), 7.92-7.96 (m, 1H), 8.03 (d, J=8.1 Hz, 1H), 8.86 (s, 1H), 8.97 (d, J=2.5 Hz, 1H), 9.31 (s, 1H), 10.74 (s, 1H), 13.14 (br, 1H).

APCI-MS (m/z); 342 [M+H]$^+$

EXAMPLE 29

(E)-N-{2-[2-(1H-indazol-3-yl)vinyl]phenyl}-1-methyl-1H-pyrrole-2-carboxamide (Compound 29)

1-Methyl-2-pyrrolecarboxylic acid (1.49 g, 11.9 mmol) was dissolved in methylene chloride (12 mL) and the solution was added with thionyl chloride (1.3 mL, 17.85 mmol) and DMF (276 μL, 3.57 mmol) at 0° C., stirred at 40° C. for 2 hours and then the mixture was concentrated. The mixture was dissolved in THF, added with a solution of (E)-2-[2-(1H-indazol-3-yl)vinyl]phenylamine (700 mg, 2.98 mmol) and triethylamine (1.25 mL, 8.93 mmol) in THF (10 mL) at room temperature, stirred at 60° C. for 4 hours. Further, potassium carbonate and methanol (10 mL) were added to the mixture and stirred for a while and then added with water. The precipitated solid was collected by filtration and reslurried with ethanol to obtain Compound 29 (703 mg, 69%).

$^1$H-NMR (270 MHz, DMSO-d$_6$) δ 3.86 (s, 3H), 6.12 (dd, J=3.8, 3.8 Hz, 1H), 7.01-7.09 (m, 2H), 7.13-7.16 (m, 1H), 7.30-7.37 (m, 4H), 7.51 (d, J=16.7 Hz, 1H), 7.50-7.54 (m, 1H), 7.63 (d, J=16.7 Hz, 1H), 7.91-7.96 (m, 1H), 7.97 (d, J=8.4 Hz, 1H), 9.77 (s, 1H), 13.1 (br, 1H).

APCI-MS (m/z); 343 [M+H]$^+$

EXAMPLE 30

(E)-N-{2-[2-(1H-indazol-3-yl)vinyl]phenyl}-2-methylbenzamide (Compound 30)

In a similar manner to Example 3, Compound 30 (76 mg, 85%) was obtained from (E)-2-[2-(1H-indazol-3-yl)vinyl]phenylamine (60 mg, 0.26 mmol), triethylamine (107 μL, 0.77 mmol) and 2-methylbenzoyl chloride (120 μL, 0.77 mmol).

$^1$H-NMR (270 MHz, DMSO-d$_6$) δ 3.17 (s, 3H), 7.14 (t, J=7.3 Hz, 1H), 7.33-7.48 (m, 7H), 7.53-7.59 (m, 3H), 7.70 (d, J=16.5 Hz, 1H), 7.93 (t, J=5.5 Hz, 1H), 8.08 (d, J=8.3 Hz, 1H), 10.18 (s, 1H), 13.19 (br, 1H).

APCI-MS (m/z); 352 [M–H]$^+$

EXAMPLE 31

(E)-N-{2-[2-(1H-indazol-3-yl)vinyl]phenyl}thiophene-3-carboxamide (Compound 31)

In a similar manner to Example 28, Compound 31 (13 mg, 15%) was obtained from 3-thiophenecarboxylic acid (79 mg, 0.61 mmol), (E)-2-[2-(1H-indazol-3-yl)vinyl]phenylamine (60 mg, 0.26 mmol), 1-hydroxybenzotriazole monohydrate (102 mg, 0.66 mmol), EDC (138 mg, 0.71 mmol) and 4-methylmorpholine (94 μL, 1.02 mmol).

$^1$H-NMR (300 MHz, DMSO-d$_6$) δ 7.04 (t, J=7.3 Hz, 1H), 7.34-7.35 (m, 4H), 7.48-7.57 (m, 2H), 7.60 (d, J=16.7 Hz, 1H), 7.69 (m, 2H), 7.92 (d, J=7.9 Hz, 1H), 7.93-7.97 (m, 1H), 8.40 (s, 1H), 10.11 (s, 1H), 13.12 (br, 1H).

APCI-MS (m/z); 346 [M+H]$^+$

EXAMPLE 32

(E)-N-{2-[2-(1H-indazol-3-yl)vinyl]phenyl}tetrahydrofuran-2-carboxamide (Compound 32)

In a similar manner to Example 29, Compound 32 (63 mg, 74%) was obtained from tetrahydrofuran-2-carboxylic acid (74 μL, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (270 MHz, DMSO-d$_6$) δ 1.87-2.08 (m, 3H), 2.10-2.28 (m, 1H), 3.83-3.91 (m, 1H), 4.03-4.11 (m, 1H), 4.47 (dd, J=8.2, 8.2 Hz, 1H), 7.20 (t, J=7.9 Hz, 1H), 7.27-7.31 (m, 2H), 7.36-7.43 (m, 2H), 7.58 (d, J=16.8 Hz, 1H), 7.49-7.57 (m, 2H), 7.86-7.90 (m, 1H), 8.10 (d, J=7.9 Hz, 1H), 9.64 (s, 1H), 13.20 (br, 1H).

APCI-MS (m/z); 334 [M+H]$^+$

EXAMPLE 33

(E)-N-{2-[2-(1H-indazol-3-yl)vinyl]phenyl}cyclopropanecarboxamide (Compound 33)

In a similar manner to Example 3, Compound 33 (64 mg, 83%) was obtained from (E)-2-[2-(1H-indazol-3-yl)vinyl]phenylamine (60 mg, 0.26 mmol), triethylamine (71 μL, 0.51 mmol) and cyclopropanecarbonyl chloride (46 μL, 0.51 mmol).

$^1$H-NMR (270 MHz, DMSO-d$_6$) δ 0.82 (d, J=5.8 Hz, 4H), 1.91-1.96 (m, 1H), 7.17-7.42 (m, 5H), 7.49-7.58 (m, 2H), 7.60 (d, J=16.8 Hz, 1H), 7.86-7.90 (m, 1H), 8.04 (d, J=8.06 Hz, 1H), 10.01 (s, 1H), 13.15 (br, 1H).

APCI-MS (m/z); 304 [M+H]$^+$

EXAMPLE 34

(E)-5-bromo-N-{2-[2-(1H-indazol-3-yl)vinyl]phenyl}thiophene-2-carboxamide (Compound 34)

In a similar manner to Example 29, Compound 34 (17 mg, 16%) was obtained from 5-bromo-2-thiophenecarboxylic acid (158 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (300 MHz, DMSO-d$_6$) δ 7.08 (t, J=7.3 Hz, 1H), 7.34-7.39 (m, 4H), 7.43 (d, J=4.0 Hz, 1H), 7.50-7.57 (m, 2H), 7.59 (d, J=16.5 Hz, 1H), 7.92-7.95 (m, 1H), 7.97-8.00 (m, 2H), 10.40 (s, 1H), 13.16 (br, 1H).

APCI-MS (m/z); 426 [M+H]$^+$

EXAMPLE 35

(E)-N-{2-[2-(1H-indazol-3-yl)vinyl]phenyl}morpholine-4-carboxamide (Compound 35)

In a similar manner to Example 3, Compound 35 (26 mg, 30%) was obtained from (E)-2-[2-(1H-indazol-3-yl)vinyl]phenylamine (60 mg, 0.26 mmol), triethylamine (71 μL, 0.51 mmol) and 4-morpholinecarbonyl chloride (60 μL, 0.51 mmol).

$^1$H-NMR (300 MHz, CDCl$_3$) δ 3.33 (br, 4H), 3.55 (br, 4H), 6.91 (s, 1H), 7.04-7.28 (m, 5H), 7.38 (d, J=7.7 Hz, 1H), 7.47 (s, 1H), 7.49 (t, J=6.6 Hz, 1H), 7.80 (d, J=8.4 Hz, 1H).

APCI-MS (m/z); 349 [M+H]$^+$

EXAMPLE 36

(E)-N-{2-[2-(1H-indazol-3-yl)vinyl]phenyl}thiazole-4-carboxamide (Compound 36)

In a similar manner to Example 29, Compound 36 (52 mg, 64%) was obtained from 4-thiazolecarboxylic acid (158 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 nmol).

$^1$H-NMR (300 MHz, CDCl$_3$) δ 7.09 (t, J=7.3 Hz, 1H), 7.29-7.37 (m, 3H), 7.49 (d, J=16.7 Hz, 1H), 7.51-7.59 (m, 3H), 7.63 (d, J=16.7 Hz, 1H), 7.89-7.93 (m, 1H), 8.00 (d, J=8.1 Hz, 1H), 8.52 (d, J=1.8 Hz, 1H), 9.32 (d, J=1.8 Hz, 1H).

APCI-MS (m/z); 347 [M+H]$^+$

EXAMPLE 37

(E)-N-{2-[2-(1H-indazol-3-yl)vinyl]phenyl}isoxazole-5-carboxamide (Compound 37)

In a similar manner to Example 28, Compound 37 (20 mg, 24%) was obtained from 5-isoxazolecarboxylic acid (69 mg, 0.61 mmol), (E)-2-[2-(1H-indazol-3-yl)vinyl]phenylamine (60 mg, 0.26 mmol), 1-hydroxybenzotriazole monohydrate (102 mg, 0.66 mmol), EDC (138 mg, 0.71 mmol) and 4-methylmorpholine (94 μL, 1.02 mmol).

$^1$H-NMR (270 MHz, DMSO-d$_6$) δ 7.11-7.15 (m, 1H), 7.30-7.40 (m, 5H), 7.52-7.59 (m, 3H), 7.97-8.01 (m, 2H), 8.85 (m, 1H), 10.79 (s, 1H), 13.16 (br, 1H).

APCI-MS (m/z); 331 [M+H]$^+$

EXAMPLE 38

(E)-N-{2-[2-(1H-indazol-3-yl)vinyl]phenyl}-N-methylbenzamide (Compound 38)

Step 1

In a similar manner to Example 3, (E)-N-{2-[2-(1-benzoyl-1-1H-indazol-3-yl)vinyl]phenyl}benzamide (128 mg, 98%) was obtained from (E)-2-[2-(1H-indazol-3-yl)vinyl]phenylamine (100 mg, 0.30 mmol), triethylamine (574 µL, 2.01 mmol) and benzoyl chloride (238 µL, 2.01 mmol).

Step 2

(E)-N-{2-[2-(1-benzoyl-1-1H-indazol-3-yl)vinyl]phenyl}benzamide (50 mg, 0.11 mmol) obtained in Step 1 was dissolved in THF (3.0 mL) and the solution was added with potassium carbonate (24.5 mg, 0.17 mmol) and methyl iodide (66 µL, 1.02 mmol) at room temperature, followed by reacting for 14 hours. The mixture was added with water and extracted with ethyl acetate. The organic layer was washed with saturated brine, dried over anhydrous magnesium sulfate and the solvent was evaporated under reduced pressure. The residue was triturated in a mixed solvent of hexane/ethyl acetate (1/1) to obtain Compound 38 (10 mg, 19%).

$^1$H-NMR (270 MHz, DMSO-$d_6$) δ 3.36 (s, 3H), 7.11 (m, 2H), 7.18-7.30 (m, 7H), 7.39-7.50 (m, 3H), 7.59 (d, J=8.2 Hz, 1H), 7.84 (d, J=7.7 Hz, 1H), 8.04 (d, J=8.2 Hz, 1H), 13.25 (br, 1H).

APCI-MS (m/z); 354 [M+H]$^+$

EXAMPLE 39

(E)-N-{2-[2-(1H-indazol-3-yl)vinyl]phenyl}-3-(thiophen-2-yl)propionamide (Compound 39)

In a similar manner to Example 28, Compound 39 (49 mg, 52%) was obtained from 3-(thiophen-2-yl)propionic acid (96 mg, 0.61 mmol), (E)-2-[2-(1H-indazol-3-yl)vinyl]phenylamine (60 mg, 0.26 mmol), 1-hydroxybenzotriazole monohydrate (102 mg, 0.66 mmol), EDC (138 mg, 0.71 mmol) and 4-methylmorpholine (94 µL, 1.02 mmol).

$^1$H-NMR (270 MHz, DMSO-$d_6$) δ 2.78 (t, J=7.2 Hz, 2H), 3.18 (t, J=7.2 Hz, 2H), 6.93-6.88 (m, 2H), 7.19 (t, J=7.2 Hz, 1H), 7.26-7.31 (m, 3H), 7.37-7.44 (m, 3H), 7.52 (d, J=13.8 Hz, 1H), 7.60 (t, J=16.8 Hz, 1H), 7.86-7.90 (m, 1H), 8.10 (d, J=8.1 Hz, 1H), 9.83 (s, 1H), 13.16 (br, 1H).

APCI-MS (m/z); 374 [M+H]$^+$

EXAMPLE 40

(E)-N-{2-[2-(1H-indazol-3-yl)vinyl]phenyl}-5-methylthiophene-2-carboxamide (Compound 40)

In a similar manner to Example 28, Compound 40 (26 mg, 28%) was obtained from 5-methyl-2-thiophenecarboxylic acid (87 mg, 0.61 mmol), (E)-2-[2-(1H-indazol-3-yl)vinyl]phenylamine (60 mg, 0.26 mmol), 1-hydroxybenzotriazole monohydrate (102 mg, 0.66 mmol), EDC (138 mg, 0.71 mmol) and 4-methylmorpholine (94 µL, 1.02 mmol).

$^1$H-NMR (270 MHz, DMSO-$d_6$) δ 2.52 (s, 3H), 6.95-6.97 (m, 1H), 7.07 (t, J=7.6 Hz, 1H), 7.34-7.39 (m, 4H), 7.52 (d, J=16.7 Hz, 1H), 7.53 (m, 1H), 7.60 (d, J=16.7 Hz, 1H), 7.89 (d, J=3.8 Hz, 1H), 7.94-7.97 (m, 2H), 10.19 (s, 1H), 13.16 (br, 1H).

APCI-MS (m/z); 360 [M+H]$^+$

EXAMPLE 41

(E)-N-{2-[2-(1H-indazol-3-yl)vinyl]phenyl}-3-methylthiophene-2-carboxamide (Compound 41)

In a similar manner to Example 29, Compound 41 (74 mg, 81%) was obtained from 3-methyl-2-thiophenecarboxylic acid (109 mg, 0.77 mmol), thionyl chloride (84 µL, 1.15 mmol), DMF (few drops), (E)-2-[2-(1H-indazol-3-yl)vinyl]phenylamine (60 mg, 0.26 mmol) and triethylamine (107 µL, 0.77 mmol).

$^1$H-NMR (270 MHz, DMSO-$d_6$) δ 3.34 (s, 3H), 7.04 (d, J=5.1 Hz, 1H), 7.10 (d, J=7.6 Hz, 1H), 7.30-7.43 (m, 4H), 7.46-7.69 (m, 4H), 7.91-7.95 (m, 1H), 8.02 (d, J=8.8 Hz, 1H), 9.83 (s, 1H), 13.17 (br, 1H).

APCI-MS (m/z); 360 [M+H]$^+$

EXAMPLE 42

(E)-N-{2-[2-(1H-indazol-3-yl)vinyl]phenyl}-1H-pyrrole-2-carboxamide (Compound 42)

In a similar manner to Example 29, Compound 42 (53 mg, 64%) was obtained from 2-pyrrolecarboxylic acid (85 mg, 0.77 mmol), thionyl chloride (84 µL, 1.15 mmol), DMF (few drops), (E)-2-[2-(1H-indazol-3-yl)vinyl]phenylamine (60 mg, 0.26 mmol) and triethylamine (107 µL, 0.77 mmol).

$^1$H-NMR (300 MHz, DMSO-$d_6$) δ 6.20 (m, 1H), 6.96 (s, 1H), 7.05 (t, J=7.7 Hz, 1H), 7.12 (s, 1H), 7.28-7.36 (m, 4H), 7.68 (d, J=16.7 Hz, 1H), 7.52 (m, 1H), 7.63 (d, J=16.7 Hz, 1H), 7.93-7.97 (m, 2H), 9.80 (s, 1H), 11.68 (s, 1H), 13.10 (br, 1H).

APCI-MS (m/z); 329 [M+H]$^+$

EXAMPLE 43

(E)-5-acetyl-N-{2-[2-(1H-indazol-3-yl)vinyl]phenyl}thiophene-2-carboxamide (Compound 43)

In a similar manner to Example 28, Compound 43 (45 mg, 46%) was obtained from 5-acetyl-2-thiophenecarboxylic acid (105 mg, 0.61 mmol), (E)-2-[2-(1H-indazol-3-yl)vinyl]phenylamine (60 mg, 0.26 mmol), 1-hydroxybenzotriazole monohydrate (102 mg, 0.66 mmol), EDC (138 mg, 0.71 mmol) and 4-methylmorpholine (94 µL, 1.02 mmol).

$^1$H-NMR (270 MHz, DMSO-$d_6$) δ 3.86 (s, 3H), 6.75 (m, 1H), 7.34-7.40 (m, 4H), 7.52-7.60 (m, 4H), 7.95-8.05 (m, 3H), 10.54 (s, 1H), 13.15 (br, 1H).

APCI-MS (m/z); 388 [M+H]$^+$

EXAMPLE 44

(E)-N-{2-[2-(1H-indazol-3-yl)vinyl]phenyl}cyclobutanecarboxamide (Compound 44)

In a similar manner to Example 3, Compound 44 (56 mg, 69%) was obtained from (E)-2-[2-(1H-indazol-3-yl)vinyl]phenylamine (60 mg, 0.26 mmol), triethylamine (71 µL, 0.51 mmol) and cyclobutanecarbonyl chloride (59 µL, 0.51 mmol).

$^1$H-NMR (300 MHz, DMSO-$d_6$) δ 2.36-2.93 (m, 6H), 3.21 (m, 1H), 7.16-7.22 (m, 1H), 7.25-7.31 (m, 2H), 7.36-7.49 (m, 2H), 7.53-7.59 (m, 2H), 7.56 (d, J=16.5 Hz, 1H), 7.88-7.90 (m, 1H), 8.07 (d, J=8.3 Hz, 1H), 9.56 (s, 1H).

APCI-MS (m/z); 318 [M+H]$^+$

EXAMPLE 45

(E)-2-ethyl-2-hydroxy-N-{2-[2-(1H-indazol-3-yl)vinyl]phenyl}butylamide (Compound 45)

In a similar manner to Example 28, Compound 45 (15 mg, 17%) was obtained from 2-ethyl-2-hydroxybutanoic acid (81 mg, 0.61 mmol), (E)-2-[2-(1H-indazol-3-yl)vinyl]phenylamine (60 mg, 0.26 mmol), 1-hydroxybenzotriazole monohydrate (102 mg, 0.66 mmol), EDC (138 mg, 0.71 mmol) and 4-methylmorpholine (94 μL, 1.02 mmol).

$^1$H-NMR (300 MHz, DMSO-$d_6$) δ 0.89 (t, J=7.3 Hz, 6H), 1.51-1.63 (m, 2H), 1.77-1.89 (m, 2H), 3.32 (m, 1H), 5.36 (br, 1H), 7.17-7.33 (m, 3H), 7.37-7.44 (m, 2H), 7.49-7.57 (m, 2H), 7.59 (d, J=16.5 Hz, 1H), 7.84 (d, J=7.7 Hz, 1H), 8.12 (d, J=8.1 Hz, 1H), 9.49 (s, 1H), 13.22 (br, 1H).

APCI-MS (m/z); 350 [M+H]$^+$

EXAMPLE 46

(E)-N-{2-[2-(1H-indazol-3-yl)vinyl]phenyl}benzo[b]thiophene-2-carboxamide (Compound 46)

In a similar manner to Example 29, Compound 46 (97 mg, 97%) was obtained from benzo[b]thiophene-2-carboxylic acid (136 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (300 MHz, DMSO-$d_6$) δ 6.98 (t, J=7.3 Hz, 1H), 7.29-7.42 (m, 4H), 7.49-7.52 (m, 3H), 7.65 (d, J=16.5 Hz, 1H), 7.58 (s, 1H), 7.97-8.05 (m, 3H), 8.08-8.11 (m, 1H), 8.43 (s, 1H), 10.60 (s, 1H), 13.13 (br, 1H).

APCI-MS (m/z); 396 [M+H]$^+$

EXAMPLE 47

(E)-N-phenyl-2-[2-(1H-indazol-3-yl)vinyl]benzamide (Compound 47)

Step 1

(1H-Indazol-3-ylmethyl)triphenylphosphonium bromide (2.5 g, 5.30 mmol) was dissolved in methanol (40 mL) and the solution was added with 2-formylbenzoic acid methyl ester (954 mg, 5.80 mmol) and potassium carbonate (2.20 g, 15.8 mmol), followed by stirring at room temperature for 2.5 hours. The reaction mixture was added with water and the precipitated solid was collected by filtration. The solid was added with 2 mol/L aqueous sodium hydroxide solution (75 mL) and heated under reflux in THF (50 mL). The mixture was extracted with ethyl acetate and the aqueous layer was neutralized by 6 mol/L hydrochloric acid. The precipitated solid was collected by filtration and the obtained solid was dried to obtain (E)-2-[2-(1H-indazol-3-yl)vinyl]benzoic acid (500 mg, 36%).

Step 2

In a similar manner to Example 28, Compound 47 (87 mg, 68%) was obtained from (E)-2-[2-(1H-indazol-3-yl)vinyl]benzoic acid (100 mg, 0.38 mmol), aniline (41 μL, 0.45 mmol), 1-hydroxybenzotriazole monohydrate (75.1 mg, 0.49 mmol), EDC (102 mg, 0.53 mmol) and 4-methylmorpholine (84 μL, 0.76 mmol).

$^1$H-NMR (270 MHz, DMSO-$d_6$) δ 7.03-7.15 (m, 2H), 7.34-7.44 (m, 4H), 7.51-7.55 (m, 4H), 7.61-7.62 (m, 1H), 7.75-7.81 (m, 3H), 7.90 (d, J=8.2 Hz, 1H), 8.03 (d, J=8.4 Hz, 1H), 13.2 (br, 1H).

APCI-MS (m/z); 340 [M+H]$^+$

EXAMPLE 48

(E)-3-amino-1-{2-[2-(1H-indazol-3-yl)vinyl]benzoyl}pyrazole (Compound 48)

In a similar manner to Example 28, Compound 48 (53 mg, 58%) was obtained from (E)-2-[2-(1H-indazol-3-yl)vinyl]benzoic acid (100 mg, 0.38 mmol), 3-aminopyrazole (37.4 mg, 0.45 mmol), 1-hydroxybenzotriazole monohydrate (75.1 mg, 0.49 mmol), EDC (102 mg, 0.53 mmol) and 4-methylmorpholine (84 μL, 0.76 mmol).

$^1$H-NMR (300 MHz, DMSO-$d_6$) δ 5.71 (s, 2H), 6.07 (d, J=3.0 Hz, 1H), 7.15 (ddd, J=8.0, 6.9, 0.8 Hz, 1H), 7.33 (d, J=16.5 Hz, 1H), 7.37 (t, J=8.0 Hz, 1H), 7.39 (ddd, J=8.0, 7.0, 1.0 Hz, 1H), 7.49 (dd, J=7.7, 1.2 Hz, 1H), 7.53 (d, J=16.5 Hz, 1H), 7.54 (d, J=8.0 Hz, 1H), 7.55 (ddd, J=8.0, 7.0, 1.2 Hz, 1H), 7.73 (d, J=8.0 Hz, 1H), 8.01 (d, J=8.0 Hz, 1H), 8.18 (br, 1H), 13.16 (br, 1H).

ESI-MS (m/z); 330 [M+H]$^+$

EXAMPLE 49

(E)-N-{2-[2-(1H-indazol-3-yl)vinyl]phenyl}benzofuran-2-carboxamide (Compound 49)

In a similar manner to Example 29, Compound 49 (78 mg, 81%) was obtained from 2-benzofurancarboxylic acid (124 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (300 MHz, DMSO-$d_6$) δ 6.99 (t, J=7.7 Hz, 1H), 7.29-7.44 (m, 5H), 7.49-7.55 (m, 3H), 7.63 (d, J=16.9 Hz, 1H), 7.72 (d, J=8.1 Hz, 1H), 7.80-7.86 (m, 2H), 7.96-8.00 (m, 2H), 10.57 (s, 1H), 13.11 (br, 1H).

APCI-MS (m/z); 380 [M+H]$^+$

EXAMPLE 50

(E)-N-{2-[2-(1H-indazol-3-yl)vinyl]phenyl}-1H-indole-2-carboxamide (Compound 50)

In a similar manner to Example 29, Compound 50 (72 mg, 74%) was obtained from 2-indolecarboxylic acid (123 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (270 MHz, DMSO-$d_6$) δ 6.94 (t, J=7.7 Hz, 1H), 7.07 (t, J=7.7 Hz, 1H), 7.19-7.51 (m, 8H), 7.56 (s, 1H), 7.63-7.71 (m, 2H), 7.93-8.01 (m, 2H), 10.28 (s, 1H), 11.78 (s, 1H), 13.10 (br, 1H).

APCI-MS (m/z); 379 [M+H]$^+$

EXAMPLE 51

(E)-N-{2-[2-(1H-indazol-3-yl)vinyl]phenyl}-5-nitrothiophene-2-carboxamide (Compound 51)

In a similar manner to Example 29, Compound 51 (256 mg, 86%) was obtained from 5-nitro-2-thiophenecarboxylic acid mg, 2.30 mmol), thionyl chloride (250 μL, 3.45 mmol), DMF (few drops), (E)-2-[2-(1H-indazol-3-yl)vinyl]phenylamine mg, 0.77 mmol) and triethylamine (321 μL, 2.30 mmol).

$^1$H-NMR (300 MHz, DMSO-$d_6$) δ 7.10 (t, J=7.5 Hz, 1H), 7.32-7.41 (m, 4H), 7.54-7.57 (m, 3H), 7.97 (d, J=7.9 Hz, 1H), 8.01 (d, J=2.8 Hz, 1H), 8.11 (d, J=3.5 Hz, 1H), 8.25 (d, J=4.4 Hz, 1H), 10.78 (s, 1H), 13.16 (br, 1H).

APCI-MS (m/z); 391 [M+H]$^+$

EXAMPLE 52

(E)-N-{2-[2-(1H-indazol-3-yl)vinyl]phenyl}-1-methyl-4-nitro-1H-pyrrole-2-carboxamide (Compound 52)

In a similar manner to Example 29, Compound 52 (60 mg, 62%) was obtained from 1-methyl-4-nitro-2-pyrrolecarboxylic acid (130 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine μL, 0.77 mmol).

$^1$H-NMR (270 MHz, DMSO-d$_6$) δ 3.93 (s, 3H), 7.06-7.11 (m, 1H), 7.34-7.38 (m, 4H), 7.47-7.65 (m, 3H), 7.79 (s, 1H), 7.93-7.96 (m, 1H), 8.00 (d, J=8.4 Hz, 1H), 8.22 (s, 1H), 10.19 (s, 1H), 13.15 (br, 1H).

APCI-MS (m/z); 388 [M+H]$^+$

EXAMPLE 53

(E)-N-{2-[2-(1H-indazol-3-yl)vinyl]phenyl}-4-methoxythiophene-3-carboxamide (Compound 53)

In a similar manner to Example 29, Compound 53 (34 mg, 36%) was obtained from 4-methoxy-3-thiophenecarboxylic acid (121 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (270 MHz, DMSO-d$_6$), δ 3.72 (s, 3H), 6.36 (d, J=3.6 Hz, 1H), 7.19-7.26 (m, 2H), 7.34-7.53 (m, 4H), 7.66 (d, J=7.6 Hz, 1H), 7.78 (d, J=16.4 Hz, 1H), 8.00 (d, J=8.1 Hz, 1H), 8.25 (d, J=3.6 Hz, 1H), 8.30 (d, J=7.9 Hz, 1H), 9.53 (s, 1H).

APCI-MS (m/z); 376 [M+H]$^+$

EXAMPLE 54

(E)-3-chloro-N-{2-[2-(1H-indazol-3-yl)vinyl]phenyl}thiophene-2-carboxamide (Compound 54)

In a similar manner to Example 29, Compound 54 (69 mg, 71%) was obtained from 3-chloro-2-thiophenecarboxylic acid (124 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (300 MHz, DMSO-d$_6$) δ 7.12 (t, J=7.0 Hz, 1H), 7.24 (d, J=5.1 Hz, 1H), 7.33-7.40 (m, 3H), 7.49-7.56 (m, 3H), 7.70 (d, J=16.9 Hz, 1H), 7.94 (d, J=5.1 Hz, 2H), 8.07 (d, J=8.1 Hz, 1H), 10.06 (s, 1H), 13.18 (br, 1H).

APCI-MS (m/z); 380 [M+H]$^+$

EXAMPLE 55

(E)-N-{2-[2-(1H-indazol-3-yl)vinyl]phenyl}-1-methyl-1H-indole-2-carboxamide (Compound 55)

In a similar manner to Example 29, Compound 55 (56 mg, 57%) was obtained from 1-methyl-1H-indole-2-carboxylic acid (134 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (300 MHz, DMSO-d$_6$) δ 4.03 (s, 3H), 7.01 (t, J=8.1 Hz, 1H), 7.16 (t, J=7.7 Hz, 1H), 7.30-7.60 (m, 9H), 7.71 (d, J=16.5 Hz, 1H), 7.72 (d, J=7.7 Hz, 1H), 7.97-8.00 (m, 1H), 8.01 (d, J=8.1 Hz, 1H), 10.32 (s, 1H), 13.14 (br, 1H).

APCI-MS (m/z); 393 [M+H]$^+$

EXAMPLE 56

(E)-5-amino-N-{2-[2-(1H-indazol-3-yl)vinyl]phenyl}thiophene-2-carboxamide (Compound 56)

Compound 51 (1.5 g, 3.84 mmol), iron powder (4.3 g, 76.8 mmol) and ammonium chloride (616 mg, 11.52 mmol) were added with ethanol (10.0 mL) and water (10.0 mL) at room temperature, stirred at 50° C. for 7 hours and the reaction mixture was filtered through celite. The filtrate was extracted with ethyl acetate and the organic layer was sequentially washed with water and saturated brine, dried over anhydrous magnesium sulfate and the solvent was evaporated under reduced pressure. The residue was triturated in a mixed solvent of chloroform/ethyl acetate to obtain Compound 56 (724 mg, 52%).

$^1$H-NMR (270 MHz, DMSO-d$_6$) δ 5.93 (d, J=4.0 Hz, 1H), 6.43 (s, 2H), 7.08 (t, J=7.3 Hz, 1H), 7.27-7.33 (m, 4H), 7.37 (d, J=6.9 Hz, 1H), 7.47 (d, J=16.5 Hz, 1H), 7.55-7.66 (m, 2H), 7.91-7.94 (m, 1H), 7.99 (d, J=8.3 Hz, 1H), 9.72 (s, 1H), 13.12 (br, 1H).

APCI-MS (m/z); 361 [M+H]$^+$

EXAMPLE 57

(E)-N-{2-[2-(1H-indazol-3-yl)vinyl]phenyl}thieno[3,2-b]thiophene-2-carboxamide (Compound 57)

In a similar manner to Example 29, Compound 57 (66 mg, 65%) was obtained from thieno[3,2-b]thiophene-2-carboxylic acid (141 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (270 MHz, DMSO-d$_6$) δ 6.99 (t, J=7.9 Hz, 1H), 7.30-7.39 (m, 4H), 7.50-7.58 (m, 3H), 7.65 (d, J=16.8 Hz, 1H), 7.90 (d, J=4.5 Hz, 1H), 7.93-8.01 (m, 2H), 8.43 (s, 1H), 10.44 (s, 1H), 13.13 (br, 1H).

APCI-MS (m/z); 402 [M+H]$^+$

EXAMPLE 58

(E)-5-chloro-N-{2-[2-(1H-indazol-3-yl)vinyl]phenyl}-3-methylbenzo[b]thiophene-2-carboxamide (Compound 58)

In a similar manner to Example 29, Compound 58 (90 mg, 75%) was obtained from 5-chloro-3-methylbenzo[b]thiophene-2-carboxylic acid (173 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (300 MHz, DMSO-d$_6$) δ 2.67 (s, 3H), 7.09 (t, J=7.9 Hz, 1H), 7.33-7.39 (m, 3H), 7.43-7.47 (m, 1H), 7.51-7.57 (m, 3H), 7.66 (d, J=16.7 Hz, 1H), 7.96-8.00 (m, 1H), 8.03-8.07 (m, 2H), 8.12 (d, J=8.8 Hz, 1H), 10.30 (s, 1H), 13.18 (br, 1H).

APCI-MS (m/z); 412 [M+H]$^+$

EXAMPLE 59

(E)-N-{2-[2-(1H-indazol-3-yl)vinyl]phenyl}-5-methyl-2-trifluoromethylfuran-3-carboxamide (Compound 59)

In a similar manner to Example 29, Compound 59 (31 mg, 30%) was obtained from 5-methyl-2-trifluoromethylfuran-3-carboxylic acid (148 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (270 MHz, DMSO-$d_6$) δ 2.43 (s, 3H), 6.87 (s, 1H), 7.12 (t, J=7.6 Hz, 1H), 7.33-7.41 (m, 3H), 7.47-7.54 (m, 2H), (d, J=16.8 Hz, 1H), 7.59 (d, J=16.8 Hz, 1H), 7.95-7.53 (m, 1H), 8.00 (d, J=8.6 Hz, 1H), 10.33 (s, 1H), 13.16 (br, 1H).

APCI-MS (m/z); 442 [M−H]$^+$

EXAMPLE 60

(E)-N-{2-[2-(1H-indazol-3-yl)vinyl]phenyl}thiophene-2-sulfonamide (Compound 60)

In a similar manner to Example 3, Compound 60 (17 mg, 18%) was obtained from (E)-2-[2-(1H-indazol-3-yl)vinyl]phenylamine (60 mg, 0.26 mmol), triethylamine (71 mL, 0.51 mmol) and 2-thiophenesulfonyl chloride (140 mg, 0.77 mmol).

$^1$H-NMR (270 MHz, DMSO-$d_6$) δ 6.90 (d, J=7.9 Hz, 1H), 7.13 (t, J=4.6 Hz, 2H), 7.20 (d, J=7.8 Hz, 1H), 7.31-7.44 (m, 3H), 7.53 (d, J=7.1 Hz, 1H), 7.58-7.60 (m, 2H), 7.72-7.75 (m, 2H), 8.06-8.12 (m, 2H), 13.23 (br, 1H).

APCI-MS (m/z); 380 [M−H]$^+$

EXAMPLE 61

(E)-N-{2-[2-(1H-indazol-3-yl)vinyl]phenyl}-5-[(thiophen-2-ylcarbonyl)amino]thiophene-2-carboxamide (Compound 61)

In a similar manner to Example 3, Compound 61 (27 mg, 45%) was obtained from Compound 56 (60 mg, 0.17 mmol), triethylamine (46 μL, 0.33 mmol) and 2-thiophenecarbonyl chloride (108 μL, 0.33 mmol).

$^1$H-NMR (300 MHz, DMSO-$d_6$) δ 6.94 (m, 1H), 7.07 (t, J=7.3 Hz, 1H), 7.26 (t, J=4.6 Hz, 1H), 7.32-7.36 (m, 4H), 7.49-7.55 (m, 2H), 7.64 (d, J=16.5 Hz, 1H), 7.90-8.00 (m, 5H), 10.11 (s, 1H), 11.90 (s, 1H), 13.13 (br, 1H).

APCI-MS (m/z); 471 [M+H]$^+$

EXAMPLE 62

(E)-N-{2-[2-(1H-indazol-3-yl)vinyl]phenyl}-5-isobutyrylaminothiophene-2-carboxamide (Compound 62)

In a similar manner to Example 3, Compound 62 (60 mg, 85%) was obtained from (E)-5-amino-N-{2-[2-(1H-indazol-3-yl)vinyl]phenyl}thiophene-2-carboxamide (60 mg, 0.17 mmol), triethylamine (46 μL, 0.33 mmol) and isobutyryl chloride (108 μL, 0.33 mmol).

$^1$H-NMR (300 MHz, DMSO-$d_6$) δ 1.14 (d, J=6.8 Hz, 6H), 4.34-4.38 (m, 1H), 6.74 (d, J=4.2 Hz, 1H), 7.06 (t, J=7.3 Hz, 1H), 7.31-7.37 (m, 4H), 7.48-7.54 (m, 2H), 7.60 (d, J=16.5 Hz, 1H), 7.86 (d, J=4.0 Hz, 1H), 7.96-7.99 (m, 2H), 10.08 (s, 1H), 11.40 (s, 1H), 13.14 (br, 1H).

APCI-MS (m/z); 431 [M+H]$^+$

EXAMPLE 63

(E)-N-{2-[2-(1H-indazol-3-yl)vinyl]phenyl}-5-nitrofuran-2-carboxamide (Compound 63)

In a similar manner to Example 29, Compound 63 (139 mg, 73%) was obtained from 5-nitro-2-furancarboxylic acid (240 mg, 1.53 mmol), thionyl chloride (112 μL, 1.53 mmol), DMF (few drops), (E)-2-[2-(1H-indazol-3-yl)vinyl]phenylamine mg, 0.51 mmol) and triethylamine (321 μL, 2.3 mmol).

$^1$H-NMR (270 MHz, DMSO-$d_6$) δ 7.13 (t, J=7.6 Hz, 1H), 7.34-7.44 (m, 4H), 7.52-7.58 (m, 3H), 7.69 (d, J=3.8 Hz, 1H), (d, J=4.0 Hz, 1H), 7.99-8.04 (m, 2H), 10.72 (s, 1H), 13.16 (br, 1H).

APCI-MS (m/z); 375 [M+H]$^+$

EXAMPLE 64

(E)-N-{2-[2-(1H-indazol-3-yl)vinyl]phenyl}-3-nitrobenzamide (Compound 64)

In a similar manner to Example 3, Compound 64 (87 mg, 89%) was obtained from (E)-2-[2-(1H-indazol-3-yl)vinyl]phenylamine (60 mg, 0.26 mmol), triethylamine (71 μL, 0.51 mmol) and 3-nitrobenzoyl chloride (95 mg, 0.51 mmol).

$^1$H-NMR (300 MHz, DMSO-$d_6$) δ 7.05 (t, J=7.3 Hz, 1H), 7.31-7.37 (m, 3H), 7.45-7.55 (m, 3H), 7.70 (d, J=16.7 Hz, 1H), 7.86 (t, J=7.7 Hz, 1H), 7.98 (m, 2H), 8.45 (d, J=7.9 Hz, 1H), 8.52 (d, J=7.7 Hz, 1H), 8.94 (s, 1H).

APCI-MS (m/z); 385 [M+H]$^+$

EXAMPLE 65

(E)-N-{2-[2-(1H-indazol-3-yl)vinyl]phenyl}-4-nitrobenzamide (Compound 65)

In a similar manner to Example 3, Compound 65 (87 mg, 89%) was obtained from (E)-2-[2-(1H-indazol-3-yl)vinyl]phenylamine (60 mg, 0.26 mmol), triethylamine (71 μL, 0.51 mmol) and 4-nitrobenzoyl chloride (95 mg, 0.51 mmol).

$^1$H-NMR (300 MHz, DMSO-$d_6$) δ 7.08 (t, J=7.2 Hz, 1H), 7.32-7.42 (m, 4H), 7.51-7.57 (m, 2H), 7.62 (d, J=16.9 Hz, 1H), 7.94 (d, J=7.7 Hz, 1H), 7.98-8.01 (m, 1H), 8.28-8.34 (m, 2H), 8.41 (d, J=8.6 Hz, 2H).

APCI-MS (m/z); 385 [M+H]$^+$

EXAMPLE 66

(E)-N-{2-[2-(1H-indazol-3-yl)vinyl]phenyl}-3-methyl-5-nitrothiophene-2-carboxamide (Compound 66)

In a similar manner to Example 29, Compound 66 (122 mg, 80%) was obtained from 3-methyl-5-nitro-2-thiophenecarboxylic acid (176 mg, 0.94 mmol), thionyl chloride (83 μL, 1.31 mmol), DMF (few drops), (E)-2-[2-(1H-indazol-3-yl)vinyl]phenylamine (100 mg, 0.377 mmol) and triethylamine (158 μL, 1.13 mmol).

$^1$H-NMR (300 MHz, DMSO-$d_6$) δ 3.31 (s, 3H), 7.15 (t, J=7.7 Hz, 1H), 7.35-7.41 (m, 3H), 7.45-7.57 (m, 3H), 7.65 (d, J=16.5 Hz, 1H), 7.95-7.99 (m, 1H), 8.07 (d, J=8.1 Hz, 1H), 8.11 (s, 1H), 10.40 (s, 1H), 13.19 (br, 1H).

APCI-MS (m/z); 405 [M+H]$^+$

EXAMPLE 67

(E)-5-amino-N-{2-[2-(1H-indazol-3-yl)vinyl]phenyl}-3-methylthiophene-2-carboxamide (Compound 67)

(E)-N-{2-[2-(1H-indazol-3-yl)vinyl]phenyl}-3-methyl-5-nitrothiophene-2-carboxamide (90 mg, 0.22 mmol), iron powder (621 mg, 11.13 mmol) and ammonium chloride (59 mg, 1.10 mmol) were added with ethanol (1.0 mL) and water (1.0 mL) at room temperature, stirred at 50° C. for 1 hour and then the reaction mixture was filtered through Celite. The filtrate was extracted with ethyl acetate and the organic layer was sequentially washed with water and saturated brine, dried over anhydrous magnesium sulfate and the solvent was evaporated under reduced pressure. The residue was triturated in ethyl acetate to obtain Compound 67 (26 mg, 32%).

$^1$H-NMR (270 MHz, DMSO-$d_6$) δ 3.31 (s, 3H), 5.79 (s, 1H), 6.30 (s, 2H), 7.09 (t, J=7.6 Hz, 1H), 7.27-7.42 (m, 4H), 7.48-7.55 (m, 2H), 7.58 (d, J=16.8 Hz, 1H), 7.87-7.90 (m, 1H), 8.00 (d, J=7.7 Hz, 1H), 9.01 (s, 1H), 13.12 (br, 1H).

APCI-MS (m/z); 375 [M+H]$^+$

EXAMPLE 68

(E)-5-acetylamino-N-{2-[2-(1H-indazol-3-yl)vinyl]phenyl}thiophene-2-carboxamide (Compound 68)

In a similar manner to Example 3, Compound 68 (20 mg, 19%) was obtained from Compound 56 (60 mg, 0.26 mmol), triethylamine (71 μL, 0.51 mmol) and acetyl chloride (37 μL, 0.51 mmol).

$^1$H-NMR (270 MHz, DMSO-$d_6$) δ 2.13 (s, 3H), 6.71 (d, J=4.0 Hz, 1H), 7.05 (t, J=7.9 Hz, 1H), 7.31-7.38 (m, 4H), 7.47-7.54 (m, 4H), 7.60 (d, J=16.5 Hz, 1H), 7.85 (d, J=4.3 Hz, 1H), 7.96 (d, J=7.6 Hz, 2H), 10.08 (s, 1H), 13.16 (br, 1H).

APCI-MS (m/z); 403 [M+H]$^+$

EXAMPLE 69

(E)-3-amino-N-{2-[2-(1H-indazol-3-yl)vinyl]phenyl}benzamide (Compound 69)

Compound 64 (60 mg, 0.13 mmol), iron powder (364 mg, 6.50 mmol) and ammonium chloride (35 mg, 0.65 mmol) were added to ethanol (1.0 mL) and water (1.0 mL) at room temperature, stirred at 50° C. for 1 hour and then the reaction mixture was filtered through Celite. The filtrate was extracted with ethyl acetate and the organic layer was sequentially washed with water and saturated brine, dried over anhydrous magnesium sulfate and the solvent was evaporated under reduced pressure. The residue was triturated in ethanol to obtain Compound 69 (11 mg, 22%).

$^1$H-NMR (300 MHz, DMSO-$d_6$) δ 5.32 (s, 2H), 6.77 (td, J=1.8, 7.7 Hz, 1H), 7.06 (t, J=7.2 Hz, 1H), 7.17-7.21 (m, 3H), 7.32-7.37 (m, 4H), 7.47-7.54 (m, 2H), 7.60 (d, J=16.7 Hz, 1H), 7.93-7.96 (m, 2H), 10.06 (s, 1H), 13.12 (br, 1H).

APCI-MS (m/z); 355 [M+H]$^+$

EXAMPLE 70

(E)-4-amino-N-{2-[2-(1H-indazol-3-yl)vinyl]phenyl}benzamide (Compound 70)

Compound 65 (60 mg, 0.13 mmol), iron powder (436 mg, 7.80 mmol) and ammonium chloride (42 mg, 0.78 mmol) were added with ethanol (1.0 mL) and water (1.0 mL) at room temperature, stirred at 50° C. for 1 hour and then the reaction mixture was filtered through Celite. The filtrate was extracted with ethyl acetate and the organic layer was sequentially washed with water and saturated brine, dried over anhydrous magnesium sulfate and the solvent was evaporated under reduced pressure. The residue was triturated in ethanol to obtain Compound 70 (15 mg, 28%).

$^1$H-NMR (270 MHz, DMSO-$d_6$) δ 5.75 (s, 2H), 6.62 (d, J=8.3 Hz, 2H), 7.02 (t, J=7.6 Hz, 1H), 7.29-7.40 (m, 4H), 7.44-7.54 (m, 2H), 7.60 (d, J=16.8 Hz, 1H), 7.80 (d, J=8.3 Hz, 2H), 7.93 (d, J=7.9 Hz, 2H), 9.80 (s, 1H), 13.11 (br, 1H).

APCI-MS (m/z); 355 [M+H]$^+$

EXAMPLE 71

(E)-N-{2-[2-(1H-indazol-3-yl)vinyl]phenyl}-4-methyl-[1,2,3]thiadiazole-5-carboxamide (Compound 71)

In a similar manner to Example 29, Compound 71 (54 mg, 58%) was obtained from 4-methyl-[1,2,3]thiadiazole-5-carboxylic acid (110 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (300 MHz, DMSO-$d_6$) δ 2.87 (s, 3H), 7.16 (t, J=7.7 Hz, 1H), 7.36-7.42 (m, 3H), 7.49-7.57 (m, 3H), 7.64 (d, J=16.5 Hz, 1H), 7.96-7.99 (m, 1H), 8.05 (d, J=8.1 Hz, 1H), 10.68 (s, 1H), 13.2 (br, 1H).

APCI-MS (m/z); 362 [M+H]$^+$

EXAMPLE 72

(E)-N-{2-[2-(1H-indazol-3-yl)vinyl]phenyl}-5-methylisoxazole-4-carboxamide (Compound 72)

In a similar manner to Example 29, Compound 72 (14 mg, 16%) was obtained from 5-methyl-4-isoxazolecarboxylic acid (97 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (300 MHz, DMSO-$d_6$) δ 3.62 (s, 3H), 6.64 (s, 1H), 7.20-7.28 (m, 3H), 7.30-7.49 (m, 2H), 7.50-7.58 (m, 2H), 7.60 (d, J=16.5 Hz, 1H), 7.88 (d, J=5.9 Hz, 1H), 8.07 (d, J=8.1 Hz, 1H), 9.88 (s, 1H), 13.19 (br, 1H).

APCI-MS (m/z); 345 [M+H]$^+$

EXAMPLE 73

(E)-N-{2-[2-(1H-indazol-3-yl)vinyl]phenyl}-2-(1-methyl-1H-pyrrol-2-yl)acetamide (Compound 73)

In a similar manner to Example 28, Compound 73 (47 mg, 52%) was obtained from (1-methylpyrrole-2-yl)acetic acid (106 mg, 0.77 mmol), (E)-2-[2-(1H-indazol-3-yl)vinyl]phenylamine (60 mg, 0.26 mmol) and EDC (146 mg, 0.77 mmol).

$^1$H-NMR (300 MHz, DMSO-$d_6$) δ 2.08 (s, 2H), 3.36 (s, 3H), 6.99 (m, 1H), 7.15-7.21 (m, 3H), 7.41-7.49 (m, 3H), 7.53 (d, J=8.4 Hz, 1H), 7.72-7.74 (m, 2H), 7.76 (d, J=16.1 Hz, 1H), 8.24 (d, J=7.3 Hz, 1H), 8.46 (d, J=8.1 Hz, 1H), 12.38 (s, 1H), 13.13 (br, 1H).

APCI-MS (m/z); 357 [M+H]$^+$

EXAMPLE 74

(E)-N-{2-[2-(1H-indazol-3-yl)vinyl]phenyl}-2-nitrobenzamide (Compound 74)

In a similar manner to Example 3, Compound 74 (75 mg, 77%) was obtained from (E)-2-[2-(1H-indazol-3-yl)vinyl]phenylamine (60 mg, 0.26 mmol), triethylamine (107 μL, 0.77 mmol) and 2-nitrobenzoyl chloride (101 μL, 0.77 mmol).

$^1$H-NMR (270 MHz, DMSO-d$_6$) δ 7.15 (t, J=7.7 Hz, 1H), 7.30-7.41 (m, 3H), 7.50 (d, J=16.5 Hz, 1H), 7.53-7.56 (m, 2H), 7.70 (d, J=16.5 Hz, 1H), 7.75-7.96 (m, 4H), 8.10 (d, J=7.9 Hz, 1H), 8.20 (d, J=8.1 Hz, 1H), 10.52 (s, 1H), 13.17 (br, 1H).

APCI-MS (m/z); 385 [M+H]$^+$

EXAMPLE 75

(E)-N-{2-[2-(1H-indazol-3-yl)vinyl]phenyl}-N,N-dimethylformamidine (Compound 75)

(E)-2-[2-(1H-indazol-3-yl)vinyl]phenylamine (60 mg, 0.26 mmol) and EDC (146 mg, 0.77 mmol) were heated for about 4 hours in DMF (5.0 mL), added with saturated aqueous sodium hydrogencarbonate solution and extracted with ethyl acetate. The organic layer was sequentially washed with water and saturated brine, dried over anhydrous magnesium sulfate and the solvent was evaporated under reduced pressure. The residue was triturated in ethyl acetate to obtain Compound 75 (36 mg, 38%).

$^1$H-NMR (270 MHz, DMSO-d$_6$) δ 3.07 (s, 6H), 6.90 (d, J=7.9 Hz, 2H), 6.99 (t, J=7.2 Hz, 1H), 7.14-7.22 (m, 2H), 7.35-7.56 (m, 2H), 7.73 (m, 2H), 8.03-8.10 (m, 2H), 13.04 (br, 1H).

APCI-MS (m/z); 291 [M+H]$^+$

EXAMPLE 76

(E)-4-amino-N-{2-[2-(1H-indazol-3-yl)vinyl]phenyl}-1-methyl-1H-pyrrole-2-carboxamide trifluoroacetate (Compound 76)

Step 1

In a similar manner to Example 28, (E)-(5-{2-[2-(1H-indazol-3-yl)vinyl]phenylcarbamoyl}-1-methyl-1H-pyrrol-3-yl)carbamic acid tert-butyl ester (39 mg, 33%) was obtained from 4-[(tert-butoxycarbonyl)amino]-1-methyl-1H-pyrrole-2-carboxylic acid (184 mg, 0.77 mmol), (E)-2-[2-(1H-indazol-3-yl)vinyl]phenylamine (60 mg, 0.26 mmol), EDC (147 mg, 0.77 mmol) and THF (10 mL).

Step 2

(E)-(5-{2-[2-(1H-indazol-3-yl)vinyl]phenylcarbamoyl}-1-methyl-1H-pyrrol-3-yl) carbamic acid tert-butyl ester (15 mg, 0.033 mmol) was dissolved in methylene chloride (1.0 mL) and trifluoroacetic acid (100 μL) was added thereto followed by stirring at room temperature for 5 hours. Then, the mixture was concentrated and dried to obtain Compound 76 (11.3 mg, 96%).

$^1$H-NMR (300 MHz, DMSO-d$_6$) δ 3.94 (s, 3H), 4.94 (br, 2H), 7.06-7.11 (s, 2H), 7.34-7.42 (m, 4H), 7.48-7.66 (m, 3H), 7.66 (d, J=16.7 Hz, 1H), 7.86-7.90 (m, 1H), 7.90 (d, J=8.3 Hz, 1H).

ESI-MS (m/z); 358 [M+H]$^+$

EXAMPLE 77

(E)-4-hydroxy-N-{2-[2-(1H-indazol-3-yl)vinyl]phenyl}benzamide (Compound 77)

In a similar manner to Example 28, Compound 78 (15 mg, 17%) was obtained from 4-hydroxybenzoic acid (106 mg, 0.77 mmol), (E)-2-[2-(1H-indazol-3-yl)vinyl]phenylamine (60 mg, 0.26 mmol), 1-hydroxybenzotriazole monohydrate (117 mg, 0.77 mmol) and EDC (146 mg, 0.77 mmol).

$^1$H-NMR (300 MHz, DMSO-d$_6$) δ 6.89 (d, J=8.6 Hz, 2H), 7.03 (t, J=7.4 Hz, 1H), 7.31-7.37 (m, 4H), 7.51 (d, J=16.7 Hz, 1H), 7.50-7.54 (m, 1H), 7.60 (d, J=16.7 Hz, 1H), 7.91-7.97 (m, 4H), 10.01 (s, 1H), 13.2 (br, 1H).

ESI-MS (m/z); 403 [M+H]$^+$

EXAMPLE 78

(E)-N-{2-[2-(1H-indazol-3-yl)vinyl]phenyl}-4-(2-methoxyethoxy)benzamide (Compound 78)

In a similar manner to Example 29, Compound 78 (49 mg, 46%) was obtained from 4-(2-methoxyethoxy)benzoic acid (150 mg, 0.77 mmol), thionyl chloride (84 μL, 1.15 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (270 MHz, DMSO-d$_6$) δ 3.29 (s, 3H), 3.70 (t, J=3.8 Hz, 2H), 4.22 (t, J=3.8 Hz, 2H), 7.04 (t, J=7.4 Hz, 1H), 7.10 (d, J=8.6 Hz, 2H), 7.32-7.36 (m, 4H), 7.47-7.54 (m, 1H), 7.51 (d, J=17.1 Hz, 1H), 7.60 (d, J=17.1 Hz, 1H), 7.60 (d, J=8.6 Hz, 1H), 7.94-7.96 (m, 1H), 8.04 (d, J=8.7 Hz, 1H), 10.12 (s, 1H), 13.11 (br, 1H).

APCI-MS (m/z); 414 [M+H]$^+$

EXAMPLE 79

(E)-4-hydroxymethyl-N-{2-[2-(1H-indazol-3-yl)vinyl]phenyl}benzamide (Compound 79)

Step 1

In a similar manner to Example 29, (E)-4-formyl-N-{2-[2-(1H-indazol-3-yl)vinyl]phenyl}benzamide (180 mg, 62%) was obtained from 4-formylbenzoic acid (556 mg, 3.70 mmol), thionyl chloride (402 μL, 5.53 mmol), DMF (few drops), (E)-2-[2-(1H-indazol-3-yl)vinyl]phenylamine (290 mg, 1.23 mmol) and triethylamine (516 μL, 3.70 mmol).

Step 2

(E)-4-formyl-N-{2-[2-(1H-indazol-3-yl)vinyl]phenyl}benzamide (100 mg, 0.27 mmol) was dissolved in methanol (1.1 mL) and the solution was added with sodium borohydride (120 mg, 2.72 mmol), stirred at room temperature for 1 hour, added with water and extracted with ethyl acetate. The organic layer was sequentially washed with water and saturated brine, dried over anhydrous magnesium sulfate and the solvent was evaporated under reduced pressure. The residue was triturated in ethanol to obtain Compound 79 (10 mg, 10%).

$^1$H-NMR (300 MHz, DMSO-d$_6$) δ 4.61 (d, J=5.5 Hz, 2H), 5.69 (t, J=5.7 Hz, 1H), 7.04 (t, J=7.3 Hz, 1H), 7.33 (d, J=8.6 Hz, 1H), 7.34-7.37 (m, 2H), 7.48-7.54 (m, 3H), 7.51 (d, J=16.7 Hz, 1H), 7.62 (d, J=16.7 Hz, 1H), 7.93 (d, J=8.3 Hz, 2H), 7.95-7.99 (m, 1H), 8.04 (d, J=8.3 Hz, 2H), 10.24 (s, 1H), 13.12 (br, 1H).

APCI-MS (m/z); 370 [M+H]$^+$

EXAMPLE 80

(E)-N-{2-[2-(1H-indazol-3-yl)vinyl]phenyl}-4-(morpholin-4-ylmethyl)benzamide (Compound 80)

(E)-4-Formyl-N-{2-[2-(1H-indazol-3-yl)vinyl] phenyl}benzamide (60 mg, 0.16 mmol) was dissolved in dichloroethane (1.5 mL) and acetic acid (10 μL) and morpholine (22 μL) and sodium triacetoxyborohydride (104 mg, 0.49 mmol) were added thereto. The mixture was stirred at room temperature for 20 hours, added with water and extracted with ethyl acetate. The organic layer was sequentially washed with water and saturated brine, dried over anhydrous magnesium sulfate and the solvent was evaporated under reduced pressure. The residue was triturated in ethyl acetate to obtain Compound 80 (21 mg, 30%).

$^1$H-NMR (270 MHz, DMSO-$d_6$) δ 2.39 (s, 2H), 3.57-3.62 (m, 8H), 7.00 (t, J=7.6 Hz, 1H), 7.30-7.37 (m, 4H), 7.48-7.54 (m, 4H), 7.60 (d, J=16.3 Hz, 1H), 7.92 (d, J=7.9 Hz, 1H), 7.96-7.99 (m, 1H), 8.03 (d, J=8.1 Hz, 2H), 10.24 (s, 1H), 13.11 (br, 1H).

APCI-MS (m/z); 439 [M+H]$^+$

EXAMPLE 81

(E)-2-chloro-N-{2-[2-(1H-indazol-3-yl)vinyl]phenyl}-4-nitrobenzamide (Compound 81)

In a similar manner to Example 29, Compound 81 (258 mg, 96%) was obtained from 2-chloro-4-nitrobenzoic acid (321 mg, mmol), thionyl chloride (139 μL, 1.91 mmol), DMF (few drops), (E)-2-[2-(1H-indazol-3-yl)vinyl]phenylamine (150 mg, mmol) and triethylamine (266 μL, 1.91 mmol).

$^1$H-NMR (300 MHz, DMSO-$d_6$) δ 7.18 (t, J=7.2 Hz, 1H), 7.27-7.41 (m, 3H), 7.50 (d, J=16.7 Hz, 1H), 7.53-7.58 (m, 2H), 7.80 (d, J=16.7 Hz, 1H), 7.92-7.96 (m, 2H), 8.10 (d, J=8.3 Hz, 1H), 8.31 (dd, J=1.8, 8.6 Hz, 1H), 8.41 (d, J=1.8 Hz, 1H).

APCI-MS (m/z); 417 [M+H]$^+$

EXAMPLE 82

(E)-N-{2-[2-(1H-indazol-3-yl)vinyl]phenyl}-4-methylsulphanylbenzamide (Compound 82)

In a similar manner to Example 29, Compound 82 (68 mg, 71%) was obtained from 4-(methylthio)benzoic acid (107 mg, 0.64 mmol), thionyl chloride (56 μL, 0.77 mmol), DMF (few drops), (E)-2-[2-(1H-indazol-3-yl)vinyl]phenylamine (60 mg, 0.26 mmol) and triethylamine (107 μL, 0.77 mmol).

$^1$H-NMR (300 MHz, DMSO-$d_6$) δ 2.56 (s, 3H), 7.05 (t, J=7.5 Hz, 1H), 7.32-7.36 (m, 5H), 7.42 (d, J=8.3 Hz, 1H), 7.51 (d, J=16.7 Hz, 1H), 7.48-7.54 (m, 1H), 7.60 (d, J=16.7 Hz, 1H), 7.92 (d, J=8.3 Hz, 1H), 7.96-7.99 (m, 1H), 8.01 (d, J=8.4 Hz, 2H), 10.23 (s, 1H), 13.12 (br, 1H).

APCI-MS (m/z); 386 [M+H]$^+$

EXAMPLE 83

(E)-4-cyano-N-{2-[2-(1H-indazol-3-yl)vinyl] phenyl}benzamide (Compound 83)

In a similar manner to Example 3, Compound 83 (72 mg, 77%) was obtained from (E)-2-[2-(1H-indazol-3-yl)vinyl] phenylamine (60 mg, 0.26 mmol), triethylamine (107 μL, 0.77 mmol) and 4-cyanobenzoyl chloride (106 mg, 0.64 mmol).

$^1$H-NMR (300 MHz, DMSO-$d_6$) δ 7.07 (t, J=8.1 Hz, 1H), 7.33-7.42 (m, 4H), 7.51 (d, J=3.9 Hz, 1H), 7.56 (t, J=5.1 Hz, 1H), 7.60 (d, J=16.7 Hz, 1H), 7.93 (d, J=8.1 Hz, 1H), 7.99 (t, J=5.1 Hz, 1H), 8.07 (d, J=8.4 Hz, 2H), 8.21 (d, J=8.3 Hz, 2H), 10.54 (s, 1H), 13.16 (br, 1H).

APCI-MS (m/z); 365 [M+H]$^+$

EXAMPLE 84

(E)-4-amino-2-chloro-N-{2-[2-(1H-indazol-3-yl) vinyl]phenyl}benzamide (Compound 84)

(E)-2-chloro-N-{2-[2-(1H-indazol-3-yl)vinyl]phenyl}-4-nitrobenzamide (60 mg, 0.14 mmol) was dissolved in acetic acid (1.0 mL) and hydrochloric acid (0.5 mL). The solution was added with tin(II) chloride (114 mg, 0.6 mmol), stirred at 40° C. for 2 hours, added with 6 mol/L sodium hydroxide to neutralize and then the mixture was extracted with ethyl acetate. The organic layer was sequentially washed with water and saturated brine, dried over anhydrous magnesium sulfate and the solvent was evaporated under reduced pressure. The residue was triturated in ethanol to obtain Compound 84 (21 mg, 38%).

$^1$H-NMR (270 MHz, DMSO-$d_6$) δ 5.78 (br, 2H), 6.56 (d, J=8.4 Hz, 1H), 6.66 (s, 1H), 7.13 (t, J=7.9 Hz, 1H), 7.29-7.44 (m, 5H), 7.53 (m, 2H), 7.70 (d, J=16.7 Hz, 1H), 7.90 (t, J=5.6 Hz, 1H), 8.10 (d, J=7.6 Hz, 1H), 9.94 (s, 1H), 13.15 (br, 1H).

APCI-MS (m/z); 390 [M+H]$^+$

EXAMPLE 85

(E)-N-{2-[2-(1H-indazol-3-yl)vinyl] phenyl}benzamide (Compound 85)

In a similar manner to Example 3, Compound 85 (557 mg, 78%) was obtained from (E)-2-[2-(1H-indazol-3-yl)vinyl] phenylamine (500 mg, 2.12 mmol), triethylamine (594 μL, 4.24 mmol) and benzoyl chloride (369 μL, 3.19 mmol).

$^1$H-NMR (300 MHz, DMSO-$d_6$) δ 7.03 (t, J=7.7 Hz, 1H), 7.33 (d, J=7.7 Hz, 1H), 7.35-7.41 (m, 3H), 7.50 (d, J=4.0 Hz, 1H), 7.53-7.57 (m, 2H), 7.61-7.65 (m, 2H), 7.63 (d, J=16.8 Hz, 1H), 7.93 (d, J=8.1 Hz, 1H), 7.96-8.00 (m, 1H), 8.07 (d, J=6.6 Hz, 2H), 10.30 (s, 1H), 13.13 (br, 1H).

APCI-MS (m/z); 340 [M+H]$^+$

EXAMPLE 86

(E)-N-{4-[2-(1H-indazol-3-yl)vinyl]-3-nitrophenyl}-4-acetylpiperazine-1-carboxamide (Compound 86)

(1H-Indazol-3-ylmethyl)triphenylphosphonium bromide (2 g, 4.23 mmol) was dissolved in methanol (20 mL) and the solution was added with 4-(4-acetylpiperazin-1-ylcarbonyl)-2-nitrobenzaldehyde (1.42 g, 4.65 mmol) and potassium carbonate (1.17 g, 8.46 mmol), followed by stirring at room temperature for 30 minutes. The reaction mixture was added with water and the precipitated solid was collected by filtration and dried. The solid was triturated in methanol to obtain Compound 86 (1.13 g, 64%).

$^1$H-NMR (300 MHz, DMSO-$d_6$) δ 2.03 (s, 3H), 3.33-3.52 (br, 8H), 7.26 (t, J=7.9 Hz, 1H), 7.43 (t, J=7.9 Hz, 1H), 7.55-7.65 (m, 1H), 7.74 (d, J=16.5 Hz, 1H), 7.78-7.81 (m, 1H), 7.84 (d, J=16.5 Hz, 1H), 8.06-8.08 (m, 1H), 8.10 (d, J=8.3 Hz, 1H), 8.22 (d, J=8.3 Hz, 1H), 13.4 (br, 1H).

APCI-MS (m/z); 418 [M+H]$^+$

EXAMPLE 87

(E)-N-{3-amino-4-[2-(1H-indazol-3-yl)vinyl]phenyl}-4-acetylpiperazine-1-carboxamide (Compound 87)

Compound 86 (150 mg, 0.36 mmol) was dissolved in ethanol (2 mL), and the solution was added with tin (92 mg, 0.77 mmol) and concentrated hydrochloric acid (1.0 mL) under ice-cooling, followed by stirring at 40° C. for 1 hour. To the reaction mixture, 6 mol/L sodium hydroxide was added to neutralize the mixture under ice-cooling. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was triturated in ethyl acetate/methanol(4/1) to obtain Compound 87 (110 mg, 79%).

$^1$H-NMR (270 MHz, DMSO-$d_6$) δ 2.03 (s, 3H), 3.29-3.48 (br, 8H), 5.54 (br, 2H), 6.60 (d, J=8.3 Hz, 1H), 6.75 (s, 1H), 7.16-7.22 (m, 1H), 7.32-7.42 (m, 2H), 7.52-7.60 (m, 3H), 8.22 (d, J=8.4 Hz, 1H), 13.10 (br, 1H).
APCI-MS (m/z); 390 [M+H]$^+$

EXAMPLE 88

(E)-N-{5-(4-acetylpiperazin-1-yl)-2-[2-(1H-indazol-3-yl)vinyl]phenyl}-3-methylthiophene-2-carboxamide (Compound 88)

In a similar manner to Example 29, Compound 88 (632 mg, 31%) was obtained from 3-methyl-2-thiophenecarboxylic acid (1.1 g, 7.70 mmol), thionyl chloride (840 μL, 11.57 mmol), DMF (few drops), Compound 87 (1.0 g, 2.57 mmol) and triethylamine (1.08 mL, 7.7 mmol).

$^1$H-NMR (270 MHz, DMSO-$d_6$) δ 2.02 (s, 3H), 3.32 (s, 3H), 3.34-3.51 (m, 8H), 7.05 (d, J=5.0 Hz, 1H), 7.10 (d, J=7.6 Hz, 1H), 7.36-7.38 (m, 2H), 7.58 (d, J=13.9 Hz, 1H), 7.47-7.60 (m, 3H), 7.70 (d, J=5.0 Hz, 1H), 8.01 (d, J=7.9 Hz, 2H), 9.97 (s, 1H), 13.20 (br, 1H).
APCI-MS (m/z); 514 [M+H]$^+$

EXAMPLE 89

(E)-N-{5-(4-acetylpiperazin-1-ylcarbonyl)-2-[2-(1H-indazol-3-yl)vinyl]phenyl}-2-(thiophen-2-yl)acetamide (Compound 89)

In a similar manner to Example 3, Compound 89 (31 mg, 30%) was obtained from Compound 87 (80 mg, 0.21 mmol), triethylamine (57 μL, 0.41 mmol) and 2-thiopheneacetyl chloride (50 μL, 0.41 mmol).

$^1$H-NMR (300 MHz, DMSO-$d_6$) δ 2.02 (s, 3H), 3.32-3.49 (br, 8H), 3.98 (s, 2H), 6.97 (t, J=4.6 Hz, 1H), 7.05 (m, 1H), 7.20 (t, J=7.5 Hz, 1H), 7.30 (d, J=8.8 Hz, 1H), 7.37-7.43 (m, 2H), 7.50-7.59 (m, 4H), 7.96 (d, J=8.3 Hz, 1H), 8.03 (d, J=8.4 Hz, 1H), 10.17 (s, 1H), 13.24 (br, 1H).
APCI-MS (m/z); 514 [M+H]$^+$

EXAMPLE 90

(E)-N-{5-(4-acetylpiperazin-1-ylcarbonyl)-2-[2-(1H-indazol-3-yl)vinyl]phenyl}benzo[b]thiophene-2-carboxamide (Compound 90)

In a similar manner to Example 29, Compound 90 (78 mg, 69%) was obtained from benzo[b]thiophene-2-carboxylic acid mg, 0.61 mmol), thionyl chloride (67 μL, 0.92 mmol), DMF (few drops), Compound 87 (80 mg, 0.20 mmol) and triethylamine (86 μL, 0.61 mmol).

$^1$H-NMR (270 MHz, DMSO-$d_6$) δ 2.04 (s, 3H), 3.53 (br, 8H), 7.03 (t, J=7.7 Hz, 1H), 7.31-7.47 (m, 2H), 7.49-7.56 (m, 4H), 7.66 (s, 2H), 8.00-8.11 (m, 4H), 8.44 (s, 1H), 10.69 (s, 1H), 13.19 (br, 1H).
APCI-MS (m/z); 550 [M+H]$^+$

EXAMPLE 91

(E)-N-{5-(4-acetylpiperazin-1-ylcarbonyl)-2-[2-(1H-indazol-3-yl)vinyl]phenyl}-1-methyl-1H-pyrrole-2-carboxamide (Compound 91)

In a similar manner to Example 29, Compound 91 (7.6 mg, 280) was obtained from 1-methyl-1H-pyrrole-2-carboxylic acid (154 mg, 1.23 mmol), thionyl chloride (119 μL, 1.64 mmol), DMF (few drops), Compound 87 (80 mg, 0.20 mmol) and triethylamine (171 μL, 1.23 mmol).

$^1$H-NMR (270 MHz, DMSO-$d_6$) δ 2.03 (s, 3H), 3.70-3.76 (m, 8H), (s, 3H), 6.13-6.16 (m, 1H), 7.04-7.17 (m, 3H), 7.34-7.42 (m, 3H), 7.52-7.56 (m, 1H), 7.62 (d, J=4.3 Hz, 2H), 7.98-8.04 (m, 2H), 9.89 (s, 1H), 13.18 (br, 1H).
APCI-MS (m/z); 497 [M+H]$^+$

EXAMPLE 92

(E)-2-[2-(1H-indazol-3-yl)vinyl]-4,5-dimethoxyphenylamine (Compound 92)

In a similar manner to Example 1, (E)-3-[2-(4,5-dimethoxy-2-nitrophenyl)vinyl]-1H-indazole was obtained from (1H-indazol-3-ylmethyl)triphenylphosphonium bromide (200 mg, 0.42 mmol), methanol (1.50 mL), 4,5-dimethoxy-2-nitrobenzaldehyde (102 mg, 0.51 mmol) and potassium carbonate (117 mg, 0.84 mmol).

Then, in a similar manner to Example 2, Compound 92 (110 mg, 89%) was obtained from (E)-3-[2-(4,5-dimethoxy-2-nitrophenyl)vinyl]-1H-indazol (132 mg, 0.38 mmol) obtained above, ethanol (2.40 mL), tin (135 mg, 1.44 mmol) and concentrated hydrochloric acid (1.0 mL).

$^1$H-NMR (270 MHz, DMSO-$d_6$) δ 3.71 (s, 3H), 3.73 (s, 3H), 5.01 (br, 2H), 6.40 (s, 1H), 7.10 (s, 1H), 7.13-7.21 (m, 2H), 7.36 (dd, J=7.4, 7.4 Hz, 1H), 7.48-7.51 (m, 2H), 8.20 (d, J=8.4 Hz, 1H), 12.9 (br, 1H).
APCI-MS (m/z); 296 [M+H]$^+$

EXAMPLE 93

(E)-2-[2-(1H-indazol-3-yl)vinyl]-6-methoxyphenylamine (Compound 93)

In a similar manner to Example 1, a product was obtained from (1H-indazol-3-ylmethyl)triphenylphosphonium bromide (200 mg, 0.42 mmol), 3-methoxy-2-nitrobenzaldehyde (84.0 mg, 0.51 mmol) and potassium carbonate (117 mg, 0.84 mmol). Then, in a similar manner to Example 2, Compound 93 (71.0 mg, 89%) was obtained from a product obtained above, tin (96.0 mg, 0.81 mmol) and concentrated hydrochloric acid (1.00 mL).

$^1$H-NMR (270 MHz, DMSO-$d_6$) δ 3.81 (s, 3H), 4.95 (br, 2H), 6.62 (dd, J=7.8, 7.8 Hz, 1H), 6.78 (d, J=7.8 Hz, 1H), 7.16-7.21 (m, 2H), 7.29 (d, J=16.5 Hz, 1H), 7.38 (dd, J=8.3, 8.3 Hz, 1H) 7.53 (d, J=8.3 Hz, 1H), 7.61 (d, J=16.5 Hz, 1H), 8.23 (d, J=8.3 Hz, 1H), 13.1 (br, 1H).
APCI-MS (m/z); 266 [M+H]$^+$

EXAMPLE 94

(E)-N-{2-[2-(1H-indazol-3-yl)vinyl]-6-methoxyphenyl}-3-methylthiophene-2-carboxamide (Compound 94)

In a similar manner to Example 29, Compound 94 (59.2 mg, 67%) was obtained from 3-methyl-2-thiophenecarboxylic acid (110 mg, 0.69 mmol), thionyl chloride (0.08 ml, 1.04 mmol), DMF (0.02 ml), Compound 93 (60.0 mg, 0.23 mmol) and triethylamine (0.09 mL, 0.69 mmol).

$^1$H-NMR (270 MHz, DMSO-$d_6$) δ 2.51 (s, 3H), 3.81 (s, 3H), 7.04 (d, J=5.3 Hz, 1H), 7.07 (dd, J=8.1, 8.1 Hz, 2H), 7.36 (dd, J=8.1, 8.1 Hz, 2H), 7.51 (d, J=16.9 Hz, 1H), 7.53 (d, J=8.4 Hz, 1H), 7.55 (d, J=8.4 Hz, 1H), 7.59 (d, J=16.9 Hz, 1H), 7.67 (d, J=5.3 Hz, 1H), 7.94 (d, J=8.4 Hz, 161-1H), 9.30 (br, 1H), 13.1 (br, 1H).

0APCI-MS (m/z); 390 [M+H]$^+$

EXAMPLE 95

(E)-N-{2-[2-(1H-indazol-3-yl)vinyl]-4,5-dimethoxyphenyl}-3-methylthiophene-2-carboxamide (Compound 95)

In a similar manner to Example 29, Compound 95 (25.4 mg, 36%) was obtained from 3-methyl-2-thiophenecarboxylic acid (82.0 mg, 0.51 mmol), thionyl chloride (0.06 ml, 0.78 mmol), DMF (0.02 ml), Compound 92 (50.0 mg, 0.17 mmol) and triethylamine (0.07 mL, 0.51 mmol).

$^1$H-NMR (270 MHz, DMSO-$d_6$) δ 2.51 (s, 3H), 3.79 (s, 3H), 3.91 (s, 3H), 6.94 (s, 1H), 7.05 (d, J=5.0 Hz, 1H), 7.03 (dd, J=7.3, 7.3 Hz, 2H), 7.53-7.49 (m, 4H), 7.69 (d, J=5.5 Hz, 1H), 8.01 (d, J=7.7 Hz, 1H), 9.73 (br, 1H), 13.1 (br, 1H).

APCI-MS (m/z); 420 [M+H]$^+$

EXAMPLE 96

(E)-N-{2-[2-(1H-indazol-3-yl)vinyl]-4,5-dimethoxyphenyl}-1-methyl-1H-pyrrole-2-carboxamide (Compound 96)

In a similar manner to Example 29, Compound 96 (44.0 mg, 64%) was obtained from 1-methyl-2-pyrrolecarboxylic acid (82.0 mg, 0.51 mmol), thionyl chloride (0.05 ml, 0.77 mmol), DMF (0.02 ml), Compound 92 (50.0 mg, 0.17 mmol) and triethylamine (0.07 mL, 0.51 mmol).

$^1$H-NMR (270 MHz, DMSO-$d_6$) δ 3.78 (s, 3H), 3.89 (d, J=7.1 Hz, 6H), 6.13 (dd, J=6.4, 6.4 Hz, 1H), 6.89 (s, 1H), 7.01-7.07 (m, 2H), 7.16 (s, 1H), 7.34 (dd, J=7.7, 7.7 Hz, 1H), 7.43 (d, J=8.6 Hz, 1H), 7.45 (d, J=16.8 Hz, 1H), 7.51 (d, J=8.6 Hz, 1H), 7.56 (d, J=16.8 Hz, 1H), 7.97 (d, J=7.8 Hz, 1H), 9.66 (br, 1H), 13.0 (br, 1H).

APCI-MS (m/z); 403 [M+H]$^+$

EXAMPLE 97

(E)-4-[2-(1H-indazol-3-yl)vinyl]-3-[(3-methylthiophen-2-ylcarbonyl)amino]benzoic acid methyl ester (Compound 97)

In a similar manner to Example 1, (1H-indazol-3-ylmethyl)triphenylphosphonium bromide (4.10 g, 8.66 mmol) was dissolved in methanol (60.0 mL) and 4-[2-(1H-indazol-3-yl)vinyl]-3-nitrobenzoic acid methyl ester was obtained from 4-formyl-3-nitrobenzoic acid methyl (2.44 g, 9.53 mmol) and potassium carbonate (2.93 g, 17.3 mmol). The crude product (0.50 g, 1.55 mmol) was dissolved in ethanol (10.0 mL), reacted with tin (0.55 g, 4.65 mmol) and concentrated hydrochloric acid (1.3 mL) at room temperature to obtain 3-amino-4-[2-(1H-indazol-3-yl)vinyl]benzoic acid methyl ester.

In a similar manner to Example 29, Compound 97 (0.84 g, 98%) was obtained from 3-methylthiophenecarboxylic acid (0.87 g, 6.15 mmol), thionyl chloride (0.67 ml, 9.22 mmol), DMF (0.10 ml), 3-amino-4-[2-(1H-indazol-3-yl)vinyl]benzoic acid methyl ester (0.60 g, 2.05 mmol) and triethylamine (0.86 ml, 6.15 mmol).

$^1$H-NMR (270 MHz, DMSO-$d_6$) δ 2.51 (s, 3H), 3.89 (s, 3H), 7.07 (d, J=4.9 Hz, 1H), 7.12 (dd, J=7.1, 7.1 Hz, 1H), 7.38 (dd, J=7.1, 7.1 Hz, 1H), 7.56 (d, J=8.4 Hz, 1H), 7.67-7.68 (m; 2H), 7.73 (d, J=4.9 Hz, 1H), 7.88 (dd, J=8.3, 8.3 Hz, 1H), 8.01-8.02 (m, 1H), 8.07 (d, J=18.1 Hz, 1H), 8.10 (d, J=18.1 Hz, 1H), 10.0 (br, 1H), 13.3 (br, 1H).

APCI-MS (m/z); 418 [M+H]$^+$

EXAMPLE 98

(E)-4-[2-(1H-indazol-3-yl)vinyl]-3-[(3-methylthiophen-2-ylcarbonyl)amino]benzoic acid (Compound 98)

Compound 97 (740 mg, 1.77 mmol) was dissolved in methanol (5.00 mL) and the solution was added with 2 mol/L aqueous sodium hydroxide solution (5.00 mL), followed by stirring at 40° C. for 1 hour. The reaction mixture was acidified by hydrochloric acid (6 mol/L) and the precipitated crystal was collected by filtration to obtain Compound 98 (603 mg, 85%).

$^1$H-NMR (270 MHz, DMSO-$d_6$) δ 2.51 (s, 3H), 7.07 (d, J=4.9 Hz, 1H), 7.12 (dd, J=7.4, 7.4 Hz, 1H), 7.38 (dd, J=6.9, 6.9 Hz, 1H), 7.56 (d, J=8.4 Hz, 1H), 7.66 (s, 2H), 7.72 (d, J=4.9 Hz, 1H), 7.87 (dd, J=8.1, 8.1 Hz, 1H), 7.97-7.98 (m, 1H), 8.05 (d, J=11.8 Hz, 1H), 8.08 (d, J=11.8 Hz, 1H), 10.0 (br, 1H), 13.3 (br, 1H).

APCI-MS (m/z); 404 [M+H]$^+$

EXAMPLE 99

(E)-N-{2-[2-(1H-indazol-3-yl)vinyl]-5-(piperazin-1-ylcarbonyl)phenyl}-3-methylthiophene-2-carboxamide (Compound 99)

In a similar manner to Example 28, a crude product of (E)-N-{5-(4-(N-1,1-dimethylethoxycarbonyl)piperazin-1-ylcarbonyl)-2-[2-(1H-indazol-3-yl)vinyl]phenyl}-3-methylthiophene-2-carboxamide was obtained from Compound 98 (35.0 mg, 0.09 mmol), N-(1,1-dimethylethoxycarbonyl) piperazine (25.0 mg, 0.14 mmol), 1-hydroxybenzotriazole monohydrate (16.0 mg, 0.12 mmol), EDC (25.0 mg, 0.13 mmol) and 4-methylmorpholine (0.02 mL, 0.18 mmol). The crude product was dissolved in methanol (0.50 mL). The solution was added with 4 mol/L hydrogen chloride-methanol solution (0.50 mL), followed by heating under reflux at 60° C. for 30 minutes. The reaction mixture was concentrated under reduced pressure and the residue was extracted after adding a saturated aqueous potassium carbonate solution and ethyl acetate. The obtained crude product was crystallized from ethyl acetate to obtain Compound 99 (33.0 mg, 78%).

$^1$H-NMR (270 MHz, DMSO-$d_6$) δ 2.58 (s, 3H), 3.13 (br, 4H), 3.74 (br, 4H), 7.07 (d, J=4.9 Hz, 1H), 7.13 (d, J=7.6 Hz, 1H), 7.39 (dd, J=7.9, 7.9 Hz, 2H), 7.56 (dd, J=7.9, 7.9 Hz, 2H), 7.59 (d, J=16.8 Hz, 1H), 7.60 (d, J=16.8 Hz, 1H), 7.72 (d, J=4.9 Hz, 1H), 8.04 (dd, J=8.2, 8.2 Hz, 2H), 10.0 (br, 1H), 13.3 (br, 1H).

ESI-MS (m/z); 472 [M+H]$^+$

EXAMPLE 100

(E)-N-{2-[2-(1H-indazol-3-yl)vinyl]-5-(morpholin-4-ylcarbonyl)phenyl}-3-methylthiophene-2-carboxamide (Compound 100)

In a similar manner to Example 28, a crude product of Compound 100 was obtained from Compound 98 (50.0 mg, 0.12 mmol), morpholine (0.02 mL, 0.18 mmol), 1-hydroxybenzotriazole monohydrate (22.0 mg, 0.15 mmol), EDC (34.0 mg, 0.17 mmol) and 4-methylmorpholine (0.03 mL, 0.24 mmol). The crude product was crystallized from a mixed solvent of ethyl acetate/hexane (1/1) to obtain Compound 100 (45.0 mg, 77%).

$^1$H-NMR (270 MHz, DMSO-$d_6$) δ 2.50 (s, 3H), 3.63 (br, 8H), 7.06 (d, J=5.0 Hz, 1H), 7.12 (d, J=7.8 Hz, 1H), 7.36-7.40 (m, 2H), 7.50 (d, J=16.7 Hz, 1H), 7.55 (d, J=8.1 Hz, 1H), 7.58 (d, J=16.7 Hz 1H), 7.58-7.62 (m, 1H), 7.72 (d, J=5.0 Hz, 1H), 8.03 (d, J=8.1 Hz, 2H), 9.98 (br, 1H), 13.2 (br, 1H).

ESI-MS (m/z); 473 [M+H]$^+$

EXAMPLE 101

(E)-N-{5-(N,N-diethylcarbamoyl)-2-[2-(1H-indazol-3-yl)vinyl]phenyl}-3-methylthiophene-2-carboxamide (Compound 101)

A crude product of Compound 101 was obtained from Compound 98 (50.0 mg, 0.12 mmol), diethylamine (0.02 mL, 0.18 mmol), 1-hydroxybenzotriazole monohydrate (22.0 mg, 0.15 mmol), EDC (34.0 mg, 0.17 mmol) and 4-methylmorpholine (0.03 mL, 0.24 mmol). The crude product was crystallized from a mixed solvent of ethyl acetate/hexane (1/1) to obtain Compound 101 (45.0 mg, 77%).

$^1$H-NMR (270 MHz, DMSO-$d_6$) δ 1.14 (br, 6H), 2.51 (s, 3H), 3.36 (br, 4H), 7.06 (d, J=5.0 Hz, 1H), 7.11 (dd, J=7.7, 7.7 Hz, 1H), 7.30 (d, J=7.7 Hz 1H), 7.35-7.40 (m, 2H), 7.54-7.62 (m, 3H), 7.71 (d, J=5.0 Hz, 1H), 8.00 (d, J=8.1 Hz, 1H), 8.05 (d, J=8.1 Hz, 1H), 9.96 (br, 1H), 13.2 (br, 1H).

ESI-MS (m/z); 459 [M+H]$^+$

EXAMPLE 102

(E)-(R)—N-{5-(3-aminopyrrolidine-1-ylcarbonyl)-2-[2-(1H-indazol-3-yl)vinyl]phenyl}-3-methylthiophene-2-carboxamide (Compound 102)

In a similar manner to Example 28, a product obtained from Compound 98 (200 mg, 0.50 mmol), (R)-(pyrrolidin-3-yl)carbamic acid tert-butyl ester (0.14 mg, 0.75 mmol), 1-hydroxybenzotriazole monohydrate (88.0 mg, 0.65 mmol), EDC (134 mg, 0.70 mmol) and 4-methylmorpholine (0.1 mL, 1.00 mmol) was dissolved in methanol (2.00 mL) and the solution was added with 4 mol/L hydrogen chloride-methanol solution (0.40 mL), followed by heating under reflux at 60° C. for 30 minutes. The reaction mixture was concentrated under reduced pressure and the residue was added with 2 mol/L aqueous sodium hydroxide solution and ethyl acetate and then extracted. The obtained crude product was crystallized from ethyl acetate to obtain Compound 102 (153 mg, 65%).

$^1$H-NMR (270 MHz, DMSO-$d_6$) δ 1.59-1.99 (m, 4H), 2.51 (s, 3H), 3.08-3.18 (m, 1H), 3.67-3.78 (m, 4H), 7.04 (d, J=5.0 Hz, 1H), 7.09 (dd, J=7.7, 7.7 Hz, 1H), 7.36 (d, J=7.7 Hz 1H), 7.42-7.45 (m, 1H), 7.51-7.62 (m, 4H), 7.69 (d, J=5.0 Hz, 1H), 8.98 (d, J=8.2 Hz, 1H), 8.03 (d, J=8.2 Hz, 1H), 9.96 (br, 1H), 13.2 (br, 1H).

APCI-MS (m/z); 472 [M+H]$^+$

EXAMPLE 103

(E)-N-{2-[2-(1H-indazol-3-yl)vinyl]-4-(2-morpholinoethoxy)phenyl}-3-methylthiophene-2-carboxamide (Compound 103)

Step 1

5-hydroxy-2-nitrobenzaldehyde (1.00 g, 5.98 mmol) was dissolved in DMF (15.0 mL) and the solution was added with morpholinoethyl chloride hydrochloride (1.11 g, 5.98 mmol) and potassium carbonate (1.65 g, 12.0 mmol), followed by heating at 80° C. for 40 minutes. The reaction mixture was concentrated under reduced pressure, added with water and extracted with ethyl acetate. The organic layer was concentrated under reduced pressure. The residue was dissolved in ethyl acetate (2.00 mL) and added with 4 mol/L hydrogen chloride-methanol solution (2.00 mL), followed by stirring at 0° C. The precipitated crystal was collected by filtration to obtain 5-(2-morpholinoethoxy)-2-nitrobenzaldehyde hydrochloride (1.80 g, 95%).

$^1$H-NMR (270 MHz, DMSO-$d_6$) δ 3.18-3.22 (m, 2H), 3.40-3.84 (m, 4H), 3.88-4.04 (m, 4H), 4.63-4.66 (m, 2H), 7.35 (d, J=2.9 Hz, 1H), 7.43 (dd, J=2.9, 9.0 Hz, 1H), 8.24 (d, J=2.9 Hz, 1H), 10.3 (s, 1H), 11.4 (br, 1H).

Step 2

In a similar manner to Example 1, 3-[2-(5-(2-morpholinoethoxy)-2-nitrophenyl)vinyl]-1H-indazole (460 mg, 66%) was obtained from (1H-indazol-3-ylmethyl)triphenylphosphonium bromide (1.00 g, 2.11 mmol), 5-(2-morpholinoethoxy)-2-nitrobenzaldehyde hydrochloride (560 mg, 1.76 mmol) obtained in Step 1 and potassium carbonate (580 mg, 4.22 mmol).

In a similar manner to Example 2, 2-[2-(1H-indazol-3-yl)vinyl]-4-(2-morpholinoethoxy)phenylamine (423 mg, 99%) was obtained from 3-[2-(5-(2-morpholinoethoxy)-2-nitrophenyl)vinyl]-1H-indazole (460 mg, 1.17 mmol), tin (420 mg, 3.51 mmol) and concentrated hydrochloric acid (9.10 mL).

$^1$H-NMR (270 MHz, DMSO-$d_6$) δ 2.52 (s, 4H), 2.73 (t, J=5.5 Hz, 2H), 3.58-3.61 (m, 4H), 4.34 (t, J=5.5 Hz, 2H); 7.07 (d, J=6.8 Hz, 1H), 7.25 (dd, J=8.2, 6.8 Hz, 1H), 7.42 (dd, J=8.2, 6.8 Hz, 1H), 7.53-7.57 (m, 2H), 7.59 (d, J=8.2 Hz, 1H), 7.70 (d, J=16.5 Hz, 1H), 7.97 (d, J=16.5 Hz, 1H), 8.05-8.12 (m, 1H), 13.2 (br, 1H).

Step 3

In a similar manner to Example 29, Compound 103 (48.9 mg, 73%) was obtained from 3-methyl-2-thiophenecarboxylic acid (60.0 mg, 0.42 mmol), thionyl chloride (0.05 ml, 0.63 mmol), DMF (0.02 mL), 2-[2-(1H-indazol-3-yl)vinyl]-4-(2-morpholinoethoxy)phenylamine (50.0 mg, 0.14 mmol) obtained in Step 2 and triethylamine (0.06 ml, 0.42 mmol).

$^1$H-NMR (270 MHz, DMSO-$d_6$) δ 2.52 (s, 7H), 2.76 (t, J=5.5 Hz, 2H), 3.58-3.61 (m, 4H), 4.34 (t, J=5.5 Hz, 2H), 6.90 (d, J=8.6 Hz, 1H), 7.03 (d, J=5.0 Hz, 1H), 7.07 (dd, J=7.7, 7.7 Hz, 1H), 7.23 (d, J=8.6 Hz, 1H), 7.35 (dd, J=7.9, 7.9 Hz, 1H), 7.47-7.54 (m, 1H), 7.51 (d, J=16.8 Hz, 1H), 7.57 (s, 2H), 7.67 (d, J=5.0 Hz, 1H), 8.01 (d, J=8.1 Hz, 1H), 9.70 (br, 1H), 13.2 (br, 1H).

ESI-MS (m/z); 489 [M+H]$^+$

EXAMPLE 104

(E)-N-{2-[2-(1H-indazol-3-yl)vinyl]-4-(2-morpholinoethoxy)phenyl}-1-methylpyrrole-2-carboxamide (Compound 104)

In a similar manner to Example 28, Compound 104 (46.3 mg, 72%) was obtained from 1-methyl-2-pyrrolecarboxylic acid β-(52.0 mg, 0.42 mmol), thionyl chloride (0.05 ml, 0.63 mmol), DMF (0.02 mL), 2-[2-(1H-indazol-3-yl)vinyl]-4-(2-morpholinoethoxy)phenylamine (50.0 mg, 0.14 mmol) obtained in Step 2 of Example 103 and triethylamine (0.06 ml, 0.42 mmol).

$^1$H-NMR (270 MHz, DMSO-$d_6$) δ 2.52 (s, 4H), 2.73 (t, J=5.9 Hz, 2H), 3.58-3.61 (m, 4H), 3.85 (s, 3H), 4.20 (t, J=5.9 Hz, 2H), 6.11 (d, J=6.4 Hz, 1H), 6.90 (d, J=8.6 Hz, 1H), 6.99-7.00 (m, 1H), 7.06 (dd, J=7.7, 7.7 Hz, 1H), 7.19 (d, J=8.8 Hz, 1H), 7.34 (dd, J=7.7, 7.7 Hz, 1H), 7.47-7.54 (m, 2H), 7.52 (d, J=8.4 Hz, 1H), 7.57 (s, 2H), 7.98 (d, J=8.3 Hz, 1H), 9.62 (br, 1H), 13.1 (br, 1H).

APCI-MS (m/z); 472 [M+H]$^+$

EXAMPLE 105

(E)-N-{5-dimethylamino-2-[2-(1H-indazol-3-yl)vinyl]phenyl}-3-methylthiophene-2-carboxamide (Compound 105)

Step 1

In a similar manner to Example 1, a crude product of {4-[2-(1H-indazol-3-yl)vinyl]-3-nitrophenyl}dimethylamine (436 mg) was obtained from (1H-indazol-3-ylmethyl)triphenylphosphonium bromide (1.00 g, 2.11 mmol), 4-dimethylamino-2-nitrobenzaldehyde (450 mg, 2.32 mmol) and potassium carbonate (580 mg, 4.22 mmol). The crude product was dissolved in ethanol (15.0 mL), and was reacted with tin (751 mg, 6.33 mmol) and concentrated hydrochloric acid (12.0 mL) in a similar manner to Example 2, to obtain {3-amino-4-[2-(1H-indazol-3-yl)vinyl]phenyl}dimethylamine (500 mg, 90%).

ESI-MS (m/z); 265 [M+H]$^+$

Step 2

In a similar manner to Example 29, Compound 105 (48.2 mg, 32%) was obtained from 3-methylthiophene-2-carboxylic acid (162 mg, 1.14 mmol), thionyl chloride (0.12 ml, 1.71 mmol), DMF (0.02 mL), {3-amino-4-[2-(1H-indazol-3-yl)vinyl]phenyl}dimethylamine (100 mg, 0.38 mmol) obtained in Step 1 and triethylamine (0.16 ml, 1.14 mmol).

$^1$H-NMR (270 MHz, DMSO-$d_6$) δ 2.50 (s, 3H), 2.96 (s, 6H), 6.70-6.77 (m, 2H), 7.00-7.05 (m, 2H), 7.25 (d, J=16.6 Hz, 1H), 7.33 (dd, J=8.3, 8.3 Hz, 1H), 7.48 (s, 1H), 7.51-7.55 (m, 1H), 7.68 (d, J=4.8 Hz, 1H), 7.76 (d, J=8.6 Hz, 1H), 7.96 (d, J=8.1 Hz, 1H), 9.72 (br, 1H), 13.0 (br, 1H).

APCI-MS (m/z); 403 [M+H]$^+$

EXAMPLE 106

(E)-5-amino-N-{2-[2-(1H-indazol-3-yl)vinyl]-4-(2-morpholinoethoxy)phenyl}thiophene-2-carboxamide (Compound 106)

In a similar manner to Example 29, a crude product of N-{2-[2-(1H-indazol-3-yl)vinyl]-4-(2-morpholinoethoxy)phenyl}-5-nitrothiophene-2-carboxamide (143 mg, 0.28 mmol) was obtained from 5-nitro-2-thiophenecarboxylic acid (143 mg, 0.81 mmol), thionyl chloride (0.09 ml, 1.21 mmol), DMF (0.02 mL), 2-[2-(1H-indazol-3-yl)vinyl]-4-(2-morpholinoethoxy)phenylamine (100 mg, 0.27 mmol) obtained in Step 2 of Example 103 and triethylamine (0.11 ml, 0.81 mmol). The product was dissolved in ethanol (2.00 mL) and water (2.00 mL), and the solution was reacted with iron powder (310 mg, 5.54 mmol) and ammonium chloride (74.0 mg, 1.35 mmol) to obtain Compound 106 (15.3 mg, 11%).

$^1$H-NMR (270 MHz, DMSO-$d_6$) δ 2.01-2.08 (m, 4H), 2.71-2.76 (m, 2H), 3.59-3.62 (m, 4H), 4.19-4.53 (m, 2H), 5.32 (dd, J=4.3, 4.3 Hz, 1H), 5.92 (d, J=4.3 Hz, 1H), 6.36 (s, 2H), 6.89 (dd, J=8.2, 8.2 Hz, 1H), 7.07 (dd, J=7.7, 7.7 Hz, 1H), 7.17 (d, J=8.6 Hz, 1H), 7.35 (dd, J=7.7, 7.7 Hz, 1H), 7.47-7.55 (m, 3H), 7.58 (d, J=16.6 Hz, 1H), 7.98 (d, J=8.4 Hz, 1H), 9.54 (br, 1H), 13.1 (br, 1H).

ESI-MS (m/z); 490 [M+H]$^+$

EXAMPLE 107

(E)-N-{5-dimethylamino-2-[2-(1H-indazol-3-yl)vinyl]phenyl}-1-methyl-1H-pyrrole-2-carboxamide (Compound 107)

In a similar manner to Example 29, Compound 107 (50.0 mg, 23%) was obtained from 1-methyl-2-pyrrolecarboxylic acid (210 mg, 1.71 mmol), thionyl chloride (0.19 ml, 2.67 mmol), DMF (0.4 mL), {3-amino-4-[2-(1H-indazol-3-yl)vinyl]phenyl}dimethylamine (150.0 mg, 0.57 mmol) obtained in Step 1 of Example 105 and triethylamine (0.24 ml, 1.71 mmol).

$^1$H-NMR (270 MHz, DMSO-$d_6$) δ 2.95 (s, 6H), 3.85 (s, 3H), 6.11-6.14 (m, 1H), 6.65 (d, J=2.6 Hz, 1H), 6.73 (dd, J=8.9, 8.9 Hz, 1H), 6.99-7.04 (m, 3H), 7.13-7.16 (m, 1H), 7.20-7.48 (m, 2H), 7.52 (d, J=16.8 Hz, 1H), 7.76 (d, J=8.9 Hz, 1H), 7.93 (d, J=8.1 Hz, 1H), 9.65 (br, 1H), 12.9 (br, 1H).

APCI-MS (m/z); 386 [M+H]$^+$

EXAMPLE 108

(E)-N-{5-hydroxymethyl-2-[2-(1H-indazol-3-yl)vinyl]phenyl}-3-methylthiophene-2-carboxamide (Compound 108)

In a similar manner to Example 1, (1H-indazol-3-ylmethyl)triphenylphosphonium bromide (4.10 g, 8.66 mmol) was dissolved in methanol (60.0 mL) and a crude product of 4-[2-(1H-indazol-3-yl)vinyl]-3-nitrobenzoic acid methyl ester (0.20 g, 0.62 mmol) was obtained from 4-formyl-3-nitrobenzoic acid methyl (2.44 g, 9.53 mmol) and potassium carbonate (2.93 g, 17.3 mmol). The product was suspended in toluene and diisobutylaluminum hydride (0.95 mol/L, 2.60 mL, 2.48 mmol) was added dropwise thereto at −78° C. Then, the reaction mixture was warmed to 0° C. and treated by sodium sulfate to obtain {4-[2-(1H-indazol-3-yl)vinyl]-3-nitrophenyl}methanol. In a similar manner to Example 2, {3-amino-4-[2-(1H-indazol-3-yl)vinyl]phenyl}methanol (86 mg, 100%) was obtained from {4-[2-(1H-indazol-3-yl)vinyl]-3-nitrophenyl}methanol (100 mg, 0.34 mmol), tin (121 mg, 1.02 mmol) and concentrated hydrochloric acid (0.30 mL).

In a similar manner to Example 29, Compound 108 (67.0 mg, 51%) was obtained from 3-methyl-2-thiophenecarboxylic acid (50.0 mg, 0.68 mmol), thionyl chloride (0.08 ml, 1.02 mmol), DMF (0.02 mL), {3-amino-4-[2-(1H-indazol-3-yl)vinyl]phenyl}methanol (86.0 mg, 0.34 mmol) and triethylamine (0.01 mL, 0.68 mmol).

¹H-NMR (270 MHz, DMSO-d₆) δ 2.50 (s, 3H), 4.54 (s, 2H), 7.05 (d, J=5.1 Hz, 1H), 7.10 (d, J=7.4 Hz, 1H), 7.28 (d, J=8.4 Hz, 1H), 7.33-7.39 (m, 2H), 7.48 (d, J=16.8 Hz, 1H), 7.53 (d, J=8.6 Hz, 1H), 7.62 (d, J=16.8 Hz, 1H), 7.69 (d, J=5.1 Hz, 1H), 7.90 (d, J=8.1 Hz, 1H), 8.02 (d, J=8.4 Hz, 1H), 9.86 (br, 1H), 13.1 (br, 1H).
APCI-MS (m/z); 390 [M+H]⁺

EXAMPLE 109

(E)-N-{2-[2-(1H-indazol-3-yl)vinyl]-6-methoxyphenyl}-1-methyl-1H-pyrrole-2-carboxamide (Compound 109)

In a similar manner to Example 29, Compound 109 (25.0 mg, 35%) was obtained from 1-methyl-2-pyrrolecarboxylic acid (71.0 mg, 0.57 mmol), thionyl chloride (0.06 ml, 0.86 mmol), DMF (0.02 ml), Compound 93 (50.0 mg, 0.19 mmol) and triethylamine (0.08 mL, 0.57 mmol).
¹H-NMR (270 MHz, DMSO-d₆) δ 3.78 (s, 3H), 3.85 (s, 3H), 6.11 (s, 1H), 6.99-7.04 (m, 3H), 7.14 (br, 1H), 7.33 (d, J=8.4 Hz, 2H), 7.48 (d, J=16.6 Hz, 1H), 7.44-7.61 (m, 2H), 7.58 (d, J=16.6 Hz, 1H), 7.88 (d, J=8.2 Hz, 1H), 9.27 (br, 1H), 13.1 (br, 1H).
APCI-MS (m/z); 373 [M+H]⁺

EXAMPLE 110

(E)-N-{4-hydroxy-2-[2-(1H-indazol-3-yl)vinyl]phenyl}-3-methylthiophene-2-carboxamide (Compound 110)

In a similar manner to Example 1, 3-[2-(5-hydroxy-2-nitrophenyl)vinyl]-1H-indazole was obtained from (1H-indazol-3-ylmethyl)triphenylphosphonium bromide (500 mg, 1.06 mmol), 5-hydroxy-2-nitrobenzaldehyde (177 mg, 1.06 mmol) and potassium carbonate (440 mg, 3.18 mmol).
In a similar manner to Example 2, {4-hydroxy-2-[2-(1H-indazol-3-yl)vinyl]phenyl}amine was obtained from 3-[2-(5-hydroxy-2-nitrophenyl)vinyl]-1H-indazole (220 mg, 0.78 mmol), tin (280 mg, 2.34 mmol) and concentrated hydrochloric acid (0.70 mL).
In a similar manner to Example 29, Compound 110 (35.3 mg, 8.9%) was obtained from 3-methyl-2-thiophenecarboxylic acid (0.33 mg, 2.34 mmol), thionyl chloride (0.26 ml, 3.51 mmol), DMF (0.01 mL), {4-hydroxy-2-[2-(1H-indazol-3-yl)vinyl]phenyl}amine (196 mg, 0.78 mmol) and triethylamine (0.33 ml, 2.34 mmol).
¹H-NMR (270 MHz, DMSO-d₆) δ 2.52 (S, 3H), 6.76 (dd, J=8.2, 8.2 Hz, 1H), 7.03 (d, J=4.6 Hz, 1H), 7.09 (d, J=7.1 Hz, 1H), 7.14 (d, J=8.4 Hz, 1H), 7.25 (d, J=2.8 Hz, 1H), 7.33-7.39 (m, 2H), 7.53 (d, J=7.1 Hz, 1H), 7.55 (d, J=17.1 Hz, 1H), 7.66 (d, J=4.6 Hz, 1H), 7.98 (d, J=7.9 Hz, 1H), 9.52 (br, 1H), 9.60 (br, 1H), 13.1 (br, 1H).
ESI-MS (m/z); 376 [M+H]⁺

EXAMPLE 111

(E)-N-{5-(4-aminopiperidin-1-ylcarbonyl)-2-[2-(1H-indazol-3-yl)vinyl]phenyl}-3-methylthiophene-2-carboxamide (Compound III)

In a similar manner to Example 99, Compound III (92.0 mg, 76%) was obtained from Compound 98 (100 mg, 0.25 mmol), piperidin-4-ylcarbamic acid tert-butyl ester (75.0 mg, 0.38 mmol), 1-hydroxybenzotriazole monohydrate (45.0 mg, 0.33 mmol), EDC (70.0 mg, 0.35 mmol), methanol (2.00 mL) and 4 moL/L hydrogen chloride-methanol solution (0.50 mL).
¹H-NMR (270 MHz, DMSO-d₆) δ 1.99 (br, 2H), 2.51 (s, 3H), 3.31 (br, 9H), 7.03 (d, J=5.0 Hz, 1H), 7.11 (dd, J=7.7, 7.7 Hz, 1H), 7.09 (br, 1H), 7.37 (d, J=7.7 Hz 1H), 7.50-7.75 (m, 5H), 7.96 (d, J=7.7 Hz, 1H)), 8.06 (d, J=8.1, Hz, 1H), 9.96 (br, 1H), 13.2 (br, 1H).
ESI-MS (m/z); 486 [M+H]⁺

EXAMPLE 112

(E)-N-{2-[2-(1H-indazol-3-yl)vinyl]-5-(N-propylcarbamoyl)-phenyl}-3-methylthiophene-2-carboxamide (Compound 112)

In a similar manner to Example 28, Compound 112 (110 mg, 99%) was obtained from Compound 98 (100 mg, 0.25 mmol), n-propylamine (0.03 mL, 0.38 mmol), 1-hydroxybenzotriazole monohydrate (44.0 mg, 0.33 mmol), EDC (67.0 mg, 0.35 mmol) and 4-methylmorpholine (0.03 mL, 0.50 mmol).
¹H-NMR (270 MHz, DMSO-d₆) δ 0.91 (t, J=7.2 Hz, 3H), 1.56 (q, J=7.2 Hz, 2H), 2.50 (s, 3H), 3.25 (q, J=7.2 Hz, 2H), 7.06 (d, J=5.0 Hz, 1H), 7.12 (d, J=8.1 Hz, 1H), 7.38 (dd, J=8.4, 8.4 Hz, 1H), 7.55 (d, J=8.6 Hz 1H), 7.63 (s, 2H), 7.72 (d, J=5.0 Hz, 1H), 7.81-7.88 (m, 2H), 8.04 (dd, J=8.1, 8.1 Hz, 2H), 8.50-8.55 (br, 1H), 9.97 (br, 1H), 13.2 (br, 1H).
ESI-MS (m/z); 445 [M+H]⁺

EXAMPLE 113

(E)-N-{5-(N-ethyl-N-methylcarbamoyl)-2-[2-(1H-indazol-3-yl)vinyl]phenyl}-3-methylthiophene-2-carboxamide (Compound 113)

In a similar manner to Example 28, Compound 113 (96.9 mg, 88%) was obtained from Compound 98 (100 mg, 0.25 mmol), N-methylethylamine (0.03 mL, 0.38 mmol), 1-hydroxybenzotriazole monohydrate (44.0 mg, 0.33 mmol), EDC (67.0 mg, 0.35 mmol) and 4-methylmorpholine (0.03 mL, 0.50 mmol).
¹H-NMR (270 MHz, DMSO-d₆) δ 1.13-1.20 (m, 3H), 1.24 (br, 3H), (s, 3H), 3.32-3.47 (m, 2H), 7.06 (d, J=5.0 Hz, 1H), (dd, J=7.9, 7.9 Hz, 1H), 7.32-7.44 (m, 3H), 7.54-7.68 (m, 1H), 7.58 (d, J=16.7 Hz, 1H), 7.65 (d, J=16.7 Hz, 1H), 7.71 (d, J=5.0 Hz, 1H), 8.03 (d, J=8.1 Hz, 2H), (br, 1H), 13.2 (br, 1H).
APCI-MS (m/z); 445 [M+H]⁺

EXAMPLE 114

(E)-N-{5-[N-(2-hydroxyethyl)carbamoyl]-2-[2-(1H-indazol-3-yl)vinyl]phenyl}-3-methylthiophene-2-carboxamide (Compound 114)

In a similar manner to Example 28, Compound 114 (79.0 mg, 84%) was obtained from Compound 98 (85.0 mg, 0.21 mmol), ethanolamine (0.02 mL, 0.32 mmol), 1-hydroxybenzotriazole monohydrate (57.0 mg, 0.27 mmol) and EDC (57.0 mg, 0.29 mmol).
¹H-NMR (270 MHz, DMSO-d₆) δ 2.51 (s, 3H), 3.36-3.38 (m, 2H), 3.54 (q, J=5.7 Hz, 2H), 4.75 (t, J=5.7 Hz, 1H), 7.07 (d, J=5.0 Hz, 1H), 7.12 (d, J=7.9 Hz, 1H), 7.38 (dd, J=7.7, 7.7 Hz, 1H), 7.55 (d, J=8.4 Hz, 1H), 7.64 (s, 2H), 7.72 (d, J=5.0 Hz, 1H), 7.82-7.89 (m, 2H), 8.05 (dd, J=8.4, 8.4 Hz, 2H), 8.50-8.54 (m, 1H), 9.99 (br, 1H), 13.2 (br, 1H).
APCI-MS (m/z); 447 [M+H]⁺

EXAMPLE 115

(E)-N-{2-[2-(1H-indazol-3-yl)vinyl]-5-(morpholin-4-ylcarbonyl)phenyl}-3-methylthiophene-2-carboxamide hydrochloride (Compound 115; hydrochloride of Compound 100)

Compound 100 (400 mg, 0.84 mmol) was dissolved in methanol (10.0 mL) and the solution was added with 4 moL/L hydrogen chloride-methanol solution (2.00 mL), followed by stirring at room temperature for 1 hour. The reaction mixture was concentrated under reduced pressure and crystallized from acetone and ethanol to obtain Compound 115 (240 mg, 56%).

$^1$H-NMR (270 MHz, DMSO-$d_6$) δ 2.50 (s, 3H), 3.63 (br, 8H), 7.06 (d, J=5.0 Hz, 1H), 7.12 (d, J=7.8 Hz, 1H), 7.36-7.40 (m, 2H), 7.50 (d, J=16.7 Hz, 1H), 7.55 (d, J=8.1 Hz, 1H), 7.58 (d, J=16.7 Hz 1H), 7.58-7.62 (m, 1H), 7.71 (d, J=5.0 Hz, 1H), 8.03 (d, J=8.1 Hz, 2H), 9.98 (br, 1H).

ESI-MS (m/z); 473 [M+H]$^+$

EXAMPLE 116

(E)-N-{2-[2-(1H-indazol-3-yl)vinyl]-5-(pyrrolidin-1-ylcarbonyl)phenyl}-3-methylthiophene-2-carboxamide (Compound 116)

In a similar manner to Example 28, Compound 116 (109 mg, 96%) was obtained from Compound 98 (100 mg, 0.25 mmol), pyrrolidine (0.03 mL, 0.38 mmol), 1-hydroxybenzotriazole monohydrate (44.0 mg, 0.33 mmol) and EDC (67.0 mg, 0.35 mmol).

$^1$H-NMR (270 MHz, DMSO-$d_6$) δ 1.87 (br, 4H), 2.51 (s, 3H), 2.74 (br, 4H), 7.06 (d, J=5.0 Hz, 1H), 7.11 (dd, J=8.1, 8.1 Hz, 1H), 7.38 (dd, J=8.1, 7.1 Hz, 1H), 7.48 (d, J=8.1 Hz, 1H), 7.53-7.61 (m, 1H), 7.57 (d, J=7.1 Hz, 1H), 7.58 (d, J=16.8 Hz, 1H), 7.66 (d, J=16.8 Hz, 1H), 7.71 (d, J=5.0 Hz, 1H), 8.03 (d, J=8.1, 8.1 Hz, 2H), 9.96 (br, 1H), 13.2 (br, 1H).

APCI-MS (m/z); 457 [M+H]$^+$

EXAMPLE 117

(E)-N-{5-(N,N-dimethylcarbamoyl)-2-[2-(1H-indazol-3-yl)vinyl]phenyl}-3-methylthiophene-2-carboxamide (Compound 117)

In a similar manner to Example 28, Compound 117 (68.0 mg, 48%) was obtained from Compound 98 (200 mg, 0.50 mmol), dimethylamine hydrochloride (61.0 mg, 0.75 mmol), EDC (134 mg, 0.70 mmol) and 4-methylmorpholine (0.09 mL, 1.00 mmol).

$^1$H-NMR (270 MHz, DMSO-$d_6$) δ 2.51 (s, 3H), 3.00 (s, 6H), 7.06 (d, J=5.0 Hz, 1H), 7.11 (dd, J=8.1, 7.1 Hz, 1H), 7.38 (dd, J=8.4, 7.1 Hz, 2H), 7.53-7.61 (m, 2H), 7.55 (d, J=8.4 Hz, 1H), 7.66 (d, J=16.8 Hz, 1H), 7.71 (d, J=4.9 Hz, 1H), 8.02 (d, J=8.4, 8.4 Hz, 2H), 9.95 (br, 1H), 13.2 (br, 1H).

ESI-MS (m/z); 431 [M+H]$^+$

EXAMPLE 118

(E)-N-{5-(N-cyclopropylcarbamoyl)-2-[2-(1H-indazol-3-yl)vinyl]phenyl}-3-methylthiophene-2-carboxamide (Compound 118)

In a similar manner to Example 28, Compound 118 (107 mg, 48%) was obtained from Compound 98 (200 mg, 0.50 mmol), cyclopropylamine (0.05 mL, 0.75 mmol) and EDC (134 mg, 0.70 mmol).

$^1$H-NMR (270 MHz, DMSO-$d_6$) δ 0.57-0.75 (m, 4H), 2.51 (s, 3H), 2.85-2.92 (m, 1H), 7.07 (d, J=4.9 Hz, 1H), 7.11 (d, J=8.9 Hz, 1H), 7.37 (dd, J=8.4, 7.1 Hz, 1H), 7.55 (d, J=8.4 Hz, 1H), 7.63 (s, 2H), 7.71 (d, J=4.9 Hz, 1H), 7.76 (d, J=17.1 Hz, 1H), 7.82 (d, J=17.1 Hz, 1H), 8.03 (dd, J=8.1, 8.1 Hz, 2H), 8.51 (d, J=4.3 Hz, 1H), 9.97 (br, 1H), 13.2 (br, 1H).

ESI-MS (m/z); 443 [M+H]$^+$

EXAMPLE 119

(E)-N-{5-(1,4-dioxa-8-azaspiro[4,5]decane-8-carbonyl)-2-[2-(1H-indazol-3-yl)vinyl]phenyl}-3-methylthiophene-2-carboxamide (Compound 119)

In a similar manner to Example 28, Compound 119 (98.9 mg, 76%) was obtained from Compound 98 (100 mg, 0.25 mmol), 1,4-dioxa-8-azaspiro[4,5]decane (0.05 mL, 0.38 mmol), 1-hydroxybenzotriazole monohydrate (44.0 mg, 0.33 mmol) and EDC (67.0 mg, 0.35 mmol).

$^1$H-NMR (270 MHz, DMSO-$d_6$) δ 1.68 (br, 4H), 2.51 (s, 3H), 3.55 (br, 4H), 3.92 (s, 4H), 7.06 (d, J=4.9 Hz, 1H), 7.12 (d, J=7.9 Hz, 1H), 7.35-7.40 (m, 2H), 7.47-7.70 (m, 3H), 7.54 (d, J=8.1 Hz, 1H), 7.71 (d, J=4.9 Hz, 1H), 8.02 (dd, J 8.1, 8.1 Hz, 2H), 9.95 (br, 1H), 13.2 (br, 1H).

ESI-MS (m/z); 529 [M+H]$^+$

EXAMPLE 120

(E)-N-{2-[2-(1H-indazol-3-yl)vinyl]-5-(4-methoxypiperidin-1-ylcarbonyl)phenyl}-3-methylthiophene-2-carboxamide (Compound 120)

In a similar manner to Example 28, Compound 120 (131 mg, 97%) was obtained from Compound 98 (100 mg, 0.25 mmol), 4-methoxypiperidine (0.05 mL, 0.38 mmol), 1-hydroxybenzotriazole monohydrate (44.0 mg, 0.33 mmol) and EDC (67.0 mg, 0.35 mmol).

$^1$H-NMR (270 MHz, DMSO-$d_6$) δ 1.48 (br, 2H), 1.85 (br, 2H), 2.51 (s, 3H), 3.27 (s, 3H), 3.44-3.61 (m, 1H), 3.90-4.07 (m, 4H), 7.06 (d, J=5.3 Hz, 1H), 7.12 (d, J=7.7 Hz, 1H), 7.33-7.44 (m, 3H), 7.53-7.62 (m, 2H), 7.55 (d, J=8.2 Hz, 1H), 7.65 (d, J=16.8 Hz, 1H), 7.71 (d, J=5.1 Hz, 1H), 8.02 (dd, J=8.1, 8.1 Hz, 1H), 9.96 (br, 1H), 13.2 (br, 1H).

APCI-MS (m/z); 501 [M+H]$^+$

EXAMPLE 121

(E)-N-{2-[2-(1H-indazol-3-yl)vinyl]-5-(methoxymethyl)phenyl}-3-methylthiophene-2-carboxamide (Compound 121)

To Compound 108 (50.0 mg, 0.13 mmol), methanol (1.00 mL) and sulfuric acid (0.07 mL, 1.30 mmol) were added and the mixture was reacted in a microwave reaction vessel at 100° C. for 5 minutes to obtain Compound 121 (31.6 mg, 61%).

$^1$H-NMR (270 MHz, DMSO-$d_6$) δ 2.51 (s, 3H), 3.33 (s, 3H), 4.46 (s, 2H), 7.05 (d, J=4.8 Hz, 1H), 7.10 (d, J=7.9 Hz, 1H), 7.26-7.52 (m, 4H), 7.56 (d, J=16.6 Hz, 1H), 7.62 (d, J=16.6 Hz, 1H), 7.70 (d, J=4.8 Hz, 1H), 7.93 (d, J=8.2 Hz, 1H), 8.02 (dd, J=8.2 Hz, 1H), 9.87 (br, 1H), 13.1 (br, 1H).

APCI-MS (m/z); 404 [M+H]$^+$

EXAMPLE 122

(E)-N-{2-[2-(1H-indazol-3-yl)vinyl]-5-(4-methanesulfonylpiperidin-1-ylcarbonyl)phenyl}-3-methylthiophene-2-carboxamide (Compound 122)

In a similar manner to Example 28, Compound 122 (69.9 mg, 52%) was obtained from Compound 98 (100 mg, 0.25 mmol), 4-(methylsulfonyl)piperidine hydrochloride (71.0 mg, 0.38 mmol), 1-hydroxybenzotriazole monohydrate (44.0 mg, 0.33 mmol), EDC (67.0 mg, 0.35 mmol) and 4-methylmorpholine (0.03 mL, 0.50 mmol).

$^1$H-NMR (270 MHz, DMSO-d$_6$) δ 1.51-1.67 (m, 1H), 1.99-2.08 (m, 2H), 2.51 (s, 3H), 2.97 (br, 2H), 3.22-3.37 (m, 4H), 3.46 (s, 3H), 7.07 (d, J=5.0 Hz, 1H), 7.12 (d, J=8.3 Hz, 1H), 7.38 (dd, J=7.4, 7.4 Hz, 2H), 7.50 (d, J=17.0 Hz, 1H), 7.55 (d, J=8.3 Hz, 1H), 7.62-7.72 (m, 1H), 7.65 (d, J=17.0 Hz, 1H), 7.72 (d, J=5.0 Hz, 1H), 8.03 (dd, J=8.3, 8.3 Hz, 2H), 9.99 (br, 1H), 13.2 (br, 1H).

APCI-MS (m/z); 549 [M+H]$^+$

EXAMPLE 123

(E)-N-{2-[2-(1H-indazol-3-yl)vinyl]-5-(morpholin-4-ylcarbonyl)phenyl}-1-methylpyrrole-2-carboxamide (Compound 123)

In a similar manner to Example 28, Compound 123 (20.1 mg, 52%) was obtained from 4-[2-(1H-indazol-3-yl)vinyl]-3-[(1-methylpyrrol-2-ylcarbonyl)amino]benzoic acid (30.0 mg, 0.08 mmol), morpholine (0.01 mL, 0.12 mmol), 1-hydroxybenzotriazole monohydrate (14.0 mg, 0.10 mmol) and EDC (22.0 mg, 0.11 mmol).

$^1$H-NMR (270 MHz, DMSO-d$_6$) δ 3.51-3.64 (m, 8H), 3.88 (s, 3H), 6.14-6.15 (m, 1H), 7.03-7.16 (m, 3H), 7.33-7.39 (m, 3H), 7.54 (d, J=7.7 Hz, 1H), 7.61 (d, J=5.6 Hz, 2H), 7.99-8.03 (m, 2H), 9.87 (br, 1H), 13.2 (br, 1H).

APCI-MS (m/z); 456 [M+H]$^+$

EXAMPLE 124

(E)-N-{5-(N,N-diethylcarbamoyl)-2-[2-(1H-indazol-3-yl)vinyl]phenyl}-3-methylthiophene-2-carboxamide hydrochloride (Compound 124; hydrochloride of Compound 101)

In a similar manner to Example 115, Compound 124 (370 mg, 76%) was obtained from Compound 101, methanol (6.0 mL) and 4 mol/L hydrogen chloride-methanol solution (2.00 mL).

$^1$H-NMR (270 MHz, DMSO-d$_6$) δ 1.14 (br, 6H), 2.51 (s, 3H), 3.36 (br, 4H), 7.06 (d, J=5.0 Hz, 1H), 7.11 (dd, J=7.7, 7.7 Hz, 1H), 7.30 (d, J=7.7 Hz 1H), 7.35-7.40 (m, 2H), 7.54-7.62 (m, 3H), 7.71 (d, J=5.0 Hz, 1H), 8.00 (d, J=8.1, Hz, 1H), 8.05 (d, J=8.1, Hz, 1H), 9.96 (br, 1H).

ESI-MS (m/z); 459 [M+H]$^+$

EXAMPLE 125

(E)-N-{5-(N,N-dimethylcarbamoyl)-2-[2-(1H-indazol-3-yl)vinyl]phenyl}-3-methylthiophene-2-carboxamide hydrochloride (Compound 125; hydrochloride of Compound 117)

In a similar manner to Example 115, Compound 125 (360 mg, 78%) was obtained from Compound 117, methanol (6.0 mL) and 4 mol/L hydrogen chloride-methanol solution (2.0 mL).

$^1$H-NMR (270 MHz, DMSO-d$_6$) δ 2.51 (s, 3H), 3.00 (s, 6H), 7.06 (d, J=5.0 Hz, 1H), 7.11 (dd, J=8.1, 7.1 Hz, 1H), 7.38 (dd, J=8.4, 7.1 Hz, 2H), 7.53-7.61 (m, 2H), 7.55 (d, J=8.4 Hz, 1H), 7.66 (d, J=16.8 Hz, 1H), 7.71 (d, J=4.9 Hz, 1H), 8.02 (dd, J=8.4, 8.4 Hz, 2H), 9.95 (br, 1H).

ESI-MS (m/z); 431 [M+H]$^+$

EXAMPLE 126

(E)-N-{2-[2-(1H-indazol-3-yl)vinyl]-5-(4-methylpiperazin-1-ylcarbonyl)phenyl}-3-methylthiophene-2-carboxamide (Compound 126)

In a similar manner to Example 28, Compound 126 (400 mg, 84%) was obtained from Compound 98 (400 mg, 0.99 mmol), 4-methylpiperazine (0.17 mL, 1.49 mmol), 1-hydroxybenzotriazole monohydrate (174 mg, 1.29 mmol) and EDC (270 mg, 1.39 mmol).

$^1$H-NMR (270 MHz, DMSO-d$_6$) δ 1.99-2.08 (m, 4H), 2.51 (s, 3H), 3.31 (s, 3H), 3.53 (br, 4H), 7.06 (d, J=5.0 Hz, 1H), 7.12 (d, J=8.1 Hz, 1H), 7.33-7.44 (m, 3H), 7.55 (d, J=8.1 Hz, 1H), 7.60-7.72 (m, 2H), 7.71 (d, J=5.0 Hz, 1H), 8.02 (dd, J=7.9, 7.9 Hz, 2H), 9.96 (br, 1H), 13.2 (br, 1H).

ESI-MS (m/z); 486 [M+H]$^+$

EXAMPLE 127

(E)-N-{2-[2-(1H-indazol-3-yl)vinyl]-5-(4-methoxypiperidin-1-ylcarbonyl)phenyl}-3-methylthiophene-2-carboxamide hydrochloride (Compound 127; hydrochloride of Compound 120)

Compound 120 (250 mg, 0.47 mmol) was added with methanol (6.00 mL) and 4 mol/L hydrogen chloride-methanol solution (2.00 mL) and the mixture was stirred at 40° C. for 1 hour. The product was crystallized from acetone to obtain Compound 127 (240 mg, 90%).

$^1$H-NMR (270 MHz, DMSO-d$_6$) δ 1.48 (br, 2H), 1.85 (br, 2H), 2.51 (s, 3H), 3.27 (s, 3H), 3.44-3.61 (m, 1H), 3.90-4.07 (m, 4H), 7.06 (d, J=5.3 Hz, 1H), 7.12 (d, J=7.7 Hz, 1H), 7.33-7.44 (m, 3H), 7.53-7.62 (m, 2H), 7.55 (d, J=8.2 Hz, 1H), 7.65 (d, J=16.8 Hz, 1H), 7.71 (d, J=5.1 Hz, 1H), 8.02 (dd, J=8.1, 8.1 Hz, 1H), 9.96 (br, 1H).

APCI-MS (m/z); 501 [M+H]$^+$

EXAMPLE 128

(E)-N-{2-[2-(1H-indazol-3-yl)vinyl]-5-(4-methylpiperazine-1-ylcarbonyl)phenyl}-3-methylthiophene-2-carboxamide hydrochloride (Compound 128; hydrochloride of Compound 126)

Compound 126 (350 mg, 0.72 mmol) was added with methanol (1.0 mL) and 4 mol/L hydrogen chloride-methanol solution (0.25 mL) and stirred at 40° C. for 1 hour. The product was crystallized from acetone to obtain Compound 128 (220 mg, 59%).

$^1$H-NMR (270 MHz, DMSO-d$_6$) δ 1.99-2.08 (m, 4H), 2.51 (s, 3H), 3.31 (s, 3H), 3.53 (br, 4H), 7.06 (d, J=5.0 Hz, 1H), 7.12 (d, J=8.1 Hz, 1H), 7.33-7.44 (m, 3H), 7.55 (d, J=8.1 Hz, 1H), 7.60-7.72 (m, 2H), 7.71 (d, J=5.0 Hz, 1H), 8.02 (dd, J=7.9, 7.9 Hz, 2H), 9.96 (br, 1H).

ESI-MS (m/z); 486 [M+H]$^+$

EXAMPLE 129

(E)-N-{5-(1,4-dioxa-8-azaspiro[4,5]decane-8-carbonyl)-2-[2-(1H-indazol-3-yl)vinyl]phenyl}-3-methylthiophene-2-carboxamide hydrochloride (Compound 132; hydrochloride of Compound 119)

Compound 119 (290 mg, 0.55 mmol) was added with 1,4-dioxane (5.00 mL) and 4 mol/L hydrogen chloride-dioxane solution (0.10 mL), and the mixture was reacted at 40° C. for 30 minutes to obtain Compound 129 (230 mg, 74%).

$^1$H-NMR (270 MHz, DMSO-$d_6$) δ 1.68 (br, 4H), 2.51 (s, 3H), 3.55 (br, 4H), 3.92 (s, 4H), 7.06 (d, J=4.9 Hz, 1H), 7.12 (d, J=7.9 Hz, 1H), 7.35-7.40 (m, 2H), 7.47-7.70 (m, 4H), 7.54 (d, J=8.1 Hz, 1H), 7.71 (d, J=4.9 Hz, 1H), 8.02 (dd, J=8.1, 8.1 Hz, 2H), 9.95 (br, 1H).

ESI-MS (m/z); 529 [M+H]$^+$

EXAMPLE 130

(E)-N-{6-[2-(1H-indazol-3-yl)vinyl]benzo[1,3]dioxol-5-yl}-3-methylthiophene-2-carboxamide (Compound 130)

Step 1

In a similar manner to Example 1, 3-[2-(4,5-methylenedioxy-2-nitrophenyl)vinyl]indazole was obtained from (1H-indazol-3-ylmethyl)triphenylphosphonium bromide (1.00 g, 2.11 mmol), 6-nitropiperonal (344 mg, 1.76 mmol) and potassium carbonate (580 mg, 4.22 mmol). Further, in a similar manner to Example 2, (E)-{6-[2-(1H-indazol-3-yl)vinyl]benzo[1,3]dioxol-5-yl}amine (470 mg, 96%) was obtained from 3-[2-(4,5-methylenedioxy-2-nitrophenyl)vinyl]indazol obtained above, tin (571 mg, 4.80 mmol) and concentrated hydrochloric acid (12.5 mL).

APCI-MS (m/z); 280 [M+H]$^+$

Step 2

In a similar manner to Example 29, Compound 130 (45.2 mg, 63%) was obtained from 3-methyl-2-thiophenecarboxylic acid (77 mg, 0.54 mmol), thionyl chloride (0.06 ml, 0.81 mmol), DMF (0.02 mL), (E)-{6-[2-(1H-indazol-3-yl)vinyl]benzo[1,3]dioxol-5-yl}amine (50.0 mg, 0.18 mmol) obtained in Step 1 and triethylamine (0.08 ml, 0.54 mmol).

$^1$H-NMR (270 MHz, DMSO-$d_6$) δ 2.52 (s, 3H), 6.66 (s, 2H), 7.49 (s, 1H), 7.61 (d, J=5.0 Hz, 1H), 7.60-7.65 (m, 1H), 7.91 (dd, J=7.1, 7.1 Hz, 1H), 7.98 (d, J=16.6 Hz, 1H), 8.08 (d, J=7.1 Hz, 1H), 8.11 (d, J=16.6 Hz, 1H), 8.12 (d, J=7.1 Hz, 1H), 8.25 (d, J=5.0 Hz, 1H), 8.56 (d, J=8.1 Hz, 1H), 10.3 (br, 1H), 13.6 (br, 1H).

APCI-MS (m/z); 404 [M+H]$^+$

EXAMPLE 131

(E)-N-{6-[2-(1H-indazol-3-yl)vinyl]benzo[1,3]dioxol-5-yl}-1-methylpyrrole-2-carboxamide (Compound 131)

In a similar manner to Example 29, Compound 131 (51.0 mg, 74%) was obtained from 1-methyl-2-pyrrolecarboxylic acid (52.0 mg, 0.42 mmol), thionyl chloride (0.05 ml, 0.63 mmol), DMF (0.02 mL), {6-[2-(1H-indazol-3-yl)vinyl]benzo[1,3]dioxol-5-yl}amine (50.0 mg, 0.14 mmol) and triethylamine (0.06 ml, 0.42 mmol).

$^1$H-NMR (270 MHz, DMSO-$d_6$) δ 3.85 (s, 3H), 6.08 (s, 2H), 6.12 (d, J=6.4 Hz, 1H), 6.87 (s, 1H), 7.00-7.13 (m, 3H), 7.30-7.48 (m, 4H), 7.54 (d, J=16.9 Hz, 1H), 7.96 (d, J=7.7 Hz, 1H), 9.66 (br, 1H), 13.0 (br, 1H).

ESI-MS (m/z); 387 [M+H]$^+$

EXAMPLE 132

(E)-5-amino-N-{6-[2-(1H-indazol-3-yl)vinyl]benzo[1,3]dioxol-5-yl}thiophene-2-carboxamide (Compound 132)

In a similar manner to Example 29, (E)-N-{6-[2-(1H-indazol-3-yl)vinyl]benzo[1,3]dioxol-5-yl}-5-nitrothiophene-2-carboxamide was obtained from 5-nitro-2-thiophenecarboxylic acid (223 mg, 1.29 mmol), thionyl chloride (0.14 ml, 1.94 mmol), DMF (0.04 mL), {6-[2-(1H-indazol-3-yl)vinyl]benzo[1,3]dioxol-5-yl}amine (120 mg, 0.43 mmol) and triethylamine (0.11 ml, 0.86 mmol).

In a similar manner to Example 2, Compound 132 (53.0 mg, 31%) was obtained from (E)-N-{6-[2-(1H-indazol-3-yl)vinyl]benzo[1,3]dioxol-5-yl}-5-nitrothiophene-2-carboxamide, ethanol (3.00 mL), water (3.00 mL), iron powder (480 mg, 8.60 mmol) and ammonium chloride (115 mg, 2.15 mmol).

$^1$H-NMR (270 MHz, DMSO-$d_6$) δ 1.99 (s, 2H), 5.92 (d, J=3.9 Hz, 1H), 6.08 (s, 2H), 6.39 (s, 2H), 6.86 (s, 1H), 7.06 (dd, J=7.9, 7.9 Hz, 1H), 7.32-7.42 (m, 1H), 7.51 (d, J=7.9 Hz, 1H), 7.53 (d, J=17.1 Hz, 1H), 7.63 (d, J=3.5 Hz, 1H), 7.97 (d, J=7.9 Hz, 1H), 9.60 (br, 1H), 13.0 (br, 1H).

ESI-MS (m/z); 405 [M+H]$^+$

EXAMPLE 133

(E)-4-acetyl-1-{2-[2-(1H-indazol-3-yl)vinyl]phenyl}piperazine (Compound 133)

Step 1

To a solution of (1H-indazol-3-ylmethyl)triphenylphosphonium bromide (3.0 g, 6.3 mmol) in methanol (18 mL), DBU (1.4 mL, 9.5 mmol) was added dropwise and 2-bromobenzaldehyde (0.81 mL, 7.0 mmol) was further added, followed by stirring at room temperature for 1.5 hours. The reaction mixture was concentrated under reduced pressure and the residue was purified by silica gel column chromatography (chloroform/methanol=100/0 to 95/5). The obtained compound was washed with methanol (15 mL) and dried under reduced pressure to obtain (E)-3-[2-(2-bromophenyl)vinyl]-1H-indazole (0.22 g, 12%).

$^1$H-NMR (300 MHz, DMSO-$d_6$) δ 7.25 (t, J=7.8 Hz, 1H), 7.25 (t, J=7.2 Hz, 1H), 7.42 (t, J=8.4 Hz, 1H), 7.45 (t, J=7.8 Hz, 1H), 7.58 (d, J=7.8 Hz, 1H), 7.60 (d, J=16.5 Hz, 1H), 7.70 (d, J=7.8 Hz, 1H), 7.80 (d, J=16.5 Hz, 1H), 8.00 (d, J=7.2 Hz, 1H), 8.10 (d, J=8.4 Hz, 1H), 13.28 (s, 1H).

APCI-MS (m/z); 299 [M+H]$^+$

Step 2

To a solution of (E)-3-[2-(2-bromophenyl)vinyl]-1H-indazole (0.26 g, 0.86 mmol) obtained in Step 1 in acetonitrile (1.0 mL), di-tert-butyl dicarbonate (0.22 g, 1.0 mmol) and 4-(dimethylamino)pyridine (0.011 g, 0.086 mmol) were added, followed by stirring at room temperature for 1.0 hour. The reaction mixture was added with water and ethyl acetate to separate the mixture into organic layer and aqueous layer and the organic layer was concentrated under reduced pressure. The residue was purified by silica gel column chromatography (chloroform) to obtain (E)-3-[2-(2-bromophenyl)vinyl]indazole-1-carboxylic acid tert-butyl ester (0.30 g, 89%).

¹H-NMR (300 MHz, DMSO-d₆) δ 1.68 (s, 9H), 7.32 (t, J=8.1 Hz, 1H), 7.45 (t, J=8.1 Hz, 1H), 7.50 (t, J=7.5 Hz, 1H), 7.66 (d, J=16.5 Hz, 1H), 7.69 (t, J=8.1 Hz, 1H), 7.73 (d, J=8.1 Hz, 1H), 7.93 (d, J=16.5 Hz, 1H), 8.10 (d, J=7.5 Hz, 1H), 8.16 (d, J=8.4 Hz, 1H), 8.21 (d, J=8.1 Hz, 1H).

ESI-MS (m/z); 399 [M+H]⁺

Step 3

To a solution of (E)-3-[2-(2-bromophenyl)vinyl]indazole-1-carboxylic acid tert-butyl ester (0.23 g, 0.57 mmol) obtained in Step 2 in toluene (1.5 mL), 1-acetylpiperazine (0.15 g, 1.1 mmol), potassium carbonate (0.20 mg, 1.4 mmol), dicyclohexyl(2',4',6'-triisopropylbiphenyl-2-yl)phosphane (0.068 g, 0.14 mmol) and tris(dibenzylideneacetone)dipalladium (0.052 g, 0.57 mmol) were sequentially added and, the mixture was stirred at 121° C. for 10 minutes under microwave (300 W) irradiation. The reaction mixture was added with water and ethyl acetate to separate the mixture into organic layer and aqueous layer and the organic layer was concentrated under reduced pressure. The residue was purified by silica gel column chromatography (hexane/ethyl acetate=90/10 to 50/50) to obtain (E)-3-{2-[2-(4-acetylpiperazin-1-yl)phenyl]vinyl}indazol-1-carboxylic acid tert-butyl ester (0.042 g, 17%).

¹H-NMR (300 MHz, CDCl₃) δ 1.75 (s, 9H), 2.13 (s, 3H), 2.94-3.05 (brt, 4H), 3.60-3.70 (brt, 2H), 3.76-3.88 (brt, 2H), 7.07 (d, J=6.9 Hz, 1H), 7.17 (t, J=7.5, 1H), 7.30 (t, J=7.5 Hz, 1H), 7.37 (d, J=17.7 Hz, 1H), 7.41 (t, J=6.9 Hz, 1H), 7.50 (d, J=17.7 Hz, 1H), 7.57 (t, J=6.9 Hz, 1H), 7.70 (d, J=7.5 Hz, 1H), 8.04 (d, J=7.5 Hz, 1H), 8.22 (d, J=7.5 Hz, 1H).

Step 4

A solution of (E)-3-{2-[2-(4-acetylpiperazin-1-yl)phenyl]vinyl}indazole-1-carboxylic acid tert-butyl ester (41 mg, 0.094 mmol) obtained in Step 3 in ethyl acetate (1.5 mL) was added with 4.0 mol/L hydrogen chloride-ethyl acetate solution (0.082 mL, 0.32 mmol) and stirred at room temperature for 2.0 hours, followed by stirring under heating and reflux for 2.0 hours. The reaction mixture was added with saturated aqueous sodium hydrogencarbonate solution and ethyl acetate to separate the mixture into organic layer and aqueous layer and the aqueous layer was extracted with ethyl acetate 2 times. All organic layers were gathered and concentrated under reduced pressure. The residue was purified by silica gel column chromatography (chloroform/methanol=90/10) to obtain Compound 133 (13 mg, 41%).

¹H-NMR (270 MHz, DMSO-d₆) δ 2.03 (s, 3H), 2.81-3.06 (br, 4H), 3.56-3.76 (brt, 4H), 7.11 (d, J=7.8 Hz, 1H), 7.12 (t, J=7.8 Hz, 1H), 7.24 (t, J=7.3 Hz, 1H), 7.28 (t, J=7.3 Hz, 1H), 7.39 (t, J=6.8 Hz, 1H), 7.50 (d, J=16.7 Hz, 1H), 7.56 (d, J=8.2 Hz, 1H), 7.79 (d, J=16.7 Hz, 1H), 7.81 (d, J=6.8 Hz, 1H), 8.07 (d, J=8.2 Hz, 1H), 13.13 (s, 1H).

APCI-MS (m/z); 347 [M+H]⁺

EXAMPLE 134

(E)-2-{2-[2-(1H-indazol-3-yl)vinyl]phenoxy}ethanol (Compound 134)

To a solution of (1H-indazol-3-ylmethyl)triphenylphosphonium bromide (0.10 g, 0.21 mmol) in methanol (0.60 mL), DBU (0.079 mL, 0.53 mmol) was added and 2-(2-hydroxyethoxybenzaldehyde (0.039 g, 0.23 mmol) was further added, followed by stirring at room temperature for 2.0 hours. The reaction mixture was concentrated under reduced pressure and the residue was purified by silica gel column chromatography (chloroform/methanol=100/0 to 95/5). The obtained compound was added with 2.0 mol/L hydrogen chloride-ethyl acetate solution (2.0 mL) and washed, then the precipitated solid was collected by filtration. The obtained solid was added with ethyl acetate and saturated aqueous sodium hydrogencarbonate solution to separate the mixture into organic layer and aqueous layer. The organic layer was concentrated under reduced pressure and the residue was dried under reduced pressure to obtain Compound 134 (0.024 g, 9%).

¹H-NMR (270 MHz, DMSO-d₆) δ 3.83 (t, J=4.8 Hz, 2H), 4.11 (t, J=4.8 Hz, 2H), 6.99 (t, J=7.9 Hz, 1H), 7.07 (d, J=7.9 Hz, 1H), 7.19 (t, J=8.1 Hz, 1H), 7.26 (t, J=6.6 Hz, 1H), 7.39 (t, J=6.6 Hz, 1H), 7.56 (d, J=8.1 Hz, 1H), 7.57 (d, J=16.6 Hz, 1H), 7.77 (d, J=8.1 Hz, 1H), 7.79 (d, J=16.6 Hz, 1H), 8.07 (d, J=8.1 Hz, 1H).

APCI-MS (m/z); 281 [M+H]⁺

EXAMPLE 135

(E)-3-[2-(2-methoxyphenyl)vinyl]-1H-indazole (Compound 135)

In a similar manner to Example 134, Compound 135 (0.015 g, 8%) was obtained from (1H-indazol-3-ylmethyl)triphenylphosphonium bromide (0.10 g, 0.21 mmol), DBU (0.047 mL, 0.32 mmol) and 2-methoxybenzaldehyde (0.028 mL, 0.23 mmol).

¹H-NMR (300 MHz, DMSO-d₆) δ 3.90 (s, 3H), 7.00 (t, J=7.2 Hz, 1H), 7.06 (d, J=8.1 Hz, 1H), 7.20 (t, J=7.2 Hz, 1H), 7.29 (t, J=8.1 Hz, 1H), 7.39 (t, J=7.2 Hz, 1H), 7.52 (d, J=16.8 Hz, 1H), 7.59 (d, J=6.3 Hz, 1H), 7.74 (d, J=16.8 Hz, 1H), 7.77 (d, J=6.3 Hz, 1H), 8.04 (d, J=8.4 Hz, 1H).

APCI-MS (m/z); 251 [M+H]⁺

EXAMPLE 136

(E)-2-[2-(1H-indazol-3-yl)vinyl]benzonitrile (Compound 136)

In a similar manner to Example 134, Compound 136 (0.012 g, 23%) was obtained from (1H-indazol-3-ylmethyl)triphenylphosphonium bromide (0.10 g, 0.21 mmol), DBU (0.047 mL, 0.32 mmol) and 2-formylbenzonitrile (0.030 g, 0.23 mmol).

¹H-NMR (270 MHz, DMSO-d₆) δ 7.26 (t, J=7.9 Hz, 1H), 7.43 (t, J=6.3 Hz, 1H), 7.48 (t, J=7.6 Hz, 1H), 7.62 (d, J=7.6 Hz, 1H), 7.72 (d, J=16.5 Hz, 1H), 7.75 (d, J=7.6 Hz, 1H), 7.88 (d, J=16.5 Hz, 1H), 7.90 (d, J=7.6 Hz, 1H), 8.08 (d, J=7.9 Hz, 1H), 8.19 (d, J=7.9 Hz, 1H).

APCI-MS (m/z); 246 [M+H]⁺

EXAMPLE 137

(E)-3-[2-{2-(morpholin-4-yl)phenyl}vinyl]-1H-indazole (Compound 137)

In a similar manner to Example 134, Compound 137 (17 mg, 54%) was obtained from (1H-indazol-3-ylmethyl)triphenylphosphonium bromide (50 mg, 0.11 mmol), DBU (24 μL, 0.16 mmol) and 2-morpholinobenzaldehyde (20 mg, 0.11 mmol).

¹H-NMR (300 MHz, DMSO-d₆) δ 2.94 (t, J=4.5 Hz, 4H), 3.82 (t, J=4.5 Hz, 4H), 7.12 (t, J=3.0 Hz, 1H), 7.14 (d, J=8.1 Hz, 1H), 7.25 (t, J=8.1 Hz, 1H), 7.30 (t, J=7.8 Hz, 1H), 7.40 (t, J=8.1 Hz, 1H), 7.45 (d, J=16.8 Hz, 1H), 7.55 (d, J=16.8 Hz, 1H), 7.76 (d, J=3.0 Hz, 1H), 7.80 (d, J=7.8 Hz, 1H), 8.07 (d, J=8.1 Hz, 1H).

APCI-MS (m/z); 306 [M+H]⁺

EXAMPLE 138

(E)-2-[2-(1H-indazol-3-yl)vinyl]-N-(thiazol-2-yl) benzamide (Compound 138)

A solution of (E)-2-[2-(1H-indazol-3-yl)vinyl]benzoic acid (30 mg, 0.11 mmol) obtained in Step 1 of Example 47 in THF (0.50 mL), was sequentially added with 4-methylmorpholine (25 μL, 0.23 mmol), 2-aminothiazole (17 mg, 0.17 mmol), EDC (31 mg, 0.16 mmol) and 1-hydroxybenzotriazole monohydrate (20 mg, 0.15 mmol), followed by stirring at room temperature for 2.0 hours. The reaction mixture was added with water and ethyl acetate to separate the mixture into organic layer and aqueous layer and the organic layer was concentrated under reduced pressure. The residue was purified by silica gel column chromatography (chloroform/methanol=100/0 to 95/5) and the obtained compound was crystallized from 4.0 mol/L hydrogen chloride-ethyl acetate solution (1.0 mL)/ethyl acetate (1.0 mL). The obtained solid was added with ethyl acetate and saturated aqueous sodium hydrogencarbonate solution to separate the mixture into organic layer and aqueous layer and the organic layer was concentrated under reduced pressure. The residue was purified by silica gel column chromatography (chloroform/methanol=15/1) to obtain Compound 138 (8.5 mg, 22%).

$^1$H-NMR (270 MHz, DMSO-$d_6$) δ 7.12 (t, J=7.6 Hz, 1H), 7.33 (d, J=3.6 Hz, 1H), 7.38 (d, J=6.9 Hz, 1H), 7.42 (d, J=6.9 Hz, 1H), 7.51-7.66 (m, 5H), 7.77 (d, J=17.2 Hz, 1H), 7.95 (d, J=8.2 Hz, 1H), 8.05 (d, J=7.9 Hz, 1H), 12.72 (s, 1H), 13.18 (s, 1H).

ESI-MS (m/z); 345 [M−H]

EXAMPLE 139

(E)-2-[2-(1H-indazol-3-yl)vinyl]-N-(1H-[1,2,4]triazol-3-yl)benzamide (Compound 139)

A solution of (E)-2-[2-(1H-indazol-3-yl)vinyl]benzoic acid (30 mg, 0.11 mmol) obtained in Step 1 of Example 47 in THF (0.50 mL) was sequentially added with 4-methylmorpholine (25 μL, 0.23 mmol), 3-amino-1,2,4-triazole (14 mg, 0.17 mmol), EDC (31 mg, 0.16 mmol) and 1-hydroxybenzotriazole monohydrate (20 mg, 0.15 mmol) followed by stirring at room temperature for 2.0 hours. The reaction mixture was added organic layer and aqueous layer and the organic layer was with water and ethyl acetate to separate the mixture into concentrated under reduced pressure. The residue was purified by silica gel column chromatography (chloroform/methanol=100/0 to 90/10) to obtain Compound 139 (17 mg, 45%).

$^1$H-NMR (300 MHz, DMSO-$d_6$) δ 7.17 (t, J=7.8 Hz, 1H), 7.38 (t, J=7.5 Hz, 1H), 7.39 (d, J=16.8 Hz, 1H), 7.42 (t, J=7.5 Hz, 1H), 7.49-7.68 (m, 5H), 7.82 (s, 1H), 7.84 (d, J=8.1 Hz, 1H), 8.04 (d, J=8.1 Hz, 1H), 13.20 (s, 1H).

ESI-MS (m/z); 331 [M+H]$^+$

EXAMPLE 140

(E)-3-{2-[2-(2-phenylethyloxy)phenyl]vinyl}-1H-indazole (Compound 140)

Step 1

A solution of 2-hydroxybenzaldehyde (0.20 mL, 1.9 mmol) in DMF (2.0 mL) was added with (2-bromoethyl)benzene (0.39 mL, 2.8 mmol) and potassium carbonate (0.78 g, 5.6 mmol), stirred at room temperature for 3.0 hours and at 80° C. for 7.5 hours. The reaction mixture was added with water and ethyl acetate to separate the mixture into organic layer and aqueous layer and the organic layer was concentrated under reduced pressure. The residue was purified by silica gel column chromatography (hexane/ethyl acetate=90/10 to 80/20) to obtain 2-(2-phenylethyloxy)benzaldehyde (0.15 g, 36%).

$^1$H-NMR (300 MHz, DMSO-$d_6$) δ 3.11 (t, J=6.6 Hz, 2H), 4.36 (t, J=6.6 Hz, 2H), 7.06 (t, J=7.2 Hz, 1H), 7.17-7.41 (m, 6H), 7.59-7.70 (m, 2H), 10.29 (s, 1H). APCI-MS (m/z); 227 [M+H]$^+$

Step 2

In a similar manner to Example 1, Compound 140 (0.079 g, 38%) was obtained from (1H-indazol-3-ylmethyl)triphenylphosphonium bromide (0.28 g, 0.61 mmol), DBU (0.14 mL, 0.91 mmol) and 2-(2-phenylethyloxy)benzaldehyde (0.15 g, 0.67 mmol) obtained in Step 1.

$^1$H-NMR (270 MHz, DMSO-$d_6$) δ 3.16 (t, J=6.3 Hz, 2H), 4.32 (t, J=6.3 Hz, 2H), 6.98 (t, J=7.2 Hz, 1H), 7.07 (d, J=8.2 Hz, 1H), 7.15-7.45 (m, 8H), 7.49 (d, J=16.8 Hz, 1H), 7.59 (d, J=7.8 Hz, 1H), 7.68 (d, J=16.8 Hz, 1H), 7.74 (d, J=7.6 Hz, 1H), 7.91 (d, J=7.6 Hz, 1H). APCI-MS (m/z); 341 [M+H]$^+$

EXAMPLE 141

(E)-2-[2-(1H-indazol-3-yl)vinyl]-N-(thiophen-2-ylmethyl)benzamide (Compound 141)

A solution of (E)-2-[2-(1H-indazol-3-yl)vinyl]benzoic acid (35 mg, 0.13 mmol) obtained in Step 1 of Example 47 in THF (1.0 mL) was sequentially added with 4-methylmorpholine (29 μL, 0.27 mmol), 2-(aminomethyl)thiophene (23 mg, 0.28 mmol) and EDC (36 mg, 0.19 mmol) and stirred at room temperature for 1.0 hour. The reaction mixture was added with water and ethyl acetate to separate the mixture into organic layer and aqueous layer and the organic layer was concentrated under reduced pressure. The residue was purified by silica gel chromatography (chloroform/methanol=100/0 to 90/10) and the obtained compound was crystallized from a mixed solvent of hexane/ethyl acetate (9/1, 1.0 mL) to obtain Compound 141 (11 mg, 17%).

$^1$H-NMR (300 MHz, DMSO-$d_6$) δ 4.66 (d, J=6.0 Hz, 2H), 6.95 (t, J=4.8 Hz, 1H), 7.06 (d, J=3.6 Hz, 1H), 7.20 (t, J=7.5 Hz, 1H), 7.30-7.62 (m, 8H), 7.83 (d, J=16.8 Hz, 1H), 7.98 (t, J=7.8 Hz, 1H), 9.14 (t, J=6.0 Hz, 1H), 13.18 (s, 1H). ESI-MS (m/z); 360 [M+H]$^+$

EXAMPLE 142

(E)-2-[2-(1H-indazol-3-yl)vinyl]-N-(pyridin-3-yl)benzamide (Compound 142)

In a similar manner to Example 141, Compound 142 (12 mg, 18%) was obtained from (E)-2-[2-(1H-indazol-3-yl)vinyl]benzoic acid (50 mg, 0.19 mmol) obtained in Step 1 of Example 47, 4-methylmorpholine (42 μL, 0.38 mmol), 3-aminopyridine (27 mg, 0.28 mmol) and EDC (51 mg, 0.27 mmol).

$^1$H-NMR (300 MHz, DMSO-$d_6$) δ 7.09 (t, J=7.8 Hz, 1H), 7.36 (t, J=6.9 Hz, 1H), 7.40-7.67 (m, 6H), 7.79 (d, J=16.5 Hz, 1H), 7.91 (d, J=7.8 Hz, 1H), 8.07 (d, J=7.8 Hz, 1H), 8.34 (d,

J=4.8 Hz, 1H), 8.92 (d, J=2.1 Hz, 1H), 10.75 (s, 1H), 13.17 (s, 1H). ESI-MS (m/z); 341 [M+H]⁺

EXAMPLE 143

(E)-2-[2-(1H-indazol-3-yl)vinyl]-N-(4-methylthiazol-2-yl)benzamide (Compound 143)

In a similar manner to Example 141, Compound 143 (0.0042 g, 3%) was obtained from (E)-2-[2-(1H-indazol-3-yl)vinyl]benzoic acid (0.10 g, 0.38 mmol) obtained in Step 1 of Example 47, 4-methylmorpholine (83 μL, 0.76 mmol), 2-amino-4-methylthiazole (0.065 g, 0.57 mmol) and EDC (0.10 g, 0.53 mmol).

¹H-NMR (300 MHz, DMSO-d₆) δ 2.30 (s, 3H), 6.87 (s, 1H), 7.12 (t, J=7.8 Hz, 1H), 7.38 (t, J=7.2 Hz, 1H), 7.42 (d, J=6.6 Hz, 1H), 7.51-7.65 (m, 4H), 7.76 (d, J=16.2 Hz, 1H), 7.95 (d, J=8.1 Hz, 1H), 8.04 (d, J=8.1 Hz, 1H), 12.63 (s, 1H), 13.18 (s, 1H).
ESI-MS (m/z); 361 [M+H]⁺

EXAMPLE 144

(E)-3-{2-[2-(4-nitrobenzyloxy)phenyl]vinyl}-1H-indazole (Compound 144)

Step 1

In a similar manner to Step 1 of Example 140, 2-(4-nitrobenzyloxy)benzaldehyde (0.20 g, 41%) was obtained from 2-hydroxybenzaldehyde (0.20 mL, 1.9 mmol), 1-bromomethyl-4-nitrobenzene (0.65 g, 2.8 mmol) and potassium carbonate (0.26 g, 5.6 mmol).

¹H-NMR (270 MHz, DMSO-d₆) δ 5.47 (s, 2H), 7.12 (t, J=8.6 Hz, 1H), 7.30 (d, J=8.6 Hz, 1H), 7.67 (t, J=7.6 Hz, 1H), 7.74 (d, J=7.6 Hz, 1H), 7.81 (d, J=8.6 Hz, 2H), 8.27 (d, J=8.2 Hz, 2H), 10.48 (s, 1H).

Step 2

In a similar manner to Example 134, Compound 144 (0.0050 g, 6%) was obtained from (1H-indazol-3-ylmethyl)triphenylphosphonium bromide (0.10 g, 0.21 mmol), DBU (47 μL, 0.32 mmol) and 2-(4-nitrobenzyloxy)benzaldehyde (0.060 g, 0.23 mmol) obtained in Step 1.

¹H-NMR (270 MHz, DMSO-d₆) δ 5.41 (s, 2H), 7.04 (t, J=7.6 Hz, 1H), 7.13 (d, J=7.8 Hz, 1H), 7.15 (t, J=7.8 Hz, 1H), 7.28 (t, J=7.6 Hz, 1H), 7.39 (t, J=7.6 Hz, 1H), 7.56 (d, J=15.9 Hz, 1H), 7.57 (d, J=7.6 Hz, 1H), 7.75-7.88 (m, 4H), 7.95 (d, J=8.1 Hz, 1H), 8.31 (d, J=7.8 Hz, 2H), 13.11 (s, 1H).
APCI-MS (m/z); 372 [M+H]⁺

EXAMPLE 145

(E)-2-[2-(1H-indazol-3-yl)vinyl]-N-([1,3,4]thiadiazol-2-yl)benzamide (Compound 145)

To a solution of (E)-2-[2-(1H-indazol-3-yl)vinyl]benzoic acid (0.13 g, 0.49 mmol) obtained in Step 1 of Example 47 in THF (2.6 mL), [1,3,4]thiadiazol-2-ylamine (0.075 g, 0.74 mmol) and EDC (0.18 g, 0.94 mmol) were added, followed by stirring at room temperature for 4.5 hours. The reaction mixture was added with water and ethyl acetate to separate the mixture into organic layer and aqueous layer and the organic layer was concentrated under reduced pressure. The residue was purified by silica gel chromatography (chloroform/methanol=100/0 to 90/10) and the obtained compound was crystallized from ethyl acetate/methanol (1/1, 2.0 mL) to obtain Compound 145 (0.020 g, 12%).

¹H-NMR (270 MHz, DMSO-d₆) δ 7.14 (t, J=8.1 Hz, 1H), 7.41 (t, J=7.8 Hz, 1H), 7.45 (t, J=7.8 Hz, 1H), 7.51-7.72 (m, 5H), 7.76 (d, J=16.5 Hz, 1H), 7.96 (d, J=8.1 Hz, 1H), 8.07 (d, J=8.1 Hz, 1H), 9.28 (s, 1H), 13.19 (s, 1H).
APCI-MS (m/z); 348 [M+H]⁺

EXAMPLE 146

(E)-3-[2-(2-methylsulfanylphenyl)vinyl]-1H-indazole (Compound 146)

Step 1

To a solution of 2-methylsulfanylbenzoic acid methyl ester (0.30 g, 1.7 mmol) in toluene (3.0 mL), diisobutylaluminum hydride (0.94 mol/L toluene solution, 3.9 mL, 3.7 mmol) was added dropwise at −78° C. and the solution was stirred for 3.5 hours. The reaction mixture was added with 2-propanol (0.20 mL), warmed to 0° C., and added with saturated aqueous potassium sodium tartrate solution to separate the mixture into organic layer and aqueous layer. The obtained organic layer was concentrated under reduced pressure and the residue was purified by silica gel chromatography (hexane/ethyl acetate=90/10 to 70/30) to obtain (2-methylsulfanylphenyl)methanol (0.22 g, 87%).

¹H-NMR (270 MHz, DMSO-d₆) δ 3.32 (s, 3H), 4.49 (d, J=5.4 Hz, 2H), 5.22 (t, J=5.4 Hz, 1H), 7.12-7.30 (m, 3H), 7.43 (d, J=6.8 Hz, 1H).

Step 2

To a solution of (2-methylsulfanylphenyl)methanol (0.20 g, 1.3 mmol) obtained in Step 1 in dichloromethane (4.0 mL), Celite (0.40 g) and pyridinium chlorochromate (0.42 g, 1.9 mmol) were added, followed by stirring at room temperature for 1.0 hour. The reaction mixture was filtered and the filtrate was concentrated under reduced pressure. The residue was purified by silica gel column chromatography (hexane/ethyl acetate=95/5 to 80/20) to obtain 2-methylsulfanylbenzaldehyde (0.14 g, 69%).

¹H-NMR (270 MHz, DMSO-d₆) δ 3.34 (s, 3H), 7.38 (t, J=7.2 Hz, 1H), 7.47 (d, J=8.1 Hz, 1H), 7.66 (t, J=7.6 Hz, 1H), 7.93 (d, J=7.6 Hz, 1H), 10.20 (s, 1H).

Step 3

A solution of (1H-indazol-3-ylmethyl)triphenylphosphonium bromide (0.10 g, 0.21 mmol) in methanol (0.60 mL) was added with DBU (0.047 mL, 0.32 mmol) and 2-methylsulfanylbenzaldehyde (0.035 g, 0.23 mmol) obtained in Step 2 was further added, followed by stirring at room temperature for 2.0 hours. The reaction mixture was concentrated under reduced pressure and the residue was purified by silica gel column chromatography (chloroform/methanol=100/0 to 95/5). The obtained compound was washed with hydrogen chloride-ethyl acetate solution and the precipitated solid was filtered. Then the solid was added with saturated aqueous sodium hydrogencarbonate solution and ethyl acetate to separate the mixture into organic layer and aqueous layer. The organic layer was concentrated under reduced pressure and the residue was washed with ethyl acetate/hexane (2/1, 1.0 mL) to obtain Compound 146 (0.016 g, 28%).

¹H-NMR (270 MHz, DMSO-d₆) δ 2.52 (s, 3H), 7.18-7.44 (m, 6H), 7.49 (d, J=16.1 Hz, 1H), 7.80 (d, J=16.1 Hz, 1H), 7.81 (d, J=7.9 Hz, 1H), 8.04 (d, J=7.6 Hz, 1H).
ESI-MS (m/z); 267 [M+H]⁺

EXAMPLE 147

(E)-3-(2-o-torylvinyl)-1H-indazole (Compound 147)

In a similar manner to Example 134, Compound 147 (0.015 g, 15%) was obtained from (1H-indazol-3-ylmethyl)triphenylphosphonium bromide (0.10 g, 0.21 mmol), DBU (0.047 mL, 0.32 mmol) and 2-methylbenzaldehyde (0.025 mL, 0.23 mmol).

$^1$H-NMR (300 MHz, DMSO-d$_6$) δ 1.24 (s, 3H), 7.17-7.30 (m, 4H), 7.40 (t, J=7.8 Hz, 1H), 7.43 (d, J=16.5 Hz, 1H), 7.56 (d, J=8.1 Hz, 1H), 7.67 (d, J=16.5 Hz, 1H), 7.78 (d, J=7.8 Hz, 1H), 8.11 (d, J=7.8 Hz, 1H), 13.15 (s, 1H).

ESI-MS (m/z); 235 [M+H]$^+$

EXAMPLE 148

(E)-7-[2-(1H-indazol-3-yl)vinyl]-2-(1-methyl-1H-pyrrol-2-yl)benzoxazole (Compound 148)

Step 1

In a similar manner to Step 1 of Example 133, (E)-2-[2-(1H-indazol-3-yl)vinyl]-6-nitrophenol (1.3 g, 44%) was obtained from (1H-indazol-3-ylmethyl)triphenylphosphonium bromide (5.0 g, 11 mmol), DBU (4.0 mL, 27 mmol), 3-nitrosalicylaldehyde (1.8 g, 11 mmol) and methanol (15 mL).

$^1$H-NMR (270 MHz, DMSO-d$_6$) δ 7.11 (t, J=8.1 Hz, 1H), 7.24 (t, J=8.1 Hz, 1H), 7.41 (t, J=8.2 Hz, 1H), 7.57 (d, J=8.2 Hz, 1H), 7.68 (d, J=16.6 Hz, 1H), 7.80 (d, J=16.6 Hz, 1H), 7.94 (d, J=8.2 Hz, 1H), 8.09 (d, J=8.2 Hz, 1H), 8.19 (d, J=8.2 Hz, 1H), 10.82 (s, 1H), 13.24 (s, 1H).

APCI-MS (m/z); 282 [M+H]$^+$

Step 2

In a similar manner to Example 2, (E)-2-amino-6-[2-(1H-indazol-3-yl)vinyl]phenol (1.2 g, 100%) was obtained from (E)-2-[2-(1H-indazol-3-yl)vinyl]-6-nitrophenol (1.3 g, 4.6 mmol) obtained in Step 1, tin (1.7 g, 14 mmol), concentrated hydrochloric acid (7.7 mL) and ethanol (26 mL).

$^1$H-NMR (300 MHz, DMSO-d$_6$) δ 6.63 (s, 2H), 6.99 (s, 1H), 7.19 (t, J=7.2 Hz, 1H), 7.20 (d, J=7.5 Hz, 1H), 7.30-7.45 (m, 3H), 7.50-7.55 (m, 2H), 7.80 (d, J=16.8 Hz, 1H), 8.11 (d, J=8.1 Hz, 1H), 13.03 (s, 1H).

APCI-MS (m/z); 252 [M+H]$^+$

Step 3

A solution of (E)-2-amino-6-[2-(1H-indazol-3-yl)vinyl]phenol (0.10 g, 0.40 mmol) obtained in Step 2 in 1,4-dioxane (1.5 mL) was added with 1-methyl-1H-pyrrole-2-carbonyl chloride (63 mg, 0.44 mmol) and stirred at 210° C. for 15 minutes under microwave irradiation. The reaction mixture was added with saturated aqueous sodium hydrogencarbonate solution and the mixture was extracted with ethyl acetate. The organic layer was concentrated under reduced pressure and the obtained residue was purified by silica gel column chromatography (chloroform to chloroform/methanol=90/10) and crystallized from ethanol to obtain Compound 148 (13 mg, 10%).

$^1$H-NMR (270 MHz, DMSO-d$_6$) δ 4.15 (s, 3H), 6.28-6.33 (br, 1H), 7.13-7.18 (br, 1H), 7.23-7.33 (m, 2H), 7.40 (t, J=8.1, Hz, 1H), 7.44 (t, J=7.3 Hz, 1H), 7.57-7.78 (m, 4H), 7.97 (d, J=16.7 Hz, 1H), 8.22 (d, J=8.1 Hz, 1H), 13.29 (s, 1H).

APCI-MS (m/z); 431 [M+H]$^+$

EXAMPLE 149

(E)-7-[2-(1H-indazol-3-yl)vinyl]-2-(thiophen-2-yl)benzoxazole (Compound 149)

Step 1

A solution of (E)-2-amino-6-[2-(1H-indazol-3-yl)vinyl]phenol (0.10 g, 0.40 mmol) obtained in Step 2 of Example 148 and pyridine (0.16 mL, 2.0 mmol) in methylene chloride (1.5 mL) was added with 2-thiophenecarbonyl chloride (85 μL, 0.80 mmol) under ice-cooling and stirred for 30 minutes. The reaction mixture was added with water and extracted with ethyl acetate. The organic layer was concentrated under reduced pressure and the residue was purified by silica gel column chromatography (chloroform/methanol=100/0 to 90/10), crystallized from ethyl acetate to obtain (E)-thiophene-2-carboxylic acid-2-[2-(1H-indazol-3-yl)vinyl]-6-[(thiophen-2-ylcarbonyl)amino]phenyl ester (38 mg, 20%).

$^1$H-NMR (300 MHz, DMSO-d$_6$) δ 7.01 (t, J=6.9 Hz, 1H), 7.13 (t, J=3.6 Hz, 1H), 7.30-7.45 (m, 5H), 7.53 (d, J=9.0 Hz, 1H), 7.56 (d, J=8.1 Hz, 1H), 7.66 (d, J=16.5 Hz, 1H), 7.74 (d, J=8.1 Hz, 1H), 7.79 (d, J=5.1 Hz, 1H), 7.83 (d, J=3.6 Hz, 1H), 7.93 (d, J=8.1 Hz, 1H), 8.11 (t, J=3.6 Hz, 1H), 10.11 (s, 1H), 13.19 (s, 1H).

APCI-MS (m/z); 472 [M+H]$^+$

Step 2

A solution of (E)-thiophene-2-carboxylic acid 2-[2-(1H-indazol-3-yl)vinyl]-6-[(thiophen-2-ylcarbonyl)amino]phenyl ester (34 mg, 0.073 mmol) obtained in Step 1 in xylene (1.0 mL) was added with p-toluenesulfonic acid monohydrate (33 mg, 0.19 mmol), followed by heating under reflux under nitrogen atomosphere for 3.0 hours. The reaction mixture was allowed to stand cool and then saturated aqueous sodium hydrogencarbonate solution was added, followed by extracting with ethyl acetate. Then, the organic layer was concentrated under reduced pressure. The residue was purified by silica gel column chromatography (chloroform to chloroform/methanol=85/15) and crystallized from ethyl acetate to obtain Compound 149 (6.0 mg, 24%).

$^1$H-NMR (300 MHz, DMSO-d$_6$) δ 7.28 (t, J=6.9 Hz, 1H), 7.37 (t, J=3.9 Hz, 1H), 7.43 (d, J=7.8 Hz, 1H), 7.46 (d, J=8.1 Hz, 1H), 7.60 (d, J=8.1 Hz, 1H), 7.69 (d, J=7.8 Hz, 1H), 7.74 (d, J=16.8 Hz, 1H), 7.76 (d, J=6.9 Hz, 1H), 7.99 (d, J=16.8 Hz, 1H), 8.01 (d, J=3.9 Hz, 1H), 8.11 (d, J=3.9 Hz, 1H), 8.25 (d, J=6.9 Hz, 1H), 13.32 (s, 1H).

ESI-MS (m/z); 344 [M+H]$^+$

EXAMPLE 150

(E)-7-[2-(1H-indazol-3-yl)vinyl]-2-(thiophen-2-ylmethyl)benzoxazole (Compound 150)

Step 1

To a mixed solution (2.3 mL) of (E)-2-amino-6-[2-(1H-indazol-3-yl)vinyl]phenol (0.15 g, 0.60 mmol) obtained in Step 2 of Example 148 in THF/DMF(2/1), thiophene-2-acetic acid (0.26 mg, 1.8 mmol), 1-hydroxybenzotriazole monohydrate (55 mg, 0.36 mmol) and EDC (0.34 g, 1.8 mmol) were added, followed by stirring at room temperature for 2.0 hours. The reaction mixture was added with water and extracted with ethyl acetate. The organic layer was concentrated under reduced pressure and the crude product was crystallized from ethyl acetate to obtain (E)-thiophen-2-ylacetic acid 2-[(thiophen-2-ylacetyl)amino]-6-{2-[1-(thiophen-2-ylacetyl)-1H-indazol-3-yl]vinyl}phenyl ester (90 mg, 24%).

$^1$H-NMR (300 MHz, DMSO-d$_6$) δ 3.95 (s, 2H), 4.33 (s, 2H), 4.82 (s, 2H), 6.90 (t, J=3.9 Hz, 1H), 6.97-7.03 (m, 3H), 7.05 (d, J=3.9 Hz, 1H), 7.10 (d, J=3.9 Hz, 1H), 7.34-7.56 (m, 5H), 7.64 (d, J=19.2 Hz, 1H), 7.69-7.74 (m, 2H), 7.78 (d, J=6.9 Hz, 1H), 7.91 (d, J=6.9 Hz, 1H), 8.11 (d, J=8.1 Hz, 1H), 8.36 (d, J=8.1 Hz, 1H), 9.79 (s, 1H).

Step 2

In a similar manner to Step 2 of Example 149, a solution of reaction mixture obtained from (E)-thiophen-2-ylacetic acid 2-[(thiophen-2-ylacetyl)amino]-6-{2-[1-(thiophen-2-ylacetyl)-1H-indazol-3-yl]vinyl}phenyl ester (90 mg, 0.14 mmol) obtained in Step 1, p-toluenesulfonic acid monohydrate (50 mg, 0.29 mmol) and xylene (1.5 mL) in methanol (3.0 mL) was added with potassium carbonate (0.10 g) and stirred for 1.5 hours. The mixture was added with water and extracted with ethyl acetate. Then, the organic layer was concentrated under reduced pressure. The residue was purified by silica gel column chromatography (chloroform to chloroform/methanol=90/10) and the crude product was crystallized from a mixed solvent of hexane/ethyl acetate (1/1) to obtain Compound 150 (32 mg, 62%).

$^1$H-NMR (300 MHz, DMSO-d$_6$) δ 4.72 (s, 2H), 7.05 (t, J=3.3 Hz, 1H), 7.18 (d, J=3.3 Hz, 1H), 7.26 (t, J=6.6 Hz, 1H), 7.42 (t, J=8.1 Hz, 1H), 7.43 (t, J=6.6 Hz, 1H), 7.50 (d, J=3.3 Hz, 1H), 7.60 (d, J=16.8 Hz, 1H), 7.61 (d, J=6.6 Hz, 1H), 7.66 (d, J=8.1 Hz, 1H), 7.69 (d, J=6.6 Hz, 1H), 7.92 (d, J=16.8 Hz, 1H), 8.17 (d, J=8.1 Hz, 1H), 13.30 (s, 1H).

ESI-MS (m/z); 358 [M+H]$^+$

EXAMPLE 151

(E)-N-2-{6-[2-(1H-indazol-3-yl)vinyl]benzo[1,3]dioxol-5-yl}isoindole-1,3-dione (Compound 151)

To a solution of (E)-{6-[2-(1H-indazol-3-yl)vinyl]benzo[1,3]dioxol-5-yl}amine (70 mg, 0.25 mmol) obtained in Step 1 of Example 130 in xylene (1.4 mL), triethylamine (7.0 μL, 0.050 mmol), phthalic acid anhydride (45 mg, 0.30 mmol) and molecular sieves 3A (70 mg) were added, followed by heating under reflux for 4.5 hours under nitrogen atomosphere. The reaction mixture was added with water and extracted with ethyl acetate. The organic layer was concentrated under reduced pressure. The residue was crystallized from a mixed solvent of methanol/water (10/1) to obtain Compound 151 (46 mg, 45%).

$^1$H-NMR (270 MHz, DMSO-d$_6$) δ 6.18 (s, 2H), 6.93-7.14 (m, 3H), 7.31 (t, J=8.4 Hz, 1H), 7.47 (s, 1H), 7.54 (d, J=16.5 Hz, 1H), 7.70 (d, J=6.8 Hz, 1H), 7.71 (s, 1H), 7.95-8.07 (m, 4H), 13.05 (s, 1H).

ESI-MS (m/z); 410 [M+H]$^+$

EXAMPLE 152

(E)-4-amino-2-{6-[2-(1H-indazol-3-yl)vinyl]benzo[1,3]dioxol-5-yl}isoindole-1,3-dione (Compound 152)

Step 1

In a similar manner to Example 151, (E)-2-{6-[2-(1H-indazol-3-yl)vinyl]benzo[1,3]dioxol-5-yl}-4-nitroisoindole-1,3-dione (94 mg, 58%) was obtained from (E)-{6-[2-(1H-indazol-3-yl)vinyl]benzo[1,3]dioxol-5-yl}amine (0.10 g, 0.36 mmol) obtained in Step 1 of Example 130, triethylamine (10 μL, 0.072 mmol), 3-nitrophthalic acid anhydride (83 mg, 0.43 mmol), molecular sieves 3A (0.10 g) and xylene (2.0 mL).

$^1$H-NMR (300 MHz, DMSO-d$_6$) δ 6.18 (s, 2H), 7.03 (t, J=7.8 Hz, 1H), 7.08 (s, 1H), 7.14 (d, J=16.5 Hz, 1H), 7.32 (t, J=7.2 Hz, 1H), 7.49 (d, J=7.2 Hz, 1H), 7.55 (d, J=16.5 Hz, 1H), 7.72 (s, 1H), 7.81 (d, J=7.8 Hz, 1H), 8.17 (t, J=7.8 Hz, 1H), 8.32 (d, J=7.2 Hz, 1H), 8.40 (d, J=7.8 Hz, 1H), 13.08 (s, 1H).

ESI-MS (m/z); 455 [M+H]$^+$

Step 2

In a similar manner to Example 2, Compound 152 (40 mg, 49%) was obtained from (E)-2-{6-[2-(1H-indazol-3-yl)vinyl]benzo[1,3]dioxol-5-yl}-4-nitroisoindole-1,3-dione (86 mg, 0.19 mmol) obtained in Step 1, tin (67 mg, 0.57 mmol), concentrated hydrochloric acid (0.33 mL) and ethanol (1.7 mL).

$^1$H-NMR (300 MHz, DMSO-d$_6$) δ 6.17 (s, 2H), 6.60 (s, 1H), 6.96-7.12 (m, 6H), 7.32 (t, J=8.1 Hz, 1H), 7.49 (d, J=5.7 Hz, 1H), 7.55 (d, J=15.3 Hz, 1H), 7.55 (s, 1H), 7.70 (s, 2H), 13.05 (s, 1H).

ESI-MS (m/z); 425 [M+H]$^+$

EXAMPLE 153

(E)-5-amino-2-{6-[2-(1H-indazol-3-yl)vinyl]benzo[1,3]dioxol-5-yl}isoindole-1,3-dione (Compound 153)

Step 1

In a similar manner to Example 151, (E)-2-{6-[2-(1H-indazol-3-yl)vinyl]benzo[1,3]dioxol-5-yl}-5-nitroisoindole-1,3-dione (55 mg, 42%) was obtained from (E)-{6-[2-(1H-indazol-3-yl)vinyl]benzo[1,3]dioxol-5-yl}amine (80 mg, 0.29 mmol) obtained in Step 1 of Example 130, triethylamine (8.0 μL, 0.057 mmol), 4-nitrophthalic anhydride (66 mg, 0.34 mmol), molecular sieves 3A (80 mg) and xylene (1.6 mL).

$^1$H-NMR (300 MHz, DMSO-d$_6$) δ 6.18 (s, 2H), 7.03 (t, J=8.1 Hz, 1H), 7.10 (s, 1H), 7.10 (d, J=16.2 Hz, 1H), 7.30 (t, J=8.1 Hz, 1H), 7.48 (d, J=8.4 Hz, 1H), 7.55 (d, J=16.2 Hz, 1H), 7.73 (s, 1H), 7.80 (d, J=8.1 Hz, 1H), 8.27 (d, J=8.4 Hz, 1H), 8.64 (s, 1H), 8.72 (d, J=8.1 Hz, 1H), 8.72 (d, J=8.1 Hz, 1H), 13.08 (s, 1H).

Step 2

In a similar manner to Example 2, Compound 153 (14 mg, 26%) was obtained from (E)-2-{6-[2-(1H-indazol-3-yl)vinyl]benzo[1,3]dioxol-5-yl}-5-nitroisoindole-1,3-dione (55 mg, 0.12 mmol) obtained in Step 1, tin (43 mg, 0.36 mmol), concentrated hydrochloric acid (0.21 mL) and ethanol (1.1 mL).

$^1$H-NMR (300 MHz, DMSO-d$_6$) δ 6.16 (s, 2H), 6.63 (s, 2H), 6.91 (d, J=8.1 Hz, 1H), 6.95-7.06 (m, 4H), 7.32 (t, J=8.1 Hz, 1H), 7.48 (s, 1H), 7.52 (d, J=16.2 Hz, 1H), 7.63 (d, J=8.1 Hz, 1H), 7.68 (s, 1H), 7.69 (d, J=6.9 Hz, 1H), 13.06 (s, 1H).

ESI-MS (m/z); 425 [M+H]$^+$

EXAMPLE 154

(E)-2-{3-chloro-2-[2-(1H-indazol-3-yl)vinyl]phenyl}isoindole-1,3-dione (Compound 154)

Step 1

In a similar manner to Step 1 of Example 133, (E)-3-[2-(2-chloro-6-nitrophenyl)vinyl]-1H-indazole (0.86 g, 53%) was obtained from (1H-indazol-3-ylmethyl)triphenylphosphonium bromide (2.6 g, 5.4 mmol), DBU (1.2 mL, 8.1 mmol), 2-chloro-6-nitrobenzaldehyde (6.6 g, 3.2 mmol) and methanol (15 mL).

$^1$H-NMR (300 MHz, DMSO-$d_6$) δ 7.11 (d, J=16.8 Hz, 1H), 7.24 (t, J=8.1 Hz, 1H), 7.43 (t, J=8.4 Hz, 1H), 7.50 (d, J=16.8 Hz, 1H), 7.59 (t, J=8.1 Hz, 1H), 7.59 (d, J=8.4 Hz, 1H), 7.92 (d, J=8.1 Hz, 1H), 7.98 (d, J=8.4 Hz, 1H), 8.07 (d, J=8.4 Hz, 1H).

ESI-MS (m/z); 300 [M+H]$^+$

Step 2

In a similar manner to Example 2, (E)-3-chloro-2-[2-(1H-indazol-3-yl)vinyl]phenylamine (0.49 g, 68%) was obtained from (E)-3-[2-(2-chloro-6-nitrophenyl)vinyl]-1H-indazole (0.80 g, 2.7 mmol) obtained in Step 1, tin (0.95 g, 6.0 mmol), concentrated hydrochloric acid (4.7 mL) and ethanol (12 mL).

$^1$H-NMR (270 MHz, DMSO-$d_6$) δ 5.43 (s, 2H), 6.70 (d, J=8.1 Hz, 1H), 6.72 (d, J=8.4 Hz, 1H), 6.98 (t, J=8.4 Hz, 1H), 7.20 (t, J=8.4 Hz, 1H), 7.31 (d, J=17.0 Hz, 1H), 7.39 (t, J=8.1 Hz, 1H), 7.42 (d, J=17.0 Hz, 1H), 7.56 (d, J=8.1 Hz, 1H), 8.07 (d, J=8.4 Hz, 1H), 13.15 (s, 1H).

ESI-MS (m/z); 270 [M+H]$^+$

Step 3

In a similar manner to Example 151, Compound 154 (83 mg, 69%) was obtained from (E)-3-chloro-2-[2-(1H-indazol-3-yl)vinyl]phenylamine (80 mg, 0.30 mmol) obtained in Step 2, triethylamine (8.4 μL, 0.059 mmol), phthalic anhydride (53 mg, 0.36 mmol), molecular sieves 3A (80 mg) and xylene (1.6 mL).

$^1$H-NMR (300 MHz, DMSO-$d_6$) δ 6.92 (d, J=16.8 Hz, 1H), 7.08 (t, J=7.5 Hz, 1H), 7.29 (d, J=16.8 Hz, 1H), 7.33 (t, J=7.5 Hz, 1H), 7.43-7.60 (m, 3H), 7.64 (d, J=8.1 Hz, 1H), 7.74 (d, J=7.5 Hz, 1H), 7.85-7.93 (m, 2H), 7.96-8.03 (m, 2H), 13.17 (s, 1H).

ESI-MS (m/z); 400 [M+H]$^+$

EXAMPLE 155

N-{2-[2-(1H-indazol-3-yl)vinyl]phenyl}-2-pyrazylamine (Compound 155)

Step 1

A solution of 2-bromobenzaldehyde (0.19 mL, 1.6 mmol), 2-aminopyrazine (0.18 g, 1.9 mmol), tris(dibenzylideneacetone)dipalladium (15 mg, 0.016 mmol), 9,9-dimethyl-4,6-bis(diphenylphosphino)xanthene (22 mg, 0.036 mmol) and cesium carbonate (0.74 g, 2.3 mmol) in 1,4-dioxane (3.2 mL) was stirred at 100° C. for 27 hours under argon atmosphere. The reaction mixture was cooled to room temperature, added with water and extracted with ethyl acetate. The organic layer was washed with saturated brine, dried over anhydrous sodium sulfate and concentrated under reduced pressure. The residue was purified by silica gel column chromatography (hexane/ethyl acetate=8/2 to 1/1) to obtain 2-(2-pyrazylamino)benzaldehyde (0.049 g, 15%).

$^1$H-NMR (270 MHz, CDCl$_3$) δ 7.10 (t, J=7.8, 1H), 7.60 (t, J=7.8 Hz, 1H), 7.66 (dd, J=1.6, 7.8 Hz, 1H), 8.08 (d, J=2.4 Hz, 1H), 8.21 (t, J=2.4 Hz, 1H), 8.30 (d, J=1.6 Hz, 1H), 8.85 (d, J=7.8 Hz, 1H), 9.94 (s, 1H), 11.12 (s, 1H).

APCI-MS (m/z); 200 [M+H]$^+$

Step 2

In a similar manner to Step 1 of Example 133, Compound 155 (47 mg, 85%) was obtained from 2-(2-pyrazylamino)benzaldehyde (35 mg, 0.18 mmol) obtained in Step 1, (1H-indazol-3-ylmethyl)triphenylphosphonium bromide (0.10 g, 0.21 mmol), DBU (0.040 mL, 0.26 mmol) and methanol (0.53 mL).

$^1$H-NMR (300 MHz, CDCl$_3$) δ 6.71 (s, 1H), 7.16 (td, J=6.8, 1.1 Hz, 1H), 7.26-7.48 (m, 5H), 7.54 (dd, J=1.2, 7.9 Hz, 1H), 7.67 (d, J=16.7 Hz, 1H), 7.76 (br, 1H), 7.79 (br, 1H), 7.98 (d, J=2.7 Hz, 1H), 8.11-8.15 (m, 2H), 10.29 (br, 1H).

ESI-MS (m/z); 314 [M+H]$^+$

EXAMPLE 156

(E)-N-{2-[2-(1H-indazol-3-yl)vinyl]phenyl}-2-methylbenzamide (Compound 156)

In a similar manner to Example 3, Compound 156 (76 mg, 85%) was obtained from o-methylbenzoyl chloride (0.12 mL, 0.77 mmol), Compound 2 (0.06 g, 0.26 mmol) and triethylamine (0.11 mL, 0.77 mmol).

$^1$H-NMR (300 MHz, DMSO-$d_6$) δ 3.18 (s, 3H), 7.14 (t, J=7.3 Hz, 1H), 7.33-7.48 (m, 6H), 7.36 (d, J=16.5 Hz, 1H), 7.53-7.59 (m, 3H), 7.72 (d, J=16.5 Hz, 1H), 7.94 (d, J=7.3 Hz, 1H), 8.08 (d, J=8.2 Hz, 1H), 10.18 (s, 1H), 13.2 (br, 1H).

APCI-MS (m/z); 354 [M+H]$^+$

EXAMPLE 157

(E)-N-{2-[2-(1H-indazol-3-yl)vinyl]phenyl}-3-methyl-4-nitrobenzamide (Compound 157)

In a similar manner to Example 29, Compound 157 (0.18 g, 89%) was obtained from 3-methyl-4-nitrobenzoic acid (0.28 g, 1.5 mmol), thionyl chloride (0.17 mL, 2.3 mmol), DMF (few drops), Compound 2 (0.12 g, 0.51 mmol) and triethylamine (0.21 mL, 1.5 mmol).

$^1$H-NMR (300 MHz, DMSO-$d_6$) δ 2.61 (s, 3H), 7.08 (t, J=7.0 Hz, 1H), 7.33-7.44 (m, 3H), 7.36 (d, J=16.7 Hz, 1H), 7.50-7.56 (m, 2H), 7.60 (d, J=16.7 Hz, 1H), 7.95-8.01 (m, 2H), 8.05-8.09 (m, 1H), 8.15-8.18 (m, 2H), 10.53 (s, 1H), 13.2 (br, 1H).

APCI-MS (m/z); 399 [M+H]$^+$

EXAMPLE 158

(E)-4-amino-N-{2-[2-(1H-indazol-3-yl)vinyl]phenyl}-3-methylbenzamide (Compound 158)

Compound 157 (0.10 g, 0.25 mmol) was dissolved in acetic acid (1.0 mL) and hydrochloric acid (1.0 mL) and the solution was added with tin(II) chloride (0.10 g, 0.5 mmol), followed by stirring at 40° C. for 2 hours. Then, the reaction mixture was neutralized by adding 6 mol/L sodium hydroxide and extracted with ethyl acetate. The organic layer was sequentially washed with water and saturated brine, dried over anhydrous magnesium sulfate and the solvent was evaporated under reduced pressure. The residue was triturated in ethanol to obtain Compound 158 (46 mg, 50%).

$^1$H-NMR (300 MHz, DMSO-$d_6$) δ 2.13 (s, 3H), 5.51 (s, 2H), 6.67 (d, J=8.4 Hz, 1H), 7.02 (t, J=7.3 Hz, 1H), 7.32-7.37 (m, 4H), 7.48 (d, J=16.7 Hz, 1H), 7.50-7.54 (m, 1H), 7.61 (d, J=16.7 Hz, 1H), 7.67-7.73 (m, 2H), 7.91-7.98 (m, 2H), 9.79 (s, 1H), 13.1 (br, 1H).

APCI-MS (m/z); 369 [M+H]$^+$

EXAMPLE 159

(E)-2-{2-[2-(1H-indazol-3-yl)vinyl]
phenyl}isoindole-1,3-dione (Compound 159)

Compound 2 (0.06 g, 0.25 mmol) was dissolved in xylene (2.0 mL) and the solution was added with phthalic anhydride (83 mg, 0.56 mmol) and triethylamine (89 μL, 0.64 mmol), followed by stirring at 60° C. for 2 hours. Then, the reaction mixture was extracted with ethyl acetate. The organic layer was sequentially washed with water and saturated brine, dried over anhydrous magnesium sulfate and the solvent was evaporated under reduced pressure. The residue was triturated in ethanol to obtain Compound 159 (4.0 mg, 4%).

$^1$H-NMR (270 MHz, DMSO-$d_6$) δ 6.92 (t, J=6.9 Hz, 1H), 7.12 (d, J=16.8 Hz, 1H), 7.23 (t, J=7.6 Hz, 1H), 7.38-7.52 (m, 4H), 7.52 (d, J=16.8 Hz, 1H), 7.64 (d, J=7.9 Hz, 1H), 7.87-7.98 (m, 4H), 8.02 (d, J=8.3 Hz, 1H), 13.1 (br, 1H).

APCI-MS (m/z); 366 [M+H]$^+$

EXAMPLE 160

(E)-N-{2-[2-(1H-indazol-3-yl)vinyl]phenyl}(3-methylthiophen-2-ylmethylene)amine (Compound 160)

Compound 2 (0.060 g, 0.25 mmol) was dissolved in toluene (3.0 mL) and the solution was added with 3-methylthiophene-2-carbaldehyde (55 μL, 0.51 mmol), p-toluenesulfonic acid (small amount), followed by stirring at 60° C. for 2 hours. Then, the reaction mixture was extracted with ethyl acetate. The organic layer was sequentially washed with water and saturated brine, dried over anhydrous magnesium sulfate and the solvent was evaporated under reduced pressure. The residue was triturated in ethanol to obtain Compound 160 (76 mg, 88%).

$^1$H-NMR (300 MHz, DMSO-$d_6$) δ 3.31 (s, 3H), 7.07 (t, J=5.1 Hz, 1H), 7.20 (t, J=7.5 Hz, 1H), 7.26-7.48 (m, 4H), 7.54 (d, J=16.7 Hz, 1H), 7.56 (d, J=8.4 Hz, 1H), 7.78 (d, J=5.1 Hz, 1H), 7.89 (d, J=7.3 Hz, 1H), 8.04 (d, J=16.7 Hz, 1H), 8.12 (d, J=8.1 Hz, 1H), 8.77 (s, 1H), 13.1 (br, 1H).

APCI-MS (m/z); 345 [M+H]$^+$

EXAMPLE 161

(E)-N-{2-[2-(1H-indazol-3-yl)vinyl]phenyl}thiourea (Compound 161)

A solution of Compound 2 (0.06 g, 0.26 mmol) in acetone mL) was added with benzoyl isothiocyanate (0.10 mL, 1.5 mmol), followed by stirring at room temperature for 1 hour. The crude product obtained by adding water to the mixture was collected by filtration, dissolved in ethanol (1 mL) and added with 1 mol/L aqueous sodium hydroxide solution (1 mL), followed by stirring at room temperature for 1 hour. The mixture was neutralized by adding 6 mol/L hydrochloric acid and the precipitated solid was collected by filtration. The residue was triturated in ethanol to obtain Compound 161 (54 mg, 72%).

$^1$H-NMR (300 MHz, DMSO-$d_6$) δ 7.20 (t, J=7.9 Hz, 1H), 7.24-7.57 (m, 6H), 7.31 (d, J=15.8 Hz, 1H), 7.60 (d, J=15.8 Hz, 1H), 7.87 (d, J=9.2 Hz, 1H), 7.94 (d, J=9.2 Hz, 1H), 8.16 (d, J=8.1 Hz, 1H), 9.56 (s, 1H), 13.2 (br, 1H).

APCI-MS (m/z); 295 [M+H]$^+$

EXAMPLE 162

(E)-3-{2-[2-(pyrrol-1-yl)phenyl]vinyl}-1H-indazole (Compound 162)

Compound 2 (0.060 g, 0.25 mmol) was dissolved in acetic acid (1.0 mL) and the solution was added with 2,5-dimethoxytetrahydrofuran (99 μL, 0.77 mmol), followed by stirring at room temperature for 2 hours. Then, to the reaction mixture, water was added and the precipitated solid was filtered. The solid was recrystallized from ethanol to obtain Compound 162 (14 mg, 20%).

$^1$H-NMR (300 MHz, DMSO-$d_6$) δ 6.33 (t, J=2.2 Hz, 2H), 6.99-7.01 (m, 2H), 7.09 (d, J=16.5 Hz, 1H), 7.11-7.15 (m, 1H), 7.33-7.52 (m, 5H), 7.52 (d, J=16.5 Hz, 1H), 7.72 (d, J=8.1 Hz, 1H), 8.03 (d, J=7.0 Hz, 1H), 13.1 (br, 1H).

APCI-MS (m/z); 286 [M+H]$^+$

EXAMPLE 163

(E)-N-{2-[2-(1H-indazol-3-yl)vinyl]phenyl}-2-pyrimidylamine (Compound 163)

Step 1

A solution of 2-bromobenzaldehyde (0.35 mL, 3.0 mmol), 2-aminopyrimidine (0.34 g, 3.6 mmol), tris(dibenzylideneacetone)dipalladium (28 mg, 0.030 mmol), 9,9-dimethyl-4,6-bis(diphenylphosphino)xanthene (38 mg, 0.066 mmol) and cesium carbonate (28 mg, 0.030 mmol) in 1,4-dioxane (6.0 mL) was stirred at 100° C. for 19 hours under argon atmosphere. After cooling to room temperature, the reaction mixture was added with water and extracted with ethyl acetate. The organic layer was washed with saturated brine, dried over anhydrous sodium sulfate and concentrated under reduced pressure. The residue was purified by silica gel column chromatography (hexane to hexane/ethyl acetate=8/2) to obtain 2-(2-pyrimidylamino)benzaldehyde (0.38 g, 64%).

$^1$H-NMR (270 MHz, CDCl$_3$) δ 6.83 (t, J=4.9 Hz, 1H), 7.11 (t, J=7.7 Hz, 1H), 7.58-7.68 (m, 2H), 8.53 (d, J=4.9 Hz, 2H), 8.94 (d, J=8.4 Hz, 1H), 9.97 (s, 1H), 11.27 (s, 1H).

Step 2

In a similar manner to Step 1 of Example 133, Compound 163 (78 mg, 68%) was obtained from 2-(pyrimidin-2-ylamino)benzaldehyde (73 mg, 0.37 mmol) obtained in Step 1, (1H-indazol-3-ylmethyl)triphenylphosphonium bromide (0.21 g, 0.44 mmol), DBU (0.082 mL, 0.55 mmol) and methanol (1.1 mL).

$^1$H-NMR (300 MHz, CDCl$_3$) δ 6.70 (t, J=4.3 Hz, 1H), 7.09 (td, J=6.8, 1.1 Hz, 1H), 7.21 (t, J=7.5 Hz, 1H), 7.30-7.44 (m, 4H), 7.60 (s, 1H), 7.63 (d, J=16.5 Hz, 1H), 7.68 (dd, J=1.5, 7.9 Hz, 1H), 7.76 (d, J=8.2 Hz, 1H), 7.88 (dd, J=1.1, 8.1 Hz, 1H), 8.42 (d, J=4.3 Hz, 2H), 10.57 (br, 1H).

APCI-MS (m/z); 314 [M+H]$^+$

EXAMPLE 164

(E)-N-{2-[2-(1H-indazol-3-yl)vinyl]phenyl}-2-pyridylamine (Compound 164)

Step 1

A solution of (E)-3-[2-(2-bromophenyl)vinyl]-1H-indazole (0.35 g, 1.2 mmol) obtained in Step 1 of Example 133, 3,4-dihydro-2H-pyrane (0.21 mL, 2.3 mmol) and p-toluenesulfonic acid monohydrate (22 mg, 0.12 mmol) in THF was stirred at 80° C. for 8 hours. After cooling to room temperature, the reaction mixture was added with saturated aqueous sodium hydrogencarbonate solution and extracted with chloroform. The organic layer was washed with saturated brine, dried over anhydrous sodium sulfate and concentrated under reduced pressure. The residue was reslurried with diisopropylether to obtain 3-[2-(2-bromophenyl)vinyl]-1-(tetrahydropyran-2-yl)-1H-indazole (0.39 g, 86%).

$^1$H-NMR (270 MHz, CDCl$_3$) δ 1.65-1.85 (m, 3H), 2.05-2.21 (m, 2H), 2.54-2.68 (m, 1H), 3.72-3.81 (m, 1H), 4.04-4.10 (m, 1H), 5.74 (dd, J=2.7, 9.2 Hz, 1H), 7.14 (t, J=8.4 Hz, 1H), 7.78-7.47 (m, 4H), 7.61 (d, J=8.1 Hz, 2H), 7.76 (d, J=6.5 Hz, 1H), 7.86 (d, J=16.7 Hz, 1H), 8.10 (d, J=8.4 Hz, 1H).

Step 2

A solution of 3-[2-(2-bromophenyl)vinyl]-1-(tetrahydropyran-2-yl)-1H-indazole (0.12 g, 0.32 mmol) obtained in Step 1,2-aminopyridine (0.38 mg, 0.38 mmol), tris(dibenzylideneacetone)dipalladium (3.1 mg, 0.0032 mmol), 9,9-dimethyl-4,6-bis(diphenylphosphino)xanthene (4.5 mg, 0.0070 mmol) and cesium carbonate (0.14 g, 0.44 mmol) in 1,4-dioxane (0.63 mL) was stirred at 100° C. for 22 hours under argon atmosphere. After cooling to room temperature, the reaction mixture was added with water and extracted with ethyl acetate. The organic layer was washed with saturated brine, dried over anhydrous sodium sulfate and concentrated under reduced pressure. The residue was purified by silica gel column chromatography (hexane/ethyl acetate=9/1 to 1/1) to obtain (E)-3-{2-[2-(2-pyridylamino)phenyl]vinyl}-1-(tetrahydropyran-2-yl)-1H-indazole (0.070 g, 56%).

$^1$H-NMR (270 MHz, CDCl$_3$) δ 1.61-1.79 (m, 3H), 2.00-2.15 (m, 2H), 2.51-2.64 (m, 1H), 3.68-3.77 (m, 1H), 4.02-4.07 (m, 1H), 5.68 (dd, J=2.7, 9.5 Hz, 1H), 6.60-6.67 (m, 2H), 7.03 (br, 1H), 7.08 (t, J=7.4 Hz, 1H), 7.18-7.54 (m, 7H), 7.66-7.79 (m, 3H), 8.17-8.20 (m, 1H).

Step 3

A solution of (E)-3-{2-[2-(2-pyridylamino)phenyl]vinyl}-1-(tetrahydropyran-2-yl)-1H-indazole (49 mg, 1.2 mmol) obtained in Step 2 and trifluoroacetic acid (1.0 mL) in methanol (0.50 mL) was stirred at room temperature for 18 hours. A 2 mol/L aqueous sodium hydroxide solution was added to neutralize the mixture and the reaction mixture was extracted with ethyl acetate. The organic layer was washed with saturated brine, dried over anhydrous sodium sulfate and then concentrated under reduced pressure. The residue was purified by silica gel column chromatography (chloroform to chloroform/methanol=97/3) to obtain Compound 164 (10 mg, 50%).

$^1$H-NMR (270 MHz, CDCl$_3$) δ 6.68-6.71 (m, 2H), 7.00 (t, J=7.7 Hz, 1H), 7.11 (br, 1H), 7.19 (t, J=7.5 Hz, 1H), 7.25-7.32 (m, 2H), 7.34-7.47 (m, 4H), 7.58-7.73 (m, 3H), 8.23 (m, 1H).

ESI-MS (m/z); 313 [M+H]$^+$

EXAMPLE 165

(E)-2-{2-[2-(1H-indazol-3-yl)vinyl] phenylamino}thiazole-5-carboxylic acid ethylester (Compound 165)

Ethyl 3-ethoxyacrylate (0.22 mL, 1.5 mmol) was dissolved in dioxane (4.0 mL) and water (4.0 mL) and after cooling to −10° C., the solution was added with N-bromosuccinimide (0.29 g, 1.6 mmol), followed by stirring at room temperature for 1 hour. The mixture was added with Compound 161 (0.40 g, 1.4 mmol), followed by stirring at 80° C. for 1 hour. The reaction mixture was added with aqueous ammonia to stop the reaction. The precipitated crude product was collected by filtration, purified by silica gel column chromatography (hexane/ethyl acetate=4/1 to 1/2) and triturated in ethyl acetate to obtain Compound 165 (45 mg, 8%).

$^1$H-NMR (300 MHz, DMSO-d$_6$) δ 1.22 (t, J=7.0 Hz, 3H), 4.17 (q, J=7.0 Hz, 2H), 7.17 (t, J=7.2 Hz, 1H), 7.31-7.41 (m, 3H), 7.51-7.57 (m, 1H), 7.53 (d, J=16.7 Hz, 1H), 7.60-7.63 (m, 1H), 7.64 (d, J=16.7 Hz, 1H), 7.86 (s, 1H), 7.96 (m, 1H), 8.00 (d, J=8.2 Hz, 1H), 10.5 (br, 1H), 13.2 (br, 1H).

APCI-MS (t/z); 391 [M+H]$^+$

EXAMPLE 166

(E)-2-{2-[2-(1H-indazol-3-yl)vinyl] phenylamino}thiazole-5-carboxylic acid (Compound 166)

Compound 165 (0.02 g, 0.051 mmol) was dissolved in methanol (1.0 mL) and 1 mol/L aqueous sodium hydroxide solution (1.0 mol) was added thereto, followed by stirring at 60° C. for 3 hours. The reaction mixture was added with water, washed with ethyl acetate and the aqueous layer was neutralized using 6 mol/L hydrochloric acid. The precipitated solid was triturated in ethyl acetate to obtain Compound 166 (13 mg, 72%).

$^1$H-NMR (270 MHz, DMSO-d$_6$) δ 7.17 (t, J=7.8 Hz, 1H), 7.28-7.41 (m, 3H), 7.49-7.56 (m, 1H), 7.53 (d, J=16.2 Hz, 1H), 7.62-7.68 (m, 1H), 7.65 (d, J=16.2 Hz, 1H), 7.79 (s, 1H), 7.95 (d, J=7.4 Hz, 1H), 8.00 (m, 1H), 10.4 (br, 1H), 13.2 (br, 1H).

APCI-MS (m/z); 363 [M+H]$^+$

EXAMPLE 167

(E)-1-{2-[2-(1H-indazol-3-yl)vinyl]phenyl}-1H-pyrrole-3-carbaldehyde (Compound 167)

Compound 2 (0.30 g, 1.3 mmol) was dissolved in acetic acid (5.0 mL) and 2,5-dimethoxy-4-tetrahydrofurancarbaldehyde (0.36 mL, 2.6 mmol) was added, followed by heating under reflux for 3 days. The reaction mixture was added with water and filtered through Celite, extracted with ethyl acetate and the organic layer was concentrated. The mixture was purified by silica gel column chromatography (hexane/ethyl acetate=4/1 to ethyl acetate) to obtain Compound 167 (88 mg, 22%).

$^1$H-NMR (270 MHz, DMSO-d$_6$) δ 6.75 (d, J=1.5 Hz, 1H), 7.05 (d, J=16.2 Hz, 1H), 7.11 (d, J=7.1 Hz, 1H), 7.19 (d, J=2.3 Hz, 1H), 7.36 (t, J=7.1 Hz, 1H), 7.48 (m, 2H), 7.51-7.61 (m, 2H), 7.60 (d, J=16.2 Hz, 1H), 7.70 (d, J=8.3 Hz, 1H), 7.93 (d, J=1.7 Hz, 1H), 8.10 (d, J=7.4 Hz, 1H), 9.81 (br, 1H), 13.2 (br, 1H).

APCI-MS (m/z); 314 [M+H]$^+$

EXAMPLE 168

(E)-1-{2-[2-(1H-indazol-3-yl)vinyl]phenyl}-1H-pyrrole-3-methanol (Compound 168)

Compound 167 (38 mg, 0.16 mmol) was dissolved in methanol (2.0 mL) and added with sodium borohydride (12 mg, 0.32 mmol) followed by stirring at room temperature for 4 hours. The reaction mixture was added with water, extracted with ethyl acetate and the organic layer was concentrated. Then, the residue was triturated in ethyl acetate to obtain Compound 168 (23 mg, 45%).

¹H-NMR (270 MHz, DMSO-d₆) δ 4.44 (d, J=5.1 Hz, 2H), 4.78 (t, J=5.3 Hz, 1H), 6.30 (t, J=2.2 Hz, 1H), 6.91 (d, J=2.3 Hz, 2H), 7.11-7.17 (m, 1H), 7.14 (d, J=16.7 Hz, 1H), 7.33-7.47 (m, 4H), 7.52 (d, J=8.4 Hz, 1H), 7.54 (d, J=16.7 Hz, 1H), 7.78 (d, J=8.3 Hz, 1H), 8.04 (d, J=9.1 Hz, 1H), 13.1 (br, 1H).

APCI-MS (m/z); 316 [M+H]⁺

EXAMPLE 169

(E)-2-{2-[2-(1H-indazol-3-yl)vinyl]phenylamino}thiazole-4-carboxylic acid ethyl ester (Compound 169)

Compound 161 (0.40 g, 1.4 mmol) was added with ethanol (3.0 mL, 1.5 mmol) and ethyl bromopyruvate (0.10 mL, 0.8 mmol) and after heating under reflux for 18 hours, aqueous ammonia was added to stop the reaction. The precipitated crude product was collected by filtration and purified by silica gel column chromatography (hexane/ethyl acetate=4/1 to 1/2). Then, the product was triturated in ethyl acetate to obtain Compound 169 (41 mg, 17%).

¹H-NMR (300 MHz, DMSO-d₆) δ 1.28 (t, J=7.2 Hz, 3H), 4.22 (q, J=7.2 Hz, 2H), 7.16 (t, J=7.3 Hz, 1H), 7.26 (t, J=7.5 Hz, 1H), 7.33-7.41 (m, 3H), 7.52 (d, J=16.7 Hz, 1H), 7.54 (d, J=8.4 Hz, 1H), 7.68-7.72 (m, 1H), 7.70 (d, J=16.7 Hz, 1H), 7.92 (d, J=6.4 Hz, 1H), 8.02 (d, J=8.1 Hz, 1H), 9.98 (br, 1H), 13.2 (br, 1H).

APCI-MS (m/z); 391 [M+H]⁺

EXAMPLE 170

(E)-2-{2-[2-(1H-indazol-3-yl)vinyl]phenylamino}thiazole-4-carboxylic acid (Compound 170)

Compound 169 (73 mg, 0.19 mmol) was dissolved in methanol (1.0 mL) and 2 mol/L sodium hydroxide (1.0 mol) was added, followed by stirring at room temperature for 1.5 hours. Water was added to the mixture and the organic layer was extracted with ethyl acetate and the aqueous layer was neutralized using 6 mol/L hydrochloric acid. The precipitated solid was triturated in ethyl acetate to obtain Compound 170 (14 mg, 21%).

¹H-NMR (270 MHz, DMSO-d₆) δ 7.16 (t, J=7.2 Hz, 1H), 7.24 (t, J=6.9 Hz, 1H), 7.31-7.41 (m, 2H), 7.50 (d, J=16.7 Hz, 1H), 7.52-7.56 (m, 2H), 7.64 (d, J=16.7 Hz, 1H), 7.76 (d, J=8.1 Hz, 1H), 7.90 (d, J=7.1 Hz, 1H), 8.02 (d, J=8.4 Hz, 1H), 9.93 (br, 1H), 13.2 (br, 1H).

APCI-MS (m/z); 363 [M+H]⁺

EXAMPLE 171

(E)-4-hydroxy-1-{2-[2-(2-(1H-indazol-3-yl)vinyl)phenylamino]thiazole-5-ylcarbonyl}piperidine (Compound 171)

In a similar manner to Example 28, Compound 171 (0.01 g, 35%) was obtained from 4-hydroxypiperidine (0.01 g, 0.10 mmol), Compound 166 (24 mg, 0.07 mmol), 1-hydroxybenzotriazole monohydrate (15 mg, 0.10 mmol), EDC (19 mg, 0.10 mmol) and 4-methylmorpholine (21 μL, 0.20 mmol).

¹H-NMR (270 MHz, DMSO-d₆) δ 1.30-1.34 (m, 2H), 1.70-1.76 (m, 2H), 3.15-3.35 (m, 2H), 3.70-3.72 (m, 1H), 3.87-3.93 (m, 2H), 4.75 (d, J=3.9 Hz, 1H), 7.17 (t, J=7.9 Hz, 1H), 7.23-7.41 (m, 3H), 7.47-7.56 (m, 2H), 7.53 (d, J=16.5 Hz, 1H), 7.66 (d, J=16.5 Hz, 1H), 7.67-7.71 (m, 1H), 7.91 (dd, J=7.1, 1.5 Hz, 1H), 8.00 (d, J=8.3 Hz, 1H), 10.1 (br, 1H), (br, 1H).

APCI-MS (m/z); 446 [M+H]⁺

EXAMPLE 172

(E)-2-{2-[2-(1H-indazol-3-yl)vinyl]phenylamino}thiazol-4-one (Compound 172)

Compound 161 (0.10 g, 0.34 mmol) was added with ethanol (3.0 mL) and chloroethyl acetate (43 μL, 0.41 mmol), and after heating under reflux for 7 hours, the aqueous ammonia was added to stop the reaction. The mixture was extracted with ethyl acetate, concentrated and purified by silica gel column chromatography (hexane/ethyl acetate=4/1 to 1/4), followed by triturating in ethyl acetate to obtain Compound 172 (13 mg, 12%).

¹H-NMR (270 MHz, DMSO-d₆) δ 3.89 (s, 2H), 6.95 (m, 1H), 7.16-7.26 (m, 3H), 7.17 (d, J=16.5 Hz, 1H), 7.35-7.45 (m, 1H), (d, J=16.5 Hz, 1H), 7.51-7.56 (m, 2H), 7.84-7.87 (m, 1H), 8.01 (d, J=8.6 Hz, 1H), 13.1 (br, 1H).

APCI-MS (m/z); 335 [M+H]⁺

EXAMPLE 173

(E)-2-{2-[2-(1H-indazol-3-yl)vinyl]phenylamino}thiazole-4-methanol (Compound 173)

Compound 169 (0.04 g, 0.10 mmol) was dissolved in THF (1.0 mL) and methylene chloride (1.0 mL) and after cooling to −78° C., diisobutylaluminum hydride (0.95 mol/L toluene solution, 0.65 mL, 0.62 mmol) was added and stirred in a temperature between −78° C. to room temperature for 19 hours. Saturated aqueous Rochelle salt solution was added to the mixture and the organic layer was extracted with ethyl acetate. The organic layer was concentrated and the residue was purified by silica gel column chromatography (chloroform/methanol=9/1). Then, the mixture was triturated in ethanol to obtain Compound 173 (16 mg, 44%).

¹H-NMR (300 MHz, DMSO-d₆) δ 4.35 (d, J=5.7 Hz, 2H), 5.10 (d, J=5.7 Hz, 1H), 6.52 (s, 1H), 7.15-7.22 (m, 2H), 7.31 (d, J=7.5 Hz, 1H), 7.38 (t, J=7.5 Hz, 1H), 7.45 (d, J=16.5 Hz, 1H), 7.54 (d, J=8.4 Hz, 1H), 7.68-7.74 (m, 1H), 7.72 (d, J=16.5 Hz, 1H), 7.86 (d, J=7.7 Hz, 1H), 8.02 (d, J=8.1 Hz, 1H), 9.64 (br, 1H), 13.1 (br, 1H).

APCI-MS (m/z); 349 [M+H]⁺

EXAMPLE 174

(E)-N-{2-[2-(1H-indazol-3-yl)vinyl]phenyl}-4-methylthiazole-5-carboxamide (Compound 174)

In a similar manner to Example 29, Compound 174 (29 mg, 19%) was obtained by treating 4-methyl-3-thiazole-5-carboxylic acid (67 mg, 0.47 mmol) with thionyl chloride (53 μL, 0.72 mmol), DMF (5.0 μL, 0.085 mmol) and dichloromethane (2.0 mL), followed by reacting with Compound 2 (0.10 g, 0.43 mmol), triethylamine (60 μL, 1.1 mmol) and THF (2.0 mL).

¹H-NMR (270 MHz, DMSO-d₆) δ 2.67 (s, 3H), 7.11 (t, J=7.8 Hz, 1H), 7.32-7.43 (m, 5H), 7.52 (d, J=16.7 Hz, 1H), 7.54 (d, J=7.8 Hz, 1H), 7.62 (d, J=16.7 Hz, 1H), 8.01 (d, J=8.4 Hz, 1H), 9.16 (s, 1H), 10.17 (s, 1H), 13.17 (s, 1H).

ESI-MS (m/z); 361 [M+H]⁺

EXAMPLE 175

(E)-4-hydroxy-1-{3-[2-(2-(1H-indazol-3-yl)vinyl)phenylamino][1,2,4]oxadiazol-5-ylcarbonyl}piperidine (Compound 175)

Step 1

Compound 136 (75 mg, 0.21 mmol) was dissolved in 2-propanol (2.0 mL) and 50 wt/vol % hydroxylamine (94 μL, 1.5 mmol) was added thereto, followed by stirring at 60° C. for 25 hours. The reaction mixture was added with water and the precipitated solid was collected by filtration and then dried. The obtained solid was triturated in ethyl acetate to obtain (E)-2-[2-(1H-indazol-3-yl)vinyl]-N-hydroxybenzamidine (44 mg, 78%).

$^1$H-NMR (270 MHz, DMSO-$d_6$) δ 5.92 (br, 2H), 7.19 (t, J=7.3 Hz, 1H), 7.29-7.56 (m, 6H), 7.89 (d, J=16.7 Hz, 1H), 7.89-7.96 (m, 1H), 8.03 (d, J=8.3 Hz, 1H), 9.55 (s, 1H), 13.1 (br, 1H).

APCI-MS (m/z); 279 [M+H]$^+$

Step 2

(E)-2-[2-(1H-indazol-3-yl)vinyl]-N-hydroxybenzamidine (0.17 g, 0.60 mmol) was dissolved in pyridine (5.0 mL) and ethyloxalyl chloride (0.12 mL, 1.1 mmol) was added thereto, followed by stirring at 90° C. for 2 hours. Methanol and 2 mol/L aqueous sodium hydroxide solution were added to the mixture and the organic layer was extracted with ethyl acetate. The aqueous layer was neutralized by 6 mol/L hydrochloric acid and the precipitated solid was collected by filtration and then dried. The obtained solid was triturated in ethanol to obtain (E)-3-{2-[2-(1H-indazol-3-yl)vinyl]phenyl}[1,2,4]oxadiazole-5-carboxylic acid (0.12 g, 50%).

$^1$H-NMR (270 MHz, DMSO-$d_6$) δ 7.27 (t, J=7.1 Hz, 1H), 7.40-7.51 (m, 2H), 7.60 (d, J=8.4 Hz, 1H), 7.73 (d, J=16.5 Hz, 1H), 7.73-7.78 (m, 1H), 7.85 (d, J=16.5 Hz, 1H), 7.85-7.90 (m, 1H), 8.09 (d, J=8.2 Hz, 1H), 8.19 (d, J=8.1 Hz, 1H), 13.2 (br, 1H).

APCI-MS (m/z); 333 [M+H]$^+$

Step 3

In a similar manner to Example 28, Compound 175 (17 mg, 76%) was obtained from 4-hydroxypiperidine (8.0 mg, 0.08 mmol), (E)-3-{2-[2-(1H-indazol-3-yl)vinyl]phenyl}[1,2,4]oxadiazole-5-carboxylic acid (18 mg, 0.05 mmol), 1-hydroxybenzotriazole monohydrate (12 mg, 0.08 mmol), EDC (16 mg, 0.08 mmol) and 4-methylmorpholine (18 μL, 0.16 mmol).

$^1$H-NMR (300 MHz, DMSO-$d_6$) δ 1.37-1.52 (m, 2H), 1.72-1.88 (m, 2H), 3.41-3.51 (m, 2H), 3.75-3.81 (m, 1H), 3.85-3.93 (m, 1H), 3.96-3.99 (m, 1H), 4.84 (d, J=4.0 Hz, 1H), 7.21 (t, J=7.1 Hz, 1H), 7.41 (t, J=7.1 Hz, 1H), 7.50-7.59 (m, 2H), 7.64-7.70 (m, 2H), 7.98 (dd, J=7.9, 1.1 Hz, 1H), 8.13 (t, J=7.1 Hz, 1H), 8.22 (d, J=16.5 Hz, 1H), 13.2 (br, 1H).

APCI-MS (m/z); 416 [M+H]$^+$

EXAMPLE 176

(E)-N,N-dimethyl-3-{2-[2-(1H-indazol-3-yl)vinyl]phenyl}[1,2,4]oxadiazole-5-carboxamide (Compound 176)

In a similar manner to Example 28, Compound 176 (28 mg, 52%) was obtained from (E)-3-{2-[2-(1H-indazol-3-yl)vinyl]phenyl}[1,2,4]oxadiazole-5-carboxylic acid (0.05 g, 0.15 mmol) obtained in Step 2 of Example 175, dimethylamine monohydrochloride (19 mg, 0.23 mmol), 1-hydroxybenzotriazole monohydrate (35 mg, 0.23 mmol), EDC (43 mg, 0.23 mmol) and 4-methylmorpholine (0.05 mL, 0.45 mmol).

$^1$H-NMR (300 MHz, DMSO-$d_6$) δ 3.10 (s, 3H), 3.24 (s, 3H), 7.21 (d, J=7.7 Hz, 1H), 7.41 (t, J=7.7 Hz, 1H), 7.52 (d, J=16.5 Hz, 1H), 7.54 (d, J=9.5 Hz, 1H), 7.59 (d, J=4.0 Hz, 1H), 7.60-7.70 (m, 1H), 8.00 (d, J=6.8 Hz, 1H), 8.12 (d, J=7.3 Hz, 1H), 8.14 (d, J=5.6 Hz, 1H), 8.24 (d, J=16.5 Hz, 1H), 13.2 (br, 1H).

APCI-MS (m/z); 360 [M+H]$^+$

EXAMPLE 177

(E)-3-{2-[2-(1H-indazol-3-yl)vinyl]phenyl}-N-methyl[1,2,4]oxadiazole-5-carboxamide (Compound 177)

In a similar manner to Example 28, Compound 177 (25 mg, 48%) was obtained from (E)-3-{2-[2-(1H-indazol-3-yl)vinyl]phenyl}[1,2,4]oxadiazole-5-carboxylic acid (0.05 g, 0.15 mmol) obtained in Step 2 of Example 175, methylamine (2.0 mol/L THF solution, 0.23 mL, 0.23 mmol), 1-hydroxybenzotriazole monohydrate (35 mg, 0.23 mmol), EDC (43 mg, 0.23 mmol) and 4-methylmorpholine (50 μL, 0.45 mmol).

$^1$H-NMR (300 MHz, DMSO-$d_6$) δ 2.87 (d, J=4.6 Hz, 3H), 7.21-7.24 (m, 1H), 7.40 (t, J=7.3 Hz, 1H), 7.53-7.65 (m, 3H), 7.64 (d, J=16.7 Hz, 1H), 8.00 (d, J=7.5 Hz, 1H), 8.13 (d, J=9.7 Hz, 1H), 8.17 (d, J=8.8 Hz, 1H), 8.24 (d, J=16.7 Hz, 1H), 9.45 (br, 1H), 13.2 (br, 1H).

APCI-MS (m/z); 346 [M+H]$^+$

EXAMPLE 178

(E)-3-{2-[2-(1H-indazol-3-yl)vinyl]phenyl}-4H-[1,2,4]oxadiazole-5-one (Compound 178)

(E)-2-[2-(1H-indazol-3-yl)vinyl]-N-hydroxybenzamidine (0.06 g, 0.22 mmol) obtained in Step 1 of Example 175 was dissolved in DMF (1.0 mL), and pyridine (35 μL, 0.43 mmol) and ethylchloroformate (0.12 mL, 1.1 mmol) were added thereto, followed by stirring at 0° C. for 30 minutes. The mixture was added with water and the precipitated solid was collected by filtration and the solid was dried. The obtained solid was dissolved in toluene (2.0 mL) at 0° C. and added with potassium tert-butoxide (85 mg, 0.76 mmol), followed by stirring at 60° C. for 2 hours. Then, the mixture was neutralized using aqueous fumaric acid solution. The reaction mixture was extracted with ethyl acetate and the organic layer was concentrated. The residue was triturated in a mixed solvent of ethyl acetate/hexane to obtain Compound 178 (18 mg, 23%).

$^1$H-NMR (300 MHz, DMSO-$d_6$) δ 7.22 (t, J=7.7 Hz, 1H), 7.40 (t, J=7.4 Hz, 1H), 7.48 (t, J=7.8 Hz, 1H), 7.55-7.67 (m, 3H), 7.62 (d, J=16.5 Hz, 1H), 8.00 (d, J=16.5 Hz, 1H), 8.10 (d, J=8.3 Hz, 2H), 13.2 (br, 1H).

APCI-MS (m/z); 305 [M+H]$^+$

EXAMPLE 179

(E)-3-{2-[2-(1H-indazol-3-yl)vinyl]phenyl}[1,2,4]oxadiazol-5-ylmethanol (Compound 179)

(E)-3-{2-[2-(1H-indazol-3-yl)vinyl]phenyl}[1,2,4]oxadiazole-5-carboxylic acid (14 mg, 0.04 mmol) obtained in Step 2 of Example 175 was dissolved in methylene chloride (1.0 mL), and thionyl chloride (5 μL, 239-0.06 mmol) and DMF (few drops) were added thereto, followed by stirring for 30 minutes. Then the mixture was concentrated and the residue was dissolved in dioxane (1.0 mL). Sodium borohydride (16 mg, 0.42 mmol) was added to the solution and the mixture was stirred at room temperature for 1 hour. Water was added to stop the reaction and the reaction mixture was extracted with ethyl acetate. The organic layer was concentrated and the residue was purified by preparative thin-layer chromatography (chloroform/acetone=4/1) to obtain Compound 179 (3.5 mg, 26%).

$^1$H-NMR (300 MHz, DMSO-$d_6$) δ 4.88 (s, 2H), 6.14 (br, 1H), 7.24 (t, J=7.5 Hz, 1H), 7.41 (t, J=7.7 Hz, 1H), 7.49 (t, J=7.7 Hz, 1H), 7.56-7.66 (m, 2H), 7.62 (d, J=16.5 Hz, 1H), 7.97 (dd, J=7.7, 1.3 Hz, 1H), 8.12 (d, J=7.7 Hz, 1H), 8.18 (d, J=8.2 Hz, 1H), 8.30 (d, J=16.5 Hz, 1H), 13.2 (br, 1H).

APCI-MS (m/z); 319 [M+H]$^+$

EXAMPLE 180

(E)-3-(3-{2-[2-(1H-indazol-3-yl)vinyl]phenyl}[1,2,4]oxadiazol-5-yl)propan-1-ol (Compound 180)

(E)-2-[2-(1H-indazol-3-yl)vinyl]-N-hydroxybenzamidine (0.08 g, 0.29 mmol) obtained in Step 1 of Example 175 was dissolved in pyridine (5.0 mL) and the solution was added with ethylsuccinyl chloride (47 µL, 0.33 mmol), followed by stirring at 90° C. for 1 hour. The reaction mixture was added with water and extracted with ethyl acetate. After the organic layer was concentrated, the residue was added to acetonitrile (5.0 mL) and stirred at 80° C. for 3.5 hours. The reaction mixture was added with water and extracted with ethyl acetate. After the organic layer was concentrated, the residue was purified by silica gel column chromatography (hexane/ethyl acetate=4/1 to 1/2) and the residue was dried. Further, the residue was dissolved in a mixed solvent of methylene chloride (1.0 mL)/THF (1.0 mL), cooled to −78° C. and diisobutylaluminum hydride (1.0 mol/L toluene solution, 1.0 mL, 1.0 mmol) was added, followed by stirring for 30 minutes. The reaction mixture was added with saturated aqueous Rochelle salt solution, extracted with ethyl acetate. The organic layer was concentrated, and the residue was purified by preparative thin-layer chromatography (chloroform/methanol=2/1) to obtain Compound 180 (18 mg, 24%).

$^1$H-NMR (300 MHz, DMSO-$d_6$) δ 2.05-1.95 (m, 2H), 3.11 (t, J=7.7 Hz, 2H), 3.54 (q, J=5.5 Hz, 2H), 4.68 (t, J=5.1 Hz, 1H), 7.24 (t, J=7.7 Hz, 1H), 7.41 (t, J=7.3 Hz, 1H), 7.48 (t, J=7.7 Hz, 1H), 7.56-7.65 (m, 3H), 7.97 (dd, J=7.7, 1.5 Hz, 1H), 8.10 (d, J=7.7 Hz, 1H), 8.14 (d, J=8.1 Hz, 1H), 8.30 (d, J=16.9 Hz, 1H), 13.2 (br, 1H).

APCI-MS (m/z); 347 [M+H]$^+$

EXAMPLE 181

(E)-2-{3-{2-[2-(1H-indazol-3-yl)vinyl]phenyl}[1,2,4]oxadiazol-5-yl}ethanol (Compound 181)

(E)-2-[2-(1H-indazol-3-yl)vinyl]-N-hydroxybenzamidine (0.08 g, 0.29 mmol) obtained in Step 1 of Example 175 was dissolved in THF (5.0 mL) and the solution was added with diisopropylethylamine (0.12 mL, 0.66 mmol) and ethylmalonyl chloride (47 µL, 0.44 mmol), followed by stirring at 80° C. for 15 minutes. Then, potassium carbonate and methanol were added to the mixture and stirred for 30 minutes. The mixture was added with water, extracted with ethyl acetate, and the organic layer was concentrated and then dried. Further, the residue was dissolved in a mixed solvent of methylene chloride (1.0 mL) and THF (1.0 mL), cooled to −78° C. and diisobutylaluminum hydride (0.95 mol/L toluene solution, 0.58 mL, 0.55 mmol) was added. The mixture was warmed to room temperature and stirred for 3 hours. The reaction mixture was added with saturated aqueous Rochelle salt solution and extracted with ethyl acetate. After the organic layer was concentrated, the residue was triturated in ethyl acetate to obtain Compound 181 (44 mg, 35%).

$^1$H-NMR (270 MHz, DMSO-$d_6$) δ 3.21 (t, J=6.3 Hz, 2H), 3.92 (q, J=6.1 Hz, 2H), 5.07 (t, J=5.5 Hz, 1H), 7.24 (t, J=7.7 Hz, 1H), 7.41 (t, J=7.3 Hz, 1H), 7.48 (t, J=7.7 Hz, 1H), 7.56-7.65 (m, 3H), 7.97 (dd, J=7.8, 1.3 Hz, 1H), 8.10 (d, J=7.8 Hz, 1H), 8.16 (d, J=8.3 Hz, 1H), 8.33 (d, J=16.7 Hz, 1H), 13.2 (br, 1H).

APCI-MS (m/z); 333 [M+H]$^+$

EXAMPLE 182

(E)-3-{2-[2-(3-morpholin-4-ylmethylpyrrol-1-yl)phenyl]vinyl}-1H-indazole (Compound 182)

Compound 167 (0.08 g, 0.26 mmol) was dissolved in dichloroethane (2.0 mL) and the solution was added with morpholine (67 µL, 0.77 mmol), acetic acid (84 µL, 0.77 mmol) and sodium borohydride (0.16 g, 0.77 mmol) followed by stirring at room temperature for 30 minutes. The reaction mixture was extracted with ethyl acetate, the organic layer was concentrated and the residue was purified by silica gel column chromatography (chloroform/methanol=9/1) to obtain Compound 182 (0.04 g, 41%).

$^1$H-NMR (300 MHz, DMSO-$d_6$) δ 3.32-3.33 (m, 4H), 3.66-3.67 (m, 2H), 3.88-3.90 (m, 2H), 4.20-4.26 (m, 2H), 6.51 (s, 1H), 7.03-7.16 (m, 2H), 7.35-7.56 (m, 8H), 7.78 (d, J=8.8 Hz, 1H), 8.06 (d, J=7.7 Hz, 1H), 13.2 (br, 1H).

APCI-MS (m/z); 385 [M+H]$^+$

EXAMPLE 183

(E)-2-{2-[2-(1H-indazol-3-yl)vinyl]phenyl}benzoxazole (Compound 183)

In a similar manner to Example 28, (E)-2-[2-(1H-indazol-3-yl)vinyl]benzoic acid (0.20 g, 0.76 mmol) obtained in Step 1 of Example 47, 2-aminophenol (91 mg, 0.83 mmol), 1-hydroxybenzotriazole monohydrate (35 mg, 0.23 mmol), EDC (0.16 mg, 0.83 mmol) and THF/DMF (2/1, 3.0 mL) were reacted. Then, in a similar manner to Step 2 of Example 150, the reaction mixture was treated with p-toluenesulfonic acid monohydrate (0.26 mg, 1.5 mmol) and xylene (5.0 mL) to obtain Compound 183 (13 mg, 5%).

$^1$H-NMR (270 MHz, DMSO-$d_6$) δ 7.31 (t, J=7.3 Hz, 1H), 7.44 (t, J=8.4 Hz, 1H), 7.47-7.72 (m, 5H), 7.66 (d, J=16.5 Hz, 1H), 7.85 (t, J=5.1 Hz, 1H), 7.93 (t, J=5.1 Hz, 1H), 8.17 (d, J=8.1 Hz, 1H), 8.21 (d, J=8.1 Hz, 1H), 8.41 (d, J=8.4 Hz, 1H), 8.87 (d, J=16.5 Hz, 1H), 13.25 (s, 1H).

ESI-MS (m/z); 336 [M−H]

EXAMPLE 184

(E)-2-{2-[2-(1H-indazol-3-yl)vinyl]phenyl}-5-nitrobenzoxazole (Compound 184)

In a similar manner to Example 28, (E)-2-[2-(1H-indazol-3-yl)vinyl]benzoic acid (0.30 g, 1.1 mmol) obtained in Step 1 of Example 47, 2-amino-4-nitrophenol (0.19 g, 1.3 mmol), 1-hydroxybenzotriazole monohydrate (52 mg, 0.34 mmol), EDC (0.24 g, 1.3 mmol) and THF/DMF (2/1, 4.5 mL) were reacted. Then, in a similar manner to Step 2 of Example 150, the reaction mixture was treated with p-toluenesulfonic acid monohydrate (0.39 mg, 2.3 mmol) and xylene (10 mL) to obtain Compound 184 (63 mg, 14%).

$^1$H-NMR (300 MHz, DMSO-d$_6$) δ 7.29 (t, J=8.1 Hz, 1H), 7.44 (t, J=7.5 Hz, 1H), 7.59 (t, J=8.1 Hz, 1H), 7.60 (d, J=8.1 Hz, 1H), 7.68 (d, J=16.5 Hz, 1H), 7.73 (t, J=7.5 Hz, 1H), 8.09 (d, J=9.0 Hz, 1H), 8.19 (d, J=7.5 Hz, 1H), 8.23 (d, J=7.5 Hz, 1H), 8.35 (d, J=8.1 Hz, 1H), 8.41 (d, J=9.0 Hz, 1H), 8.71 (s, 1H), 8.76 (d, J=16.5 Hz, 1H), 13.28 (s, 1H).

ESI-MS (m/z); 383 [M+H]$^+$

EXAMPLE 185

(E)-2-{2-[2-(1H-indazol-3-yl)vinyl]phenyl}benzoxazol-5-ylamine (Compound 185)

In a similar manner to Example 2, Compound 185 (18 mg, 43%) was obtained from (E)-2-{2-[2-(1H-indazol-3-yl)vinyl]phenyl}-5-nitrobenzoxazole (45 mg, 0.12 mmol) obtained in Example 184, tin (41 mg, 0.35 mmol), concentrated hydrochloric acid (0.21 mL) and ethanol (0.89 mL).

$^1$H-NMR (300 MHz, DMSO-d$_6$) δ 5.21 (s, 2H), 6.74 (d, J=8.4 Hz, 1H), 7.02 (s, 1H), 7.33 (t, J=8.1 Hz, 1H), 7.45 (t, J=8.4 Hz, 1H), 7.46 (d, J=8.4 Hz, 1H), 7.51 (t, J=8.1 Hz, 1H), 7.57-7.64 (m, 2H), 7.64 (d, J=16.8 Hz, 1H), 8.14 (d, J=8.1 Hz, 2H), 8.48 (d, J=8.1 Hz, 1H), 8.95 (d, J=16.8 Hz, 1H), 13.24 (s, 1H).

ESI-MS (m/z); 353 [M+H]$^+$

EXAMPLE 186

(E)-N'-(1-{2-[2-(1H-indazol-3-yl)vinyl]phenyl}-1H-pyrrol-3-ylmethyl)-N,N-dimethylethane-1,2-diamine (Compound 186)

Compound 167 (0.06 g, 0.19 mmol) was dissolved in dichloroethane (2.0 mL) and the solution was added with N,N-dimethylethylenediamine (62 μL, 0.57 mmol), acetic acid (63 μL, 0.57 mmol) and sodium triacetoxyborohydride (0.12 g, 0.57 mmol), followed by stirring at room temperature for 1 hour. The reaction mixture was added with water, extracted with ethyl acetate and the organic layer was concentrated. The residue was purified by silica gel column chromatography (ethyl acetate/methanol=9/1) to obtain Compound 186 (0.01 g, 14%).

$^1$H-NMR (300 MHz, DMSO-d$_6$) δ 2.04 (m, J=4.2 Hz, 2H), 2.08 (m, 6H), 2.29 (d, J=6.4 Hz, 2H), 2.63 (d, J=6.4 Hz, 2H), (d, J=2.0 Hz, 1H), 6.89-6.93 (m, 2H), 7.11 (d, J=16.7 Hz, 1H), 7.14 (d, J=6.7 Hz, 1H), 7.34-7.52 (m, 5H), (d, J=16.7 Hz, 1H), 7.73 (d, J=8.1 Hz, 1H), 8.02 (d, J=6.6 Hz, 1H), 13.1 (br, 1H).

APCI-MS (m/z); 386 [M+H]$^+$

EXAMPLE 187

(E)-2-(1-{2-[2-(1H-indazol-3-yl)vinyl]phenyl}-1H-pyrrol-3-ylmethylamino)ethanol (Compound 187)

Compound 167 (0.06 g, 0.19 mmol) was dissolved in dichloroethane (2.0 mL) and the solution was added with ethanolamine (35 μL, 0.57 mmol), acetic acid (63 μL, 0.57 mmol) and sodium triacetoxyborohydride (0.12 g, 0.57 mmol), followed by stirring at room temperature for 1 hour. The reaction mixture was added with water, extracted with ethyl acetate and the organic layer was concentrated. The residue was purified by silica gel column chromatography (ethyl acetate/methanol=9/1) to obtain Compound 187 (24 mg, 35%).

$^1$H-NMR (270 MHz, DMSO-d$_6$) δ 2.64 (d, J=5.6 Hz, 2H), 3.45 (m, 2H), 3.64 (m, 2H), 4.43 (br, 1H), 6.28 (t, J=2.0 Hz, 1H), 6.89-6.91 (m, 2H), 7.09-7.16 (m, 1H), 7.15 (d, J=16.8 Hz, 1H), 7.33-7.51 (m, 5H), 7.51 (d, J=16.5 Hz, 1H), 7.74 (d, J=8.6 Hz, 1H), 8.02 (d, J=7.3 Hz, 1H), 13.2 (br, 1H).

APCI-MS (m/z); 359 [M+H]$^+$

EXAMPLE 188

(E)-N-(1-{2-[2-(1H-indazol-3-yl)vinyl]phenyl}-1H-pyrrol-3-ylmethyl)-N,N',N'-trimethylethane-1,2-diamine (Compound 188)

Compound 167 (0.06 g, 0.19 mmol) was dissolved in dichloroethane (2.0 mL) and the solution was added with N,N,N'-trimethylethylenediamine (62 μL, 0.57 mmol), acetic acid (63 μL, 0.57 mmol) and sodium triacetoxyborohydride (0.12 g, 0.57 mmol), followed by stirring at room temperature for 1 hour. The reaction mixture was added with water, extracted with ethyl acetate and the organic layer was concentrated. The residue was purified by silica gel column chromatography (ethyl acetate/methanol=9/1) to obtain Compound 188 (41 mg, 54%).

$^1$H-NMR (270 MHz, DMSO-d$_6$) δ 2.08 (s, 6H), 2.16 (s, 3H), 2.29-2.34 (m, 2H), 2.40-2.45 (m, 2H), 3.44 (s, 2H), 6.24 (t, J=1.7 Hz, 1H), 6.86 (m, 1H), 6.92 (t, J=2.3 Hz, 1H), 7.08-7.15 (m, 2H), 7.33-7.56 (m, 6H), 7.72 (d, J=8.3 Hz, 1H), 8.00 (d, J=7.9 Hz, 1H), 13.2 (br, 1H).

APCI-MS (m/z); 400 [M+H]$^+$

EXAMPLE 189

(E)-3-cyclopropylmethylaminomethyl-1-{2-[2-(1H-indazol-3-yl)vinyl]phenyl}pyrrole (Compound 189)

Compound 167 (0.06 g, 0.19 mmol) was dissolved in dichloroethane (2.0 mL) and the solution was added with cyclopropanemethylamine (50 μL, 0.57 mmol), acetic acid (63 μL, 0.57 mmol) and sodium triacetoxyborohydride (0.12 g, 0.57 mmol), followed by stirring at room temperature for 1 hour. The reaction mixture was added with water, extracted with ethyl acetate and the organic layer was concentrated. The residue was purified by silica gel column chromatography (ethyl acetate/methanol=9/1) to obtain Compound 189 (0.01 g, 14%).

$^1$H-NMR (300 MHz, DMSO-d$_6$) δ 0.28-0.30 (m, 2H), 0.32-0.33 (m, 2H), 0.81-0.83 (m, 1H), 2.38 (d, J=6.6 Hz, 2H), 3.61 (s, 2H), 6.25 (m, 1H), 6.85 (t, J=2.6 Hz, 2H), 7.04-7.12 (m, 2H), 7.30-7.50 (m, 6H), 7.69 (d, J=8.3 Hz, 1H), 7.97 (d, J=7.2 Hz, 1H), 13.1 (br, 1H).

APCI-MS (m/z); 369 [M+H]$^+$

EXAMPLE 190

(E)-3-[(2-{2-(2,5-dimethylpyrrol-1-yl)phenyl]vinyl}-1H-indazole (Compound 190)

Compound 2 (0.50 g, 2.1 mmol) was dissolved in toluene (10 mL) and the solution was added with 2,5-hexanedione (0.75 mL, 6.4 mmol), molecular sieves 4A and p-toluenesulfonic acid (small amount), followed by stirring at 110° C. for 4 hours. The mixture was added with water and extracted with ethyl acetate. The organic layer was concentrated and the residue was purified by silica gel column chromatography (hexane/ethyl acetate=100/1 to 1/1) to obtain Compound 190 (0.62 g, 92%).

¹H-NMR (300 MHz, DMSO-d₆) δ 1.89 (s, 6H), 5.95 (m, 2H), 6.60 (d, J=16.8 Hz, 1H), 7.11 (t, J=7.3 Hz, 1H), 7.31-7.38 (m, 2H), 7.37 (d, J=16.7 Hz, 1H), 7.46 (dt, J=7.7 Hz, 1.5 Hz, 1H), 7.52 (d, J=9.2 Hz, 1H), 7.54 (d, J=16.7 Hz, 1H), 7.60 (d, J=8.1 Hz, 1H), 8.07 (d, J=6.6 Hz, 1H), 13.2 (br, 1H).

APCI-MS (m/z); 314 [M+H]⁺

EXAMPLE 191

(E)-1-{2-[2-(1H-indazol-3-yl)vinyl]phenyl}-2,5-dimethyl-1H-pyrrol-3-ylmethanol (Compound 191)

After cooling DMF (1.0 mL) to 0° C., phosphonyl chloride (0.20 mL, 2.1 mmol) was added thereto and stirred for 15 minutes. Then, Compound 190 (0.06 g, 0.19 mmol) dissolved in DMF (1.0 mL) was added to the mixture and after stirring at room temperature for 30 minutes, the reaction mixture was added with ice water. Further, the mixture was added with 1 mol/L aqueous sodium hydroxide solution (10 mL) and stirred at room temperature for 1 hour, extracted with ethyl acetate and then the organic layer was concentrated. The residue was dissolved in methanol (3.0 mL) and the solution was added with sodium borohydride (17 mg, 0.44 mmol), stirred at room temperature for 1 hour, and the reaction mixture was added with water and extracted with ethyl acetate. After the organic layer was concentrated, the residue was triturated in hexane/ethyl acetate (4/1) to obtain Compound 191 (19 mg, 29%).

¹H-NMR (270 MHz, DMSO-d₆) δ 1.86 (s, 6H), 4.37 (d, J=5.0 Hz, 2H), 4.55 (t, J=5.0 Hz, 1H), 6.00 (s, 1H), 6.58 (d, J=17.0 Hz, 1H), 7.11 (t, J=7.9 Hz, 1H), 7.28-7.35 (m, 1H), 7.35 (d, J=15.2 Hz, 1H), 7.42-7.56 (m, 3H), 7.45 (d, J=15.2 Hz, 1H), 7.59 (d, J=7.9 Hz, 1H), 8.07 (d, J=6.3 Hz, 1H), 13.1 (br, 1H).

APCI-MS (m/z); 344 [M+H]⁺

EXAMPLE 192

(E)-2-{2-[2-(1H-indazol-3-yl)vinyl]phenyl}-5-nitroisoindole-1,3-dione (Compound 192)

In a similar manner to Example 151, Compound 192 (97 mg, 56%) was obtained from Compound 2 (0.10 g, 0.43 mmol), triethylamine (12 μL, 0.085 mmol), 4-nitrophthalic anhydride (99 mg, 0.51 mmol), molecular sieves 3A (0.12 g) and xylene (2.0 mL).

¹H-NMR (300 MHz, DMSO-d₆) δ 7.05 (t, J=7.4 Hz, 1H), 7.26 (d, J=16.5 Hz, 1H), 7.33 (d, J=7.4 Hz, 1H), 7.45-7.63 (m, 4H), 7.62 (d, J=16.5 Hz, 1H), 7.84 (d, J=7.9 Hz, 1H), 8.13 (d, J=7.4 Hz, 1H), 8.29 (d, J=8.1 Hz, 1H), 8.65 (s, 1H), 8.73 (d, J=7.9 Hz, 1H), 13.13 (s, 1H).

ESI-MS (m/z); 409 [M–H]

EXAMPLE 193

(E)-5-amino-2-{2-[2-(1H-indazol-3-yl)vinyl]phenyl}isoindole-1,3-dione (Compound 193)

In a similar manner to Example 2, Compound 193 (11 mg, 23%) was obtained from (E)-2-{2-[2-(1H-indazol-3-yl)vinyl]phenyl}-5-nitroisoindole-1,3-dioen (50 mg, 0.12 mmol) obtained in Example 192, tin (43 mg, 0.37 mmol), concentrated hydrochloric acid (0.22 mL) and ethanol (1.0 mL).

¹H-NMR (270 MHz, DMSO-d₆) δ 6.64 (s, 2H), 6.91 (d, J=8.1 Hz, 1H), 7.02 (t, J=6.9 Hz, 1H), 7.05 (s, 1H), 7.16 (d, J=16.8 Hz, 1H), 7.29-7.48 (m, 4H), 7.52 (d, J=8.7 Hz, 1H), 7.58 (d, J=16.8 Hz, 1H), 7.64 (d, J=8.7 Hz, 1H), 7.72 (d, J=8.1 Hz, 1H), 8.08 (d, J=7.5 Hz, 1H), 13.13 (s, 1H).

ESI-MS (m/z); 381 [M+H]⁺

EXAMPLE 194

(E)-4-amino-2-{2-[2-(1H-indazol-3-yl)vinyl]phenyl}isoindole-1,3-dione (Compound 194)

Step 1

In a similar manner to Example 151, (E)-2-{2-[2-(1H-indazol-3-yl)vinyl]phenyl}-4-nitroisoindole-1,3-dione (0.24 mg, 45%) was obtained from Compound 2 (0.30 mg, 1.3 mmol), triethylamine (36 μL, 0.26 mmol), 3-nitrophthalic anhydride (0.30 g, 1.5 mmol), molecular sieves 3A (0.30 g) and xylene (6.0 mL).

¹H-NMR (270 MHz, DMSO-d₆) δ 7.05 (t, J=7.8 Hz, 1H), 7.29 (d, J=16.5 Hz, 1H), 7.34 (d, J=7.3 Hz, 1H), 7.46-7.62 (m, 4H), 7.62 (d, J=16.8 Hz, 1H), 7.85 (d, J=8.4 Hz, 1H), 8.12 (d, J=6.8 Hz, 1H), 8.18 (d, J=7.3 Hz, 1H), 8.32 (d, J=7.8 Hz, 1H), 8.40 (d, J=7.8 Hz, 1H), 13.15 (s, 1H).

Step 2

In a similar manner to Example 2, Compound 194 (87 mg, 47%) was obtained from (E)-2-{2-[2-(1H-indazol-3-yl)vinyl]phenyl}-4-nitroisoindole-1,3-dione (0.20 g, 0.49 mmol) obtained in Step 1, tin (0.17 mg, 1.5 mmol), concentrated hydrochloric acid (0.86 mL) and ethanol (4.0 mL).

¹H-NMR (270 MHz, DMSO-d₆) δ 6.61 (s, 2H), 7.02 (t, J=8.1 Hz, 1H), 7.09 (t, J=3.0 Hz, 1H), 7.12 (d, J=1.6 Hz, 1H), 7.19 (d, J=15.9 Hz, 1H), 7.33 (t, J=7.0 Hz, 1H), 7.43 (d, J=1.6 Hz, 1H), 7.44-7.65 (m, 5H), 7.74 (d, J=8.6 Hz, 1H), 8.10 (d, J=8.1 Hz, 1H), 13.13 (s, 1H).

ESI-MS (m/z); 381 [M+H]⁺

EXAMPLE 195

(E)-2-{2-[2-(1H-indazol-3-yl)vinyl]phenyl}-3H-imidazole-4-carboxylic acid methyl ester (Compound 195)

(E)-2-[2-(1H-indazol-3-yl)vinyl]-N-hydroxybenzamidine (0.30 g, 0.83 mmol) obtained in Step 1 of Example 175 was dissolved in methanol (8.0 mL) and after heating methyl propiolate (0.21 mL, 2.5 mmol) under reflux for 5 hours, water was added to stop the reaction. The mixture was extracted with ethyl acetate and the organic layer was concentrated. The residue was purified by preparative thin-layer chromatography (chloroform/acetone=4/1) to obtain Compound 195 (13 mg, 5%).

¹H-NMR (270 MHz, DMSO-d₆) δ 3.64 (s, 3H), 7.14 (t, J=7.9 Hz, 1H), 7.34-7.59 (m, 5H), 7.56 (d, J=16.7 Hz, 1H), 7.73 (d, J=16.7 Hz, 1H), 7.96-8.01 (m, 2H), 8.02 (d, J=7.9 Hz, 1H), 13.2 (br, 1H).

APCI-MS (m/z); 345 [M+H]⁺

EXAMPLE 196

(E)-5-chloro-2-{2-[2-(1H-indazol-3-yl)vinyl]phenyl}isoindole-1,3-dione (Compound 196)

In a similar manner to Example 151, Compound 196 (90 mg, 66%) was obtained from Compound 2 (80 mg, 0.34 mmol), triethylamine (9.6 μL, 0.068 mmol), 4-chlorophthalic anhydride (68 mg, 0.37 mmol), molecular sieves 3A (40 mg) and xylene (1.6 mL).

¹H-NMR (270 MHz, DMSO-d₆) δ 7.04 (t, J=7.8 Hz, 1H), 7.22 (d, J=16.5 Hz, 1H), 7.34 (d, J=8.4 Hz, 1H), 7.45-7.62 (m, 4H), 7.61 (d, J=16.5 Hz, 1H), 7.78 (d, J=7.8 Hz, 1H), 7.99-8.16 (m, 4H), 13.13 (s, 1H).
ESI-MS (m/z); 400 [M+H]⁺

EXAMPLE 197

(E)-2-{2-[2-(1H-indazol-3-yl)vinyl]phenyl}-5-methylisoindole-1,3-dione (Compound 197)

In a similar manner to Example 151, Compound 197 (54 mg, 42%) was obtained from Compound 2 (80 mg, 0.34 mmol), triethylamine (9.6 μL, 0.068 mmol), 4-methylphthalic anhydride (61 mg, 0.37 mmol), molecular sieves 3A (80 mg) and xylene (1.6 mL).

¹H-NMR (270 MHz, DMSO-d₆) δ2.56 (s, 3H), 7.01 (t, J=7.3 Hz, 1H), 7.18 (d, J=16.2 Hz, 1H), 7.33 (t, J=7.3 Hz, 1H), 7.44-7.60 (m, 4H), 7.60 (d, J=16.2 Hz, 1H), 7.73 (d, J=8.1 Hz, 1H), 7.77 (d, J=8.6 Hz, 1H), 7.87 (s, 1H), 7.92 (d, J=7.3 Hz, 1H), 8.11 (d, J=8.1 Hz, 1H), 13.12 (s, 1H).
ESI-MS (m/z); 380 [M+H]⁺

EXAMPLE 198

(E)-2-{2-[2-(1H-indazol-3-yl)vinyl]phenyl}pyrrolo[3,4-c]pyridine-1,3-dione hydrochloride (Compound 198)

In a similar manner to Example 151, (E)-2-{2-[2-(1H-indazol-3-yl)vinyl]phenyl}pyrrolo[3,4-c]pyridine-1,3-dione was obtained from (E)-2-[2-(1H-indazol-3-yl)vinyl]phenylamine (80 mg, 0.34 mmol) obtained in Example 2, triethylamine (9.6 μL, 0.068 mmol), 3,4-pyridinedicarboxylic anhydride (61 mg, 0.41 mmol), molecular sieves 3A (80 mg) and xylene (1.6 mL). Further, the product was dissolved in ethyl acetate (1.0 mL) and 4.0 mol/L hydrogen chloride-ethyl acetate solution (1.0 mL) was added thereto, followed by stirring at room temperature for 30 minutes. The precipitated crystal was collected by filtration to obtain Compound 198 (60 mg, 44%).

¹H-NMR (300 MHz, DMSO-d₆) δ 7.24 (t, J=8.1 Hz, 1H), 7.38-7.47 (m, 3H), 7.47 (d, J=16.5 Hz, 1H), 7.58 (d, J=8.4 Hz, 1H), 7.61 (d, J=8.4 Hz, 1H), 7.64 (d, J=8.1 Hz, 1H), 8.00-8.05 (m, 2H), 8.34 (d, J=4.8 Hz, 1H), 9.22 (d, J=4.8 Hz, 1H), 9.29 (s, 1H).
ESI-MS (m/z); 367 [M+H]⁺

EXAMPLE 199

(E)-4-fluoro-2-{2-[2-(1H-indazol-3-yl)vinyl]phenyl}isoindole-1,3-dione (Compound 199)

In a similar manner to Example 151, Compound 199 (37 mg, 29%) was obtained from Compound 2 (80 mg, 0.34 mmol), triethylamine (9.5 μL, 0.068 mmol), 3-fluorophthalic anhydride (68 mg, 0.41 mmol), molecular sieves 3A (80 mg) and xylene (1.6 mL).

¹H-NMR (270 MHz, DMSO-d₆) δ 7.03 (t, J=7.6 Hz, 1H), 7.24 (d, J=16.5 Hz, 1H), 7.33 (t, J=7.6 Hz, 1H), 7.46-7.66 (m, 4H), 7.61 (d, J=16.5 Hz, 1H), 7.80 (t, J=8.4 Hz, 1H), 7.81 (d, J=7.6 Hz, 1H), 7.89 (d, J=7.6 Hz, 1H), 7.97-8.06 (m, 1H), 8.11 (d, J=7.8 Hz, 1H), 13.15 (s, 1H).
ESI-MS (m/z); 384 [M+H]⁺

EXAMPLE 200

(E)-4-hydroxy-2-{2-[2-(1H-indazol-3-yl)vinyl]phenyl}isoindole-1,3-dione (Compound 200)

In a similar manner to Example 151, Compound 200 (64 mg, 49%) was obtained from Compound 2 (80 mg, 0.34 mmol), triethylamine (67 μL, 0.48 mmol), 3-hydroxyphthalic anhydride (66 mg, 0.41 mmol), molecular sieves 3A (80 mg) and xylene (1.6 mL).

¹H-NMR (270 MHz, DMSO-d₆) δ 6.97 (t, J=7.6 Hz, 1H), 7.03-7.23 (m, 2H), 7.33 (d, J=8.4 Hz, 1H), 7.38 (d, J=16.5 Hz, 1H), 7.42-7.60 (m, 4H), 7.51 (d, J=8.1 Hz, 1H), 7.67 (d, J=16.5 Hz, 1H), 7.72 (d, J=8.4 Hz, 1H), 7.74 (d, J=7.6 Hz, 1H), 8.10 (d, J=7.6 Hz, 1H), 13.13 (s, 1H).
ESI-MS (m/z); 382 [M+H]⁺

EXAMPLE 201

(E)-5-ethylamino-2-{2-[2-(1H-indazol-3-yl)vinyl]phenyl}isoindole-1,3-dione (Compound 201)

To a solution of (E)-5-amino-2-{2-[2-(1H-indazol-3-yl)vinyl]phenyl}isoindole-1,3-dione (40 mg, 0.11 mmol) obtained in Example 193 in THF (1.0 mL), acetaldehyde (5.2 μL, 0.12 mmol) and sodium triacetoxyborohydride (33 mg, 0.16 mmol) were added and stirred at room temperature for 2.5 hours. The reaction mixture was added with saturated aqueous sodium hydrogencarbonate solution, extracted with ethyl acetate and the organic layer was concentrated under reduced pressure. The residue was purified by silica gel column chromatography (chloroform to chloroform/methanol=90/10) to obtain Compound 201 (16 mg, 38%).

¹H-NMR (270 MHz, DMSO-d₆) δ 1.22 (t, J=7.3 Hz, 3H), 3.45 (q, J=7.3 Hz, 2H), 6.93 (d, J=8.4 Hz, 1H), 7.01 (t, J=7.6 Hz, 1H), 7.04 (s, 1H), 7.17 (d, J=16.5 Hz, 1H), 7.17 (t, J=8.4 Hz, 1H), 7.33 (t, J=7.6 Hz, 1H), 7.38 (d, J=8.1 Hz, 1H), 7.45 (t, J=7.6 Hz, 1H), 7.52 (d, J=8.1 Hz, 1H), 7.58 (d, J=16.5 Hz, 1H), 7.69 (d, J=8.4 Hz, 1H), 7.70 (t, J=8.4 Hz, 1H), 8.08 (d, J=7.6 Hz, 1H), 13.13 (s, 1H).
ESI-MS (m/z); 409 [M+H]⁺

EXAMPLE 202

(E)-2-{2-[2-(1H-indazol-3-yl)vinyl]phenyl}benzo[f]isoindole-1,3-dione (Compound 202)

In a similar manner to Example 151, Compound 202 (36 mg, 26%) was obtained from Compound 2 (80 mg, 0.34 mmol), triethylamine (9.5 μL, 0.068 mmol), 2,3-naphthalenedicarboxylic anhydride (81 mg, 0.41 mmol), molecular sieves 3A (80 mg) and xylene (1.6 mL).

¹H-NMR (270 MHz, DMSO-d₆) δ 6.89 (t, J=7.6 Hz, 1H), 7.23 (d, J=16.5 Hz, 1H), 7.26 (t, J=8.6 Hz, 1H), 7.46 (d, J=8.6 Hz, 1H), 7.49-7.61 (m, 3H), 7.63 (d, J=7.6 Hz, 1H), 7.72 (d, J=8.6 Hz, 1H), 7.84 (dd, J=3.0, 3.0 Hz, 2H), 8.13 (d, J=7.6 Hz, 1H), 8.33 (dd, J=3.0, 3.0 Hz, 2H), 8.70 (s, 2H), 13.07 (s, 1H).
ESI-MS (m/z); 416 [M+H]⁺

EXAMPLE 203

(E)-2-{2-[2-(1H-indazol-3-yl)vinyl]phenyl}-4,5,6,7-tetrahydroisoindole-1,3-dione (Compound 203)

To a solution of Compound 2 (50 mg, 0.21 mmol) in acetic acid (1.0 mL), 4,5,6,7-tetrahydroisobenzofuran-1,3-dione (39 mg, 0.26 mmol) was added followed by heating under reflux for 1.0 hour. The reaction mixture was added with saturated aqueous sodium hydrogencarbonate solution, extracted with ethyl acetate and the organic layer was concentrated under reduced pressure. The residue was purified by silica gel column chromatography (chloroform to chloroform/methanol=90/10) and crystallized from ethyl acetate to obtain Compound 203 (37 mg, 46%).

$^1$H-NMR (300 MHz, DMSO-$d_6$) δ 1.75-1.84 (br, 4H), 2.34-2.44 (br, 4H), 7.14 (d, J=16.5 Hz, 1H), 7.17 (t, J=6.3 Hz, 1H), 7.30 (d, J=8.1 Hz, 1H), 7.39 (t, J=7.8 Hz, 1H), 7.42 (d, J=7.8 Hz, 1H), 7.51 (d, J=6.3 Hz, 1H), 7.55 (t, J=6.3 Hz, 1H), 7.59 (d, J=16.5 Hz, 1H), 7.84 (d, J=8.4 Hz, 1H), 8.08 (d, J=8.4 Hz, 1H), 13.21 (s, 1H).

ESI-MS (m/z); 370 [M+H]$^+$

EXAMPLE 204

(E)-1-{2-[2-(1H-indazol-3-yl)vinyl]phenyl}-3,4-dimethylpyrrole-2,5-dione (Compound 204)

In a similar manner to Example 203, Compound 204 (53 mg, 45%) was obtained from Compound 2 (80 mg, 0.34 mmol), 2,3-dimethylmaleic anhydride (52 mg, 0.41 mmol) and acetic acid (1.6 mL).

$^1$H-NMR (300 MHz, DMSO-$d_6$) δ 2.05 (s, 6H), 7.14 (d, J=16.5 Hz, 1H), 7.18 (t, J=8.1 Hz, 1H), 7.30 (d, J=7.8 Hz, 1H), 7.39 (t, J=8.1 Hz, 1H), 7.42 (t, J=7.8 Hz, 1H), 7.53 (t, J=7.8 Hz, 1H), 7.56 (d, J=8.1 Hz, 1H), 7.59 (d, J=16.5 Hz, 1H), 7.86 (d, J=8.1 Hz, 1H), 8.07 (d, J=7.8 Hz, 1H), 13.20 (s, 1H).

ESI-MS (m/z); 344 [M+H]$^+$

EXAMPLE 205

(E)-6-{2-[2-(1H-indazol-3-yl)vinyl]phenyl}pyrrolo[3,4-b]pyridine-5,7-dione (Compound 205)

Step 1

To a solution of Compound 2 (0.10 g, 0.43 mmol) in THF (2.0 mL), pyridine (0.10 μL, 1.3 mmol) and 2,3-pyridinedicarboxylic anhydride (76 mg, 0.51 mmol) were added and stirred at room temperature for 1.5 hours. The reaction mixture was added with water, extracted with ethyl acetate and the organic layer was concentrated under reduced pressure. The residue was purified by silica gel column chromatography (chloroform to chloroform/methanol=90/10), crystallized from ethyl acetate to obtain (E)-2-{2-[2-(1H-indazol-3-yl)vinyl]phenylcarbamoyl}nicotinic acid or (E)-3-{2-[2-(1H-indazol-3-yl)vinyl]phenylcarbamoyl}pyridine-2-carboxylic acid (63 mg, 39%).

ESI-MS (m/z); 385 [M+H]$^+$

Step 2

To a solution of (E)-2-{2-[2-(1H-indazol-3-yl)vinyl]phenylcarbamoyl}nicotinic acid or (E)-3-{2-[2-(1H-indazol-3-yl)vinyl]phenylcarbamoyl}pyridine-2-carboxylic acid (20 mg, 0.052 mmol) obtained in Step 1 in THF (1.0 mL), 1-hydroxybenzotriazole monohydrate (1.6 mg, 0.010 mmol) and EDC (15 mg, 0.078 mmol) were added, followed by heating under reflux for 30 minutes. The reaction mixture was added with water, extracted with ethyl acetate and the organic layer was concentrated under reduced pressure. The residue was purified by silica gel column chromatography (chloroform to chloroform/methanol=90/10), crystallized from DMF/water (1/1) to obtain Compound 205 (7.2 mg, 38%).

$^1$H-NMR (270 MHz, DMSO-$d_6$) δ 7.03 (t, J=8.1 Hz, 1H), 7.27 (d, J=16.2 Hz, 1H), 7.33 (t, J=6.8 Hz, 1H), 7.46-7.62 (m, 4H), 7.61 (d, J=16.2 Hz, 1H), 7.82 (d, J=8.4 Hz, 1H), 7.91 (t, J=4.9 Hz, 1H), 8.11 (d, J=6.8 Hz, 1H), 8.46 (d, J=8.4 Hz, 1H), 9.10 (d, J=4.9 Hz, 1H), 13.12 (s, 1H).

ESI-MS (m/z); 367 [M+H]$^+$

EXAMPLE 206

(E)-1-{2-[2-(1H-indazol-3-yl)vinyl]phenyl}piperidin-2-one (Compound 206)

Step 1

In a similar manner to Example 3, (E)-N-{2-[2-(1H-indazol-3-yl)vinyl]phenyl}-5-bromopentamide (49 mg, 37%) was obtained from Compound 2 (80 mg, 0.34 mmol), 5-bromovalerylchloride (55 μL, 0.41 mmol), pyridine (83 μL, 1.0 mmol) and THF (1.6 mL).

$^1$H-NMR (270 MHz, DMSO-$d_6$) δ 1.72-1.97 (m, 4H), 2.44 (t, J=7.1 Hz, 2H), 3.56 (t, J=6.4 Hz, 2H), 7.18-7.45 (m, 6H), 7.55 (d, J=7.1 Hz, 1H), 7.60 (d, J=15.9 Hz, 1H), 7.86-7.92 (m, 1H), 8.10 (d, J=8.1 Hz, 1H), 9.77 (s, 1H), 13.17 (s, 1H).

ESI-MS (m/z); 399 [M+H]$^+$

Step 2

To a solution of (E)-N-{2-[2-(1H-indazol-3-yl)vinyl]phenyl}-5-bromopentamide (40 mg, 0.10 mmol) obtained in Step 1 in THF (1.0 mL), potassium t-butoxide (24 mg, 0.21 mmol) was added, followed by stirring at room temperature for 2.0 hours. The reaction mixture was added with water, extracted with ethyl acetate and the organic layer was concentrated under reduced pressure. The residue was purified by silica gel column chromatography (chloroform to chloroform/methanol=90/10) to obtain Compound 206 (32 mg, 100%).

$^1$H-NMR (270 MHz, DMSO-$d_6$) δ 1.06 (t, J=6.2 Hz, 1H), 1.18 (t, J=6.2 Hz, 1H), 1.83-2.01 (br, 4H), 3.35-3.48 (br, 1H), 3.55-3.67 (br, 1H), 7.18-7.30 (m, 2H), 7.33-7.44 (m, 4H), 7.56 (t, J=8.1 Hz, 1H), 7.56 (d, J=16.5 Hz, 1H), 7.97 (d, J=8.6 Hz, 2H), 13.20 (s, 1H).

ESI-MS (m/z); 318 [M+H]$^+$

EXAMPLE 207

(E)-3,4-dichloro-1-{2-[2-(1H-indazol-3-yl)vinyl]phenyl}pyrrole-2,5-dione (Compound 207)

In a similar manner to Example 203, Compound 207 (0.11 mg, 46%) was obtained from Compound 2 (0.15 g, 0.638 mmol), 2,3-dichloromaleic anhydride (0.13 mg, 0.77 mmol) and acetic acid (2.3 mL).

$^1$H-NMR (300 MHz, DMSO-$d_6$) δ 7.16 (t, J=7.8 Hz, 1H), 7.34 (d, J=16.5 Hz, 1H), 7.37-7.56 (m, 5H), 7.60 (d, J=16.5 Hz, 1H), 7.99 (d, J=8.4 Hz, 1H), 8.09 (d, J=7.8 Hz, 1H), 13.21 (s, 1H).

ESI-MS (m/z); 384 [M]$^+$

EXAMPLE 208

(E)-1-{2-[2-(1H-indazol-3-yl)vinyl]phenyl}pyrrolidin-2-one (Compound 208)

In a similar manner to Example 3, Compound 208 (0.16 g, 98%) was obtained from Compound 2 (0.10 mg, 0.43 mmol), 4-bromobutyryl chloride (59 μL, 0.51 mmol), pyridine (0.10 mL, 1.3 mmol) and THF (2.0 mL).

$^1$H-NMR (300 MHz, DMSO-$d_6$) δ 2.20 (t, J=7.5 Hz, 2H), 2.44-2.57 (m, 2H), 3.75 (t, J=7.5 Hz, 2H), 7.29-7.44 (m, 6H), 7.55 (d, J=16.5 Hz, 1H), 7.57 (d, J=8.4 Hz, 1H), 7.98 (d, J=7.8 Hz, 2H), 13.19 (s, 1H).

ESI-MS (m/z); 304 [M+H]$^+$

EXAMPLE 209

(E)-5-{2-[2-(1H-indazol-3-yl)vinyl]phenyl}thieno[2,3-c]pyrrole-4,6-dione (Compound 209)

Step 1

To a solution of (E)-N-{2-[2-(1H-indazol-3-yl)vinyl]phenyl}thiophene-2-carboxamide (0.28 g, 0.81 mmol) obtained in Example 14 in THF (5.6 mL), n-butyllithium (2.7 mol/L n-hexane solution, 3.0 mL, 8.1 mmol) was added dropwise at −78° C. under nitrogen atomosphere, followed by stirring for 1.0 hour. Then, under carbon dioxide gas atmosphere, the mixture was stirred at −78° C. for 30 minutes and at 0° C. for 2.0 hours. The reaction mixture was added with 2-propanol and saturated aqueous ammonium chloride solution, extracted with ethyl acetate and the organic layer was concentrated under reduced pressure. The residue was purified by silica gel column chromatography (chloroform/methanol=100/0 to 80/20) to obtain (E)-2-{2-[2-(1H-indazol-3-yl)vinyl]phenylcarbamoyl}thiophene-3-carboxylic acid (0.14 g, 44%).

$^1$H-NMR (300 MHz, DMSO-d$_6$) δ 7.14 (t, J=8.1 Hz, 1H), 7.24-7.41 (m, 3H), 7.46-7.56 (m, 3H), 7.65 (d, J=7.5 Hz, 1H), 7.72 (d, J=4.8 Hz, 1H), 7.89 (d, J=16.2 Hz, 1H), 7.92 (d, J=7.5 Hz, 1H), 8.23 (d, J=7.8 Hz, 1H), 13.15 (s, 1H).

ESI-MS (m/z); 390 [M+H]$^+$

Step 2

In a similar manner to Step 2 of Example 205, Compound 209 (29 mg, 22%) was obtained from (E)-2-{2-[2-(1H-indazol-3-yl)vinyl]phenylcarbamoyl}thiophene-3-carboxylic acid (0.14 g, 0.36 mmol) obtained in Step 1,1-hydroxybenzotriazole monohydrate (11 mg, 0.072 mmol), EDC (0.10 g, 0.54 mmol) and THF (7.0 mL).

$^1$H-NMR (300 MHz, DMSO-d$_6$) δ 7.06 (t, J=7.5 Hz, 1H), 7.26 (d, J=16.8 Hz, 1H), 7.35 (t, J=7.5 Hz, 1H), 7.44-7.62 (m, 5H), 7.65 (d, J=4.8 Hz, 1H), 7.79 (d, J=8.7 Hz, 1H), 8.10 (d, J=7.5 Hz, 1H), 8.38 (d, J=4.8 Hz, 1H), 13.16 (s, 1H).

ESI-MS (m/z); 372 [M+H]$^+$

EXAMPLE 210

(E)-2-{2-[2-(1H-indazol-3-yl)vinyl]phenyl}-5,6-dihydro-4H-cyclopenta[c]pyrrole-1,3-dione (Compound 210)

Step 1

In a similar manner to Example 151, (E)-2-(N-{2-[2-(1H-indazol-3-yl)vinyl]phenyl}carbamoyl)cyclopentene-1-carboxylic acid (0.12 g, 74%) was obtained from Compound 2 (0.10 g, 0.43 mmol), triethylamine (12 μL, 0.085 mmol), cyclopentene-1,2-dicarboxylic anhydride (70 mg, 0.51 mmol), molecular sieves 3A (0.10 mg) and xylene (2.0 mL).

$^1$H-NMR (300 MHz, DMSO-d$_6$) δ 1.90-1.99 (br, 2H), 2.66-2.75 (br, 2H), 2.81-2.91 (br, 2H), 7.19 (t, J=7.2 Hz, 1H), 7.26-7.46 (m, 3H), 7.48 (d, J=16.5 Hz, 1H), 7.55 (d, J=8.4 Hz, 1H), 7.59-7.65 (m, 1H), 7.64 (d, J=16.5 Hz, 1H), 7.91 (d, J=7.2 Hz, 1H), 8.11 (d, J=8.1 Hz, 1H).

ESI-MS (m/z); 374 [M+H]$^+$

Step 2

In a similar manner to Step 2 of Example 205, Compound 210 (14 mg, 12%) was obtained from (E)-2-(N-{2-[2-(1H-indazol-3-yl)vinyl]phenyl}carbamoyl)cyclopentene-1-carboxylic acid (0.12 g, 0.31 mmol) obtained in Step 1, 1-hydroxybenzotriazole monohydrate (9.6 mg, 0.063 mmol), EDC (90 mg, 0.47 mmol) and THF (4.0 mL).

$^1$H-NMR (270 MHz, DMSO-d$_6$) δ 2.42-2.52 (br, 2H), 2.69-2.78 (br, 4H), 7.19 (t, J=7.7 Hz, 1H), 7.20 (d, J=16.3 Hz, 1H), 7.30 (d, J=7.7 Hz, 1H), 7.39 (t, J=8.3 Hz, 1H), 7.42 (t, J=8.3 Hz, 1H), 7.52 (t, J=7.7 Hz, 1H), 7.56 (d, J=8.3 Hz, 1H), 7.59 (d, J=16.3 Hz, 1H), 7.88 (d, J=8.3 Hz, 1H), 8.06 (d, J=7.7 Hz, 1H), 13.16 (s, 1H).

ESI-MS (m/z); 356 [M+H]$^+$

EXAMPLE 211

(E)-1-{2-[2-(1H-indazol-3-yl)vinyl]phenyl}pyrrolidine-2,5-dione (Compound 211)

In a similar manner to Example 151, Compound 211 (34 mg, 31%) was obtained from Compound 2 (80 mg, 0.34 mmol), triethylamine (9.6 μL, 0.068 mmol), succinic anhydride (41 mg, 0.41 mmol), molecular sieves 3A (80 mg) and xylene (1.6 mL).

$^1$H-NMR (300 MHz, DMSO-d$_6$) δ 2.84-2.99 (m, 4H), 7.15 (d, J=16.5 Hz, 1H), 7.21-7.28 (m, 2H), 7.40 (t, J=8.7 Hz, 1H), 7.42 (t, J=8.1 Hz, 1H), 7.52 (t, J=8.1 Hz, 1H), 7.56 (d, J=8.7 Hz, 1H), 7.58 (d, J=16.5 Hz, 1H), 7.96 (d, J=8.1 Hz, 1H), 8.06 (d, J=8.1 Hz, 1H), 13.21 (s, 1H).

ESI-MS (m/z); 318 [M+H]$^+$

EXAMPLE 212

(E)-3-{2-[2-(1H-indazol-3-yl)vinyl]phenyl}imidazolidine-2,4-dione (Compound 212)

Step 1

A solution of Compound 2 (0.15 g, 0.64 mmol) in THF (3.8 mL) was ice-cooled and ethyl isocyanoacetate (93 μL, 0.83 mmol) was added thereto, followed by stirring at room temperature overnight. The reaction mixture was added with water, extracted with ethyl acetate and the organic layer was concentrated under reduced pressure. The residue was purified by silica gel column chromatography (chloroform/methanol=100/0 to 90/10) and crystallized from ethyl acetate to obtain (E)-(3-{2-[2-(1H-indazol-3-yl)vinyl]phenyl}ureido)oxoacetic acid ethyl ester (87 mg, 37%).

$^1$H-NMR (270 MHz, DMSO-d$_6$) δ 1.20 (t, J=7.0 Hz, 3H), 3.91 (d, J=5.7 Hz, 2H), 4.21 (q, J=7.3 Hz, 2H), 6.83 (t, J=7.3 Hz, 1H), 7.09 (d, J=7.3 Hz, 1H), 7.12 (d, J=7.6 Hz, 1H), 7.21 (t, J=7.3 Hz, 1H), 7.24 (t, J=7.6 Hz, 1H), 7.40 (t, J=7.6 Hz, 1H), 7.43 (d, J=16.2 Hz, 1H), 7.56 (d, J=7.6 Hz, 1H), 7.64 (d, J=16.2 Hz, 1H), 7.67 (d, J=7.6 Hz, 1H), 8.14 (d, J=7.3 Hz, 1H), 8.44 (s, 1H), 13.21 (s, 1H).

Step 2

(E)-(3-{2-[2-(1H-indazol-3-yl)vinyl]phenyl}ureido)oxoacetic acid ethyl ester (50 mg, 0.14 mmol) obtained in Step 1 was heated under reflux in a mixed solvent of 6.0 mol/L hydrochloric acid/acetone (1/1, 2.5 mL) under nitrogen atomosphere for 60 hours. The reaction mixture was added with saturated aqueous sodium hydrogencarbonate solution, extracted with ethyl acetate and the organic layer was concentrated under reduced pressure. The residue was purified by silica gel column chromatography (chloroform to chloroform/methanol=90/10) to obtain Compound 212 (38 mg, 87%).

$^1$H-NMR (300 MHz, DMSO-d$_6$) δ 4.17 (d, J=17.7 Hz, 1H), 4.27 (d, J=17.7 Hz, 1H), 7.21 (t, J=7.8 Hz, 1H), 7.24 (d, J=16.8 Hz, 1H), 7.30 (d, J=7.2 Hz, 1H), 7.40 (t, J=7.2 Hz, 1H), 7.42 (t, J=7.8 Hz, 1H), 7.52 (t, J=8.1 Hz, 1H), 7.56 (d, J=8.1 Hz, 1H), 7.58 (d, J=16.8 Hz, 1H), 7.95 (d, J=8.1 Hz, 1H), 8.06 (d, J=7.8 Hz, 1H), 8.44 (s, 1H), 13.21 (s, 1H).

ESI-MS (m/z); 319 [M+H]$^+$

EXAMPLE 213

(E)-2-{2-[2-(1H-indazol-3-yl)vinyl]phenyl}-2,3-dihydroisoindole-1-one (Compound 213)

Step 1

In a similar manner to Example 3, (E)-2-chloromethyl-N-{2-[2-(1H-indazol-3-yl)vinyl]phenyl}benzamide (40 mg, 30%) was obtained from Compound 2 (80 mg, 0.34 mmol), 2-(chloromethyl)benzoyl chloride (96 mg, 0.51 mmol), pyridine (96 μL, 1.2 mmol) and THF (1.0 mL).

$^1$H-NMR (300 MHz, DMSO-$d_6$) δ 5.00 (s, 2H), 7.13 (t, J=7.5 Hz, 1H), 7.31-7.38 (m, 1H), 7.37 (d, J=5.7 Hz, 1H), 7.39 (t, J=8.1 Hz, 1H), 7.44-7.65 (m, 6H), 7.68-7.78 (m, 2H), 7.73 (d, J=16.5 Hz, 1H), 7.96 (d, J=5.7 Hz, 1H), 8.09 (d, J=8.4 Hz, 0.1H), 10.38 (s, 1H), 13.17 (s, 1H).

ESI-MS (m/z); 388 [M+H]$^+$

Step 2

In a similar manner to Step 2 of Example 206, Compound 213 (23 mg, 73%) was obtained from (E)-2-chloromethyl-N-{2-[2-(1H-indazol-3-yl)vinyl]phenyl}benzamide (35 mg, 0.090 mmol) obtained in Step 1, potassium t-butoxide (31 mg, 0.28 mmol) and THF (1.0 mL).

$^1$H-NMR (270 MHz, DMSO-$d_6$) δ 4.94 (s, 2H), 6.94 (t, J=7.0 Hz, 1H), 7.25 (d, J=16.5 Hz, 1H), 7.31 (t, J=7.8 Hz, 1H), 7.41-7.55 (m, 5H), 7.58-7.66 (m, 2H), 7.69 (d, J=8.4 Hz, 1H), 7.70 (d, J=16.5 Hz, 1H), 7.86 (d, J=7.6 Hz, 1H), 8.05 (d, J=6.2 Hz, 1H), 13.09 (s, 1H).

ESI-MS (m/z); 352 [M+H]$^+$

EXAMPLE 214

(E)-5,6-dichloro-2-{2-[2-(1H-indazol-3-yl)vinyl]phenyl}isoindole-1,3-dione (Compound 214)

Step 1

In a similar manner to Example 29, (E)-4,5-dichloro-N-{2-[2-(1H-indazol-3-yl)vinyl]phenyl}phthalamide (48 mg, 31%) was obtained from 4,5-dichlorophthalic acid (0.16 g, mmol), thionyl chloride (0.11 mL, 1.5 mmol), DMF (26 μL, mmol) and methylene chloride (1.6 mL) and Compound 2 (80 mg, 0.34 mmol) obtained in Example 2, triethylamine (0.19 mL, 1.4 mmol) and THF (1.6 mL).

$^1$H-NMR (270 MHz, DMSO-$d_6$) δ 7.16 (t, J=7.3 Hz, 1H), 7.26-7.42 (m, 3H), 7.48 (d, J=16.8 Hz, 1H), 7.54 (d, J=8.1 Hz, 1H), 7.56 (t, J=8.1 Hz, 1H), 7.74 (d, J=16.8 Hz, 1H), 7.91 (d, J=16.8 Hz, 1H), 7.91 (d, J=4.3 Hz, 1H), 7.97 (s, 1H), 8.08 (s, 1H), 8.16 (d, J=8.1 Hz, 1H).

Step 2

In a similar manner to Step 2 of Example 205, Compound 214 (28 mg, 73%) was obtained from (E)-4,5-dichloro-N-{2-[2-(1H-indazol-3-yl)vinyl]phenyl}phthalamide (40 mg, 0.088 mmol) obtained in Step 1,1-hydroxybenzotriazole monohydrate (2.7 mg, 0.018 mmol), EDC (25 mg, 0.13 mmol) and THF (2.0 mL).

$^1$H-NMR (300 MHz, DMSO-$d_6$) δ 7.07 (t, J=7.2 Hz, 1H), 7.23 (d, J=16.5 Hz, 1H), 7.34 (t, J=8.1 Hz, 1H), 7.44-7.62 (m, 4H), 7.61 (d, J=16.5 Hz, 1H), 7.83 (d, J=8.1 Hz, 1H), 8.12 (d, J=8.1 Hz, 1H), 8.38 (s, 2H), 13.15 (s, 1H).

ESI-MS (m/z); 434 [M+H]$^+$

EXAMPLE 215

(E)-N-{2-[2-(1H-indazol-3-yl)vinyl]phenyl}-4-methanesulfonylbenzamide (Compound 215)

In a similar manner to Example 29, Compound 215 (59 mg, 47%) was obtained from 4-(methylsulfonyl)benzoic acid (151 mg, 0.75 mmol), thionyl chloride (66 μL, 0.91 mmol), DMF (70 μL, 0.91 mmol) and methylene chloride (2.0 mL), and Compound 2 (80 mg, 0.30 mmol), triethylamine (253 μL, 1.8 mmol) and THF (2.0 mL).

$^1$H-NMR (270 MHz, DMSO-$d_6$) δ 3.27 (s, 3H), 7.07 (t, J=8.3 Hz, 1H), 7.36 (t, J=8.6 Hz, 1H), 7.39 (d, J=5.3 Hz, 2H), 7.53 (d, J=8.3 Hz, 1H), 7.57 (d, J=5.3 Hz, 2H), 7.92-8.08 (m, 4H), 8.15 (d, J=16.6 Hz, 1H), 8.16 (d, J=8.6 Hz, 1H), 8.29 (d, J=8.3 Hz, 1H), 10.54 (s, 1H), 13.13 (s, 1H).

ESI-MS (m/z); 418 [M+H]$^+$

EXAMPLE 216

(E)-4-amino-2-{2-[2-(1H-indazol-3-yl)vinyl]phenyl}-2,3-dihydroisoindole-1-one (Compound 216)

Step 1

To a solution of Compound 2 (70 mg, 0.26 mmol) in DMF (1.4 mL), triethylamine (91 μL, 0.68 mmol) and 2-bromomethyl-3-nitrobenzoic acid methyl ester (79 mg, 0.29 mmol) were added, followed by stirring at 80° C. for 7.0 hours under nitrogen atomosphere. The reaction mixture was added with water, extracted with ethyl acetate and the organic layer was concentrated under reduced pressure. The residue was purified by silica gel column chromatography (chloroform to chloroform/methanol=90/10) to obtain (E)-2-{2-[2-(1H-indazol-3-yl)vinyl]phenyl}-4-nitro-2,3-dihydroisoindol-1-one (61 mg, 60%).

$^1$H-NMR (300 MHz, DMSO-$d_6$) δ 5.39 (s, 2H), 6.99 (t, J=7.5 Hz, 1H), 7.30 (d, J=16.5 Hz, 1H), 7.32 (t, J=8.4 Hz, 1H), 7.43-7.63 (m, 5H), 7.78 (d, J=8.4 Hz, 1H), 7.93 (d, J=7.5 Hz, 1H), 8.08 (d, J=7.5 Hz, 1H), 8.32 (d, J=7.5 Hz, 1H), 8.56 (d, J=8.4 Hz, 1H), 13.11 (s, 1H).

ESI-MS (m/z); 397 [M+H]$^+$

Step 2

To a solution of (E)-2-{2-[2-(1H-indazol-3-yl)vinyl]phenyl}-4-nitro-2,3-dihydroisoindol-1-one (54 mg, 0.14 mmol) obtained in Step 1 in ethanol/water (2/1, 3.3 mL), ammonium chloride (40 mg, 0.75 mmol) and iron (38 mg, 0.68 mmol) were added, followed by heating under reflux for 4.0 hours under nitrogen atomosphere. The reaction mixture was added with water, extracted with ethyl acetate and the organic layer was concentrated under reduced pressure. The residue was purified by silica gel column chromatography (chloroform to chloroform/methanol=90/10) and crystallized from hexane/ethyl acetate (1/1) to obtain Compound 216 (10 mg, 20%).

$^1$H-NMR (300 MHz, DMSO-$d_6$) δ 4.64 (s, 2H), 5.52 (s, 2H), 6.87 (d, J=8.1 Hz, 1H), 6.96 (t, J=7.8 Hz, 1H), 7.03 (d, J=6.9 Hz, 1H), 7.25 (d, J=16.8 Hz, 1H), 7.28 (d, J=6.9 Hz, 1H), 7.32 (t, J=7.8 Hz, 1H), 7.39-7.53 (m, 4H), 7.56 (d, J=16.8 Hz, 1H), 7.70 (d, J=8.1 Hz, 1H), 8.05 (d, J=7.8 Hz, 1H), 13.10 (s, 1H).

ESI-MS (m/z); 367 [M+H]$^+$

EXAMPLE 217

(E)-N-{2-[2-(1H-indazol-3-yl)vinyl]-5-(morpholin-4-ylcarbonyl)phenyl}-N-methylpyrrole-2-carboxamide hydrochloride (Compound 217, hydrochloride of Compound 123)

Step 1

In a similar manner to Example 1, (1H-indazol-3-ylmethyl)triphenylphosphonium bromide (4.1 g, 8.7 mmol) was dissolved in methanol (60 mL) and 4-[2-(1H-indazol-3-yl)vinyl]-3-nitrobenzoic acid methyl ester was obtained from 4-formyl-3-nitrobenzoic acid methyl (2.4 g, 9.5 mmol) and potassium carbonate (2.9 g, 17 mmol). In a similar manner to Example 2, said 4-[2-(1H-indazol-3-yl)vinyl]-3-nitrobenzoic acid methyl ester (0.50 g, 1.6 mmol) was dissolved in ethanol (10 mL) and 3-amino-4-[2-(1H-indazol-3-yl)vinyl]benzoic acidmethyl was obtained using tin (0.55 g, 4.7 mmol) and concentrated hydrochloric acid (1.3 mL) at room temperature.

APCI-MS (m/z); 294 [M+H]$^+$

Step 2

In a similar manner to Example 29, (E)-4-[2-(1H-indazol-3-yl)vinyl]-3-[(N-methylpyrrol-2-ylcarbonyl)amino]benzoic acid methyl ester was obtained from 3-amino-4-[2-(1H-indazol-3-yl)vinyl]benzoic acid methyl ester (1.4 g, 4.8 mmol) obtained in step 1, THF (25 mL), triethylamine (1.3 ml, 9.6 mmol) and N-methylpyrrolecarbonyl chloride (2.1 g, 14 mmol). In a similar manner to Example 98, (E)-4-[2-(1H-indazol-3-yl)vinyl]-3-[(N-methylpyrrol-2-ylcarbonyl)amino]benzoic acid (1.5 g, 81%) was obtained by stirring at 60° C. for 1 hour using methanol (20 mL) and 2 mol/L aqueous sodium hydroxide solution (20 mL).

$^1$H-NMR (270 MHz, DMSO-d$_6$) δ 3.88 (s, 3H), 6.16 (d, J=5.1 Hz, 1H), 7.04 (s, 1H), 7.08-7.14 (m, 1H), 7.17-7.19 (m, 1H), 7.38 (dd, J=8.4, 8.4 Hz, 1H), 7.56 (d, J=8.9 Hz, 1H), 7.67 (s, 2H), 7.85 (d, J=8.6 Hz, 1H), 7.93 (s, 1H), 8.02 (d, J=7.9 Hz, 1H), 8.08 (d, J=8.4 Hz, 1H), 9.92 (br, 1H), 13.2 (br, 1H).

APCI-MS (m/z); 387 [M+H]$^+$

Step 3

In a similar manner to Example 28, a product was obtained from (E)-4-[2-(1H-indazol-3-yl)vinyl]-3-[(N-methylpyrrol-2-ylcarbonyl)amino]benzoic acid (0.20 g, 0.52 mmol) obtained in Step 2, morpholine (70 μL, 0.78 mmol), 1-hydroxybenzotriazole monohydrate (91 mg, 0.68 mmol) and EDC (0.14 g, 0.73 mmol). Further, the product was added with methanol (2.0 mL) and 4 mol/L hydrogen chloride-methanol solution (1.0 mL), stirred at room temperature for 2 hours and crystallized from a mixed solvent of acetone/ethanol (2/1) to obtain Compound 217 (0.10 g, 39%).

$^1$H-NMR (270 MHz, DMSO-d$_6$) δ 3.63-3.84 (m, 8H), 3.88 (s, 3H), 6.14 (d, J=6.4 Hz, 1H), 7.04 (s, 1H), 7.10-7.12 (m, 1H), 7.16-7.16 (m, 1H), 7.33-7.39 (m, 2H), 7.39 (d, J=16.7 Hz, 1H), 7.54 (d, J=8.2 Hz, 1H), 7.61 (d, J=7.5 Hz, 2H), 7.99-8.03 (m, 2H), 9.86 (br, 1H).

APCI-MS (m/z); 456 [M+H]$^+$

EXAMPLE 218

(E)-N-{2-[2-(1H-indazol-3-yl)vinyl]-5-(4-formylpiperazin-1-ylcarbonyl)phenyl}-3-methylthiophene-2-carboxamide hydrochloride (Compound 218)

In a similar manner to Example 28, (E)-N-{2-[2-(1H-indazol-3-yl)vinyl]-5-(4-formylpiperazin-1-ylcarbonyl)phenyl}-3-methylthiophene-2-carboxamide was obtained from Compound 98 (0.20 g, 0.50 mmol), N-formylpiperazine (86 mg, 0.75 mmol), 1-hydroxybenzotriazole monohydrate (88 mg, 0.65 mmol) and EDC (0.13 g, 0.70 mmol). Further, the product was added with methanol (5.0 mL) and 4 mol/L hydrogen chloride-methanol solution (2.0 mL), stirred at room temperature for 2 hours and crystallized from a mixed solvent of acetone/ethanol (2/1) to obtain Compound 218 (0.16 g, 61%).

$^1$H-NMR (270 MHz, DMSO-d$_6$) δ 2.51 (s, 3H), 3.76-4.15 (m, 8H), 7.07 (d, J=5.0 Hz, 1H), 7.13 (d, J=7.9 Hz, 1H), 7.35-7.44 (m, 2H), 7.54-7.56 (m, 2H), 7.62-7.64 (m, 2H), 7.72 (d, J=5.0 Hz, 1H), 8.05 (d, J=8.2 Hz, 2H), 9.26 (br, 1H), 10.0 (br, 1H).

ESI-MS (m/z); 498 [M+H]$^+$

EXAMPLE 219

(E)-N-{2-[2-(1H-indazol-3-yl)vinyl]-5-(4-hydroxypiperidin-1-ylcarbonyl)phenyl}-3-methylthiophene-2-carboxamide hydrochloride (Compound 219)

In a similar manner to Example 28, (E)-N-{2-[2-(1H-indazol-3-yl)vinyl]-5-(4-hydroxypiperidin-1-ylcarbonyl)phenyl}-3-methylthiophene-2-carboxamide was obtained from Compound 98 (0.10 g, 0.25 mmol), 4-hydroxypiperidine (38 mg, 0.38 mmol), 1-hydroxybenzotriazole monohydrate (44 mg, 0.33 mmol) and EDC (67 mg, 0.35 mmol). Further, the product was added with methanol (5.0 mL) and 4 mol/L hydrogen chloride-methanol solution (2.0 mL), stirred at room temperature for 2 hours and crystallized from a mixed solvent of acetone/ethanol (2/1) to obtain Compound 219 (0.10 g, 77%).

$^1$H-NMR (270 MHz, DMSO-d$_6$) δ 1.40 (s, 2H), 1.77 (s, 2H), 2.50 (s, 3H), 3.18-3.65 (m, 5H), 7.06 (d, J=5.0 Hz, 1H), 7.12 (d, J=8.1 Hz, 1H), 7.34 (d, J=8.1, 8.1 Hz, 1H), 7.42 (d, J=8.1 Hz, 1H), 7.53-7.61 (m, 2H), 7.57 (d, J=16.8 Hz, 1H), 7.64 (d, J=16.8 Hz, 1H), 7.71 (d, J=5.0 Hz, 1H), 8.02 (dd, J=8.1, 8.1 Hz, 2H), 9.96 (br, 1H).

APCI-MS (m/z); 487 [M+H]$^+$

EXAMPLE 220

(E)-(R)—N-{2-[2-(1H-indazol-3-yl)vinyl]-5-(3-hydroxypyrrolidin-1-ylcarbonyl)phenyl}-3-methylthiophene-2-carboxamide hydrochloride (Compound 220)

In a similar manner to Example 28, (E)-(R)—N-{2-[2-(1H-indazol-3-yl)vinyl]-5-(3-hydroxypyrrolidin-1-ylcarbonyl)phenyl}-3-methylthiophene-2-carboxamide was obtained from Compound 98 (0.20 g, 0.50 mmol), (R)-3-hydroxypyrrolidine (93 mg, 0.75 mmol), 1-hydroxybenzotriazole monohydrate (88 mg, 0.65 mmol) and EDC (0.13 g, 0.68 mmol). Further, the product was added with methanol (5.0 mL) and 4 mol/L hydrogen chloride-methanol solution (2.0 mL), stirred at room temperature for 2 hours and crystallized from ethanol to obtain Compound 220 (95 mg, 37%).

$^1$H-NMR (270 MHz, DMSO-d$_6$) δ 1.84-1.95 (m, 2H), 2.50 (s, 3H), 3.32-3.66 (m, 5H), 4.27-4.34 (m, 1H), 7.06 (d, J=4.9 Hz, 1H), 7.12 (d, J=7.9 Hz, 1H), 7.34 (dd, J=8.2, 8.2 Hz, 1H), 7.47 (d, J=8.6 Hz, 1H), 7.55 (d, J=8.2 Hz, 1H), 7.58-7.62 (m, 2H), 7.65 (d, J=17.1 Hz, 1H), 7.71 (d, J=4.9 Hz, 1H), 8.02 (dd, J=8.4, 8.4 Hz, 2H), 9.97 (br, 1H).

APCI-MS (m/z); 473 [M+H]$^+$

EXAMPLE 221

(E)-(R)—N-{2-[2-(1H-indazol-3-yl)vinyl]-5-(3-aminopyrrolidin-1-ylcarbonyl)phenyl}-3-methylthiophene-2-carboxamide hydrochloride (Compound 221: hydrochloride of Compound 102)

In a similar manner to Example 115, Compound 221 (81 mg, 73%) was obtained from Compound 102 (96 mg, 0.20 mmol), methanol (1.0 mL) and 4 mol/L hydrogen chloride-methanol solution (1.0 mL).

$^1$H-NMR (270 MHz, DMSO-d$_6$) δ 2.09-2.23 (m, 2H), 2.50 (s, 3H), 3.57-4.26 (m, 5H), 4.27-4.34 (m, 1H), 7.07 (d, J=4.9 Hz, 1H), 7.13 (d, J=7.9 Hz, 1H), 7.38 (dd, J=7.9, 7.9 Hz, 1H), 7.56 (d, J=8.4 Hz, 1H), 7.50-7.64 (m, 3H) 7.72 (d, J=4.9 Hz, 1H), 8.05 (dd, J=8.4, 8.4 Hz, 2H), 8.23-8.34 (m, 2H), 10.0 (br, 1H).

ESI-MS (m/z); 472 [M+H]$^+$

EXAMPLE 222

(E)-N-{2-[2-(1H-indazol-3-yl)vinyl]-5-(4-methanesulfonylpiperazin-1-ylcarbonyl)phenyl}-3-methylthiophene-2-carboxamide hydrochloride (Compound 222)

In a similar manner to Example 28, (E)-N-{2-[2-(1H-indazol-3-yl)vinyl]-5-(4-methanesulfonylpiperazin-1-ylcarbonyl)phenyl}-3-methylthiophene-2-carboxamide was obtained from Compound 98 (0.20 g, 0.50 mmol), 4-methanesulfonylpiperazine (0.15 g, 0.75 mmol), 1-hydroxybenzotriazole monohydrate (88 mg, 0.65 mmol), EDC (0.13 g, 0.70 mmol) and N-methylmorpholine (0.11 g, 1.0 mmol). Further, in a similar manner to Example 115, the product was added with methanol (1.0 mL) and 4 mol/L hydrogen chloride-methanol solution (0.50 mL), stirred at room temperature for 2 hours and crystallized from ethanol to obtain Compound 222 (0.10 g, 35%).

$^1$H-NMR (270 MHz, DMSO-d$_6$) δ 2.50 (s, 3H), 2.90 (s, 3H), 3.21 (br, 4H), 4.22 (br, 4H), 7.07 (d, J=4.9 Hz, 1H), 7.12 (d J=8.1 Hz, 1H), 7.38 (dd, J=7.6, 7.6 Hz, 2H), 7.50-7.62 (m, 4H) 7.72 (d, J=4.9 Hz, 1H), 8.04 (d, J=8.4 Hz, 2H), 9.99 (br, 1H).

APCI-MS (m/z); 550 [M+H]$^+$

EXAMPLE 223

(E)-N-{2-[2-(1H-indazol-3-yl)vinyl]-5-(cis-2,6-dimethylmorpholin-4-ylcarbonyl)phenyl}-3-methylthiophene-2-carboxamide hydrochloride (Compound 223)

In a similar manner to Example 28, (E)-N-{2-[2-(1H-indazol-3-yl)vinyl]-5-(cis-2,6-dimethylmorpholin-4-ylcarbonyl)phenyl}-3-methylthiophene-2-carboxamide was obtained from Compound 98 (0.20 g, 0.50 mmol), cis-2,6-dimethylmorpholine (85 mg, 0.75 mmol), 1-hydroxybenzotriazole monohydrate (88 mg, 0.65 mmol), EDC (0.13 g, 0.70 mmol) and N-methylmorpholine (0.11 g, 1.0 mmol). Further, in a similar manner to Example 115, the product was added with methanol (5.0 mL) and 4 mol/L hydrogen chloride-methanol solution (2.0 mL), stirred at room temperature for 3 hours and crystallized from ethanol to obtain Compound 223 (0.14 g, 60%).

$^1$H-NMR (270 MHz, DMSO-d$_6$) δ 1.10-1.20 (m, 6H), 2.50 (s, 3H), 3.57-3.62 (m, 4H), 4.40 (br, 2H), 7.06 (d, J=4.9 Hz, 1H), 7.12 (dd, J=7.6, 7.6 Hz, 1H), 7.38 (dd, J=8.2, 8.2 Hz, 2H), 7.48 (s, 1H), 7.54-7.56 (m, 1H), 7.60 (d, J=16.8 Hz, 1H), 7.66 (d, J=16.8 Hz, 1H), 7.72 (d, J=4.9 Hz, 1H), 8.04 (dd, J=7.6, 7.6 Hz, 2H), 9.99 (br, 1H).

APCI-MS (m/z); 501 [M+H]$^+$

EXAMPLE 224

(E)-N-{2-[2-(1H-indazol-3-yl)vinyl]-5-(morpholin-4-ylmethyl)phenyl}-3-methylthiophene-2-carboxamide hydrochloride (Compound 224)

Step 1

Compound 108 (0.30 g, 0.77 mmol) was dissolved in DMF (12 mL) and the solution was added with triphenylphosphine (0.45 g, 1.5 mmol) and carbon tetrabromide (0.51 g, 1.5 mmol), followed by stirring at room temperature for 1 hour. After the reaction, the mixture was added with ethyl acetate and washed with saturated aqueous sodium hydrogencarbonate solution. The organic layer was concentrated under reduced pressure to obtain (E)-N-{2-[2-(1H-indazol-3-yl)vinyl]-5-(bromomethyl)phenyl}-3-methylthiophene-2-carboxamide.

$^1$H-NMR (270 MHz, DMSO-d$_6$) δ 2.51 (s, 3H), 4.54 (d, J=5.7 Hz, 2H), 5.28 (t, J=5.7 Hz, 1H), 7.04-7.11 (m, 2H), 7.27-7.70 (m, 7H), 7.90 (d, J=8.3 Hz, 1H), 8.02 (d, J=8.3 Hz, 1H), 9.87 (br, 1H), 13.1 (br, 1H). APCI-MS (m/z); 390 [M+H]$^+$.

Step 2

The bromide obtained in Step 1 was dissolved in THF and the solution was added with triethylamine (0.32 mL, 2.3 mmol) and morpholine (0.22 mL, 2.3 mmol), followed by stirring at room temperature for 1 hour. After the reaction, the mixture was added with ethyl acetate, washed with saturated brine and the organic layer was concentrated under reduced pressure. The obtained crude product was purified by silica gel column chromatography (chloroform to chloroform/methanol=9/1). Compound 224 (0.17 g, 42%) was obtained from methanol (5.0 mL) and 4 mol/L hydrogen chloride-methanol solution (1.0 mL).

$^1$H-NMR (270 MHz, DMSO-d$_6$) δ 2.51 (s, 3H), 3.14-3.32 (m, 4H), 3.73-3.99 (m, 4H), 4.38 (br, 2H), 7.07 (d, J=5.1 Hz, 1H), 7.13 (d, J=7.4 Hz, 1H), 7.38 (dd, J=8.4, 8.4 Hz, 1H) 7.54-7.64 (m, 3H), 7.58 (d, J=16.8 Hz, 1H), 7.66 (d, J=16.8 Hz, 1H), 7.72 (d, J=4.8 Hz, 1H), 8.05 (dd, J=8.4, 8.4 Hz, 2H), 10.0 (br, 1H), 10.7 (br, 1H).

APCI-MS (m/z); 459 [M+H]$^+$

EXAMPLE 225

(E)-N-{2-[2-(1H-indazol-3-yl)vinyl]-4-(morpholin-4-yl)phenyl}-3-methylthiophene-2-carboxamide hydrochloride (Compound 225)

In a similar manner to Example 1, (1H-indazol-3-ylmethyl)triphenylphosphonium bromide (0.12 g, 0.25 mmol) was dissolved in methanol (6.0 mL) and crude 3-{2-[5-(morpholin-4-yl)-2-nitrophenyl]vinyl}-1H-indazole was obtained from 5-morpholino-2-nitrobenzaldehyde (65 mg, 0.25 mmol) and potassium carbonate (0.10 g, 0.75 mmol). In a similar manner to Example 2, crude 3-{2-[5-(morpholin-4-yl)-2-nitrophenyl]vinyl}-1H-indazole (0.80 g, 2.3 mmol) was dissolved in ethanol (25 mL) and the solution was added with tin (0.82 g, 6.9 mmol) and concentrated hydrochloric acid (4.0 mL) and heated from room temperature to 40° C. to obtain 2-[2-(1H-indazol-3-yl)vinyl]-4-(morpholin-4-yl)phenylamine. Further, in a similar manner to Example 29, 2-[2-(1H-indazol-3-yl)vinyl]-4-(morpholin-4-yl)phenylamine (0.45 g, 1.4 mmol) was dissolved in THF (10 mL) and the solution was added with triethylamine (0.61 ml, 4.2 mmol) and 3-methylthiophenecarbonylchloride (0.20 g, 1.4 mmol) and stirred at room temperature for 1 hour. The reaction mixture was added with saturated aqueous sodium hydrogencarbonate solution, extracted with ethyl acetate and the organic layer was concentrated under reduced pressure to obtain free base of Compound 225. Further, said free base was treated by 4 mol/L hydrogen chloride-methanol solution (1.0 mL) to obtain Compound 225 (0.40 g, 55%).

$^1$H-NMR (270 MHz, DMSO-$d_6$) δ 2.50 (s, 3H), 3.95 (s, 4H), 4.92 (s, 4H), 7.05 (d, J=5.1 Hz, 1H), 7.11 (d, J=5.1 Hz, 1H), 7.30-7.40 (m, 3H), 7.55 (d, J=8.6 Hz, 1H), 7.61 (s, 2H), 7.70 (d, J=5.1 Hz, 1H), 7.85 (s, 1H), 8.02 (d, J=8.2 Hz, 1H), 9.84 (br, 1H).

APCI-MS (m/z); 445 [M+H]$^+$

EXAMPLE 226

(E)-N-{2-[2-(1H-indazol-3-yl)vinyl]-4-(morpholin-4-yl)phenyl}-1-methyl-1H-pyrrole-2-carboxamide hydrochloride (Compound 226)

2-[2-(1H-indazol-3-yl)vinyl]-4-(morpholin-4-yl)phenylamine (0.30 g, 0.94 mmol) synthesized in Example 225 was dissolved in THF (10 mL) and the solution was added with triethylamine (0.40 mL, 2.9 mmol) and N-methylpyrrolecarbonyl chloride (0.41 g, 2.8 mmol), followed by stirring at room temperature for 1 hour. The reaction mixture was added with saturated aqueous sodium hydrogencarbonate solution, extracted with ethyl acetate and the organic layer was concentrated under reduced pressure to obtain free base of Compound 226. Further, said free base was treated by 4 mol/L hydrogen chloride-methanol solution (1.0 mL) to obtain Compound 226 (0.23 g, 49%).

$^1$H-NMR (270 MHz, DMSO-$d_6$) δ 2.50 (s, 3H), 3.32 (s, 4H), 3.87 (s, 4H), 6.00-6.14 (m, 1H), 7.01-7.14 (m, 4H), 7.24 (d, J=8.6 Hz, 1H), 7.36 (dd, J=8.1, 8.1 Hz, 1H), 7.53 (d, J=8.6 Hz, 1H), 7.58-7.59 (m, 3H), 7.99 (d, J=8.2 Hz, 1H), 9.84 (br, 1H).

APCI-MS (m/z); 428 [M+H]$^+$

EXAMPLE 227

(E)-N-{2-[2-(1H-indazol-3-yl)vinyl]-4-(4-methanesulfonylpiperidin-1-yl)phenyl}-3-methylthiophene-2-carboxamide hydrochloride (Compound 227)

Step 1

In a similar manner to Example 1, (1H-indazol-3-ylmethyl)triphenylphosphonium bromide (0.30 g, 0.63 mmol) was dissolved in methanol (15 mL) and crude 3-{2-[5-(4-methanesulfonylpiperidin-1-yl)-2-nitrophenyl]vinyl}-1H-indazole was obtained from 5-(4-methanesulfonyl piperidin-1-yl)-2-nitrobenzaldehyde (0.20 g, 0.64 mmol) and potassium carbonate (0.26 g, 1.9 mmol).

APCI-MS (m/z); 427 [M+H]$^+$

Step 2

In a similar manner to Example 2, said crude 3-{2-[5-(4-methanesulfonylpiperidin-1-yl)-2-nitrophenyl]vinyl}-1H-indazole (0.23 g, 0.54 mmol) obtained in Step 1 was dissolved in ethanol (7.0 mL) and 2-[2-(1H-indazol-3-yl)vinyl]-4-(4-methanesulfonylpiperidin-1-yl)phenylamine was obtained from tin (0.19 g, 1.6 mmol) and concentrated hydrochloric acid (1.0 mL) at room temperature. In a similar manner to Example 29, a solution of 2-[2-(1H-indazol-3-yl)vinyl]-4-(4-methanesulfonylpiperidin-1-yl)phenylamine (0.22 g, 0.54 mmol) in THF (10 mL) was added with triethylamine (0.23 ml, 1.6 mmol) and 3-methylthiophenecarbonyl chloride (0.09 g, 0.54 mmol), followed by stirring at room temperature for 1 hour. The reaction mixture was added with saturated aqueous sodium hydrogencarbonate solution, extracted with ethyl acetate and the organic layer was concentrated under reduced pressure to obtain crude (E)-N-{2-[2-(1H-indazol-3-yl)vinyl]-4-(4-methanesulfonylpiperidin-1-yl)phenyl}-3-methylthiophene-2-carboxamide. Further, Compound 227 (68 mg, 22%) was obtained using 4 mol/L hydrogen chloride-methanol solution (1.0 mL).

$^1$H-NMR (270 MHz, DMSO-$d_6$) δ 2.24 (s, 2H), 2.50 (s, 3H), 3.01-3.03 (m, 2H), 3.40-3.45 (m, 1H), 3.47-3.94 (m, 7H), 7.05 (d, J=4.9 Hz, 1H), 7.11 (d, J=7.6 Hz, 1H), 7.34-7.40 (m, 3H), 7.55 (d, J=8.4 Hz, 1H), 7.59 (s, 3H), 7.70 (d, J=4.9 Hz, 1H) 8.02 (d, J=8.1 Hz, 1H), 9.88 (br, 1H).

APCI-MS (m/z); 521 [M+H]$^+$

EXAMPLE 228

(E)-N-{2-[2-(1H-indazol-3-yl)vinyl]-4-(4-methylpiperazin-1-yl)phenyl}-3-methylthiophene-2-carboxamide (Compound 228)

Step 1

In a similar manner to Example 1, (1H-indazol-3-ylmethyl)triphenylphosphonium bromide (0.40 g, 0.85 mmol) was dissolved in methanol (20 mL) and crude 3-{2-[5-(4-methylpiperazin-1-yl)-2-nitrophenyl]vinyl}-1H-indazole was obtained from 5-(4-methylpiperazin-1-yl)-2-nitrobenzaldehyde (0.21 g, 0.85 mmol) and potassium carbonate (0.35 g, 2.6 mmol).

APCI-MS (m/z); 334 [M+H]$^+$

Step 2

In a similar manner to Example 2, crude 3-{2-[5-(4-methylpiperazin-1-yl)-2-nitrophenyl]vinyl}-1H-indazole (262 mg, 0.72 mmol) obtained in Step 1 was dissolved in ethanol (10 mL) and was reacted with tin (0.26 g, 2.2 mmol) and concentrated hydrochloric acid (1.3 mL) at room temperature to obtain 2-[2-(1H-indazol-3-yl)vinyl]-4-(4-methylpiperazine-1-yl)phenylamine. In a similar manner to Example 29, 2-[2-(1H-indazol-3-yl)vinyl]-4-(4-methylpiperazin-1-yl)phenylamine (0.10 g, 0.30 mmol) was dissolved in THF (5.0 mL) and the solution was added with triethylamine (0.13 ml, 0.90 mmol) and 3-methylthiophenecarbonyl chloride (0.05 g, 0.31 mmol), followed by stirring at room temperature for 1 hour. The reaction mixture was added with saturated aqueous sodium hydrogencarbonate solution and extracted with ethyl acetate. The organic layer was concentrated under reduced pressure and the obtained crude product was triturated in ethyl acetate to obtain Compound 228 (0.10 g, 73%).

$^1$H-NMR (270 MHz, DMSO-$d_6$) δ 2.26 (s, 4H), 2.50 (s, 3H), 3.31 (s, 4H), 3.79 (s, 3H), 6.92-6.95 (m, 1H), 7.02-7.11 (m, 2H), 7.17-7.20 (m, 1H), 7.33-7.40 (m, 1H), 7.51-7.57 (m, 4H), 7.66 (d, J=4.9 Hz, 1H), 8.03 (d, J=8.1 Hz, 1H), 9.62 (br, 1H), 13.1 (s, 1H).

APCI-MS (m/z); 458 [M+H]$^+$

EXAMPLE 229

(E)-N-{5-[2-(dimethylamino)ethylcarbamoyl]-2-[2-(1H-indazol-3-yl)vinyl]phenyl}-3-methylthiophene-2-carboxamide hydrochloride (Compound 229)

In a similar manner to Example 28, crude (E)-N-{5-[2-(dimethylamino)ethylcarbamoyl]-2-[2-(1H-indazol-3-yl)vinyl]phenyl}-3-methylthiophene-2-carboxamide was obtained from Compound 98 (0.11 g, 0.25 mmol), N,N-dimethylethylenediamine (0.04 g, 0.37 mmol), 1-hydroxybenzotriazole monohydrate (44 mg, 0.32 mmol) and EDC (67 mg, 0.35 mmol). Further, the product was added with methanol (2.0 mL) and 4 mol/L hydrogen chloride-methanol solution (0.50 mL), stirred at room temperature for 2 hours and crystallized from ethanol to obtain Compound 229 (95 mg, 76%).

$^1$H-NMR (270 MHz, DMSO-$d_6$) δ 2.50 (s, 3H), 2.81-2.83 (m, 6H), 3.41-3.44 (m, 2H), 3.67-3.69 (m, 2H), 7.06 (d, J=4.6 Hz, 1H), 7.12 (d, J=6.9 Hz, 1H), 7.37 (dd, J=8.2, 8.2 Hz, 1H), 7.56 (d, J=8.2 Hz, 1H), 7.65 (s, 2H), 7.72 (d, J=4.6 Hz, 1H), 7.95 (d, J=7.2 Hz, 2H), 8.05 (d, J=8.9 Hz, 2H), 8.99 (br, 1H), 10.7 (br, 1H).

APCI-MS (m/z); 474 [M+H]$^+$

EXAMPLE 230

(E)-N-{5-(2-diethylaminoethylcarbamoyl)-2-[2-(1H-indazol-3-yl)vinyl]phenyl}-3-methylthiophene-2-carboxamide hydrochloride (Compound 230)

In a similar manner to Example 28, crude (E)-N-{5-(2-diethylaminoethylcarbamoyl)-2-[2-(1H-indazol-3-yl)vinyl]phenyl}-3-methylthiophene-2-carboxamide was obtained from Compound 98 (0.10 g, 0.25 mmol), N,N-diethylethylenediamine (0.05 g, 0.37 mmol), 1-hydroxybenzotriazole monohydrate (44 mg, 0.32 mmol) and EDC (67 mg, 0.35 mmol). Further, the product was added with methanol (2.0 mL) and 4 mol/L hydrogen chloride-methanol solution (0.50 mL), stirred at room temperature for 2 hours and crystallized from ethanol to obtain Compound 230 (75 mg, 75%).

$^1$H-NMR (270 MHz, DMSO-$d_6$) δ 1.25 (t, J=7.1 Hz, 6H), 2.50 (s, 3H), 3.18-3.24 (m, 6H), 3.42-3.69 (m, 2H), 7.07 (d, J=5.0 Hz, 1H), 7.12 (d, J=7.6 Hz, 1H), 7.38 (dd, J=7.4, 7.4 Hz, 1H), 7.56 (d, J=8.6 Hz, 1H), 7.65 (s, 2H), 7.72 (d, J=5.0 Hz, 1H), 7.89-7.93 (m, 2H), 8.06 (dd, J=8.1, 8.1 Hz, 2H), 8.95 (br, 1H), 10.2 (br, 1H). APCI-MS (m/z); 502 [M+H]$^+$

EXAMPLE 231

(S)-(E)-N-{2-[2-(1H-indazol-3-yl)vinyl]-5-[4-(pyrrolidin-2-ylcarbonyl)piperazin-1-ylcarbonyl]phenyl}-3-methylthiophene-2-carboxamide (Compound 231)

N-(tert-butoxycarbonyl)-L-proline (0.20 g, 0.42 mmol) was dissolved in THF (10 mL) and the solution was added with Compound 99 (0.14 g, 0.42 mmol), 1-hydroxybenzotriazole monohydrate (75 mg, 0.54 mmol) and EDC (0.11 g, 0.59 mmol), followed by stirring at 60° C. for 2 hours. After the reaction, the reaction mixture was added with ethyl acetate, washed with saturated aqueous sodium hydrogencarbonate solution and the organic layer was concentrated under reduced pressure. The obtained (S)-(E)-N-2-(4-{4-[2-(1H-indazol-3-yl)vinyl]-3-[(3-methylthiophene-2-carbonyl)amino]benzoyl}piperazine-1-carbonyl)pyrrolidine-1-carboxylic acid tert-butyl ester was dissolved in methanol (5.0 mL) and 4 mol/L hydrogen chloride-methanol solution (1.0 mL) was added thereto, followed by heating under reflux at 60° C. for 2 hours. The reaction mixture was concentrated under reduced pressure and the residue was added with saturated aqueous sodium hydrogencarbonate solution and ethyl acetate and then extracted. The obtained crude product was crystallized from ethanol to obtain Compound 231 (0.14 g, 56%).

$^1$H-NMR (270 MHz, DMSO-$d_6$) δ 2.01-2.04 (m, 4H), 2.50 (s, 3H), 3.02-3.38 (m, 8H), 4.45 (br, 2H), 5.33 (br, 1H), 7.07-7.12 (m, 2H), 7.40 (d, J=6.1 Hz, 2H), 7.54-7.63 (m, 4H), 7.73 (d, J=4.6 Hz, 1H), 8.05 (d, J=8.1 Hz, 2H), 10.0 (br, 1H), 13.2 (br, 1H).

ESI-MS (m/z); 569 [M+H]$^+$

EXAMPLE 232

(E)-N-{2-[2-(1H-indazol-3-yl)vinyl]-5-(4-methanesulfonylpiperazin-1-ylmethyl)phenyl}-3-methylthiophene-2-carboxamide (Compound 232)

In a similar manner to Step 2 of Example 224, Compound 232 (18 mg, 15%) was obtained from (E)-N-{2-[2-(1H-indazol-3-yl)vinyl]-5-(bromomethyl)phenyl}-3-methylthiophene-2-carboxamide (0.10 g, 0.22 mmol) obtained in Step 1 of Example 224, triethylamine (0.14 mL, 0.99 mmol) and methanesulfonylpiperazine (67 mg, 0.33 mmol).

$^1$H-NMR (270 MHz, DMSO-$d_6$) δ 2.50 (s, 3H), 2.90 (s, 3H), 3.21 (br, 4H), 4.22 (br, 4H), 4.38 (br, 2H), 7.03-7.09 (m, 2H), 7.38 (d, J=8.4 Hz, 2H) 7.41-7.57 (m, 3H), 7.64 (s, 2H), 8.05 (d, J=7.9 Hz, 2H), 10.0 (br, 1H), 13.2 (br, 1H).

APCI-MS (m/z); 536 [M+H]$^+$

EXAMPLE 233

(R)-(E)-N-{5-(3-aminopyrrolidin-1-ylmethyl)-2-[2-(1H-indazol-3-yl)vinyl]phenyl}-3-methylthiophene-2-carboxamide (Compound 233)

In a similar manner to Step 2 of Example 224, (R)-(E)-1-{4-[2-(1H-indazol-3-yl)vinyl]-3-[(3-methylthiophen-2-ylcarbonyl)amino]benzyl}pyrrolidin-3-yl)carbamic acid tert-butyl ester was obtained from (E)-N-{2-[2-(1H-indazol-3-yl)vinyl]-5-(bromomethyl)phenyl}-3-methylthiophene-2-carboxamide (0.40 g, 0.88 mmol) obtained in Step 1 of Example 224, triethylamine (0.37 mL, 2.6 mmol), (R)-(pyrrolidin-3-yl)carbamic acid tert-butyl ester (0.2 g, 1.1 mmol). The product was dissolved in methanol (5.0 mL) and 4 mol/L hydrogen chloride-methanol solution (1.0 mL) was added thereto, followed by heating under reflux at 60° C. for 1 hour. The reaction mixture was concentrated under reduced pressure and the residue was added with saturated aqueous sodium hydrogencarbonate solution and ethyl acetate and then extracted. The obtained crude product was crystallized from ethyl acetate to obtain Compound 233 (35 mg, 10%).

$^1$H-NMR (270 MHz, DMSO-$d_6$) δ 1.90-2.19 (m, 4H), 2.50 (s, 3H), 2.68-2.73 (m, 3H), 3.31 (br, 2H), 3.58-3.62 (m, 2H), 7.05 (d, J=4.9 Hz, 1H), 7.09 (d, J=7.9 Hz, 1H), 7.27 (d, J=7.6 Hz, 1H), 7.31-7.39 (m, 2H), 7.47 (d, J=16.8 Hz, 1H) 7.53 (d, J=8.4 Hz, 1H), 7.61 (d, J=16.8 Hz, 1H), 7.69 (d, J=4.9 Hz, 1H), 7.88 (d, J=8.4 Hz, 1H), 8.02 (d, J=8.4 Hz, 1H), 9.84 (br, 1H), 13.2 (br, 1H).

ESI-MS (m/z); 458 [M+H]$^+$

EXAMPLE 234

(E)-N-{2-[2-(1H-indazol-3-yl)vinyl]-5-(4-methylpiperazin-1-ylmethyl)phenyl}-3-methylthiophene-2-carboxamide (Compound 234)

In a similar manner to Step 2 of Example 224, Compound 234 (51 mg, 14%) was obtained from (E)-N-{2-[2-(1H-indazol-3-yl)vinyl]-5-(bromomethyl)phenyl}-3-methylthiophene-2-carboxamide (0.35 g, 0.76 mmol) obtained in Step 1 of Example 224, triethylamine (0.32 mL, 2.3 mmol) and 1-methylpiperazine (0.25 mL, 2.3 mmol).

$^1$H-NMR (270 MHz, DMSO-$d_6$) δ 2.17 (s, 3H), 2.37-2.46 (m, 8H), 2.51 (s, 3H), 3.49 (br, 2H), 7.05 (d, J=4.9 Hz, 1H), 7.09 (d, J=7.9 Hz, 1H), 7.25-7.39 (m, 3H), 7.47 (d, J=16.6 Hz, 1H), 7.53 (d, J=8.4 Hz, 1H), 7.60 (d, J=16.6 Hz, 1H), 7.69 (d, J=4.9 Hz, 1H), 7.89 (d, J=8.1 Hz, 1H), 8.00 (d, J=8.1 Hz, 1H), 9.84 (br, 1H), 13.1 (br, 1H).

ESI-MS (m/z); 472 [M+H]$^+$

EXAMPLE 235

(E)-N-{2-[2-(1H-indazol-3-yl)vinyl]-5-(4-methanesulfonylpiperidin-1-ylmethyl)phenyl}-3-methylthiophene-2-carboxamide (Compound 235)

In a similar manner to Step 2 of Example 224, Compound 235 (7.2 mg, 3%) was obtained from (E)-N-{2-[2-(1H-indazol-3-yl)vinyl]-5-(bromomethyl)phenyl}-3-methylthiophene-2-carboxamide (0.20 g, 0.44 mmol) obtained in Step 1 of Example 224, triethylamine (0.18 mL, 1.3 mmol), 4-methanesulfonylpiperidine (0.23 mg, 0.66 mmol).

$^1$H-NMR (270 MHz, DMSO-$d_6$) δ 1.97 (br, 2H), 2.02 (br, 2H), 2.51 (s, 3H), 2.91 (s, 3H), 2.96-3.01 (m, 3H), 3.27-3.31 (m, 2H), 3.53 (br, 2H), 7.05 (d, J=4.9 Hz, 1H), 7.09 (d, J=7.9. Hz, 1H), 7.26-7.39 (m, 3H), 7.48 (d, J=16.9 Hz, 1H), 7.51-7.55 (m, 1H), 7.61 (d, J=16.9 Hz, 1H), 7.70 (d, J=4.9 Hz, 1H), 7.90 (d, J=8.1 Hz, 1H), 8.00 (d, J=8.1 Hz, 1H), 9.85 (br, 1H), 13.1 (br, 1H).

ESI-MS (m/z); 535 [M+H]$^+$

EXAMPLE 236

(E)-N-{5-[(2-diethylaminoethylamino)methyl]-2-[2-(1H-indazol-3-yl)vinyl]phenyl}-3-methylthiophene-2-carboxamide (Compound 236)

In a similar manner to Step 2 of Example 224, Compound 236 (0.26 g, 81%) was obtained from (E)-N-{2-[2-(1H-indazol-3-yl)vinyl]-5-(bromomethyl)phenyl}-3-methylthiophene-2-carboxamide (0.30 g, 0.66 mmol) obtained in Step 1 of Example 224, triethylamine (0.28 mL, 2.0 mmol) and diethylaminoethylamine (0.29 mL, 2.0 mmol).

$^1$H-NMR (270 MHz, DMSO-$d_6$) δ 0.94 (t, J=7.0 Hz, 6H), 2.41-2.46 (m, 7H), 2.51 (s, 3H), 2.55-2.57 (m, 2H), 3.74 (br, 2H), (d, J=4.9 Hz, 1H), 7.10 (d, J=8.1 Hz, 1H), 7.28-7.39 (m, 3H), 7.48 (d, J=16.7 Hz, 1H), 7.53 (d, J=8.1 Hz, 1H), 7.61 (d, J=16.7 Hz, 1H), 7.70 (d, J=4.9 Hz, 1H), 7.89 (d, J=8.1 Hz, 1H), 8.01 (d, J=8.1 Hz, 1H), 9.85 (br, 1H), 13.1 (br, 1H).

ESI-MS (m/z); 488 [M+H]$^+$

EXAMPLE 237

(E)-N-{2-[2-(1H-indazol-3-yl)vinyl]-4-(2-diethylaminoethoxy)phenyl}-3-methylthiophene-2-carboxamide (Compound 237)

Step 1

In a similar manner to Example 1, (1H-indazol-3-ylmethyl)triphenylphosphonium bromide (3.6 g, 7.6 mmol) was dissolved in methanol (50 mL) and crude (E)-N-(2-{3-[2-(1H-indazol-3-yl)vinyl]-4-nitrophenyloxy}ethyl)diethylamine was obtained from 5-(2-diethylaminoethoxy)-2-nitrobenzaldehyde (2.0 g, 7.5 mmol) and potassium carbonate (3.2 g, 23 mmol).

ESI-MS (m/z); 351 [M+H]$^+$

Step 2

Crude (E)-N-(2-{3-[2-(1H-indazol-3-yl)vinyl]-4-nitrophenyloxy}ethyl)diethylamine (2.0 g, 5.2 mmol) obtained in Step 1 was dissolved in ethanol (20 mL) and the solution was treated by tin (1.9 g, 16 mmol) and concentrated hydrochloric acid (1.0 mL) at room temperature in a similar manner to Example 2, to obtain (E)-{4-[2-(diethylamino)ethoxy]-2-[2-(1H-indazol-3-yl)vinyl]phenyl}amine. In a similar manner to Example 29, (E)-{4-[2-(diethylamino)ethoxy]-2-[2-(1H-indazol-3-yl)vinyl]phenyl}amine (0.49 g, 1.4 mmol) was dissolved in THF (15 mL) and the solution was added with triethylamine (0.58 ml, 4.2 mmol) and 3-methylthiophenecarbonyl chloride (0.23 g, 1.4 mmol), followed by stirring at room temperature for 1 hour. The reaction mixture was added with saturated aqueous sodium hydrogencarbonate solution and extracted with ethyl acetate. The organic layer was concentrated under reduced pressure and the residue was triturated in ethyl acetate to obtain Compound 237 (0.42 g, 63%).

$^1$H-NMR (270 MHz, DMSO-$d_6$) δ 0.87 (t, J=6.9 Hz, 6H), 2.51 (s, 3H), 2.55-2.63 (m, 4H), 2.82 (t, J=6.0 Hz, 2H), 4.15 (t, J=6.0 Hz, 2H), 6.89-6.93 (m, 1H), 7.04 (d, J=4.9 Hz, 1H), 7.10 (d, J=7.1 Hz, 1H), 7.23-7.26 (m, 1H), 7.34-7.39 (m, 1H), 7.46-7.47 (m, 1H), 7.53 (d, J=8.2 Hz, 1H), 7.58 (s, 2H), 7.68 (d, J=4.9 Hz, 1H), 8.02 (d, J=8.2 Hz, 1H), 9.70 (br, 1H), 13.1 (s, 1H).

ESI-MS (m/z); 475 [M+H]$^+$

EXAMPLE 238

(E)-N-{2-[2-(1H-indazol-3-yl)vinyl]-4-[N-(2-methoxyethyl)-2-(morpholin-4-yl)ethylamino]phenyl}-3-methylthiophene-2-carboxamide (Compound 238)

Step 1

In a similar manner to Example 1, (1H-indazol-3-ylmethyl)triphenylphosphonium bromide (0.14 g, 0.30 mmol) was dissolved in methanol (2.0 mL) and crude (E)-3-[2-(1H-indazol-3-yl)vinyl]-N-(2-methoxyethyl)-N-[2-(morpholin-4-yl)ethyl]-4-nitroaniline was obtained from 5-[N-(2-methoxyethyl)-2-(morpholin-4-yl)ethylamino]-2-nitrobenzaldehyde (0.10 g, 0.30 mmol) and potassium carbonate (0.12 g, 0.90 mmol).

ESI-MS (m/z); 422 [M+H]$^+$

Step 2

In a similar manner to Example 2, the crude product obtained in Step 1 (75 mg, 0.17 mmol) was dissolved in ethanol (5.0 mL), treated by tin (0.06 g, 0.51 mmol) and concentrated hydrochloric acid (1.0 mL) at room temperature to obtain (E)-4-amino-3-[2-(1H-indazol-3-yl)vinyl]-N-(2-methoxyethyl)-N-(2-morpholin-4-ylethyl)aniline. In a similar manner to Example 29, said compound (72 mg, 0.17 mmol) was dissolved in THF (2.0 mL) and the solution was added with triethylamine (0.07 ml, 0.51 mmol) and 3-methylthiophene-2-carbonylchloride (27 mg, 0.17 mmol), followed by stirring at room temperature for 2 hours. The reaction mixture was added with saturated aqueous sodium hydrogencarbonate solution and extracted with ethyl acetate. The organic layer was concentrated under reduced pressure and the residue was triturated in ethyl acetate to obtain Compound 238 (46 mg, 51%).

$^1$H-NMR (270 MHz, DMSO-$d_6$) δ 2.51 (s, 3H), 3.18 (s, 2H), 3.56-3.58 (m, 5H), 3.62-3.64 (m, 2H), 2.89-4.10 (m, 10H), 6.82-6.86 (m, 1H), 7.03 (d, J=4.9 Hz, 1H), 7.06-7.10 (m, 1H), 7.15-7.22 (m, 2H), 7.36 (dd, J=8.2, 8.2 Hz, 1H), 7.53 (d, J=8.2 Hz, 1H), 7.59 (s, 2H), 7.67 (d, J=4.9 Hz, 1H), 8.07 (d, J=8.2 Hz, 1H), 9.61 (br, 1H), 13.1 (s, 1H).

ESI-MS (m/z); 546 [M+H]$^+$

EXAMPLE 239

(E)-N-{5-[4-(2-hydroxyethyl)piperazin-1-ylmethyl]-2-[2-(1H-indazol-3-yl)vinyl]phenyl}-3-methylthiophene-2-carboxamide (Compound 239)

In a similar manner to Step 2 of Example 224, Compound 239 (1.3 g, 50%) was obtained from (E)-N-{2-[2-(1H-indazol-3-yl)vinyl]-5-(bromomethyl)phenyl}-3-methylthiophene-2-carboxamide (2.3 g, 5.1 mmol) obtained in Step 1 of Example 224, triethylamine (2.0 mL, 15 mmol) and 1-(2-hydroxyethyl)piperazine (2.0 mL, 15 mmol).

$^1$H-NMR (270 MHz, DMSO-$d_6$) δ 2.35-2.42 (m, 8H), 2.51 (s, 3H), 3.30-3.32 (m, 2H), 3.44-3.51 (m, 4H), 4.36 (t, J=5.3 Hz, 1H), 7.05 (d, J=5.0 Hz, 1H), 7.09 (d, J=8.1 Hz, 1H), 7.24-7.39 (m, 3H), 7.47 (d, J=16.7 Hz, 1H), 7.53 (d, J=8.1 Hz, 1H), 7.60 (d, J=16.7 Hz, 1H), 7.69 (d, J=5.0 Hz, 1H), 7.89 (d, J=8.1 Hz, 1H), 8.00 (d, J=8.1 Hz, 1H), 9.85 (br, 1H), 13.1 (br, 1H).

ESI-MS (m/z); 502 [M+H]$^+$

EXAMPLE 240

(E)-N-{2-[2-(1H-indazol-3-yl)vinyl]-5-(piperidin-4-ylcarbamoyl)phenyl}-3-methylthiophene-2-carboxamide hydrochloride (Compound 240)

In a similar manner to Example 28, crude 4-{4-[2-(1H-indazol-3-yl)vinyl]-3-[(3-methylthiophenecarbonyl)amino]benzoylamino}piperidine-1-carboxylic acid tert-butyl ester was obtained from Compound 98 (0.40 g, 1.0 mmol), (piperidin-4-yl)carbamic acid tert-butyl ester (0.22 g, 1.1 mmol), 1-hydroxybenzotriazole monohydrate (41 mg, 0.30 mmol) and EDC (0.21 g, 1.1 mmol). Further, Compound 240 (0.34 g, 61%) was obtained using methanol (1.0 mL) and 4 mol/L hydrogen chloride-methanol solution (1.0 mL).

$^1$H-NMR (270 MHz, DMSO-$d_6$) δ 1.78-2.01 (m, 4H), 2.52 (s, 3H), 3.29 (s, 2H), 3.34 (s, 2H), 4.09 (s, 1H), 7.07 (d, J=4.9 Hz, 1H), 7.11 (d, J=7.6 Hz, 1H), 7.38 (d, J=7.6, 7.6 Hz, 1H), 7.55 (d, J=8.2 Hz, 1H), 7.64 (s, 2H), 7.73 (d, J=4.9 Hz, 1H), 7.87-7.96 (m, 2H), 8.05 (dd, J=8.2, 8.2 Hz, 2H), 8.61 (d, J=7.6 Hz, 1H), 9.06 (br, 1H), 10.0 (br, 1H).

ESI-MS (m/z); 486 [M+H]$^+$

EXAMPLE 241

(E)-N-{5-[N-(2-dimethylaminoethyl)-N-(2-methoxyethyl)carbamoyl]-2-[2-(1H-indazol-3-yl)vinyl]phenyl}-3-methylthiophene-2-carboxamide hydrochloride (Compound 241)

In a similar manner to Example 28, crude (E)-N-{5-[(2-dimethylaminoethyl)-(2-methoxyethyl)carbamoyl]-2-[2-(1H-indazol-3-yl)vinyl]phenyl}-3-methylthiophene-2-carboxamide was obtained from Compound 98 (0.30 g, 0.74 mmol), N-(2-dimethylaminoethyl)-2-methoxyethylamine (0.12 g, 0.81 mmol), 1-hydroxybenzotriazole monohydrate (30 mg, 0.22 mmol) and EDC (0.16 g, 0.81 mmol). Further, Compound 241 (0.14 g, 35%) was obtained using methanol (1.0 mL) and 4 mol/L hydrogen chloride-methanol solution (1.0 mL).

$^1$H-NMR (270 MHz, DMSO-$d_6$) δ 2.52 (s, 3H), 2.86 (br, 6H), 3.22 (s, 3H), 3.34-3.36 (m, 2H), 3.55-3.57 (m, 2H), 3.84 (s, 4H), (d, J=4.9 Hz, 1H), 7.12 (d, J=7.9 Hz, 1H), 7.36-7.44 (m, 2H), 7.53-7.62 (m, 3H), 7.66 (d, J=16.9 Hz, 1H), (d, J=4.9 Hz, 1H), 8.05 (dd, J=7.9, 7.9 Hz, 2H), 10.0 (br, 1H).

ESI-MS (m/z); 532 [M+H]$^+$

EXAMPLE 242

(E)-N-{2-[2-(1H-indazol-3-yl)vinyl]-5-piperazin-1-ylmethyl}phenyl}-3-methylthiophene-2-carboxamide (Compound 242)

In a similar manner to Step 2 of Example 224, crude product was obtained from (E)-N-{2-[2-(1H-indazol-3-yl)vinyl]-5-(bromomethyl)phenyl}-3-methylthiophene-2-carboxamide (1.2 g, 2.6 mmol) obtained in Step 1 of Example 224, triethylamine (1.1 mL, 7.7 mmol) and 1-(tert-butoxycarbonyl)piperazine (0.57 g, 3.1 mmol). Further, the product was dissolved in methanol (10 mL), added with 4 mol/L hydrogen chloride-methanol solution (1.0 mL) and reacted at 60° C. for 1 hour. The reaction mixture was concentrated under reduced pressure, neutralized by aqueous sodium hydroxide solution and crystallized from ethyl acetate to obtain Compound 242 (0.47 g, 40%).

$^1$H-NMR (270 MHz, DMSO-$d_6$) δ 2.33 (br, 4H), 2.51 (s, 3H), 2.69-2.72 (m, 4H), 3.46 (s, 2H), 7.05 (d, J=4.9 Hz, 1H), 7.09 (d, J=8.1 Hz, 1H), 7.25-7.39 (m, 3H), 7.47 (d, J=16.7 Hz, 1H), 7.53 (d, J=8.1 Hz, 1H), 7.60 (d, J=16.7 Hz, 1H), 7.70 (d, J=4.9 Hz, 1H), 7.89 (d, J=8.1 Hz, 1H), 8.00 (d, J=8.1 Hz, 1H), 9.84 (br, 1H), 13.1 (br, 1H).

ESI-MS (m/z); 458 [M+H]$^+$

EXAMPLE 243

(R)-(E)-{3-[2-(3-aminopyrrolidin-1-yl)ethoxy]-6-[2-(1H-indazol-3-yl)vinyl]-2-methoxyphenyl}-3-methylthiophene-2-carboxamide (Compound 243)

Step 1

In a similar manner to Step 5 of Example 339, (R)-(E)-[1-(2-{4-[2-(1H-indazol-3-yl)vinyl]-2-methoxy-3-[(3-methylthiophene-2-carbonyl)amino]phenoxy}ethyl)pyrrolidin-3-yl]carbamic acid tert-butyl ester (83 mg, 61%) was obtained from (E)-(3-(2-chloroethoxy)-2-methoxy-6-{2-[1-(3-methylthiophene-2-carbonyl)-1H-indazol-3-yl]vinyl}phenyl)-3-methylthiophene-2-carboxamide obtained in Step 3 of Example 349 (0.13 g, 0.22 mmol), (3R)-(+)-3-(tert-butoxycarbonylamino)pyrrolidine (0.41 g, 2.2 mmol), sodium iodide (50 mg, 0.33 mmol) and N,N-dimethylacetamide (2.6 mL).

$^1$H-NMR (300 MHz, DMSO-$d_6$) δ 1.37 (s, 9H), 1.58 (m, 2H), 2.35-2.67 (m, 4H), 2.52 (s, 3H), 2.82 (m, 2H), 3.76 (s, 3H), 4.00 (m, 1H), 4.17 (t, J=5.9 Hz, 2H), 6.95 (d, J=6.3 Hz, 1H), 7.05 (d, J=4.9 Hz, 1H), 7.07 (d, J=7.1 Hz, 1H), 7.13 (d, J=8.3 Hz, 1H), 7.36 (t, J=7.1 Hz, 1H), 7.40 (d, J=16.7 Hz, 1H), 7.51 (d, J=16.7 Hz, 1H), 7.52 (d, J=8.3 Hz, 1H), 7.66 (d, J=7.1 Hz, 1H), 7.68 (d, J=4.9 Hz, 1H), 7.94 (d, J=7.1 Hz, 1H), 9.49 (s, 1H), 13.11 (s, 1H).

ESI-MS (m/z); 618 [M+H]$^+$

Step 2

In a similar manner to Step 2 of Example 346, Compound 243 (43 mg, 63%) was obtained from (R)-(E)-[1-(2-{4-[2-(1H-indazol-3-yl)vinyl]-2-methoxy-3-[(3-methylthiophene-2-carbonyl)amino]phenoxy}ethyl)pyrrolidin-3-yl]carbamic acid tert-butyl ester (82 mg, 0.13 mmol) obtained in Step 1, 10% hydrogen chloride-methanol solution (0.82 mL) and methanol (0.82 mL).

$^1$H-NMR (270 MHz, DMSO-$d_6$) δ 1.35 (m, 1H), 1.99 (m, 1H), 2.25 (m, 1H), 2.44-2.72 (m, 5H), 2.52 (s, 3H), 2.74-2.90 (m, 3H), 3.77 (s, 3H), 4.17 (t, J=5.7 Hz, 2H), 7.05 (d, J=4.6 Hz, 1H), 7.07 (d, J=8.4 Hz, 1H), 7.13 (d, J=7.3 Hz, 1H), 7.36 (t, J=8.4 Hz, 1H), 7.39 (d, J=16.5 Hz, 1H), 7.51 (d, J=16.5 Hz, 1H), 7.53 (d, J=8.4 Hz, 1H), 7.66 (d, J=7.3 Hz, 1H), 7.68 (d, J=4.6 Hz, 1H), 7.94 (d, J=8.4 Hz, 1H), 9.49 (s, 1H), 13.08 (s, 1H).

ESI-MS (m/z); 518 [M+H]

EXAMPLE 244

(E)-N-{2-[2-(1H-indazol-3-yl)vinyl]-5-[4-(2-methoxyacetyl)piperazin-1-ylmethyl]phenyl}-3-methylthiophene-2-carboxamide (Compound 244)

In a similar manner to Example 28, Compound 242 (0.20 g, 0.44 mmol) was dissolved in DMF (5.0 mL) and Compound 244 (62 mg, 27%) was obtained from methoxyacetic acid (31 mg, 0.40 mmol), 1-hydroxybenzotriazole monohydrate (16 mg, 0.13 mmol) and EDC (85 mg, 0.48 mmol).

$^1$H-NMR (270 MHz, DMSO-$d_6$) δ 2.49 (br, 4H), 2.51 (s, 3H), 3.27 (s, 3H), 3.40-3.46 (m, 4H), 3.53 (s, 2H), 4.07 (s, 2H), 7.05 (d, J=4.9 Hz, 1H), 7.09 (d, J=7.6 Hz, 1H), 7.27-7.39 (m, 3H), 7.48 (d, J=16.7 Hz, 1H), 7.45-7.64 (m, 1H), 7.61 (d, J=16.7 Hz, 1H), 7.70 (d, J=4.9 Hz, 1H), 7.91 (d, J=8.1 Hz, 1H), 8.00 (d, J=8.1 Hz, 1H), 9.86 (br, 1H), 13.1 (br, 1H).

ESI-MS (m/z); 530 [M+H]$^+$

EXAMPLE 245

(E)-N-{2-[2-(1H-indazol-3-yl)vinyl]-5-[2-(morpholin-4-yl)ethylaminomethyl]phenyl}-3-methylthiophene-2-carboxamide (Compound 245)

In a similar manner to Step 2 of Example 224, Compound 245 (0.52 g, 11%) was obtained from (E)-N-{2-[2-(1H-indazol-3-yl)vinyl]-5-(bromomethyl)phenyl}-3-methylthiophene-2-carboxamide (0.42 g, 0.94 mmol) obtained in Step 1 of Example 224, triethylamine (0.40 mL, 2.8 mmol) and 2-morpholinoethylamine (0.37 g, 2.8 mmol).

$^1$H-NMR (270 MHz, DMSO-$d_6$) δ 2.35-2.37 (m, 4H), 2.42 (t, J=6.3 Hz, 2H), 2.51 (s, 3H), 2.64 (t, J=6.3 Hz, 2H), 3.55-3.58 (m, 4H), 3.77 (s, 2H), 7.05 (d, J=4.9 Hz, 1H), 7.10 (d, J=8.1 Hz, 1H), 7.28-7.39 (m, 3H), 7.48 (d, J=16.7 Hz, 1H), 7.54 (d, J=8.6 Hz, 1H), 7.61 (d, J=16.7 Hz, 1H), 7.69 (d, J=4.9 Hz, 1H), 7.89 (d, J=8.1 Hz, 1H), 8.01 (d, J=8.6 Hz, 1H), 9.85 (br, 1H), 13.1 (br, 1H).

ESI-MS (m/z); 502 [M+H]$^+$

EXAMPLE 246

(E)-{2-[2-(1H-indazol-3-yl)vinyl]-5-(morpholin-4-yl)phenyl}-1-methyl-1H-pyrrole-2-carboxamide monohydrochloride (Compound 246)

Step 1

(1H-Indazol-3-ylmethyl)triphenylphosphonium bromide (0.64 g, 1.3 mmol) was dissolved in methanol (8.0 mL) and the solution was added with 4-(morpholin-4-yl)-2-nitrobenzaldehyde (0.35 g, 1.5 mmol) and potassium carbonate (0.37 g, 2.7 mmol), followed by stirring at room temperature for 1 hour. The reaction mixture was added with water and the precipitated solid was collected by filtration and dried. The obtained solid was triturated in methanol to obtain (E)-3-([2-[4-(morpholin-4-yl)-2-nitrophenyl]vinyl]-1H-indazole (0.41 g, 86%).

$^1$H-NMR (300 MHz, DMSO-$d_6$) δ 3.26-3.29 (m, 4H), 3.74-3.77 (m, 4H), 7.22 (t, J=7.9 Hz, 1H), 7.33-7.42 (m, 2H), 7.52 (d, J=16.5 Hz, 1H), 7.54-7.65 (m, 4H), 7.99 (d, J=9.0 Hz, 1H), 8.02 (d, J=8.4 Hz, 1H), 13.2 (br, 1H). APCI-MS (m/z); 351 [M+H]$^+$

Step 2

In a similar manner to Example 2, (E)-3-{[2-[4-(morpholin-4-yl)-2-nitrophenyl]vinyl]-1H-indazole (0.41 g, 1.2 mmol) obtained in Step 1 was dissolved in ethanol (5.0 mL), and the solution was added with tin (0.29 g, 2.4 mmol) and concentrated hydrochloric acid (2.5 mL) under ice-cooling, followed by stirring at 40° C. for 2 hours. To the reaction mixture under ice-cooling, 6 mol/L aqueous sodium hydroxide solution was added to neutralize the mixture. Then the mixture was filtered. The filtrate was added with saturated aqueous sodium hydrogencarbonate solution and extracted with ethyl acetate. The organic layer was washed with water and saturated brine, dried over anhydrous magnesium sulfate and then evaporated under reduced pressure. The residue was triturated in ethyl acetate to obtain (E)-2-[2-(1H-indazol-3-yl)vinyl]-5-(morpholin-4-yl)phenylamine (0.28 g, 75%).

$^1$H-NMR (270 MHz, DMSO-$d_6$) δ 3.04-3.08 (m, 4H), 3.71-3.74 (m, 4H), 5.20 (br, 2H), 6.29 (d, J=10.2 Hz, 2H), 7.08 (d, J=16.5 Hz, 1H), 7.12-7.18 (m, 1H), 7.33-7.42 (m, 2H), 7.47 (d, J=5.8 Hz, 1H), 7.52 (m, 1H), 8.18 (d, J=7.6 Hz, 1H), 12.9 (br, 1H). APCI-MS (m/z); 321 [M+H]$^+$

Step 3

In a similar manner to Example 29, (E)-{2-[2-(1H-indazol-3-yl)vinyl]-5-(morpholin-4-yl)phenyl}-1-methyl-1H-pyrrole-2-carboxamide was obtained from 1-methyl-1H-pyrrole-2-carboxylic acid (0.23 g, 1.9 mmol), thionyl chloride (0.18 mL, 2.5 mmol), DMF (few drops), (E)-2-[2-(1H-indazol-3-yl)vinyl]-5-(morpholin-4-yl)phenylamine (0.1 g, 0.31 mmol) obtained in Step 2 and triethylamine (0.26 mL, 1.9 mmol). Further, the reaction mixture was added with 1 mol/L hydrogen chloride-ethanol solution (2.0 mL), stirred for 1 hour and concentrated. The residue was triturated in acetone to obtain Compound 246 (68 mg, 51%).

$^1$H-NMR (270 MHz, DMSO-$d_6$) δ 3.15-3.17 (m, 4H), 3.76 (m, 4H), 3.86 (s, 3H), 6.11 (t, J=3.8 Hz, 1H), 6.89 (m, 1H), 6.93-7.06 (m, 3H), 7.14-7.13 (m, 1H), 7.29 (d, J=16.5 Hz, 1H), 7.32 (d, J=8.3 Hz, 1H), 7.49 (d, J=8.3 Hz, 1H), 7.51 (d, J=16.5 Hz, 1H), 7.80 (d, J=8.8 Hz, 1H), 7.93 (d, J=8.3 Hz, 1H), 9.69 (br, 1H). APCI-MS (m/z); 428 [M+H]$^+$

EXAMPLE 247

(E)-N-{2-[2-(1H-indazol-3-yl)vinyl]-5-morpholin-4-ylphenyl}-3-methylthiophene-2-carboxamide monohydrochloride (Compound 247)

In a similar manner to Example 29, a free base of Compound 247 was synthesized from 3-methylthiophene-2-carboxylic acid (0.13 g, 0.94 mmol), thionyl chloride (0.10 mL, 1.4 mmol), DMF (few drops), (E)-2-[2-(1H-indazol-3-yl)vinyl]-5-(morpholin-4-yl)phenylamine (0.10 g, 0.31 mmol)

obtained in Step 2 of Example 246 and triethylamine (0.13 mL, 0.94 mmol). Further, said free base was added with 1 mol/L hydrogen chloride-ethanol solution (2.0 mL), stirred for 1 hour and then the reaction mixture was concentrated. The residue was triturated in acetone to obtain Compound 247 (61 mg, 44%).

$^1$H-NMR (300 MHz, DMSO-d$_6$) δ 3.14-3.18 (m, 4H), 3.34 (s, 3H), 3.73-7.76 (m, 4H), 6.92-6.97 (m, 2H), 7.01-7.06 (m, 2H), 7.28-7.36 (m, 1H), 7.34 (d, J=16.7 Hz, 1H), 7.49 (d, J=8.2 Hz, 1H), 7.51 (d, J=16.7 Hz, 1H), 7.67 (d, J=4.9 Hz, 1H), 7.80 (d, J=8.6 Hz, 1H), 7.97 (d, J=7.8 Hz, 1H), 9.77 (br, 1H). APCI-MS (m/z); 445 [M+H]$^+$

EXAMPLE 248

(E)-N-{2-[2-(1H-indazol-3-yl)vinyl]-5-[4-(2-hydroxyacetyl)piperazin-1-ylmethyl]phenyl}-3-methylthiophene-2-carboxamide (Compound 248)

In a similar manner to Example 28, Compound 248 (49 mg, 43%) was obtained from Compound 242 (0.10 g, 0.22 mmol), DMF (5.0 mL), glycolic acid (19 mg, 0.20 mmol), 1-hydroxybenzotriazole monohydrate (10 mg, 0.13 mmol) and EDC (63 mg, 0.33 mmol).

$^1$H-NMR (270 MHz, DMSO-d$_6$) δ 2.46 (br, 4H), 2.51 (s, 3H), 3.49 (br, 4H), 3.53 (s, 2H), 4.07 (d, J=5.3 Hz, 2H), 4.53 (t, J=5.3 Hz, 1H), 7.05 (d, J=4.9 Hz, 1H), 7.09 (d, J=7.9 Hz, 1H), 7.27-7.39 (m, 3H), 7.48 (d, J=16.7 Hz, 1H), 7.51-7.58 (m, 1H), 7.61 (d, J=16.8 Hz, 1H), 7.69 (d, J=4.9 Hz, 1H), 7.91 (d, J=7.9 Hz, 1H), 8.00 (d, J=8.6 Hz, 1H), 9.86 (br, 1H), 13.1 (br, 1H).

ESI-MS (m/z); 516 [M+H]$^+$

EXAMPLE 249

(E)-N-(2-[2-(1H-indazol-3-yl)vinyl]-5-{N-(2-methoxyethyl)-N-[2-(morpholin-4-yl)ethyl]carbamoyl}phenyl)-3-methylthiophene-2-carboxamide (Compound 249)

In a similar manner to Example 28, Compound 249 (0.23 g, 80%) was obtained from Compound 98 (0.20 g, 0.50 mmol), N-(2-methoxyethyl)-2-(morpholin-4-yl)ethylamine (0.11 g, 0.50 mmol), 1-hydroxybenzotriazole monohydrate (20 mg, 0.15 mmol) and EDC (0.11 g, 1.7 mmol).

$^1$H-NMR (270 MHz, DMSO-d$_6$) δ 2.24 (br, 2H), 2.52 (s, 3H), 3.16-3.18 (m, 4H), 3.29 (s, 3H), 3.56 (br, 10H), 7.06 (d, J=4.9 Hz, 1H), 7.11 (d, J=7.9 Hz, 1H), 7.31-7.41 (m, 3H), 7.53-7.60 (m, 2H), 7.65 (d, J=16.8 Hz, 1H), 7.71 (d, J=4.9 Hz, 1H), 8.03 (dd, J=8.7, 8.7 Hz, 2H), 9.96 (br, 1H), 13.2 (br, 1H).

ESI-MS (m/z); 574 [M+H]$^+$

EXAMPLE 250

(E)-2-{4-fluoro-2-[2-(1H-indazol-3-yl)vinyl]phenyl}isoindole-1,3-dione (Compound 250)

Step 1

In a similar manner to Step 1 of Example 133, (E)-3-[2-(5-fluoro-2-nitrophenyl)vinyl]-1H-indazole (0.80 g, 48%) was obtained from bromo(1H-indazol-3-ylmethyl)triphenylphosphonium (2.8 g, 5.9 mmol), DBU (1.3 mL, 8.9 mmol), 5-fluoro-2-nitrobenzaldehyde (1.0 g, 5.9 mmol) and methanol (17 mL).

$^1$H-NMR (270 MHz, DMSO-d$_6$) δ 7.21 (t, J=8.1 Hz, 1H), 7.36 (d, J=3.5 Hz, 1H), 7.45 (t, J=8.1 Hz, 1H), 7.60 (d, J=8.1 Hz, 1H), 7.81 (s, 1H), 7.81 (d, J=3.5 Hz, 1H), 8.05 (d, J=16.5 Hz, 1H), 8.13 (d, J=8.1 Hz, 1H), 8.14 (d, J=16.5 Hz, 1H).

ESI-MS (m/z); 284 [M+H]$^+$

Step 2

In a similar manner to Example 2, (E)-4-fluoro-2-[2-(1H-indazol-3-yl)vinyl]phenylamine (0.21 g, 30%) was obtained from (E)-3-[2-(5-fluoro-2-nitrophenyl)vinyl]-1H-indazole (0.79 g, 2.8 mmol) obtained in Step 1, tin (0.99 g, 8.4 mmol), concentrated hydrochloric acid (4.9 mL) and ethanol (16 mL).

$^1$H-NMR (270 MHz, DMSO-d$_6$) δ 5.20 (s, 2H), 6.70 (s, 1H), 6.85 (t, J=8.1 Hz, 1H), 7.19 (d, J=8.1 Hz, 1H), 7.39 (s, 2H), 7.40 (d, J=6.6 Hz, 1H), 7.51 (d, J=6.6 Hz, 1H), 7.54 (d, J=8.4 Hz, 1H), 8.22 (d, J=8.4 Hz, 1H), 13.12 (s, 1H).

ESI-MS (m/z); 254 [M+H]$^+$

Step 3

In a similar manner to Example 151, Compound 250 (64 mg, 53%) was obtained from (E)-4-fluoro-2-[2-(1H-indazol-3-yl)vinyl]phenylamine (80 mg, 0.32 mmol) obtained in Step 2, triethylamine (8.8 μL, 0.063 mmol), phthalic acid anhydride (56 mg, 0.38 mmol), molecular sieves 3A (80 mg) and xylene (1.6 mL).

$^1$H-NMR (270 MHz, DMSO-d$_6$) δ 6.98 (t, J=7.6 Hz, 1H), 7.10 (d, J=16.5 Hz, 1H), 7.24-7.35 (m, 2H), 7.49-7.58 (m, 2H), 7.55 (s, 1H), 7.69-7.78 (m, 2H), 7.95-8.08 (m, 4H).

ESI-MS (m/z); 384 [M+H]$^+$

EXAMPLE 251

(E)-N-{2-[2-(1H-indazol-3-yl)vinyl]-5-[2-(morpholin-4-yl)ethoxy]phenyl}-3-methylthiophene-2-carboxamide (Compound 251)

(1H-Indazol-3-ylmethyl)triphenylphosphonium bromide (34 mg, 0.07 mmol) was dissolved in methanol (1.5 mL) and the solution was added with 4-[2-(morpholin-4-yl)ethoxy]-2-nitrobenzaldehyde (23 mg, 0.07 mmol) and potassium carbonate (0.02 g, 0.14 mmol), followed by stirring at room temperature for 1 hour. The reaction mixture was added with water and the precipitated solid was collected by filtration and dried. The solid was dissolved in ethanol (1.0 mL) and the solution was added with tin (31 mg, 0.26 mmol) and concentrated hydrochloric acid (0.5 mL) under ice-cooling, followed by stirring at 40° C. for 2 hours. To the reaction mixture under ice-cooling, 6 mol/L aqueous sodium hydroxide solution was added to neutralize the mixture. Then the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. In a similar manner to Example 29, Compound 251 (7.2 mg, 21%) was obtained by treating the residue with 3-methylthiophene-2-carboxylic acid (48 mg, 0.34 mmol), thionyl chloride (37 μL, 0.51 mmol), DMF (few drops) and triethylamine (48 μL, 0.34 mmol).

$^1$H-NMR (270 MHz, DMSO-d$_6$) δ 2.71 (t, J=5.5 Hz, 2H), 3.31 (s, 3H), 3.57-3.61 (m, 8H), 4.14 (t, J=5.5 Hz, 2H), 6.93 (d, J=2.5 Hz, 1H), 6.96-7.10 (m, 3H), 7.35 (d, J=16.7 Hz, 1H), 7.35-7.38 (m, 1H), 7.52 (d, J=7.6 Hz, 1H), 7.56 (d, J=16.7 Hz,

1H), 7.69 (d, J=5.1 Hz, 1H), 7.86 (d, J=8.4 Hz, 1H), 8.00 (d, J=8.3 Hz, 1H), 9.84 (br, 1H), 13.1 (br, 1H). APCI-MS (m/z); 489 [M+H]$^+$

EXAMPLE 252

(E)-N-{2-[2-(1H-indazol-3-yl)vinyl]-5-[N-(2-methoxyethyl)methylaminomethyl]phenyl}-3-methylthiophene-2-carboxamide (Compound 252)

In a similar manner to Step 2 of Example 224, Compound 252 (0.20 g, 67%) was obtained from (E)-N-{2-[2-(1H-indazol-3-yl)vinyl]-5-(bromomethyl)phenyl}-3-methylthiophene-2-carboxamide (0.30 g, 0.64 mmol) obtained in Step 1 of Example 224, triethylamine (0.30 mL, 2.0 mmol) and N-(2-methoxyethyl)methylamine (0.20 g, 2.0 mmol).

$^1$H-NMR (270 MHz, DMSO-d$_6$) δ 2.20 (s, 3H), 2.51 (s, 3H), 2.56 (t, J=5.9 Hz, 2H), 3.33 (s, 3H), 3.48 (t, J=5.9 Hz, 2H), 3.54 (s, 2H), 7.05 (d, J=4.9 Hz, 1H), 7.10 (d, J=7.4 Hz, 1H), 7.25-7.39 (m, 3H), 7.49 (d, J=16.8 Hz, 1H), 7.51-7.55 (m, 1H), 7.62 (d, J=16.8 Hz, 1H), 7.70 (d, J=4.9 Hz, 1H), 7.90 (d, J=8.1 Hz, 1H), 8.01 (d, J=8.1 Hz, 1H), 9.86 (br, 1H), 13.1 (br, 1H).

ESI-MS (m/z); 461 [M+H]$^+$

EXAMPLE 253

(E)-N-{5-[N-(2-hydroxyethyl)-2-(morpholin-4-yl)ethylaminomethyl]-2-[2-(1H-indazol-3-yl)vinyl]phenyl}-3-methylthiophene-2-carboxamide (Compound 253)

In a similar manner to Step 2 of Example 224, Compound 253 (0.17 g, 49%) was obtained from (E)-N-{2-[2-(1H-indazol-3-yl)vinyl]-5-(bromomethyl)phenyl}-3-methylthiophene-2-carboxamide (0.30 g, 0.64 mmol) obtained in Step 1 of Example 224, triethylamine (0.30 mL, 2.0 mmol) and N-(2-hydroxyethyl)-2-(morpholin-4-yl)ethylamine (0.35 g, 2.0 mmol).

$^1$H-NMR (270 MHz, DMSO-d$_6$) δ 2.35 (s, 4H), 2.40-2.46 (m, 2H), 2.51 (s, 3H), 2.56-2.63 (m, 4H), 3.47-3.51 (m, 2H), 3.52-3.56 (m, 4H), 3.68 (s, 2H), 4.60 (br, 1H), 7.05 (d, J=4.9 Hz, 1H), 7.10 (d, J=7.4 Hz, 1H), 7.28-7.39 (m, 3H), 7.48 (d, J=16.8 Hz, 1H), 7.55-7.64 (m, 1H), 7.61 (d, J=16.8 Hz, 1H), 7.70 (d, J=4.9 Hz, 1H), 7.89 (d, J=8.1 Hz, 1H), 8.01 (d, J=8.1 Hz, 1H), 9.85 (br, 1H), 13.1 (br, 1H).

ESI-MS (m/z); 546 [M+H]$^+$

EXAMPLE 254

(E)-4-amino-2-{4-fluoro-2-[2-(1H-indazol-3-yl)vinyl]phenyl}isoindole-1,3-dione (Compound 254)

Step 1

In a similar manner to Example 151, (E)-2-{4-fluoro-2-[2-(1H-indazol-3-yl)vinyl]phenyl}-4-nitroisoindole-1,3-dione (0.12 g, 69%) was obtained from (E)-4-fluoro-2-[2-(1H-indazol-3-yl)vinyl]phenylamine (0.10 g, 0.40 mmol) obtained in Step 2 of Example 250, triethylamine (11 µL, 0.068 mmol), 3-nitrophthalic acid anhydride (92 mg, 0.47 mmol), molecular sieves 3A (0.10 g) and xylene (2.0 mL).

$^1$H-NMR (300 MHz, DMSO-d$_6$) δ 7.08 (t, J=7.5 Hz, 1H), 7.25 (d, J=16.2 Hz, 1H), 7.29-7.38 (m, 2H), 7.49-7.59 (m, 2H), 7.75 (d, J=16.2 Hz, 1H), 7.88 (d, J=8.1 Hz, 1H), 8.03 (d, J=8.1 Hz, 1H), 8.17 (d, J=7.8 Hz, 1H), 8.32 (d, J=7.5 Hz, 1H), 8.40 (d, J=7.8 Hz, 1H), 13.20 (s, 1H)

ESI-MS (m/z); 429 [M+H]$^+$.

Step 2

In a similar manner to Example 2, Compound 254 (49 mg, 46%) was obtained from (E)-2-{4-fluoro-2-[2-(1H-indazol-3-yl) vinyl]phenyl}-4-nitroisoindole-1,3-dione (0.10 g, 0.23 mmol) obtained in Step 1, tin (83 mg, 0.70 mmol), concentrated hydrochloric acid (0.41 mL) and ethanol (2.0 mL).

$^1$H-NMR (270 MHz, DMSO-d$_6$) δ 6.61 (s, 2H), 7.05 (t, J=7.3, 1H), 7.08-7.17 (m, 3H), 7.25-7.38 (m, 2H), 7.46-7.60 (m, 3H), 7.73 (d, J=16.7 Hz, 1H), 7.78 (d, J=9.2 Hz, 1H), 8.00 (d, J=7.6 Hz, 1H), 13.18 (s, 1H).

ESI-MS (m/z); 399 [M+H]$^+$

EXAMPLE 255

(E)-N-(5-{N-[2-(diethylamino)ethyl]-N-(2-hydroxyethyl) carbamoyl}-2-[2-(1H-indazol-3-yl)vinyl]phenyl)-3-methylthiophene-2-carboxamide (Compound 255)

In a similar manner to Example 28, Compound 255 (0.10 g, 25%) was obtained from Compound 98 (0.30 g, 0.74 mmol), 2-(2-diethylaminoethyl)ethanol (0.13 g, 0.81 mmol), 1-hydroxybenzotriazole monohydrate (20 mg, 0.15 mmol) and EDC (0.16 g, 0.81 mmol).

$^1$H-NMR (270 MHz, DMSO-d$_6$) δ 0.97 (br, 3H), 1.00 (br, 3H), 2.33 (br, 2H), 2.52 (s, 3H), 2.66 (br, 2H), 3.33 (br, 4H), 3.51 (br, 4H), 7.06 (d, J=4.9 Hz, 1H), 7.13 (d, J=7.4 Hz, 1H), 7.32-7.45 (m, 3H), 7.56 (d, J=8.1 Hz, 1H), 7.58 (d, J=17.1 Hz, 1H), 7.65 (d, J=17.1 Hz, 1H), 7.71 (d, J=4.9 Hz, 1H), 8.02 (dd, J=8.2, 8.2 Hz, 2H), 9.96 (br, 1H), 13.2 (br, 1H).

ESI-MS (m/z); 546 [M+H]$^+$

EXAMPLE 256

(E)-N-{5-[N-(2-hydroxyethyl)-N-(3-methoxypropyl)carbamoyl]-2-[2-(1H-indazol-3-yl) vinyl]phenyl}-3-methylthiophene-2-carboxamide (Compound 256)

In a similar manner to Example 28, Compound 256 (0.23 g, 60%) was obtained from Compound 98 (0.30 g, 0.74 mmol), 2-(3-methoxypropylamino)ethanol (0.10 g, 0.81 mmol), 1-hydroxybenzotriazole monohydrate (20 mg, 0.15 mmol) and EDC (0.16 g, 0.81 mmol).

$^1$H-NMR (270 MHz, DMSO-d$_6$) δ 1.84 (br, 2H), 2.52 (s, 3H), 3.14-3.26 (m, 4H), 3.32 (s, 3H), 3.41-3.49 (m, 4H), 4.81 (t, J=5.4 Hz, 1H), 7.06 (d, J=4.9 Hz, 1H), 7.12 (d, J=7.6 Hz, 1H), 7.32-7.42 (m, 3H), 7.53-7.62 (m, 3H), 7.71 (d, J=4.9 Hz, 1H), 8.02 (dd, J=8.4, 8.4 Hz, 2H), 9.96 (br, 1H), 13.2 (br, 1H).

ESI-MS (m/z); 519 [M+H]$^+$

EXAMPLE 257

(E)-{5-chloro-2-[2-(1H-indazol-3-yl) vinyl]phenyl}thiophene-2-carboxamide (Compound 257)

Step 1

In a similar manner to Step 1 of Example 133, (E)-3-[2-(4-chloro-2-nitrophenyl)vinyl]-1H-indazole (2.5 g, 76%) was obtained from (1H-indazol-3-ylmethyl)triphenylphosphonium bromide (5.1 g, 11 mmol), DBU (2.4 mL, 16 mmol), 4-chloro-2-nitrobenzaldehyde (2.0 g, 11 mmol) and methanol (31 mL).

$^1$H-NMR (270 MHz, DMSO-d$_6$) δ 7.25 (t, J=8.1 Hz, 1H), 7.42 (t, J=8.1 Hz, 1H), 7.59 (d, J=8.1 Hz, 1H), 7.73 (s, 2H), 7.84 (d, J=8.6 Hz, 1H), 8.08 (d, J=8.1 Hz, 1H), 8.14 (s, 1H), 8.18 (d, J=8.6 Hz, 1H), 13.35 (s, 1H).

ESI-MS (m/z); 300 [M+H]$^+$

Step 2

In a similar manner to Example 2, (E)-5-chloro-2-[2-(1H-indazol-3-yl)vinyl]phenylamine (0.43 g, 48%) was obtained from (E)-3-[2-(4-chloro-2-nitrophenyl)vinyl]-1H-indazole (1.0 g, 3.3 mmol) obtained in Step 1, tin (1.2 g, 10 mmol), concentrated hydrochloric acid (5.9 mL) and ethanol (15 mL).

$^1$H-NMR (300 MHz, DMSO-d$_6$) δ 5.65 (s, 2H), 6.59 (d, J=8.4 Hz, 1H), 6.75 (s, 1H), 7.18 (t, J=7.2 Hz, 1H), 7.36 (d, J=16.2 Hz, 1H), 7.39 (t, J=7.2 Hz, 1H), 7.50 (d, J=16.2 Hz, 1H), 7.50-7.57 (m, 2H), 8.21 (d, J=8.4 Hz, 1H), 13.09 (s, 1H).

ESI-MS (m/z); 270 [M+H]$^+$

Step 3

In a similar manner to Example 3, Compound 257 (30 mg, 26%) was obtained from (E)-5-chloro-2-[2-(1H-indazol-3-yl)vinyl]phenylamine (80 mg, 0.30 mmol) obtained in Step 2, 2-thenoyl chloride (32 µL, 0.30 mmol), pyridine (60 µL, 0.74 mmol) and THF (1.6 mL).

$^1$H-NMR (270 MHz, DMSO-d$_6$) δ 7.08 (t, J=7.0 Hz, 1H), 7.29 (t, J=4.9 Hz, 1H), 7.36 (t, J=7.0 Hz, 1H), 7.42 (d, J=8.6 Hz, 1H), 7.50 (s, 1H), 7.54 (d, J=8.6 Hz, 1H), 7.58 (s, 2H), 7.92 (d, J=4.9 Hz, 1H), 7.97 (d, J=8.6 Hz, 1H), 8.02 (d, J=8.6 Hz, 1H), 8.10 (d, J=4.9 Hz, 1H), 10.42 (s, 1H), 13.18 (s, 1H).

ESI-MS (m/z); 380 [M+H]$^+$

EXAMPLE 258

(E)-2-{5-chloro-2-[2-(1H-indazol-3-yl) vinyl]phenyl}isoindole-1,3-dione (Compound 258)

In a similar manner to Example 151, Compound 258 (41 mg, 34%) was obtained from (E)-5-chloro-2-[2-(1H-indazol-3-yl)vinyl]phenylamine (80 mg, 0.30 mmol) obtained in Step 2 of Example 257, triethylamine (8.4 µL, 0.059 mmol), phthalic anhydride (53 mg, 0.36 mmol), molecular sieves 3A (80 mg) and xylene (1.6 mL).

$^1$H-NMR (300 MHz, DMSO-d$_6$) δ 7.03 (t, J=7.5 Hz, 1H), 7.17 (d, J=16.5 Hz, 1H), 7.33 (t, J=7.5 Hz, 1H), 7.51 (d, J=8.1 Hz, 1H), 7.62-7.71 (m, 3H), 7.78 (d, J=8.4 Hz, 1H), 7.93-8.01 (m, 2H), 8.02-8.08 (m, 2H), 8.17 (d, J=8.1 Hz, 1H), 13.17 (s, 1H).

ESI-MS (m/z); 400 [M+H]$^+$

EXAMPLE 259

(E)-N-{5-[N-(2-hydroxyethyl)-N-(2-morpholinoethyl) carbamoyl]-2-[2-(1H-indazol-3-yl) vinyl]phenyl}-3-methylthiophene-2-carboxamide (Compound 259)

In a similar manner to Example 28, Compound 259 (72 mg, 20%) was obtained from Compound 98 (0.30 g, 0.74 mmol), 2-[2-(morpholin-4-yl)ethylamino]ethanol (0.14 g, 0.81 mmol), 1-hydroxybenzotriazole monohydrate (20 mg, 0.15 mmol) and EDC (0.16 g, 0.81 mmol).

$^1$H-NMR (270 MHz, DMSO-d$_6$) δ 2.24 (br, 2H), 2.52 (s, 3H), 3.16-3.18 (m, 4H), 3.29 (s, 3H), 3.56 (br, 8H), 7.06 (d, J=4.9 Hz, 1H), 7.12 (d, J=7.6 Hz, 1H), 7.34-7.44 (m, 3H), 7.53-7.60 (m, 2H), 7.65 (d, J=16.8 Hz, 1H), 7.72 (d, J=4.9 Hz, 1H), 8.02 (dd, J=8.9, 8.9 Hz, 2H), 9.96 (br, 1H), 13.2 (br, 1H).

ESI-MS (m/z); 560 [M+H]$^+$

EXAMPLE 260

(E)-N-{2-[2-(1H-indazol-3-yl)vinyl]-5-[N-(2-methoxyethyl)-N-methylcarbamoyl]phenyl}-3-methylthiophene-2-carboxamide (Compound 260)

In a similar manner to Example 28, Compound 260 (0.29 g, 82%) was obtained from Compound 98 (0.30 g, 0.74 mmol), N-(2-methoxyethyl)methylamine (73 mg, 0.81 mmol), 1-hydroxybenzotriazole monohydrate (20 mg, 0.15 mmol) and EDC (0.16 mg, 0.81 mmol).

$^1$H-NMR (270 MHz, DMSO-d$_6$) δ 2.52 (s, 3H), 3.01 (s, 3H), 3.22 (br, 3H), 3.48 (br, 4H), 7.06 (d, J=4.9 Hz, 1H), 7.11 (d J=7.9 Hz, 1H), 7.31-7.41 (m, 3H), 7.53-7.60 (m, 2H), 7.65 (d, J=16.8 Hz, 1H), 7.71 (d, J=4.9 Hz, 1H), 8.03 (dd, J=8.7, 8.7 Hz, 2H), 9.96 (br, 1H), 13.2 (br, 1H).

ESI-MS (m/z); 475 [M+H]$^+$

EXAMPLE 261

(E)-N-{6-[2-(1H-indazol-3-yl)vinyl]-2,3-dimethoxyphenyl}-3-methylthiophene-2-carboxamide (Compound 261)

(1H-Indazol-3-ylmethyl)triphenylphosphonium bromide (0.26 g, 0.56 mmol) was dissolved in methanol (3.0 mL) and the solution was added with 3,4-dimethoxy-2-nitrobenzaldehyde (0.12 g, 0.56 mmol) and potassium carbonate (0.16 g, 1.1 mmol), followed by stirring at room temperature for 4 hours. The reaction mixture was added with water and the precipitated solid was collected by filtration and dried. The solid was dissolved in ethanol (2.0 mL), and the solution was added with tin (0.12 g, 0.96 mmol) and concentrated hydrochloric acid (1.0 mL) under ice-cooling, followed by stirring at 40° C. for 2 hours. To the reaction mixture under ice-cooling, 6 mol/L sodium hydroxide was added to neutralize the mixture. Then, the mixture was filtered. The filtrate was added with saturated aqueous sodium hydrogencarbonate solution and the mixture was extracted with ethyl acetate. The organic layer was washed with water and saturated brine, dried over anhydrous magnesium sulfate and the solvent was evaporated under reduced pressure. In a similar manner to Example 29, Compound 261 (36 mg, 14%) was obtained by treating the residue with 3-methylthiophene-2-carboxylic acid (0.25 g, 1.8 mmol), thionyl chloride (0.19 mL, 2.7 mmol), DMF (few drops) and triethylamine (0.25 mL, 1.8 mmol).

$^1$H-NMR (300 MHz, DMSO-d$_6$) δ 3.32 (s, 3H), 3.72 (s, 3H), 3.87 (s, 3H), 7.03-7.09 (m, 3H), 7.31-7.39 (m, 1H), 7.39 (d, J=16.3 Hz, 1H), 7.49 (d, J=16.3 Hz, 1H), 7.50-7.52 (m, 1H), 7.68-7.70 (m, 2H), 7.92 (d, J=8.4 Hz, 1H), 9.51 (br, 1H), 13.1 (br, 1H). APCI-MS (m/z); 420 [M+H]$^+$

EXAMPLE 262

(E)-N-{2-[2-(1H-indazol-3-yl)vinyl]-5-(4-methylpiperazin-1-yl)phenyl}-3-methylthiophene-2-carboxamide (Compound 262)

(1H-Indazol-3-ylmethyl)triphenylphosphonium bromide (0.15 g, 0.32 mmol) was dissolved in methanol (3.0 mL) and the solution was added with 4-(4-methylpiperazin-1-yl)-2-nitrobenzaldehyde (0.12 g, 0.48 mmol) and potassium carbonate (88 mg, 0.64 mmol), followed by stirring at room temperature for 2 hours. The reaction mixture was added with water and the precipitated solid was collected by filtration and dried. The solid was dissolved in ethanol (1.0 mL) and under ice-cooling, the solution was added with tin (53 mg, 0.44 mmol) and concentrated hydrochloric acid (0.5 mL), followed by stirring at 40° C. for 1 hour. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. In a similar manner to Example 29, Compound 262 (24 mg, 30%) was obtained by treating the residue with 3-methylthiophene-2-carboxylic acid (73 mg, 0.17 mmol), thionyl chloride (56 μL, 0.77 mmol), DMF (few drops) and triethylamine (71 μL, 0.51 mmol).

$^1$H-NMR (300 MHz, DMSO-d$_6$) δ 2.22 (s, 3H), 2.45-2.49 (m, 4H), 3.19-3.31 (m, 4H), 3.33 (s, 3H), 6.90-6.95 (m, 2H), 7.01-7.06 (m, 2H), 7.30 (d, J=16.7 Hz, 1H), 7.33 (t, J=8.1 Hz, 1H), 7.49 (d, J=8.1 Hz, 1H), 7.51 (d, J=16.7 Hz, 1H), 7.67 (d, J=5.1 Hz, 1H), 7.77 (d, J=8.6 Hz, 1H), 7.97 (d, J=7.9 Hz, 1H), 9.75 (br, 1H), 13.0 (br, 1H). APCI-MS (m/z); 458 [M+H]$^+$

EXAMPLE 263

(E)-N-{3-(2-diethylaminoethoxy)-6-[2-(1H-indazol-3-yl)vinyl]-2-methoxymephenyl}-3-methylthiophene-2-carboxamide (Compound 263)

Step 1

A solution of 4-hydroxy-3-methoxy-2-nitrobenzaldehyde (4.4 g, 22 mmol) in DMF (30 mL) was added with potassium carbonate (6.2 g, 24 mmol) and 2-(diethylamino)ethylbromide hydrobromide (6.2 g, 45 mmol), followed by stirring at 60° C. for 4 hours. Further, the reaction mixture was concentrated, added with water and extracted with ethyl acetate. The organic layer was washed with saturated brine, dried over anhydrous sodium sulfate and concentrated to obtain crude product. The obtained product was dissolved in ethyl acetate and the solution was added with 4 mol/L hydrogen chloride-ethyl acetate solution. The obtained white crystal was collected by filtration and dried to obtain 4-(diethylamino)ethoxy-3-methoxy-2-nitrobenzaldehyde hydrochloride (2.2 g, 29%).

$^1$H-NMR (270 MHz, DMSO-d$_6$) δ 1.27 (t, J=7.0 Hz, 6H), 3.18-3.28 (m, 4H), 3.60-3.63 (m, 2H), 3.87 (s, 3H), 4.63 (t, J=5.4 Hz, 2H), 7.55 (d, J=8.6 Hz, 1H), 7.94 (d, J=8.6 Hz, 1H), 9.82 (s, 1H).

ESI-MS (m/z); 297 [M+H]$^+$

Step 2

In a similar manner to Example 1, (E)-3-(2-{4-[2-(diethylamino)ethoxy]-3-methoxy-2-nitrophenyl}vinyl)-1H-indazole (3.0 g, 82%) was obtained from 4-(diethylamino)ethoxy-3-methoxy-2-nitrobenzaldehyde hydrochloride (2.9 g, 8.8 mmol) obtained in Step 1, bromo(1H-indazol-3-ylmethyl)triphenylphosphonium (4.2 g, 8.8 mmol), potassium carbonate (2.4 g, 18 mmol) and methanol (70 mL).

$^1$H-NMR (270 MHz, DMSO-d$_6$) δ 0.97 (t, J=7.0 Hz, 6H), 2.55 (q, J=7.0 Hz, 4H), 2.82 (t, J=5.9 Hz, 2H), 3.89 (s, 3H), 4.18 (t, J=5.9 Hz, 2H), 7.06 (d, J=16.2 Hz, 1H), 7.21 (t, J=8.1 Hz, 1H), 7.37 (d, J=8.9 Hz, 1H), 7.37 (d, J=8.9 Hz, 1H), 7.39 (t, J=8.1 Hz, 1H), 7.55 (d, J=8.1 Hz, 1H), 7.60 (d, J=16.2 Hz, 1H), 7.81 (d, J=8.9 Hz, 1H), 7.93 (d, J=8.1 Hz, 1H).

ESI-MS (m/z); 411 [M+H]$^+$

Step 3

In a similar manner to Example 2, (E)-3-[2-(diethylamino)ethoxy]-6-[2-(1H-indazol-3-yl)vinyl]-2-methoxyphenylamine (1.9 g, 69%) was obtained from (E)-3-(2-{4-[2-(diethylamino)ethoxy]-3-methoxy-2-nitrophenyl}vinyl)-1H-indazole (3.0 g, 7.3 mmol) obtained in Step 2, tin (2.7 g, 23 mmol), concentrated hydrochloric acid (20 mL) and ethanol (70 mL).

ESI-MS (m/z); 381 [M+H]$^+$

Step 4

In a similar manner to Example 29, a crude product was obtained from (E)-3-[2-(diethylamino)ethoxy]-6-[2-(1H-indazol-3-yl)vinyl]-2-methoxyphenylamine (1.0 g, 2.6 mmol) obtained in Step 3, 3-methylthiophenecarboxylic acid (0.41 g, 2.9 mmol), thionyl chloride (0.25 mL, 3.5 mmol), DMF-(0.28 mL, 3.6 mmol), methylene chloride (14 mL), triethylamine (1.4 mL, 10 mmol) and THF (20 mL). The product was purified by silica gel column chromatography [amino-silica gel chromatorex (trade mark) NH, manufactured by Fuji Silysia, ethyl acetate/hexane=3/7 to ethyl acetate], to obtain Compound 263 (0.49 g, 37%).

$^1$H-NMR (300 MHz, DMSO-d$_6$) δ 1.01 (t, J=7.0 Hz, 6H), 2.51 (s, 3H), 2.59 (q, J=7.0 Hz, 4H), 2.84 (t, J=6.0 Hz, 2H), 3.78 (s, 3H), 4.13 (t, J=6.0 Hz, 2H), 7.02 (d, J=5.1 Hz, 1H), 7.06 (t, J=8.4 Hz, 1H), 7.11 (d, J=8.7 Hz, 1H), 7.34 (t, J=8.4 Hz, 1H), 7.36 (d, J=16.9 Hz, 1H), 7.50 (d, J=8.4 Hz, 1H), 7.51 (d, J=16.9 Hz, 1H), 7.61 (d, J=8.7 Hz, 1H), 7.63 (d, J=5.1 Hz, 1H), 7.92 (d, J=8.4 Hz, 1H), 9.33 (s, 1H), 13.9 (br, 1H).

ESI-MS (m/z); 505 [M+H]$^+$

EXAMPLE 264

(E)-N-{2-[2-(1H-indazol-3-yl)vinyl]-5-(piperidin-4-ylaminomethyl)phenyl}-3-methylthiophene-2-carboxamide (Compound 264)

In a similar manner to Step 2 of Example 224, a crude product was obtained from (E)-N-{2-[2-(1H-indazol-3-yl)vinyl]-5-(bromomethyl)phenyl}-3-methylthiophene-2-carboxamide (0.42 g, 0.94 mmol) obtained in Step 1 of Example 224, triethylamine (0.40 mL, 2.8 mmol) and (piperidin-4-yl)carbamic acid tert-butyl ester (0.57 g, 2.8 mmol). The product was dissolved in methanol (5.0 mL) and the solution was added with 4 mol/L hydrogen chloride-methanol solution (1.0 mL), followed by reacting at 60° C. for 1 hour. The reaction mixture was concentrated under reduced pressure, neutralized by aqueous sodium hydroxide solution and crystallized from ethanol and acetone to obtain Compound 264 (0.78 g, 18%).

$^1$H-NMR (270 MHz, DMSO-d$_6$) δ 1.10-1.24 (m, 3H), 1.77-1.99 (m, 2H), 2.43-2.46 (m, 3H), 2.52 (s, 3H), 2.76-2.92 (m, 3H), 3.77 (s, 2H), 7.05 (d, J=4.9 Hz, 1H), 7.09 (d, J=7.6 Hz, 1H), 7.30-7.39 (m, 3H), 7.47 (d, J=16.8 Hz, 1H), 7.53 (d, J=8.2 Hz, 1H), 7.60 (d, J=16.8 Hz, 1H), 7.69 (d, J=4.9 Hz, 1H), 7.87 (d, J=8.2 Hz, 1H), 8.00 (d, J=8.2 Hz, 1H), 9.85 (br, 1H), 13.1 (br, 1H).

ESI-MS (m/z); 472 [M+H]$^+$

EXAMPLE 265

(E)-N-{5-fluoro-2-[2-(1H-indazol-3-yl)vinyl]phenyl}-3-methylthiophene-2-carboxamide (Compound 265)

(1H-Indazol-3-ylmethyl)triphenylphosphonium bromide (0.83 g, 1.8 mmol) was dissolved in methanol (3.0 mL) and the solution was added with 4-fluoro-2-nitrobenzaldehyde (0.36 g, 2.1 mmol) and potassium carbonate (0.49 g, 3.5 mmol), followed by stirring at room temperature for 1 hour. The reaction mixture was added with water and the precipitated solid was collected by filtration and dried. The solid was dissolved in ethanol (2.0 mL), and the solution was added with tin (88 mg, 0.74 mmol) and concentrated hydrochloric acid (1.0 mL) under ice-cooling, followed by stirring at 40° C. for 1 hour. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. In a similar manner to Example 29, Compound 265 (66 mg, 48%) was obtained by treating the residue with 3-methylthiophene-2-carboxylic acid (0.16 g, 1.1 mmol), thionyl chloride (0.12 mL, 1.7 mmol), DMF (few drops) and triethylamine (0.11 mL, 1.1 mmol).

$^1$H-NMR (270 MHz, DMSO-$d_6$) δ 3.33 (s, 3H), 7.03-7.23 (m, 2H), 7.32-7.43 (m, 2H), 7.48-7.78 (m, 5H), 7.93-8.08 (m, 2H), 9.98 (br, 1H), 13.2 (br, 1H). APCI-MS (m/z); 378 [M+H]$^+$

EXAMPLE 266

(E)-N-{6-[2-(1H-indazol-3-yl)vinyl]-2-methoxy-3-(2-morpholinoethoxy)phenyl}-3-methylthiophene-2-carboxamide (Compound 266)

(1H-Indazol-3-ylmethyl)triphenylphosphonium bromide (0.32 g, 0.68 mmol) was dissolved in methanol (3.0 mL) and the solution was added with 3-methoxy-4-(2-morpholin-4-ylethoxy)-2-nitrobenzaldehyde (0.21 g, 0.68 mmol) synthesized in a similar manner to Step 1 of Example 263 and potassium carbonate (0.19 g, 1.4 mmol), followed by stirring at room temperature for 1 hour. The reaction mixture was added with water and the precipitated solid was collected by filtration and dried. The filtrate was dissolved in ethanol (4.0 mL), and the solution was added with tin (0.12 g, 1.0 mmol) and concentrated hydrochloric acid (2.0 mL) under ice-cooling, followed by stirring at 40° C. for 1 hour. To the reaction mixture under ice-cooling, 6 mol/L aqueous sodium hydroxide solution was added to neutralize the mixture. Then the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. In a similar manner to Example 29, Compound 266 (87 mg, 32%) was obtained by treating the residue with 3-methylthiophene-2-carboxylic acid (0.23 g, 1.6 mmol), thionyl chloride (0.17 mL, 2.4 mmol), DMF (few drops) and triethylamine (0.22 mL, 1.6 mmol).

$^1$H-NMR (270 MHz, DMSO-$d_6$) δ 2.73-2.78 (m, 2H), 3.34 (s, 3H), 3.36 (m, 4H), 3.57-3.59 (m, 4H), 3.78 (s, 3H), 4.18-4.23 (m, 2H), 7.04-7.16 (m, 2H), 7.32-7.38 (m, 1H), 7.38 (d, J=16.5 Hz, 1H), 7.43-7.54 (m, 2H), 7.51 (d, J=16.5 Hz, 1H), 7.65-7.69 (m, 2H), 7.93 (d, J=8.3 Hz, 1H), 9.50 (br, 1H), 13.1 (br, 1H). APCI-MS (m/z); 519 [M+H]$^+$

EXAMPLE 267

(E)-N-{2-[2-(1H-indazol-3-yl)vinyl]-5-[N-(2-methoxyethyl)-2-(morpholinoethyl)amino]phenyl}-3-methylthiophene-2-carboxamide (Compound 267)

Step 1

4-Fluoro-2-nitrobenzaldehyde (0.20 g, 1.2 mmol), N-(2-methoxyethyl)-2-morpholinoethylamine (1.2 g, 6.5 mmol) and DMSO (3.5 mL) were added and stirred at 100° C. for 3 hours. The reaction mixture was added with water and extracted with ethyl acetate. The organic layer was washed with water and saturated brine, dried over anhydrous magnesium sulfate and the solvent was evaporated under reduced pressure. The residue was purified by silica gel column chromatography (hexane/ethyl acetate=1/1 to ethyl acetate). In a similar manner to Example 1, the obtained 4-[N-(2-methoxyethyl)-N-(2-morpholinoethyl)amino]-2-nitrobenzaldehyde was dissolved in methanol (8.0 mL) and the solution was added with (1H-indazol-3-ylmethyl)triphenylphosphonium bromide (0.21 g, 0.62 mmol) and potassium carbonate (0.17 g, 1.3 mmol) followed by stirring at room temperature for 1 hour. The reaction mixture was added with water and extracted with ethyl acetate. The organic layer was washed with water and saturated brine, dried over anhydrous magnesium sulfate and the solvent was evaporated under reduced pressure. The residue was purified by silica gel column chromatography (chloroform to chloroform/methanol=9/1) to obtain (E)-N-{4-[2-(1H-indazol-3-yl)vinyl]-3-nitrophenyl}-N-(2-methoxyethyl)-2-morpholinoethylamine (45 mg, 20%).

$^1$H-NMR (270 MHz, CDCl$_3$) δ 2.52-2.61 (m, 6H), 3.37 (s, 3H), 3.55-3.63 (m, 6H), 3.71-3.76 (m, 4H), 6.95 (dt, J=8.9, 2.6 Hz, 1H), 7.21-7.30 (m, 2H), 7.35-7.49 (m, 3H), 7.70 (d, J=8.9 Hz, 1H), 7.95 (d, J=16.5 Hz, 1H), 8.07 (d, J=8.3 Hz, 1H). APCI-MS (m/z); 452 [M+H]$^+$

Step 2

(E)-N-{4-[2-(1H-indazol-3-yl)vinyl]-3-nitrophenyl}-N-(2-methoxyethyl)-2-morpholinoethylamine (45 mg, 0.10 mmol) obtained in Step 1 was dissolved in ethanol (2.0 mL), and the solution was added with tin (25 mg, 0.21 mmol) and concentrated hydrochloric acid (1.0 mL) under ice-cooling, followed by stirring at 40° C. for 5 hours. To the reaction mixture under ice-cooling, 6 mol/L sodium hydroxide was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. In a similar manner to Example 29, Compound 267 (24 mg, 30%) was obtained by treating the residue with 3-methylthiophene-2-carboxylic acid (46 mg, 0.32 mmol), thionyl chloride (35 μL, 0.48 mmol), DMF (few drops) and triethylamine (45 μL, 0.32 mmol).

$^1$H-NMR (300 MHz, DMSO-$d_6$) δ 2.45-2.48 (m, 8H), 3.28 (s, 3H), 3.32 (s, 3H), 3.34-3.46 (m, 4H), 3.47-3.60 (m, 4H), 6.67-6.71 (m, 2H), 7.02 (d, J=7.3 Hz, 1H), 7.05 (d, J=5.1 Hz, 1H), 7.23 (d, J=16.9 Hz, 1H), 7.34 (t, J=8.1 Hz, 1H), 7.48 (d, J=8.1 Hz, 1H), 7.49 (d, J=16.9 Hz, 1H), 7.68 (d, J=5.1 Hz, 1H), 7.73 (d, J=8.8 Hz, 1H), 7.97 (d, J=8.1 Hz, 1H), 9.74 (br, 1H), 13.0 (br, 1H). APCI-MS (m/z); 546 [M+H]$^+$

EXAMPLE 268

(E)-N-{5-[4-(2-cyanoethyl)piperazin-1-ylmethyl]-2-[2-(1H-indazol-3-yl)vinyl]phenyl}-3-methylthiophene-2-carboxamide (Compound 268)

In a similar manner to Step 2 of Example 224, Compound 268 (0.17 g, 31%) was obtained from (E)-N-{2-[2-(1H-indazol-3-yl)vinyl]-5-(bromomethyl)phenyl}-3-methylthiophene-2-carboxamide (0.49 g, 1.1 mmol) obtained in Step 1 of Example 224, triethylamine (0.45 mL, 3.2 mmol) and 3-piperazin-1-ylpropionitrile (0.45 g, 3.2 mmol).

¹H-NMR (270 MHz, DMSO-d₆) δ 2.44-2.49 (m, 8H), 2.51 (s, 3H), 2.56-2.66 (m, 2H), 3.29 (s, 2H), 3.50 (s, 2H), 7.05 (d, J=4.9 Hz, 1H), 7.09 (d, J=7.7 Hz, 1H), 7.25-7.45 (m, 3H), 7.52-7.55 (m, 2H), 7.61 (d, J=16.6 Hz, 1H), 7.69 (d, J=4.9 Hz, 1H), 7.90 (d, J=8.1 Hz, 1H), 8.00 (d, J=8.1 Hz, 1H), 9.85 (br, 1H), 13.1 (br, 1H).
ESI-MS (m/z); 511 [M+H]⁺

EXAMPLE 269

(E)-N-{5-(4-acetylpiperazin-1-ylmethyl)-2-[2-(1H-indazol-3-yl)vinyl]phenyl}-3-methylthiophene-2-carboxamide (Compound 269)

In a similar manner to Step 2 of Example 224, Compound 269 (88 mg, 16%) was obtained from (E)-N-{2-[2-(1H-indazol-3-yl)vinyl]-5-(bromomethyl)phenyl}-3-methylthiophene-2-carboxamide (0.49 g, 1.1 mmol) obtained in Step 1 of Example 224, triethylamine (0.45 mL, 3.2 mmol) and 4-acetylpiperazine (0.42 g, 3.2 mmol).

¹H-NMR (270 MHz, DMSO-d₆) δ 1.99 (s, 3H), 2.35-2.41 (m, 4H), (s, 3H), 3.44 (br, 4H), 3.53 (br, 2H), 7.05 (d, J=4.9 Hz, 1H), 7.10 (d, J=7.7 Hz, 1H), 7.27-7.39 (m, 3H), 7.46-7.55 (m, 2H), 7.61 (d, J=16.6 Hz, 1H), 7.70 (d, J=4.9 Hz, 1H), 7.91 (d, J=8.1 Hz, 1H), 8.00 (d, J=8.1 Hz, 1H), (br, 1H), 13.1 (br, 1H).
ESI-MS (m/z); 500 [M+H]⁺

EXAMPLE 270

(E)-N-{5-(4-formylpiperazin-1-ylmethyl)-2-[2-(1H-indazol-3-yl)vinyl]phenyl}-3-methylthiophene-2-carboxamide (Compound 270)

In a similar manner to Step 2 of Example 224, Compound 270 (43 mg, 8%) was obtained from (E)-N-{2-[2-(1H-indazol-3-yl)vinyl]-5-(bromomethyl)phenyl}-3-methylthiophene-2-carboxamide (0.49 g, 1.1 mmol) obtained in Step 1 of Example 224, triethylamine (0.45 mL, 3.2 mmol) and 4-formylpiperazine (0.37 g, 3.2 mmol).

¹H-NMR (270 MHz, DMSO-d₆) δ 2.42-2.49 (m, 4H), 2.51 (s, 3H), 3.39 (br, 4H), 3.55 (br, 2H), 7.05 (d, J=4.9 Hz, 1H), 7.10 (d, J=7.7 Hz, 1H), 7.27-7.37 (m, 3H), 7.39-7.55 (m, 2H), 7.61 (d, J=17.1 Hz, 1H), 7.70 (d, J=4.9 Hz, 1H), 7.91 (d, J=8.2 Hz, 1H), 7.99-8.06 (m, 2H), 9.86 (br, 1H), 13.1 (br, 1H).
ESI-MS (m/z); 486 [M+H]⁺

EXAMPLE 271

(E)-N-{2-[2-(1H-indazol-3-yl)vinyl]-5-[4-(2-methoxyethyl)piperazin-1-ylmethyl]phenyl}-3-methylthiophene-2-carboxamide (Compound 271)

In a similar manner to Step 2 of Example 224, Compound 271 (63 mg, 11%) was obtained from (E)-N-{2-[2-(1H-indazol-3-yl)vinyl]-5-(bromomethyl)phenyl}-3-methylthiophene-2-carboxamide (0.49 g, 1.1 mmol) obtained in Step 1 of Example 224, triethylamine (0.45 mL, 3.2 mmol) and 1-(2-methoxyethyl)piperazine (0.47 g, 3.2 mmol).

¹H-NMR (270 MHz, DMSO-d₆) δ 2.44-2.50 (m, 10H), 2.51 (s, 3H), 3.22 (s, 3H), 3.42 (t, J=5.9 Hz, 2H), 3.48 (br, 2H), 7.05 (d, J=4.9 Hz, 1H), 7.09 (d, J=7.4 Hz, 1H), 7.24-7.39 (m, 3H), 7.47 (d, J=16.6 Hz, 1H), 7.51-7.55 (m, 1H), 7.60 (d, J=16.6 Hz, 1H), 7.69 (d, J=4.9 Hz, 1H), 7.89 (d, J=8.2 Hz, 1H), 8.00 (d, J=8.2 Hz, 1H), 9.85 (br, 1H), 13.1 (br, 1H)
ESI-MS (m/z); 516 [M+H]⁺.

EXAMPLE 272

(E)-N-{2-[2-(1H-indazol-3-yl)vinyl]-5-(4-methanesulfonylpiperazin-1-yl)phenyl}-3-methylthiophene-2-carboxamide (Compound 272)

Step 1

A solution of 4-fluoro-2-nitrobenzaldehyde (0.20 g, 1.2 mmol) in DMSO (3.5 mL) was added with 1-methanesulfonylpiperazine (0.71 g, 3.5 mmol), followed by stirring at 100° C. for 1 hour. The reaction mixture was added with water and the organic layer was extracted with hexane/ethyl acetate (4/1) to remove impurities. The aqueous layer was extracted with ethyl acetate and the obtained organic layer was washed with water and saturated brine, dried over anhydrous magnesium sulfate and evaporated under reduced pressure to obtain 4-(4-methanesulfonylpiperazin-1-yl)-2-nitrobenzaldehyde (0.36 g, ¹H-NMR (270 MHz, DMSO-d₆) δ 2.92 (s, 3H), 3.23 (t, J=5.1 Hz, 1H), 3.63 (t, J=5.1 Hz, 1H), 7.31 (dt, J=8.9 Hz, 2.4 Hz, 1H), 7.49 (d, J=2.4 Hz, 1H), 7.85 (d, J=8.9 Hz, 1H), 9.86 (s, 1H). APCI-MS (m/z); 314 [M+H]⁺

Step 2

To a solution of 4-(4-methanesulfonylpiperazin-1-yl)-2-nitrobenzaldehyde (0.36 g, 1.1 mmol) obtained in Step 1 in methanol (5.0 mL), (1H-indazol-3-ylmethyl) triphenylphosphonium bromide (0.54 g, 1.1 mmol) and potassium carbonate (0.31 g, 2.3 mmol) were added, followed by stirring at room temperature for 1 hour. The reaction mixture was added with water and extracted with ethyl acetate. The organic layer was washed with water and saturated brine, dried over anhydrous magnesium sulfate and the solvent was evaporated under reduced pressure. The filtrate was purified by silica gel column chromatography (hexane/ethyl acetate=4/1 to ethyl acetate) to obtain (E)-3-{2-[4-(4-methanesulfonylpiperazin-1-yl)-2-nitrophenyl]vinyl}-1H-indazole (0.48 g, 26%).

¹H-NMR (300 MHz, CDCl₃) δ 2.78 (s, 3H), 2.97 (t, J=5.1 Hz, 4H), 3.20 (t, J=5.1 Hz, 4H), 7.41-7.49 (m, 2H), 7.52-7.58 (m, 2H), 7.63-7.70 (m, 2H), 7.79 (d, J=8.6 Hz, 1H), 8.00 (d, J=16.7 Hz, 1H), 8.09 (d, J=8.6 Hz, 1H). APCI-MS (m/z); 428 [M+H]⁺

Step 3

(E)-3-{2-[4-(4-methanesulfonylpiperazin-1-yl)-2-nitrophenyl]vinyl}-1H-indazole (0.13 g, 0.29 mmol) obtained in Step 2 was dissolved in ethanol (2.0 mL), and the solution was added with tin (73 mg, 0.62 mmol) and concentrated hydrochloric acid (1.0 mL) under ice-cooling, followed by stirring at 40° C. for 1 hour. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was triturated in ethyl acetate to obtain (E)-2-[2-(1H-indazol-3-yl)vinyl]-5-(4-methanesulfonylpiperazin-1-yl)phenylamine (0.06 g, 52%).

¹H-NMR (300 MHz, DMSO-d₆) δ 2.93 (s, 3H), 3.23-3.41 (m, 4H), 3.90-4.16 (m, 4H), 6.32 (br, 2H), 7.12 (d, J=16.3 Hz, 1H), 7.13-7.18 (m, 1H), (t, J=7.9 Hz, 1H), 7.42 (d, J=9.3 Hz, 1H), 7.47-7.52 (m, 1H), 7.52 (d, J=16.3 Hz, 1H), 8.19 (d, J=7.9 Hz, 1H), 12.9 (br, 1H). APCI-MS (m/z); 398 [M+H]⁺

Step 4

In a similar manner to Example 29, Compound 272 (37 mg, 51%) was obtained from (E)-2-[2-(1H-indazol-3-yl)vinyl]-5-(4-methanesulfonylpiperazin-1-yl)phenylamine (55 mg, 0.14 mmol) obtained in Step 3,3-methylthiophene-2-carboxylic acid (59 mg, 0.42 mmol), thionyl chloride (46 μL, 0.62 mmol), DMF (few drops) and triethylamine (58 μL, 0.42 mmol).

$^1$H-NMR (270 MHz, DMSO-$d_6$) δ 2.94 (s, 3H), 3.35 (s, 3H), 3.31-3.51 (m, 8H), 6.67-7.08 (m, 4H), 7.32 (d, J=9.9 Hz, 1H), 7.35 (d, J=16.7 Hz, 1H), 7.50 (d, J=7.8 Hz, 1H), 7.52 (d, J=16.7 Hz, 1H), 7.69 (d, J=5.0 Hz, 1H), 7.82 (d, J=8.6 Hz, 1H), 7.98 (d, J=8.3 Hz, 1H), 9.79 (br, 1H), 13.0 (br, 1H). APCI-MS (m/z); 522 [M+H]$^+$

EXAMPLE 273

(E)-N-{5-[4-(2-hydroxyethyl)piperazin-1-yl]-2-[2-(1H-indazol-3-yl)vinyl]phenyl}-3-methylthiophene-2-carboxamide (Compound 273)

Step 1

4-Fluoro-2-nitrobenzaldehyde (0.20 g, 1.2 mmol), 1-hydroxyethylpiperazin (0.80 mL, 6.5 mmol) and DMSO (3.5 mL) were added and stirred at 100° C. for 1.5 hours. The reaction mixture was added with water and was washed with hexane/ethyl acetate=4/1 to remove impurities. After removing impurities, the reaction mixture was extracted with ethyl acetate, and the organic layer was washed with water and saturated brine and dried over anhydrous magnesium sulfate. Then, the solvent was evaporated under reduced pressure to obtain 4-[4-(2-hydroxyethyl)piperazin-1-yl]-2-nitrobenzaldehyde (0.34 g, 100%).

$^1$H-NMR (270 MHz, CDCl$_3$) δ 2.65 (t, J=5.1 Hz, 2H), 2.70 (t, J=5.3 Hz, 4H), 3.49 (t, J=5.1 Hz, 4H), 3.70 (t, J=5.3 Hz, 1H), 7.07 (dd, J=8.9, 2.6 Hz, 1H), 7.34 (d, J=2.7 Hz, 1H), 7.93 (d, J=8.8 Hz, 1H), 10.2 (s, 1H). APCI-MS (m/z); 280 [M+H]$^+$

Step 2

A solution of 4-[4-(2-hydroxyethyl)piperazin-1-yl]-2-nitrobenzaldehyde (0.33 g, 1.2 mmol) obtained in Step 1 in methanol (4.0 mL) was added with (1H-indazol-3-ylmethyl)triphenylphosphonium bromide (0.54 g, 1.1 mmol) and potassium carbonate (0.33 g, 2.4 mmol), followed by stirring at room temperature for 1.5 hours. The reaction mixture was added with water and extracted with ethyl acetate. The organic layer was washed with water and saturated brine, dried over anhydrous magnesium sulfate and the solvent was evaporated under reduced pressure. The filtrate was purified by silica gel column chromatography (hexane/ethyl acetate=4/1 to ethyl acetate) to obtain (E)-2-(4-{(4-[2-(1H-indazol-3-yl)vinyl]-3-nitrophenyl}piperazin-1-yl)ethanol (0.26 g, 56%).

$^1$H-NMR (300 MHz, CDCl$_3$) δ 2.65 (t, J=5.5 Hz, 2H), 2.72 (t, J=5.1 Hz, 4H), 3.35 (t, J=5.1 Hz, 4H), 3.69 (t, J=5.5 Hz, 2H), 7.16 (dd, J=9.0, 2.7 Hz, 1H), 7.38 (d, J=16.5 Hz, 1H), 7.44-7.49 (m, 2H), 7.63-7.70 (m, 2H), 7.76 (d, J=8.8 Hz, 1H), 7.99 (d, J=16.5 Hz, 1H), 8.10 (d, J=8.4 Hz, 1H). APCI-MS (m/z); 386 [M+H]$^+$

Step 3

(E)-2-(4-{4-[2-(1H-indazol-3-yl)vinyl]-3-nitrophenyl}piperazin-1-yl)ethanol (0.26 g, 0.66 mmol) obtained in Step 2 was dissolved in ethanol (3.0 mL), and the solution was added with tin (0.17 g, 1.4 mmol) and concentrated hydrochloric acid (1.5 mL) under ice-cooling, followed by stirring at 40° C. for 1 hour. To the reaction mixture under ice-cooling, 6 mol/L aqueous sodium hydroxide solution was added to neutralize the mixture. Then the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was triturated in ethyl acetate to obtain (E)-2-(4-{3-amino-4-[2-(1H-indazol-3-yl)vinyl]phenyl}piperazin-1-yl)ethanol (0.24 g, 100%).

$^1$H-NMR (300 MHz, CDCl$_3$) δ 2.62 (t, J=5.5 Hz, 2H), 2.68 (t, J=4.8 Hz, 4H), 3.24 (t, J=4.8 Hz, 4H), 3.68 (t, J=5.5 Hz, 2H), 6.27 (br, 2H), 6.45 (dd, J=8.8, 2.6 Hz, 1H), 7.18-7.26 (m, 2H), 7.41-7.49 (m, 4H), 7.56 (d, J=16.2 Hz, 1H), 7.99 (d, J=8.4 Hz, 1H). APCI-MS (m/z); 356 [M+H]$^+$

Step 4

In a similar manner to Example 29, Compound 273 (82 mg, 25%) was obtained from (E)-2-(4-{3-amino-4-[2-(1H-indazol-3-yl)vinyl]phenyl}piperazin-1-yl)ethanol (0.24 g, 0.68 mmol) obtained in Step 3, 3-methylthiophene-2-carboxylic acid (0.29 g, 2.0 mmol), thionyl chloride (0.21 mL, 2.8 mmol), DMF (few drops) and triethylamine (0.28 mL, 2.0 mmol).

$^1$H-NMR (270 MHz, DMSO-$d_6$) δ 2.51-2.65 (m, 4H), 2.73 (t, J=5.6 Hz, 2H), 3.21-3.33 (m, 4H), 3.34-3.39 (m, 5H), 4.38 (t, J=5.6 Hz, 1H), 6.91-6.97 (m, 1H), 7.01-7.08 (m, 2H), 7.31 (d, J=16.8 Hz, 1H), 7.33 (t, J=8.3 Hz, 1H), 7.52 (d, J=8.3 Hz, 1H), 7.54 (d, J=16.8 Hz, 1H), 7.77 (d, J=2.1 Hz, 1H), 7.79 (d, J=2.1 Hz, 2H), 7.97 (d, J=8.3 Hz, 1H), 9.75 (br, 1H), 13.0 (br, 1H). APCI-MS (m/z); 488 [M+H]$^+$

EXAMPLE 274

(E)-N-{2-[2-(1H-indazol-3-yl)vinyl]-5-piperazin-1-ylphenyl}-3-methylthiophene-2-carboxamide (Compound 274)

Step 1

A solution of 4-fluoro-2-nitrobenzaldehyde (0.50 g, 3.0 mmol) in DMSO (5.0 mL) was added with 1-(tert-butoxycarbonyl)piperazine (1.7 g, 8.9 mmol), followed by stirring at 80° C. for 5 hours. The reaction mixture was added with water and the precipitated solid was collected by filtration to obtain 4-(4-formyl-3-nitrophenyl)piperazine-1-carboxylic acid tert-butyl ester (1.7 g, 100%).

$^1$H-NMR (300 MHz, CDCl$_3$) δ 1.46 (s, 9H), 2.84 (t, J=5.5 Hz, 4H), 3.63 (t, J=5.5 Hz, 4H), 7.04 (dd, J=8.8, 2.6 Hz, 1H), 7.33 (d, J=2.6 Hz, 1H), 7.93 (d, J=8.8 Hz, 1H), (s, 1H). APCI-MS (m/z); 336 [M+H]$^+$

Step 2

A solution of 4-(4-formyl-3-nitrophenyl)piperazine-1-carboxylic acid tert-butyl ester (1.4 g, 3.0 mmol) obtained in Step 1 in methanol (10 mL) was added with (1H-indazol-3-ylmethyl)triphenylphosphonium bromide (0.99 g, 3.0 mmol) and potassium carbonate (0.82 g, 5.9 mmol), followed by stirring at room temperature for 1.5 hours. The reaction mixture was added with water and extracted with ethyl acetate. The organic layer was washed with water and saturated brine, dried over anhydrous magnesium sulfate and the solvent was evaporated under reduced pressure. The filtrate was purified by silica gel column chromatography (hexane/ethyl acetate=4/1 to ethyl acetate) to obtain (E)-4-{4-[2-(1H-indazol-3-yl)vinyl]-3-nitrophenyl}piperazine-1-carboxylic acid tert-butyl ester (0.22 g, 16%).

¹H-NMR (300 MHz, CDCl₃) δ 1.60 (s, 9H), 2.81 (t, J=5.2 Hz, 2H), 3.28 (t, J=5.1 Hz, 2H), 3.39 (t, J=5.1 Hz, 2H), (t, J=5.2 Hz, 1H), 7.17 (dd, J=8.6, 2.6 Hz, 1H), (d, J=16.5 Hz, 1H), 7.43-7.50 (m, 2H), 7.63-7.71 (m, 2H), 7.78 (d, J=8.8 Hz, 1H), 7.99 (d, J=16.5 Hz, 1H), 8.09 (d, J=8.2 Hz, 1H). APCI-MS (m/z); 450 [M+H]⁺

Step 3

(E)-4-{4-[2-(1H-indazol-3-yl)vinyl]-3-nitrophenyl}piperazine-1-carboxylic acid tert-butyl ester (0.20 g, 0.45 mmol) obtained in Step 2 was dissolved in ethanol (1.0 mL), and the solution was added with iron (0.50 g, 8.9 mmol) and water (1.0 mL) under ice-cooling, followed by stirring at 40° C. for 1 hour. To the reaction mixture under ice-cooling, water was added and the mixture was neutralized. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was triturated in ethyl acetate to obtain (E)-4-{3-amino-4-[2-(1H-indazol-3-yl)vinyl]phenyl}piperazine-1-carboxylic acid tert-butyl ester (63 mg, 34%).

¹H-NMR (300 MHz, CDCl₃) δ 1.49 (s, 9H), 3.16 (t, J=5.3 Hz, 4H), 3.58 (t, J=5.3 Hz, 4H), 6.24 (br, 2H), 6.45 (dd, J=8.6 Hz, 2.2 Hz, 1H), 7.19-7.25 (m, 2H), 7.41-7.50 (m, 4H), 7.54 (d, J=16.3 Hz, 1H), 8.00 (d, J=8.1 Hz, 1H). APCI-MS (m/z); 420 [M+H]⁺

Step 4

In a similar manner to Example 29, (E)-4-{4-[2-(1H-indazol-3-yl)vinyl]-3-[(3-methylthiophene-2-carbonyl) amino]phenyl}piperazine-1-carboxylic acid tert-butyl ester (51 mg, 19%) was obtained from (E)-4-{3-amino-4-[2-(1H-indazol-3-yl)vinyl]phenyl}piperazine-1-carboxylic acid tert-butyl ester (63 mg, 0.5 mmol) obtained in Step 3, 3-methylthiophene-2-carboxylic acid (0.19 g, 1.5 mmol), thionyl chloride (0.16 mL, 2.2 mmol), DMF (few drops) and triethylamine (0.21 mL, 1.5 mmol).

¹H-NMR (270 MHz, CDCl₃) δ 1.49 (s, 9H), 2.60 (s, 3H), 3.27 (m, 4H), 3.60 (m, 4H), 3.27 (br, 2H), 6.94 (d, J=5.0 Hz, 1H), 7.19-7.34 (m, 2H), 7.41-7.51 (m, 2H), 7.59 (d, J=16.5 Hz, 1H), 7.56-7.59 (m, 1H), 7.73 (d, J=6.6 Hz, 1H), 7.96 (d, J=7.6 Hz, 1H). APCI-MS (m/z); 544 [M+H]⁺

Step 5

(E)-4-{4-[2-(1H-indazol-3-yl)vinyl]-3-[(3-methylthiophene-2-carbonyl)amino]phenyl}piperazine-1-carboxylic acid tert-butyl ester (51 mg, 0.09 mmol) obtained in Step 4 was dissolved in ethanol (2.0 ml) and the solution was added with 1 mol/L hydrogen chloride-ethanol solution (1.0 mL), followed by stirring for 1 hour. To the reaction mixture under ice-cooling, 6 mol/L aqueous sodium hydroxide solution was added to neutralize the mixture. Then the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was triturated in methanol to obtain Compound 274 (22 mg, 55%).

¹H-NMR (300 MHz, DMSO-d₆) δ 2.83 (m, 4H), 3.32 (s, 3H), 3.10 (m, 4H), 6.87-6.94 (m, 2H), 7.00-7.06 (m, 2H), 7.30 (d, J=16.3 Hz, 1H), 7.32 (t, J=8.6 Hz, 1H), 7.51 (d, J=16.3 Hz, 1H), 7.50 (t, J=8.6 Hz, 1H), 7.67 (d, J=4.9 Hz, 1H), 7.76 (d, J=8.8 Hz, 1H), 7.96 (d, J=8.4 Hz, 1H), 9.74 (br, 1H), 13.0 (br, 1H). APCI-MS (m/z); 444 [M+H]⁺

EXAMPLE 275

(E)-N-{2-[2-(1H-indazol-3-yl)vinyl]-5-(2-methoxyethoxy)phenyl}-3-methylthiophene-2-carboxamide (Compound 275)

Step 1

4-Fluoro-2-nitrobenzaldehyde (0.20 g, 1.2 mmol), methoxyethanol (0.28 mL, 3.6 mmol) and DMSO (2.0 mL) were added and stirred at 60° C. for 1.5 hours. The reaction mixture was added with water and was washed with hexane/ethyl acetate=4/1 to remove impurities. After removing impurities, the reaction mixture was extracted with ethyl acetate, and the organic layer was washed with water and saturated brine and dried over anhydrous magnesium sulfate. Then, the solvent was evaporated under reduced pressure. The filtrate was purified by silica gel column chromatography (hexane/ethyl acetate=4/1 to 1/1) and concentrated to obtain 4-(2-methoxyethoxy)-2-nitrobenzaldehyde (28 mg, 10%).

¹H-NMR (300 MHz, CDCl₃) δ 3.46 (s, 3H), 3.81 (t, J=4.5 Hz, 2H), 4.28 (t, J=4.5 Hz, 2H), 7.28 (dd, J=8.6, 2.4 Hz, 1H), 7.56 (d, J=2.4 Hz, 1H), 7.97 (d, J=8.6 Hz, 1H), 10.3 (s, 1H). APCI-MS (m/z); 226 [M+H]⁺

Step 2

A solution of 4-(2-methoxyethoxy)-2-nitrobenzaldehyde (27 mg, 0.12 mmol) obtained in Step 1 in methanol (1.0 mL) was added with (1H-indazol-3-ylmethyl)triphenylphosphonium bromide (57 mg, 0.12 mmol) and potassium carbonate (33 mg, 0.24 mmol), followed by stirring at room temperature for 1.5 hours. The reaction mixture was washed with water and extracted with ethyl acetate. The organic layer was washed with water and saturated brine, dried over anhydrous magnesium sulfate and the solvent was evaporated under reduced pressure. The filtrate was purified by silica gel column chromatography (ethyl acetate) to obtain (E)-3-{2-[4-(2-methoxyethoxy)-2-nitrophenyl]vinyl}-1H-indazole (0.04 g, 100%).

¹H-NMR (300 MHz, CDCl₃) δ 3.47 (s, 3H), 3.79 (t, J=4.6 Hz, 2H), 4.21 (t, J=4.6 Hz, 2H), 7.20-7.24 (m, 1H), 7.37 (t, J=8.0 Hz, 1H), 7.42-7.49 (m, 2H), 7.51-7.58 (m, 1H), 7.64-7.12 (m, 1H), 7.78 (d, J=8.8 Hz, 1H), 7.99 (d, J=16.5 Hz, 1H), 8.07 (d, J=8.2 Hz, 1H). APCI-MS (m/z); 339 [M+H]⁺

Step 3

(E)-3-{2-[4-(2-methoxyethoxy)-2-nitrophenyl]vinyl}-1H-indazole (0.04 g, 0.12 mmol) obtained in Step 2 was dissolved in ethanol (1.0 mL), and the solution was added with tin (0.03 g, 0.25 mmol) and concentrated hydrochloric acid (1.0 mL) under ice-cooling, followed by stirring at 40° C. for 2.5 hours. To the reaction mixture under ice-cooling, 6 mol/L aqueous sodium hydroxide solution was added to neutralize the mixture. Then the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was triturated in ethyl acetate to obtain (E)-2-[2-(1H-indazol-3-yl)vinyl]-5-(2-methoxyethoxy)phenylamine (36 mg, 100%).

¹H-NMR (270 MHz, CDCl₃) δ 3.45 (s, 3H), 3.72-3.76 (m, 2H), 4.08-4.16 (m, 2H), 6.31 (br, 2H), 6.43 (dd, J=8.6, 2.5 Hz, 1H), 7.19 (d, J=7.1 Hz, 1H), 7.39 (d, J=6.1 Hz, 1H), 7.40-7.58 (m, 3H), 7.63-7.72 (m, 2H), 7.97 (d, J=8.1 Hz, 1H). APCI-MS (m/z); 310 [M+H]⁺

Step 4

In a similar manner to Example 29, Compound 275 (0.03 g, 58%) was obtained from (E)-2-[2-(1H-indazol-3-yl)vinyl]-5-(2-methoxyethoxy)phenylamine (36 mg, 0.12 mmol) obtained in Step 3, 3-methylthiophene-2-carboxylic acid (0.05 g, 0.35 mmol), thionyl chloride (40 μL, 0.54 mmol), DMF (few drops) and triethylamine (49 μL, 0.35 mmol).

$^1$H-NMR (300 MHz, DMSO-$d_6$) δ 3.32 (s, 6H), 3.65-3.69 (m, 2H), 4.11-4.15 (m, 2H), 6.94 (d, J=8.8 Hz, 1H), 6.99-7.08 (m, 2H), 7.32-7.39 (m, 1H), 7.33 (d, J=16.7 Hz, 1H), 7.49-7.62 (m, 2H), 7.55 (d, J=16.7 Hz, 1H), 7.69 (d, J=4.9 Hz, 1H), 7.85 (d, J=9.9 Hz, 1H), 7.99 (d, J=8.1 Hz, 1H), 9.85 (br, 1H), 13.1 (br, 1H). APCI-MS (m/z); 434 [M+H]$^+$

EXAMPLE 276

(E)-N-{2-[2-(1H-indazol-3-yl)vinyl]-5-(morpholin-4-ylcarbonyl)phenyl}isoindole-1,3-dione (Compound 276)

Step 1

A solution of (E)-4-[2-(1H-indazol-3-yl)vinyl]-3-nitrobenzoic acid methyl ester (1.0 g, 3.1 mmol) obtained in Step 1 of Example 217 in methanol (20 mL) was added with 2 mol/L aqueous sodium hydroxide solution (10 mL) and stirred at 60° C. for 1 hour. The reaction mixture was acidified by hydrochloric acid (6 mol/L) and the precipitated crystal was collected by filtration to obtain 4-[2-(1H-indazol-3-yl)vinyl]-3-nitrobenzoic acid.

ESI-MS (m/z); 310 [M+H]$^+$

Step 2

Crude 4-[2-(1H-indazol-3-yl)vinyl]-3-nitrobenzoic acid (1.0 g, 3.2 mmol) obtained in Step 1 was dissolved in ethanol (30 mL) and the solution was added with tin (1.2 g, 9.7 mmol) and concentrated hydrochloric acid (7.0 mL), followed by reacting at 40° C. to obtain 3-amino-4-[2-(1H-indazol-3-yl)vinyl]benzoic acid. The crude product (0.65 g, 2.3 mmol) was added with xylene (20 mL), triethylamine (0.16 mL, 1.2 mmol), phthalic anhydride (0.41 g, 2.8 mmol) and molecular sieves 3A (0.65 mg), followed by heating at 140° C. for 4 hours. The reaction mixture was filtered and the filtrate was acidified by hydrochloric acid (2 mol/L). The precipitated crystal was collected by filtration to obtain 3-(1,3-dioxo-1,3-dihydroisoindol-2-yl)-4-[2-(1H-indazol-3-yl)vinyl]benzoic acid.

ESI-MS (m/z); 410 [M+H]$^+$

Step 3

Compound 276 (46 mg, 48%) was obtained from 3-(1,3-dioxo-1,3-dihydroisoindol-2-yl)-4-[2-(1H-indazol-3-yl)vinyl]benzoic acid (80 mg, 0.20 mmol) obtained in Step 2, morpholine (22 mg, 0.22 mmol), 1-hydroxybenzotriazole monohydrate (8.0 mg, 0.06 mmol) and EDC (42 mg, 0.22 mmol).

$^1$H-NMR (270 MHz, DMSO-$d_6$) δ 3.64 (br, 8H), 7.03 (d, J=8.2, 1H), 7.23 (d, J=16.5 Hz, 1H), 7.33 (d, J=8.2 Hz, 1H), 7.46-7.53 (m, 2H), 7.62 (d, J=8.1 Hz, 1H), 7.70 (d, J=16.5 Hz, 1H), 7.78 (d, J=8.2 Hz, 1H), 7.96-8.07 (m, 4H), 8.20 (d, J=8.2 Hz, 1H), 13.2 (br, 1H).

ESI-MS (m/z); 479 [M+H]$^+$

EXAMPLE 277

(E)-N-{5-[4-(3-hydroxypropyl)piperazin-1-ylmethyl]-2-[2-(1H-indazol-3-yl)vinyl]phenyl}-3-methylthiophene-2-carboxamide (Compound 277)

In a similar manner to Step 2 of Example 224, Compound 277 (0.11 g, 27%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and 3-(piperazin-1-yl)propan-1-ol (0.33 g, 2.3 mmol).

$^1$H-NMR (270 MHz, DMSO-$d_6$) δ 1.98-2.03 (m, 2H), 2.24-2.49 (m, 10H), 2.51 (s, 3H), 3.32 (br, 2H), 3.49 (br, 2H), 5.32 (br, 1H), 7.05 (d, J=4.9 Hz, 1H), 7.09 (d, J=8.1 Hz, 1H), 7.25-7.50 (m, 4H), 7.53 (d, J=8.1 Hz, 1H), 7.60 (d, J=16.6 Hz, 1H), 7.69 (d, J=4.9 Hz, 1H), 7.89 (d, J=8.1 Hz, 1H), 8.00 (d, J=8.6 Hz, 1H), 9.85 (br, 1H), 13.1 (br, 1H).

ESI-MS (m/z); 516 [M+H]$^+$

EXAMPLE 278

(E)-N-{2-[2-(1H-indazol-3-yl)vinyl]-5-(3-methylpyrrolidin-1-ylmethyl)phenyl}-3-methylthiophene-2-carboxamide (Compound 278)

In a similar manner to Step 2 of Example 224, a crude product was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and 3-[N-(tert-butoxycarbonyl)methylamino]pyrrolidine (0.46 g, 2.3 mmol). Further, the product was dissolved in methanol (5.0 mL) and the solution was added with 4 mol/L hydrogen chloride-methanol solution (2.0 mL), followed by reacting at 60° C. for 1 hour. The reaction mixture was concentrated under reduced pressure, neutralized by aqueous sodium hydroxide solution and crystallized from ethyl acetate to obtain Compound 278 (98 mg, 22%).

$^1$H-NMR (270 MHz, DMSO-$d_6$) δ 1.44-1.50 (m, 2H), 1.94-2.01 (m, 2H), 2.20 (s, 3H), 2.23-2.25 (m, 2H), 2.51 (s, 3H), 2.69-2.75 (m, 1H), 3.08-3.29 (m, 1H), 3.58 (br, 2H), 7.05 (d, J=4.9 Hz, 1H), 7.09 (d, J=8.1 Hz, 1H), 7.25-7.39 (m, 3H), (d, J=16.8 Hz, 1H), (d, 7.53 (d, J=8.1 Hz, 1H), (d, J=16.8 Hz, 1H), 7.69 (d, J=4.9 Hz, 1H), 7.88 (d, J=8.1 Hz, 1H), 8.00 (d, J=8.1 Hz, 1H), 9.84 (br, 1H), (br, 1H).

ESI-MS (m/z); 472 [M+H]$^+$

EXAMPLE 279

(E)-N-{2-[2-(1H-indazol-3-yl)vinyl]-5-[4-(2-methoxyethyl)piperazin-1-yl]phenyl}-3-methylthiophene-2-carboxamide (Compound 279)

Step 1

4-Fluoro-2-nitrobenzaldehyde (0.20 g, 1.2 mmol), 1-(2-methoxyethyl)piperazine (0.94 mL, 6.5 mmol) and DMSO (3.5 mL) were added and stirred at 100° C. for 1.0 hour. The reaction mixture was added with water and was washed with hexane/ethyl acetate (4/1) to remove impurities. After removing impurities, the reaction mixture was extracted with ethyl acetate, and the organic layer was washed with water and saturated brine and dried over anhydrous magnesium sulfate. Then, the solvent was evaporated under reduced pressure and the residue was purified by silica gel column chromatography (ethyl acetate) to obtain 4-[4-(2-methoxyethyl) piperazin-1-yl]-2-nitrobenzaldehyde (0.23 g, 68%).

$^1$H-NMR (300 MHz, CDCl$_3$) δ 2.63-2.69 (m, 8H), 3.38 (s, 3H), 3.49 (t, J=5.1 Hz, 2H), 3.56 (t, J=5.3 Hz, 2H), 7.04 (dd, J=8.8, 2.6 Hz, 1H), 7.32 (d, J=2.6 Hz, 1H), 7.92 (d, J=9.0 Hz, 1H), 10.2 (s, 1H). APCI-MS (m/z); 294 [M+H]$^+$

Step 2

A solution of 4-[4-(2-methoxyethyl)piperazin-1-yl]-2-nitrobenzaldehyde (0.23 g, 0.68 mmol) obtained in Step 1 was dissolved in methanol (8.0 mL) and the solution was added with (1H-indazol-3-ylmethyl)triphenylphosphonium bromide (0.32 g, 0.68 mmol) and potassium carbonate (0.19 g, 1.4 mmol), followed by stirring at room temperature for 1.5 hours. The reaction mixture was added with water and extracted with ethyl acetate. The organic layer was washed with water and saturated brine, dried over anhydrous magnesium sulfate and the solvent was evaporated under reduced pressure. The residue was purified by silica gel column chromatography (ethyl acetate) to obtain (E)-3-{2-[4-(2-methoxyethyl)piperazin-1-yl]-2-nitrophenyl}vinyl}-1H-indazole (0.48 g, 100%).

$^1$H-NMR (270 MHz, CDCl$_3$) δ 2.77 (m, 8H), 3.35-3.42 (m, 5H), 3.62-3.64 (m, 2H), 7.11 (dd, J=8.6, 2.6 Hz, 1H), 7.21-7.36 (m, 1H), 7.40-7.58 (m, 2H), 7.61-7.69 (m, 2H), 7.73 (d, J=8.9 Hz, 1H), 7.93 (d, J=16.5 Hz, 1H), 8.04 (d, J=7.9 Hz, 1H). APCI-MS (m/z); 408 [M+H]$^+$

Step 3

A solution of (E)-3-{2-[4-(2-methoxyethyl)piperazin-1-yl]-2-nitrophenyl}vinyl}-1H-indazole (0.28 mg, 0.68 mmol) obtained in Step 2 in ethanol (3.0 mL) was added with tin (0.17 g, 1.4 mmol) and concentrated hydrochloric acid (1.5 mL) under ice-cooling, followed by stirring at 40° C. for 2.5 hours. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was triturated in ethyl acetate to obtain (E)-2-[2-(1H-indazol-3-yl)vinyl]-5-[4-(2-methoxyethyl)piperazin-1-yl]phenylamine (0.26 g, 100%).

$^1$H-NMR (300 MHz, CDCl$_3$) δ 2.65-2.69 (m, 8H), 3.26 (t, J=5.5 Hz, 2H), 3.38 (s, 3H), 3.57 (t, J=5.5 Hz, 2H), 6.26 (br, 2H), 6.45 (dd, J=8.4, 2.2 Hz, 1H), 7.18-7.26 (m, 2H), 7.41-7.49 (m, 4H), 7.54 (d, J=16.3 Hz, 1H), 7.99 (d, J=8.1 Hz, 1H). APCI-MS (m/z); 378 [M+H]$^+$

Step 4

In a similar manner to Example 29, Compound 279 (0.03 g, 58%) was obtained from (E)-2-[2-(1H-indazol-3-yl)vinyl]-5-[4-(2-methoxyethyl)piperazin-1-yl]phenylamine (0.26 g, 0.68 mmol) obtained in Step 3,3-methylthiophene-2-carboxylic acid (0.29 g, 2.1 mmol), thionyl chloride (0.20 mL, 2.7 mmol), DMF (few drops) and triethylamine (0.29 mL, 2.1 mmol).

$^1$H-NMR (300 MHz, DMSO-d$_6$) δ 2.53 (t, J=5.7 Hz, 2H), 3.26 (s, 3H), 3.29 (s, 3H), 3.31-3.43 (m, 8H), 3.48 (t, J=5.7 Hz, 2H), 6.90-6.96 (m, 2H), 7.02-7.06 (m, 2H), 7.31 (d, J=16.7 Hz, 1H), 7.32-7.37 (m, 1H), 7.50 (d, J=9.0 Hz, 1H), 7.52 (d, J=16.7 Hz, 1H), 7.69 (d, J=4.9 Hz, 1H), 7.79 (d, J=8.8 Hz, 1H), 7.98 (d, J=7.9 Hz, 1H), 9.77 (br, 1H), 13.0 (br, 1H). APCI-MS (m/z); 502 [M+H]$^+$

EXAMPLE 280

(E)-N-{5-[N-(2-hydroxyethyl)methylamino]-2-(1H-indazol-3-yl)vinyl}phenyl}-3-methylthiophene-2-carboxamide (Compound 280)

Step 1

A solution of 4-fluoro-2-nitrobenzaldehyde (0.20 g, 1.2 mmol) in DMSO (3.5 mL) was added with 2-methylaminoethanol (0.52 mL, 6.5 mmol) and stirred at 100° C. for 5.0 hours. The reaction mixture was added with water and was washed with hexane/ethyl acetate (4/1) to remove impurities. After removing the impurities, the reaction mixture was extracted with ethyl acetate, and the organic layer was washed with water and saturated brine and dried over anhydrous magnesium sulfate. Then, the solvent was evaporated under reduced pressure. The residue was purified by silica gel column chromatography (ethyl acetate) to obtain 4-[N-(2-hydroxyethyl) methylamino]-2-nitrobenzaldehyde (0.20 g, 75%).

$^1$H-NMR (300 MHz, CDCl$_3$) δ 3.18 (s, 3H), 3.67 (t, J=5.5 Hz, 2H), 3.91 (t, J=5.5 Hz, 2H), 6.93 (dd, J=9.0, 2.6 Hz, 1H), 7.18 (d, J=2.6 Hz, 1H), 7.90 (d, J=9.0 Hz, 1H), 10.1 (s, 1H). APCI-MS (m/z); 225 [M+H]$^+$

Step 2

A solution of 4-[N-(2-hydroxyethyl)methylamino]-2-nitrobenzaldehyde (0.20 g, 0.88 mmol) obtained in Step 1 in methanol (8.0 mL) was added with (1H-indazol-3-ylmethyl) triphenylphosphonium bromide (0.42 g, 0.88 mmol) and potassium carbonate (0.24 g, 1.8 mmol), followed by stirring at room temperature for 1.5 hours. The reaction mixture was added with water and extracted with ethyl acetate. The organic layer was washed with water and saturated brine, dried over anhydrous magnesium sulfate and the solvent was evaporated under reduced pressure. The residue was purified by silica gel column chromatography (ethyl acetate) to obtain (E)-2-(N-{4-[2-(1H-indazol-2-yl)vinyl]-3-nitrophenyl}methylamino)ethanol (0.22 g, 75%).

$^1$H-NMR (270 MHz, CDCl$_3$) δ 3.12 (s, 3H), 3.61 (d, J=5.6 Hz, 2H), 3.87 (d, J=5.6 Hz, 2H), 7.24-7.54 (m, 4H), 7.61-7.69 (m, 4H), 8.10 (m, 1H). APCI-MS (m/z); 338 [M+H]$^+$

Step 3

A solution of (E)-2-(N-{4-[2-(1H-indazol-2-yl)vinyl]-3-nitrophenyl}methylamino)ethanol (0.22 g, 0.65 mmol) obtained in Step 2 in ethanol (3.0 mL) was added with tin (0.16 g, 1.4 mmol) and concentrated hydrochloric acid (1.5 mL) under ice-cooling, followed by stirring at 40° C. for 2.5 hours. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was triturated in ethyl acetate to obtain (E)-2-(N-{3-amino-4-[2-(1H-indazol-3-yl) vinyl]phenyl}methylamino)ethanol (0.18 g, 92%).

$^1$H-NMR (300 MHz, CDCl$_3$) δ 2.99 (s, 3H), 3.49 (t, J=5.7 Hz, 2H), 3.84 (t, J=5.7 Hz, 2H), 6.15 (br, 2H), 6.34 (dd, J=8.8, 2.6 Hz, 1H), 7.15-7.24 (m, 3H), 7.38-7.53 (m, 3H), 7.59 (d, J=8.4 Hz, 1H), 8.00 (d, J=8.1 Hz, 1H). APCI-MS (m/z); 308 [M+H]$^+$

Step 4

In a similar manner to Example 29, Compound 280 (89 mg, 34%) was obtained from (E)-2-(N-{3-amino-4-[2-(1H-indazol-3-yl)vinyl]phenyl}methylamino)ethanol (0.18 g, 0.60 mmol) obtained in Step 3,3-methylthiophene-2-carboxylic acid (0.34 g, 2.4 mmol), thionyl chloride (0.22 mL, 3.0 mmol), DMF (few drops) and triethylamine (0.33 mL, 2.4 mmol).

$^1$H-NMR (300 MHz, DMSO-$d_6$) δ 2.99 (s, 3H), 3.24-3.33 (m, 2H), 3.41 (s, 3H), 3.55-3.59 (m, 2H), 4.74 (t, J=5.1 Hz, 1H), 6.66 (m, 1H), 6.69-6.74 (m, 1H), 6.99-7.06 (m, 2H), 7.23 (d, J=16.5 Hz, 1H), 7.33 (t, J=8.2 Hz, 1H), 7.48 (d, J=16.5 Hz, 1H), 7.49 (d, J=8.2 Hz, 1H), 7.69 (d, J=5.1 Hz, 1H), 7.74 (d, J=9.0 Hz, 1H), 7.95 (d, J=8.3 Hz, 1H), 9.74 (br, 1H), 13.0 (br, 1H). APCI-MS (m/z); 433 [M+H]$^+$

EXAMPLE 281

(E)-N-{5-[4-(2-hydroxyethyl)piperazin-1-ylcarbonyl]-2-[2-(1H-indazol-3-yl)vinyl]phenyl}-3-methylthiophene-2-carboxamide (Compound 281)

In a similar manner to Example 28, Compound 281 (83 mg, 22%) was obtained from Compound 98 (0.30 g, 0.74 mmol), 1-(2-hydroxyethyl)piperazine (0.11 g, 0.81 mmol), 1-hydroxybenzotriazole monohydrate (20 mg, 0.15 mmol) and EDC (0.16 g, 0.81 mmol).

$^1$H-NMR (270 MHz, DMSO-$d_6$) δ 2.41-2.46 (m, 8H), 2.52 (s, 3H), 3.46-3.55 (m, 4H), 4.41-4.45 (m, 1H), 7.06 (d, J=5.1 Hz, 1H), 7.12 (d, J=8.1 Hz, 1H), 7.33-7.44 (m, 3H), 7.53-7.61 (m, 1H), 7.55 (d, J=8.4 Hz, 1H), 7.65 (d, J=16.6 Hz, 1H), 7.72 (d, J=5.1 Hz, 1H), 8.00-8.05 (m, 2H), 9.96 (br, 1H), 13.2 (br, 1H).

ESI-MS (m/z); 516 [M+H]$^+$

EXAMPLE 282

(E)-N-(2-[2-(1H-indazol-3-yl)vinyl]-5-{N-[2-(morpholin-4-yl)ethyl]carbamoyl}phenyl)-3-methylthiophene-2-carboxamide (Compound 282)

In a similar manner to Example 28, Compound 282 (0.27 g, 70%) was obtained from Compound 98 (0.30 g, 0.74 mmol), 2-morpholinoethylamine (0.11 g, 0.81 mmol), 1-hydroxybenzotriazole monohydrate (20 mg, 0.15 mmol) and EDC (0.16 g, 0.81 mmol).

$^1$H-NMR (270 MHz, DMSO-$d_6$) δ 2.41-2.49 (m, 6H), 2.52 (s, 3H), 3.38-3.45 (m, 2H), 3.58 (t, J=4.4 Hz, 4H), 7.07 (d, J=5.1 Hz, 1H), 7.12 (d, J=7.9 Hz, 1H), 7.38 (dd, J=7.7, 7.7 Hz, 1H), 7.55 (d, J=8.4 Hz, 1H), 7.64 (s, 2H), 7.72 (d, J=5.1 Hz, 1H), 7.80-8.08 (m, 4H), 8.49 (t, J=5.4 Hz, 1H), 9.99 (br, 1H), 13.2 (br, 1H).

ESI-MS (m/z); 516 [M+H]$^+$

EXAMPLE 283

(E)-N-{2-[2-(1H-indazol-3-yl)vinyl]-5-[3-(methylamino)pyrrolidin-1-ylcarbonyl]phenyl}-3-methylthiophene-2-carboxamide (Compound 283)

In a similar manner to Example 28, a crude product was obtained from Compound 98 (0.50 g, 1.2 mmol), 3-[N-(tert-butoxycarbonyl)methylamino]pyrrolidine (0.26 g, 1.2 mmol), 1-hydroxybenzotriazole monohydrate (34 mg, 0.25 mmol) and EDC (0.24 g, 1.2 mmol). Further, the product was dissolved in methanol (10 mL), added with 4 mol/L hydrogen chloride-methanol solution (2.0 mL), followed by reacting at 60° C. for 1 hour. The reaction mixture was concentrated under reduced pressure, neutralized by aqueous sodium hydroxide solution and crystallized from ethyl acetate to obtain Compound 283 (0.45 g, 75%).

$^1$H-NMR (270 MHz, DMSO-$d_6$) δ 1.99 (br, 3H), 2.36 (br, 2H), (s, 3H), 3.33-3.70 (m, 6H), 7.06 (d, J=4.9 Hz, 1H), (d, J=7.6 Hz, 1H), 7.38 (t, J=7.6 Hz, 1H), 7.49-7.62 (m, 4H), 7.67 (d, J=16.9 Hz, 1H), 7.72 (d, J=4.9 Hz, 1H), 8.04 (dd, J=7.6, 7.6 Hz, 2H), 9.99 (br, 1H), 13.2 (br, 1H).

ESI-MS (m/z); 486 [M+H]$^+$

EXAMPLE 284

(E)-N-{5-[N-(2-dimethylaminoethyl)-2-(methoxyethyl) amino]-2-[2-(1H-indazol-3-yl)vinyl]phenyl}-3-methylthiophene-2-carboxamide (Compound 284)

Step 1

A solution of 4-fluoro-2-nitrobenzaldehyde (0.10 g, 0.60 mmol) in DMSO (1.5 mL) was added with N'-(2-methoxyethyl)-N, N-dimethylethane-1,2-diamine (0.48 g, 3.3 mmol) and stirred at 100° C. for 5.0 hours. The reaction mixture was added with water and was washed with hexane/ethyl acetate (4/1) to remove impurities. After removing the impurities, the reaction mixture was extracted with ethyl acetate, and the organic layer was washed with water and saturated brine and dried over anhydrous magnesium sulfate. Then, the solvent was evaporated under reduced pressure. The filtrate was purified by silica gel column chromatography (ethyl acetate) to obtain 4-[N-(2-dimethylaminoethyl)-2-(methoxyethyl) amino]-2-nitrobenzaldehyde (95 mg, 55%).

$^1$H-NMR (300 MHz, CDCl$_3$) δ 2.31 (s, 6H), 2.52 (t, J=7.5 Hz, 2H), 3.36 (s, 3H), 3.56-3.67 (m, 6H), 6.89 (dd, J=9.0, 2.6 Hz, 1H), 7.17 (d, J=2.6 Hz, 1H), 7.90 (d, J=8.8 Hz, 1H), 10.1 (s, 1H). APCI-MS (m/z); 296 [M+H]$^+$

Step 2

A solution of 4-[N-(2-dimethylaminoethyl)-2-(methoxyethyl) amino]-2-nitrobenzaldehyde (95 mg, 0.32 mmol) obtained in Step 1 in methanol (4.0 mL) was added with (1H-indazol-3-ylmethyl)triphenylphosphonium bromide (0.15 g, 0.33 mmol) and potassium carbonate (89 mg, 0.64 mmol), followed by stirring at room temperature for 2.0 hours. The reaction mixture was added with water and extracted with ethyl acetate. The organic layer was washed with water and saturated brine, dried over anhydrous magnesium sulfate and the solvent was evaporated under reduced pressure. The residue was purified by silica gel column chromatography (ethyl acetate) and the obtained product was dissolved in ethanol (2.0 mL), added with tin (0.08 g, 0.67 mmol) and concentrated hydrochloric acid (1.0 mL) under ice-cooling, followed by stirring at 40° C. for 2.5 hours. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. In a similar manner to Example 29, Compound 284 (35 mg, 22%) was obtained by treating the residue with 3-methylthiophene-2-carboxylic acid (91 mg, 0.63 mmol), thionyl chloride (62 μL, 0.85 mmol), DMF (few drops) and triethylamine (88 μL, 0.63 mmol).

$^1$H-NMR (300 MHz, DMSO-$d_6$) δ 2.21 (s, 9H), 2.39-2.46 (m, 4H), 3.43-3.52 (m, 7H), 6.65-6.70 (m, 2H), 7.01 (d, J=7.5 Hz, 1H), 7.04 (d, J=5.0 Hz, 1H), 7.24 (d, J=16.5 Hz, 1H), 7.33

(t, J=7.5 Hz, 1H), 7.48 (d, J=16.5 Hz, 1H), 7.50 (d, J=8.1 Hz, 1H), 7.68 (d, J=4.9 Hz, 1H), 7.74 (d, J=8.4 Hz, 1H), 7.96 (d, J=8.1 Hz, 1H), 9.74 (br, 1H), 13.0 (br, 1H). APCI-MS (m/z); 504 [M+H]$^+$

EXAMPLE 285

(E)-3-(1,3-dioxo-1,3-dihydroisoindol-2-yl)-4-[2-(1H-indazol-3-yl)vinyl]-N,N-dimethylbenzamide (Compound 285)

In a similar manner to Step 3 of Example 276, Compound 285 (0.10 g, 63%) was obtained from 3-(1,3-dioxo-1,3-dihydroisoindol-2-yl)-4-[2-(1H-indazol-3-yl)vinyl]benzoic acid (0.15 g, 0.37 mmol) obtained in Step 2 of Example 276, dimethylamine hydrochloride (33 mg, 0.41 mmol), 1-hydroxybenzotriazole monohydrate (55 mg, 0.41 mmol) and EDC (99 mg, 0.52 mmol) and methylmorpholine (0.06 mL, 0.55 mmol).

$^1$H-NMR (270 MHz, DMSO-d$_6$) δ 3.01 (s, 3H), 3.02 (s, 3H), 7.04 (d, J=8.2 Hz, 1H), 7.22 (d, J=16.8 Hz, 1H), 7.33-7.36 (m, 1H), 7.51 (d, J=8.4 Hz, 1H), 7.60-7.63 (m, 2H), 7.69 (d, J=16.8 Hz, 1H), 7.78 (d, J=8.2 Hz, 1H), 7.96-8.06 (m, 4H), 8.18 (d, J=8.4 Hz, 1H), 13.2 (br, 1H).

ESI-MS (m/z); 437 [M+H]$^+$

EXAMPLE 286

(E)-2-[5-[4-(2-hydroxyethyl)piperazin-1-ylcarbonyl]-2-[2-(1H-indazol-3-yl)vinyl]phenyl]isoindole-1,3-dione (Compound 286)

In a similar manner to Step 3 of Example 276, Compound 286 (34 mg, 27%) was obtained from 3-(1,3-dioxo-1,3-dihydroisoindol-2-yl)-4-[2-(1H-indazol-3-yl)vinyl]benzoic acid (0.10 g, 0.24 mmol) obtained in Step 2 of Example 276, 1-(2-hydroxyethyl)piperazine (33 mg, 0.26 mmol), 1-hydroxybenzotriazole monohydrate (17 mg, 0.12 mmol) and EDC (51 mg, 0.26 mmol).

$^1$H-NMR (270 MHz, DMSO-d$_6$) δ 2.41-2.43 (m, 6H), 3.41-3.55 (m, 6H), 4.42-4.46 (m, 1H), 7.03 (d, J=7.6 Hz, 1H), 7.22 (d, J=16.6 Hz, 1H), 7.33-7.36 (m, 1H), 7.50-7.63 (m, 3H), 7.69 (d, J=16.5 Hz, 1H), 7.77 (d, J=8.6 Hz, 1H), 7.96-8.07 (m, 4H), 8.19 (d, J=8.4 Hz, 1H), 13.2 (br, 1H).

ESI-MS (m/z); 522 [M+H]$^+$

EXAMPLE 287

(E)-2-[2-(1H-indazol-3-yl)vinyl]-5-(4-methylpiperazin-1-ylcarbonyl)phenyl]isoindole-1,3-dione (Compound 287)

In a similar manner to Step 3 of Example 276, Compound 287 (60 mg, 33%) was obtained from 3-(1,3-dioxo-1,3-dihydroisoindol-2-yl)-4-[2-(1H-indazol-3-yl)vinyl]benzoic acid (0.15 g, 0.37 mmol) obtained in Step 2 of Example 276, N-methylpiperazine (45 mg, 0.41 mmol), 1-hydroxybenzotriazole monohydrate (55 mg, 0.41 mmol) and EDC (99 mg, 0.52 mmol).

$^1$H-NMR (270 MHz, DMSO-d$_6$) δ 2.21 (s, 3H), 2.36 (br, 4H), 3.51 (br, 4H), 7.04 (d, J=7.6, 1H), 7.22 (d, J=16.5 Hz, 1H), 7.34 (d, J=7.6 Hz, 1H), 7.52 (d, J=8.4 Hz, 1H), 7.57-7.60 (m, 2H), 7.69 (d, J=16.5 Hz, 1H), 7.78 (d, J=8.4 Hz, 1H), 7.96-8.07 (m, 4H), 8.19 (d, J=8.4 Hz, 1H), 13.2 (br, 1H).

ESI-MS (m/z); 492 [M+H]$^+$

EXAMPLE 288

(E)-4-amino-N-{2-[2-(1H-indazol-3-yl)vinyl]-5-(morpholin-4-ylcarbonyl)phenyl}isoindole-1,3-dione (Compound 288)

Step 1

To 3-amino-4-[2-(1H-indazol-3-yl)vinyl]benzoic acid (1.7 g, 6.2 mmol) obtained in Step 2 of Example 276, xylene (55 mL), triethylamine (0.45 mL, 3.1 mmol), 3-nitrophthalic anhydride (1.4 g, 7.4 mmol), molecular sieves 3A (2.0 g) were added, followed by heating at 140° C. for 4 hours. Molecular sieves 3A was filtered off and the reaction mixture was acidified by hydrochloric acid (2 mol/L). The precipitated crystal was collected by filtration to obtain (E)-4-[2-(1H-indazol-3-yl)vinyl]-3-(4-nitro-1,3-dioxo-1,3-dihydroisoindol-2-yl)benzoic acid.

$^1$H-NMR (270 MHz, DMSO-d$_6$) δ 7.07 (d, J=8.6 Hz, 1H), 7.26-7.49 (m, 1H), 7.50-7.69 (m, 3H), 7.81-7.98 (m, 2H), 8.02-8.18 (m, 3H), 8.30-8.10 (m, 2H), 13.2 (br, 1H).

ESI-MS (m/z); 455 [M+H]$^+$

Step 2

In a similar manner to Step 3 of Example 276, (E)-2-{2-[2-(1H-indazol-3-yl)vinyl]-5-(morpholin-4-ylcarbonyl)phenyl}-4-nitroisoindole-1,3-dione was obtained from (E)-4-[2-(1H-indazol-3-yl)vinyl]-3-(4-nitro-1,3-dioxo-1,3-dihydroisoindol-2-yl)benzoic acid (0.86 g, 1.9 mmol) obtained in Step 1, morpholine (0.25 g, 2.9 mmol), 1-hydroxybenzotriazole monohydrate (0.33 g, 2.5 mmol) and EDC (0.51 g, 2.7 mmol).

$^1$H-NMR (270 MHz, DMSO-d$_6$) δ 3.63 (br, 8H), 6.62 (br, 2H), 7.02-7.13 (m, 3H), 7.21 (d, J=16.5 Hz, 1H), 7.34 (dd, J=8.1, 8.1 Hz, 1H), 7.51-7.60 (m, 4H), 7.69 (d, J=16.5 Hz, 1H), 7.77 (d, J=8.2 Hz, 1H), 8.18 (d, J=8.2 Hz, 1H), 13.2 (br, 1H).

ESI-MS (m/z); 524 [M+H]$^+$

Step 3

In a similar manner to Example 2, (E)-2-{2-[2-(1H-indazol-3-yl)vinyl]-5-(morpholin-4-ylcarbonyl)phenyl}-4-nitroisoindole-1,3-dione (0.30 g, 0.57 mmol) obtained in Step 2 was dissolved in ethanol (30 mL) and was reacted with tin (0.2 g, 1.7 mmol) and concentrated hydrochloric acid (7.0 mL) at room temperature to obtain Compound 288 (46 mg, 53%).

$^1$H-NMR (270 MHz, DMSO-d$_6$) δ 3.63 (br, 8H), 6.62 (br, 2H), 7.02-7.13 (m, 3H), 7.21 (d, J=16.5 Hz, 1H), 7.34 (dd, J=8.1, 8.1 Hz, 1H), 7.51-7.60 (m, 4H), 7.69 (d, J=16.5 Hz, 1H), 7.77 (d, J=8.2 Hz, 1H), 8.18 (d, J=8.2 Hz, 1H), 13.2 (br, 1H).

ESI-MS (m/z); 494 [M+H]$^+$

EXAMPLE 289

(E)-N-{5-[4-(2-hydroxyethyl)piperazin-1-ylcarbonyl]-2-[2-(1H-indazol-3-yl)vinyl]phenyl}thiophene-2-carboxamide (Compound 289)

Step 1

A solution of 3-amino-4-[2-(1H-indazol-3-yl)vinyl]benzoic acid methyl ester (0.51 g, 1.8 mmol) obtained in Step 1 of Example 217 and triethylamine (0.73 ml, 5.3 mmol) in THF (20 mL) was added with 2-thiophenecarbonyl chloride (0.20 g, 1.9 mmol) and stirred for 2 hours. The reaction mixture was added with saturated aqueous sodium hydrogencarbonate solution and extracted with ethyl acetate. The organic layer was concentrated under reduced pressure to obtain crude product. Further, the product was dissolved in methanol (10 mL) and 2 mol/L aqueous sodium hydroxide solution (2.0 mL) was added thereto, followed by stirring at 60° C. for 1 hour. The reaction mixture was acidified by hydrochloric acid (6 mol/L) and the precipitated crystal was collected by filtration to obtain (E)-4-[2-(1H-indazol-3-yl)vinyl]-3-[(thiophen-2-ylcarbonyl)amino]benzoic acid (0.28 g, 41%).

$^1$H-NMR (270 MHz, DMSO-d$_6$) δ 7.08 (dd, J=8.1, 8.1 Hz, 1H), 7.28-7.30 (m, 1H), 7.34-7.55 (m, 2H), 7.62 (d, J=16.6 Hz, 1H), 7.71 (d, J=16.6 Hz, 1H), 7.87-8.00 (m, 4H), 8.13 (t, J=4.4 Hz, 2H), 10.5 (br, 1H), 13.2 (br, 1H).

ESI-MS (m/z); 390 [M+H]$^+$

Step 2

In a similar manner to Example 28, Compound 289 (0.15 g, 83%) was obtained from (E)-4-[2-(1H-indazol-3-yl)vinyl]-3-[(thiophen-2-ylcarbonyl)amino]benzoic acid (0.14 g, 0.36 mmol) obtained in Step 1,1-(2-hydroxyethyl)piperazine (0.05 g, 0.40 mmol), 1-hydroxybenzotriazole monohydrate (24 mg, 0.18 mmol) and EDC (76 mg, 0.36 mmol).

$^1$H-NMR (270 MHz, DMSO-d$_6$) δ 2.46 (br, 4H), 3.56 (br, 8H), 5.40 (br, 1H), 7.08 (dd, J=8.1, 8.1 Hz, 1H), 7.27-7.30 (m, 1H), 7.34-7.41 (m, 2H), 7.44-7.63 (m, 4H), 7.91 (d, J=4.9 Hz, 1H), 7.98 (d, J=8.1 Hz, 1H), 8.06 (d, J=8.1 Hz, 1H), 8.11 (d, J=3.8 Hz, 1H), 10.4 (br, 1H), 13.2 (br, 1H).

ESI-MS (m/z); 502 [M+H]$^+$

EXAMPLE 290

(E)-N-{5-[(4-(2-hydroxyethyl)piperazin-1-ylcarbonyl)-2-[2-(1H-indazol-3-yl)vinyl]phenyl}benzamide (Compound 290)

Step 1

A solution of 3-amino-4-[2-(1H-indazol-3-yl)vinyl]benzoic acid methyl ester (0.30 g, 1.0 mmol) obtained in Step 1 of Example 217 and triethylamine (0.43 ml, 3.1 mmol) in THF (10 mL) was added with benzoyl chloride (0.13 mL, 1.1 mmol) followed by stirring for 4 hours. The reaction mixture was extracted with ethyl acetate. The organic layer was washed with saturated aqueous sodium hydrogencarbonate solution and concentrated under reduced pressure to obtain crude product. Further, the product was dissolved in methanol (20 mL) and the solution was added with 2 mol/L aqueous sodium hydroxide solution (5.0 mL), followed by stirring at 60° C. for 1 hour. The reaction mixture was acidified by hydrochloric acid (6 mol/L) and the precipitated crystal was collected by filtration to obtain (E)-4-[2-(1H-indazol-3-yl)vinyl]-3-(benzoylamino)benzoic acid (0.35 g, 89%).

$^1$H-NMR (270 MHz, DMSO-d$_6$) δ 7.07 (dd, J=7.6, 7.6 Hz, 1H), 7.33-7.42 (m, 1H), 7.53-7.74 (m, 6H), 7.87-8.14 (m, 6H), 10.4 (br, 1H), 13.2 (br, 1H).

ESI-MS (m/z); 384 [M+H]$^+$

Step 2

In a similar manner to Example 28, Compound 290 (96 mg, 49%) was obtained from (E)-4-[2-(1H-indazol-3-yl)vinyl]-3-(benzoylamino)benzoic acid (0.15 g, 0.39 mmol) obtained in Step 1, 1-(2-hydroxyethyl)piperazine (0.05 g, 0.43 mmol), 1-hydroxybenzotriazole monohydrate (26 mg, 0.20 mmol) and EDC (83 mg, 0.43 mmol).

$^1$H-NMR (270 MHz, DMSO-d$_6$) δ 2.41-2.46 (m, 8H), 3.49-3.55 (m, 4H), 4.43 (t, 1H), 7.06 (dd, J=7.6, 7.6 Hz, 1H), 7.33-7.42 (m, 2H), 7.52-7.55 (m, 1H), 7.58-7.65 (m, 6H), 7.96 (d, J=8.2 Hz, 1H), 8.05 (d, J=8.2 Hz, 2H), 8.09 (br, 1H), 10.4 (br, 1H), 13.2 (br, 1H).

ESI-MS (m/z); 496 [M+H]$^+$

EXAMPLE 291

(E)-N-{5-[4-(3-hydroxypropyl)piperazin-1-ylcarbonyl]-2-[2-(1H-indazol-3-yl)vinyl]phenyl}furan-2-carboxamide (Compound 291)

Step 1

A solution of 3-amino-4-[2-(1H-indazol-3-yl)vinyl]benzoic acid methyl ester (0.30 g, 1.0 mmol) obtained in Step 1 of Example 217 and triethylamine (0.43 ml, 3.1 mmol) in THF (10 mL) was added with furan-2-carbonyl chloride (0.11 mL, 1.1 mmol), followed by stirring for 4 hours. The reaction mixture was extracted with ethyl acetate and saturated aqueous sodium hydrogencarbonate solution. The organic layer was concentrated under reduced pressure to obtain crude product. Further, the product was dissolved in methanol (20 mL) and added with 2 mol/L aqueous sodium hydroxide solution (5.0 mL), followed by stirring at 60° C. for 1 hour. The reaction mixture was acidified by hydrochloric acid (6 mol/L) and the precipitated crystal was collected by filtration to obtain (E)-4-[2-(1H-indazol-3-yl) vinyl]-3-[(furan-2-carbonyl)amino]benzoic acid (0.31 g, 82%).

$^1$H-NMR (270 MHz, DMSO-d$_6$) δ 6.74-6.76 (m, 1H), 7.13 (br, 1H), 7.38-7.41 (m, 2H), 7.54-7.66 (m, 3H), 7.98-8.12 (m, 5H), 10.3 (br, 1H), 13.2 (br, 1H).

ESI-MS (m/z); 374 [M+H]$^+$

Step 2

In a similar manner to Example 28, Compound 291 (0.12 g, 64%) was obtained from (E)-4-[2-(1H-indazol-3-yl)vinyl]-3-[(furan-2-carbonyl)amino]benzoic acid (0.15 g, 0.39 mmol) obtained in Step 1,1-(3-hydroxypropyl)piperazine (0.06 g, 0.43 mmol), 1-hydroxybenzotriazole monohydrate (26 mg, 0.20 mmol) and EDC (82 mg, 0.43 mmol).

$^1$H-NMR (270 MHz, DMSO-d$_6$) δ 1.57-1.62 (m, 2H), 2.35-2.49 (br, 8H), 3.32-3.47 (m, 4H), 4.44 (br, 1H), 6.74-6.76 (m, 1H), 7.13 (dd, J=7.6, 7.6 Hz, 1H), 7.34-7.41 (m, 4H), 7.55 (d, J=8.4 Hz, 1H), 7.60 (s, 2H), 7.98-8.05 (m, 3H), 10.3 (br, 1H), 13.2 (br, 1H).

ESI-MS (m/z); 500 [M+H]$^+$

EXAMPLE 292

(E)-N-{2-[2-(1H-indazol-3-yl)vinyl]-4-methoxy-5-[3-(morpholin-4-yl)propyloxy]phenyl}-3-methylthiophene-2-carboxamide (Compound 292)

Step 1

4-(3-Chloropropyloxy)-5-methoxy-2-nitrobenzaldehyde (0.40 g, 1.5 mmol) was dissolved in toluene (6.0 mL) and the solution was added with potassium carbonate (1.0 g, 7.3 mmol) dissolved in morpholine (0.38 mL, 4.4 mmol), sodium iodide (0.44 g, 2.9 mmol), tetrabutylammonium bromide (24 mg, 0.007 mmol) and water (2.0 mL), followed by stirring at 100° C. for 19 hours. The reaction mixture was added with water and extracted with ethyl acetate. The organic layer was washed with water and saturated brine, dried over anhydrous magnesium sulfate and the solvent was evaporated under reduced pressure. The filtrate was purified by silica gel column chromatography (hexane/ethyl acetate=100/0 to 0/100) and concentrated to obtain 5-methoxy-4-[3-(morpholin-4-yl) propyloxy]-2-nitrobenzaldehyde (0.26 g, 54%).

¹H-NMR (300 MHz, CDCl₃) δ 2.45-2.11 (m, 2H), 2.55 (t, J=7.0 Hz, 2H), 3.71-3.75 (m, 8H), 4.01 (s, 3H), 4.23 (t, J=6.6 Hz, 2H), 7.42 (s, 1H), 7.64 (s, 1H), 10.4 (s, 1H). APCI-MS (m/z); 325 [M+H]⁺

Step 2

A solution of 5-methoxy-4-[3-(morpholin-4-yl) propyloxy]-2-nitrobenzaldehyde (0.26 g, 0.79 mmol) obtained in Step 1 in methanol (8.0 mL) was added with (1H-indazol-3-ylmethyl)triphenylphosphonium bromide (0.73 g, 1.5 mmol) and potassium carbonate (0.34 g, 2.8 mmol), followed by stirring at room temperature for 3.5 hours. The reaction mixture was added with water and the precipitated solid was triturated in methanol to obtain (E)-3-{2-[5-methoxy-4-[3-(morpholin-4-yl)propyloxy]-2-nitrophenyl]vinyl}-1H-indazole (0.39 g, 100%).

¹H-NMR (270 MHz, DMSO-d₆) δ 1.89-1.95 (m, 2H), 2.37-2.43 (m, 2H), 3.56-3.60 (m, 8H), 4.03 (s, 3H), 4.14 (t, J=6.2 Hz, 2H), 7.24 (t, J=7.6 Hz, 1H), 7.42 (t, J=7.6 Hz, 1H), 7.49 (s, 1H), 7.56-7.68 (m, 3H), 7.95 (d, J=16.5 Hz, 1H), 8.09 (d, J=8.3 Hz, 1H), 13.3 (br, 1H). APCI-MS (m/z); 439 [M+H]⁺

Step 3

(E)-3-{2-[5-methoxy-4-(3-(morpholin-4-yl) propyloxy)-2-nitrophenyl]vinyl}-1H-indazole (0.39 g, 0.89 mmol) obtained in Step 2 was dissolved in ethanol (3.0 mL), and the solution was added with tin (0.22 g, 1.9 mmol) and concentrated hydrochloric acid (1.5 mL) under ice-cooling, followed by stirring at 40° C. for 6 hours. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The filtrate was purified by silica gel column chromatography (chloroform to chloroform/methanol=9/1) to obtain (E)-2-[2-(1H-indazol-3-yl)vinyl]-4-methoxy-5-[3-(morpholin-4-yl)propyloxy]phenylamine (0.32 g, 89%).

¹H-NMR (270 MHz, DMSO-d₆) δ 1.84-1.91 (m, 2H), 2.36-2.50 (m, 8H), 3.58 (t, J=4.6 Hz, 2H), 3.73 (s, 3H), 3.93 (t, J=6.6 Hz, 2H), 5.00 (br, 2H), 6.40 (s, 1H), 7.10-7.21 (m, 3H), 7.37 (t, J=7.6 Hz, 1H), 7.47-7.53 (m, 2H), 8.20 (d, J=8.2 Hz, 1H), 13.0 (br, 1H). APCI-MS (m/z); 409 [M+H]⁺

Step 4

In a similar manner to Example 29, Compound 292 (0.16 mg, 38%) was obtained from (E)-2-[2-(1H-indazol-3-yl)vinyl]-4-methoxy-5-[3-(morpholin-4-yl)propyloxy]phenylamine (0.32 g, 0.79 mmol) obtained in Step 2,3-methylthiophene-2-carboxylic acid (0.34 g, 2.4 mmol), thionyl chloride (0.23 mL, 3.2 mmol), DMF (few drops) and triethylamine (0.33 mL, 2.4 mmol).

¹H-NMR (300 MHz, DMSO-d₆) δ 1.89 (t, J=6.6 Hz, 2H), 2.35-2.46 (m, 6H), 3.32 (s, 3H), 3.54-3.57 (m, 4H), 3.89 (s, 3H), 4.01 (t, J=6.2 Hz, 2H), 6.93 (m, 1H), 7.02-7.12 (m, 2H), 7.34 (t, J=8.1 Hz, 1H), 7.44 (d, J=16.7 Hz, 1H), 7.43-7.52 (m, 2H), 7.52 (d, J=16.7 Hz, 1H), 7.67 (d, J=4.9 Hz, 1H), 7.99 (d, J=8.1 Hz, 1H), 9.71 (br, 1H), 13.07 (br, 1H). APCI-MS (m/z); 533 [M+H]⁺

EXAMPLE 293

(E)-N-{2-[2-(1H-indazol-3-yl)vinyl]-4-methoxy-5-[2-(morpholin-4-yl)ethoxy]phenyl}-3-methylthiophene-2-carboxamide (Compound 293)

Step 1

In a similar manner to Step 2 of Example 292, (E)-3-{2-[5-methoxy-4-[2-(morpholin-4-yl)ethoxy]-2-nitrophenyl]vinyl}-1H-indazol (0.26 g, 64%) was obtained from 5-methoxy-4-[2-(morpholin-4-yl)ethoxy]-2-nitrobenzaldehyde (0.30 g, 0.97 mmol) which can be synthesized in a similar manner to Step 1 of Example 292, methanol (8.0 mL), (1H-indazol-3-ylmethyl) triphenylphosphonium bromide (0.50 g, 1.0 mmol) and potassium carbonate (0.27 g, 1.9 mmol).

¹H-NMR (270 MHz, DMSO-d₆) δ 2.73 (t, J=5.6 Hz, 2H), 3.57-3.60 (m, 8H), 4.03 (s, 3H), 4.22 (t, J=5.6 Hz, 2H), 7.24 (t, J=6.9 Hz, 1H), 7.42 (d, J=6.9 Hz, 1H), 7.49-7.69 (m, 4H), 7.96 (d, J=16.3 Hz, 1H), 8.10 (d, J=7.6 Hz, 1H), 13.3 (br, 1H). APCI-MS (m/z); 425 [M+H]⁺

Step 2

In a similar manner to Step 3 of Example 292, (E)-2-[2-(1H-indazol-3-yl)vinyl]-4-methoxy-5-(2-(morpholin-4-yl)ethoxy)phenylamine (0.23 g, 96%) was obtained from (E)-3-{2-[5-methoxy-4-(2-(morpholin-4-yl)ethoxy)-2-nitrophenyl]vinyl}-1H-indazole (0.26 g, 0.62 mmol) obtained in Step 1, ethanol (3.0 mL), tin (0.16 g, 1.3 mmol) and concentrated hydrochloric acid (1.5 mL).

¹H-NMR (300 MHz, DMSO-d₆) δ 2.63-2.72 (m, 2H), 3.55-3.60 (m, 8H), 3.74 (s, 3H), 3.99-4.04 (m, 2H), 4.99 (br, 2H), 6.42 (s, 1H), 7.11-7.19 (m, 3H), 7.37 (t, J=8.0 Hz, 1H), 7.45-7.53 (m, 2H), 8.20 (d, J=7.9 Hz, 1H), 13.0 (br, 1H). APCI-MS (m/z); 395 [M+H]⁺

Step 3

In a similar manner to Example 29, Compound 293 (0.14 g, 48%) was obtained from (E)-2-[2-(1H-indazol-3-yl)vinyl]-4-methoxy-5-(2-morpholin-4-ylethoxy)phenylamine (0.23 g, 0.59 mmol) obtained in Step 2,3-methylthiophene-2-carboxylic acid (0.25 g, 1.8 mmol), thionyl chloride (0.17 mL, 2.4 mmol), DMF (few drops) and triethylamine (0.25 mL, 1.8 mmol).

¹H-NMR (300 MHz, DMSO-d₆) δ 2.70 (t, J=5.9 Hz, 2H), 3.32 (s, 3H), 3.55-3.71 (m, 8H), 3.89 (s, 3H), 4.09 (t, J=5.9 Hz, 2H), 6.97-7.13 (m, 3H), 7.34 (t, J=7.0 Hz, 1H), 7.42 (d, J=16.4 Hz, 1H), 7.44-7.52 (m, 1H), 7.52 (d, J=16.4 Hz, 1H), 7.61 (t, J=4.8 Hz, 1H), 7.67 (d, J=4.9 Hz, 1H), 8.00 (d, J=8.2 Hz, 1H), 9.70 (br, 1H), 13.08 (br, 1H). APCI-MS (m/z); 519 [M+H]⁺

EXAMPLE 294

(E)-N-{5-[3-(dimethylamino)pyrrolidin-1-ylmethyl]-2-[2-(1H-indazol-3-yl)vinyl]phenyl}-3-methylthiophene-2-carboxamide (Compound 294)

In a similar manner to Step 2 of Example 224, Compound 294 (0.16 g, 44%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and 3-(dimethylamino)pyrrolidine (0.33 g, 2.3 mmol).

¹H-NMR (270 MHz, DMSO-d₆) δ 2.13 (s, 6H), 2.51 (s, 3H), 2.59-2.79 (m, 3H), 3.32 (br, 4H), 3.51-3.67 (m, 2H), 7.05 (d, J=4.9 Hz, 1H), 7.10 (d, J=8.1 Hz, 1H), 7.25-7.39 (m, 3H), 7.48 (d, J=16.8 Hz, 1H), 7.52-7.55 (m, 1H), 7.61 (d, J=16.8

Hz, 1H), 7.69 (d, J=4.9 Hz, 1H), 7.89 (d, J=8.2 Hz, 1H), 8.01 (d, J=8.2 Hz, 1H), 9.84 (br, 1H), 13.1 (br, 1H).
ESI-MS (m/z); 486 [M+H]$^+$

EXAMPLE 295

(E)-N-{5-[3-(dimethylamino)pyrrolidin-1-ylcarbonyl]-2-[2-(1H-indazol-3-yl)vinyl]phenyl}-3-methylthiophene-2-carboxamide (Compound 295)

In a similar manner to Example 28, Compound 295 (0.21 g, 56%) was obtained from Compound 98 (0.30 g, 0.74 mmol), 3-dimethylaminopyrrolidine (94 mg, 0.81 mmol), 1-hydroxybenzotriazole monohydrate (20 mg, 0.15 mmol) and EDC (0.16 g, 0.81 mmol).

$^1$H-NMR (270 MHz, DMSO-d$_6$) δ 2.13 (s, 3H), 2.20 (s, 3H), 2.52 (s, 3H), 2.70 (s, 1H), 3.31-3.54 (m, 6H), 7.06 (d, J=4.9 Hz, 1H), 7.11 (d, J=7.9 Hz, 1H), 7.38 (dd, J=7.9, 7.9 Hz, 1H), 7.48-7.62 (m, 5H), 7.71 (d, J=4.9 Hz, 1H), 7.99-8.06 (m, 2H), 9.98 (br, 1H), 13.2 (br, 1H).
ESI-MS (m/z); 500 [M+H]$^+$

EXAMPLE 296

(E)-N-{2-[2-(1H-indazol-3-yl)vinyl]-5-[4-(morpholin-4-yl)piperidin-1-ylmethyl]phenyl}-3-methylthiophene-2-carboxamide (Compound 296)

In a similar manner to Step 2 of Example 224, Compound 296 (44 mg, 11%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and 4-(piperidin-4-yl)morpholine (0.39 g, 2.3 mmol).

$^1$H-NMR (270 MHz, DMSO-d$_6$) δ 1.39-1.43 (m, 2H), 1.73-2.01 (m, 5H), 2.45-2.49 (m, 4H), 2.51 (s, 3H), 2.87-2.90 (m, 2H), 3.48-3.57 (m, 6H), 7.05 (d, J=4.9 Hz, 1H), 7.09 (d, J=8.1 Hz, 1H), 7.24-7.36 (m, 3H), 7.47 (d, J=16.8 Hz, 1H), 7.53 (d, J=8.2 Hz, 1H), 7.60 (d, J=16.8 Hz, 1H), 7.69 (d, J=4.9 Hz, 1H), 7.89 (d, J=8.2 Hz, 1H), 8.00 (d, J=8.2 Hz, 1H), 9.84 (br, 1H), 13.1 (br, 1H).
ESI-MS (m/z); 542 [M+H]$^+$

EXAMPLE 297

(E)-N-{2-[2-(1H-indazol-3-yl)vinyl]-5-[N-methyl-N-(piperidine-4-yl)carbamoyl]phenyl}-3-methylthiophene-2-carboxamide (Compound 297)

In a similar manner to Example 28, a crude product was obtained from Compound 98 (0.30 g, 0.74 mmol), (N-methylpiperidin-1-yl)carbamic acid tert-butyl ester (0.18 g, 0.81 mmol), 1-hydroxybenzotriazole monohydrate (20 mg, 0.15 mmol) and EDC (0.16 g, 0.81 mmol). Further, the product was dissolved in methanol (10 mL), added with 4 mol/L hydrogen chloride-methanol solution (2.0 mL) and reacted at 60° C. for 1 hour. The reaction mixture was concentrated under reduced pressure, neutralized by aqueous sodium hydroxide solution and crystallized from ethyl acetate to obtain Compound 297 (0.26 g, 71%).

$^1$H-NMR (270 MHz, DMSO-d$_6$) δ 1.60 (br, 4H), 2.52 (s, 3H), 2.86 (s, 3H), 2.96-3.17 (m, 1H), 3.32 (br, 4H), 7.06 (d, J=4.9 Hz, 1H), 7.11 (d, J=7.9 Hz, 1H), 7.31-7.42 (m, 3H), 7.54-7.55 (m, 2H), 7.60 (d, J=16.8 Hz, 1H), 7.71 (d, J=4.9 Hz, 1H), 8.01 (d, J=8.2 Hz 1H), 8.05 (d, J=8.2 Hz 1H), 9.96 (br, 1H), 13.2 (br, 1H)
ESI-MS (m/z); 500 [M+H]$^+$ .

EXAMPLE 298

(E)-N-{2-[2-(1H-indazol-3-yl)vinyl]-4-methoxy-5-{3-[N-(2-methoxyethyl)methylamino]propyloxy}phenyl}-3-methylthiophene-2-carboxamide (Compound 298)

Step 1

In a similar manner to Step 1 of Example 292, 5-methoxy-4-{3-[N-(2-methoxyethyl)methylamino]propyloxy}-2-nitrobenzaldehyde (0.47 g, 99%) was obtained from 4-(3-chloropropyloxy)-5-methoxy-2-nitrobenzaldehyde (0.40 g, 1.5 mmol), N-(2-methoxyethyl)methylamine (0.79 mL, 7.3 mmol), sodium iodide (0.44 g, 2.9 mmol), tetrabutylammoniumbromide (24 mg, 0.007 mmol) and potassium carbonate (1.0 g, 7.3 mmol).

$^1$H-NMR (300 MHz, CDCl$_3$) δ 2.04-2.10 (m, 2H), 2.31 (s, 3H), 2.58-2.63 (m, 4H), 3.33 (s, 3H), 3.48 (t, J=5.5 Hz, 2H), 4.01 (s, 3H), 4.24 (d, J=6.6 Hz, 2H), 7.41 (s, 1H), 7.66 (s, 1H), 10.4 (s, 1H). APCI-MS (m/z); 327 [M+H]$^+$

Step 2

In a similar manner to Step 2 of Example 292, (E)-N-(3-{4-[2-(1H-indazol-3-yl)vinyl]-2-methoxy-5-nitrophenoxypropyl)-N-(2-methoxyethyl)methylamine (0.86 g, 100%) was obtained from 5-methoxy-4-{3-[N-(2-methoxyethyl)methylamino]propyloxy}-2-nitrobenzaldehyde (0.47 g, 1.5 mmol) obtained in Step 1, methanol (5.0 mL), (1H-indazol-3-ylmethyl)triphenylphosphonium bromide (0.76 g, 1.6 mmol) and potassium carbonate (0.26 g, 1.9 mmol).

$^1$H-NMR (270 MHz, DMSO-d$_6$) δ 1.84-1.98 (m, 2H), 2.19 (s, 3H), 2.49 (m, 2H), 3.20 (s, 3H), 3.23-3.31 (m, 4H), 4.02 (s, 3H), 4.08-4.13 (m, 2H), 6.98-7.01 (m, 1H), 7.40 (t, J=7.1 Hz, 1H), 7.47-7.67 (m, 4H), 7.94 (d, J=16.5 Hz, 1H), 8.09 (d, J=8.6 Hz, 1H), 13.3 (br, 1H). APCI-MS (m/z); 441 [M+H]$^+$

Step 3

(E)-N-(3-{4-[2-(1H-indazol-3-yl)vinyl]-2-methoxy-5-nitrophenoxypropyl)-N-(2-methoxyethyl)methylamine (0.64 g, 1.5 mmol) obtained in Step 2 was dissolved in ethanol (6.0 mL), and the solution was added with tin (0.36 g, 3.1 mmol) and concentrated hydrochloric acid (3.0 mL) under ice-cooling, followed by stirring at 40° C. for 5 hours. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and evaporated under reduced pressure. In a similar manner to Example 29, Compound 298 (0.15 g, 30%) was obtained by treating the residue with 3-methylthiophene-2-carboxylic acid (0.40 g, 2.9 mmol), thionyl chloride (0.28 mL, 3.8 mmol), DMF (few drops) and triethylamine (0.40 mL, 2.9 mmol), THF (6.0 mL).

$^1$H-NMR (300 MHz, DMSO-d$_6$) δ 1.85 (t, J=6.6 Hz, 2H), 2.16-2.46 (m, 4H), 2.49 (m, 8H), 3.32 (s, 3H), 3.90 (s, 3H), 3.96-4.00 (m, 2H), 6.92 (m, 1H), 7.02-7.08 (m, 2H), 7.34 (t, J=8.1 Hz, 1H), 7.41-7.57 (m, 2H), 7.44 (d, J=16.5 Hz, 1H), 7.52 (d, J=16.5 Hz, 1H), 7.67 (d, J=5.1 Hz, 1H), 8.00 (d, J=8.1 Hz, 1H), 9.71 (br, 1H), 13.1 (br, 1H). APCI-MS (m/z); 535 [M+H]$^+$

EXAMPLE 299

(E)-2-{5-[4-(2-hydroxyethyl)piperazin-1-yl]-2-[2-(1H-indazol-3-yl)vinyl]phenyl}isoindole-1,3-dione (Compound 299)

(E)-2-(4-{3-amino-4-[2-(1H-indazol-3-yl)vinyl]phenyl}piperazin-1-yl)ethanol (0.10 g, 0.28 mmol) obtained in Step 3 of Example 273 was dissolved in p-xylene (3.5 mL) and the solution was added with phthalic anhydride (49 mg, 0.33 mmol), triethylamine (0.02 mL, 0.14 mmol), molecular sieves 3A (0.10 g), followed by stirring at 140° C. for 25 hours. The solution was added with water and extracted with ethyl acetate. The organic layer was washed with saturated brine, dried over anhydrous magnesium sulfate and the solvent was evaporated under reduced pressure. The filtrate was reslurried with ethyl acetate to obtain Compound 299 (4.5 mg, 3%).

$^1$H-NMR (300 MHz, DMSO-$d_6$) δ 2.49-2.72 (m, 6H), 3.22-3.44 (m, 6H), 4.40 (m, 1H), 6.95-7.15 (m, 3H), 7.15-7.25 (m, 2H), 7.25 (d, J=16.4 Hz, 1H), 7.26-7.47 (m, 1H), 7.46 (d, J=16.4 Hz, 1H), 7.65-7.69 (m, 1H), 7.90-8.01 (m, 4H), 13.0 (br, 1H). APCI-MS (m/z); 494 [M+H]$^+$

EXAMPLE 300

(E)-N-{5-[3-(diethylamino)propyloxy]-2-[2-(1H-indazol-3-yl)vinyl]-4-methoxyphenyl}-3-methylthiophene-2-carboxamide (Compound 300)

Step 1

In a similar manner to Step 1 of Example 292, 4-[3-(diethylamino)propyloxy]-5-methoxy-2-nitrobenzaldehyde (0.30 g, 65%) was obtained from 4-(3-chloropropyloxy)-5-methoxy-2-nitrobenzaldehyde (0.40 g, 1.5 mmol), diethylamine (1.5 mL, 15 mmol), sodium iodide (0.44 g, 2.9 mmol), tetrabutylammonium bromide (24 mg, 0.07 mmol) and potassium carbonate (1.0 g, 7.3 mmol).

$^1$H-NMR (300 MHz, CDCl$_3$) δ 1.03-1.09 (m, 8H), 2.03-2.12 (m, 2H), 2.57-2.65 (m, 4H), 4.00 (s, 3H), 4.19-4.26 (m, 2H), 7.41 (s, 1H), 7.63 (s, 1H), 10.4 (s, 1H). APCI-MS (m/z); 311 [M+H]$^+$

Step 2

A solution of 4-[3-(diethylamino)propyloxy]-5-methoxy-2-nitrobenzaldehyde (0.30 g, 0.96 mmol) obtained in Step 1 in methanol (5.0 mL) was added with (1H-indazol-3-ylmethyl)triphenylphosphonium bromide (0.50 g, 1.1 mmol) and potassium carbonate (0.26 g, 1.9 mmol), followed by stirring at room temperature for 2.0 hours. The reaction mixture was added with water and extracted with ethyl acetate. The organic layer was washed with saturated brine, dried over anhydrous magnesium sulfate and the solvent was evaporate under reduced pressure. The filtrate was purified by silica gel column chromatography (ethyl acetate). The product was dissolved in ethanol (2.0 mL), and the solution was added with tin (0.28 g, 2.4 mmol) and concentrated hydrochloric acid (4.0 mL) under ice-cooling, followed by stirring at 40° C. for 4.5 hours. To the reaction mixture under ice-cooling, 6 mol/L sodium hydroxide was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. In a similar manner to Example 29, Compound 300 (46 mg, 49%) was obtained by treating the residue with 3-methylthiophene-2-carboxylic acid (77 mg, 0.54 mmol), thionyl chloride (52 μL, 0.72 mmol), DMF (few drops) and triethylamine (76 μL, 0.54 mmol).

$^1$H-NMR (300 MHz, DMSO-$d_6$) δ 0.90-0.97 (m, 8H), 1.81-1.86 (m, 2H), 2.43-2.50 (m, 4H), 3.32 (s, 3H), 3.91 (s, 3H), 3.99-4.04 (m, 2H), 6.93-7.09 (m, 3H), 7.35 (t, J=7.6 Hz, 1H), 7.44 (d, J=16.5 Hz, 1H), 7.44-7.54 (m, 2H), 7.58 (d, J=16.5 Hz, 1H), 7.68 (d, J=4.8 Hz, 1H), 8.01 (d, J=8.2 Hz, 1H), 9.72 (br, 1H), 13.1 (br, 1H). APCI-MS (m/z); 519 [M+H]$^+$

EXAMPLE 301

(E)-N-{5-[4-(acetylamino)piperidin-1-ylcarbonyl]-2-[2-(1H-indazol-3-yl)vinyl]phenyl}-3-methylthiophene-2-carboxamide (Compound 301)

In a similar manner to Example 28, Compound 301 (0.24 g, 60%) was obtained from Compound 98 (0.30 g, 0.74 mmol), N-(piperidin-4-yl)acetamide (0.20 g, 1.1 mmol), 1-hydroxybenzotriazole monohydrate (0.13 g, 0.97 mmol) and EDC (0.20 g, 1.0 mmol).

$^1$H-NMR (270 MHz, DMSO-$d_6$) δ 1.17-1.32 (m, 4H), 1.80 (s, 3H), 2.52 (s, 3H), 3.14 (br, 2H), 3.82-3.99 (m, 2H), 4.02-4.07 (m, 1H), 7.06 (d, J=4.9 Hz, 1H), 7.10 (d, J=7.7 Hz, 1H), 7.31-7.45 (m, 3H), 7.54-7.61 (m, 2H), 7.66 (d, J=16.6 Hz, 1H), 7.72 (d, J=4.9 Hz, 1H), 7.86 (d, J=7.7 Hz 1H), 8.01-8.06 (m, 2H), 9.97 (br, 1H), 13.2 (br, 1H).

ESI-MS (m/z); 528 [M+H]$^+$

EXAMPLE 302

(E)-(S)—N-{5-[4-(2,3-dihydroxypropyl)piperazin-1-ylmethyl]-2-[2-(1H-indazol-3-yl)vinyl]phenyl}-3-methylthiophene-2-carboxamide (Compound 302)

In a similar manner to Step 2 of Example 224, Compound 302 (44 mg, 11%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and (S)-3-(piperazin-1-yl)propane-1,2-diole (0.39 g, 2.3 mmol).

$^1$H-NMR (270 MHz, DMSO-$d_6$) δ 2.51 (br, 11H), 3.34 (br, 5H), 3.52 (br, 2H), 3.65 (br, 1H), 4.52 (br, 1H), 7.05 (d, J=4.9 Hz, 1H), 7.09 (d, J=8.2 Hz, 1H), 7.25-7.39 (m, 3H), 7.48 (d, J=16.8 Hz, 1H), 7.52-7.55 (m, 1H), 7.61 (d, J=16.6 Hz, 1H), 7.70 (d, J=4.9 Hz, 1H), 7.90 (d, J=8.2 Hz, 1H), 8.00 (d, J=8.2 Hz, 1H), 9.86 (br, 1H), 13.1 (br, 1H).

ESI-MS (m/z); 532 [M+H]$^+$

EXAMPLE 303

(E)-N-{5-[N-(1-acetylpiperidin-4-yl)carbamoyl]-2-[2-(1H-indazol-3-yl)vinyl]phenyl}-3-methylthiophene-2-carboxamide (Compound 303)

In a similar manner to Example 28, Compound 303 (0.24 g, 61%) was obtained from Compound 98 (0.30 g, 0.74 mmol), 1-acetyl-4-aminopiperidine (0.20 g, 1.1 mmol), 1-hydroxybenzotriazole monohydrate (0.13 g, 0.97 mmol) and EDC (0.20 g, 1.0 mmol).

$^1$H-NMR (270 MHz, DMSO-$d_6$) δ 1.43-1.52 (m, 2H), 1.80-1.99 (m, 2H), 2.02 (s, 3H), 2.52 (s, 3H), 2.63-2.72 (m, 1H), 3.10-3.46 (m, 2H), 3.82-3.87 (m, 1H), 4.01-4.07 (m, 1H), 4.35-4.38 (m, 1H), 7.07 (d, J=4.9 Hz, 1H), 7.11 (d, J=7.6 Hz, 1H), 7.37 (dd, J=7.6, 7.6 Hz, 1H), 7.53-7.72 (m, 3H), 7.82-7.87 (m, 2H), 8.04 (dd, J=8.4, 8.4 Hz, 2H), 8.38 (d, J=7.7 Hz, 1H), 9.99 (br, 1H), 13.2 (br, 1H).

ESI-MS (m/z); 528 [M+H]$^+$

EXAMPLE 304

(E)-N-{2-[2-(1H-indazol-3-yl)vinyl]-5-[4-(3-methoxypropyl)piperazin-1-ylmethyl]phenyl}-3-methylthiophene-2-carboxamide (Compound 304)

In a similar manner to Step 2 of Example 224, Compound 304 (85 mg, 18%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and 1-(3-methoxypropyl)piperazine (0.37 g, 2.3 mmol).

$^1$H-NMR (270 MHz, DMSO-d$_6$) δ 1.58-1.68 (m, 2H), 2.28-2.49 (m, 10H), 2.51 (br, 3H), 3.20 (s, 3H), 3.30 (br, 2H), 3.49 (br, 2H), 7.05 (d, J=4.9 Hz, 1H), 7.09 (d, J=8.2 Hz, 1H), 7.24-7.39 (m, 3H), 7.47 (d, J=16.8 Hz, 1H), 7.52-7.55 (m, 1H), 7.60 (d, J=16.8 Hz, 1H), 7.69 (d, J=4.9 Hz, 1H), 7.89 (d, J=8.1 Hz, 1H), 8.00 (d, J=8.1 Hz, 1H), 9.85 (br, 1H), 13.1 (br, 1H).

ESI-MS (m/z); 530 [M+H]$^+$

EXAMPLE 305

(E)-N-{5-[N-(2-hydroxyethyl)methylamino]-2-[2-(1H-indazol-3-yl)vinyl]phenyl}-1-methyl-1H-pyrrole-2-carboxamide (Compound 305)

In a similar manner to Example 29, Compound 305 (56 mg, 84%) was obtained from (E)-2-(N-{3-amino-4-[2-(1H-indazol-3-yl)vinyl]phenyl}methylamino)ethanol (0.05 g, 0.16 mmol) obtained in Step 3 of Example 280, 1-methyl-1H-pyrrole-2-carboxylic acid (0.06 g, 0.48 mmol), thionyl chloride (53 µL, 0.72 mmol), DMF (few drops) and triethylamine (67 µL, 0.48 mmol).

$^1$H-NMR (300 MHz, DMSO-d$_6$) δ 2.98 (s, 3H), 3.42-3.45 (m, 2H), 3.57-3.59 (m, 2H), 3.87 (s, 3H), 4.73 (t, J=4.9 Hz, 1H), 6.13 (t, J=2.6 Hz, 1H), 6.61 (d, J=2.6 Hz, 1H), 6.70 (d, J=9.2 Hz, 1H), 6.98-7.01 (m, 2H), 7.03-7.15 (m, 1H), 7.20 (d, J=16.7 Hz, 1H), 7.32 (t, J=7.7 Hz, 1H), 7.50 (d, J=16.7 Hz, 1H), 7.52 (d, J=9.5 Hz, 1H), 7.74 (d, J=9.2 Hz, 1H), 7.91 (d, J=7.7 Hz, 1H), 9.65 (br, 1H), 12.94 (br, 1H). APCI-MS (m/z); 416 [M+H]$^+$

EXAMPLE 306

(E)-4-amino-2-{5-[4-(3-hydroxypropyl)piperazin-1-ylmethyl]-2-[2-(1H-indazol-3-yl)vinyl]phenyl}isoindole-1,3-dione (Compound 306)

Step 1

To a solution of (E)-4-[2-(1H-indazol-3-yl)vinyl]-3-[(3-methylthiophen-2-ylcarbonyl)amino]benzoic acid methyl ester (6.3 g, 19 mmol) obtained in Example 97 in THF (0.25 L), diisobutylaluminum hydride (0.94 mol/L n-hexane solution, 72 mL, 68 mmol) was added dropwise under nitrogen atomosphere at 0° C., followed by stirring at 0° C. for 1.0 hour and at room temperature for 2.0 hours. The reaction mixture was added with 2-propanol at 0° C. and then added with saturated aqueous potassium sodium tartrate solution. The mixture was extracted with ethyl acetate and the organic layer was concentrated under reduced pressure. The residue was crystallized from methanol to obtain (E)-{4-[2-(1H-indazol-3-yl)vinyl]-3-nitrophenyl}methanol (4.1 g, 72%).

$^1$H-NMR (300 MHz, DMSO-d$_6$) δ 4.62 (d, J=5.1 Hz, 2H), 5.52 (t, J=6.0 Hz, 1H), 7.25 (t, J=8.1 Hz, 1H), 7.42 (t, J=8.1 Hz, 1H), 7.59 (d, J=8.1 Hz, 1H), 7.64 (d, J=16.5 Hz, 1H), 7.69 (d, J=8.1 Hz, 1H), 7.82 (d, J=16.5 Hz, 1H), 7.96 (s, 1H), 8.08 (d, J=3.3 Hz, 1H), 8.10 (d, J=3.3 Hz, 1H), 13.31 (s, 1H).

ESI-MS (m/z); 296 [M+H]$^+$

Step 2

In a similar manner to Steps 1 and 2 of Example 224, a crude product obtained from (E)-{4-[2-(1H-indazol-3-yl)vinyl]-3-nitrophenyl}methanol (0.30 g, 1.0 mmol) obtained in Step 1, carbon tetrabromide (0.98 g, 3.0 mmol), triphenylphosphine (0.80 g, 3.1 mmol) and DMF (6.0 mL), 1-(3-hydroxypropyl)piperazine (0.44 g, 3.1 mmol), triethylamine (0.43 mL, 3.1 mmol) and THF (6.0 mL) which was not isolated but treated with tin (0.41 g, 3.4 mmol), concentrated hydrochloric acid (1.5 mL) and ethanol (9.0 mL) in a similar manner to Example 2 to obtain (E)-3-(4-{3-amino-4-[2-(1H-indazol-3-yl)vinyl]benzyl}piperazin-1-yl)propan-1-ol (0.29 g, 74%).

$^1$H-NMR (300 MHz, DMSO-d$_6$) δ 1.56 (t, J=6.9 Hz, 2H), 2.24-2.45 (br, 8H), 2.49 (t, J=6.9 Hz, 2H), 3.31 (s, 1H), 3.42 (t, J=6.9 Hz, 2H), 5.29 (s, 2H), 6.53 (d, J=7.8 Hz, 1H), 6.67 (s, 1H), 7.17 (t, J=7.2 Hz, 1H), 7.25 (d, J=16.5 Hz, 1H), 7.38 (d, J=7.2 Hz, 1H), 7.44 (d, J=8.1 Hz, 1H), 7.53 (d, J=7.8 Hz, 1H), 7.54 (d, J=16.5 Hz, 1H), 8.21 (d, J=8.1 Hz, 1H), 13.04 (s, 1H).

Step 3

In a similar manner to Example 151, (E)-2-{5-[4-(3-hydroxypropyl)piperazin-1-ylmethyl]-2-[2-(1H-indazol-3-yl)vinyl]phenyl}-4-nitroisoindole-1,3-dione (92 mg, 64%) was obtained from (E)-3-(4-{3-amino-4-[2-(1H-indazol-3-yl)vinyl]benzyl}piperazin-1-yl)propan-1-ol (0.10 g, 0.26 mmol) obtained in Step 2, triethylamine (7.1 µL, 0.051 mmol), 3-nitrophthalic acid anhydride (59 mg, 0.31 mmol) and xylene (2.0 mL).

$^1$H-NMR (300 MHz, DMSO-d$_6$) δ 1.61-1.76 (br, 2H), 2.62-2.84 (br, 2H), 3.21-3.50 (br, 10H), 3.55-3.66 (br, 2H), 7.05 (t, J=6.9 Hz, 1H), 7.27 (d, J=16.5 Hz, 1H), 7.34 (t, J=6.9 Hz, 1H), 7.43 (s, 1H), 7.51 (d, J=8.1 Hz, 1H), 7.60 (d, J=16.5 Hz, 1H), 7.84 (d, J=8.1 Hz, 1H), 8.10 (d, J=7.8 Hz, 1H), 8.17 (t, J=7.8 Hz, 1H), 8.18 (d, J=7.8 Hz, 1H), 8.31 (d, J=6.9 Hz, 1H), 8.40 (d, J=6.9 Hz, 1H), 13.16 (s, 1H).

ESI-MS (m/z); 567 [M+H]$^+$

Step 4

In a similar manner to Example 2, Compound 306 (7.4 mg, 9%) was obtained from (E)-2-{5-[4-(3-hydroxypropyl)piperazin-1-ylmethyl]-2-[2-(1H-indazol-3-yl)vinyl]phenyl}-4-nitroisoindole-1,3-dione (91 mg, 0.16 mmol) obtained in Step 3, tin (76 mg, 0.64 mmol), concentrated hydrochloric acid (0.28 mL) and ethanol (2.3 mL).

$^1$H-NMR (270 MHz, DMSO-d$_6$) δ 1.56 (t, J=6.8 Hz, 2H), 2.30-2.55 (br, 10H), 3.42 (t, J=6.8 Hz, 2H), 3.54 (s, 2H), 6.61 (s, 1H), 7.02 (t, J=7.8 Hz, 1H), 7.07-7.21 (m, 3H), 7.32 (d, J=6.2 Hz, 1H), 7.33 (t, J=7.8 Hz, 1H), 7.47-7.59 (m, 2H), 7.49 (d, J=16.8 Hz, 1H), 7.57 (d, J=16.8 Hz, 1H), 7.73 (d, J=8.4 Hz, 1H), 8.04 (d, J=8.4 Hz, 1H), 9.14 (s, 2H), 13.09 (s, 1H).

ESI-MS (m/z); 537 [M+H]$^+$

EXAMPLE 307

(E)-4-amino-2-{5-[4-(2-hydroxyethyl)piperazin-1-ylmethyl]-2-[2-(1H-indazol-3-yl)vinyl]phenyl}isoindole-1,3-dione (Compound 307)

Step 1

In a similar manner to Steps 1 and 2 of Example 224, a crude product obtained from (E)-{4-[2-(1H-indazol-3-yl)vinyl]-3-nitrophenyl}methanol (0.30 g, 1.0 mmol) obtained in Step 1 of Example 306, carbon tetrabromide (1.0 g, 3.1 mmol), triphenylphosphine (0.80 mg, 3.1 mmol) and DMF (6.0 mL) and 1-(2-hydroxyethyl)piperazine (0.40 mg, 3.1 mmol), triethylamine (0.43 mL, 3.1 mmol) and THF (6.0 mL), which was not isolated but treated with tin (0.17 g, 1.5 mmol), concentrated hydrochloric acid (0.86 mL) and ethanol (10 mL) in a similar manner to Example 2 to obtain (E)-2-(4-{3-amino-4-[2-(1H-indazol-3-yl)vinyl]benzyl}piperazin-1-yl)ethanol (0.26 g, 66%).

$^1$H-NMR (300 MHz, DMSO-$d_6$) δ 2.23-2.55 (br, 8H), 3.49 (t, J=5.4 Hz, 2H), 4.09 (t, J=5.4 Hz, 2H), 4.37 (s, 1H), 5.29 (s, 2H), 6.53 (d, J=8.1 Hz, 1H), 6.67 (s, 1H), 7.18 (t, J=7.2 Hz, 1H), 7.25 (d, J=16.5 Hz, 1H), 7.38 (t, J=7.2 Hz, 1H), 7.44 (d, J=8.1 Hz, 1H), 7.51 (d, J=8.1 Hz, 1H), 7.54 (d, J=16.5 Hz, 1H), 8.21 (d, J=8.1 Hz, 1H), 13.03 (s, 1H).

ESI-MS (m/z); 378 [M+H]$^+$

Step 2

In a similar manner to Example 151, (E)-2-{5-[4-(2-hydroxyethyl)piperazin-1-ylmethyl]-2-[2-(1H-indazol-3-yl)vinyl]phenyl}-4-nitroisoindole-1,3-dione (0.11 g, 54%) was obtained from (E)-2-(4-{3-amino-4-[2-(1H-indazol-3-yl)vinyl]benzyl}piperazin-1-yl)ethanol (0.13 g, 0.35 mmol) obtained in Step 2, triethylamine (9.8 µL, 0.070 mmol), 3-nitrophthalic anhydride (82 mg, 0.42 mmol) and xylene/DMF (4/1, 3.3 mL).

$^1$H-NMR (300 MHz, DMSO-$d_6$) δ 1.06 (t, J=7.0 Hz, 1H), 2.37-2.65 (br, 10H), 3.51 (t, J=7.0 Hz, 2H), 3.55 (s, 2H), 7.05 (t, J=7.8 Hz, 2H), 7.26 (d, J=16.5 Hz, 1H), 7.33 (t, J=8.4 Hz, 1H), 7.42 (s, 1H), 7.46-7.54 (m, 2H), 7.59 (d, J=16.5 Hz, 1H), 7.84 (d, J=8.4 Hz, 1H), 8.07 (d, J=8.4 Hz, 1H), 8.17 (d, J=7.8 Hz, 1H), 8.30 (d, J=7.3 Hz, 1H), 8.39 (d, J=7.8 Hz, 1H), 13.13 (s, 1H).

Step 3

In a similar manner to Step 2 of Example 216, Compound 307 (14 mg, 100%) was obtained from (E)-2-{5-[4-(2-hydroxyethyl)piperazin-1-ylmethyl]-2-[2-(1H-indazol-3-yl)vinyl]phenyl}-4-nitroisoindole-1,3-dione (14 mg, 0.026 mmol) obtained in Step 2, ammonium chloride (7.6 mg, 0.14 mmol), iron (7.2 mg, 0.13 mmol) and ethanol/water (2/1, 0.86 mL).

$^1$H-NMR (270 MHz, DMSO-$d_6$) δ 1.06 (t, J=6.2 Hz, 1H), 2.32-2.60 (br, 10H), 3.42-3.51 (m, 2H), 3.53 (s, 2H), 6.61 (s, 2H), 7.02 (t, J=7.0 Hz, 1H), 7.11 (d, J=7.0 Hz, 1H), 7.16 (d, J=16.8 Hz, 1H), 7.32 (d, J=7.8 Hz, 1H), 7.33 (d, J=16.8 Hz, 1H), 7.44-7.61 (m, 4H), 7.73 (d, J=8.1 Hz, 1H), 8.04 (d, J=7.8 Hz, 1H), 13.12 (s, 1H).

ESI-MS (m/z); 523 [M+H]$^+$

EXAMPLE 308

(E)-{5-[N-(2-hydroxyethyl)-2-(morpholin-4-yl)ethylamino]-2-[2-(1H-indazol-3-yl)vinyl]phenyl}-1-methyl-1H-pyrrole-2-carboxamide (Compound 308)

4-Fluoro-2-nitrobenzaldehyde (0.20 g, 1.2 mmol), 2-[2-(morpholin-4-yl)ethylamino]ethanol (0.95 g, 5.5 mmol) and DMSO (3.0 mL) were added and stirred at 100° C. for 5.0 hours. The reaction mixture was added with water, extracted with hexane/ethyl acetate (4/1) to remove impurities. Next, the mixture was extracted with ethyl acetate. The organic layer was washed with saturated brine, dried over anhydrous magnesium sulfate and the solvent was evaporated under reduced pressure. The residue was purified by silica gel column chromatography (ethyl acetate). The obtained product was dissolved in methanol (3.0 mL) and the solution was added with (1H-indazol-3-ylmethyl)triphenylphosphonium bromide (0.15 g, 0.33 mmol) and potassium carbonate (89 mg, 0.64 mmol), followed by stirring at room temperature for 1.0 hour. The reaction mixture was added with water and extracted with ethyl acetate. The organic layer was washed with water and saturated brine, dried over anhydrous magnesium sulfate and the solvent was evaporated under reduced pressure. The residue was purified by silica gel column chromatography (ethyl acetate). The obtained product was dissolved in ethanol (2.0 mL), and the solution was added with tin (76 mg, 0.63 mmol) and concentrated hydrochloric acid (1.0 mL) under ice-cooling, followed by stirring at 40° C. for 2.5 hours. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with saturated brine, dried over anhydrous magnesium sulfate and the solvent was evaporated under reduced pressure. In a similar manner to Example 29, Compound 308 (35 mg, 1%) was obtained by treating the residue with 1-methyl-1H-pyrrole-2-carboxylic acid (91 mg, 0.73 mmol), thionyl chloride (65 µL, 0.9 mmol), DMF (few drops) and triethylamine (0.10 mL, 0.73 mmol).

$^1$H-NMR (300 MHz, DMSO-$d_6$) δ 2.50 (m, 4H), 3.34-3.59 (m, 12H), 3.88 (s, 3H), 4.94 (m, 1H), 6.13 (m, 1H), 6.60 (m, 1H), 6.68 (d, J=7.9 Hz, 1H), 7.01 (m, 2H), 7.14 (m, 1H), 7.20 (d, J=16.5 Hz, 1H), 7.31 (t, J=6.8 Hz, 1H), 7.50 (t, J=16.5 Hz, 1H), 7.52 (d, J=7.9 Hz, 1H), 7.73 (d, J=9.5 Hz, 1H), 7.92 (d, J=8.1 Hz, 1H), 9.65 (br, 1H), 12.9 (br, 1H). APCI-MS (m/z); 515 [M+H]$^+$

EXAMPLE 309

(E)-4-amino-2-{2-[2-(1H-indazol-3-yl)vinyl]-5-[4-(3-methoxypropyl)piperazin-1-ylcarbonyl]phenyl}isoindole-1,3-dione (Compound 309)

In a similar manner to Example 28, a crude product was obtained from (E)-4-[2-(1H-indazol-3-yl)vinyl]-3-(4-nitro-1,3-dioxo-1,3-dihydroisoindol-2-yl)benzoic acid (0.10 g, 0.22 mmol) obtained in Step 1 of Example 288, 1-(3-methoxypropyl)piperazine (52 mg, 0.33 mmol), 1-hydroxybenzotriazole monohydrate (39 mg, 0.29 mmol) and EDC (59 mg, 0.31 mmol). The product was dissolved in ethanol (2.0 mL), and the solution was added with tin (38 mg, 0.32 mmol) and concentrated hydrochloric acid (1.0 mL) under ice-cooling, followed by stirring at 40° C. for 1 hour. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was purified by preparative thin-layer chromatography (chloroform/methanol=9/1) to obtain Compound 309 (0.01 g, 15%).

$^1$H-NMR (300 MHz, DMSO-$d_6$) δ 1.64-1.69 (m, 2H), 2.32-2.38 (m, 8H), 3.21 (s, 3H), 3.32-3.36 (m, 4H), 6.63 (br, 2H), 7.04 (t, J=8.1 Hz, 1H), 7.09-7.13 (m, 2H), 7.20 (d, J=16.5 Hz, 1H), 7.34 (t, J=8.1 Hz, 1H), 7.50-7.58 (m, 4H), 7.70 (d, J=16.5 Hz, 1H), 7.78 (d, J=8.1 Hz, 1H), 8.16 (d, J=8.2 Hz, 1H), 13.22 (br, 1H). APCI-MS (m/z); 565 [M+H]$^+$

EXAMPLE 310

(E)-4-amino-2-{2-[2-(1H-indazol-3-yl)vinyl]-5-(4-methoxypiperidin-1-ylcarbonyl)phenyl}-2,3-dihydroisoindole-1-one (Compound 310)

In a similar manner to Example 28, a crude product was obtained from (E)-4-[2-(1H-indazol-3-yl)vinyl]-3-(4-nitro-1,3-dioxo-1,3-dihydroisoindol-2-yl)benzoic acid (0.10 g, 0.22 mmol) obtained in Step 1 of Example 288, 4-methoxypiperidine (0.04 mL, 0.33 mmol), 1-hydroxybenzotriazole monohydrate (39 mg, 0.29 mmol) and EDC (59 mg, 0.31 mmol). The product was dissolved in ethanol (2.0 mL), and the solution was added with tin (55 mg, 0.46 mmol) and concentrated hydrochloric acid (1.0 mL) under ice-cooling, followed by stirring at 40° C. for 3 hours. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was purified by preparative thin-layer chromatography (chloroform/methanol=9/1) to obtain Compound 310 (22 mg, 20%).

$^1$H-NMR (300 MHz, DMSO-$d_6$) δ 1.47-1.50 (m, 2H), 1.87 (m, 2H), 3.27 (s, 3H), 3.35-3.95 (m, 4H), 4.68 (s, 2H), 5.52 (br, 2H), 6.87 (d, J=7.9 Hz, 1H), 6.96-7.04 (m, 2H), 7.26 (d, J=16.5 Hz, 1H), 7.26-7.35 (m, 2H), 7.46-7.56 (m, 4H), 7.63 (d, J=16.5 Hz, 1H), 7.73 (d, J=8.4 Hz, 1H), 8.10 (d, J=8.2 Hz, 1H), 13.16 (br, 1H). APCI-MS (m/z); 508 [M+H]$^+$

EXAMPLE 311

(E)-N-{5-[4-(2-hydroxyethyl)piperidin-1-ylmethyl]-2-[2-(1H-indazol-3-yl)vinyl]phenyl}-3-methylthiophene-2-carboxamide (Compound 311)

In a similar manner to Step 2 of Example 224, Compound 311 (73 mg, 20%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and 4-(2-hydroxyethyl)piperidine (0.28 g, 2.3 mmol).

$^1$H-NMR (270 MHz, DMSO-$d_6$) δ 1.36 (br, 2H), 1.91-1.99 (m, 1H), 2.51 (s, 3H), 2.83 (br, 4H), 3.30 (br, 4H), 3.42-3.44 (m, 4H), 4.33 (br, 1H), 7.05 (d, J=4.9 Hz, 1H), 7.10 (d, J=7.9 Hz, 1H), 7.33-7.39 (m, 3H), 7.52-7.34 (m, 3H), 7.70 (d, J=4.9 Hz, 1H), 7.88 (br, 1H), 8.00 (d, J=8.4 Hz, 1H), 9.87 (br, 1H), 13.1 (br, 1H).

ESI-MS (m/z); 501 [M+H]$^+$

EXAMPLE 312

(E)-N-{5-[4-(2-hydroxy-2-methylpropyl) piperazin-1-ylmethyl]-2-[2-(1H-indazol-3-yl)vinyl]phenyl}-3-methylthiophene-2-carboxamide (Compound 312)

In a similar manner to Step 2 of Example 224, Compound 312 (35 mg, 9%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and 2-methyl-1-(piperazin-1-yl)propan-2-ol (0.36 g, 2.3 mmol).

$^1$H-NMR (270 MHz, DMSO-$d_6$) δ 1.07 (s, 6H), 2.14-2.20 (m, 4H), 2.42-2.49 (m, 4H), 2.51 (s, 3H), 3.06-3.10 (m, 2H), 3.48 (br, 2H), 4.03 (br, 1H), 7.05 (d, J=4.9 Hz, 1H), 7.09 (d, J=7.6 Hz, 1H), 7.24-7.39 (m, 3H), 7.47 (d, J=16.8 Hz, 1H), 7.51-7.55 (m, 1H), 7.60 (d, J=16.8 Hz, 1H), 7.70 (d, J=4.9 Hz, 1H), 7.89 (d, J=8.4 Hz, 1H), 8.00 (d, J=8.4 Hz, 1H), 9.85 (br, 1H), 13.1 (br, 1H).

ESI-MS (m/z); 530 [M+H]$^+$

EXAMPLE 313

(E)-{2-[2-(1H-indazol-3-yl)vinyl]-5-[4-(3-oxobutyl) piperazin-1-ylmethyl]phenyl}-3-methylthiophene-2-carboxamide (Compound 313)

Compound 242 (35 mg, 0.077 mmol) was dissolved in a mixed solvent of ethyl acetate (5.0 mL) and THF (1.0 mL) and the solution was added with methyl vinyl ketone (0.020 mL, 0.24 mmol), followed by stirring at room temperature for 1 hour. The reaction mixture was concentrated and purified by silica gel column chromatography (chloroform to methanol/chloroform=1/3) to obtain Compound 313 (33 mg, 82%).

$^1$H-NMR (300 MHz, DMSO-$d_6$) δ 2.09 (s, 3H), 2.30-2.60 (m, 10H), 2.51 (s, 3H), 3.31 (s, 2H), 3.48 (s, 2H), 7.05 (d, J=5.1 Hz, 1H), 7.09 (d, J=8.1 Hz, 1H), 7.27 (t, J=8.4 Hz, 1H), 7.31 (s, 1H), 7.36 (t, J=8.4 Hz, 1H), 7.48 (d, J=16.6 Hz, 1H), 7.53 (d, J=8.4 Hz, 1H), 7.60 (d, J=16.6 Hz, 1H), 7.70 (d, J=5.1 Hz, 1H), 7.89 (d, J=8.1 Hz, 1H), 8.01 (d, J=8.4 Hz, 1H), 9.86 (s, 1H), 13.1 (br, 1H).

ESI-MS (m/z); 528 [M+H]$^+$

EXAMPLE 314

(E)-4-amino-2-{5-[4-(3-hydroxypropyl)piperazin-1-ylmethyl]-2-[2-(1H-indazol-3-yl)vinyl]phenyl}-2,3-dihydroisoindole-1-one (Compound 314)

Step 1

In a similar manner to Step 1 of Example 216, (E)-2-{5-[4-(3-hydroxypropyl)piperazin-1-ylmethyl]-2-[2-(1H-indazol-3-yl)vinyl]phenyl}-4-nitro-2,3-dihydroisoindole-1-one (45 mg) was obtained from (E)-3-(4-{3-amino-4-[2-(1H-indazol-3-yl)vinyl]benzyl}piperazin-1-yl)propan-1-ol (77 mg, 0.20 mmol) obtained in Step 2 of Example 306, triethylamine (68 μL, 0.49 mmol), 2-bromomethyl-3-nitrobenzoic acid methyl ester (59 mg, 0.22 mmol) and DMF (1.5 mL).

ESI-MS (m/z); 553 [M+H]$^+$

Step 2

In a similar manner to Step 2 of Example 216, Compound 314 (10 mg, 10%) was obtained from (E)-2-{5-[4-(3-hydroxypropyl)piperazin-1-ylmethyl]-2-[2-(1H-indazol-3-yl)vinyl]phenyl}-4-nitro-2,3-dihydroisoindole-1-one (44 mg) obtained in Step 1, ammonium chloride (23 mg, 0.44 mmol), iron (22 mg, 0.40 mmol) and ethanol/water (2/1, 2.6 mL).

¹H-NMR (270 MHz, DMSO-d₆) δ 1.06 (t, J=6.9 Hz, 1H), 1.56 (t, J=6.9 Hz, 2H), 2.32 (t, J=6.9 Hz, 2H), 2.32-2.48 (br, 8H), 3.43 (t, J=6.9 Hz, 2H), 3.52 (s, 2H), 4.64 (s, 2H), 5.51 (s, 2H), 6.87 (d, J=7.8 Hz, 1H), 6.96 (t, J=7.2 Hz, 1H), 7.02 (d, J=7.2 Hz, 1H), 7.22 (d, J=16.5 Hz, 1H), 7.29 (t, J=7.8 Hz, 1H), 7.32 (t, J=7.8 Hz, 1H), 7.38 (s, 1H), 7.40 (d, J=7.8 Hz, 1H), 7.50 (d, J=7.2 Hz, 1H), 7.53 (d, J=16.5 Hz, 1H), 7.69 (d, J=8.1 Hz, 1H), 7.99 (d, J=8.1 Hz, 1H), 13.09 (s, 1H).
ESI-MS (m/z); 523 [M+H]⁺

EXAMPLE 315

(E)-4-amino-2-{2-[2-(1H-indazol-3-yl)vinyl]-5-(4-methylpiperazin-1-ylcarbonyl)phenyl}isoindole-1,3-dione (Compound 315)

In a similar manner to Example 28, a crude product was obtained from (E)-4-[2-(1H-indazol-3-yl)vinyl]-3-(4-nitro-1,3-dioxo-1,3-dihydroisoindol-2-yl)benzoic acid (0.60 g, 1.3 mmol) obtained in Step 1 of Example 288, 1-methylpiperazine (0.22 mL, 2.0 mmol), 1-hydroxybenzotriazole monohydrate (0.23 g, 1.7 mmol) and EDC (0.35 g, 1.8 mmol). The product was dissolved in ethyl acetate (8.0 mL), and the solution was added with tin(II) chloride dehydrate (0.9 g, 4.2 mmol) under ice-cooling, followed by stirring at room temperature for 9.0 hours. The reaction mixture was filtered, added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was purified by silica gel column chromatography (chloroform/methanol=9/1 to 4/1) to obtain Compound 315 (0.12 g, 18%).
¹H-NMR (300 MHz, DMSO-d₆) δ 2.21 (s, 3H), 2.27-2.35 (m, 4H), 2.50-3.63 (m, 4H), 6.62 (br, 2H), 7.05 (t, J=7.7 Hz, 1H), 7.09-7.13 (m, 2H), 7.20 (d, J=16.7 Hz, 1H), 7.34 (d, J=7.7 Hz, 1H), 7.50-7.58 (m, 4H), 7.70 (d, J=16.7 Hz, 1H), 7.78 (d, J=8.1 Hz, 1H), 8.17 (d, J=8.1 Hz, 1H), 13.20 (br, 1H).
APCI-MS (m/z); 507 [M+H]⁺

EXAMPLE 316

(E)-7-amino-2-{2-[2-(1H-indazol-3-yl)vinyl]-5-(4-methylpiperazin-1-ylcarbonyl)phenyl}-2,3-dihydroisoindole-1-one (Compound 316)

In a similar manner to Example 28, a crude product was obtained from 4-[2-(1H-indazol-3-yl)vinyl]-3-(4-nitro-1,3-dioxo-1,3-dihydroisoindol-2-yl)benzoic acid (0.20 g, 0.44 mmol) obtained in Step 1 of Example 288, 1-methylpiperazine (72 μL, 0.66 mmol), 1-hydroxybenzotriazole monohydrate (78 mg, 0.57 mmol) and EDC (0.12 g, 0.62 mmol). The product was dissolved in ethanol (1.0 mL), and the solution was added with tin (43 mg, 0.36 mmol) and concentrated hydrochloric acid (0.50 mL) under ice-cooling, followed by stirring at 40° C. for 1.5 hours. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was purified by preparative thin-layer chromatography (chloroform/methanol=9/1) to obtain Compound 316 (3.1 mg, 5%).
¹H-NMR (300 MHz, DMSO-d₆) δ 2.21 (s, 3H), 2.35-2.50 (m, 4H), 3.33-3.61 (m, 4H), 5.34 (s, 2H), 6.21 (br, 2H), 6.92 (d, J=7.9 Hz, 1H), 6.95-7.00 (m, 2H), 7.29-7.35 (m, 3H), 7.46-7.52 (m, 3H), 7.61 (d, J=16.7 Hz, 1H), 7.77 (d, J=8.1 Hz, 1H), 8.11 (d, J=8.4 Hz, 1H), 13.14 (br, 1H).
APCI-MS (m/z); 493 [M+H]⁺

EXAMPLE 317

(E)-4-amino-2-{2-[2-(1H-indazol-3-yl)vinyl]-5-[4-(morpholin-4-yl)piperidin-1-ylcarbonyl]phenyl}isoindole-1, 3-dione (Compound 317)

In a similar manner to Example 28, a crude product was obtained from 4-[2-(1H-indazol-3-yl)vinyl]-3-(4-nitro-1,3-dioxo-1,3-dihydroisoindol-2-yl)benzoic acid (0.10 g, 0.22 mmol) obtained in Step 1 of Example 288, 4-(piperidin-4-yl)morpholine (56 mg, 0.33 mmol), 1-hydroxybenzotriazole monohydrate (39 mg, 0.29 mmol) and EDC (59 mg, 0.31 mmol). The product was dissolved in ethanol (2.0 mL), and the solution was added with tin (55 mg, 0.46 mmol) and concentrated hydrochloric acid (1.0 mL) under ice-cooling, followed by stirring at 40° C. for 1.5 hours. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was purified by preparative thin-layer chromatography (chloroform/methanol=9/1) to obtain Compound 317 (3.0 mg, 2%).
¹H-NMR (300 MHz, DMSO-d₆) δ 1.33 (m, 4H), 1.79 (m, 4H), 3.30-3.33 (m, 4H), 3.56 (m, 4H), 6.62 (br, 2H), 7.05 (d, J=7.3 Hz, 1H), 7.08-7.13 (m, 3H), 7.20 (d, J=16.5 Hz, 1H), 7.34 (t, J=7.3 Hz, 1H), 7.50-7.58 (m, 4H), 7.68 (d, J=16.5 Hz, 1H), 7.77 (d, J=7.9 Hz, 1H), 8.16 (d, J=8.1 Hz, 1H), 13.21 (br, 1H).
APCI-MS (m/z); 577 [M+H]⁺

EXAMPLE 318

(E)-N-{5-{4-[2-(2-hydroxyethoxy)ethyl]piperazin-1-ylmethyl}-2-[2-(1H-indazol-3-yl)vinyl]-phenyl}-3-methylthiophene-2-carboxamide (Compound 318)

In a similar manner to Step 2 of Example 224, Compound 318 (24 mg, 6%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and 1-[2-(2-hydroxyethoxy)ethyl]piperazine (0.40 g, 2.3 mmol).
¹H-NMR (270 MHz, DMSO-d₆) δ 2.44-2.49 (m, 8H), 2.51 (s, 3H), 3.37-3.41 (m, 2H), 3.46-3.52 (m, 8H), 4.01-4.04 (m, 1H), 7.05 (d, J=4.9 Hz, 1H), 7.09 (d, J=7.4 Hz, 1H), 7.24-7.39 (m, 3H), 7.47 (d, J=16.8 Hz, 1H), 7.53 (d, J=8.1 Hz, 1H), 7.60 (d, J=16.8 Hz, 1H), 7.69 (d, J=4.9 Hz, 1H), 7.89 (d, J=8.1 Hz, 1H), 8.00 (d, J=8.1 Hz, 1H), 9.85 (br, 1H), 13.1 (br, 1H).
ESI-MS (m/z); 546 [M+H]⁺

EXAMPLE 319

(E)-N-{2-[2-(1H-indazol-3-yl)vinyl]-5-{4-[2-(morpholin-4-yl)ethyl]piperazine]-1-ylmethyl}phenyl}-3-methylthiophene-2-carboxamide (Compound 319)

In a similar manner to Step 2 of Example 224, Compound 319 (24 mg, 5%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and 4-[2-(piperazin-1-yl)ethyl]morpholine (0.46 g, 2.3 mmol).

$^1$H-NMR (270 MHz, DMSO-$d_6$) δ 2.34-2.49 (m, 18H), 2.51 (s, 3H), 3.48-3.56 (m, 4H), 7.05 (d, J=4.9 Hz, 1H), 7.09 (d, J=7.2 Hz, 1H), 7.24-7.39 (m, 3H), 7.47 (d, J=16.8 Hz, 1H), 7.53 (d, J=8.1 Hz, 1H), 7.60 (d, J=16.8 Hz, 1H), 7.70 (d, J=4.9 Hz, 1H), 7.89 (d, J=8.1 Hz, 1H), 8.00 (d, J=8.1 Hz, 1H), 9.85 (br, 1H), 13.1 (br, 1H).

ESI-MS (m/z); 571 [M+H]$^+$

EXAMPLE 320

(E)-{2-[2-(1H-indazol-3-yl)vinyl]-5-(N-methoxy N-methylcarbamoyl)phenyl}-3-methyl-2-carboxamide (Compound 320)

In a similar manner to Example 1, Compound 320 (24 mg, 17%) was obtained from Compound 98 (0.13 g, 0.32 mmol), EDC (79 mg, 0.41 mmol), 1-hydroxybenzotriazole monohydrate (56 mg, 0.41 mmol), triethylamine (0.088 mL, 0.63 mmol), N,O-dimethylamine hydrochloride (37 mg, 0.38 mmol) and DMF (2.0 mL).

$^1$H-NMR (270 MHz, DMSO-$d_6$) δ 2.50 (s, 3H), 3.28 (s, 3H), 3.61 (s, 3H), 7.05 (d, J=5.1 Hz, 1H), 7.10 (t, J=8.4 Hz, 1H), 7.37 (t, J=8.4 Hz, 1H), 7.53-7.68 (m, 5H), 7.70 (d, J=5.1 Hz, 1H), 8.02 (d, J=8.4 Hz, 1H), 8.03 (d, J=8.1 Hz, 1H), 9.97 (s, 1H), 13.2 (br, 1H).

ESI-MS (m/z); 447 [M+H]$^+$

EXAMPLE 321

(E)-4-amino-2-{5-[4-(3-methoxypropyl)piperazin-1-ylmethyl]-2-[2-(1H-indazol-3-yl)vinyl]phenyl}-2,3-dihydroisoindole-1-one (Compound 321)

Step 1

In a similar manner to Step 1 of Example 224, bromide was obtained from (E)-{4-[2-(1H-indazol-3-yl)vinyl]-3-nitrophenyl}methanol (0.30 g, 1.0 mmol) obtained in Step 1 of Example 306, carbon tetrabromide (1.0 g, 3.1 mmol) and triphenylphosphine (0.80 mg, 3.1 mmol). Further, in a similar manner to Step 2 of Example 224, a crude product was obtained from DMF (6.0 mL) and 1-(3-methoxypropyl)piperazine (0.48 g, 3.1 mmol), triethylamine (0.43 mL, 3.1 mmol) and THF (6.0 mL), and the product was used for next step without isolation. In a similar manner to Example 2, the crude product was treated with tin (0.39 g, 3.3 mmol), concentrated hydrochloric acid (1.4 mL) and ethanol (8.9 mL), to obtain (E)-2-[2-(1H-indazol-3-yl)vinyl]-5-[4-(3-methoxypropyl)piperazin-1-ylmethyl]phenylamine (0.34 g, 81%).

$^1$H-NMR (270 MHz, DMSO-$d_6$) δ 1.63 (t, J=6.9 Hz, 2H), 2.24-2.43 (br, 10H), 2.29 (t, J=6.9 Hz, 2H), 3.31 (s, 3H), 3.34 (s, 2H), 5.28 (s, 2H), 6.53 (d, J=8.1 Hz, 1H), 6.66 (s, 1H), 7.17 (t, J=7.3 Hz, 1H), 7.25 (d, J=16.3 Hz, 1H), 7.37 (t, J=7.3 Hz, 1H), 7.44 (d, J=8.1 Hz, 1H), 7.52 (d, J=7.3 Hz, 1H), 7.55 (d, J=16.3 Hz, 1H), 8.20 (d, J=7.3 Hz, 1H), 13.03 (s, 1H).

ESI-MS (m/z); 406 [M+H]$^+$

Step 2

In a similar manner to Example 151, (E)-2-{2-[2-(1H-indazol-3-yl)vinyl]-5-[4-(3-methoxypropyl)piperazin-1-ylmethyl]phenyl}-4-nitroisoindole-1,3-dione (0.13 g, 41%) was obtained from (E)-2-[2-(1H-indazol-3-yl)vinyl]-5-[4-(3-methoxypropyl)piperazin-1-ylmethyl]phenylamine (0.23 g, 0.56 mmol) obtained in Step 1, triethylamine (16 μL, 0.11 mmol), 3-nitrophthalic anhydride (0.13 g, 0.67 mmol) and xylene/DMF (4/1, 5.7 mL).

$^1$H-NMR (270 MHz, DMSO-$d_6$) δ 1.71-1.86 (br, 2H), 3.13-3.57 (br, 10H), 3.17 (s, 2H), 3.22 (s, 3H), 3.36 (t, J=6.2 Hz, 2H), (s, 2H), 7.05 (t, J=7.6 Hz, 1H), 7.27 (d, J=16.5 Hz, 1H), 7.34 (t, J=7.6 Hz, 1H), 7.43 (s, 1H), 7.51 (d, J=8.1 Hz, 1H), 7.61 (d, J=16.5 Hz, 1H), 7.84 (d, J=8.1 Hz, 1H), 8.10 (d, J=7.8 Hz, 1H), 8.12 (t, J=7.8 Hz, 1H), (d, J=7.6 Hz, 1H), 8.31 (d, J=7.6 Hz, 1H), 8.40 (d, J=7.8 Hz, 1H), 13.15 (s, 1H).

ESI-MS (m/z); 581 [M+H]$^+$

Step 3

In a similar manner to Step 2 of Example 216, Compound 321 (43 mg, 36%) was obtained from (E)-2-{2-[2-(1H-indazol-3-yl)vinyl]-5-[4-(3-methoxypropyl)piperazin-1-ylmethyl]phenyl}-4-nitroisoindole-1,3-dione (0.13 g, 0.22 mmol) obtained in Step 2, ammonium chloride (63 mg, 1.2 mmol), iron (60 mg, 1.1 mmol) and ethanol/water (2/1, 7.5 mL).

$^1$H-NMR (300 MHz, DMSO-$d_6$) δ 1.63 (t, J=6.9 Hz, 2H), 2.24-2.56 (br, 8H), 2.29 (t, J=6.9 Hz, 2H), 3.20 (s, 3H), 3.38-3.50 (m, 2H), 3.53 (s, 2H), 6.61 (s, 2H), 7.02 (t, J=7.2 Hz, 1H), 7.07-7.13 (m, 2H), 7.16 (d, J=16.8 Hz, 1H), 7.31 (s, 1H), 7.33 (t, J=7.2 Hz, 1H), 7.43-7.61 (m, 4H), 7.73 (d, J=9.0 Hz, 1H), 8.05 (d, J=8.4 Hz, 1H), 13.12 (s, 1H).

ESI-MS (m/z); 551 [M+H]$^+$

EXAMPLE 322

(E)-N-{5-[4-(3-hydroxy-3-methylbutyl)piperidin-1-ylmethyl]-2-[2-(1H-indazol-3-yl)vinyl]phenyl}-3-methylthiophene-2-carboxamide (Compound 322)

In a similar manner to Step 2 of Example 224, Compound 322 (25 mg, 6%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol), 2-methyl-4-piperazin-1-ylbutan-2-ol (0.40 g, 2.3 mmol).

$^1$H-NMR (270 MHz, DMSO-$d_6$) δ 1.08 (s, 6H), 1.48-1.53 (m, 2H), 2.48-2.50 (m, 8H), 2.51 (s, 3H), 3.32 (br, 2H), 3.48 (br, 2H), 4.70 (br, 1H), 7.05 (d, J=4.9 Hz, 1H), 7.09 (d, J=7.2 Hz, 1H), 7.24-7.39 (m, 3H), 7.47 (d, J=16.8 Hz, 1H), 7.53 (d, J=8.2 Hz, 1H), 7.60 (d, J=16.8 Hz, 1H), 7.69 (d, J=4.9 Hz, 1H), 7.89 (d, J=8.2 Hz, 1H), 8.00 (d, J=8.2 Hz, 1H), 9.85 (br, 1H), 13.1 (br, 1H).

ESI-MS (m/z); 544 [M+H]$^+$

EXAMPLE 323

(E)-4-amino-2-{2-[2-(1H-indazol-3-yl)vinyl]-5-[4-(3-methoxypropyl)piperazin-1-ylmethyl]phenyl}-2,3-dihydroisoindol-1-one (Compound 323)

In a similar manner to Step 1 of Example 216, a crude product was obtained from (E)-2-[2-(1H-indazol-3-yl)vinyl]-5-[4-(3-methoxypropyl)piperazin-1-ylmethyl]phenylamine (0.11 g, 0.28 mmol) obtained in Step 1 of Example 321, triethylamine (97 μL, 0.70 mmol), 2-bromomethyl-3-nitrobenzoic acid methyl ester (84 mg, 0.31 mmol) and DMF (2.3 mL). The product was treated by ammonium chloride (63 mg, 1.2 mmol), iron (60 mg, 1.1 mmol) and ethanol/water (2/1, 7.5 mL) in a similar manner to Step 2 of Example 216, to obtain Compound 323 (43 mg, 36%).

$^1$H-NMR (300 MHz, DMSO-$d_6$) δ 1.63 (t, J=7.2 Hz, 2H), 2.30 (t, J=7.2 Hz, 2H), 2.33-2.47 (m, 4H), 3.20 (s, 3H), 3.27-3.44 (br, 6H), 3.52 (s, 2H), 4.64 (s, 2H), 5.51 (s, 2H), 6.87 (d, J=7.5 Hz, 1H), 6.96 (t, J=7.8 Hz, 1H), 7.02 (d, J=7.5 Hz, 1H), 7.22 (d, J=16.8 Hz, 1H), 7.28 (t, J=7.5 Hz, 1H), 7.31 (t, J=7.8 Hz, 1H), 7.38 (s, 1H), 7.39 (d, J=7.8 Hz, 1H), 7.49 (d, J=7.8 Hz, 1H), 7.53 (d, J=16.8 Hz, 1H), 7.69 (d, J=7.8 Hz, 1H), 8.00 (d, J=7.8 Hz, 1H), 13.09 (s, 1H).

ESI-MS (m/z); 537 [M+H]$^+$

EXAMPLE 324

(E)-4-amino-2-{2-[2-(1H-indazol-3-yl)vinyl]-5-(morpholin-4-ylcarbonyl)phenyl}-2,3-dihydroisoindole-1-one (Compound 324)

Step 1

In a similar manner to Example 28, (E)-4-{3-amino-4-[2-(1H-indazol-3-yl)vinyl]benzoyl}morpholine (34 mg, 9%) was obtained from (E)-3-amino-4-[2-(1H-indazol-3-yl)vinyl]benzoic acid (0.30 g, 1.07 mmol) obtained in Step 2 of Example 276, morpholine (0.11 mL, 1.3 mmol), 1-hydroxybenzotriazole monohydrate (33 mg, 0.21 mmol), EDC (0.25 g, 1.3 mmol) and a mixed solvent of THF/DMF (5/1, 5.4 mL).

$^1$H-NMR (270 MHz, DMSO-d$_6$) δ 3.25-3.68 (br, 8H), 5.53 (s, 2H), 6.60 (d, J=7.8 Hz, 1H), 6.74 (s, 1H), 7.19 (t, J=7.0 Hz, 1H), 7.35 (d, J=17.0 Hz, 1H), 7.38 (t, J=7.0 Hz, 1H), 7.51-7.62 (m, 3H), 8.22 (d, J=8.4 Hz, 1H), 13.11 (s, 1H).

ESI-MS (m/z); 349 [M+H]$^+$

Step 2

In a similar manner to Step 1 of Example 216, a crude product was obtained from (E)-4-{3-amino-4-[2-(1H-indazol-3-yl)vinyl]benzoyl}morpholine (32 mg, 0.092 mmol) obtained in Step 1, triethylamine (32 μL, 0.23 mmol), 2-bromomethyl-3-nitrobenzoic acid methyl ester (28 mg, 0.28 mmol) and DMF (0.64 mL). The product was treated with ammonium chloride (39 mg, 0.73 mmol), iron (37 mg, 0.66 mmol) and a mixed solvent of ethanol/water (2/1, 4.0 mL), in a similar manner to Step 2 of Example 216, to obtain Compound 324 (17 mg, 39%).

$^1$H-NMR (300 MHz, DMSO-d$_6$) δ 3.22-3.73 (br, 8H), 4.68 (s, 2H), 5.53 (s, 2H), 6.87 (d, J=7.8 Hz, 1H), 6.98 (t, J=7.5 Hz, 1H), 7.03 (d, J=7.5 Hz, 1H), 7.25 (d, J=16.5 Hz, 1H), 7.29 (t, J=7.5 Hz, 1H), 7.32 (t, J=7.5 Hz, 1H), 7.51 (d, J=8.4 Hz, 2H), 7.58 (s, 1H), 7.65 (d, J=16.5 Hz, 1H), 7.73 (d, J=8.7 Hz, 1H), 8.13 (d, J=8.7 Hz, 1H), 13.18 (s, 1H).

ESI-MS (m/z); 480 [M+H]$^+$

EXAMPLE 325

(E)-4-amino-2-{2-[(2-(1H-indazol-3-yl)vinyl]-5-(4-methoxypiperidin-1-ylcarbonyl)phenyl}isoindole-1,3-dione (Compound 325)

In a similar manner to Example 28, a crude product (0.02 mg, 0.036 mmol) was obtained from 4-methoxypiperidine (0.24 mL, 2.0 mmol), 4-[2-(1H-indazol-3-yl)vinyl]-3-(4-nitro-1,3-dioxo-1,3-dihydroisoindol-2-yl)benzoic acid (0.30 g, 0.66 mmol) obtained in Step 1 of Example 288, 1-hydroxybenzotriazole monohydrate (230 mg, 1.7 mmol) and EDC (350 mg, 1.9 mmol). The product was dissolved in DMF (2.0 mL) and the solution was added with sodium hydrosulfite (0.2 g, 1.2 mmol), followed by stirring at 50° C. for 5.0 hours. The reaction mixture was added with water and extracted with ethyl acetate. The organic layer was washed with water and saturated brine, dried over anhydrous magnesium sulfate and the solvent was evaporated under reduced pressure. The residue was purified by preparative thin-layer chromatography (chloroform/methanol=9/1) to obtain Compound 325 (15 mg, 58%).

$^1$H-NMR (300 MHz, CDCl$_3$) δ 1.46-1.49 (m, 4H), 1.86-1.99 (m, 4H), 3.27 (s, 3H), 3.32-3.35 (m, 1H), 6.62 (br, 2H), 7.05 (t, J=7.1 Hz, 1H), 7.11 (dd, J=3.3, 6.6 Hz, 1H), 7.21 (d, J=16.7 Hz, 1H), 7.34 (t, J=7.1 Hz, 1H), 7.44 (dd, J=3.3, 6.6 Hz, 1H), 7.50-7.58 (m, 3H), 7.69 (d, J=16.7 Hz, 1H), 7.78 (d, J=8.2 Hz, 1H), 7.90 (dd, J=3.3, 6.6 Hz, 1H), 8.17 (d, J=8.1 Hz, 1H), 13.2 (br, 1H).

APCI-MS (m/z); 522 [M+H]$^+$

EXAMPLE 326

(E)-3-(4-amino-1,3-dioxo-1,3-dihydroisoindol-2-yl)-4-[2-(1H-indazol-3-yl)vinyl]-N,N-dimethylbenzamide (Compound 326)

In a similar manner to Example 28, a crude product was obtained from dimethylamine (160 mg, 2.0 mmol), 4-[2-(1H-indazol-3-yl)vinyl]-3-(4-nitro-1,3-dioxo-1,3-dihydroisoindol-2-yl)benzoic acid (0.30 g, 0.66 mmol) obtained in Step 1 of Example 288, 1-hydroxybenzotriazole monohydrate (230 mg, 1.7 mmol) and EDC (350 mg, 1.9 mmol). The product was dissolved in ethyl acetate (1.0 mL), and the solution was added with tin(II) chloride (47 mg, 0.21 mmol) under ice-cooling, followed by stirring at room temperature for 5.0 hours. Then, the reaction mixture was filtered through Celite. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. The residue was purified by preparative thin-layer chromatography (chloroform/methanol=9/1) to obtain Compound 326 (15 mg, 82%).

$^1$H-NMR (300 MHz, CDCl$_3$) δ 2.89 (s, 3H), 2.96 (s, 3H), 5.36 (br, 2H), 6.94 (d, J=8.1 Hz, 1H), 7.09 (t, J=7.4 Hz, 1H), 7.28 (m, 1H), 7.34 (d, J=8.9 Hz, 1H), 7.38 (m, 2H), 7.43-7.52 (m, 2H), 7.60 (d, J=6.9 Hz, 1H), 7.74 (d, J=8.3 Hz, 1H), 7.96 (d, J=8.1 Hz, 1H), 8.02 (s, 1H).

APCI-MS (m/z); 452 [M+H]$^+$

EXAMPLE 327

(E)-N-{5-[N-(2-hydroxyethyl)-N-methylcarbamoyl]-2-[2-(1H-indazol-3-yl)vinyl]phenyl}-3-methylthiophene-2-carboxamide (Compound 327)

In a similar manner to Example 28, Compound 327 (0.12 g, 35%) was obtained from Compound 98 (0.30 g, 0.74 mmol), 2-(methylamino)ethanol (90 mg, 1.1 mmol), 1-hydroxybenzotriazole monohydrate (0.13 g, 0.97 mmol) and EDC (0.20 g, 1.0 mmol).

$^1$H-NMR (270 MHz, DMSO-d$_6$) δ 2.52 (s, 3H), 3.02 (s, 3H), 3.38-3.63 (m, 4H), 4.82 (t, J=5.6 Hz, 1H), 7.06 (d, J=4.9 Hz, 1H), 7.12 (d, J=7.1 Hz, 1H), 7.35-7.46 (m, 3H), 7.53-7.60 (m, 2H), 7.65 (d, J=16.6 Hz, 1H), 7.71 (d, J=4.9 Hz, 1H), 7.98-8.05 (m, 2H), 9.95 (br, 1H), 13.2 (br, 1H).

ESI-MS (m/z); 461 [M+H]$^+$

EXAMPLE 328

(E)-N-{2-[2-(1H-indazol-3-yl)vinyl]-5-[N-methyl-N-(1-methylpiperidin-4-yl)carbamoyl]phenyl}-3-methylthiophene-2-carboxamide (Compound 328)

In a similar manner to Example 28, Compound 328 (0.23 g, 60%) was obtained from Compound 98 (0.30 g, 0.74 mmol), N-(1-methylpiperidin-4-yl)methylamine (0.16 g, 1.1 mmol), 1-hydroxybenzotriazole monohydrate (0.13 g, 0.97 mmol) and EDC (0.20 g, 1.0 mmol).

$^1$H-NMR (270 MHz, DMSO-d$_6$) δ 1.59-2.13 (m, 8H), 2.52 (s, 3H), 2.86 (br, 4H), 3.32 (s, 3H), 7.06 (d, J=4.9 Hz, 1H), 7.11 (d, J=7.7 Hz, 1H), 7.31-7.48 (m, 3H), 7.53-7.61 (m, 2H), 7.66 (d, J=16.8 Hz, 1H), 7.71 (d, J=4.9 Hz, 1H), 8.00 (d, J=8.2 Hz, 1H), 8.05 (d, J=8.2 Hz, 1H), 9.96 (br, 1H), 13.2 (br, 1H).

ESI-MS (m/z); 514 [M+H]$^+$

EXAMPLE 329

(E)-N-{2-[2-(1H-indazol-3-yl)vinyl]-5-(4-methyl-3-oxopiperazine-1-ylmethyl)phenyl}-3-methylthiophene-2-carboxamide (Compound 329)

In a similar manner to Step 2 of Example 224, Compound 329 (25 mg, 7%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and 1-methylpiperazin-2-one (0.35 g, 2.3 mmol).

$^1$H-NMR (270 MHz, DMSO-d$_6$) δ 2.51 (s, 3H), 2.67-2.71 (m, 2H), 2.83 (s, 3H), 2.99 (s, 2H), 3.27-3.29 (m, 2H), 3.58 (s, 2H), 7.05 (d, J=4.9 Hz, 1H), 7.10 (d, J=7.7 Hz, 1H), 7.27-7.39 (m, 3H), 7.46-7.55 (m, 2H), 7.61 (d, J=16.6 Hz, 1H), 7.70 (d, J=4.9 Hz, 1H), 7.91 (d, J=8.1 Hz, 1H), 8.01 (d, J=7.9 Hz, 1H), 9.86 (br, 1H), 13.1 (br, 1H).

ESI-MS (m/z); 486 [M+H]$^+$

EXAMPLE 330

(R)-(E)-N-{5-(3-hydroxypyrrolidin-1-ylmethyl)-2-[2-(1H-indazol-3-yl)vinyl]phenyl}-3-methylthiophene-2-carboxamide (Compound 330)

In a similar manner to Step 2 of Example 224, Compound 330 (77 mg, 22%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and (R)-(−)-3-pyrrolidinole hydrochloride (1.1 g, 8.3 mmol).

$^1$H-NMR (270 MHz, DMSO-d$_6$) δ 2.02-2.07 (m, 2H), 2.49 (br, 2H), 2.51 (s, 3H), 2.67-2.76 (m, 2H), 3.66 (br, 2H), 4.23 (br, 1H), 4.77 (br, 1H), 7.05 (d, J=4.9 Hz, 1H), 7.11 (d, J=7.7 Hz, 1H), 7.27-7.39 (m, 3H), 7.46-7.55 (m, 2H), 7.61 (d, J=16.6 Hz, 1H), 7.70 (d, J=4.9 Hz, 1H), 7.90 (d, J=8.1 Hz, 1H), 8.01 (d, J=8.1 Hz, 1H), 9.86 (br, 1H), 13.1 (br, 1H).

ESI-MS (m/z); 459 [M+H]$^+$

EXAMPLE 331

(R)-(E)-N-{2-[2-(1H-indazol-3-yl)vinyl]-5-(2-methylpiperazin-1-ylmethyl)phenyl}-3-methylthiophene-2-carboxamide (Compound 331)

In a similar manner to Example 29, (E)-N-{5-hydroxymethyl-2-[2-(1H-indazol-3-yl)vinyl]phenyl}-N-methylpyrrole-2-carboxamide (0.52 g, 74%) was obtained from N-methylpyrrole-2-carboxylic acid (0.47 g, 3.8 mmol), thionyl chloride (0.41 mL, 5.5 mmol), DMF (20 µL, 0.19 mmol) and methylene chloride (15 mL), and {3-amino-4-[2-(1H-indazol-3-yl)vinyl]phenyl}methanol (0.50 g, 1.9 mmol) obtained in Step 1 of Example 108, triethylamine (0.79 mL, 5.7 mmol) and THF (10 mL).

$^1$H-NMR (270 MHz, DMSO-d$_6$) δ 2.01-2.08 (m, 2H), 2.24-2.41 (m, 2H), 2.51 (s, 3H), 2.58-2.79 (m, 2H), 3.31 (br, 5H), 3.93-3.98 (m, 1H), 7.05 (d, J=4.9 Hz, 1H), 7.11 (d, J=7.7 Hz, 1H), 7.25-7.43 (m, 3H), 7.49-7.55 (m, 2H), 7.59 (d, J=16.8 Hz, 1H), 7.69 (d, J=4.9 Hz, 1H), 7.88 (d, J=8.1 Hz, 1H), 7.98 (d, J=8.1 Hz, 1H), 9.84 (br, 1H), 13.1 (br, 1H).

ESI-MS (m/z); 472 [M+H]$^+$

EXAMPLE 332

(E)-N-{2-[2-(1H-indazol-3-yl)vinyl]-5-piperazin-1-ylmethyl}phenyl}-N-methylpyrrole-2-carboxamide (Compound 332)

Step 1

In a similar manner to Example 29, (E)-N-{5-hydroxymethyl-2-[2-(1H-indazol-3-yl)vinyl]phenyl}-N-methylpyrrole-2-carboxamide (0.52 g, 74%) was obtained from N-methylpyrrolecarboxylic acid (0.47 g, 3.8 mmol), thionyl chloride (0.41 mL, 5.5 mmol), DMF (20 µL, 0.19 mmol) and methylene chloride (15 mL), and {3-amino-4-[2-(1H-indazol-3-yl)vinyl]phenyl}methanol (0.50 g, 1.9 mmol) obtained in Step 1 of Example 108, triethylamine (0.79 mL, 5.7 mmol) and THF (10 mL).

$^1$H-NMR (270 MHz, DMSO-d$_6$) δ 3.88 (s, 3H), 4.53-4.57 (m, 2H), 5.24-5.33 (m, 1H), 6.12-6.17 (m, 1H), 7.01-7.66 (m, 9H), 7.87-8.00 (m, 2H), 9.89 (s, 1H), 13.1 (s, 1H).

ESI-MS (m/z); 373 [M+H]$^+$

Step 2

In a similar manner to Step 1 of Example 224, (E)-N-{2-[2-(1H-indazol-3-yl)vinyl]-5-(bromomethyl)phenyl}-N-methylpyrrole-2-carboxamide was obtained from (E)-N-{5-hydroxymethyl-2-[2-(1H-indazol-3-yl)vinyl]phenyl}-N-methylpyrrole-2-carboxamide (0.50 g, 1.3 mmol) obtained in Step 1, DMF (30 mL), triphenylphosphine (0.79 g, 2.7 mmol) and carbon tetrabromide (0.89 g, 2.7 mmol). Further, in a similar manner to Step 2 of Example 224, a crude product was obtained from 1-(tert-butoxycarbonyl)piperazine (0.75 g, 4.1 mmol) and triethylamine (0.56 mL, 4.1 mmol). Then, the product was dissolved in methanol (5.0 mL) and the solution was added with 4 mol/L hydrogen chloride-methanol solution (1.0 mL), followed by and reacting at 60° C. for 1 hour. The reaction mixture was concentrated under reduced pressure, neutralized by aqueous sodium hydroxide solution and crystallized from ethyl acetate to obtain Compound 332 (0.16 g, 26%).

$^1$H-NMR (270 MHz, DMSO-d$_6$) δ 2.32-2.49 (m, 4H), 2.68-2.70 (m, 4H), 3.31 (s, 3H), 3.88 (s, 2H), 6.12-6.15 (m, 1H), 7.02-7.09 (m, 1H), 7.14-7.25 (m, 4H), 7.32-7.38 (m, 1H), 7.46 (d, J=16.6 Hz, 1H), 7.53 (d, J=8.4 Hz, 1H), 7.61 (d, J=16.6 Hz, 1H), 7.88 (d, J=8.1 Hz, 1H), 7.96 (d, J=8.4 Hz, 1H), 9.75 (br, 1H), 13.1 (br, 1H).

ESI-MS (m/z); 441 [M+H]$^+$

EXAMPLE 333

(E)-N-{6-[2-(1H-indazol-3-yl)vinyl]-2-methoxy-3-[2-(4-methylpiperazin-1-yl)-2-oxoethoxy]phenyl}-3-methylthiophene-2-carboxamide (Compound 333)

Step 1

In a similar manner to Example 28, (E)-1-{4-[2-(1H-indazol-3-yl)vinyl]-2-methoxy-3-nitrophenoxyacetyl}-4-methylpiperazine (0.18 g, 17%) was obtained from (E)-{4-[2-(1H-indazol-3-yl)vinyl]-2-methoxy-3-nitrophenoxy}acetic acid (0.2 g, 0.5 mmol) obtained in Step 3 of Example 335, N-methylpiperazine (0.10 mL, 0.81 mmol), 1-hydroxybenzotriazole monohydrate (95 mg, 0.70 mmol) and EDC (0.15 g, 1.1 mmol).

$^1$H-NMR (300 MHz, DMSO-$d_6$) δ 2.29 (s, 3H), 2.35-2.38 (m, 4H), 3.41-3.46 (m, 4H), 3.94 (s, 3H), 5.12 (s, 2H), 7.07 (d, J=16.0 Hz, 1H), 7.20-7.30 (m, 2H), 7.38-7.43 (m, 1H), 7.55-7.64 (m, 1H), 7.61 (d, J=16.0 Hz, 1H), 7.80 (d, J=9.1 Hz, 1H), 7.93 (d, J=8.4 Hz, 1H), 13.3 (br, 1H).

ESI-MS (m/z); 452 [M+H]$^+$

Step 2

In a similar manner to Example 2, (E)-4-{3-amino-4-[2-(1H-indazol-3-yl)vinyl]-2-methoxyphenoxyacetyl}-1-methylpiperazine (0.20 g, 100%) was obtained from (E)-1-{4-[2-(1H-indazol-3-yl)vinyl]-2-methoxy-3-nitrophenoxyacetyl}-4-methylpiperazine (0.18 g, 0.4 mmol) obtained in Step 1, tin (0.14 g, 1.2 mmol), concentrated hydrochloric acid (1.0 mL) and ethanol (10 mL).

ESI-MS (m/z); 422 [M+H]$^+$

Step 3

In a similar manner to Example 29, Compound 333 (35 mg, 16%) was obtained from (E)-4-{3-amino-4-[2-(1H-indazol-3-yl)vinyl]-2-methoxyphenoxyacetyl}-1-methylpiperazine (0.20 g, 0.4 mmol) obtained in Step 2,3-methylthiophene-2-carboxylic acid (0.12 g, 0.81 mmol), thionyl chloride (0.10 mL, 1.2 mmol), DMF (1 µL, 0.08 mmol), methylene chloride (2 mL), triethylamine (0.17 mL, 1.2 mmol) and THF (10.0 mL).

$^1$H-NMR (300 MHz, DMSO-$d_6$) δ 2.21 (s, 3H), 2.30-2.37 (m, 4H), 2.51 (s, 3H), 3.32-3.49 (m, 4H), 3.80 (s, 3H), 4.97 (s, 2H), 7.01-7.10 (m, 3H), 7.33-7.64 (m, 5H), 7.68 (d, J=4.9 Hz, 1H), 7.93 (d, J=8.2 Hz, 1H), 9.50 (s, 1H), 13.1 (br, 1H).

ESI-MS (m/z); 546 [M+H]$^+$

EXAMPLE 334

(E)-N-{6-[2-(1H-indazol-3-yl)vinyl]-2-methoxy-3-[2-(2,5-dioxoimidazolidin-1-yl)ethoxy]phenyl}-3-methylthiophene-2-carboxamide (Compound 334)

Step 1

A solution of 2-(4-dimethoxymethyl-2-methoxy-3-nitrophenoxy)ethylamine (0.16 g, 0.56 mmol) obtained in Step 3 of Example 338 in THF (5.0 mL) was added with triethylamine (0.23 mL, 1.7 mmol) and ethyl isocyanoacetate (0.09 mL, 0.84 mmol), followed by stirring at room temperature for 1 hour. The reaction mixture was added with water and extracted with ethyl acetate. The organic layer was washed with saturated brine, dried over anhydrous magnesium sulfate and the solvent was evaporated under reduced pressure to obtain crude product. The product was added with a mixed solvent of acetone (2.0 mL) and 6 mol/L hydrochloric acid (1.0 ml) and heated under reflux for 2.5 hours. The reaction mixture was neutralized by 2 mol/L aqueous sodium hydroxide solution and then extracted with ethyl acetate. The organic layer was washed with saturated brine, dried over anhydrous magnesium sulfate and the solvent was evaporated under reduced pressure to obtain 4-[2-(2,5-dioxoimidazolidin-1-yl)ethoxy]-3-methoxy-2-nitrobenzaldehyde (0.08 g, 42%).

$^1$H-NMR (300 MHz, CDCl$_3$) δ 3.93 (s, 3H), 4.01-4.08 (m, 4H), 4.36 (t, J=5.5 Hz, 2H), 6.07 (br, 1H), 7.11 (d, J=8.6 Hz, 1H), 7.63 (d, J=8.6 Hz, 1H), 9.78 (s, 1H).

APCI-MS (m/z); 324 [M+H]$^+$

Step 2

(1H-indazol-3-ylmethyl)triphenylphosphonium bromide (0.12 g, 0.26 mmol), 4-[2-(2,5-dioxoimidazolidin-1-yl)ethoxy]-3-methoxy-2-nitrobenzaldehyde (0.08 g, 0.24 mmol) obtained in Step 1 and potassium carbonate (0.07 g, 0.47 mmol) were dissolved in methanol (3.0 mL), followed by stirring at room temperature for 1.0 hour. The reaction mixture was added with water and extracted with ethyl acetate. The organic layer was washed with saturated brine, dried over anhydrous magnesium sulfate and the solvent was evaporated under reduced pressure. The residue was purified by silica gel column chromatography (chloroform/methanol=9/1) to obtain (E)-3-(2-{4-[2-(1H-indazol-3-yl)vinyl]-2-methoxy-3-nitrophenoxy}ethyl)imidazolidine 2,4-dione (0.03 g, 32%).

$^1$H-NMR (300 MHz, CDCl$_3$) δ 3.92 (s, 3H), 4.00-4.04 (m, 4H), 4.30 (t, J=5.5 Hz, 2H), 6.04 (br, 1H), 7.03 (d, J=8.8 Hz, 1H), 7.23 (d, J=8.1 Hz, 1H), 7.35-7.50 (m, 5H), 7.89 (d, J=7.9 Hz, 1H).

APCI-MS (m/z); 438 [M+H]$^+$

Step 3

(E)-3-(2-{4-[2-(1H-indazol-3-yl)vinyl]-2-methoxy-3-nitrophenoxy}ethyl)imidazolidine-2,4-dione (0.03 g, 0.07 mmol) obtained in Step 2 was dissolved in ethanol (2 mL), and the solution was added with tin (0.026 g, 0.2 mmol) and concentrated hydrochloric acid (1.0 mL) under ice-cooling, followed by stirring at room temperature for 4 hours. To the reaction mixture under ice-cooling, 6 mol/L aqueous sodium hydroxide solution was added to neutralize the mixture. Then, the mixture was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure. In a similar manner to Example 29, Compound 334 (1.7 mg, 5%) was obtained by treating obtained crude product with 3-methylthiophene-2-carboxylic acid (0.013 g, 0.09 mmol), thionyl chloride (0.01 mL, 0.12 mmol), DMF (0.01 mL) and triethylamine (0.017 mL, 0.12 mmol).

$^1$H-NMR (300 MHz, DMSO-$d_6$) δ 2.75 (s, 3H), 3.71 (s, 3H), 3.82 (t, J=5.4 Hz, 2H), 3.94-3.96 (m, 2H), 4.22 (t, J=5.4 Hz, 2H), 7.04-7.13 (m, 3H), 7.34 (d, J=8.2 Hz, 1H), 7.41 (d, J=16.5 Hz, 1H), 7.49 (d, J=9.0 Hz, 1H), 7.51 (d, J=16.5 Hz, 1H), 7.64-7.69 (m, 2H), 7.94 (d, J=7.9 Hz, 1H), 8.11 (br, 1H), 9.48 (br, 1H), 13.1 (br, 1H).

APCI-MS (m/z); 532 [M+H]$^+$

EXAMPLE 335

(E)-N-{6-[2-(1H-indazol-3-yl)vinyl]-2-methoxy-3-(2-morpholin-4-yl-2-oxoethoxy)phenyl}-3-methylthiophene-2-carboxamide (Compound 335)

Step 1

A solution of 4-hydroxy-3-methoxy-2-nitrobenzaldehyde (2.0 g, 10 mmol) in DMF (10 mL) was added with methyl bromoacetate (1.1 mL, 11 mmol) and potassium carbonate (2.1 g, 15 mmol), followed by stirring for 1.5 hours. The solvent was evaporated under reduced pressure and the residue was purified by silica gel column chromatography (chloroform/methanol=9/1) to obtain methyl (4-formyl-2-methoxy-3-nitrophenoxy)acetate (2.2 g, 84%).

$^1$H-NMR (300 MHz, DMSO-$d_6$) δ 3.74 (s, 3H), 3.91 (s, 3H), 5.15 (s, 2H), 7.49 (d, J=8.6 Hz, 1H), 7.86 (d, J=8.6 Hz, 1H), 9.81 (s, 1H).

APCI-MS (m/z); 270 [M+H]$^+$

Step 2

Methyl (4-formyl-2-methoxy-3-nitrophenoxy)acetate (2.3 g, 8.5 mmol) obtained in Step 1, (1H-indazol-3-ylmethyl)triphenylphosphonium bromide (4.4 g, 9.4 mmol) and potassium carbonate (2.4 g, 17 mmol) were dissolved in methanol (15 mL) and the solution was stirred at room temperature for 2.0 hours. The reaction mixture was added with water and extracted with ethyl acetate. The organic layer was washed with saturated brine, dried over anhydrous magnesium sulfate and the solvent was evaporated under reduced pressure. The obtained crude product was reslurried with ethanol to obtain methyl (E)-{4-[2-(1H-indazol-3-yl)vinyl]-2-methoxy-3-nitrophenoxy}acetate (2.8 g, 87%).

$^1$H-NMR (270 MHz, DMSO-$d_6$) δ 3.74 (s, 3H), 3.94 (s, 3H), 5.06 (s, 2H), 7.08 (d, J=16.3 Hz, 1H), 7.23 (t, J=7.8 Hz, 1H), 7.34 (d, J=9.1 Hz, 1H), 7.40 (t, J=7.8 Hz, 1H), 7.55-7.63 (m, 1H), 7.63 (d, J=16.3 Hz, 1H), 7.82 (d, J=8.9 Hz, 1H), 7.94 (d, J=8.1 Hz, 1H), 13.3 (br, 1H).

APCI-MS (m/z); 384 [M+H]$^+$

Step 3

A solution of methyl (E)-{4-[2-(1H-indazol-3-yl)vinyl]-2-methoxy-3-nitrophenoxy}acetate obtained in Step 2 in methanol (20 mL) was added with 2 mol/L aqueous sodium hydroxide solution (10 mL) and stirred at 60° C. for 1 hour. To the reaction mixture under ice-cooling, 2 mol/L hydrochloric acid was added to neutralize the mixture. The precipitated solid was collected by filtration to obtain (E)-{4-[2-(1H-indazol-3-yl)vinyl]-2-methoxy-3-nitrophenoxy}acetic acid (1.9 g, 100%).

$^1$H-NMR (270 MHz, DMSO-$d_6$) δ 3.93 (s, 3H), 4.94 (s, 2H), 7.08 (d, J=16.2 Hz, 1H), 7.23 (t, J=7.4 Hz, 1H), 7.32 (d, J=8.9 Hz, 1H), 7.40 (t, J=7.4 Hz, 1H), 7.56 (d, J=8.8 Hz, 1H), 7.63 (d, J=16.2 Hz, 1H), 7.82 (d, J=8.9 Hz, 1H), 7.94 (d, J=7.8 Hz, 1H), 13.3 (br, 1H).

APCI-MS (m/z); 370 [M+H]$^+$

Step 4

In a similar manner to Example 28, (E)-4-{4-[2-(1H-indazol-3-yl)vinyl]-2-methoxy-3-nitrophenoxyacetyl}morpholine (0.2 g, 86%) was obtained from morpholine (0.1 mL, 1.6 mmol), (E)-{4-[2-(1H-indazol-3-yl)vinyl]-2-methoxy-3-nitrophenoxy}acetic acid (0.2 g, 0.54 mmol) obtained in Step 3, 1-hydroxybenzotriazole monohydrate (0.19 g, 1.4 mmol) and EDC (0.29 g, 1.5 mmol).

$^1$H-NMR (300 MHz, DMSO-$d_6$) δ 3.47 (m, 4H), 3.59-3.65 (m, 4H), 3.94 (s, 3H), 5.14 (s, 2H), 7.08 (d, J=16.5 Hz, 1H), 7.23 (t, J=7.3 Hz, 1H), 7.30 (d, J=9.2 Hz, 1H), 7.40 (t, J=7.3 Hz, 1H), 7.56 (d, J=9.2 Hz, 1H), 7.61 (d, J=16.5 Hz, 1H), 7.80 (d, J=8.8 Hz, 1H), 7.92 (d, J=8.1 Hz, 1H), 13.3 (br, 1H).

APCI-MS (m/z); 439 [M+H]$^+$

Step 5

A solution of (E)-4-{4-[2-(1H-indazol-3-yl)vinyl]-2-methoxy-3-nitrophenoxyacetyl}morpholine (0.2 g, 0.46 mmol) obtained in Step 4 in ethanol (4.0 mL) was ice-cooled and the solution was added with tin (0.16 g, 1.4 mmol) and concentrated hydrochloric acid (2.0 mL), followed by stirring at room temperature for 3 hours. To the reaction mixture under ice-cooling, 6 mol/L sodium hydroxide was added to neutralize the mixture. Then, the obtained solid was filtered. The filtrate was added with saturated aqueous sodium hydrogencarbonate solution and extracted with ethyl acetate. The organic layer was washed with water and saturated brine, dried over anhydrous magnesium sulfate and the solvent was evaporated under reduced pressure to obtain (E)-4-{3-amino-4-[2-(1H-indazol-3-yl)vinyl]-2-methoxyphenoxyacetyl}morpholine (0.17 g, 93%).

$^1$H-NMR (300 MHz, CDCl$_3$) δ 3.66-3.70 (m, 8H), 3.88 (s, 3H), 4.76 (s, 2H), 6.44 (d, J=8.6 Hz, 1H), 7.19-7.24 (m, 2H), 7.28 (m, 1H), 7.42 (dt, J=0.9, 7.3 Hz, 1H), 7.49 (d, J=8.2 Hz, 1H), 7.50 (d, J=16.5 Hz, 1H), 8.00 (d, J=8.2 Hz, 1H).

APCI-MS (m/z); 409 [M+H]$^+$

Step 6

In a similar manner to Example 29, Compound 335 (46 mg, 49%) was obtained from (E)-4-{3-amino-4-[2-(1H-indazol-3-yl)vinyl]-2-methoxyphenoxyacetyl}morpholine (0.17 g, 0.43 mmol) obtained in Step 5, 3-methylthiophene-2-carboxylic acid (0.18 g, 1.3 mmol), thionyl chloride (0.12 mL, 1.7 mmol), DMF (few drops) and triethylamine (0.18 mL, 1.3 mmol).

$^1$H-NMR (300 MHz, DMSO-$d_6$) δ 3.31 (s, 3H), 3.49-3.52 (m, 4H), 3.60-3.63 (m, 4H), 3.81 (s, 3H), 4.99 (s, 2H), 7.03-7.10 (m, 3H), 7.33-7.38 (m, 1H), 7.38 (d, J=16.7 Hz, 1H), 7.51 (d, J=16.7 Hz, 1H), 7.53 (d, J=8.4 Hz, 1H), 7.64 (d, J=9.0 Hz, 1H), 7.68 (d, J=4.9 Hz, 1H), 7.92 (d, J=8.2 Hz, 1H), 9.51 (s, 1H), 13.1 (br, 1H).

APCI-MS (m/z); 533 [M+H]$^+$

EXAMPLE 336

(E)-(S)—N-{2-[2-(1H-indazol-3-yl)vinyl]-5-(2-methylpiperazin-1-ylmethyl)phenyl}-3-methylthiophene-2-carboxamide (Compound 336)

In a similar manner to Step 2 of Example 224, Compound 336 (51 mg, 14%) was obtained from (E)-N-{2-[2-(1H-indazol-3-yl)vinyl]-5-(bromomethyl)phenyl}-3-methylthiophene-2-carboxamide (0.35 g, 0.77 mmol) obtained in Step 1 of Example 224, triethylamine (0.32 mL, 2.3 mmol) and (S)-3-methylpiperazine-1-carboxylic acid tert-butyl ester (0.46 g, 2.3 mmol).

$^1$H-NMR (270 MHz, DMSO-$d_6$) δ 2.01-2.08 (m, 2H), 2.24-2.41 (m, 2H), 2.51 (s, 3H), 2.58-2.79 (m, 2H), 3.31 (br, 5H), 3.93-3.98 (m, 1H), 7.05 (d, J=4.9 Hz, 1H), 7.11 (d, J=7.7 Hz, 1H), 7.25-7.43 (m, 3H), 7.49-7.55 (m, 2H), 7.59 (d, J=16.8 Hz, 1H), 7.69 (d, J=4.9 Hz, 1H), 7.88 (d, J=8.1 Hz, 1H), 7.98 (d, J=8.1 Hz, 1H), 9.84 (br, 1H), 13.1 (br, 1H).

ESI-MS (m/z); 472 [M+H]$^+$

EXAMPLE 337

(E)-N-{6-[2-(1H-indazol-3-yl)vinyl]-2-methoxy-3-[2-(2-oxopyrrolidin-1-yl)ethoxy]phenyl}-3-methylthiophene-2-carboxamide (Compound 337)

Step 1

In a similar manner to Example 1, (E)-1-(2-{4-[2-(1H-indazol-3-yl)vinyl]-2-methoxy-3-nitrophenoxyethyl)pyrrolidine-2-one (0.70 g, 92%) was obtained from 4-(2-oxopyrrolidin-1-ylethoxy)-3-methoxy-2-nitrobenzaldehyde (0.55 g, 1.8 mmol); (1H-indazol-3-ylmethyl)triphenylphosphonium bromide (0.85 g, 1.8 mmol), potassium carbonate (0.75 g, 5.4 mmol) and methanol (20 mL). $^1$H-NMR (270 MHz, DMSO-d$_6$) δ 1.93-1.97 (m, 2H), 2.19-2.25 (m, 2H), 3.47 (t, J=7.1 Hz, 2H), 3.63 (t, J=5.3 Hz, 2H), 3.85 (s, 3H), 4.26 (t, J=5.3 Hz, 2H), 7.06 (d, J=16.4 Hz, 1H), 7.18-7.24 (m, 1H), 7.36-7.41 (m, 2H), 7.55 (d, J=8.4 Hz, 1H), 7.61 (d, J=16.4 Hz, 1H), 7.82 (d, J=8.9 Hz, 1H), 7.93 (d, J=8.1 Hz, 1H), 13.3 (s, 1H).

ESI-MS (m/z); 423 [M+H]$^+$

Step 2

In a similar manner to Example 2, (E)-1-(2-{3-amino-4-[2-(1H-indazol-3-yl)vinyl]-2-methoxyphenoxy}ethyl)pyrrolidin-2-one (0.64 g, 98%) was obtained from (E)-1-(2-{4-[2-(1H-indazol-3-yl)vinyl]-2-methoxy-3-nitrophenoxy}ethyl)pyrrolidin-2-one (0.70 g, 1.7 mmol) obtained in Step 1, tin (0.61 g, 5.1 mmol), concentrated hydrochloric acid (5.0 mL) and ethanol (50 mL).

ESI-MS (m/z); 393 [M+H]$^+$

Step 3

In a similar manner to Example 29, Compound 337 (0.43 g, 50%) was obtained from (E)-1-(2-{3-amino-4-[2-(1H-indazol-3-yl)vinyl]-2-methoxyphenoxy}ethyl)pyrrolidine-2-one (0.63 g, 1.6 mmol) obtained in Step 2, 3-methylthiophenecarboxylic acid (0.35 g, 2.4 mmol), thionyl chloride (0.27 mL, 3.7 mmol), DMF (20 µL, 0.24 mmol), methylene chloride (3 mL), triethylamine (0.67 mL, 4.8 mmol) and THF (5.0 mL).

$^1$H-NMR (300 MHz, DMSO-d$_6$) δ 1.89-2.00 (m, 2H), 2.24 (t, J=8.1 Hz, 2H), 2.51 (s, 3H), 3.52 (t, J=7.1 Hz, 2H), 3.63-3.70 (m, 2H), 3.75 (s, 3H), 4.19 (t, J=5.3 Hz, 2H), 7.04-7.14 (m, 3H), 7.33-7.54 (m, 4H), 7.65-7.69 (m, 2H), 7.94 (d, J=8.2 Hz, 1H), 9.49 (s, 1H), 13.1 (br, 1H).

ESI-MS (m/z); 517 [M+H]$^+$

EXAMPLE 338

(E)-N-{6-[2-(1H-indazol-3-yl)vinyl]-2-methoxy-3-[2-(propylsulfonylamino)ethoxy]phenyl}-3-methylthiophene-2-carboxamide (Compound 338)

Step 1

A solution of 4-hydro-3-methoxy-2-nitrobenzaldehyde (2.0 g, 10 mmol) in DMF (10 mL) was added with N-(2-bromoethyl)phthalimide (2.8 g, 11 mmol) and potassium carbonate (2.1 g, 15 mmol), followed by stirring for 5 hours. Then, the solvent was evaporated under reduced pressure. The residue was purified by silica gel column chromatography (chloroform/methanol=9/1) to obtain 4-[2-(phtalimido)ethoxy]-3-methoxy-2-nitrobenzaldehyde (0.8 g, 21%).

$^1$H-NMR (300 MHz, DMSO-d$_6$) δ 3.74 (s, 3H), 4.08 (t, J=5.3 Hz, 2H), 4.47 (t, J=5.3 Hz, 2H), 7.52 (d, J=8.6 Hz, 1H), 7.63 (d, J=8.6 Hz, 1H), 7.83-7.92 (m, 4H), 9.78 (s, 1H).

APCI-MS (m/z); 371 [M+H]$^+$

Step 2

A solution of 4-[2-(phtalimido)ethoxy]-3-methoxy-2-nitrobenzaldehyde (0.7 g, 1.9 mmol) obtained in Step 1 in methanol (2.0 mL) was added with 1 mol/L hydrogen chloride-methanol solution (1.0 mL) and stirred for 2 hours, then excess amount of potassium carbonate was added thereto, followed by stirring for 1 hour. The reaction mixture was concentrated, added with saturated aqueous sodium hydrogen carbonate solution and extracted with ethyl acetate. The organic layer was washed with saturated brine, dried over anhydrous magnesium sulfate and the solvent was evaporated under reduced pressure. The residue was reslurried with ethyl acetate to obtain 2-[2-(4-dimethoxymethyl-2-methoxy-3-nitrophenoxy)ethyl]phtalimide (0.7 g, 94%).

$^1$H-NMR (300 MHz, DMSO-d$_6$) δ 3.20 (s, 6H), 3.71 (s, 3H), 4.05 (t, J=5.1 Hz, 2H), 4.35 (t, J=5.1 Hz, 2H), 5.40 (s, 1H), 7.23 (d, J=8.8 Hz, 1H), 7.30 (d, J=8.8 Hz, 1H), 7.82-7.91 (m, 4H).

APCI-MS (m/z); 417 [M+H]$^+$

Step 3

A solution of 2-[2-(4-dimethoxymethyl-2-methoxy-3-nitrophenoxy)ethyl]phtalimide (0.05 g, 0.12 mmol) obtained in Step 2 in ethanol (1.0 mL) was added with hydrazine monohydrate (6.4 µL, 0.13 mmol) and heated under reflux for 3 hours. The reaction mixture was cooled to room temperature and added with water, followed by extracting with ethyl acetate. The organic layer was washed with saturated brine, dried over anhydrous magnesium sulfate and the solvent was evaporated under reduced pressure to obtain 2-(4-dimethoxymethyl-2-methoxy-3-nitrophenoxy)ethylamine (0.04 g, 100%).

$^1$H-NMR (300 MHz, DMSO-d$_6$) δ 2.92 (t, J=5.5 Hz, 2H), 3.23 (s, 6H), 3.42 (br, 2H), 3.85 (s, 3H), 4.05 (t, J=5.5 Hz, 2H), 5.42 (s, 1H), 7.32 (d, J=7.9 Hz, 1H), 7.46 (d, J=7.9 Hz, 1H).

APCI-MS (m/z); 287 [M+H]$^+$

Step 4

A solution of 2-(4-dimethoxymethyl-2-methoxy-3-nitrophenoxy)ethylamine (0.5 g, 1.8 mmol) obtained in Step 3 in THF (10 mL) was added with triethylamine (0.38 mL, 2.7 mmol) and n-propanesulfonyl chloride (0.24 mL, 2.2 mmol), followed by stirring at room temperature for 3 hours. The reaction mixture was added with water and extracted with ethyl acetate. The organic layer was washed with saturated brine, dried over anhydrous magnesium sulfate and the solvent was evaporated under reduced pressure. The residue was added with methanol (6.0 mL) and 1 mol/L hydrochloric acid, followed by stirring for 15 minutes. The reaction mixture was added with water and extracted with ethyl acetate. The organic layer was washed with saturated brine, dried over anhydrous magnesium sulfate and the solvent was evaporated under reduced pressure to obtain [2-(4-formyl-2-methoxy-3-nitrophenoxy)ethyl]propane-1-sulfonamide (0.39 g, 62%).

$^1$H-NMR (300 MHz, CDCl$_3$) δ 1.04 (t, J=7.5 Hz, 3H), 1.26 (t, J=7.1 Hz, 2H), 1.80-1.90 (m, 2H), 3.05-3.09 (m, 2H), 3.94 (s, 3H), 4.29 (t, J=4.8 Hz, 2H), 5.56 (t, J=5.7 Hz, 1H), 7.18 (d, J=8.4 Hz, 1H), 7.63 (d, J=8.4 Hz, 1H), 9.75 (s, 1H).

APCI-MS (m/z); 347 [M+H]$^+$

Step 5

A solution of (1H-indazol-3-ylmethyl)triphenylphosphonium bromide (0.58 g, 1.2 mmol) and [2-(4-formyl-2-methoxy-3-nitrophenoxy)ethyl]propane-1-sulfonamide (0.39 g, 1.1 mmol) obtained in Step 4 in methanol (5.0 mL) was added with potassium carbonate (0.3 g, 2.2 mmol) and stirred at room temperature for 2.0 hours. The reaction mixture was added with water and extracted with ethyl acetate. The organic layer was washed with saturated brine, dried over anhydrous magnesium sulfate and the solvent was evaporated under reduced pressure. The residue was purified by silica gel column chromatography (chloroform/methanol=9/1) to obtain (E)-N-({4-[2-(1H-indazol-3-yl)vinyl]-2-methoxy-3-nitrophenoxy}ethyl)propane-1-sulfonamide (0.3 g, 60%).

$^1$H-NMR (300 MHz, CDCl$_3$) δ 1.07 (t, J=7.5 Hz, 3H), 1.81-1.94 (m, 2H), 3.06-3.11 (m, 2H), 3.55-3.61 (m, 2H), 3.91 (s, 3H), 4.19 (t, J=5.1 Hz, 2H), 5.45 (br, 2H), 7.02 (d, J=8.8 Hz, 1H), 7.25-7.28 (m, 2H), 7.33 (s, 1H), 7.38-7.48 (m, 2H), 7.50 (d, J=7.5 Hz, 1H), 7.89 (d, J=8.2 Hz, 1H).

APCI-MS (m/z); 461 [M+H]$^+$

Step 6

A solution of (E)-N-({4-[2-(1H-indazol-3-yl)vinyl]-2-methoxy-3-nitrophenoxy}ethyl)propane-1-sulfonamide (0.3 g, 0.68 mmol) obtained in Step 5 in ethanol (10 mL) was added with tin (0.24 g, 2.0 mmol) and concentrated hydrochloric acid (5.0 mL) under ice-cooling, followed by stirring at room temperature for 1 hour. To the reaction mixture under ice-cooling, 6 mol/L sodium hydroxide was added to neutralize the mixture. Then, the mixture was filtered. The filtrate was added with saturated aqueous sodium hydrogen carbonate solution and extracted with ethyl acetate. The organic layer was washed with water and saturated brine, dried over anhydrous magnesium sulfate and the solvent was evaporated under reduced pressure. In a similar manner to Example 29, Compound 338 (0.14 g, 41%) was obtained by treating the residue with 3-methylthiophene-2-carboxylic acid (0.14 g, 1.0 mmol), thionyl chloride (0.16 mL, 1.4 mmol), DMF (few drops) and triethylamine (0.19 mL, 1.4 mmol).

$^1$H-NMR (300 MHz, DMSO-d$_6$) δ 0.98 (t, J=7.3 Hz, 3H), 1.63-1.74 (m, 2H), 3.04-3.10 (m, 2H), 3.35 (s, 3H), 3.37-3.40 (m, 3H), 3.79 (s, 3H), 4.13 (t, J=5.5 Hz, 2H), 7.05 (d, J=4.9 Hz, 1H), 7.08 (d, J=7.5 Hz, 1H), 7.13 (d, J=9.0 Hz, 1H), 7.34 (d, J=8.1 Hz, 1H), 7.40 (d, J=16.5 Hz, 1H), 7.51 (d, J=16.5 Hz, 1H), 7.52 (d, J=8.2 Hz, 1H), 7.66 (d, J=3.7 Hz, 1H), 7.69 (s, 1H), 7.94 (d, J=8.2 Hz, 1H), 9.51 (s, 1H), 13.1 (br, 1H).
APCI-MS (m/z); 555 [M+H]$^+$

EXAMPLE 339

(E)-N-{3-{3-[N-ethyl(2-hydroxyethyl)amino]propoxy}-6-[2-(1H-indazol-3-yl)vinyl]-2-methoxyphenyl}-3-methylthiophene-2-carboxamide (Compound 339)

Step 1

In a similar manner to Step 1 of Example 263, 4-(3-chloropropoxy)-3-methoxy-2-nitrobenzaldehyde (8.3 g, 100%) was obtained from 4-hydroxy-3-methoxy-2-nitrobenzaldehyde (6.0 g, 30 mmol), potassium carbonate (11 g, 82 mmol), 1-bromo-3-chloropropane (5.0 mL, 61 mmol) and DMF (120 mL).

$^1$H-NMR (300 MHz, DMSO-d$_6$) δ 2.29 (t, J=6.0 Hz, 2H), 3.83 (t, J=6.0 Hz, 2H), 3.87 (s, 3H), 4.36 (t, J=6.0 Hz, 2H), 7.50 (d, J=8.4 Hz, 1H), 7.89 (d, J=8.4 Hz, 1H), 9.81 (s, 1H).
ESI-MS (m/z); 274 [M+H]$^+$

Step 2

In a similar manner to Example 1, (E)-3-{2-[4-(3-chloropropoxy)-3-methoxy-2-nitrophenyl]vinyl}-1H-indazol (11 g, 100%) was obtained from 4-(3-chloropropoxy)-3-methoxy-2-nitrobenzaldehyde (8.0 g, 29 mmol) obtained in Step 1, (1H-indazol-3-ylmethyl)triphenylphosphonium bromide (14 g, 29 mmol), DBU (6.5 mL, 44 mmol) and methanol (83 mL).

$^1$H-NMR (300 MHz, DMSO-d$_6$) δ 2.26 (t, J=6.0 Hz, 2H), 3.84 (t, J=6.0 Hz, 2H), 3.89 (s, 3H), 4.24-4.33 (m, 2H), 7.08 (d, J=15.9 Hz, 1H), 7.23 (t, J=8.1 Hz, 1H), 7.40 (t, J=8.1 Hz, 1H), 7.42 (d, J=8.7 Hz, 1H), 7.52-7.68 (m, 2H), 7.85 (d, J=8.7 Hz, 1H), 7.95 (d, J=8.3 Hz, 1H), 13.29 (s, 1H).
ESI-MS (m/z); 388 [M+H]$^+$

Step 3

In a similar manner to Example 2, (E)-3-(3-chloropropoxy)-6-[2-(1H-indazol-3-yl)vinyl]-2-methoxyphenylamine (10 g, 100%) was obtained from (E)-3-{2-[4-(3-chloropropoxy)-3-methoxy-2-nitrophenyl]vinyl}-1H-indazole (11 g, 29 mmol) obtained in Step 2, tin (10 g, 87 mmol), concentrated hydrochloric acid (51 mL) and ethanol (0.28 L).

$^1$H-NMR (300 MHz, DMSO-d$_6$) δ 2.19 (t, J=5.9 Hz, 2H), 3.38-3.51 (m, 2H), 3.71 (s, 3H), 3.83 (t, J=5.9 Hz, 2H), 5.10 (s, 2H), 6.39 (d, J=8.6 Hz, 1H), 7.17 (t, J=7.8 Hz, 1H), 7.20 (d, J=16.2 Hz, 1H), 7.27 (d, J=8.6 Hz, 1H), 7.37 (t, J=7.8 Hz, 1H), 7.48-7.70 (m, 2H), 8.21 (d, J=7.8 Hz, 1H), 13.00 (s, 1H).

Step 4

In a similar manner to Example 29, (E)-N-(3-(3-chloropropoxy)-2-methoxy-6-{2-[1-(3-methylthiophene-2-carbonyl)-1H-indazol-3-yl]vinyl}phenyl)-3-methylthiophene-2-carboxamide (3.7 g, 36%) was obtained from (E)-3-(3-chloropropoxy)-6-[2-(1H-indazol-3-yl)vinyl]-2-methoxyphenylamine (6.0 g, 17 mmol) obtained in Step 3, 3-methylthiophene carboxylic acid (2.6 g, 18 mmol), thionyl chloride (2.1 mL, 29 mmol), DMF (0.20 mL, 3.3 mmol), methylene chloride (0.12 L), triethylamine (5.9 mL, 42 mmol) and THF (0.12 L).
ESI-MS (m/z); 606 [M]$^+$ Step 5

A solution of (E)-N-(3-(3-chloropropoxy)-2-methoxy-6-{2-[1-(3-methylthiophene-2-carbonyl)-1H-indazol-3-yl]vinyl}phenyl)-3-methylthiophene-2-carboxamide (0.30 g, 0.49 mmol) obtained in Step 4 in N,N-dimethylacetamide (6.0 mL) was added with 2-(ethylamino)ethanol (0.97 mL, 9.9 mmol) and sodium iodide (0.11 g, 0.74 mmol), followed by stirring at 90° C. for 3.0 hours. After cooling the reaction mixture to room temperature, aqueous sodium hydroxide solution (2.0 mol/L, 3.0 mL) was added and the mixture was stirred for 1.0 hour. The mixture was added with water and extracted with ethyl acetate. The organic layer was concentrated under reduced pressure and the residue was purified by silica gel column chromatography [amino-silica gel chromatorex (trade mark) NH, manufactured by Fuji Silysia; hexane/ethyl acetate=60/40 to ethyl acetate] and crystallized from hexane/ethyl acetate (1/1) to obtain Compound 339 (91 mg, 34%).

$^1$H-NMR (300 MHz, DMSO-d$_6$) δ 1.88 (t, J=6.6 Hz, 2H), 1.99 (s, 3H), 2.46-2.55 (m, 2H), 2.62 (t, J=6.6 Hz, 2H), 3.45 (q, J=6.4 Hz, 2H), 3.77 (s, 3H), 3.98-4.07 (m, 5H), 4.12 (t, J=6.4 Hz, 2H), 4.31 (t, J=5.6 Hz, 1H), 7.07 (d, J=17.1 Hz, 1H), 7.07 (d, J=4.7 Hz, 1H), 7.10 (t, J=8.6 Hz, 1H), 7.36 (t, J=8.6 Hz, 1H), 7.45 (d, J=17.1 Hz, 1H), 7.49 (d, J=8.6 Hz, 1H), 7.52 (d, J=8.6 Hz, 1H), 7.66 (d, J=8.2 Hz, 1H), 7.68 (d, J=4.7 Hz, 1H), 7.94 (d, J=8.2 Hz, 1H), 9.48 (s, 1H), 13.08 (s, 1H).
ESI-MS (m/z); 535 [M+H]$^+$

EXAMPLE 340

(E)-(s)-N-{3-[3-(2-hydroxymethylpyrrolidin-1-yl)propoxy]-6-[2-(1H-indazol-3-yl)vinyl]-2-methoxyphenyl}-3-methylthiophene-2-carboxamide (Compound 340)

In a similar manner to Step 5 of Example 339, Compound 340 (0.22 g, 48%) was obtained from (E)-N-(3-(3-chloropropoxy)-2-methoxy-6-{2-[1-(3-methylthiophene-2-carbonyl)-1H-indazol-3-yl]vinyl}phenyl)-3-methylthiophene-2-carboxamide (0.50 g, 0.83 mmol) obtained in Step 4 of Example 339, L-prolinol (1.63 mL, 17 mmol), sodium iodide (0.19 g, 1.2 mmol) and N,N-dimethylacetamide (10 mL).

$^1$H-NMR (300 MHz, DMSO-d$_6$) δ 1.49-1.71 (m, 3H), 1.73-1.97 (m, 3H), 2.11-2.22 (m, 1H), 2.36-2.48 (m, 1H), 2.48 (s, 3H), 2.93-3.12 (m, 2H), 3.14-3.25 (m, 1H), 3.26-3.36 (m, 1H), 3.36-3.47 (m, 1H), 3.77 (s, 3H), 4.07-4.18 (m, 2H), 4.32 (t, J=5.4 Hz, 1H), 7.05 (d, J=5.1 Hz, 1H), 7.07 (d, J=17.4 Hz, 1H), 7.10 (t, J=8.4 Hz, 1H), 7.36 (t, J=8.4 Hz, 1H), 7.45

(d, J=17.4 Hz, 1H), 7.49 (d, J=8.4 Hz, 1H), 7.52 (d, J=8.4 Hz, 1H), 7.66 (d, J=8.4 Hz, 1H), 7.68 (d, J=5.1 Hz, 1H), 7.94 (d, J=8.4 Hz, 1H), 9.48 (s, 1H), 13.08 (s, 1H).

ESI-MS (m/z); 547 [M+H]$^+$

EXAMPLE 341

(E)-N-{6-[2-(1H-indazol-3-yl)vinyl]-2-methoxy-3-[3-(3-oxopiperazin-1-yl)propoxy]phenyl}-3-methylthiophene-2-carboxamide (Compound 341)

In a similar manner to Step 5 of Example 339, Compound 341 (0.15 g, 41%) was obtained from (E)-N-(3-(3-chloropropoxy)-2-methoxy-6-{2-[1-(3-methylthiophene-2-carbonyl)-1H-indazol-3-yl]vinyl}phenyl)-3-methylthiophene-2-carboxamide (0.40 g, 0.66 mmol) obtained in Step 4 of Example 339, 2-piperazinone (0.66 g, 6.6 mmol), sodium iodide (0.15 g, 0.99 mmol) and N,N-dimethylacetamide (8.0 mL).

$^1$H-NMR (300 MHz, DMSO-d$_6$) δ 1.96 (t, J=7.1 Hz, 2H), 2.52 (s, 3H), 2.47-2.63 (m, 4H), 2.95 (s, 2H), 3.18-3.22 (br, 2H), 3.77 (s, 3H), 4.13 (t, J=5.7 Hz, 2H), 7.05 (d, J=4.7 Hz, 1H), 7.07 (d, J=17.9 Hz, 1H), 7.13 (t, J=7.3 Hz, 1H), 7.36 (t, J=7.3 Hz, 1H), 7.45 (d, J=17.9 Hz, 1H), 7.49 (d, J=7.3 Hz, 1H), 7.52 (d, J=8.2 Hz, 1H), 7.66 (d, J=7.3 Hz, 1H), 7.68 (d, J=7.3 Hz, 1H), 7.73 (s, 1H), 7.94 (d, J=8.2 Hz, 1H), 9.49 (s, 1H), 13.08 (s, 1H).

ESI-MS (m/z); 546 [M+H]$^+$

EXAMPLE 342

(E)-N-{6-[2-(1H-indazol-3-yl)vinyl]-2-methoxy-3-(3-morpholin-4-yl)propoxyphenyl}-3-methylthiophene-2-carboxamide (Compound 342)

In a similar manner to Step 5 of Example 339, Compound 342 (0.15 g, 48%) was obtained from (E)-N-(3-(3-chloropropoxy)-2-methoxy-6-{2-[1-(3-methylthiophene-2-carbonyl)-1H-indazol-3-yl]vinyl}phenyl)-3-methylthiophene-2-carboxamide (0.35 g, 0.58 mmol) obtained in Step 4 of Example 339, morpholine (0.50 mL, 5.8 mmol), sodium iodide (0.13 g, 0.87 mmol) and N,N-dimethylacetamide (7.0 mL).

$^1$H-NMR (300 MHz, DMSO-d$_6$) δ 1.94 (t, J=6.2 Hz, 2H), 2.34-2.43 (br, 4H), 2.43-2.53 (m, 2H), 2.51 (s, 3H), 3.59 (t, J=4.6 Hz, 4H), 3.76 (s, 3H), 4.13 (t, J=6.2 Hz, 2H), 7.05 (d, J=4.9 Hz, 1H), 7.07 (d, J=17.7 Hz, 1H), 7.11 (t, J=6.9 Hz, 1H), 7.36 (t, J=6.9 Hz, 1H), 7.45 (d, J=17.7 Hz, 1H), 7.49 (d, J=6.9 Hz, 1H), 7.52 (d, J=7.7 Hz, 1H), 7.66 (d, J=6.9 Hz, 1H), 7.68 (d, J=4.9 Hz, 1H), 7.94 (d, J=7.7 Hz, 1H), 9.49 (s, 1H), 13.08 (s, 1H).

ESI-MS (m/z); 533 [M+H]$^+$

EXAMPLE 343

(E)-N—(R)-{6-[2-(1H-indazol-3-yl)vinyl]-2-methoxy-3-[(3-hydroxypyrrolidine-1-ylcarbonyl)acetyloxy]phenyl}-3-methylthiophene-2-carboxamide (Compound 343)

Step 1

In a similar manner to Example 28, (R)-(E)-3-hydroxy-1-({4-[2-(1H-indazol-3-yl)vinyl]-2-methoxy-3-nitrophenoxy}acetyl)pyrrolidine (0.24 g, 31%) was obtained from (E)-4-[2-(1H-indazol-3-yl)-vinyl]-2-methoxy-3-nitrophenoxy acetic acid (0.4 g, 1.1 mmol) obtained in Step 3 of Example 335, (R)-3-pyrrolidinol hydrochloride (0.20 g, 1.6 mmol), 1-hydroxybenzotriazole monohydrate (0.19 g, 1.4 mmol) and EDC (0.29 g, 1.5 mmol).

$^1$H-NMR (300 MHz, DMSO-d$_6$) δ 1.97-2.00 (m, 2H), 3.30-3.42 (m, 3H), 3.56-3.60 (m, 1H), 3.91 (s, 3H), 4.20-4.38 (m, 1H), 4.97-5.08 (m, 2H), 7.03-7.09 (m, 1H), 7.21-7.29 (m, 2H), 7.36-7.41 (m, 1H), 7.51-7.71 (m, 2H), 7.77 (d, J=8.6 Hz, 1H), 7.91 (d, J=8.1 Hz, 1H), 13.3 (br, 1H).

ESI-MS (m/z); 439 [M+H]$^+$

Step 2

In a similar manner to Example 2, (R)-(E)-3-hydroxy-1-({3-amino-4-[2-(1H-indazol-3-yl)vinyl]-2-methoxyphenoxy}acetyl)pyrrolidine (0.20 g, 100%) was obtained from (R)-(E)-3-hydroxy-1-({4-[2-(1H-indazol-3-yl)vinyl]-2-methoxy-3-nitrophenoxy}acetyl)pyrrolidine (0.24 g, 0.5 mmol) obtained in Step 1, tin (0.19 g, 1.5 mmol), concentrated hydrochloric acid (1.0 mL) and ethanol (10 mL).

ESI-MS (m/z); 409 [M+H]$^+$

Step 3

In a similar manner to Example 29, Compound 343 (51 mg, 19%) was obtained from (R)-(E)-3-hydroxy-1-({3-amino-4-[2-(1H-indazol-3-yl)vinyl]-2-methoxyphenoxy}acetyl)pyrrolidine (0.20 g, 0.49 mmol) obtained in Step 2, 3-methylthiophene carboxylic acid (0.12 g, 0.83 mmol), thionyl chloride (0.10 mL, 1.2 mmol), DMF (1 μL, 0.08 mmol), methylene chloride (2 mL), triethylamine (0.22 mL, 1.6 mmol) and THF (5.0 mL).

$^1$H-NMR (300 MHz, DMSO-d$_6$) δ 1.79-1.99 (m, 2H), 2.51 (s, 3H), 3.39-3.45 (m, 2H), 3.58-3.66 (m, 2H), 3.81 (s, 3H), 4.28-4.38 (m, 1H), 4.85-4.90 (m, 2H), 7.01-7.10 (m, 3H), 7.33-7.64 (m, 5H), 7.68 (d, J=4.9 Hz, 1H), 7.93 (d, J=8.2 Hz, 1H), 9.50 (s, 1H), 13.1 (br, 1H).

ESI-MS (m/z); 533 [M+H]$^+$

EXAMPLE 344

(E)-N-{3-[3-(4-hydroxypiperidin-1-yl)propoxy]-6-[2-(1H-indazol-3-yl)vinyl]-2-methoxyphenyl}-3-methylthiophene-2-carboxamide (Compound 344)

In a similar manner to Step 5 of Example 339, Compound 344 (0.11 g, 33%) was obtained from (E)-N-(3-(3-chloropropoxy)-2-methoxy-6-{2-[1-(3-methylthiophene-2-carbonyl)-1H-indazol-3-yl]vinyl}phenyl)-3-methylthiophene-2-carboxamide (0.35 g, 0.58 mmol) obtained in Step 4 of Example 339, 4-hydroxypiperidine (0.58 g, 5.8 mmol), sodium iodide (0.13 g, 0.87 mmol) and N,N-dimethylacetamide (7.0 mL).

$^1$H-NMR (300 MHz, DMSO-d$_6$) δ 1.32-1.46 (m, 2H), 1.64-1.76 (m, 2H), 1.86-1.95 (m, 2H), 1.96-2.08 (m, 2H), 2.45 (t, J=7.0 Hz, 2H), 2.51 (s, 3H), 2.65-2.78 (m, 2H), 3.76 (s, 3H), 3.98-4.07 (m, 1H), 4.11 (t, J=5.9 Hz, 2H), 4.52 (d, J=4.2 Hz, 1H), 7.05 (d, J=4.9 Hz, 1H), 7.07 (t, J=17.4 Hz, 1H), 7.10 (t, J=6.3 Hz, 1H), 7.36 (t, J=6.3 Hz, 1H), 7.45 (d, J=17.4 Hz, 1H), 7.49 (d, J=8.6 Hz, 1H), 7.52 (d, J=6.3 Hz, 1H), 7.66 (d, J=6.3 Hz, 1H), 7.68 (d, J=4.9 Hz, 1H), 7.94 (d, J=8.6 Hz, 1H), 9.49 (s, 1H), 13.08 (s, 1H).

ESI-MS (m/z); 547 [M+H]$^+$

EXAMPLE 345

(E)-4-amino-2-{5-[4-(2-hydroxyethyl)piperazin-1-ylmethyl]-2-[2-(1H-indazol-3-yl)vinyl]phenyl}-2,3-dihydroisoindole-1-one (Compound 345)

In a similar manner to Step 1 of Example 216, a crude product was obtained from (E)-2-(4-{3-amino-4-[2-(1H-indazol-3-yl)vinyl]benzyl}piperazin-1-yl)ethanol (0.11 g, 0.28 mmol) obtained in Step 1 of Example 307, triethylamine (68 µL, 0.49 mmol), 2-(bromomethyl)-3-nitrobenzoic acid methyl ester (59 mg, 0.22 mmol) and DMF (1.5 mL). The product was treated with ammonium chloride (43 mg, 0.80 mmol), iron (40 mg, 0.72 mmol) and ethanol/water (2/1, 4.7 mL), in a similar manner to Step 2 of Example 216, to obtain Compound 345 (17 mg, 23%).

$^1$H-NMR (270 MHz, DMSO-$d_6$) δ 1.06 (t, J=6.8 Hz, 2H), 2.30-2.63 (br, 8H), 3.46 (t, J=6.8 Hz, 2H), 3.52 (s, 2H), 4.64 (s, 2H), 5.50 (s, 2H), 6.87 (d, J=8.4 Hz, 1H), 6.96 (t, J=6.8 Hz, 1H), 7.02 (d, J=7.8 Hz, 1H), 7.22 (d, J=16.7 Hz, 1H), 7.25-7.35 (m, 2H), 7.38 (s, 1H), 7.39 (d, J=7.8 Hz, 1H), 7.50 (d, J=8.4 Hz, 1H), 7.54 (d, J=16.7 Hz, 1H), 7.69 (d, J=8.4 Hz, 1H), 7.99 (d, J=6.8 Hz, 1H), 13.07 (s, 1H).

ESI-MS (m/z); 509 [M+H]$^+$

EXAMPLE 346

(R)-(E)-N-{3-[3-(3-aminopyrrolidin-1-yl)propoxy]-6-[2-(1H-indazol-3-yl)vinyl]-2-methoxyphenyl}-3-methylthiophene-2-carboxamide (Compound 346)

Step 1

In a similar manner to Step 5 of Example 339, (R)-(E)—N-{3-[3-(3-N-tert-butoxycarbonylaminopyrrolidin-1-yl)propoxy]-2-methoxy-6-[2-(1H-indazol-3-yl)vinyl]phenyl}-3-methylthiophene-2-carboxamide (0.33 g, 80%) was obtained from (E)-N-(3-(3-chloropropoxy)-2-methoxy-6-{2-[1-(3-methylthiophene-2-carbonyl)-1H-indazol-3-yl]vinyl}phenyl)-3-methylthiophene-2-carboxamide (0.40 g, 0.66 mmol) obtained in Step 4 of Example 339, (3R)-(+)-3-(tert-butoxycarbonylamino)pyrrolidine (0.62 g, 3.3 mmol), sodium iodide (0.15 g, 0.99 mmol) and N,N-dimethylacetamide (8.0 mL).

$^1$H-NMR (300 MHz, DMSO-$d_6$) δ 1.37 (s, 9H), 1.73-2.09 (m, 3H), 2.23-2.32 (m, 2H), 2.52 (s, 3H), 2.69-2.84 (m, 2H), 3.73-3.96 (m, 4H), 3.76 (s, 3H), 4.13 (t, J=6.0 Hz, 2H), 6.94 (d, J=6.3 Hz, 1H), 7.05 (d, J=5.0 Hz, 1H), 7.06 (d, J=9.3 Hz, 1H), 7.12 (t, J=9.3 Hz, 1H), 7.36 (t, J=8.4 Hz, 1H), 7.39 (d, J=16.4 Hz, 1H), 7.51 (d, J=16.4 Hz, 1H), 7.51 (t, J=8.4 Hz, 1H), 7.66 (d, J=8.4 Hz, 1H), 7.68 (d, J=5.0 Hz, 1H), 7.94 (d, J=8.4 Hz, 1H), 9.48 (s, 1H), 13.09 (s, 1H).

ESI-MS (m/z); 632 [M+H]$^+$

Step 2

A solution of (R)-(E)-N-{3-[3-(3-N-tert-butoxycarbonylaminopyrrolidin-1-yl)propoxy]-2-methoxy-6-[2-(1H-indazol-3-yl)vinyl]phenyl}-3-methylthiophene-2-carboxamide (0.32 g, 0.51 mmol) obtained in Step 1 in mixed solvent of ethyl acetate/methanol (3.2 mL/3.0 mL) was added with 4.0 mol/L hydrogen chloride-ethyl acetate solution (0.45 mL, 1.8 mmol), followed by stirring at room temperature for 1.5 hours and at 40° C. for 9.0 hours. The reaction mixture was added with saturated aqueous sodium hydrogencarbonate solution and extracted with ethyl acetate. The organic layer was concentrated under reduced pressure The residue was purified by silica gel column chromatography [amino-silica gel chromatorex(trade mark)NH, manufactured by Fuji Silysia; ethyl acetate to ethyl acetate/methanol=80/20] and crystallized from a mixed solvent of hexane/ethyl acetate (2/1) to obtain Compound 346 (108 mg, 40%).

$^1$H-NMR (300 MHz, DMSO-$d_6$) δ 1.28-1.40 (m, 2H), 1.86-2.05 (m, 4H), 2.42-2.61 (m, 4H), 2.51 (s, 3H), 2.65-2.75 (m, 2H), 3.48 (m, 1H), 3.76 (s, 3H), 4.13 (t, J=6.2 Hz, 2H), 7.05 (d, J=4.9 Hz, 1H), 7.06 (d, J=7.8 Hz, 1H), 7.12 (d, J=7.8 Hz, 1H), 7.36 (t, J=8.2 Hz, 1H), 7.38 (d, J=17.0 Hz, 1H), 7.51 (d, J=17.0 Hz, 1H), 7.51 (t, J=8.2 Hz, 1H), 7.66 (d, J=8.2 Hz, 1H), 7.68 (d, J=4.9 Hz, 1H), 7.94 (d, J=8.2 Hz, 1H), 9.47 (s, 1H).

ESI-MS (m/z); 532 [M+H]

EXAMPLE 347

(E)-N-{3-{3-[(2-hydroxyethyl)methylamino]propoxy}-6-[2-(1H-indazol-3-yl)vinyl]-2-methoxyphenyl}-3-methylthiophene-2-carboxamide (Compound 347)

In a similar manner to Step 5 of Example 339, Compound 347 (0.13 g, 50%) was obtained from (E)-N-(3-(3-chloropropoxy)-2-methoxy-6-{2-[1-(3-methylthiophene-2-carbonyl)-1H-indazol-3-yl]vinyl}phenyl)-3-methylthiophene-2-carboxamide (0.30 g, 0.50 mmol) obtained in Step 4 of Example 339, 2-(methylamino)ethanol (0.41 g, 5.0 mmol), sodium iodide (0.11 g, 0.75 mmol) and N,N-dimethylacetamide (6.0 mL).

$^1$H-NMR (300 MHz, DMSO-$d_6$) δ 1.91-2.01 (m, 4H), 2.22 (s, 3H), 2.52 (s, 3H), 3.49 (t, J=6.2 Hz, 2H), 3.77 (s, 3H), 4.12-4.14 (m, 2H), 4.35-4.36 (m, 2H), 5.34 (br, 1H), 7.04-7.14 (m, 3H), 7.36-7.54 (m, 4H), 7.64-7.69 (m, 2H), 7.94 (d, J=8.4 Hz, 1H), 9.48 (br, 1H), 13.08 (br, 1H).

ESI-MS (m/z); 521 [M+H]$^+$

EXAMPLE 348

(E)-N-(6-[2-(1H-indazol-3-yl)vinyl]-2-methoxy-3-{3-[(3R*,4R*)-3-methoxy-4-(methylamino)pyrrolidin-1-yl]propoxy}phenyl)-3-methylthiophene-2-carboxamide (Compound 348)

In a similar manner to Step 5 of Example 339, Compound 348 (60 mg, 21%) was obtained from (E)-N-(3-(3-chloropropoxy)-2-methoxy-6-{2-[1-(3-methylthiophene-2-carbonyl)-1H-indazol-3-yl]vinyl}phenyl)-3-methylthiophene-2-carboxamide (0.30 g, 0.50 mmol) obtained in Step 4 of Example 339, trans-N-(4-methoxypyrrolidin-3-yl)methylamine (0.65 g, 5.0 mmol), sodium iodide (0.11 g, 0.75 mmol) and N,N-dimethylacetamide (6.0 mL).

$^1$H-NMR (300 MHz, DMSO-$d_6$) δ 1.23-1.25 (m, 2H), 1.91-1.94 (m, 2H), 2.14 (m, 1H), 2.26 (s, 3H), 2.52 (s, 3H), 2.58 (m, 2H), (t, J=6.3 Hz, 2H), 3.32 (s, 3H), 3.50 (br, 1H), 3.73 (s, 3H), 4.12 (t, J=6.3 Hz, 2H), 7.04-7.13 (m, 3H), 7.33-7.51 (m, 4H), 7.64-7.69 (m, 2H), 7.94 (d, J=8.2 Hz, 1H), (s, 1H), 13.08 (s, 1H).

ESI-MS (m/z); 576 [M+H]$^+$

EXAMPLE 349

(E)-{3-[2-(4-hydroxypiperidin-1-yl)ethoxy]-6-[2-(1H-indazol-3-yl)vinyl]-2-methoxyphenyl}-3-methylthiophene-2-carboxamide (Compound 349)

Step 1

In a similar manner to Step 1 of Example 263, 4-(2-chloroethoxy)-3-methoxy-2-nitrobenzaldehyde (4.3 g, 66%) was obtained from 4-hydroxy-3-methoxy-2-nitrobenzaldehyde (5.0 g, 25 mmol), potassium carbonate (11 g, 76 mmol), 1-bromo-2-chloroethane (3.2 mL, 38 mmol) and DMF (0.10 L).

$^1$H-NMR (300 MHz, DMSO-$d_6$) δ 3.91 (s, 3H), 4.07 (t, J=5.0 Hz, 2H), 4.53 (t, J=5.0 Hz, 2H), 7.54 (d, J=8.6 Hz, 1H), 7.89 (d, J=8.6 Hz, 1H), 9.82 (s, 1H).

Step 2

In a similar manner to Example 1, a crude product was obtained from 4-(2-chloroethoxy)-3-methoxy-2-nitrobenzaldehyde (2.5 g, 9.6 mmol) obtained in Step 1, (1H-indazol-3-ylmethyl)triphenylphosphonium bromide (4.6 g, 9.6 mmol), DBU (2.2 mL, 14.4 mmol) and methanol (27 mL). The product was treated with tin (3.4 g, 29 mmol), concentrated hydrochloric acid (17 mL) and ethanol (83 mL), in a similar manner to Example 2, to obtain (E)-3-(2-chloroethoxy)-6-[2-(1H-indazol-3-yl)vinyl]-2-methoxyphenylamine (3.3 g, 100%).

ESI-MS (m/z); 344 [M+H]$^+$

Step 3

In a similar manner to Example 29, (E)-(3-(2-chloroethoxy)-2-methoxy-6-{2-[1-(3-methylthiophene-2-carbonyl)-1H-indazol-3-yl]vinyl}phenyl)-3-methylthiophene-2-carboxamide (2.6 g, 49%) was obtained from (E)-3-(2-chloroethoxy)-6-[2-(1H-indazol-3-yl)vinyl]-2-methoxyphenylamine (3.0 g, 8.8 mmol) obtained in Step 3, 3-methylthiophenecarboxylic acid (3.4 g, 24 mmol), thionyl chloride (2.5 mL, 34 mmol), DMF (0.28 mL, 4.8 mmol), methylene chloride (60 mL), triethylamine (7.1 mL, 50 mmol) and THF (60 mL).

ESI-MS (m/z); 593 [M]$^+$

Step 4

In a similar manner to Step 5 of Example 339, Compound 349 (41 mg, 35%) was obtained from (E)-(3-(2-chloroethoxy)-2-methoxy-6-{2-[1-(3-methylthiophene-2-carbonyl)-1H-indazol-3-yl]vinyl}phenyl)-3-methylthiophene-2-carboxamide (0.13 g, 0.22 mmol) obtained in Step 3,4-hydroxypiperidine (0.22 g, 22 mmol), sodium iodide (50 mg, 0.33 mmol) and N,N-dimethylacetamide (2.6 mL).

$^1$H-NMR (270 MHz, DMSO-d$_6$) δ 1.40 (m, 2H), 1.71 (m, 2H), 2.16 (m, 2H), 2.52 (s, 3H), 2.73 (t, J=5.7 Hz, 2H), 2.82 (m, 2H), 3.42 (m, 1H), 3.77 (s, 3H), 4.18 (t, J=5.7 Hz, 2H), 4.54 (d, J=4.3 Hz, 1H), 7.05 (d, J=4.9 Hz, 1H), 7.07 (t, J=7.8 Hz, 1H), 7.14 (d, J=9.2 Hz, 1H), 7.35 (t, J=7.8 Hz, 1H), 7.39 (d, J=17.0 Hz, 1H), 7.51 (d, J=17.0 Hz, 1H), 7.52 (d, J=9.2 Hz, 1H), 7.66 (d, J=7.8 Hz, 1H), 7.68 (d, J=4.9 Hz, 1H), 7.94 (d, J=7.8 Hz, 1H), 9.49 (s, 1H), 13.09 (s, 1H).

ESI-MS (m/z); 533 [M+H]$^+$

EXAMPLE 350

(E)-N-(3-{3-[4-(hydroxymethyl)piperidin-1-yl]propoxy}-6-[2-(1H-indazol-3-yl)vinyl]-2-methoxyphenyl)-3-methylthiophene-2-carboxamide (Compound 350)

In a similar manner to Step 5 of Example 339, Compound 350 (80 mg, 30%) was obtained from (E)-N-(3-(3-chloropropoxy)-2-methoxy-6-{2-[1-(3-methylthiophene-2-carbonyl)-1H-indazol-3-yl]vinyl}phenyl)-3-methylthiophene-2-carboxamide (0.30 g, 0.50 mmol) obtained in Step 4 of Example 339, piperidin-4-ylmethanol (0.58 g, 5.0 mmol), sodium iodide (0.11 g, 0.75 mmol) and N,N-dimethylacetamide (6.0 mL).

$^1$H-NMR (300 MHz, DMSO-d$_6$) δ 1.17-1.24 (m, 5H), 1.62-1.99 (m, 6H), 2.52 (s, 3H), 2.86-2.90 (m, 2H), 3.24 (t, J=6.1 Hz, 2H), 3.76 (s, 3H), 4.11 (t, J=6.1 Hz, 2H), 4.39 (t, J=5.3 Hz, 1H), 7.04-7.13 (m, 3H), 7.33-7.54 (m, 4H), 7.64-7.69 (m, 2H), 7.94 (d, J=8.1 Hz, 1H), 9.49 (br, 1H), 13.08 (br, 1H).

ESI-MS (m/z); 561 [M+H]$^+$

EXAMPLE 351

(E)-{2-[2-(1H-indazol-3-yl)vinyl]phenyl}-3-methylbenzo[b]thiophene-2-carboxamide (Compound 351)

In a similar manner to Example 29, 3-methylbenzo[b]thiophene-2-carboxylic acid (0.14 g, 0.70 mmol) was treated with thionyl chloride (79 μL, 1.1 mmol), DMF (7.4 μL, 0.13 mmol) and dichloromethane (3.0 mL), followed by reacting with Compound 2 (0.15 g, 0.64 mmol), triethylamine (0.23 mL, 1.6 mmol) and THF (3.0 mL) to obtain Compound 351 (261 mg, 100%).

$^1$H-NMR (300 MHz, DMSO-d$_6$) δ 2.70 (s, 3H), 7.08 (d, J=7.5 Hz, 1H), 7.31-7.59 (m, 8H), 7.69 (d, J=16.5 Hz, 1H), 7.91-8.01 (m, 2H), 8.07 (d, J=7.2 Hz, 2H), 10.22 (s, 1H), 13.18 (s, 1H).

ESI-MS (m/z); 410 [M+H]$^+$

EXAMPLE 352

(E)-N-{2-[2-(1H-indazol-3-yl)vinyl]phenyl}-1-methyl-1H-imidazole-2-carboxamide (Compound 352)

In a similar manner to Example 29, 1-methyl-1H-imidazole-2-carboxylic acid (59 mg, 0.47 mmol) was treated with thionyl chloride (53 μL, 0.72 mmol), DMF (5.0 μL, 0.085 mmol) and dichloromethane (2.0 mL), followed by reacting with Compound 2 (0.10 g, 0.43 mmol), triethylamine (60 μL, 1.1 mmol) and THF (2.0 mL) to obtain Compound 352 (50 mg, 34%).

$^1$H-NMR (270 MHz, DMSO-d$_6$) δ 4.00 (s, 3H), 7.14 (t, J=7.2 Hz, 1H), 7.15 (s, 1H), 7.27-7.36 (m, 2H), 7.38 (t, J=7.2 Hz, 1H), 7.46-7.61 (m, 4H), 7.68 (d, J=16.8 Hz, 1H), 7.91 (d, J=7.2 Hz, 1H), 8.11 (d, J=8.4 Hz, 1H), 10.26 (s, 1H), 13.17 (s, 1H).

EXAMPLE 353

(E)-N-{2-[2-(1H-indazol-3-yl)vinyl]phenyl}-4-bromo-3-methylthiophene-2-carboxamide (Compound 353)

In a similar manner to Example 29, 4-bromo-3-methylthiophene-2-carboxylic acid (0.10 g, 0.47 mmol) was treated with thionyl chloride (53 μL, 0.72 mmol), DMF (5.0 μL, 0.085 mmol) and dichloromethane (2.0 mL), followed by reacting with Compound 2 (0.10 g, 0.43 mmol), triethylamine (60 μL, 1.1 mmol) and THF (2.0 mL) to obtain Compound 353 (44 mg, 24%).

$^1$H-NMR (300 MHz, DMSO-d$_6$) δ 2.46 (s, 3H), 7.11 (t, J=7.2 Hz, 1H), 7.33-7.47 (m, 5H), 7.52 (d, J=16.5 Hz, 1H), 7.55 (d, J=8.4 Hz, 1H), 7.62 (d, J=16.5 Hz, 1H), 7.97 (s, 1H), 8.01 (d, J=8.4 Hz, 1H), 10.12 (s, 1H), 13.17 (s, 1H).

ESI-MS (m/z); 440 [M+H]$^+$

EXAMPLE 354

(E)-N-{2-[2-(1H-indazol-3-yl)vinyl]phenyl}-5-(methylsulfonyl)thiophene-2-carboxamide (Compound 354)

In a similar manner to Example 29, 5-(methylsulfonyl)thiophene-2-carboxylic acid (97 mg, 0.47 mmol) was treated with thionyl chloride (53 μL, 0.72 mmol), DMF (5.0 μL, 0.085 mmol) and dichloromethane (2.0 mL), followed by reacting with Compound 2 (0.10 g, 0.43 mmol), triethylamine (60 μL, 1.1 mmol) and THF (2.0 mL) to obtain Compound 354 (58 mg, 32%).

$^1$H-NMR (270 MHz, DMSO-$d_6$) δ 3.44 (s, 3H), 7.10 (t, J=7.3 Hz, 1H), 7.33-7.44 (m, 4H), 7.54-7.59 (m, 2H), 7.56 (d, J=16.5 Hz, 1H), 7.92-8.04 (m, 3H), 8.14 (d, J=3.2 Hz, 1H), 10.67 (s, 1H), 13.16 (s, 1H).

ESI-MS (m/z); 424 [M+H]$^+$

EXAMPLE 355

Preparation Example (Tablet)

Tablet having the following formulation is prepared in a conventional manner.

| | |
|---|---|
| Compound 2 | 5 mg |
| Lactose | 60 mg |
| Potato starch | 30 mg |
| Poly(vinyl alcohol) | 2 mg |
| Magnesium stearate | 1 mg |
| Tar pigment | trace amount |

INDUSTRIAL APPLICABILITY

The present invention provides an IGF-1R inhibitor comprising, as an active ingredient, an indazole derivative or a pharmaceutically acceptable salt thereof, and the like.

The invention claimed is:

1. An indazole derivative represented by Formula (IIIb):

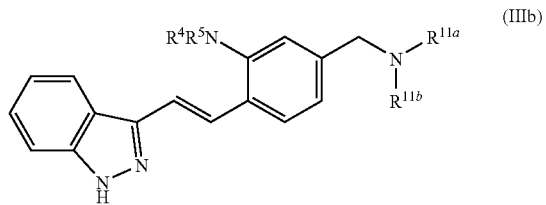

(IIIb)

{wherein $R^4$ represents a hydrogen atom or substituted or unsubstituted lower alkyl, $R^5$ represents a hydrogen atom, substituted or unsubstituted lower alkyl, a substituted or unsubstituted heterocyclic group, —C(=S)NH$_2$, —C(=O)R$^6$ [wherein R$^6$ represents a hydrogen atom, substituted or unsubstituted lower alkyl, substituted or unsubstituted lower alkoxy, substituted or unsubstituted aryl, a substituted or unsubstituted heterocyclic group, or —NR$^{7a}$R$^{7b}$ (wherein R$^{7a}$ and R$^{7b}$ may be the same or different and each represents a hydrogen atom, substituted or unsubstituted lower alkyl, substituted or unsubstituted lower alkoxy, substituted or unsubstituted aryl, or a substituted or unsubstituted heterocyclic group, or R$^{7a}$ and R$^{7b}$ are combined together with the adjacent nitrogen atom thereto to form a substituted or unsubstituted heterocyclic group)] or —S(O)$_2$R$^8$ (wherein R$^8$ represents substituted or unsubstituted lower alkyl or substituted or unsubstituted aryl), or R$^4$ and R$^5$ are combined together with the adjacent nitrogen atom thereto to form nitro, a substituted or unsubstituted heterocyclic group, —N=CH—R$^{18}$ (wherein R$^{18}$ represents substituted or unsubstituted aryl, or a substituted or unsubstituted heterocyclic group), or —N=CH—NR$^{9a}$R$^{9b}$ (wherein R$^{9a}$ and R$^{9b}$ may be the same or different and each represents a hydrogen atom or lower alkyl), and R$^{11a}$ and R$^{11b}$ have the same meanings as R$^{7a}$ and R$^{7b}$ defined above, respectively}, or a pharmaceutically acceptable salt thereof.

2. The indazole derivative or the pharmaceutically acceptable salt thereof according to claim 1, wherein R$^{11a}$ and R$^{11b}$ are combined together with the adjacent nitrogen atom thereto to form a substituted or unsubstituted heterocyclic group.

3. The indazole derivative or the pharmaceutically acceptable salt thereof according to claim 1, wherein R$^{11a}$ and R$^{11b}$ may be the same or different and each is substituted or unsubstituted lower alkyl.

4. The indazole derivative or the pharmaceutically acceptable salt thereof according to claim 1, wherein R$^4$ is a hydrogen atom and R$^5$ is —C(=O)R$^{6d}$ (wherein R$^{6d}$ represents a substituted or unsubstituted heterocyclic group).

5. The indazole derivative or the pharmaceutically acceptable salt thereof according to claim 2, wherein R$^4$ is a hydrogen atom and R$^5$ is —C(=O)R$^{6d}$ (wherein R$^{6d}$ represents a substituted or unsubstituted heterocyclic group).

6. The indazole derivative or the pharmaceutically acceptable salt thereof according to claim 3, wherein R$^4$ is a hydrogen atom and R$^5$ is —C(=O)R$^{6d}$ (wherein R$^{6d}$ represents a substituted or unsubstituted heterocyclic group).

7. The indazole derivative or the pharmaceutically acceptable salt thereof according to claim 5, wherein R$^{6d}$ methylthiophen-2-yl.

8. The indazole derivative or the pharmaceutically acceptable salt thereof according to claim 4, wherein R$^{11a}$ and R$^{11b}$ are combined together with the adjacent nitrogen atom thereto to form a substituted or unsubstituted piperazinyl.

9. The indazole derivative or the pharmaceutically acceptable salt thereof according to claim 8, wherein R$^{6d}$ is 3-methylthiophen-2-yl.

10. An indazole derivative selected from the group consisting of:
(E)-N-{2-[2-(1H-indazol-3-yl)vinyl]-5-(4-methylpiperazin-1-ylmethyl)phenyl}-3-methylthiophene-2-carboxamide,
(E)-N-{5-[4-(2-hydroxyethyl)piperazin-1-ylmethyl]-2-[2-(1H-indazol-3-yl)vinyl]phenyl}-3-methylthiophene-2-carboxamide,
(E)-N-{2-[2-(1H-indazol-3-yl)vinyl]-5-piperazin-1-ylmethyl}phenyl]-3-methylthiophene-2-carboxamide,
(E)-N-{2-[2-(1H-indazol-3-yl)vinyl]-5-[4-(2-methoxyacetyl)piperazin-1-ylmethyl]phenyl}-3-methylthiophene-2-carboxamide,
(E)-N-{2-[2-(1H-indazol-3-yl)vinyl]-5-[4-(2-hydroxyacetyl)piperazin-1-ylmethyl]phenyl}-3-methylthiophene-2-carboxamide,
(E)-N-{5-(4-acetylpiperazin-1-ylmethyl)-2-[2-(1H-indazol-3-yl)vinyl]phenyl}-3-methylthiophene-2-carboxamide,
(E)-N-{2-[2-(1H-indazol-3-yl)vinyl]-5-[4-(2-methoxyethyl)piperazin-1-ylmethyl]phenyl}-3-methylthiophene-2-carboxamide,
(E)-N-{5-[4-(3-hydroxypropyl)piperazin-1-ylmethyl]-2-[2-(1H-indazol-3-yl)vinyl]phenyl}-3-methylthiophene-2-carboxamide,
(E)-N-{5-[4-(2-hydroxy-2-methylpropyl)piperazin-1-ylmethyl]-2-[2-(1H-indazol-3-yl)vinyl]phenyl}-3-methylthiophene-2-carboxamide,
(E)-{2-[2-(1H-indazol-3-yl)vinyl]-5-[4-(3-oxobutyl)piperazin-1-ylmethyl]phenyl}-3-methylthiophene-2-carboxamide, and (E)-N-{5-[4-(3-hydroxy-3-methylbutyl)piperidin-1-ylmethyl]-2-[2-(1H-indazol-3-yl)vinyl]phenyl}-3-methylthiophene-2-carboxamide, or a pharmaceutically acceptable salt thereof.

11. An indazole derivative selected from the group consisting of:

(E)-N-{2-[2-(1H-indazol-3-yl)vinyl]-5-(4-methyl-3-oxopiperazin-1-ylmethyl)phenyl}-3-methylthiophene-2-carboxamide, (R)-(E)-N-{2-[2-(1H-indazol-3-yl)vinyl]-5-(2-methylpiperazin-1-ylmethyl)phenyl}-3-methylthiophene-2-carboxamide, and (S)-(E)-N-{2-[2-(1H-indazol-3-yl)vinyl]-5-(2-methylpiperazin-1-ylmethyl)phenyl}-3-methylthiophene-2-carboxamide, or a pharmaceutically acceptable salt thereof.

12. An indazole derivative selected from the group consisting of:

(E)-N-{2-[2-(1H-indazol-3-yl)vinyl]-5-(piperazin-1-ylcarbonyl)phenyl}-3-methylthiophene-2-carboxamide, (E)-N-{2-[2-(1H-indazol-3-yl)vinyl]-5-(4-methanesulfonylpiperazin-1-ylcarbonyl)phenyl}-3-methylthiophene-2-carboxamide, (S)-(E)-N-{2-[2-(1H-indazol-3-yl)vinyl]-5-[4-(pyrrolidin-2-ylcarbonyl)piperazin-1-ylcarbonyl]phenyl}-3-methylthiophene-2-carboxamide, and (E)-N-{5-[4-(2-hydroxyethyl)piperazin-1-ylcarbonyl]-2-[2-(1H-indazol-3-yl)vinyl]phenyl}-3-methylthiophene-2-carboxamide, or a pharmaceutically acceptable salt thereof.

13. An indazole derivative selected from the group consisting of:

(E)-N-{-2-[2-(1H-indazol-3-yl)vinyl]-5-(N-propylcarbamoyl)phenyl}-3-methylthiophene-2-carboxamide, (E)-N-{-2-[2-(1H-indazol-3-yl)vinyl]-5-[2-(morpholin-4-yl)ethylaminomethyl]phenyl}-3-methylthiophene-2-carboxamide, and (E)-N-{-2-[2-(1H-indazol-3-yl)vinyl]-5-[N-(2-methoxyethyl)methylaminomethyl]phenyl}-3-methylthiophene-2-carboxamide, or a pharmaceutically acceptable salt thereof.

14. A method for inhibiting type I insulin-like growth factor receptor comprising administering to a mammal an effective amount of the indazole derivative or the pharmaceutically acceptable salt thereof described in any one of claims 1 to 4, 5, 6 and 7 to 13.

15. A method for treating solid carcinoma selected from the group consisting of colon cancer and pancreatic cancer comprising administering to a mammal an effective amount of the indazole derivative or the pharmaceutically acceptable salt thereof described in any one of claims 1 to 4, 5, 6 and 7 to 13.

16. A method for treating multiple myeloma comprising administering to a mammal an effective amount of the indazole derivative or the pharmaceutically acceptable salt thereof described in any one of claims 1 to 4, 5, 6 and 7 to 13.

* * * * *

UNITED STATES PATENT AND TRADEMARK OFFICE
CERTIFICATE OF CORRECTION

PATENT NO. : 7,605,272 B2  Page 1 of 11
APPLICATION NO. : 11/814753
DATED : October 20, 2009
INVENTOR(S) : Yutaka Kanda et al.

It is certified that error appears in the above-identified patent and that said Letters Patent is hereby corrected as shown below:

ON THE TITLE PAGE ITEM [57] ABSTRACT:

Line 8, "or the like," should be deleted.

COLUMN 1:

Line 49, "an" should read --a--; and
Line 65, "1-phenyltetrahydronaphtalene" should read
--1-phenyltetrahydronaphthalene--.

COLUMN 4:

Line 50, " 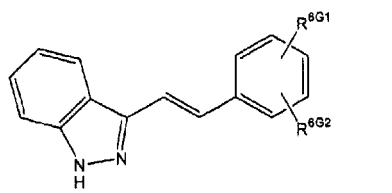 "

should read

-- 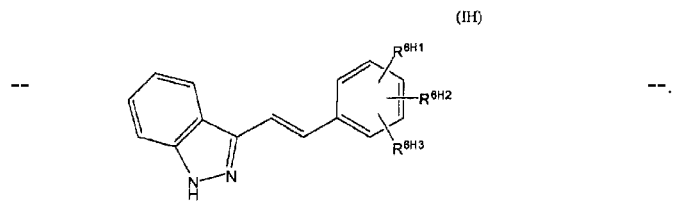 --.

COLUMN 6:

Line 28, "—$CX^1X^1$—$N^{11a}R^{11b}$" should read -- —$CX^1X^2$—$N^{11a}R^{11b}$--.

COLUMN 8:

Line 22, " 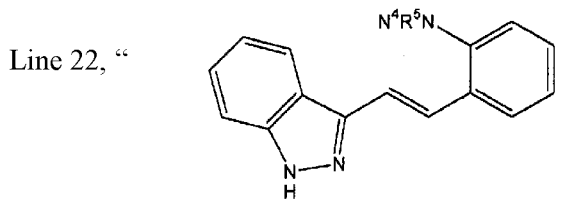 " should read

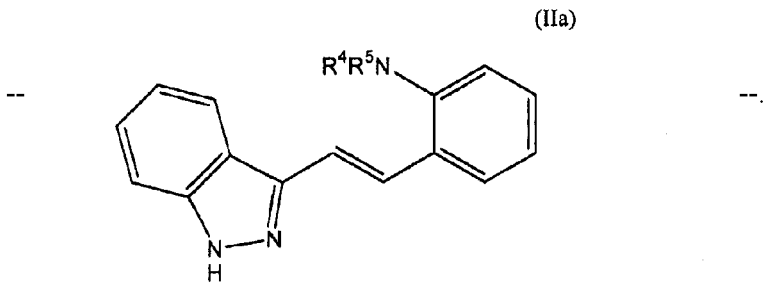

(IIa)

COLUMN 12:

Line 43, "tetrahydrophtalimido, 1,2-cyclopentenedicarboxyImido," should read
--tetrahydrophthalimido, 1,2-cyclopentenedicarboxyimido,--.

COLUMN 13:

Line 23, "groups" should read --group--;
Line 24, "(v)," should read --(V),--;
Line 25, "atoms" should read --atom--; and
Line 62, "heteroatom" should read --heteroatoms--.

COLUMN 14:

Line 13, "heteroatom" should read --heteroatoms--; and
Line 42, "naphtalenedicarboxamido," should read
--naphthalenedicarboxamido,--.

COLUMN 15:

Line 56, "cyclopropylcarbonyl," (second occurrence) should be deleted.

COLUMN 17:

Line 61, after "like" insert --or the like--; and
Line 45, "like]}" should read --like]};--.

COLUMN 19:

Line 54, "each" should be deleted.

COLUMN 20:

Line 64, "δ 6" should be deleted.

CERTIFICATE OF CORRECTION (continued)
U.S. Pat. No. 7,605,272 B2

COLUMN 45:

No. 171, " 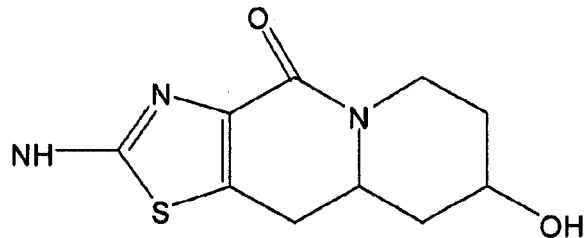 " should read

-- 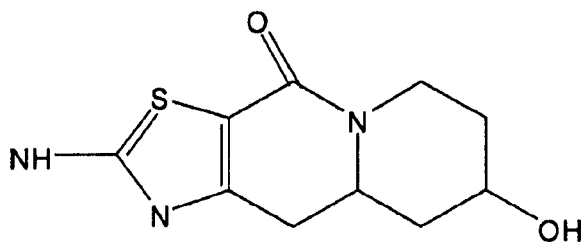 --.

COLUMN 98:

Line 6, "(d, J=8.1Hz, 1H)," should read --7.90 (d, J=8.1Hz, 1H),--.

COLUMN 105:

Line 14, "352 [M-H]$^+$" should read --352 [M+H]$^+$--.

COLUMN 110:

Line 64, "mg, 0.77 mmol)" should read --180 mg, 0.77 mmol)--.

COLUMN 111:

Line 15, "triethylamine μL, 0.77" should read --triethylamine (107 μL, 0.77--.

COLUMN 113:

Line 15, "(d, J=16.8 Hz, 1H)," should read --7.53 (d, J=16.8 Hz, 1H)--
and "7.95-7.53" should read --7.95-7.98--;
Line 17, "442 [M-H]$^+$" should read --442 [M+H]$^+$--; and
Line 33, "380 [M-H]$^+$" should read --380 [M+H]$^+$--.

COLUMN 114:

Line 13, "(d, J=4.0 Hz, 1H)," should read --7.87 (d, J=4.0 Hz, 1H),--.

COLUMN 119:

Line 32, "mg, mmol)" should read --mg, 0.64 mmol)--.

COLUMN 121:

Line 67, "acid mg, 0.61 mmol)," should read --acid (110 mg, 0.61 mmol),--.

COLUMN 122:

Line 16, "280)" should read --28%--.

COLUMN 123:

Line 15, "7.94 (d, J=8.4 Hz, 161-1H)," should read --7.94 (d, J=8.4 Hz, 1H),--; and
Line 17, "OAPCI-MS" should read --APCI-MS--.

COLUMN 127:

Line 9, "β-(52.0 mg, 0.42 mmol)," should read --(52.0 mg, 0.42 mmol),--.

COLUMN 129:

Line 61, "(Compound III)" should read --(Compound 111)--; and
Line 63, "Compound III" should read --Compound 111--.

COLUMN 130:

Line 25, "7.55 (d, J=8.6 Hz 1H)," should read --7.55 (d, J=8.6 Hz, 1H),--;
Line 43, "(s, 3H)," should read --2.51 (s, 3H),--; and
Line 46, "(br, 1H)," should read --9.96 (br, 1H),--.

COLUMN 133:

Line 53, "8.00 (d, J=8.1, Hz, 1H)," should read --8.00 (d, J=8.1 Hz, 1H),--.

COLUMN 135:

Line 6, "pound 132;" should read --pound 129;--.

COLUMN 137:

Line 62, "hydroxyethoxybenzaldehyde" should read --hydroxyethoxy)benzaldehyde--.

COLUMN 139:

Line 31, "345 [M-H]" should read --345 [M+H]$^+$--;
    Line 45, "added organic" should read --added with water and ethyl acetate to separate the mixture into organic--;
    Line 46, "with water and ethyl acetate to separate the mixture" should be deleted; and
    Line 47, "into" should be deleted.

COLUMN 140:

Line 11, "APCI-MS" should read --¶ APCI-MS--;
    Line 25, "APCI-MS" should read --¶ APCI-MS--; and
    Line 49, "ESI-MS" should read --¶ ESI-MS--.

COLUMN 141:

Line 2, "ESI-MS" should read --¶ ESI-MS--.

COLUMN 146:

Line 42, "8.72 (d, J=8.1 Hz," should be deleted; and
    Line 43, "1H)," should be deleted.

COLUMN 154:

Line 2, "(br," should read --13.2 (br,--; and
    Line 21, "(d, J=16.5 Hz, 1H)," should read --7.42 (d, J=16.5 Hz, 1H),--.

COLUMN 156:

Line 67, "(5μL, 239-0.06 mmol)" should read --(5μL, 0.06 mmol)--.

COLUMN 158:

Line 55, "336 [M-H]" should read --336 [M+H]$^+$--.

COLUMN 159:

Line 48, "(d, J=2.0 Hz, 1H)," should read --6.29 (d, J=2.0 Hz, 1H),--; and
    Line 49, "(d, J=16.7 Hz, 1H)," should read --7.52 (d, J=16.7 Hz, 1H),--.

COLUMN 160:

Line 55, "(E)-3-[(2-{2-(2,5-dimethylpyrrol-1-yl)phenyl]vinyl}-" should read --(E)-3-{2-[2-(2,5-dimethylpyrrol-1-yl)phenyl]vinyl}- --.

COLUMN 161:

Line 52, "409 [M-H]" should read --409 [M+H]$^+$--; and
    Line 61, "nyl]phenyl}-5-nitroisoindole-1,3-dioen" should read
        --nyl]phenyl}-5-nitroisoindole-1,3-dione--.

COLUMN 163:

Line 18, "δ2.56" should read --δ 2.56--.

COLUMN 174:

Line 25, "APCI-MS" should read --¶ APCI-MS--; and
    Line 42, "7.38 (dd, J=8.4, 8.4, 1H)" should read --7.38 (dd, J=8.4, 8.4, 1H),--.

COLUMN 177:

Line 46, "APCI-MS" should read --¶ APCI-MS--.

COLUMN 179:

Line 53, "(d, J=4.9 Hz, 1H)," should read --7.05 d, (J=4.9 Hz, 1H),--.

COLUMN 182:

Line 9, "(d, J=4.9 Hz, 1H)," should read --7.07 (d, J=4.9 Hz, 1H),--; and
    Line 10, "(d, J=4.9" should read --7.72 (d, J=4.9--.

COLUMN 183:

Line 17, "518 [M+H]" should read --518 [M+H]$^+$--.

COLUMN 184:

Line 12, "APCI-MS" should read --¶ APCI-MS--;
    Line 35, "APCI-MS" should read --¶ APCI-MS--; and
    Line 54, "APCI-MS" should read --¶ APCI-MS--.

COLUMN 185:

Line 12, "APCI-MS" should read --¶ APCI-MS--.

COLUMN 187:

Line 2, "APCI-MS" should read --¶ APCI-MS--.

COLUMN 190:

Line 53, "APCI-MS" should read --¶ APCI-MS--.

COLUMN 191:

Line 24, "APCI-MS" should read --¶ APCI-MS--.

COLUMN 193:

Line 19, "APCI-MS" should read --¶ APCI-MS--; and
  Line 56, "APCI-MS" should read --¶ APCI-MS--.

COLUMN 194:

Line 27, "APCI-MS" should read --¶ APCI-MS--; and
  Line 53, "APCI-MS" should read --¶ APCI-MS--.

COLUMN 196:

Line 19, "(0.36 g," should read --(0.36 g, 96%).--;
  Line 23, "APCI-MS" should read --¶ APCI-MS--;
  Line 42, "APCI-MS" should read --¶ APCI-MS--; and
  Line 67, "APCI-MS" should read --¶ APCI-MS--.

COLUMN 197:

Line 37, "APCI-MS" should read --¶ APCI-MS--; and
  Line 58, "APCI-MS" should read --¶ APCI-MS--.

COLUMN 198:

Line 15, "APCI-MS" should read --¶ APCI-MS--;
  Line 31, "APCI-MS" should read --¶ APCI-MS--;
  Line 50, "(s, 1H)." should read --10.2 (s, 1H).--; and
  Line 51, "APCI-MS" should read --¶ APCI-MS--.

COLUMN 199:

Line 2, "(t," should read --3.62 (t,--;
  Line 3, "(d, J=16.5 Hz," should read --7.33 (d, J=16.5 Hz,--;
  Line 5, "APCI- " should read --¶ APCI- --;
  Line 27, "APCI-MS" should read --¶ APCI-MS--;
  Line 44, "APCI-MS" should read --¶ APCI-MS--; and
  Line 67, "APCI-MS" should read --¶ APCI-MS--.

COLUMN 200:

Line 44, "APCI-MS" should read --¶ APCI-MS--; and
    Line 67, "APCI-MS" should read --¶ APCI-MS--.

COLUMN 201:

Line 14, "APCI-MS" should read --¶ APCI-MS--.

COLUMN 202:

Line 45, "(d, J=16.8 Hz, 1H), (d, 7.53 (d, J=8.1 Hz, 1H), (d, J=16.8 Hz,"
        should read --7.48 (d, J=16.8 Hz, 1H), 7.53 (d, J=8.1 Hz, 1H), 7.61 (d,
        J=16.8 Hz,--; and
    Line 47, "(br, 1H)." should read --13.1 (br, 1H).--.

COLUMN 203:

Line 6, "APCI-MS" should read --¶ APCI-MS--; and
    Line 29, "APCI-MS" should read --¶ APCI-MS--.

COLUMN 204:

Line 45, "APCI-MS" should read --¶ APCI-MS--; and
    Line 66, "APCI-MS" should read --¶ APCI-MS--.

COLUMN 205:

Line 15, "APCI-MS" should read --¶ APCI-MS--.

COLUMN 206:

Line 6, "(s, 3H)," should read --2.52 (s, 3H),-- and "(d," should read --7.11(d,--; and
    Line 35, "APCI-MS" should read --¶ APCI-MS--.

COLUMN 207:

Line 3, "APCI-MS" should read --¶ APCI-MS--.

COLUMN 211:

Line 3, "APCI-MS" should read --¶ APCI-MS--;
    Line 22, "APCI-MS" should read --¶ APCI-MS--;
    Line 50, "APCI-MS" should read --¶ APCI-MS--; and
    Line 66, "APCI-MS" should read --¶ APCI-MS--.

COLUMN 212:

Line 48, "APCI-MS" should read --¶ APCI-MS--.

COLUMN 214:

Line 22, "APCI-MS" should read --¶ APCI-MS--;
　　　Line 38, "APCI-MS" should read --¶ APCI-MS--; and
　　　Line 66, "APCI-MS" should read --¶ APCI-MS--.

COLUMN 215:

Line 23, "APCI-MS" should read --¶ APCI-MS--;
　　　Line 41, "APCI-MS" should read --¶ APCI-MS--; and
　　　Line 53, "evaporate" should read --evaporated--.

COLUMN 216:

Line 9, "APCI-MS" should read --¶ APCI-MS--; and
　　　Line 42, "-1,2-diole" should read -- -1,2-dione--.

COLUMN 217:

Line 46, "APCI-MS" should read --¶ APCI-MS--.

COLUMN 220:

Line 41, "APCI-MS" should read --¶ APCI-MS--.

COLUMN 221:

Line 10, "APCI-MS" should read --¶ APCI-MS--; and
　　　Line 45, "APCI-MS" should read --¶ APCI-MS--.

COLUMN 226:

Line 6, "(s, 2H)," should read --3.64 (s, 2H),--; and
　　　Line 9, "(d, J=7.6 Hz, 1H)," should read --8.18 (d, J=7.6 Hz, 1H),--.

COLUMN 227:

Line 53, "(E)-4-amino-2-{2-[(2-" should read --(E)-4-amino-2-{2-[2- --.

CERTIFICATE OF CORRECTION (continued)
U.S. Pat. No. 7,605,272 B2

COLUMN 229:

Line 65, "Example 29, (E)-N-{5-hydroxym-" should read --Step 2 of Example
        224, Compound 331 (75 mg, 21%) was obtained from
        (E)-N-{2-[2-(lH-indazol-3-yl)vinyl]-5-(bromomethyl)phenyl}-
        3-methylthiophene-2-carboxamide (0.35 g, 0.77 mmol) obtained in
        Step 1 of Example 224, triethylamine (0.32 mL, 2.3 mmol) and
        (R)-3-methylpiperazine-1-carboxylic acid tert-butyl ester (0.46 g, 2.3 mmol).--; and
    Lines 66-67 should be deleted.

COLUMN 230:

Lines 1-6 should be deleted;
    Line 28, "thylpyrrolecarboxylic" should read --thylpyrrole-2-carboxylic--; and
    Line 55, "by and" should read --by--.

COLUMN 234:

Line 62, "-3-nitrophenoxyethyl)pyrro-" should read
        --3-nitrophenoxy}ethyl)pyrro- --; and
    Line 67, "$^1$H-NMR" should read --¶ $^1$H-NMR--.

COLUMN 235:

Line 47, "4-[2-(phtalimido)" should read --4-[2-(phthalimido)--;
    Line 55, "4-[2-(phtalimido)ethoxy]" should read --4-[2-(phthalimido)ethoxy]--;
        and
    Line 67, "phtalimide" should read --phthalimide--.

COLUMN 236:

Line 9, "phtalimide" should read --phthalimide--.

COLUMN 246:

Line 28, after "$R^{6d}$" insert --is 3- -- and "methylth-" should read --is methylth- --.

COLUMN 248:

Line 11, "or" should read --¶ or--;
Line 16, "claims 1 to 4," should read --claims 1 to 13.--;
Line 17, "5, 6 and 7 to 13." should be deleted;
Line 23, "claims 1 to 4, 5, 6 and 7 to 13." should read --claims 1 to 13.--; and
Line 27, "claims 1 to 4, 5, 6 and 7 to 13." should read --claims 1 to 13.--.

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO.        : 7,605,272 B2
APPLICATION NO.   : 11/814753
DATED             : October 20, 2009
INVENTOR(S)       : Yutaka Kanda et al.

It is certified that error appears in the above-identified patent and that said Letters Patent is hereby corrected as shown below:

COLUMN 14:

Line 43, "tetrahydrophtalimido, 1,2-cyclopentenedicarboxyImido," should read
--tetrahydrophthalimido, 1,2-cyclopentenedicarboxyimido,--.

Signed and Sealed this

Eighteenth Day of May, 2010

David J. Kappos
*Director of the United States Patent and Trademark Office*